US012655149B2

(12) United States Patent
Ha et al.

(10) Patent No.: US 12,655,149 B2
(45) Date of Patent: Jun. 16, 2026

(54) ORGANIC LIGHT-EMITTING DIODE

(71) Applicant: LG CHEM, LTD., Seoul (KR)

(72) Inventors: Jae Seung Ha, Daejeon (KR); Yeon Hwan Kim, Daejeon (KR); Min Woo Lee, Daejeon (KR); Hyeon Jin Mun, Daejeon (KR)

(73) Assignee: LG CHEM, LTD., Seoul (KR)

( * ) Notice: Subject to any disclaimer, the term of this patent is extended or adjusted under 35 U.S.C. 154(b) by 388 days.

(21) Appl. No.: 16/757,990

(22) PCT Filed: Jan. 11, 2019

(86) PCT No.: PCT/KR2019/000488
§ 371 (c)(1),
(2) Date: Apr. 21, 2020

(87) PCT Pub. No.: WO2019/139419
PCT Pub. Date: Jul. 18, 2019

(65) Prior Publication Data

US 2020/0343450 A1 Oct. 29, 2020

(30) Foreign Application Priority Data

Jan. 11, 2018 (KR) ........................ 10-2018-0003772

(51) Int. Cl.
*H10K 50/15* (2023.01)
*C07C 211/61* (2006.01)
(Continued)

(52) U.S. Cl.
CPC .......... *C07D 487/04* (2013.01); *C07C 211/61* (2013.01); *C07D 221/20* (2013.01);
(Continued)

(58) Field of Classification Search
CPC .. H10K 85/631; H10K 85/633; H10K 85/636; H10K 85/6572; H10K 85/626;
(Continued)

(56) References Cited

U.S. PATENT DOCUMENTS 9,496,506 B2 11/2016 Lecloux et al.
2004/0251816 A1 12/2004 Leo et al.
(Continued)

FOREIGN PATENT DOCUMENTS

CN 107459478 A * 12/2017 .......... C07D 209/80
KR 10-20000051826 8/2000
(Continued)

*Primary Examiner* — Alexander R Pagano
*Assistant Examiner* — Frank S. Hou

(74) *Attorney, Agent, or Firm* — Bryan Cave Leighton Paisner LLP

(57) ABSTRACT

Provided is an organic light-emitting diode comprising: a positive electrode; a negative electrode provided to face the positive electrode; a light-emitting layer provided between the positive electrode and the negative electrode; a hole adjusting layer having one or more layers provided between the positive electrode and the light-emitting layer, in which one or more layers of the hole adjusting layers includes at least one compound of Formulae 1 or Formula 2, and the light-emitting layer includes a compound of Formula 3;

[Formula 1]

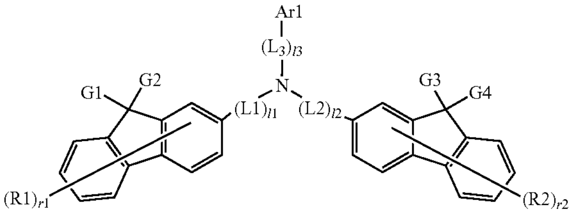

[Formula 2]

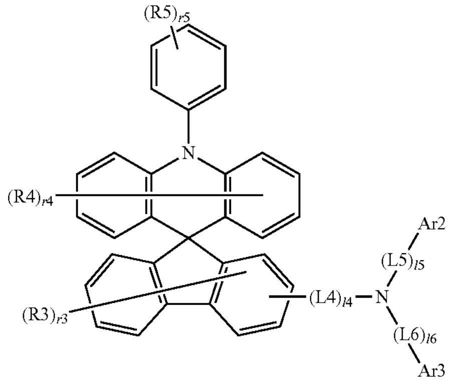

[Formula 3]

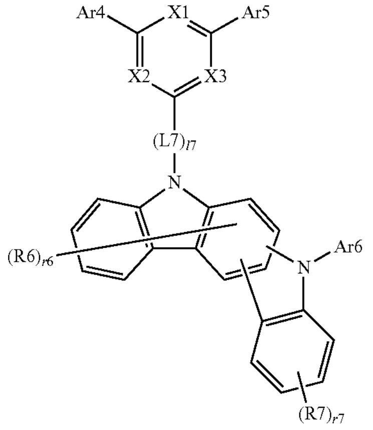

wherein:

G1 to G4 are each independently a substituted or unsubstituted alkyl or aryl group;

(Continued)

L1 to L7 are each independently a direct bond, or a substituted or unsubstituted arylene or heteroarylene group;

at least one of X1 to X3 is N, and any remaining is each CR8; and

Ar1 to Ar6 are each independently a substituted or unsubstituted aryl or heteroaryl group, or Ar2 and Ar3 together form a substituted or unsubstituted hetero ring.

5 Claims, 1 Drawing Sheet

(51) Int. Cl.

| | |
|---|---|
| ***C07D 221/20*** | (2006.01) |
| ***C07D 333/76*** | (2006.01) |
| ***C07D 401/12*** | (2006.01) |
| ***C07D 405/12*** | (2006.01) |
| ***C07D 487/04*** | (2006.01) |
| ***C09K 11/06*** | (2006.01) |
| ***H10K 50/11*** | (2023.01) |
| ***H10K 50/12*** | (2023.01) |
| ***H10K 50/17*** | (2023.01) |
| ***H10K 85/30*** | (2023.01) |
| ***H10K 85/60*** | (2023.01) |
| *H10K 101/10* | (2023.01) |

(52) U.S. Cl.

CPC ......... *C07D 333/76* (2013.01); *C07D 401/12* (2013.01); *C07D 405/12* (2013.01); *C09K 11/06* (2013.01); *H10K 85/633* (2023.02); *H10K 85/636* (2023.02); *H10K 85/654* (2023.02); *H10K 85/6572* (2023.02); *C07C 2603/18* (2017.05); *C09K 2211/1007* (2013.01); *C09K 2211/1011* (2013.01); *C09K 2211/1014* (2013.01); *C09K 2211/1018* (2013.01); *H10K 50/11* (2023.02); *H10K 50/15* (2023.02); *H10K 50/17* (2023.02); *H10K 85/626* (2023.02); *H10K 85/6574* (2023.02); *H10K 85/6576* (2023.02); *H10K 2101/10* (2023.02)

(58) Field of Classification Search

CPC .... H10K 50/156; H10K 85/615; H10K 50/15; C07D 487/04; C09K 11/06

See application file for complete search history.

(56) References Cited

U.S. PATENT DOCUMENTS

| | | | | |
|---|---|---|---|---|
| 2012/0104940 | A1* | 5/2012 | Shin | H10K 85/6572 585/27 |
| 2014/0138632 | A1 | 5/2014 | Kim et al. | |
| 2015/0243891 | A1* | 8/2015 | Kato | C09K 11/06 257/40 |
| 2016/0301005 | A1 | 10/2016 | Pfister et al. | |
| 2017/0125697 | A1 | 5/2017 | Cho et al. | |
| 2017/0125699 | A1* | 5/2017 | Ahn | H10K 85/342 |
| 2017/0133599 | A1 | 5/2017 | Cho et al. | |
| 2017/0186978 | A1* | 6/2017 | Kim | H10K 85/633 |
| 2017/0194569 | A1 | 7/2017 | Kim et al. | |
| 2017/0365788 | A1 | 12/2017 | Cha et al. | |
| 2018/0069180 | A1 | 3/2018 | Cha et al. | |
| 2018/0145261 | A1 | 5/2018 | Ha et al. | |
| 2018/0277762 | A1 | 9/2018 | Ha et al. | |
| 2018/0287068 | A1 | 10/2018 | Ha et al. | |
| 2019/0131542 | A1 | 5/2019 | Kim et al. | |
| 2019/0259947 | A1* | 8/2019 | Lee | H10K 85/633 |
| 2019/0288209 | A1 | 9/2019 | Pfister et al. | |

FOREIGN PATENT DOCUMENTS

| | | | | |
|---|---|---|---|---|
| KR | 10-20100131939 | | 12/2010 | |
| KR | 10-20120101032 | | 9/2012 | |
| KR | 20140006708 | * | 9/2014 | C09K 11/06 |
| KR | 10-20160033587 | | 3/2016 | |
| KR | 10-20160078506 | | 7/2016 | |
| KR | 10-20160150016 | | 12/2016 | |
| KR | 10-20170051762 | | 5/2017 | |
| KR | 10-20170075877 | | 7/2017 | |
| KR | 10-20170076600 | | 7/2017 | |
| KR | 10-20170119291 | | 10/2017 | |
| KR | 10-20170134163 | | 12/2017 | |
| WO | 2003012890 | | 2/2003 | |
| WO | 2017/061779 | A1 | 4/2017 | |
| WO | 2017/061785 | A1 | 4/2017 | |
| WO | 2017/061832 | A1 | 4/2017 | |
| WO | 2017/073932 | A1 | 5/2017 | |

* cited by examiner

[Figure 1]
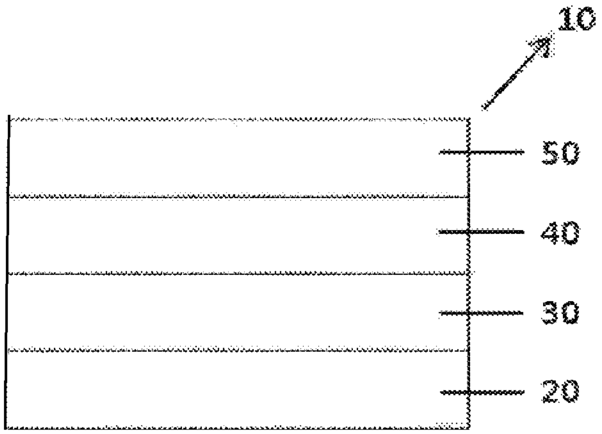
[Figure 2]
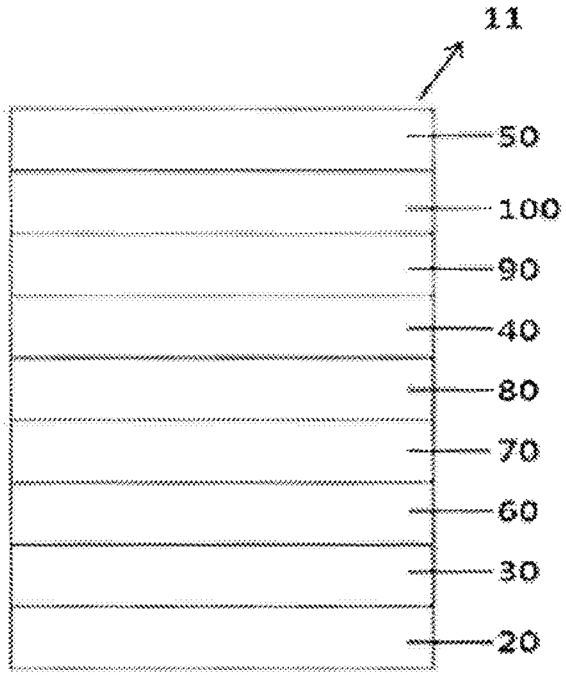

ORGANIC LIGHT-EMITTING DIODE

CROSS-REFERENCE TO RELATED APPLICATIONS

This application is a National Stage Application of International Application No. PCT/KR2019/000488 filed on Jan. 11, 2019, which claims priority to and the benefit of Korean Patent Application No. 10-2018-0003772 filed in the Korean Intellectual Property Office on Jan. 11, 2018, the entire contents of which are incorporated herein by reference.

TECHNICAL FIELD

The present specification relates to an organic light emitting diode.

BACKGROUND

In general, an organic light emitting phenomenon refers to a phenomenon in which electric energy is converted into light energy by using an organic material. An organic light emitting diode using the organic light emitting phenomenon usually has a structure including a positive electrode, a negative electrode, and an organic material layer interposed therebetween. Here, the organic material layer has in many cases a multi-layered structure composed of different materials in order to improve the efficiency and stability of the organic light emitting diode, and for example, can be composed of a hole injection layer, a hole transport layer, a light emitting layer, an electron transport layer, an electron injection layer, and the like. In the structure of the organic light emitting diode, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting diode.

BRIEF DESCRIPTION

Technical Problem

The present specification provides an organic light emitting diode.

Technical Solution

The present specification provides an organic light emitting diode including: a positive electrode; a negative electrode provided to face the positive electrode; a light emitting layer provided between the positive electrode and the negative electrode; and a hole adjusting layer having one or more layers provided between the positive electrode and the light emitting layer, in which one or more layers of the hole adjusting layer include at least one compound selected from the following Formulae 1 and 2, and the light emitting layer includes a compound of the following Formula 3:

[Formula 1]

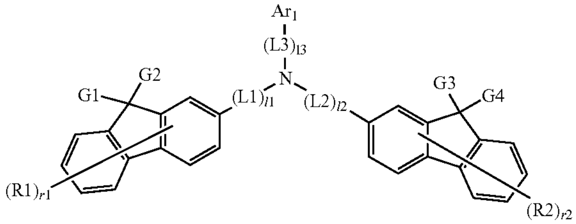

[Formula 2]

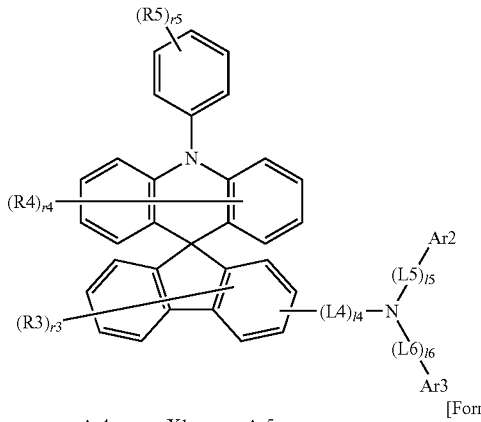

[Formula 3]

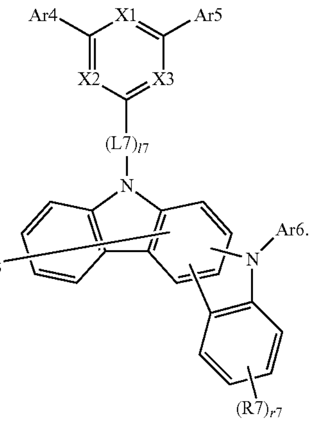

In Formulae 1 to 3:

G1 to G4 are the same as or different from each other, and are each independently a substituted or unsubstituted alkyl group or a substituted or unsubstituted aryl group;

L1 to L7 are the same as or different from each other, and are each independently a direct bond, a substituted or unsubstituted arylene group, or a substituted or unsubstituted heteroarylene group;

at least one of X1 to X3 is N, and any remaining one is CR8;

Ar1 to Ar6 are the same as or different from each other, and are each independently a substituted or unsubstituted aryl group or a substituted or unsubstituted heteroaryl group, or Ar2 and Ar3 are bonded to each other to form a substituted or unsubstituted hetero ring;

R1 to R8 are the same as or different from each other, and are each independently hydrogen, deuterium, a halogen group, a nitrile group, a nitro group, a hydroxyl group, a carbonyl group, an ester group, an imide group, an amide group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted arylphosphine group, a substituted or unsubstituted phosphine oxide group, a substituted or unsubstituted aryl group, or a substituted or unsubstituted heteroaryl group;

r1 to r3 are each an integer from 1 to 7;

r4 is an integer from 1 to 8;

r5 and l1 to l7 are each an integer from 1 to 5;

r6 is an integer from 1 to 6;

r7 is an integer from 1 to 4; and when r1 to r7 and l1 to l7 are each 2 or more, two or more structures in the parenthesis are the same as or different from each other.

Advantageous Effects

An organic light emitting diode according to an exemplary embodiment of the present specification can lower a driving voltage, improve the light efficiency, and improve the service life characteristics of the device by the thermal stability of a compound.

BRIEF DESCRIPTION OF DRAWINGS

FIG. 1 illustrates an organic light emitting diode 10 according to an exemplary embodiment of the present specification.

FIG. 2 illustrates an organic light emitting diode 11 according to another exemplary embodiment of the present specification.

EXPLANATION OF REFERENCE NUMERALS AND SYMBOLS

10, 11: Organic light emitting diode
20: Substrate
30: Positive electrode
40: Light emitting layer
50: Negative electrode
60: Hole injection layer
70: Hole transport layer
80: Hole adjusting layer
90: Electron transport layer
100: Electron injection layer

DETAILED DESCRIPTION

Hereinafter, the present specification will be described in more detail.

The present specification provides an organic light emitting diode including: a positive electrode; a negative electrode provided to face the positive electrode; a light emitting layer provided between the positive electrode and the negative electrode; and a hole adjusting layer having one or more layers provided between the positive electrode and the light emitting layer, in which one or more layers of the hole adjusting layer include at least one of the compounds of Formulae 1 and/or 2, and the light emitting layer includes a compound of Formula 3.

According to an exemplary embodiment of the present specification, in the compound of Formula 1, two substituents among tri-substituted amine substituents are composed of a fluorene unit, and the compound of Formula 2 is composed of a structure in which an amine group is bonded to an acridine fused ring. Accordingly, since Formulae 1 and 2 include an amine group having excellent hole adjusting capability, when the compound of Formula 1 and/or the compound of Formula 2 are/is used as a hole adjusting layer of an organic light emitting diode, the organic light emitting diode has low driving voltage, high efficiency, long service life, and device stability.

According to an exemplary embodiment of the present specification, the compound of Formula 3 has a structure in which a monocyclic hetero ring is substituted with an indolocarbazole core through a linking group, and the conjugation of N unshared electron pairs with indolocarbazole and a monocyclic hetero ring is appropriately maintained, so that an organic light emitting diode using the compound in a light emitting layer of the organic light emitting diode has better service life and efficiency of the device than those of an organic light emitting diode using an anthracene derivative and a pyrene derivative in the related art as a host of a light emitting layer.

Accordingly, an organic light emitting diode including a positive electrode, a negative electrode, and an organic material layer formed therebetween, in which the organic material layer contains the material according to exemplary embodiments described in the present specification, has a low driving voltage and a long service life. In the present specification, effects of low voltage, high efficiency, and long service life are derived by a combination of materials between a light emitting layer and a hole adjusting layer, or a combination of the light emitting layer and the hole adjusting layer having a plurality of layers. According to exemplary embodiments of the present specification, when a material having a structure in which a fluorene unit in a tertiary amine structure is substituted and/or a structure in which an amine group is bonded to an acridine fused ring are/is introduced as a material for a hole adjusting layer, it is possible to bring about improvement in device characteristics caused by transporting holes and adjusting carriers. In particular, as a material for a light emitting layer, a combination with a unit in which a monocyclic hetero ring is bonded to an indolocarbazole core exhibits the best characteristics in terms of voltage. In particular, when the hole adjusting layer has a plurality of layers, an improved result is exhibited due to more finely subdivided energy levels.

When one part "includes" one constituent element in the present specification, unless otherwise specifically described, this does not mean that another constituent element is excluded, but means that another constituent element can be further included.

When one member is disposed "on" another member in the present specification, this includes not only a case where the one member is brought into contact with another member, but also a case where still another member is present between the two members.

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent can be substituted, and when two or more are substituted, the two or more substituents can be the same as or different from each other.

In the present specification, the term "substituted or unsubstituted" means being substituted with one or two or more substituents selected from the group consisting of deuterium, a halogen group, a nitrile group, a nitro group, an imide group, an amide group, a carbonyl group, an ether group, an ester group, a hydroxy group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted arylphosphine group, a substituted or unsubstituted phosphine oxide group, a substituted or unsubstituted aryl group, and a substituted or unsubstituted heterocyclic group or being substituted with a substituent to which two or more substituents are linked among the substituents exemplified above, or having no substituent. For example, "the substituent to which two or more substituents are linked" can be a biphenyl group. That is, the biphenyl group can also be an aryl group, and can be interpreted as a substituent to which two phenyl groups are linked.

In the present specification, means a moiety bonded to another substituent or a bonding portion.

In the present specification, a halogen group can be fluorine, chlorine, bromine or iodine.

In the present specification, the number of carbon atoms of an imide group is not particularly limited, but is preferably 1 to 30. Specifically, the imide group can be a compound having the following structures, but is not limited thereto:

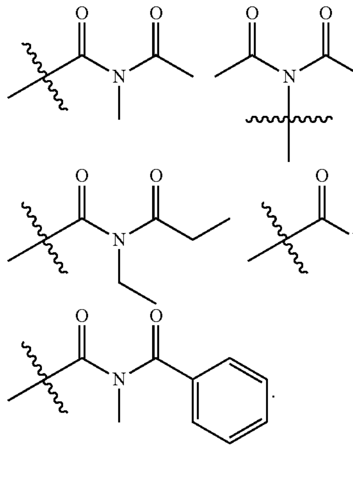

In the present specification, for an amide group, the nitrogen of the amide group can be substituted with hydrogen, a straight-chained, branched, or cyclic alkyl group having 1 to 30 carbon atoms, or an aryl group having 6 to 30 carbon atoms. Specifically, the amide group can be a compound having the following structural formulae, but is not limited thereto:

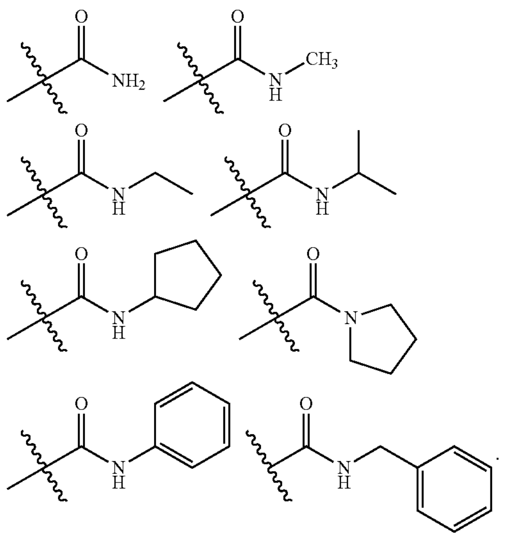

In the present specification, the number of carbon atoms of a carbonyl group is not particularly limited, but is preferably 1 to 30. Specifically, the carbonyl group can be a compound having the following structures, but is not limited thereto:

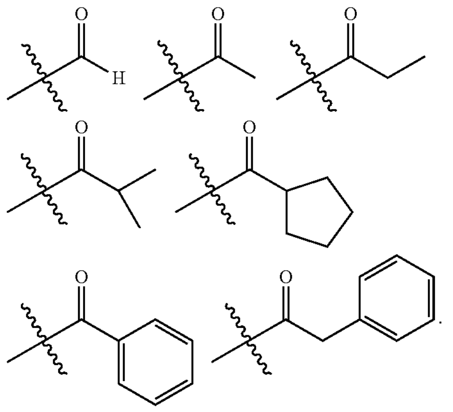

In the present specification, for an ester group, the oxygen of the ester group can be substituted with a straight-chained, branched, or cyclic alkyl group having 1 to 25 carbon atoms, or an aryl group having 6 to 30 carbon atoms. Specifically, the ester group can be a compound having the following structural formulae, but is not limited thereto:

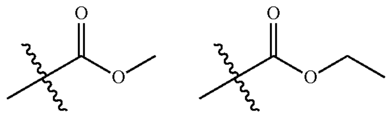

-continued

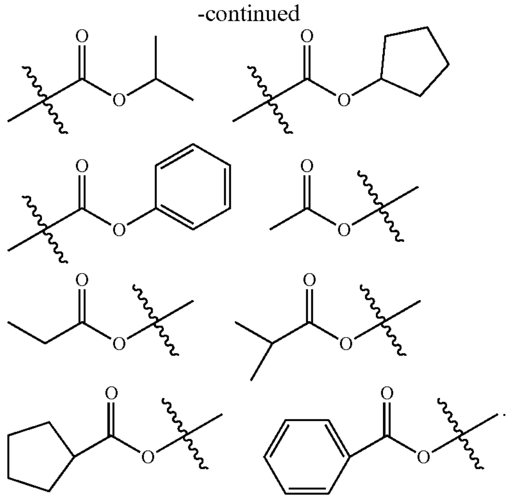

In the present specification, for an ether group, the oxygen of the ether group can be substituted with a straight-chained, branched, or cyclic alkyl group having 1 to 25 carbon atoms, or an aryl group having 6 to 30 carbon atoms. Specifically, the ether group can be a compound having the following structural formulae, but is not limited thereto:

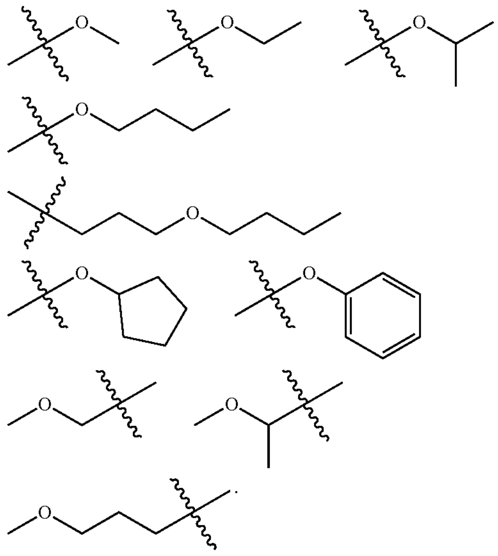

In the present specification, the alkyl group can be straight-chained or branched, and the number of carbon atoms thereof is not particularly limited, but is preferably 1 to 30. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methyl-hexyl, and the like, but are not limited thereto.

In the present specification, a cycloalkyl group is not particularly limited, but has preferably 3 to 30 carbon atoms, and specific examples thereof include cyclopropyl, cyclobutyl, cyclopentyl, 3-methylcyclopentyl, 2,3-dimeth-ylcyclopentyl, cyclohexyl, 3-methylcyclohexyl, 4-methyl-cyclohexyl, 2,3-dimethyl-cyclohexyl, 3,4,5-trimethyl-cyclo-hexyl, 4-tert-butylcyclohexyl, cycloheptyl, cyclooctyl, and the like, but are not limited thereto.

In the present specification, the alkoxy group can be straight-chained, branched, or cyclic. The number of carbon atoms of the alkoxy group is not particularly limited, but is preferably 1 to 30. Specific examples thereof include methoxy, ethoxy, n-propoxy, isopropoxy, i-propyloxy, n-butoxy, isobutoxy, tert-butoxy, sec-butoxy, n-pentyloxy, neo-pentyloxy, isopentyloxy, n-hexyloxy, 3,3-dimethyl-butyloxy, 2-ethylbutyloxy, n-octyloxy, n-nonyloxy, n-decyloxy, benzyloxy, p-methylbenzyloxy, and the like, but are not limited thereto.

In the present specification, an amine group can be selected from the group consisting of —$NH_2$, a monoalkylamine group, a dialkylamine group, an N-alkylarylamine group, a monoarylamine group, a diarylamine group, an N-arylheteroarylamine group, an N-alkyl-heteroarylamine group, a monoheteroarylamine group, and a diheteroarylamine group, and the number of carbon atoms thereof is not particularly limited, but is preferably 1 to 30. Specific examples of the amine group include a methylamine group, a dimethylamine group, an ethylamine group, a diethylamine group, a phenylamine group, a naphthyl-amine group, a biphenylamine group, an anthracenylamine group, a 9-methyl-anthracenylamine group, a diphenylamine group, a ditolylamine group, an N-phenyltolylamine group, a triphenylamine group, an N-phenyl-biphenylamine group, an N-phenylnaphthylamine group, an N-biphenyl-naphthylamine group, an N-naphthylfluorenylamine group, an N-phenyl-phenanthrenylamine group, an N-biphenylphenanthrenylamine group, an N-phenyl-fluorenylamine group, an N-phenyl terphenylamine group, an N-phenanthrenylfluorenylamine group, an N-biphenylfluorenylamine group, and the like, but are not limited thereto.

In the present specification, an N-alkylarylamine group means an amine group in which an alkyl group and an aryl group are substituted with N of the amine group.

In the present specification, an N-arylheteroarylamine group means an amine group in which an aryl group and a heteroaryl group are substituted with N of the amine group.

In the present specification, an N-alkylheteroarylamine group means an amine group in which an alkyl group and a heteroaryl group are substituted with N of the amine group.

In the present specification, examples of an alkylamine group include a substituted or unsubstituted monoalkylamine group or a substituted or unsubstituted dialkylamine group. The alkyl group in the alkylamine group can be a straight-chained or branched alkyl group. The alkylamine group including two or more alkyl groups can include a straight-chained alkyl group, a branched alkyl group, or both a straight-chained alkyl group and a branched alkyl group. For example, the alkyl group in the alkylamine group can be selected from the above-described examples of the alkyl group.

In the present specification, the alkyl group in the N-alkylarylamine group, the alkylthioxy group, the alkylsulfoxy group, and the N-alkylheteroarylamine group is the same as the above-described examples of the alkyl group. Specifically, examples of the alkylthioxy group include a methylthioxy group, an ethylthioxy group, a tert-butylthioxy group, a hexylthioxy group, an octylthioxy group, and the like, and examples of the alkylsulfoxy group include a methylsulfoxy group, an ethylsulfoxy group, a propylsulfoxy group, a butylsulfoxy group, and the like, but the examples are not limited thereto.

In the present specification, the alkenyl group can be straight-chained or branched, and the number of carbon atoms thereof is not particularly limited, but is preferably 2 to 30. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenyl-vinyl-1-yl, 2-phenyl-2-(naphthyl-1-yl)vinyl-1-yl, 2,2-bis(di-phenyl-1-yl)vinyl-1-yl, a stilbenyl group, a styrenyl group, and the like, but are not limited thereto.

In the present specification, specific examples of a silyl group include a trimethylsilyl group, a triethylsilyl group, a t-butyl-dimethylsilyl group, a vinyldimethylsilyl group, a propyldimethylsilyl group, a triphenylsilyl group, a diphenylsilyl group, a phenylsilyl group, and the like, but are not limited thereto.

In the present specification, a boron group can be $-BR_{100}R_{101}$, and $R_{100}$ and $R_{101}$ are the same as or different from each other, and can be each independently selected from the group consisting of hydrogen, deuterium, halogen, a nitrile group, a substituted or unsubstituted monocyclic or polycyclic cycloalkyl group having 3 to 30 carbon atoms, a substituted or unsubstituted straight-chained or branched alkyl group having 1 to 30 carbon atoms, a substituted or unsubstituted monocyclic or polycyclic aryl group having 6 to 30 carbon atoms, and a substituted or unsubstituted monocyclic or polycyclic heteroaryl group having 2 to 30 carbon atoms.

In the present specification, specific examples of a phosphine oxide group include a diphenylphosphine oxide group, a dinaphthylphosphine oxide group, and the like, but are not limited thereto.

In the present specification, an aryl group is not particularly limited, but has preferably 6 to 30 carbon atoms, and the aryl group can be monocyclic or polycyclic.

When the aryl group is a monocyclic aryl group, the number of carbon atoms thereof is not particularly limited, but is preferably 6 to 30. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 30. Specific examples of the polycyclic aryl group include a naphthyl group, an anthracenyl group, a phenanthryl group, a triphenylenyl group, a pyrenyl group, a phenalenyl group, a perylenyl group, a chrysenyl group, a fluorenyl group, and the like, but are not limited thereto.

In the present specification, the fluorenyl group can be substituted, and adjacent substituents can be bonded to each other to form a ring.

When the fluorenyl group is substituted, the substituent can be

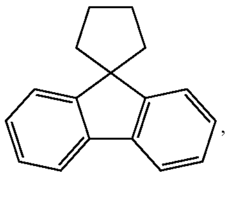
,
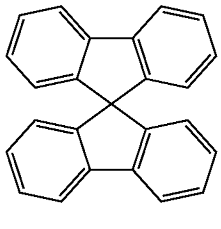
,

-continued

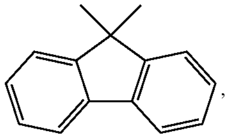
,
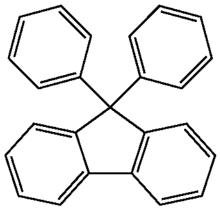
,
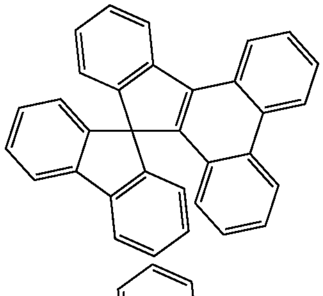
,
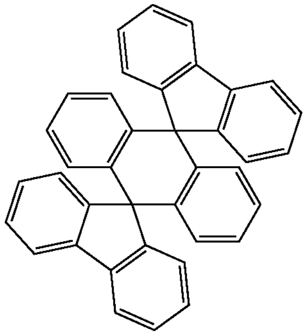

and the like. However, the substituent is not limited thereto.

In the present specification, the "adjacent" group can mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring can be interpreted as groups which are "adjacent" to each other.

In the present specification, the aryl group in the aryloxy group, the arylthioxy group, the arylsulfoxy group, the N-arylalkylamine group, the N-arylheteroarylamine group, and the arylphosphine group is the same as the above-described examples of the aryl group. Specifically, examples of the aryloxy group include a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyl-oxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group, and the like, examples of the arylthioxy group include a phenylthioxy group, a 2-methylphenylthioxy group, a 4-tert-butyl-phenylthioxy group, and the like, and examples of the arylsulfoxy group include a benzenesulfoxy group, a p-toluenesulfoxy group, and the like, but the examples are not limited thereto.

In the present specification, examples of an arylamine group include a substituted or unsubstituted monoarylamine group or a substituted or unsubstituted diarylamine group. The aryl group in the arylamine group can be a monocyclic aryl group or a polycyclic aryl group. The arylamine group including two or more aryl groups can include a monocyclic aryl group, a polycyclic aryl group, or both a monocyclic aryl group and a polycyclic aryl group. For example, the aryl group in the arylamine group can be selected from the above-described examples of the aryl group.

In the present specification, a heterocyclic group includes one or more atoms other than carbon, that is, one or more heteroatoms, and specifically, the heteroatom can include one or more atoms selected from the group consisting of O, N, Se, S, and the like. The number of carbon atoms thereof is not particularly limited, but is preferably 2 to 30, and the heterocyclic group can be monocyclic or polycyclic. The heterocyclic group can have an aliphatic ring, an aromatic ring, or a structure in which an aliphatic ring and an aromatic ring are fused. Examples of the heterocyclic group include a thiophene group, a furanyl group, a pyrrole group, an imidazolyl group, a thiazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthridine group, a phenanthrolinyl group (phenanthroline), an isoxazolyl group, a thiadiazolyl group, a phenothiazinyl group, a dibenzofuran group, and the like, but are not limited thereto.

In the present specification, a heteroaryl group means a substituent including an aromatic hetero ring, and specifically means an aromatic heterocyclic group or a heterocyclic group in which an aromatic ring and an aliphatic ring are fused. The above-described description of the heterocyclic group can be applied to the heteroaryl group, except that the aromatic hetero ring is included.

In the present specification, examples of a heteroarylamine group include a substituted or unsubstituted monoheteroarylamine group or a substituted or unsubstituted diheteroarylamine group. The heteroarylamine group including two or more heteroaryl groups can include a monocyclic heteroaryl group, a polycyclic heteroaryl group, or both a monocyclic heteroaryl group and a polycyclic heteroaryl group. For example, the heteroaryl group in the heteroarylamine group can be selected from the above-described examples of the heteroaryl group.

In the present specification, examples of the heteroaryl group in the N-arylheteroarylamine group and the N-alkylheteroarylamine group are the same as the above-described examples of the heteroaryl group.

In the present specification, in a substituted or unsubstituted ring formed by bonding adjacent groups, the "ring" means a substituted or unsubstituted hydrocarbon ring, or a substituted or unsubstituted hetero ring.

In the present specification, a hydrocarbon ring can be an aromatic ring, an aliphatic ring, or a fused ring of the aromatic ring and the aliphatic ring, and can be selected from the examples of the cycloalkyl group or the aryl group, except for the hydrocarbon ring which is not monovalent.

In the present specification, an aromatic ring can be monocyclic or polycyclic, and can be selected from the examples of the aryl group, except for the aromatic ring which is not monovalent.

In the present specification, a hetero ring includes one or more atoms other than carbon, that is, one or more heteroatoms, and specifically, the heteroatom can include one or more atoms selected from the group consisting of O, N, Se, S, and the like. The hetero ring can be monocyclic or polycyclic, can be an aromatic ring, an aliphatic ring, or a fused ring of the aromatic ring and the aliphatic ring, and can be selected from the examples of the heteroaryl group or the heterocyclic group, except for the hetero ring which is not monovalent.

The arylene group means that there are two bonding positions in an aryl group, that is, a divalent group, and the above-described description on the aryl group can be cited, except that the arylene group is a divalent group.

The heteroarylene group means that there are two bonding positions in a heteroaryl group, that is, a divalent group, and the above-described description on the heteroaryl group can be cited, except that the heteroarylene group is a divalent group.

According to an exemplary embodiment of the present specification, Formula 1 is any one of the following Formulae 1-1 to 1-3:

[Formula 1-1]

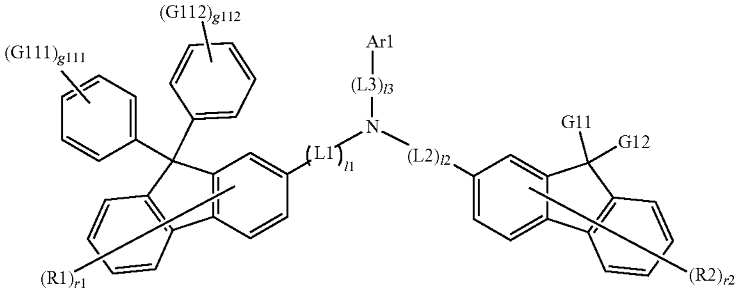

-continued

[Formula 1-2]

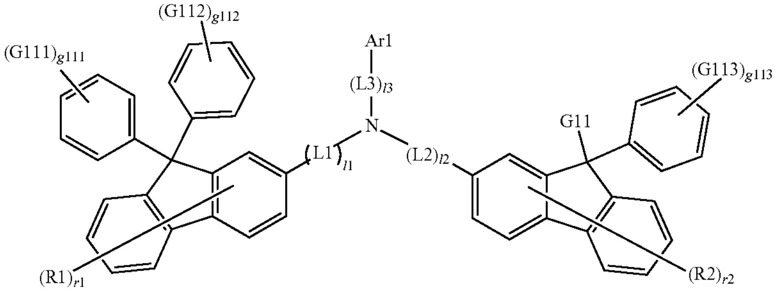

[Formula 1-3]

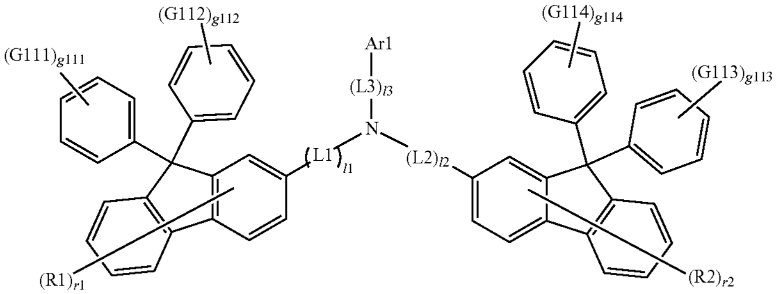

wherein in Formulae 1-1 to 1-3:

the definitions of R1, R2, r1, r2, L1 to L3, l1 to l3, and Ar1 are the same as those defined in Formula 1;

G11 and G12 are the same as or different from each other, and are each independently a substituted or unsubstituted alkyl group;

G111 to G114 are the same as or different from each other, and are each independently hydrogen, a substituted or unsubstituted alkyl group, or a substituted or unsubstituted aryl group;

g111 to g114 are each an integer from 1 to 5; and when gill to g114 are each 2 or more, two or more structures in the parenthesis are the same as or different from each other.

According to an exemplary embodiment of the present specification, Formula 2 is any one of the following Formulae 2-1 to 2-4.

[Formula 2-1]

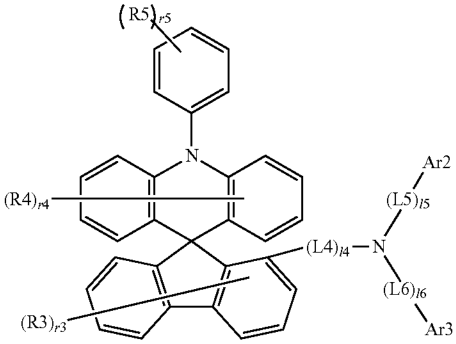

-continued

[Formula 2-2]

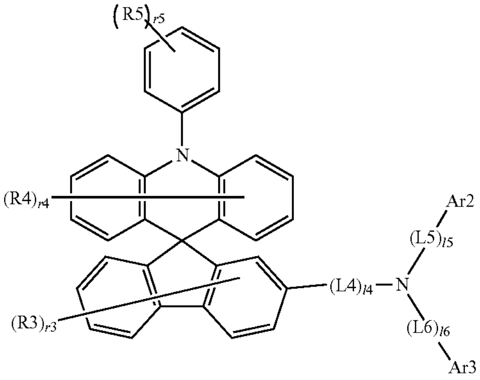

[Formula 2-3]

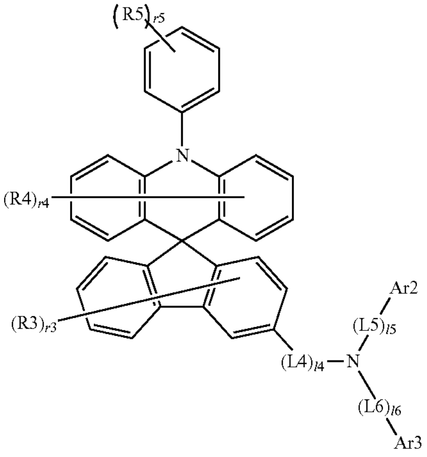

-continued
[Formula 2-4]
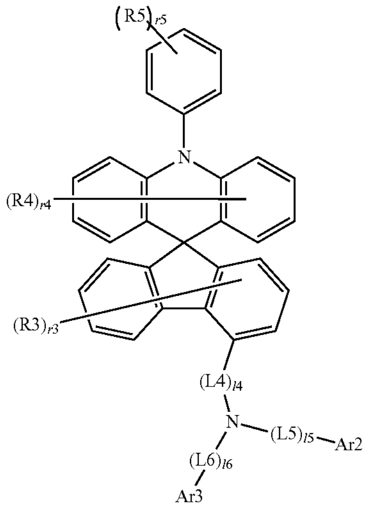
wherein in Formulae 2-1 to 2-4:
the definitions of R3 to R5, L4 to L6, Ar2, Ar3, r3 to r5, and 14 to 16 are the same as those defined in Formula 2.
According to an exemplary embodiment of the present specification, Formula 3 is any one of the following Formulae 3-1 to 3-6:
[Formula 3-1]
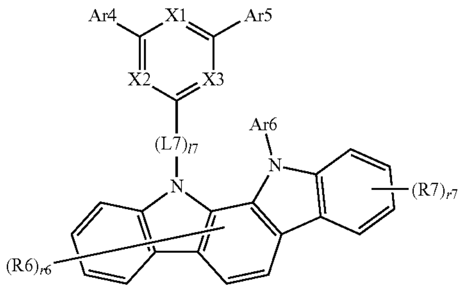
[Formula 3-2]
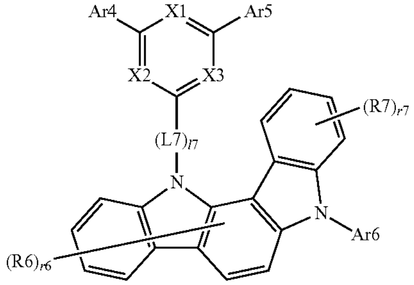
-continued
[Formula 3-3]
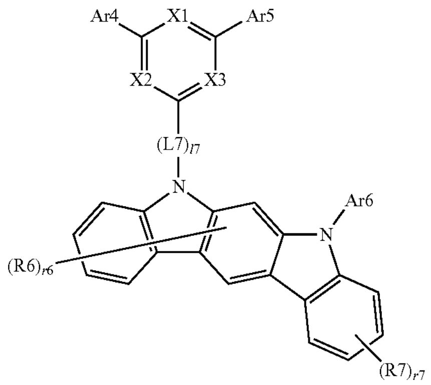
[Formula 3-4]
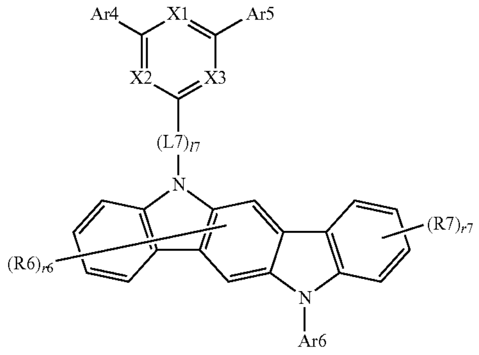
[Formula 3-5]
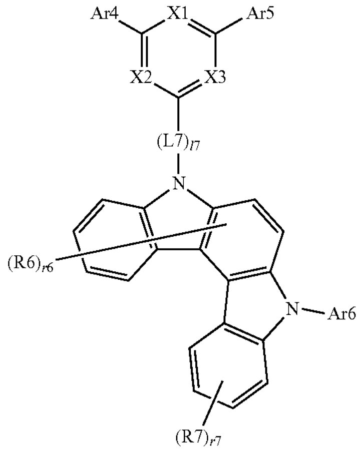

-continued

[Formula 3-6]

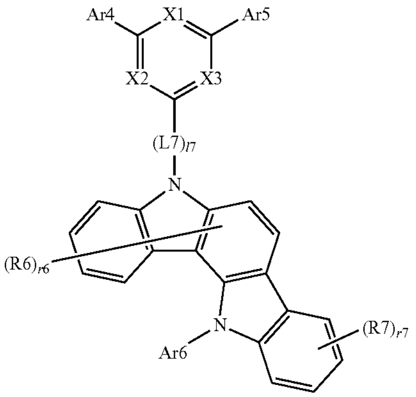

wherein in Formulae 3-1 to 3-6:

the definitions of X1 to X3, L7, l7, Ar4 to Ar6, R6, R7, r6, and r7 are the same as those defined in Formula 3.

According to an exemplary embodiment of the present specification, L1 to L7 are the same as or different from each other, and are each independently a direct bond, or an arylene group that is unsubstituted or substituted with one or more selected from the group consisting of an alkyl group and an aryl group.

According to an exemplary embodiment of the present specification, L1 to L7 are the same as or different from each other, and are each independently a direct bond, a phenylene group, a biphenylylene group, a naphthylene group, or a fluorenylene group that is unsubstituted or substituted with one or more selected from the group consisting of an alkyl group and an aryl group.

According to an exemplary embodiment of the present specification, L1 to L7 are the same as or different from each other, and are each independently a direct bond, a phenylene group, a biphenylylene group, a naphthylene group, or a fluorenylene group that is unsubstituted or substituted with one or more selected from the group consisting of a methyl group and a phenyl group.

According to an exemplary embodiment of the present specification, Ar1 to Ar6 are the same as or different from each other, and are each independently an aryl group that is unsubstituted or substituted with one or more selected from the group consisting of an alkyl group and an aryl group, or a heteroaryl group that is unsubstituted or substituted with an aryl group.

According to an exemplary embodiment of the present specification, Ar1 to Ar6 are the same as or different from each other, and are each independently a phenyl group that is unsubstituted or substituted with an aryl group; a biphenyl group that is unsubstituted or substituted with an aryl group; a terphenyl group that is unsubstituted or substituted with an aryl group; a quaterphenyl group; a naphthyl group; a fluorenyl group that is unsubstituted or substituted with one or more selected from the group consisting of an alkyl group and an aryl group; a carbazolyl group; a dibenzofuran group; a dibenzothiophene group; or a spiroacridinefluorene group that is unsubstituted or substituted with an aryl group.

According to an exemplary embodiment of the present specification, Ar1 to Ar6 are the same as or different from each other, and are each independently a phenyl group that is unsubstituted or substituted with a phenyl group, a biphenyl group, or a terphenyl group; a biphenyl group that is unsubstituted or substituted with a phenyl group or a biphenyl group; a terphenyl group that is unsubstituted or substituted with a phenyl group; a quaterphenyl group; a naphthyl group; a fluorenyl group that is unsubstituted or substituted with one or more selected from the group consisting of a methyl group and a phenyl group; a carbazolyl group; a dibenzofuran group; a dibenzothiophene group; or a spiroacridinefluorene group that is unsubstituted or substituted with a phenyl group.

According to an exemplary embodiment of the present specification, R1 to R8 are the same as or different from each other, and are each independently hydrogen, an alkyl group, or an aryl group.

According to an exemplary embodiment of the present specification, R1 to R8 are the same as or different from each other, and are each independently hydrogen, a methyl group, a t-butyl group, or a phenyl group.

According to an exemplary embodiment of the present specification, in Formula 1, L1 to L3 are the same as or different from each other, and are each independently a direct bond, or an arylene group that is unsubstituted or substituted with one or more selected from the group consisting of an alkyl group and an aryl group.

According to an exemplary embodiment of the present specification, in Formula 1, L1 to L3 are the same as or different from each other, and are each independently a direct bond, a phenylene group, a biphenylylene group, or a fluorenylene group that is unsubstituted or substituted with one or more selected from the group consisting of an alkyl group and an aryl group.

According to an exemplary embodiment of the present specification, in Formula 1, L1 to L3 are the same as or different from each other, and are each independently a direct bond, a phenylene group, a biphenylylene group, or a fluorenylene group that is unsubstituted or substituted with one or more selected from the group consisting of a methyl group and a phenyl group.

According to an exemplary embodiment of the present specification, in Formula 1, l1 to l3 are each 1 or 2.

According to an exemplary embodiment of the present specification, in Formula 1, Ar1 is an aryl group that is unsubstituted or substituted with one or more selected from the group consisting of an alkyl group and an aryl group, or a heteroaryl group.

According to an exemplary embodiment of the present specification, in Formula 1, Ar1 is a phenyl group that is unsubstituted or substituted with an aryl group; a biphenyl group that is unsubstituted or substituted with an aryl group; a terphenyl group; a naphthyl group; a fluorenyl group that is unsubstituted or substituted with one or more selected from the group consisting of an alkyl group and an aryl group; a carbazolyl group; a dibenzofuran group; or a dibenzothiophene group.

According to an exemplary embodiment of the present specification, in Formula 1, Ar1 is a phenyl group that is unsubstituted or substituted with a phenyl group, or a biphenyl group; a biphenyl group that is unsubstituted or substituted with a phenyl group; a terphenyl group; a naphthyl group; a fluorenyl group that is unsubstituted or substituted with one or more selected from the group consisting of a methyl group and a phenyl group; a carbazolyl group; a dibenzofuran group; or a dibenzothiophene group.

According to an exemplary embodiment of the present specification, in Formula 1, R1 and R2 are the same as or different from each other, and are each independently hydrogen, an alkyl group, or an aryl group.

According to an exemplary embodiment of the present specification, in Formula 1, R1 and R2 are the same as or different from each other, and are each independently hydrogen, a methyl group, a t-butyl group, or a phenyl group.

According to an exemplary embodiment of the present specification, in Formula 1, G1 to G4 are the same as or different from each other, and are each independently an alkyl group, or an aryl group that is unsubstituted or substituted with an alkyl group, or an aryl group.

According to an exemplary embodiment of the present specification, in Formula 1, G1 to G4 are the same as or different from each other, and are each independently a methyl group, a phenyl group that is unsubstituted or substituted with an alkyl group, or an aryl group; or a biphenyl group.

According to an exemplary embodiment of the present specification, in Formula 1, G1 to G4 are the same as or different from each other, and are each independently a methyl group; a phenyl group that is unsubstituted or substituted with a methyl group, a t-butyl group, or a phenyl group; or a biphenyl group.

According to an exemplary embodiment of the present specification, in Formulae 1-1 and 1-2, G11 and G12 are the same as or different from each other, and are each independently an alkyl group.

According to an exemplary embodiment of the present specification, in Formulae 1-1 and 1-2, G11 and G12 are a methyl group.

According to an exemplary embodiment of the present specification, in Formulae 1-1 to 1-3, G111 to G114 are the same as or different from each other, and are each independently hydrogen, an alkyl group, an aryl group.

According to an exemplary embodiment of the present specification, in Formulae 1-1 to 1-3, G111 to G114 are the same as or different from each other, and are each independently hydrogen, a methyl group, a t-butyl group, or a phenyl group.

According to an exemplary embodiment of the present specification, in Formula 2, L4 to L6 are the same as or different from each other, and are each independently a direct bond, or an arylene group that is unsubstituted or substituted with one or more selected from the group consisting of an alkyl group and an aryl group.

According to an exemplary embodiment of the present specification, in Formula 2, L4 to L6 are the same as or different from each other, and are each independently a direct bond, a phenylene group, a biphenylylene group, or a fluorenylene group that is unsubstituted or substituted with one or more selected from the group consisting of an alkyl group and an aryl group.

According to an exemplary embodiment of the present specification, in Formula 2, L4 to L6 are the same as or different from each other, and are each independently a direct bond, a phenylene group, a biphenylylene group, or a fluorenylene group that is unsubstituted or substituted with one or more selected from the group consisting of a methyl group and a phenyl group.

According to an exemplary embodiment of the present specification, in Formula 2, L4 to L6 are each 1 or 2.

According to an exemplary embodiment of the present specification, in Formula 2, Ar2 and Ar3 are the same as or different from each other, and are each independently an aryl group that is unsubstituted or substituted with one or more selected from the group consisting of an alkyl group and an aryl group, or a heteroaryl group that is unsubstituted or substituted with an aryl group.

According to an exemplary embodiment of the present specification, in Formula 2, Ar2 and Ar3 are the same as or different from each other, and are each independently a phenyl group that is unsubstituted or substituted with an aryl group; a biphenyl group that is unsubstituted or substituted with an aryl group; a terphenyl group that is unsubstituted or substituted with an aryl group; a quaterphenyl group; a naphthyl group; a fluorenyl group that is unsubstituted or substituted with one or more selected from the group consisting of an alkyl group and an aryl group; a carbazolyl group; a dibenzofuran group; a dibenzothiophene group; or a spiroacridinefluorene group that is unsubstituted or substituted with an aryl group.

According to an exemplary embodiment of the present specification, in Formula 2, Ar2 and Ar3 are the same as or different from each other, and are each independently a phenyl group that is unsubstituted or substituted with a phenyl group, a biphenyl group, or a terphenyl group; a biphenyl group that is unsubstituted or substituted with a phenyl group, or a biphenyl group; a terphenyl group that is unsubstituted or substituted with a phenyl group; a quaterphenyl group; a naphthyl group; a fluorenyl group that is unsubstituted or substituted with one or more selected from the group consisting of a methyl group and a phenyl group; a carbazolyl group; a dibenzofuran group; a dibenzothiophene group; or a spiroacridinefluorene group that is unsubstituted or substituted with a phenyl group.

According to an exemplary embodiment of the present specification, in Formula 2, R3 to R5 are hydrogen.

According to an exemplary embodiment of the present specification, in Formula 3, L7 is an arylene group.

According to an exemplary embodiment of the present specification, in Formula 3, L7 is a phenylene group, a biphenylylene group, or a naphthylene group.

According to an exemplary embodiment of the present specification, in Formula 3, L7 is 1 or 2.

According to an exemplary embodiment of the present specification, in Formula 3, Ar4 to Ar6 are the same as or different from each other, and are each independently an aryl group that is unsubstituted or substituted with an aryl group.

According to an exemplary embodiment of the present specification, in Formula 3, Ar4 to Ar6 are the same as or different from each other, and are each independently a phenyl group that is unsubstituted or substituted with an aryl group, a biphenyl group, or a naphthyl group.

According to an exemplary embodiment of the present specification, in Formula 3, Ar4 to Ar6 are the same as or different from each other, and are each independently a phenyl group that is unsubstituted or substituted with a phenyl group, a biphenyl group, or a naphthyl group.

According to an exemplary embodiment of the present specification, in Formula 3, R6 and R7 are hydrogen.

According to an exemplary embodiment of the present specification, Formula 1 is selected from among the following compounds:

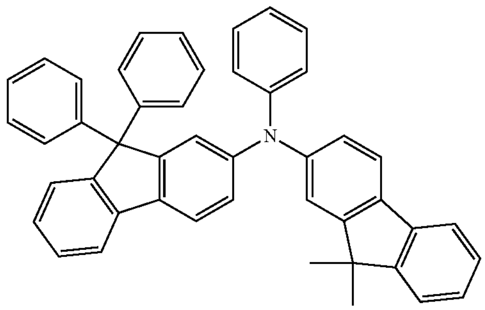

-continued
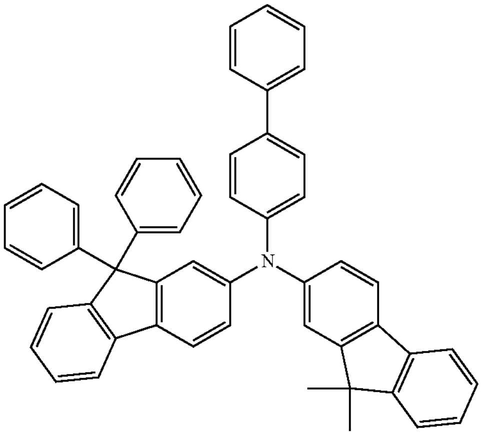
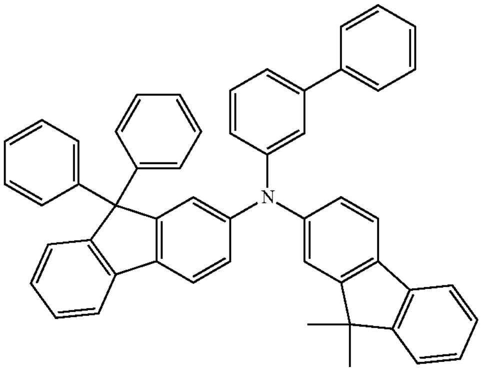
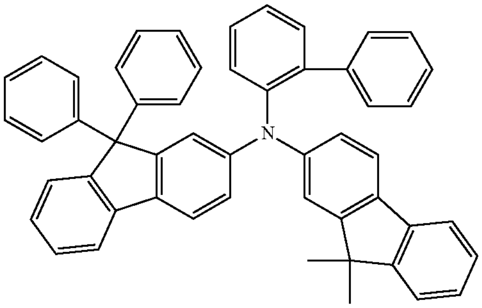
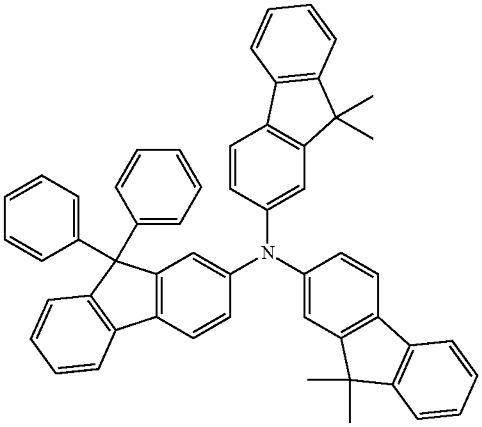
-continued
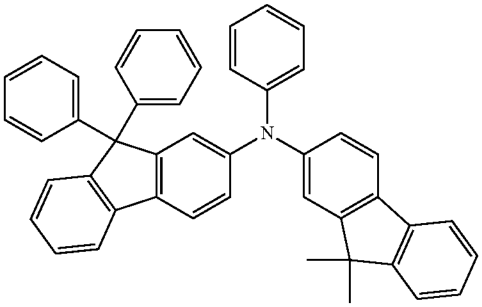
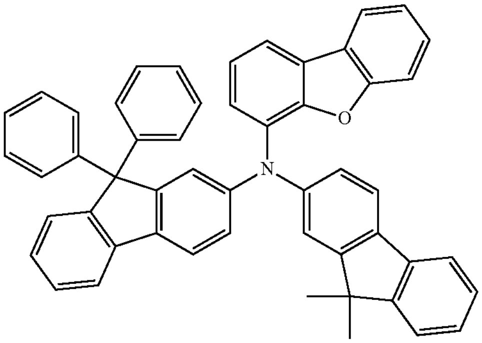
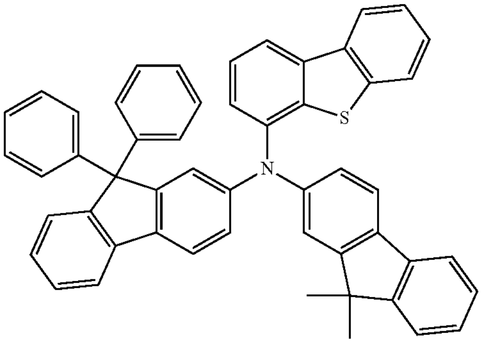
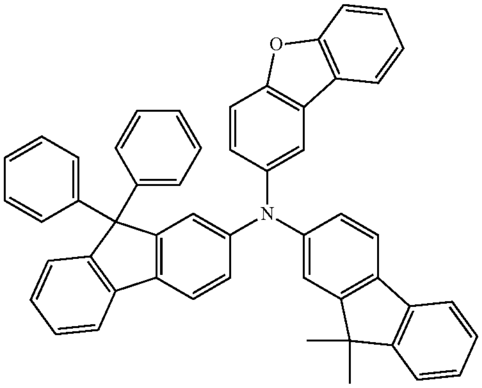

-continued
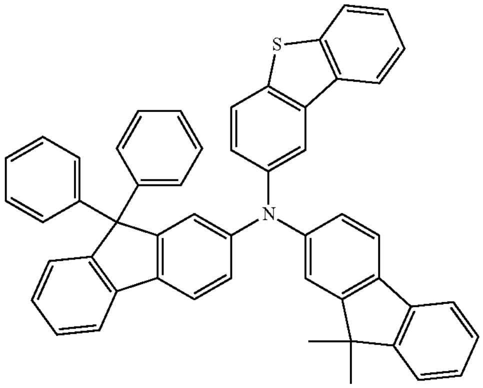
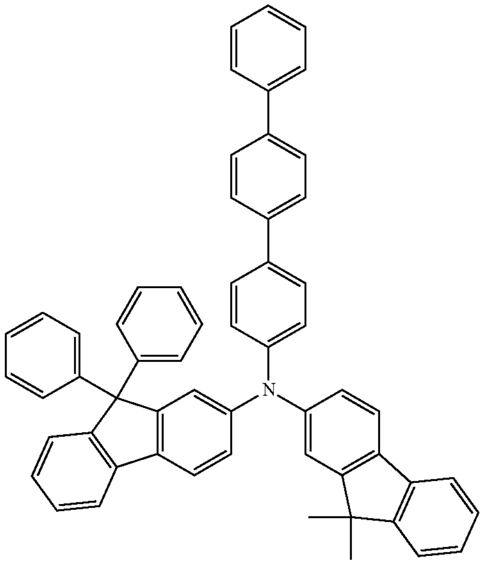
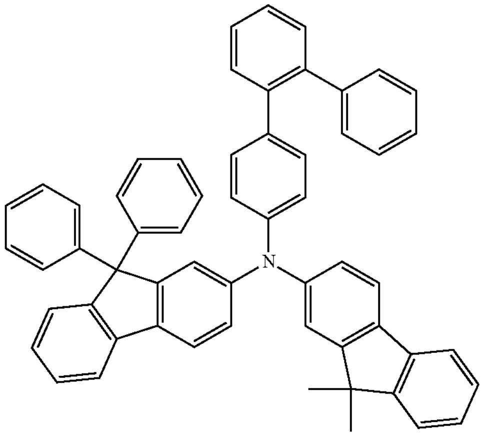
-continued
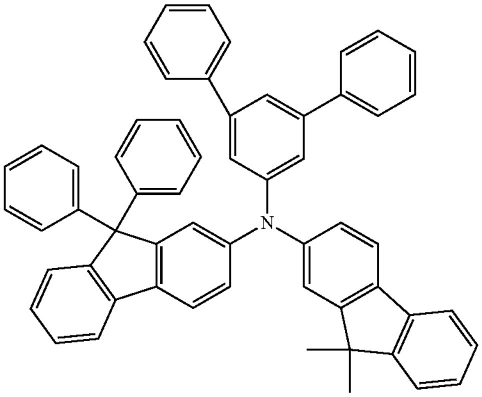
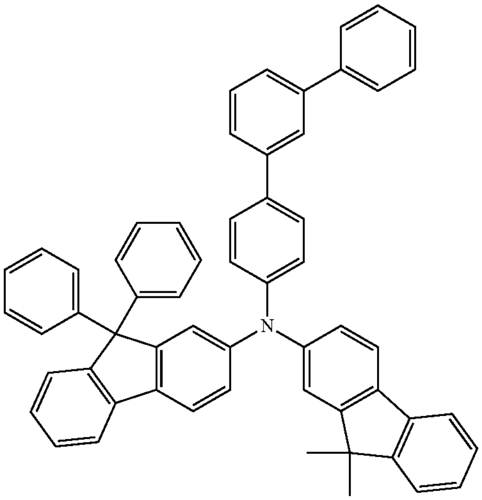
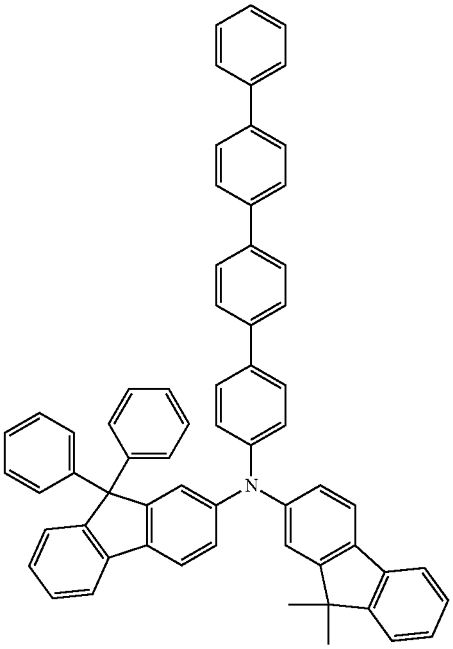

-continued
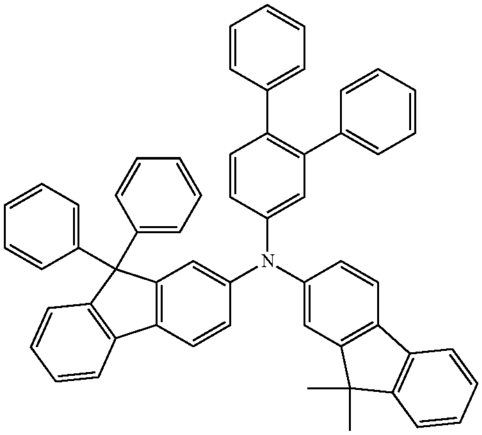
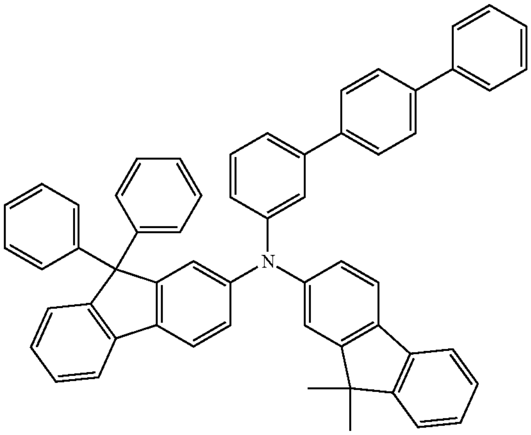
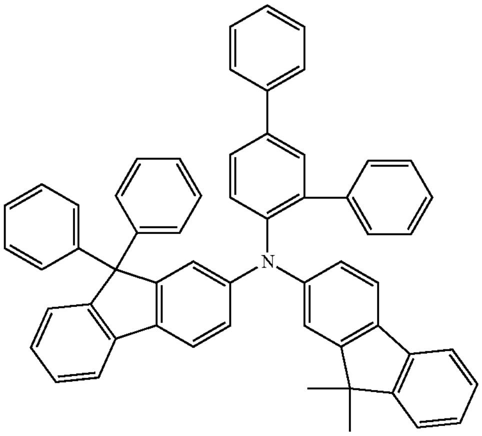
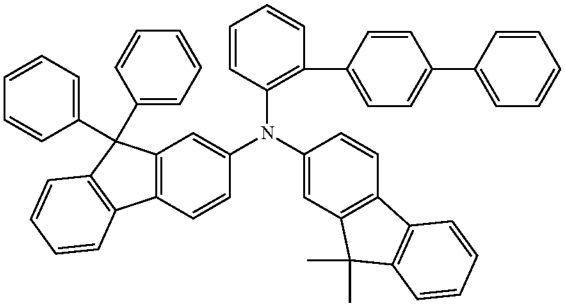
-continued
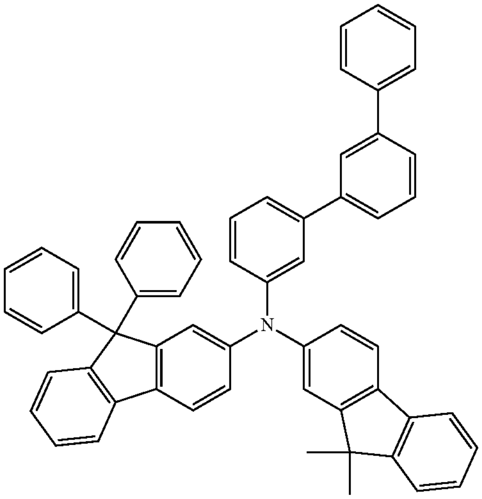
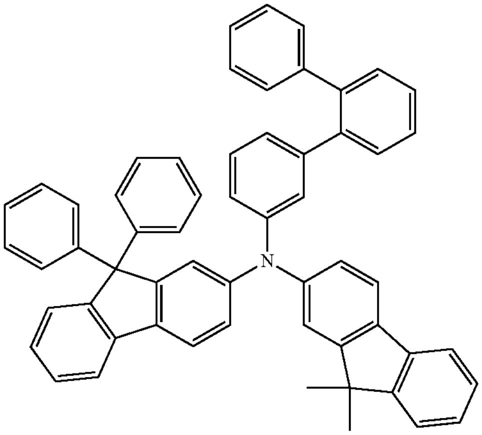
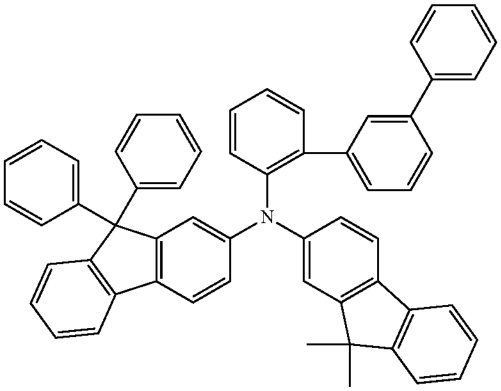
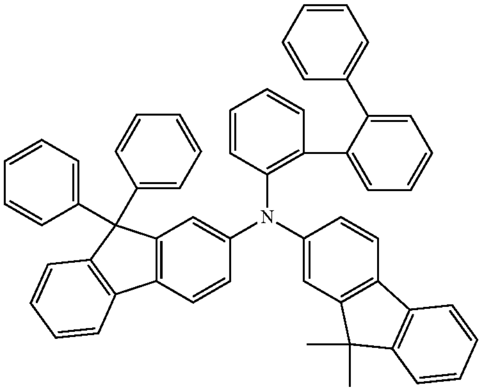

-continued
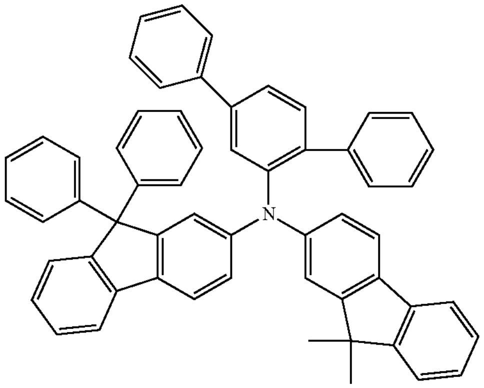
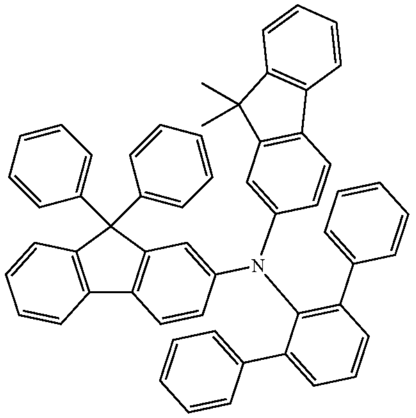
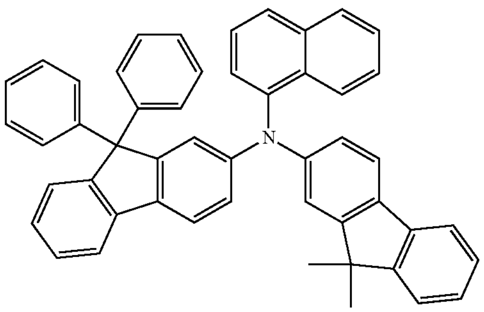
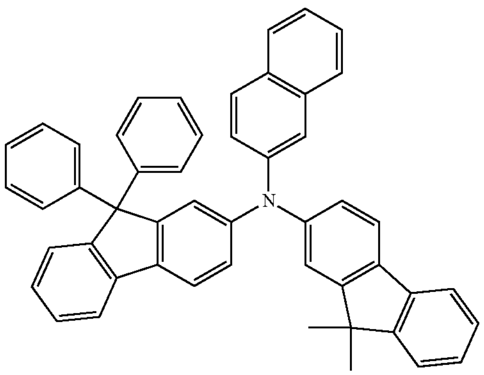
-continued
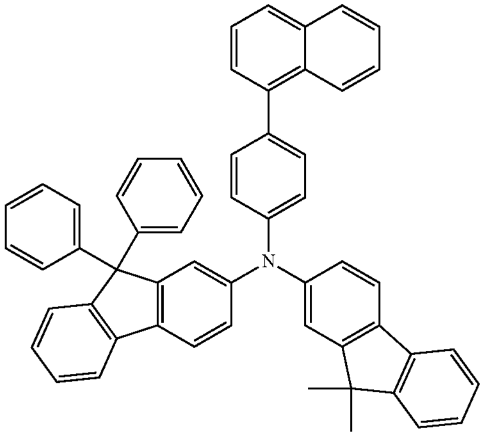
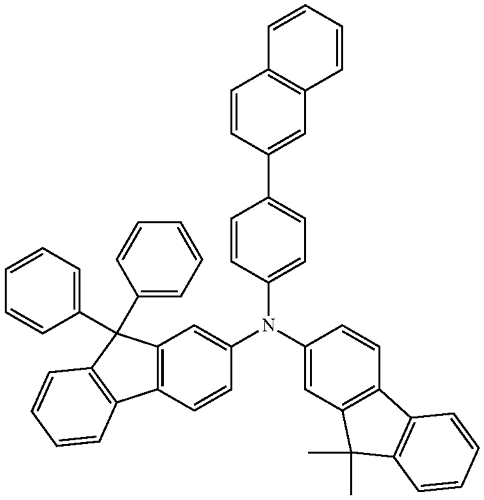
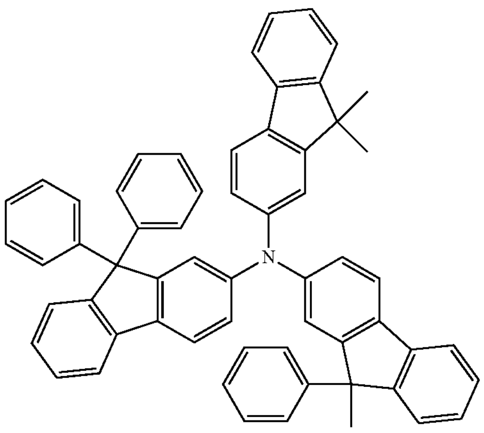

-continued
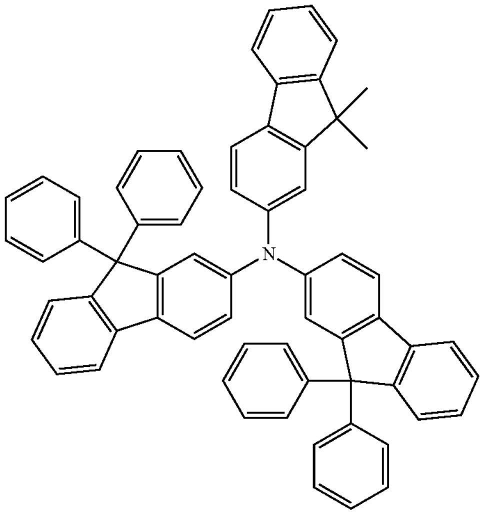 [SMILES: CC1(C)c2ccccc2-c2ccc(N(c3ccc4c(c3)C(c3ccccc3)(c3ccccc3)c3ccccc3-4)c3ccc4c(c3)C(c3ccccc3)(c3ccccc3)c3ccccc3-4)cc21]
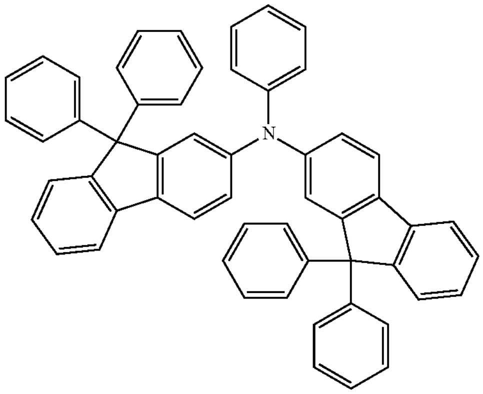
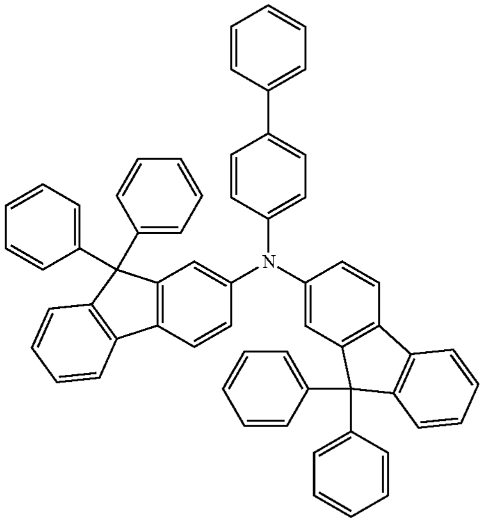
-continued
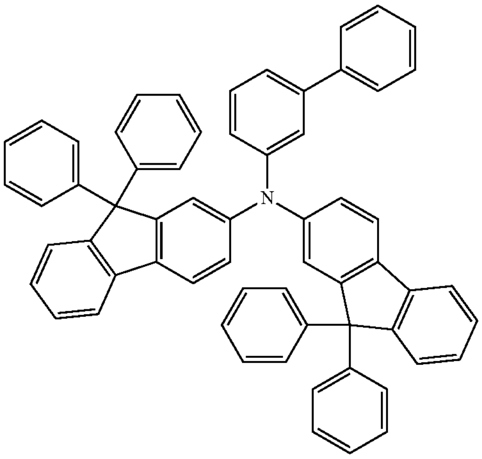
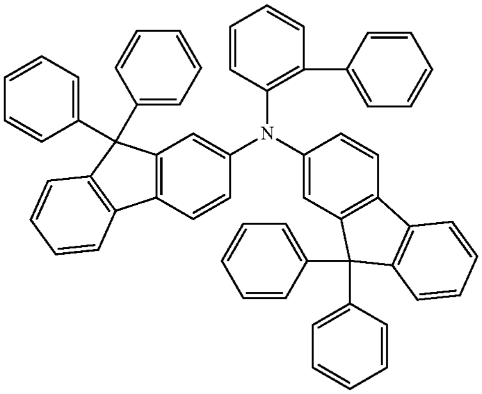
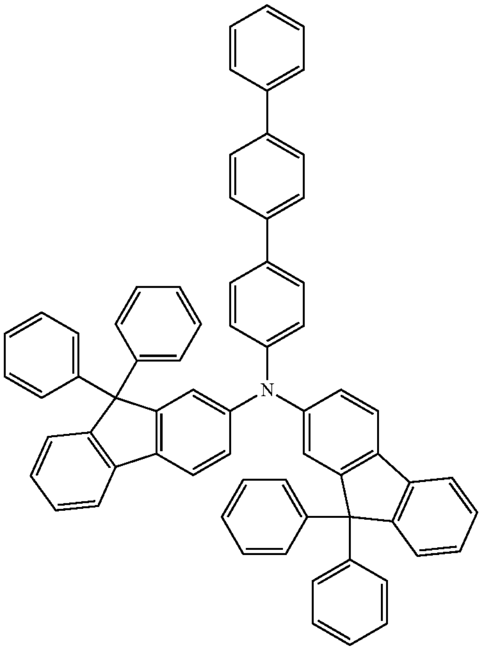

-continued
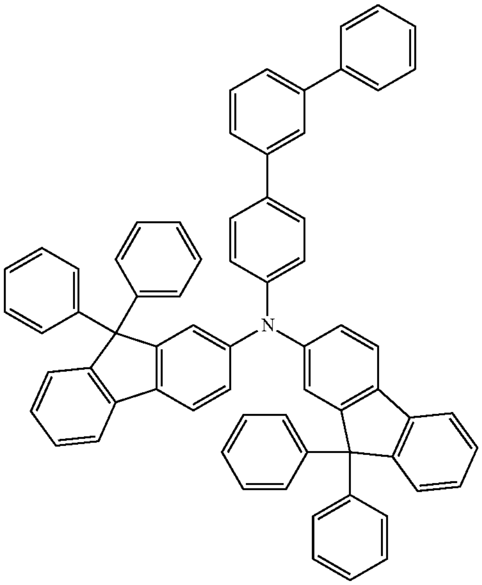
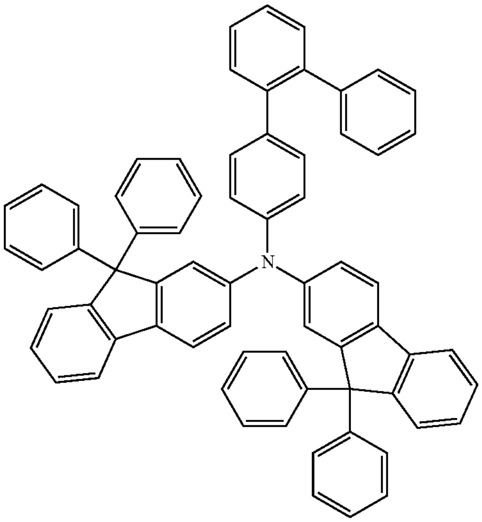
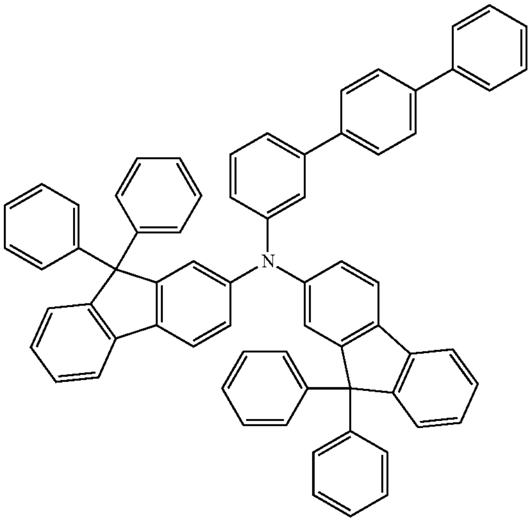
-continued
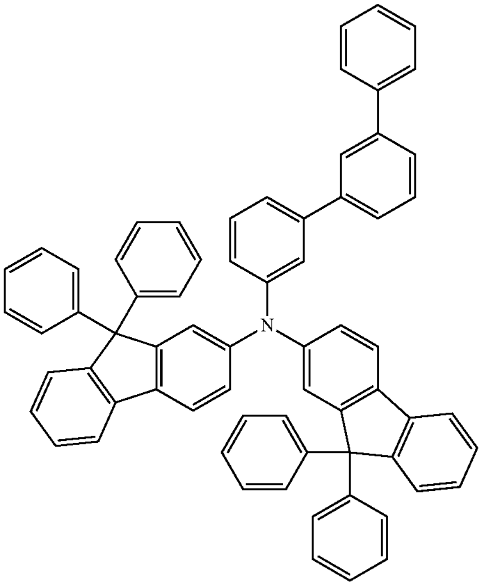
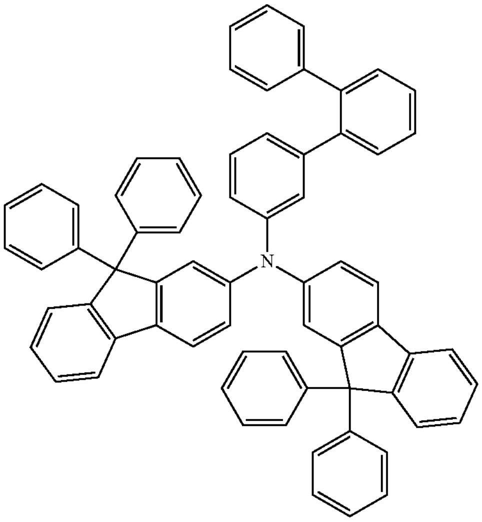
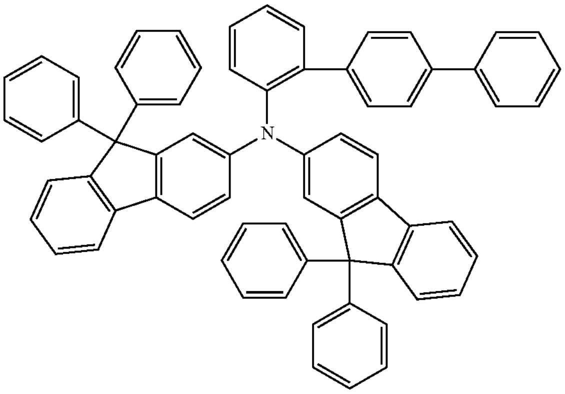

-continued
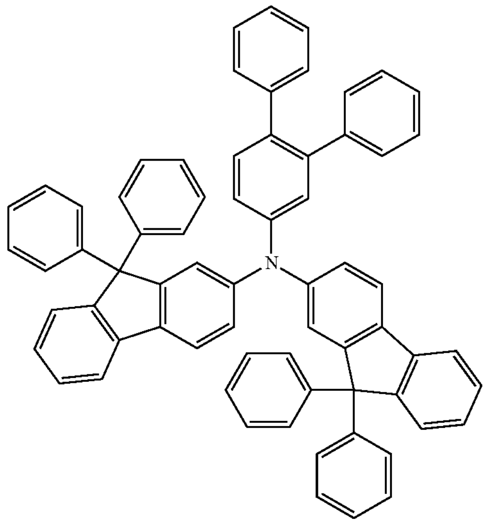
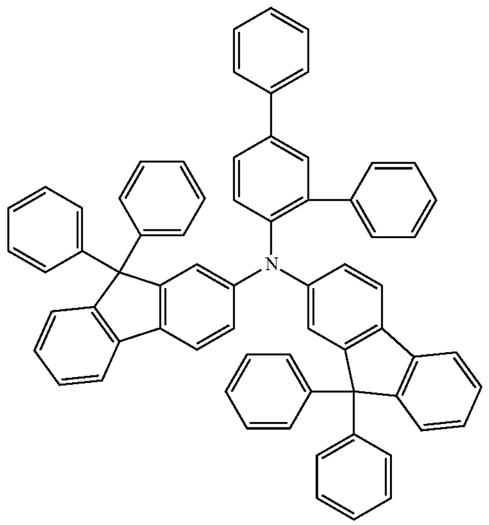
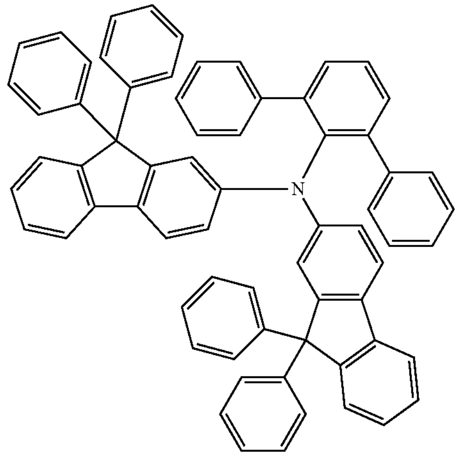
-continued
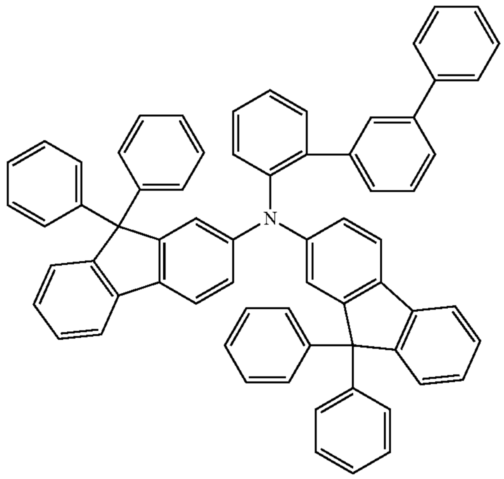
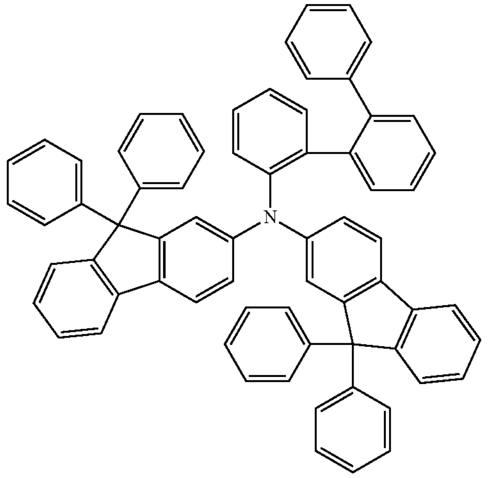
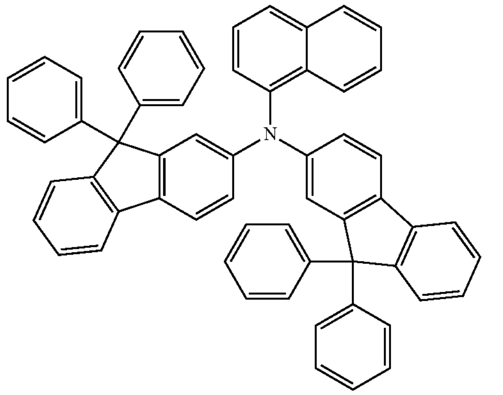

-continued
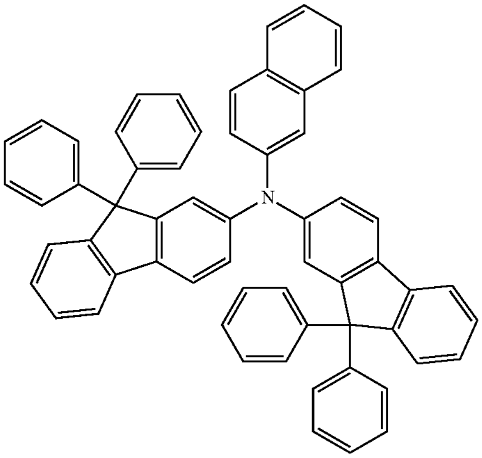
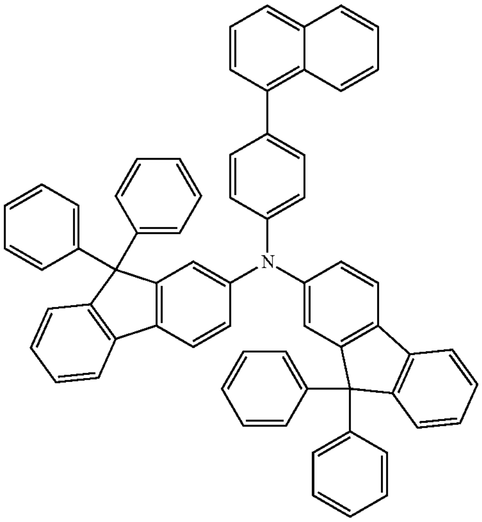
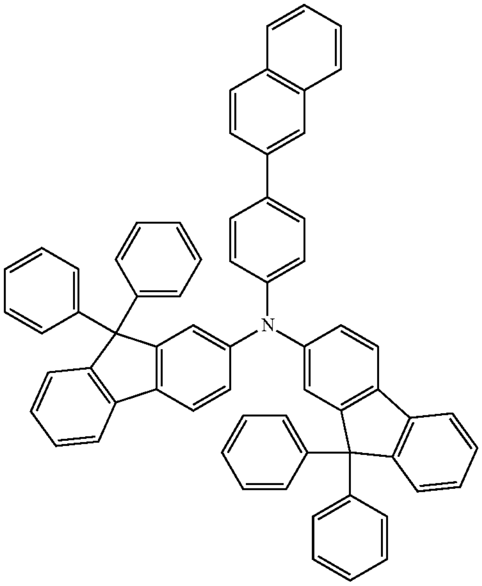
-continued
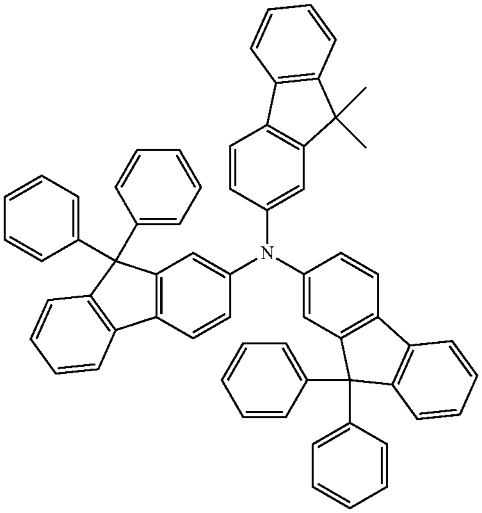
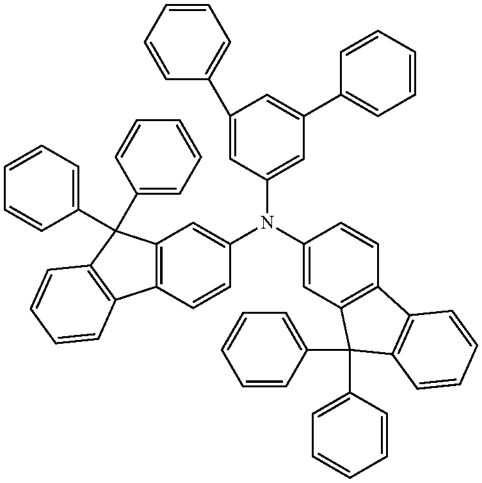
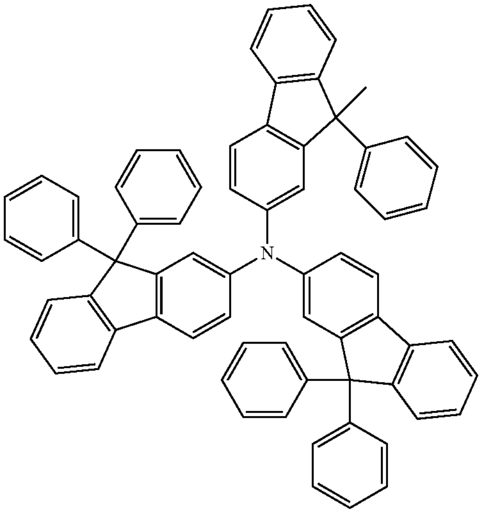

-continued
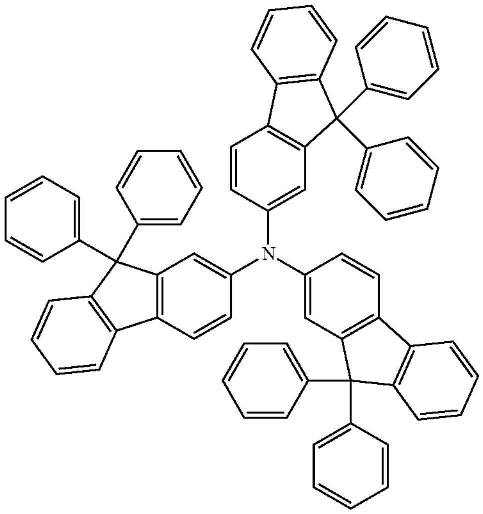
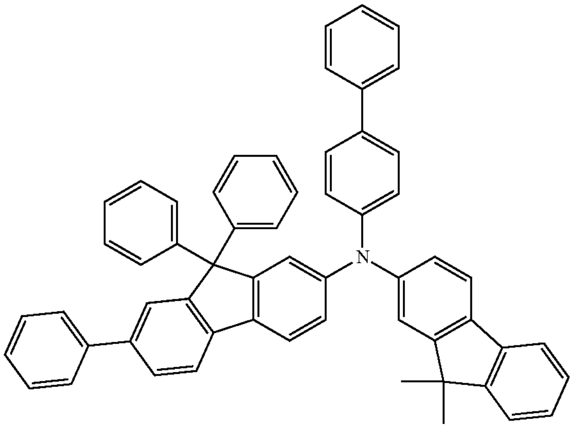
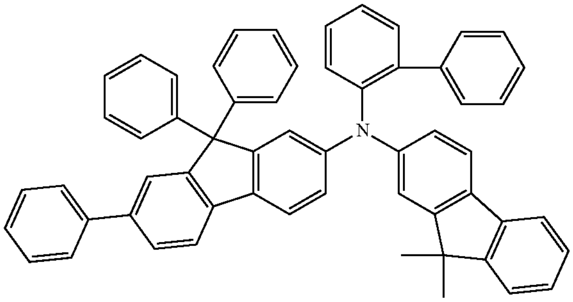
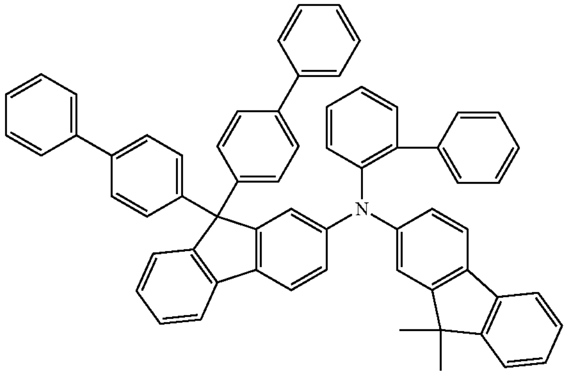
-continued
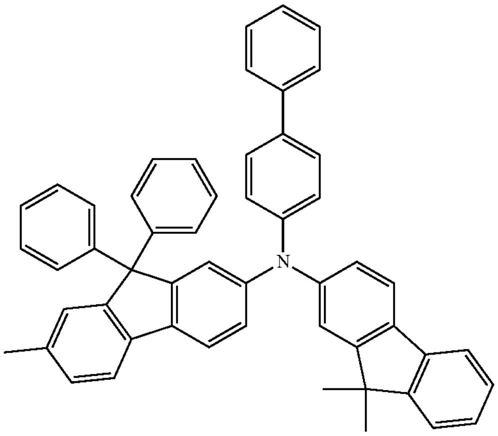
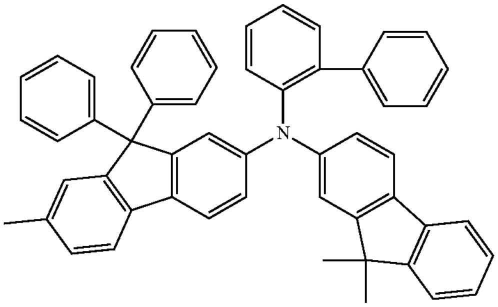
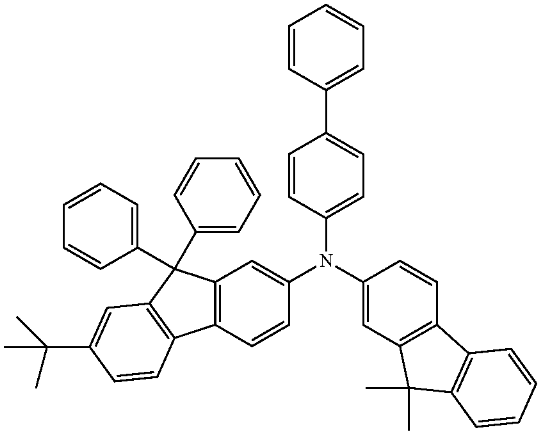
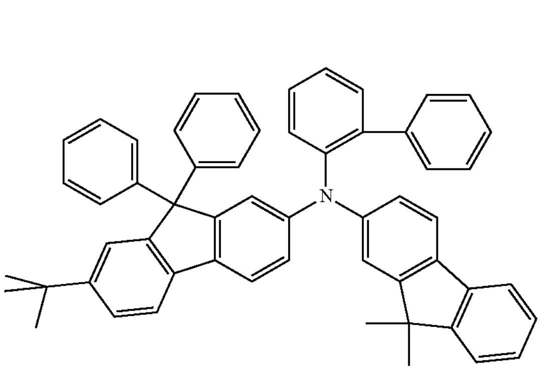

-continued
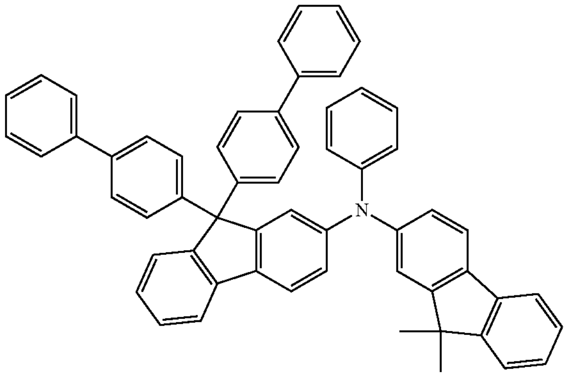
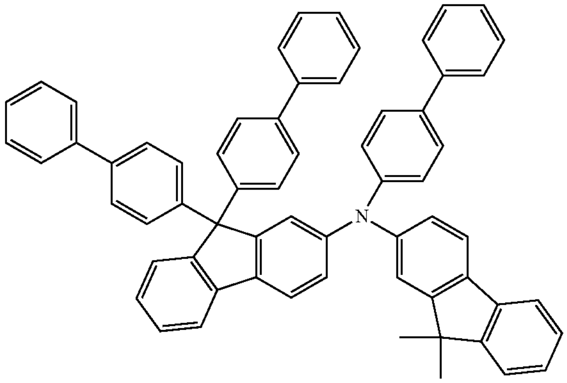
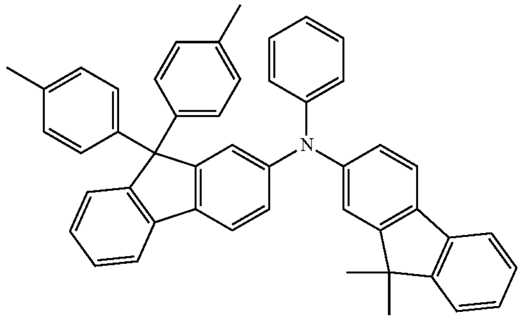
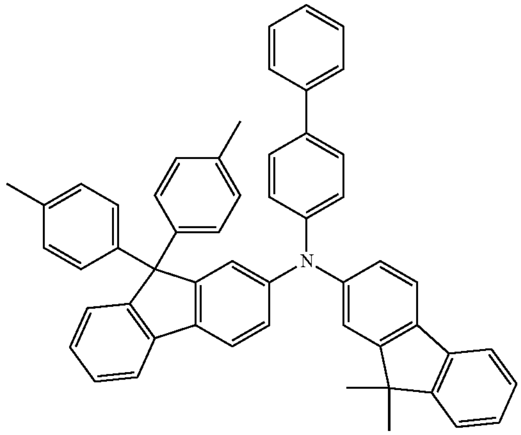
-continued
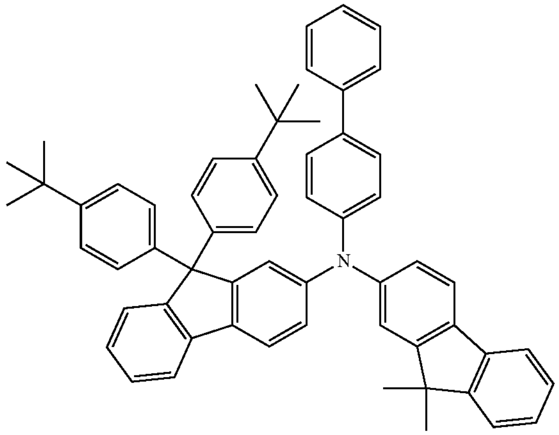
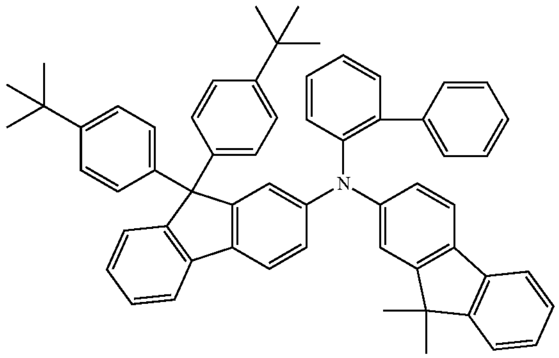
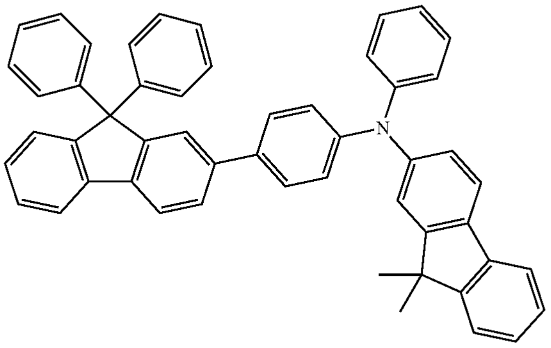
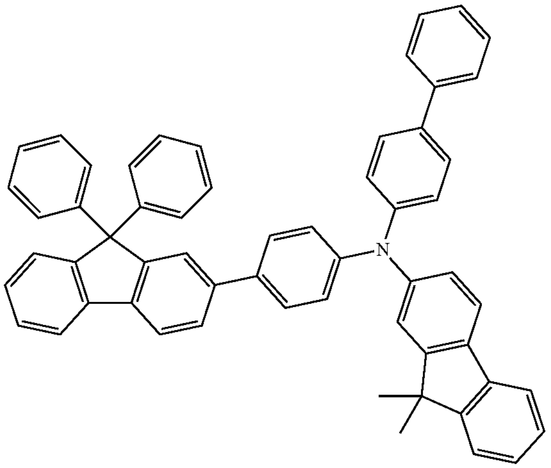

-continued
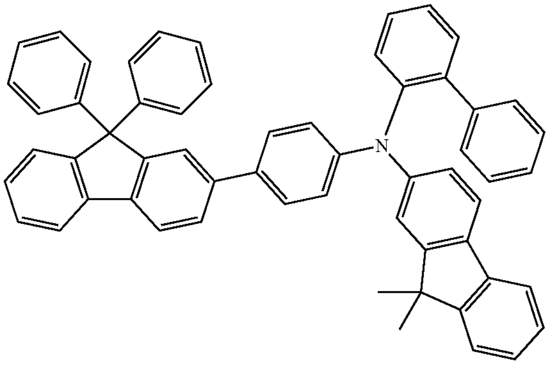
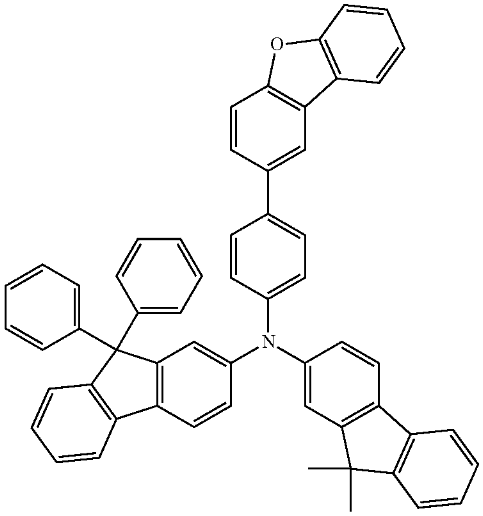
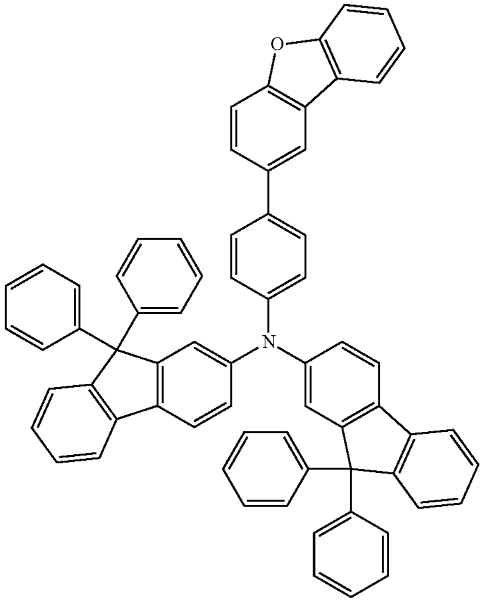
-continued
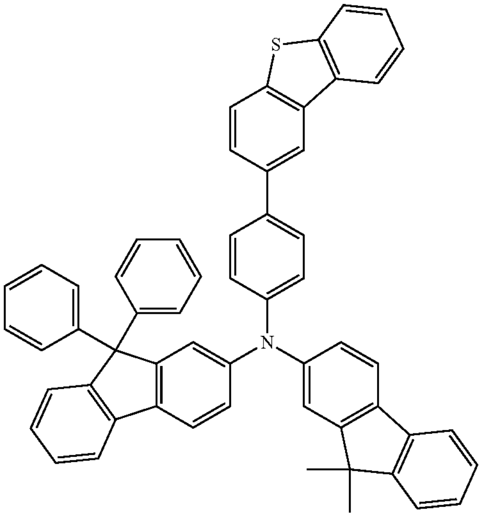
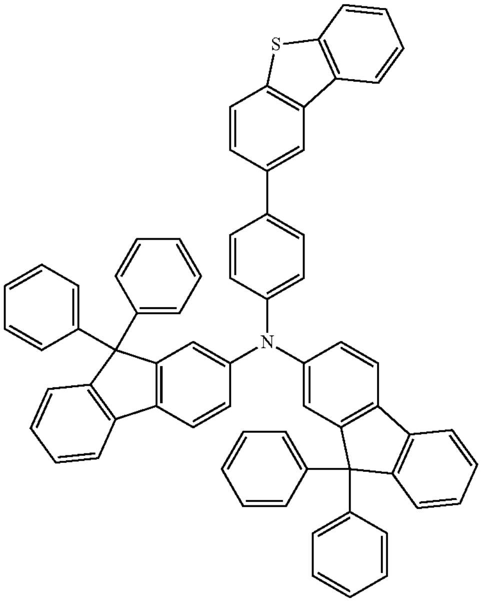
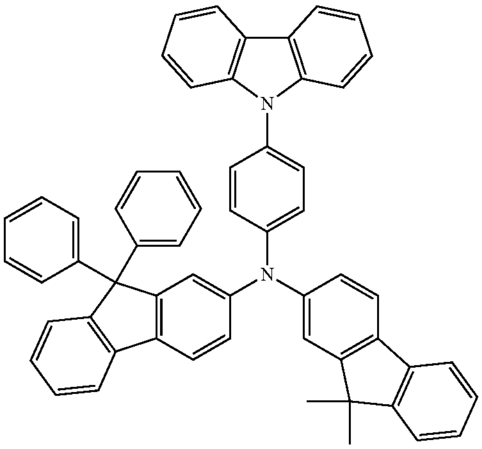

-continued
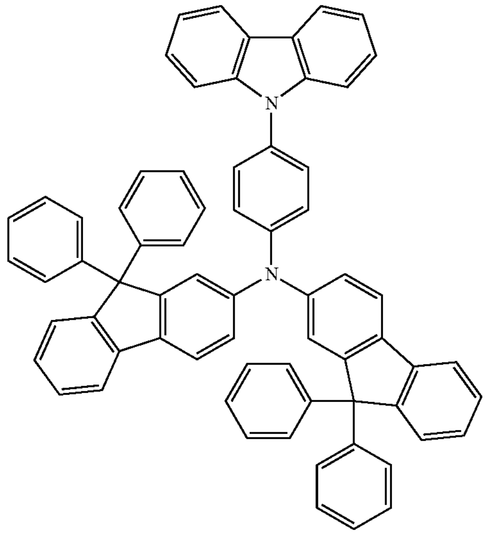
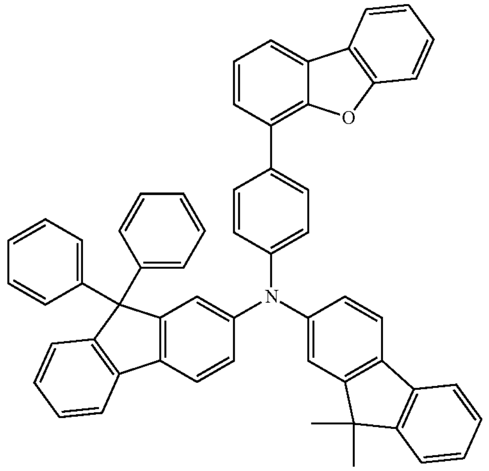
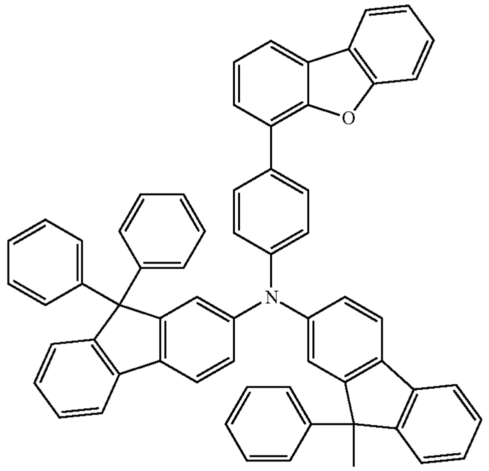
-continued
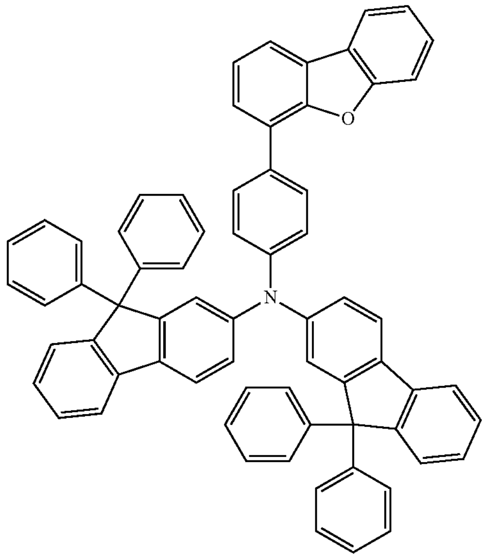
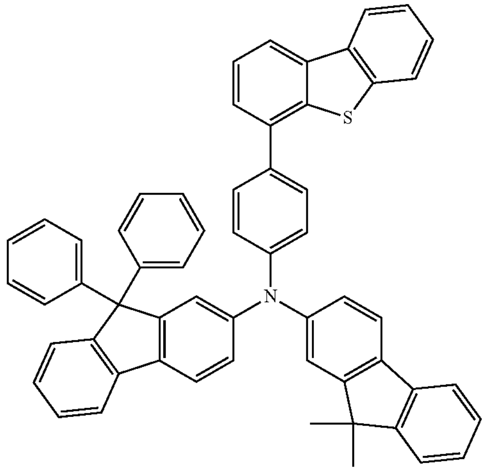
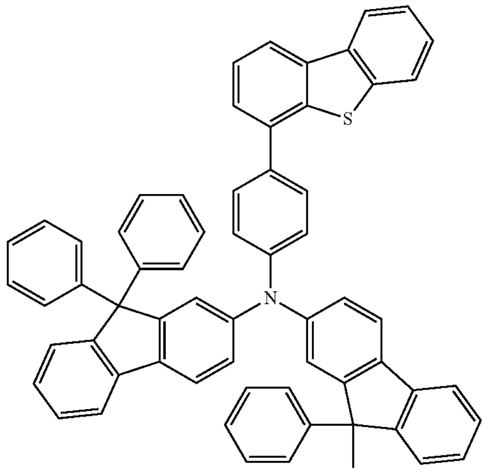

-continued
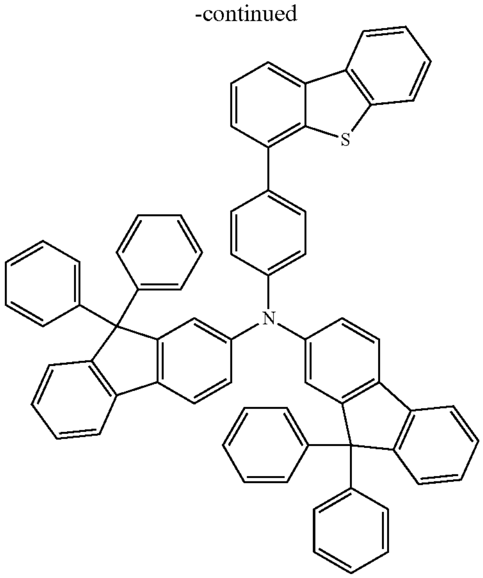
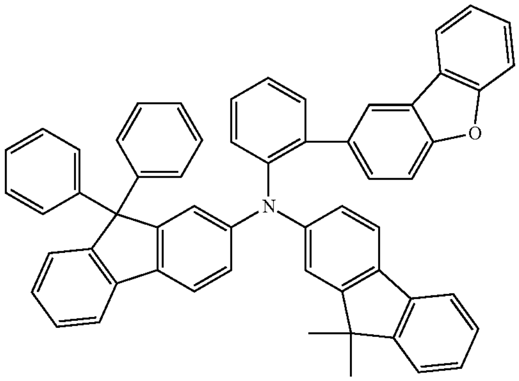
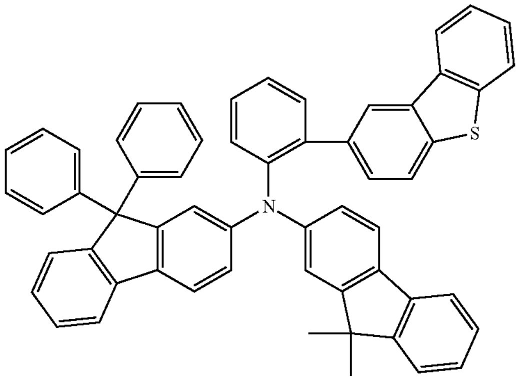
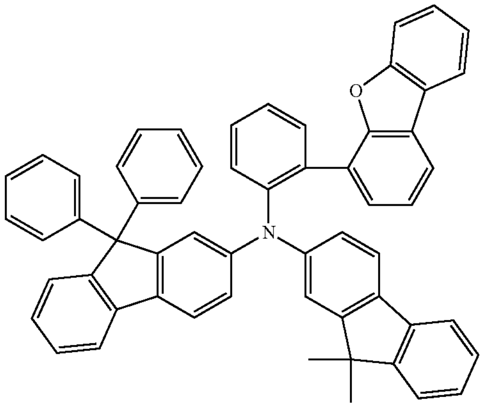
-continued
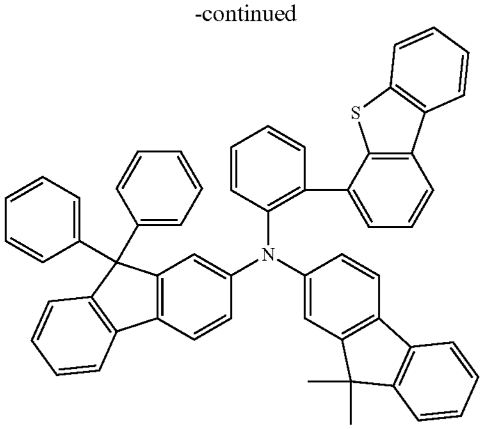
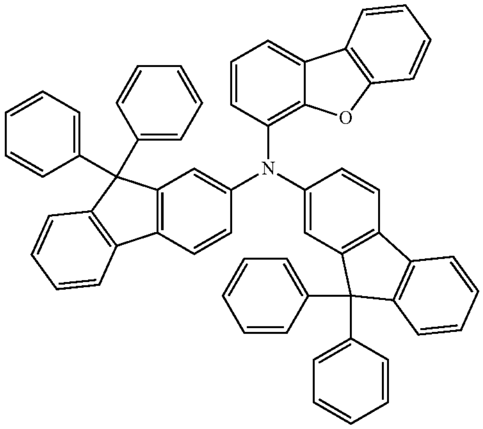
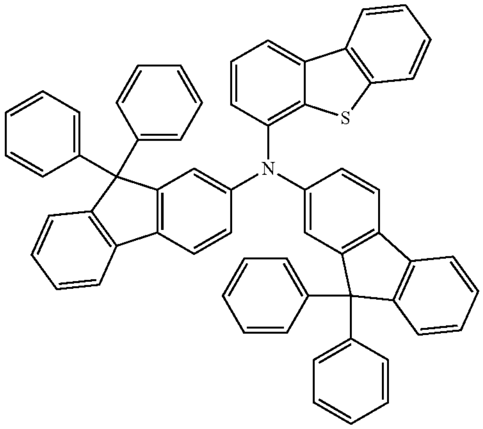
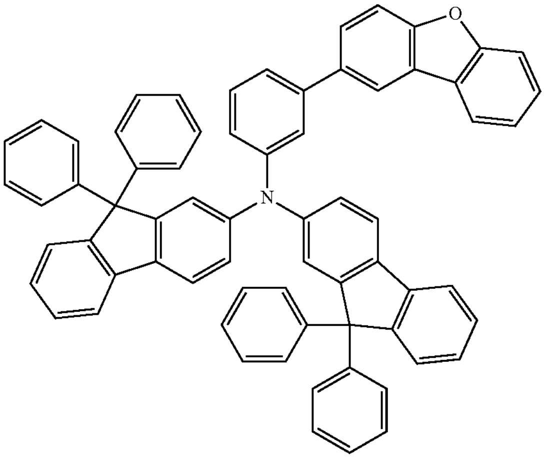

-continued
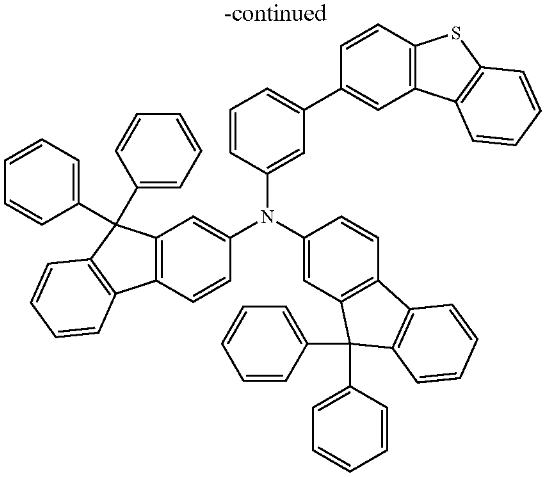
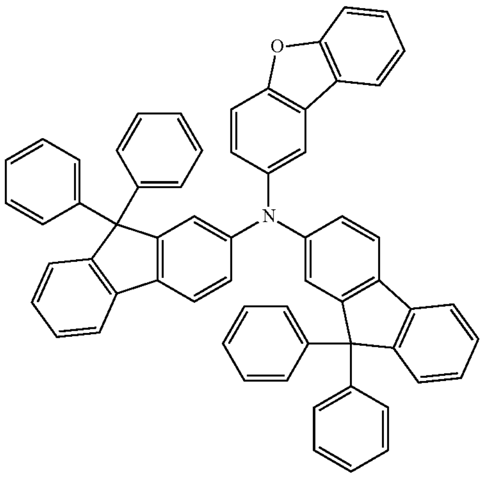
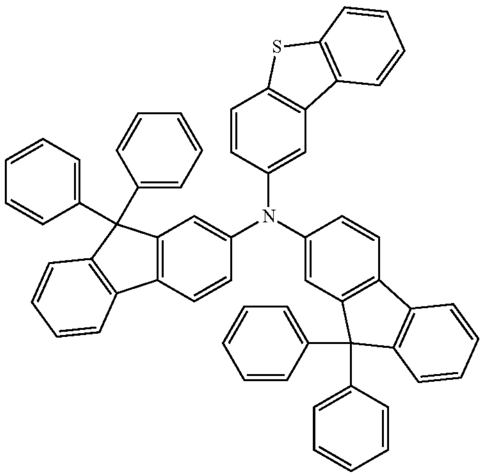
-continued
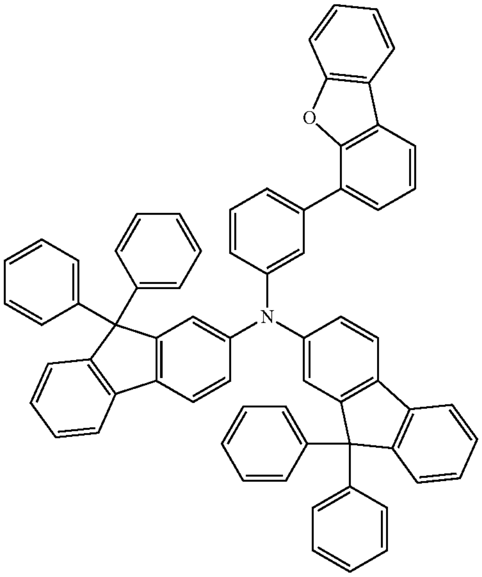
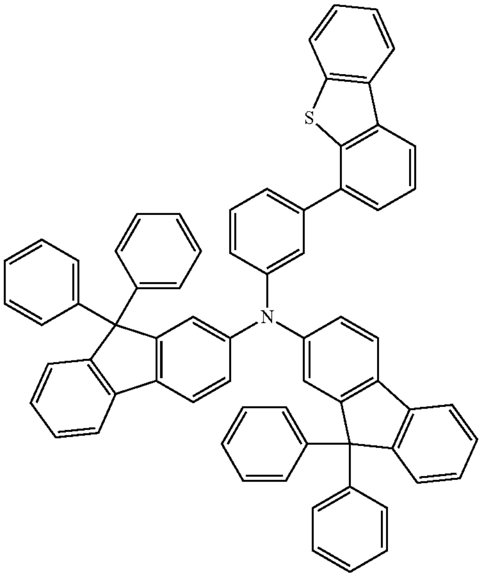
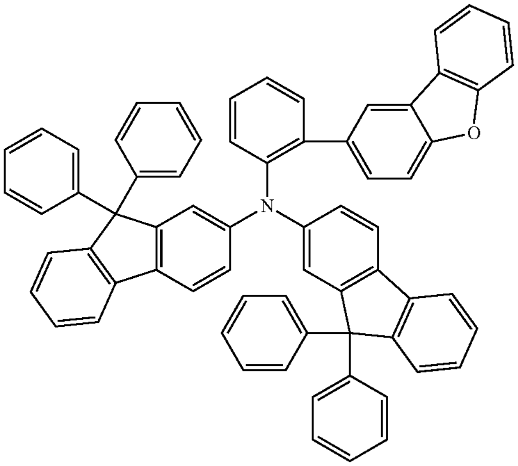

-continued
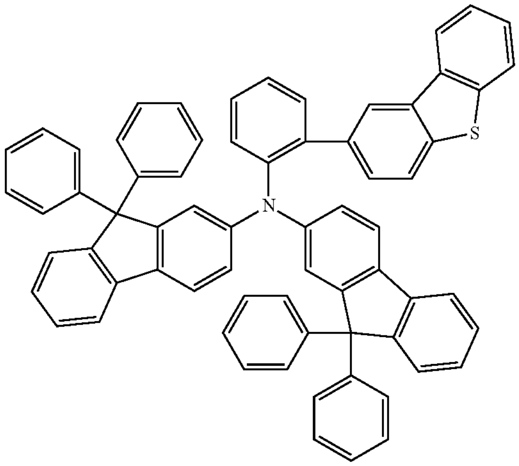
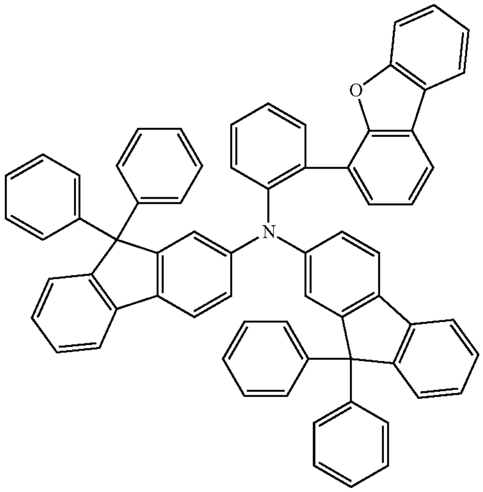
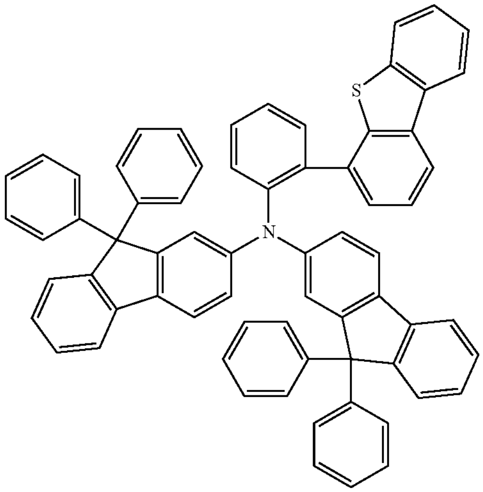
-continued
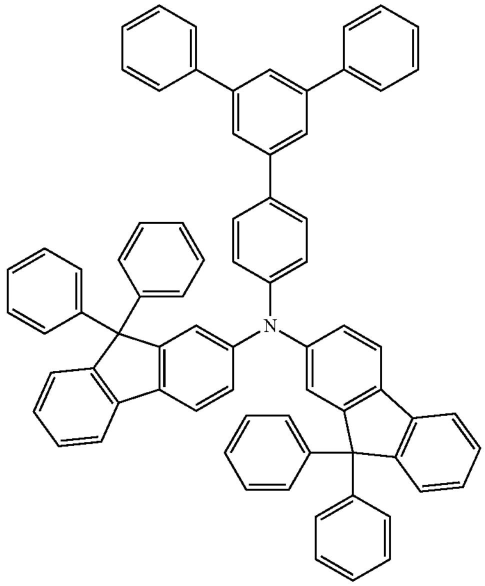
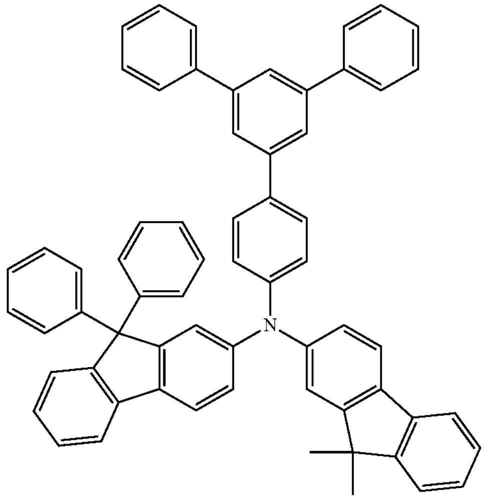
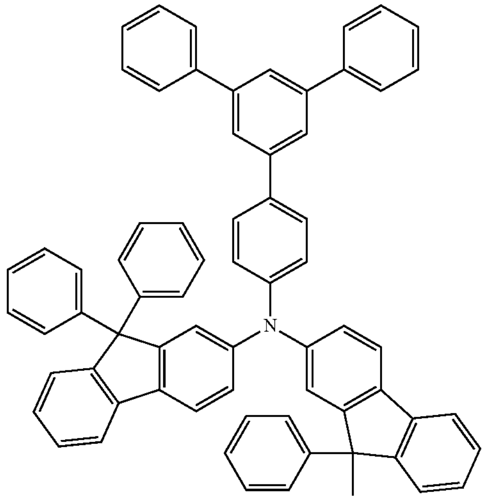

-continued
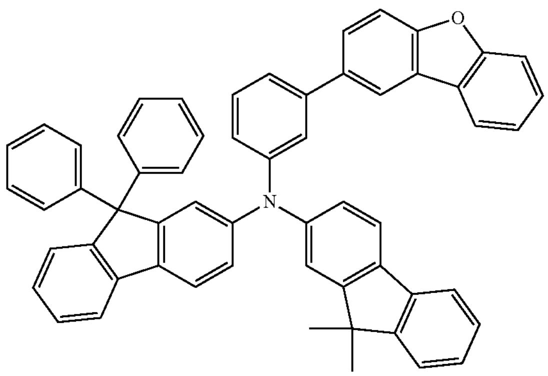
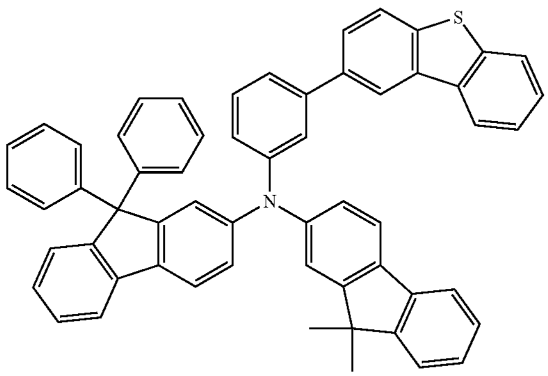
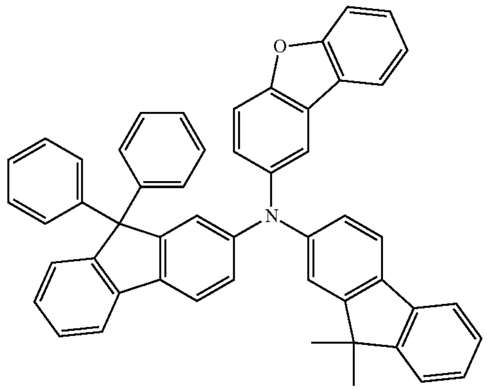
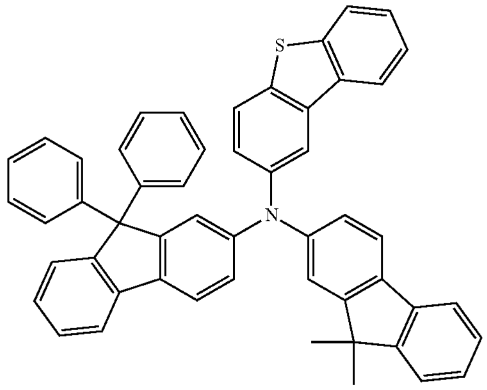
-continued
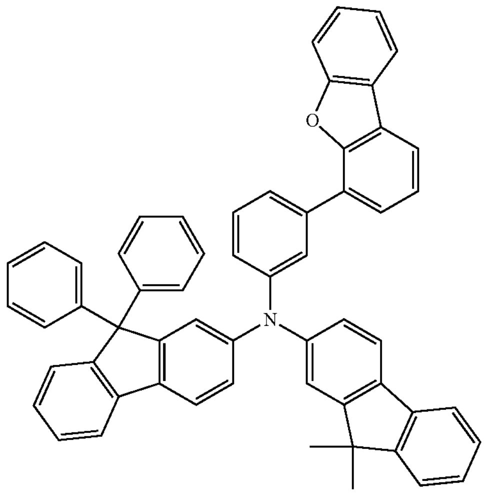
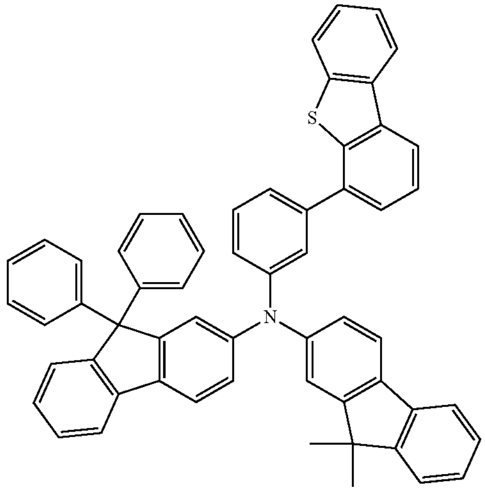
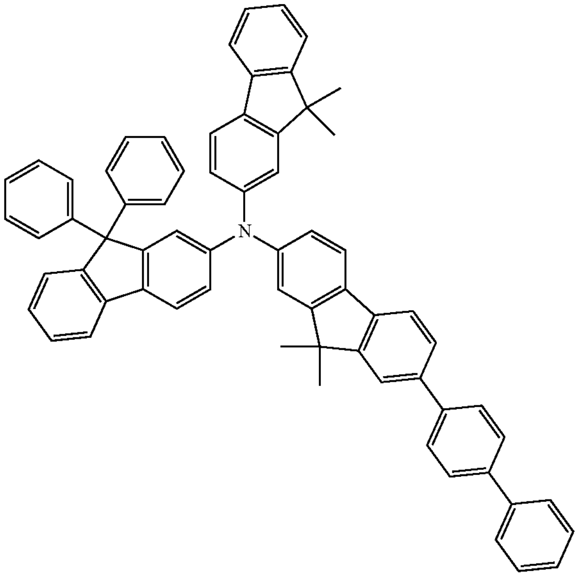

-continued
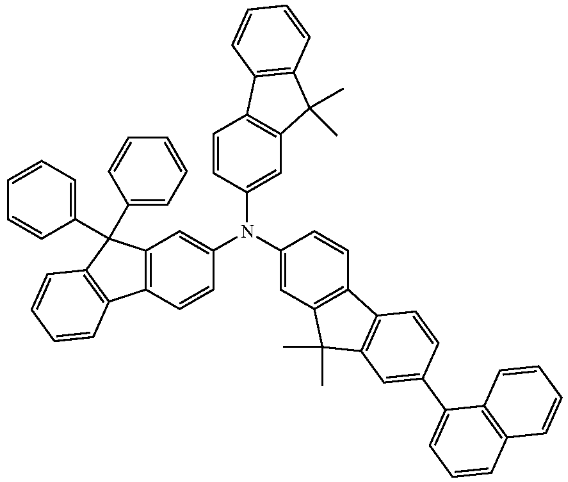
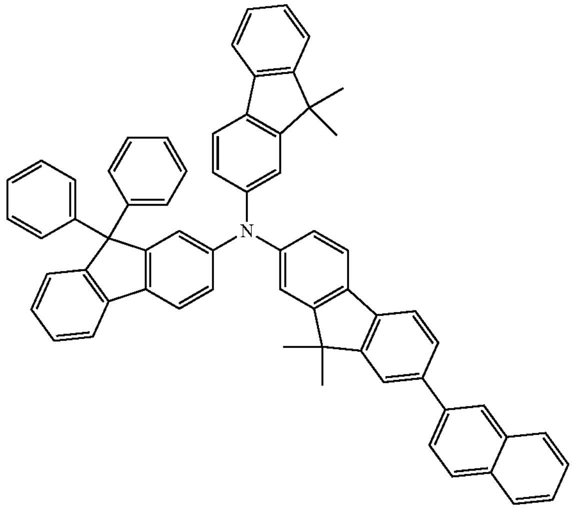
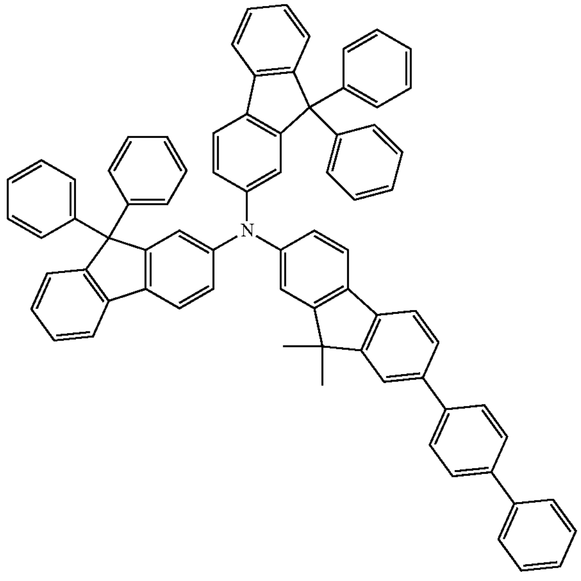
-continued
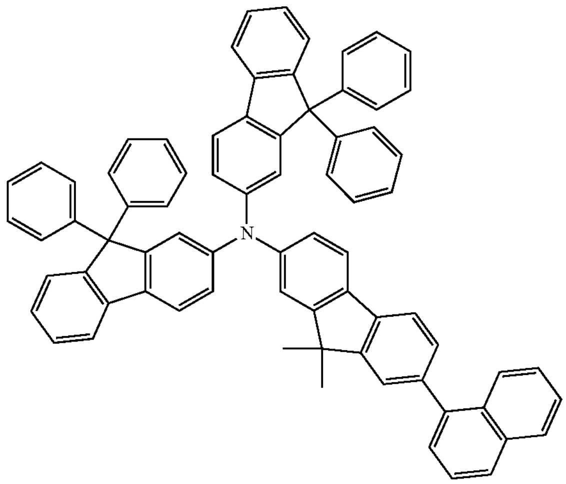
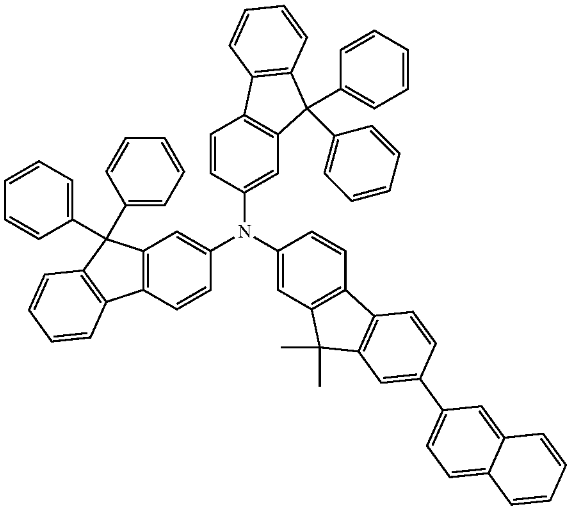
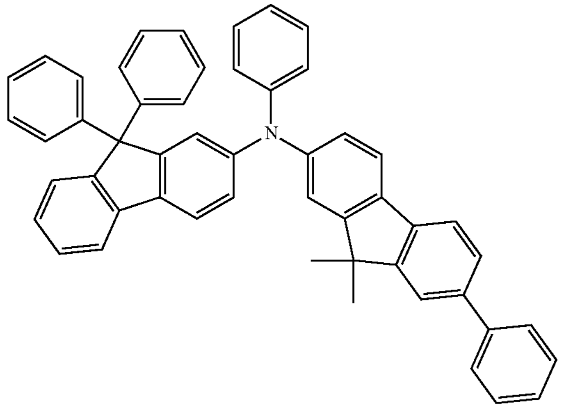

-continued
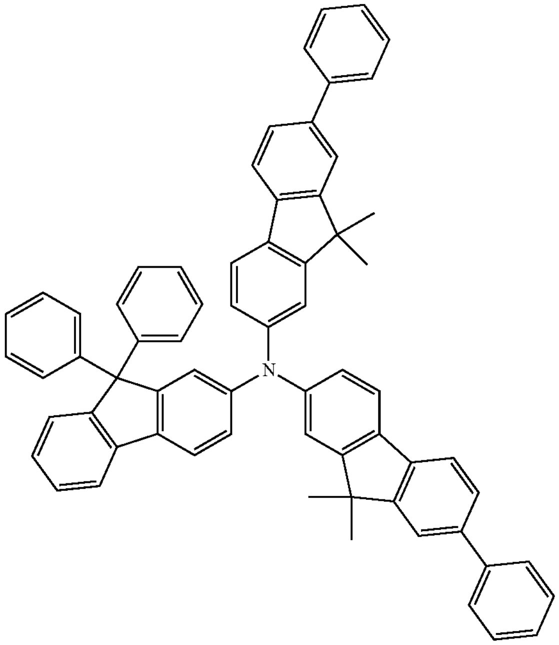
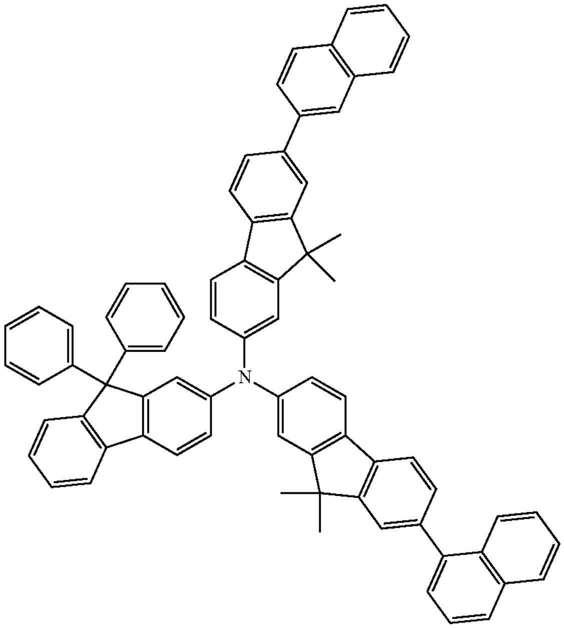
-continued
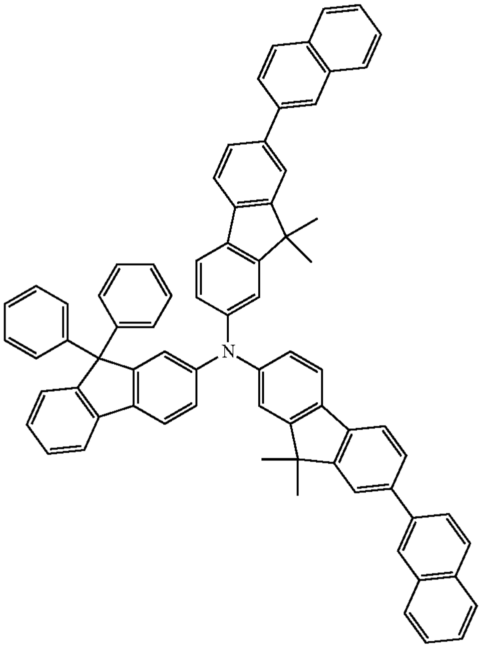
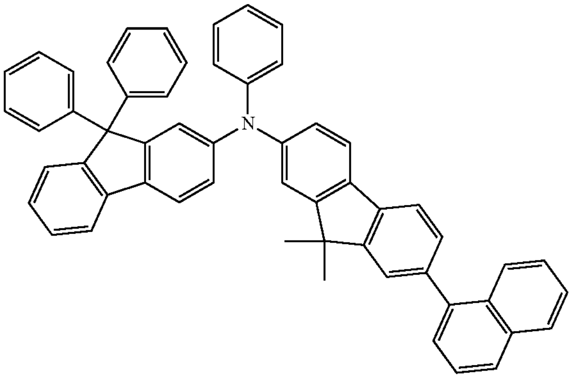
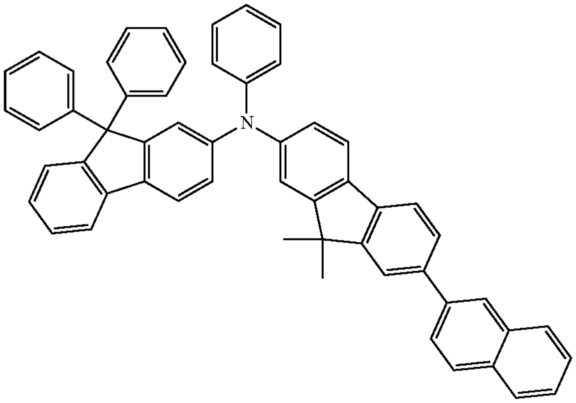

-continued
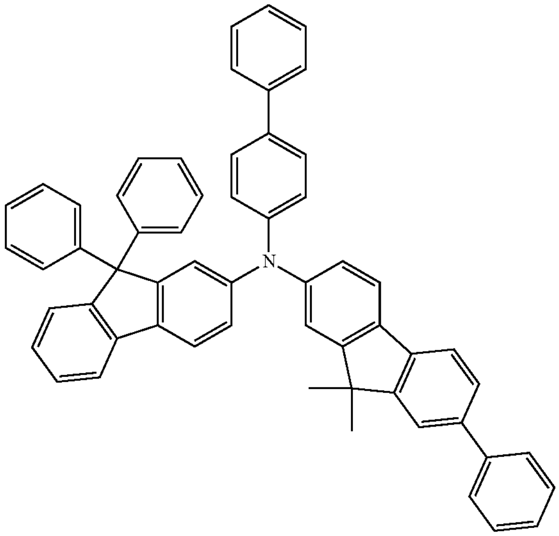
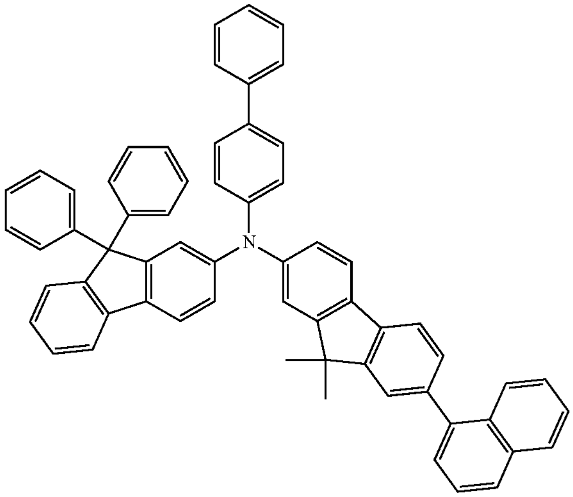
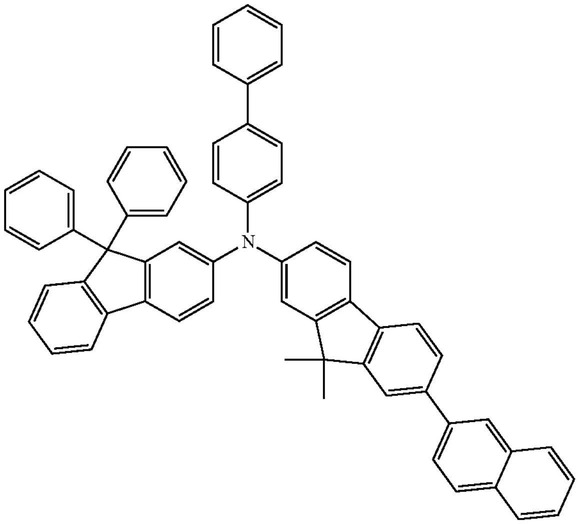
-continued
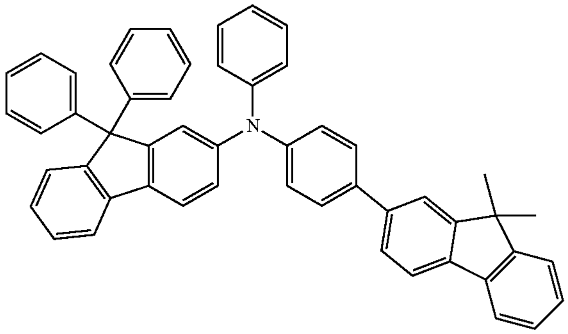
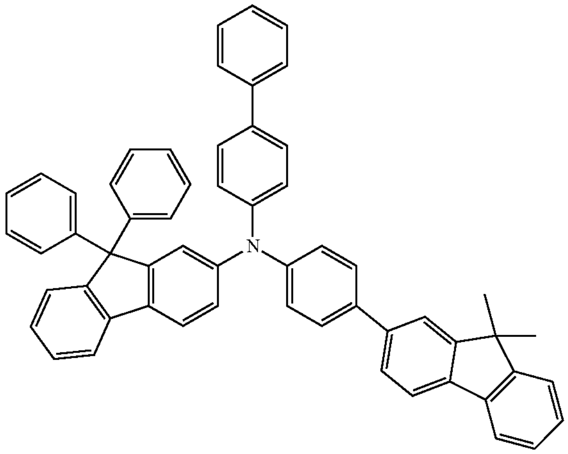
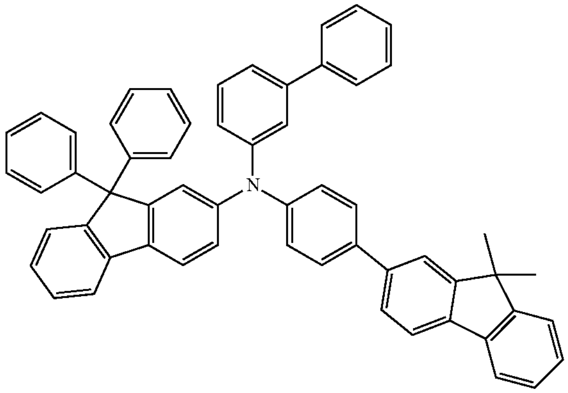
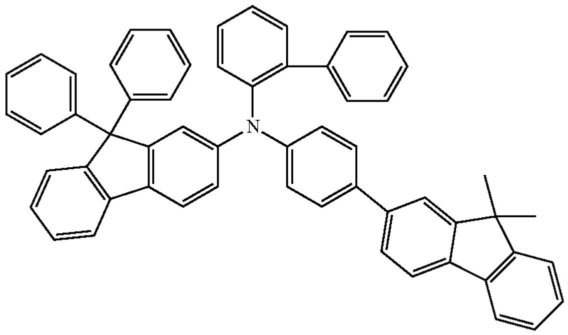

-continued
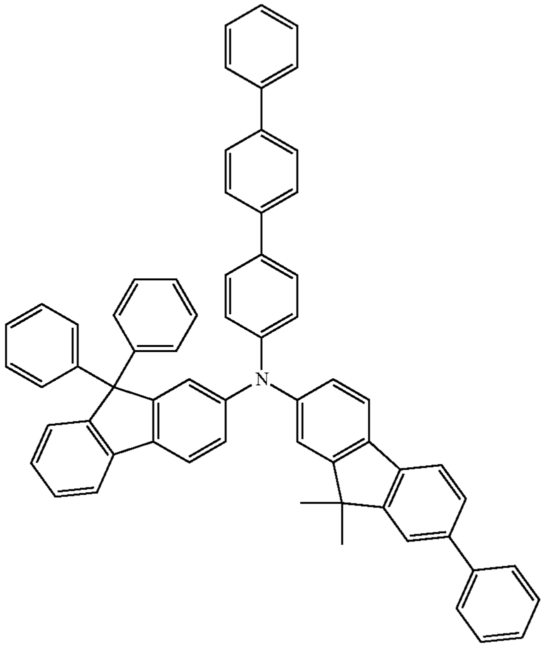
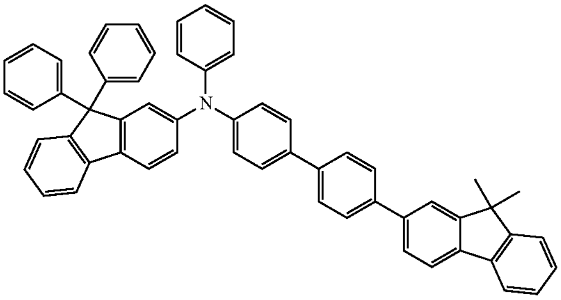
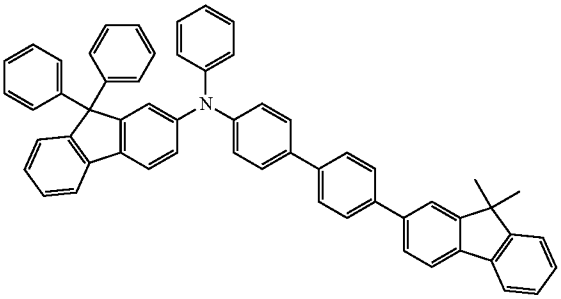
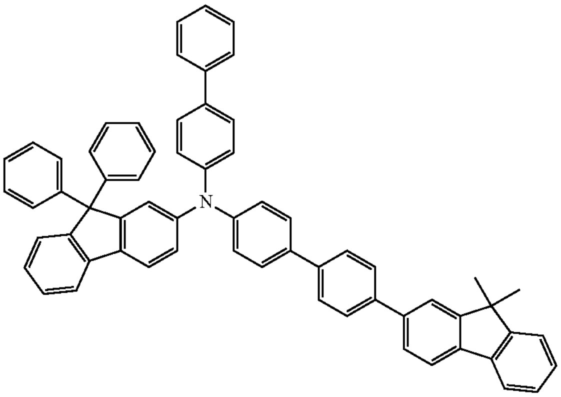
-continued
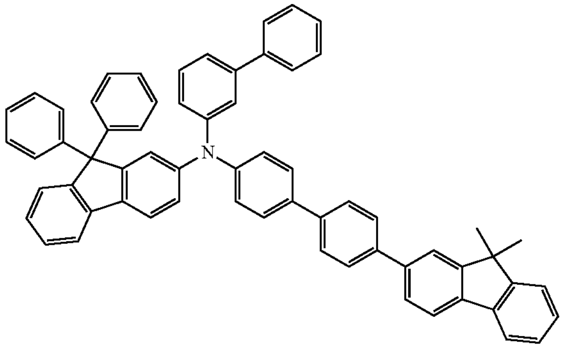
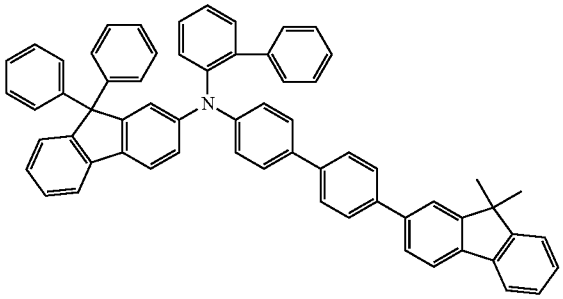
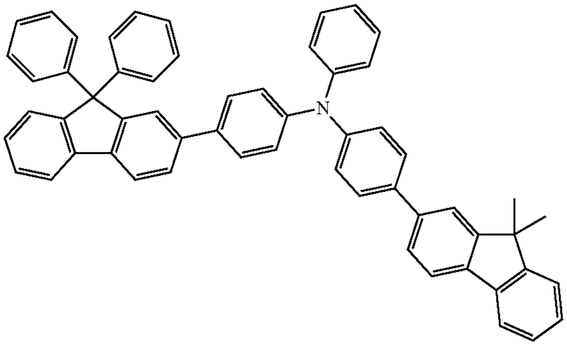
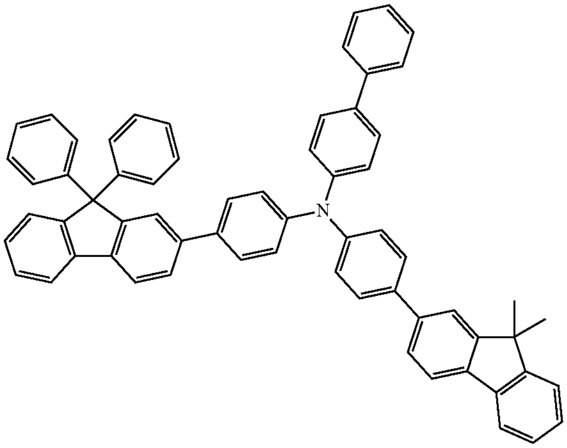

-continued
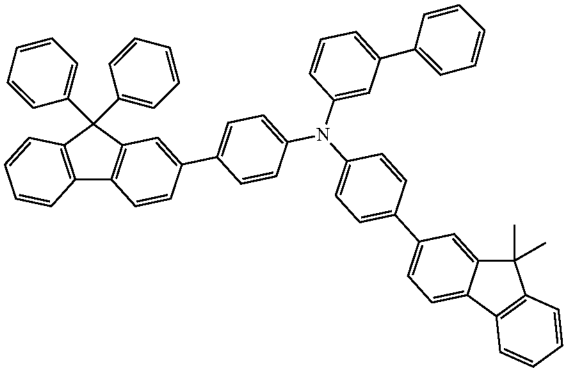
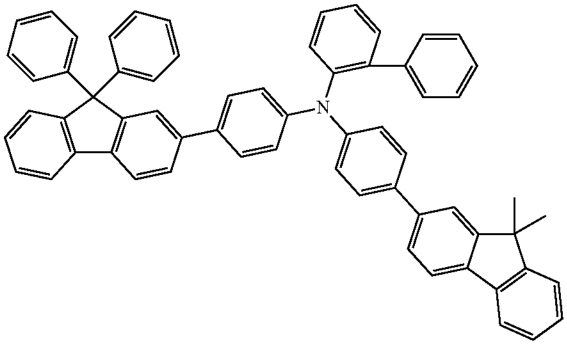
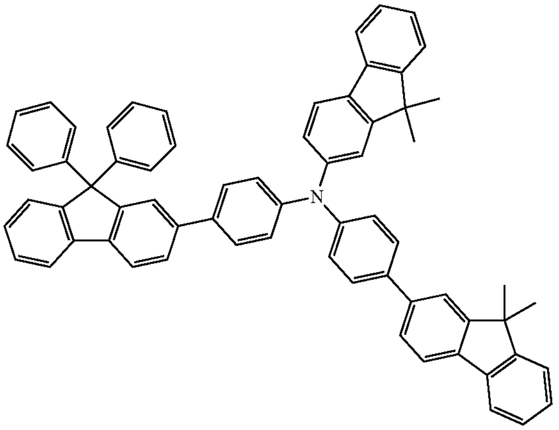
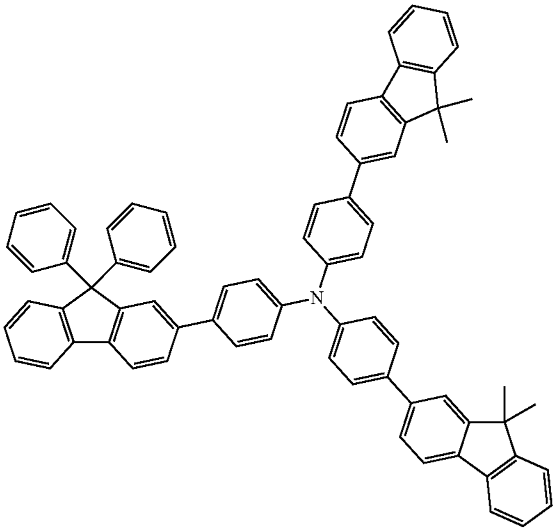
-continued
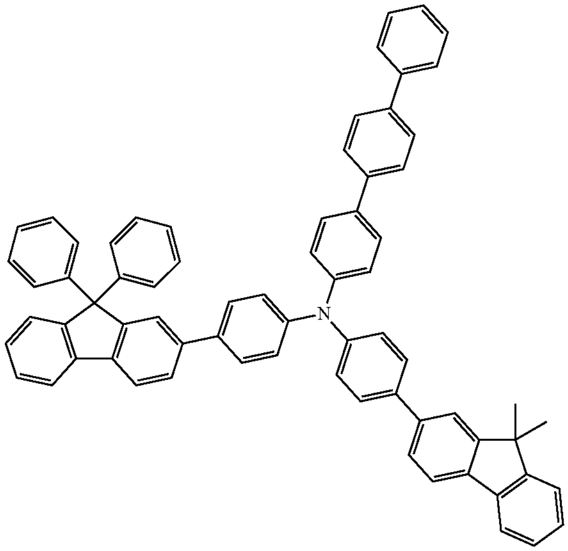
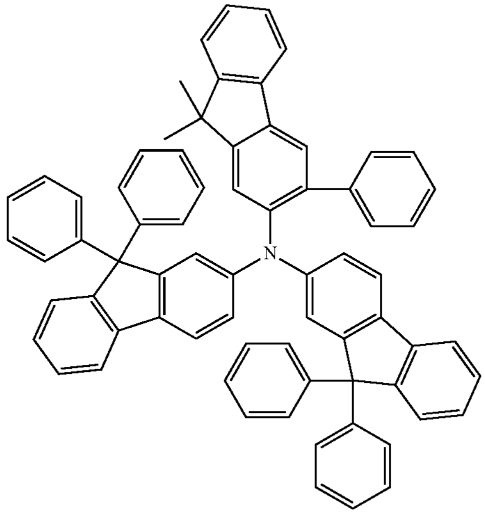
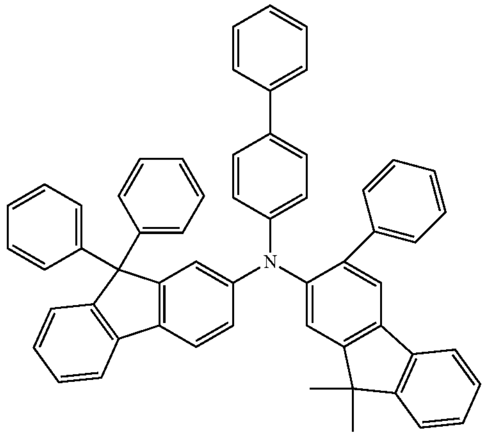

-continued
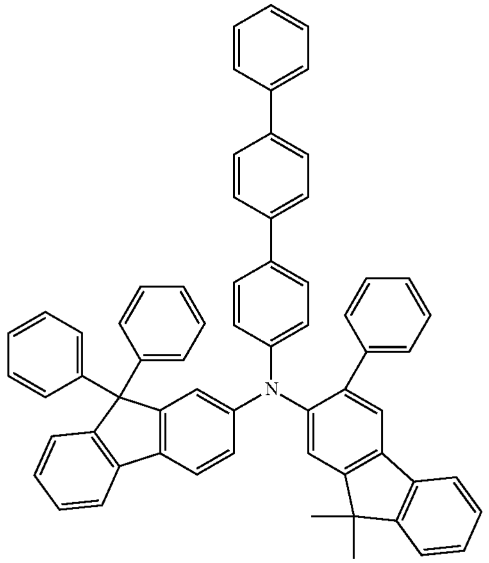
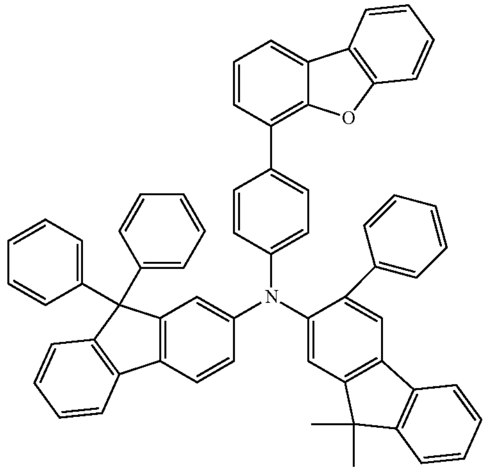
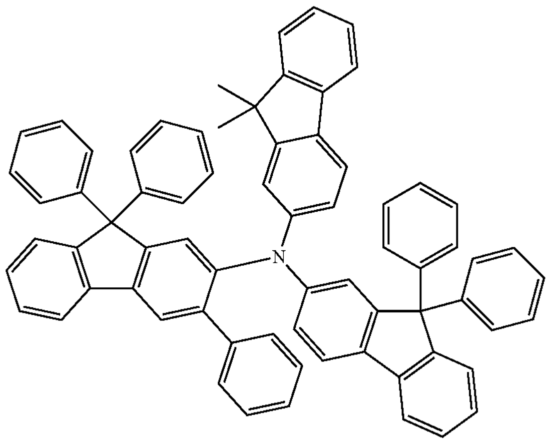
-continued
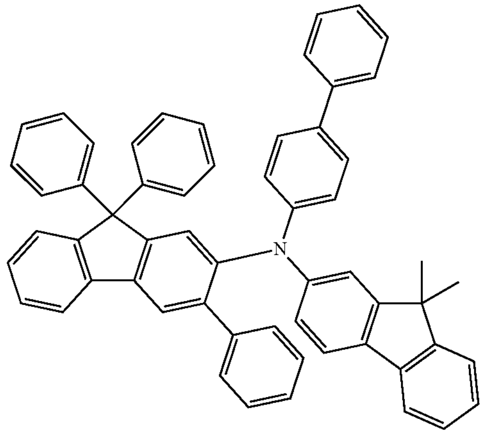
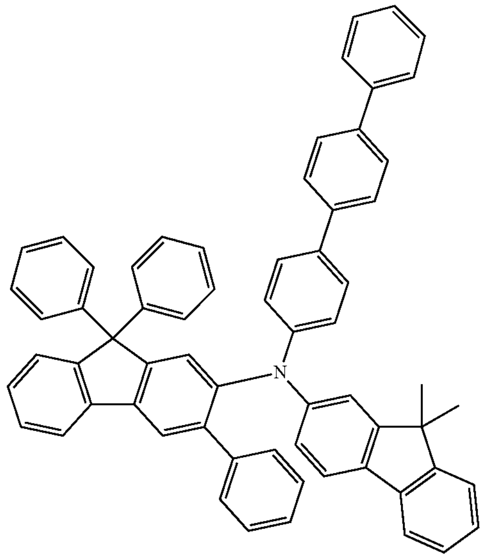
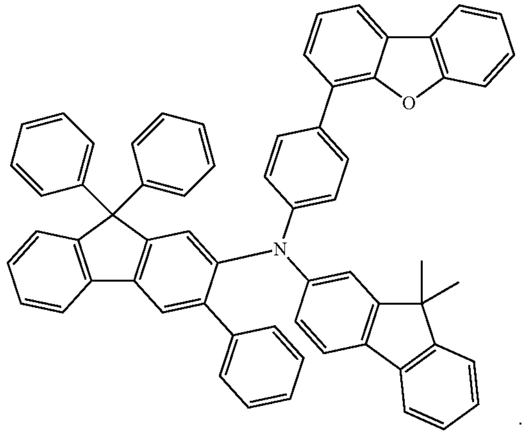
.
According to an exemplary embodiment of the present specification, Formula 2 is selected from among the following compounds:

-continued
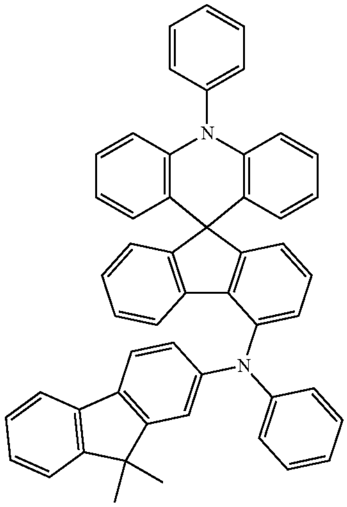
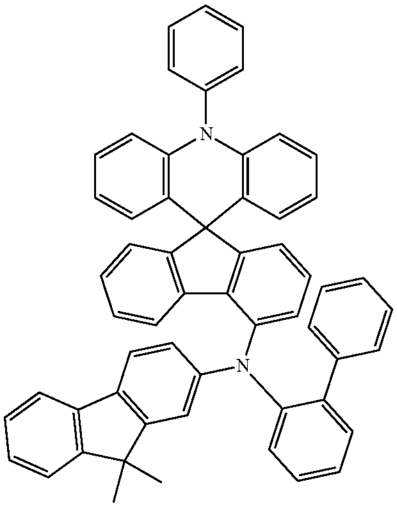
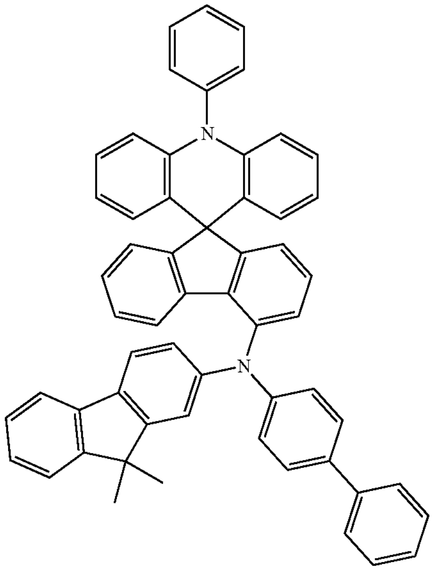
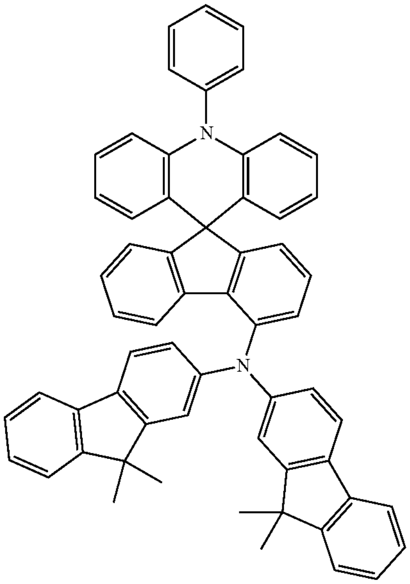
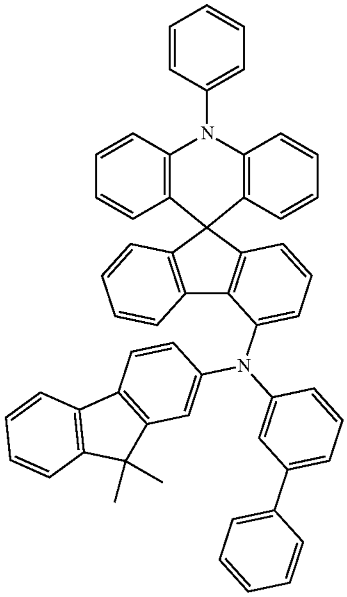
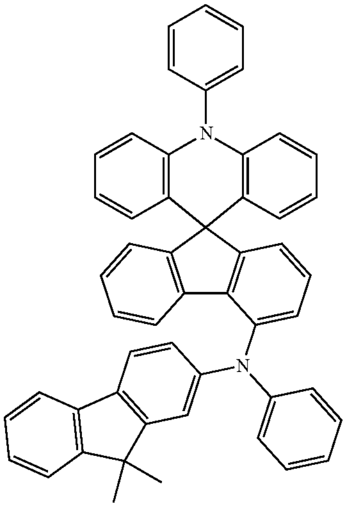

-continued
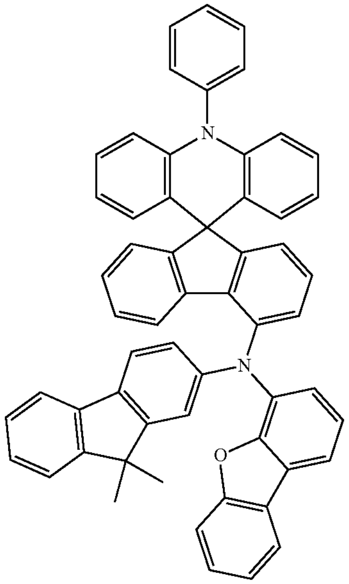
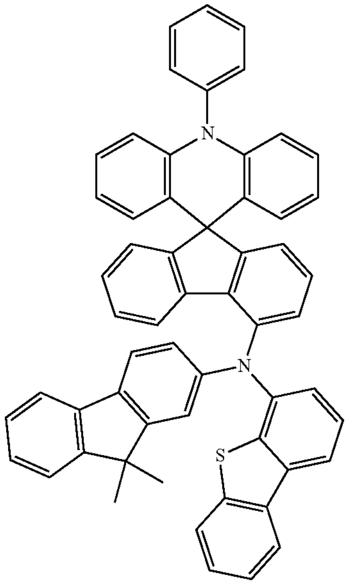
-continued
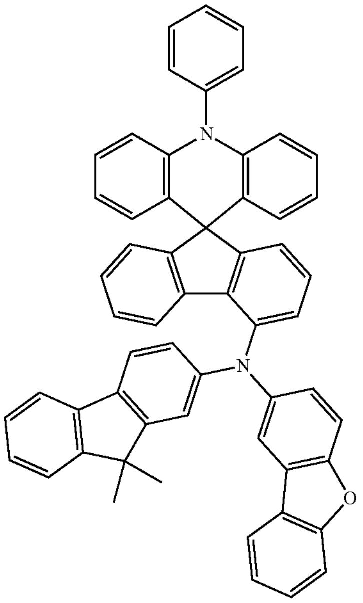
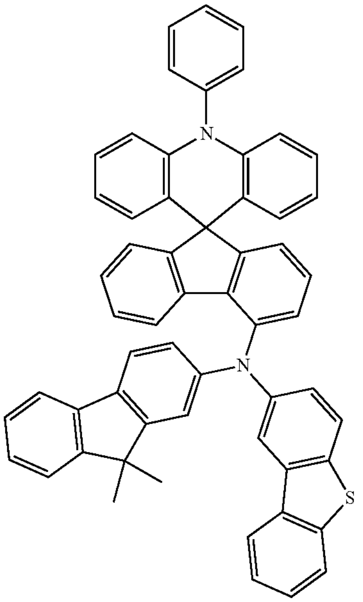

-continued
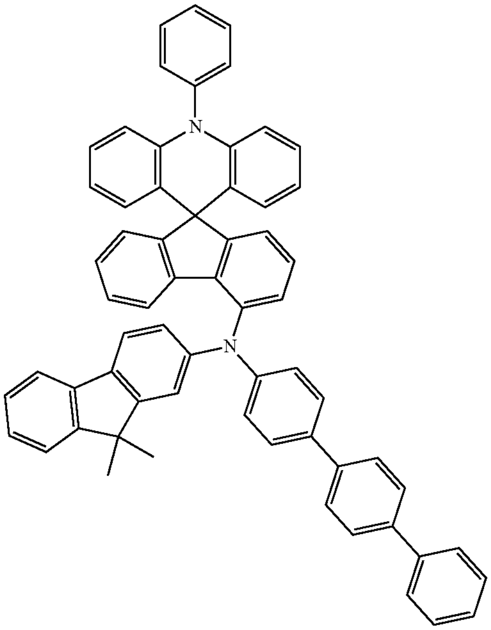
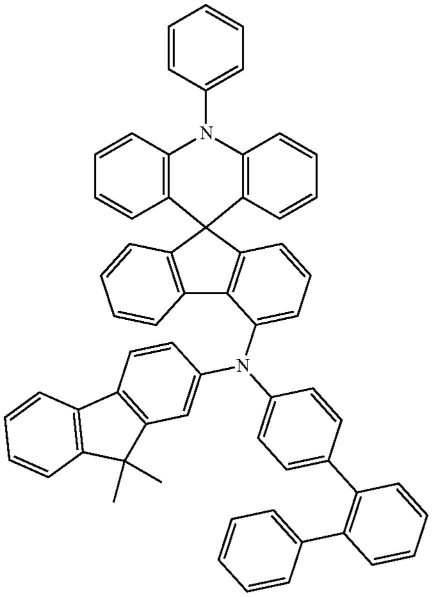
-continued
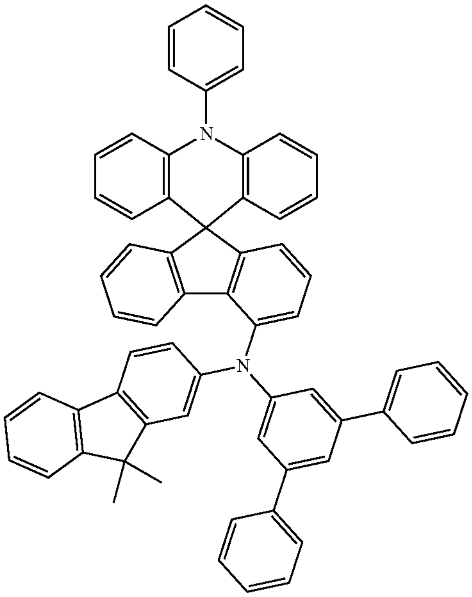
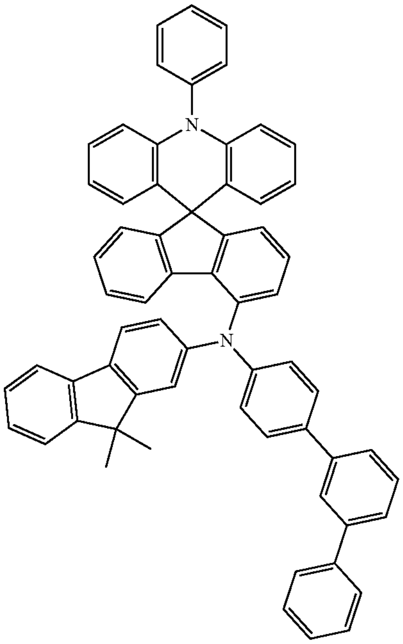

-continued
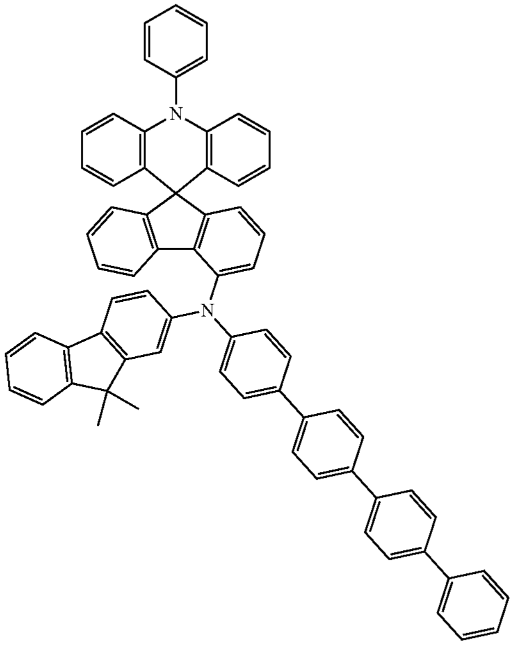
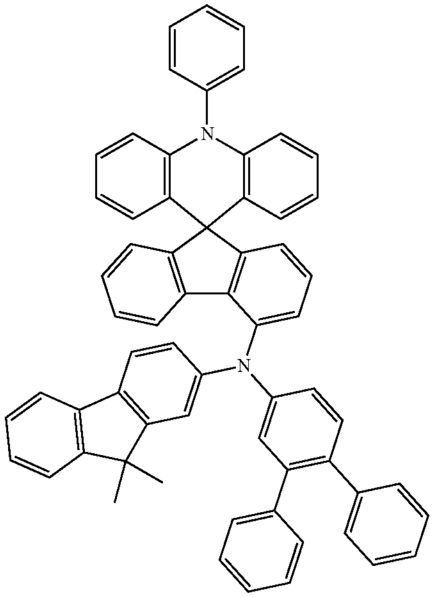
-continued
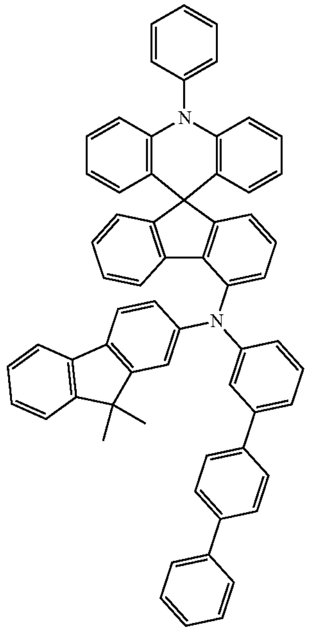
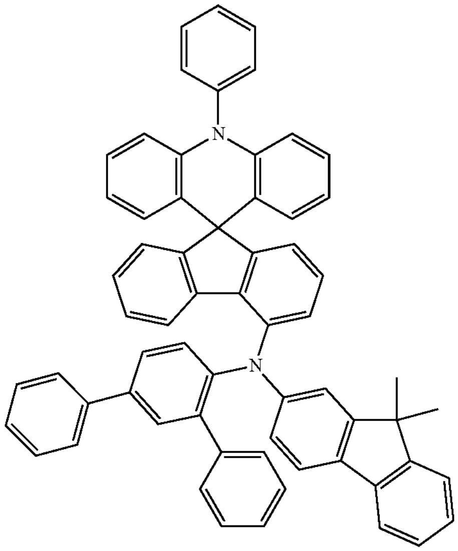

-continued
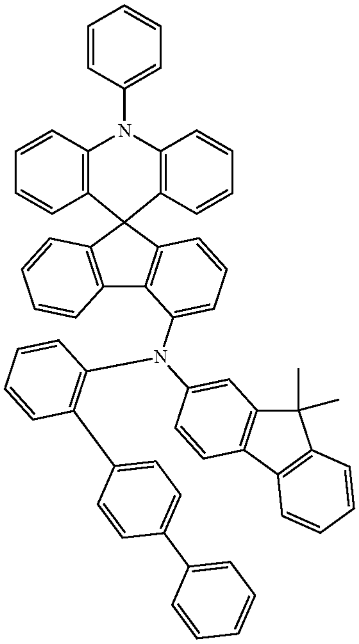
-continued
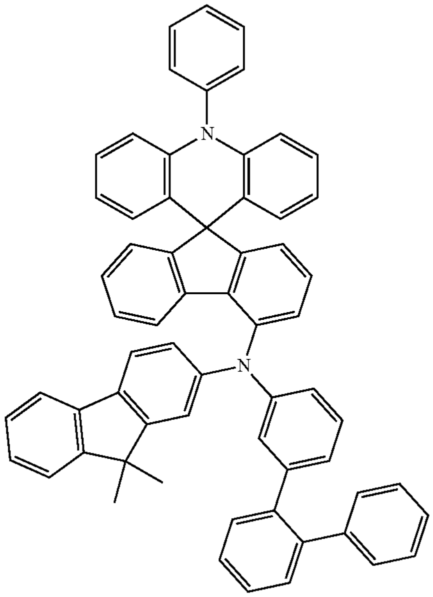
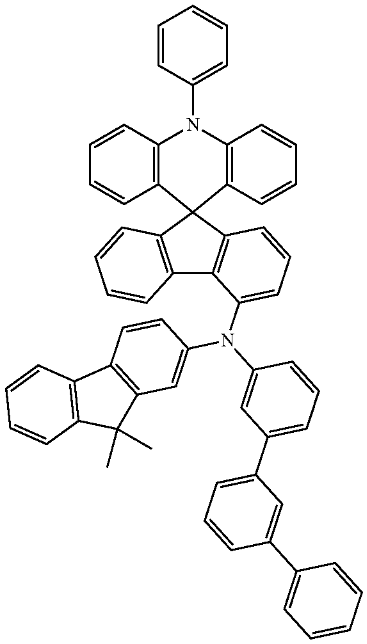
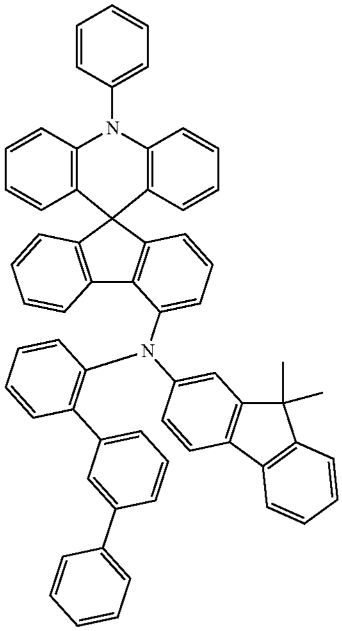

-continued
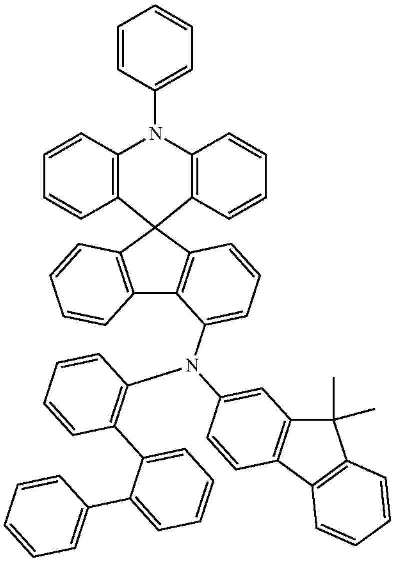
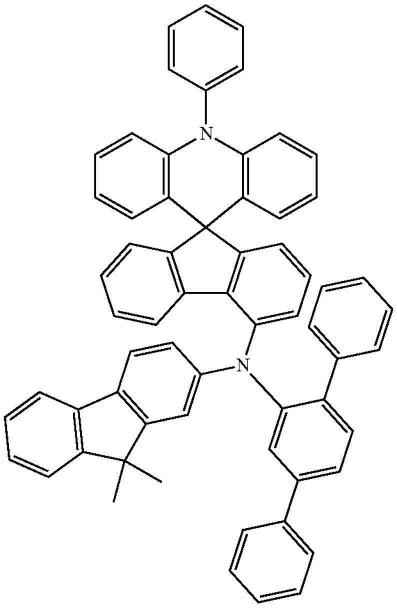
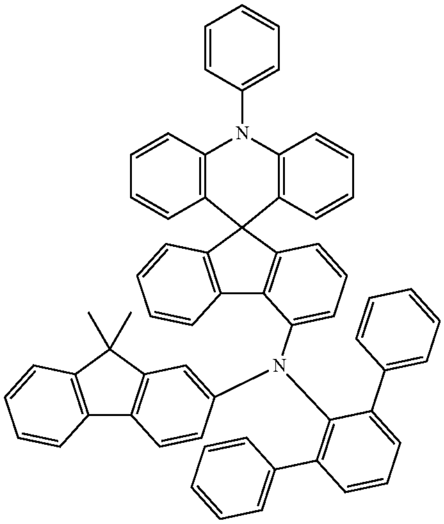
-continued
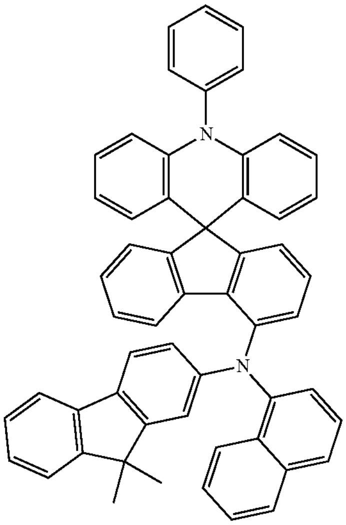
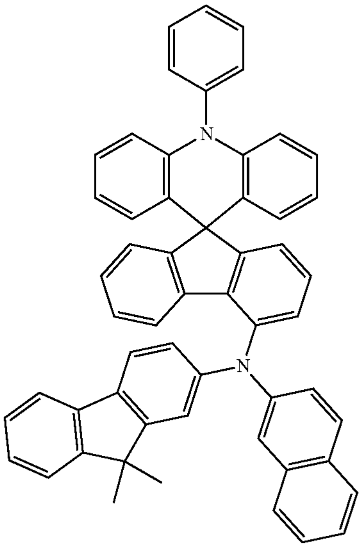
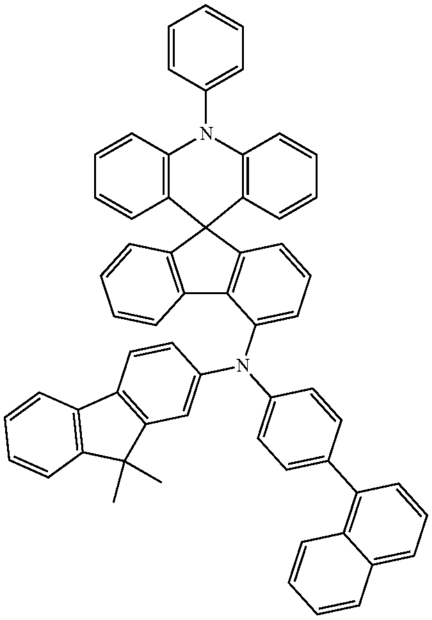

-continued
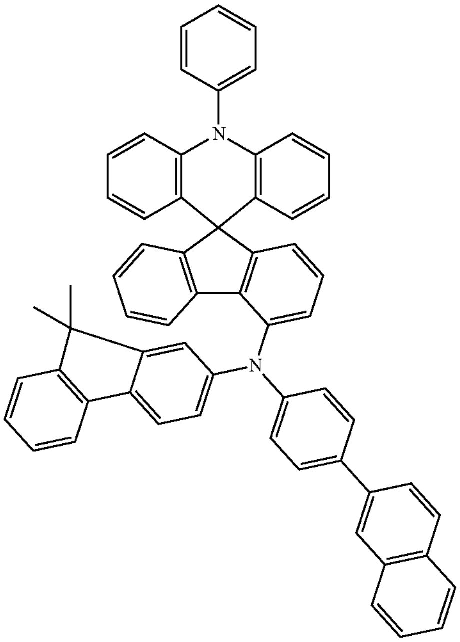
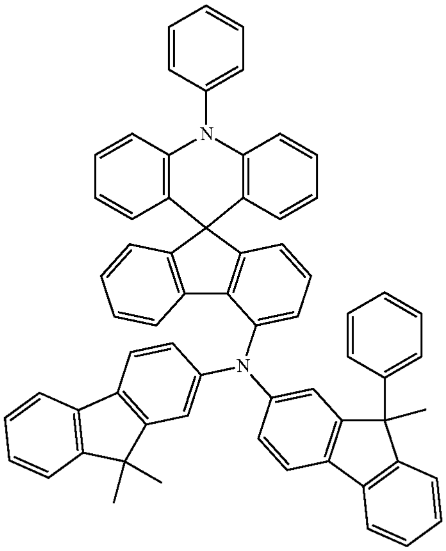
-continued
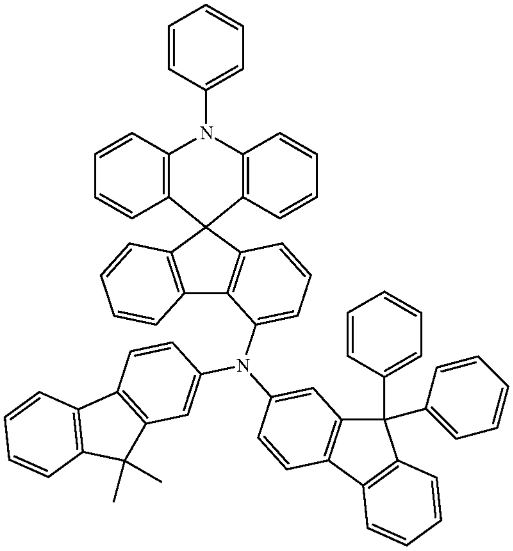
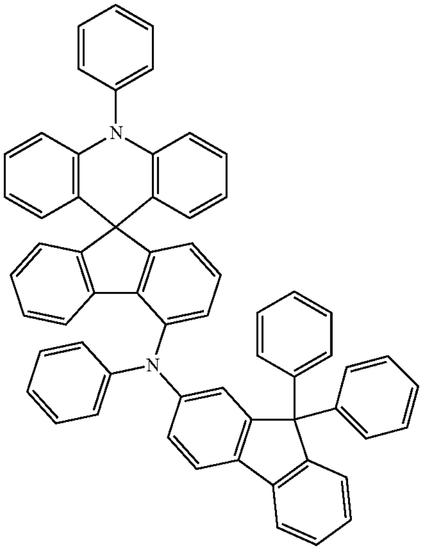
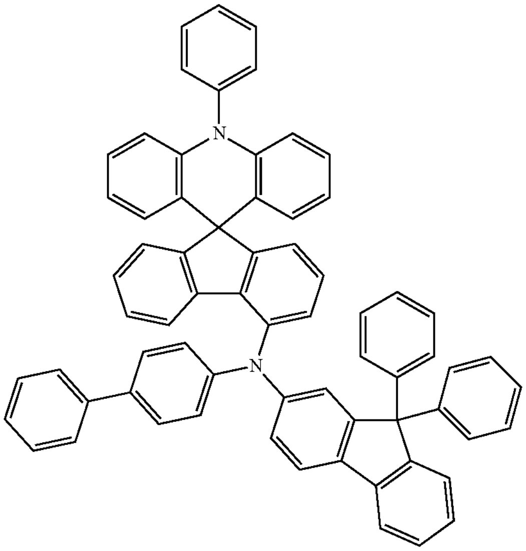

-continued
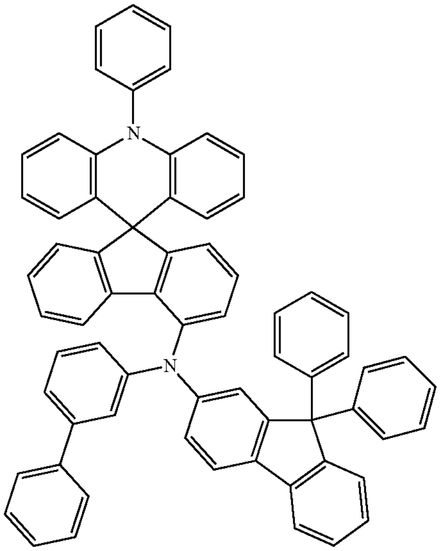
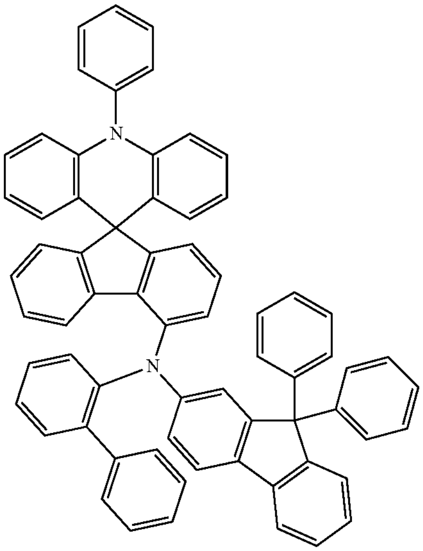
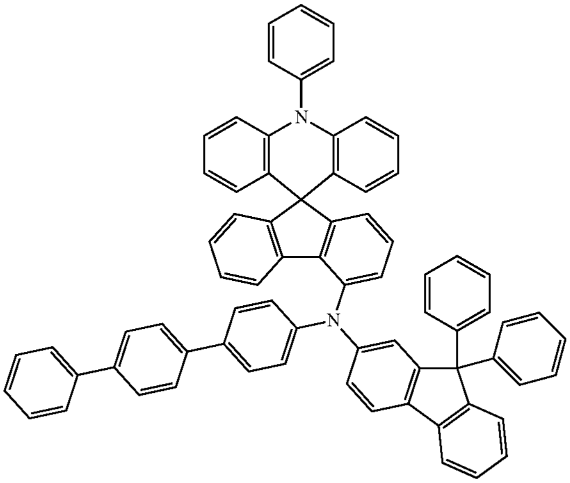
-continued
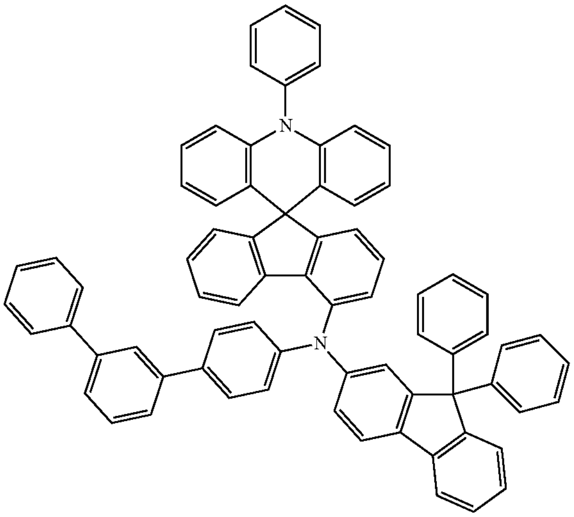
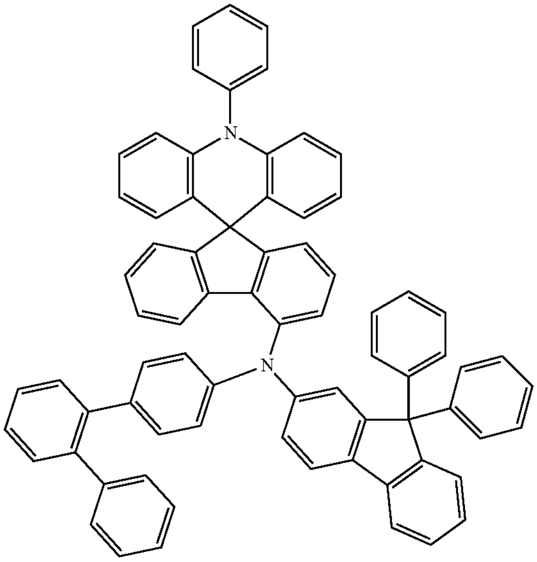
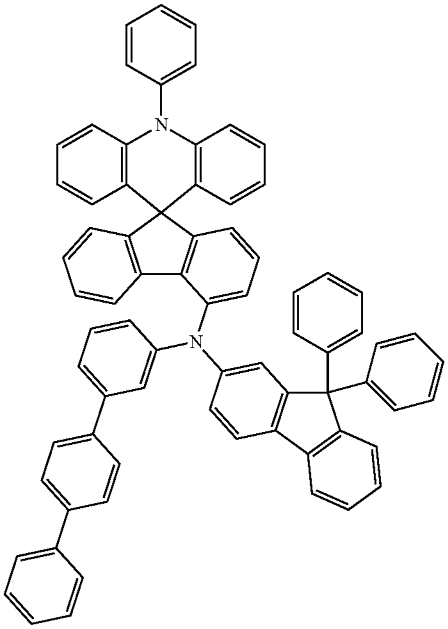

-continued
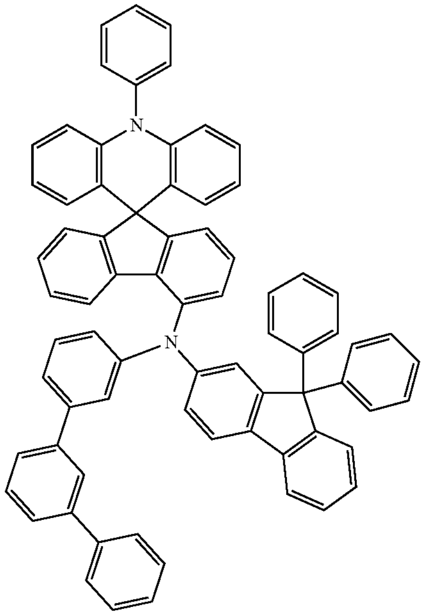
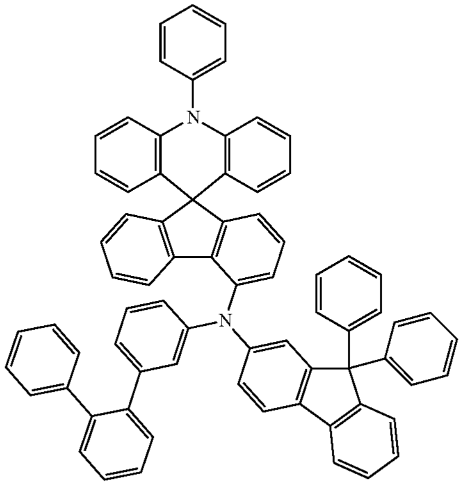
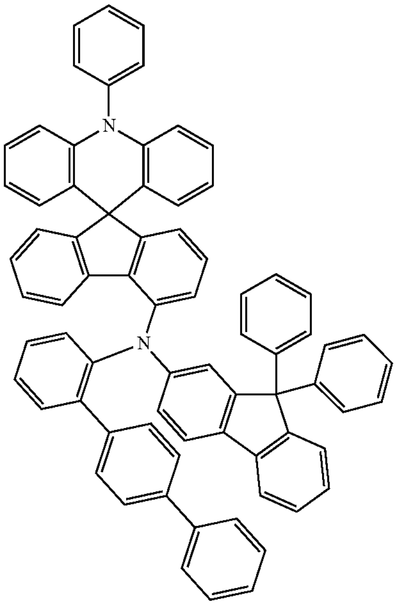
-continued
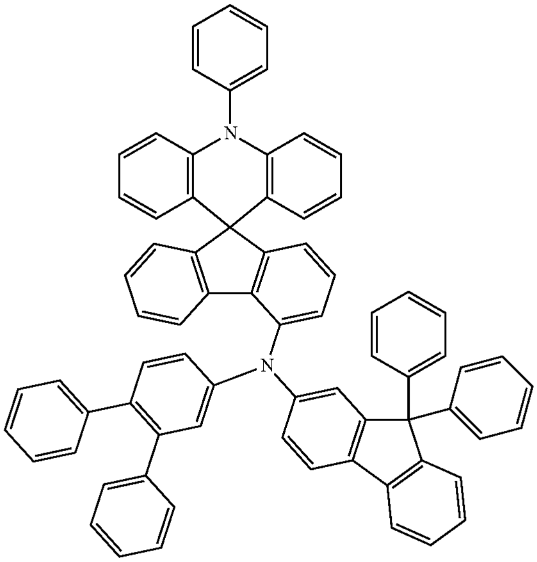
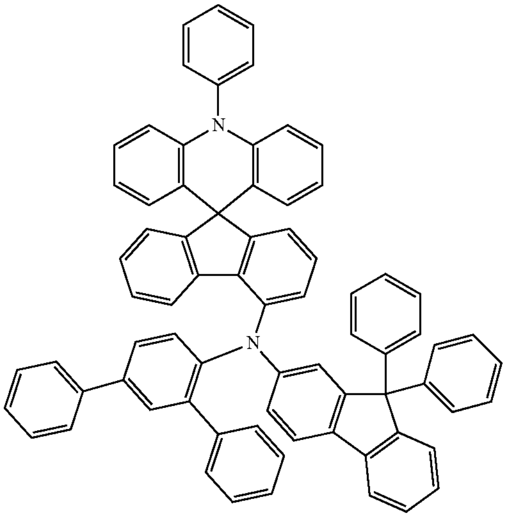
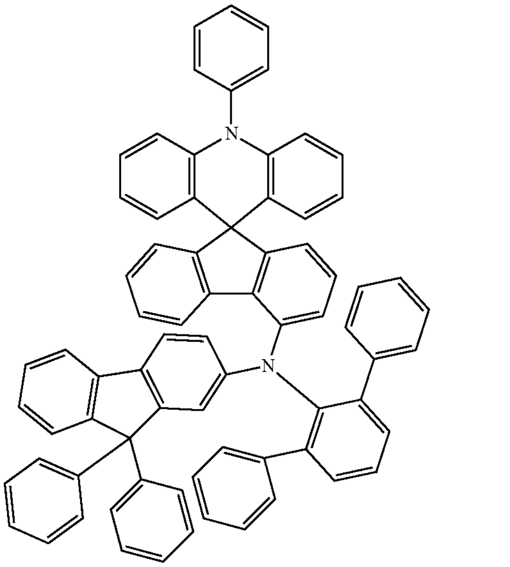

-continued
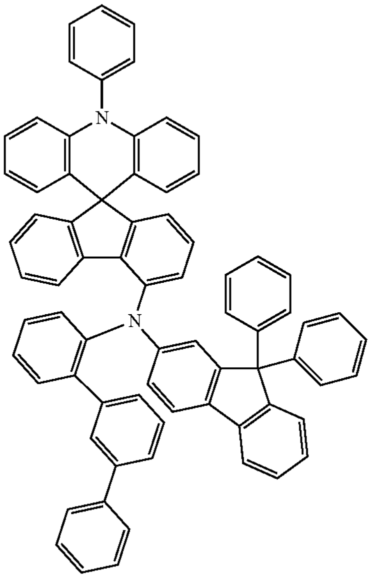
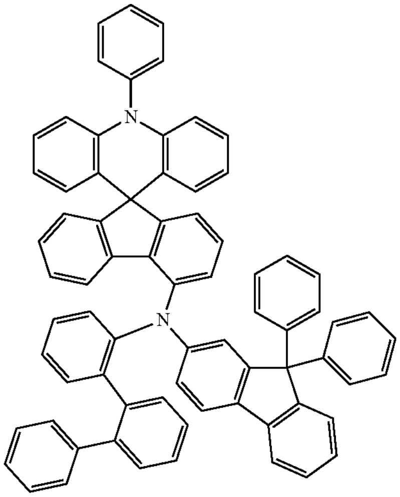
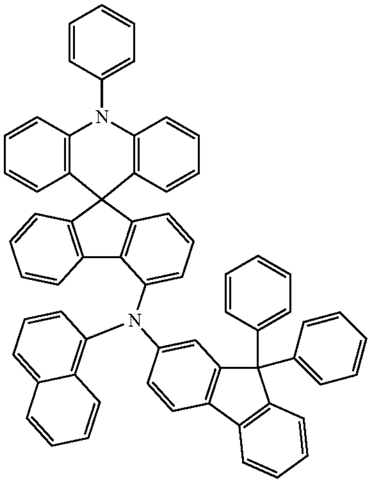
-continued
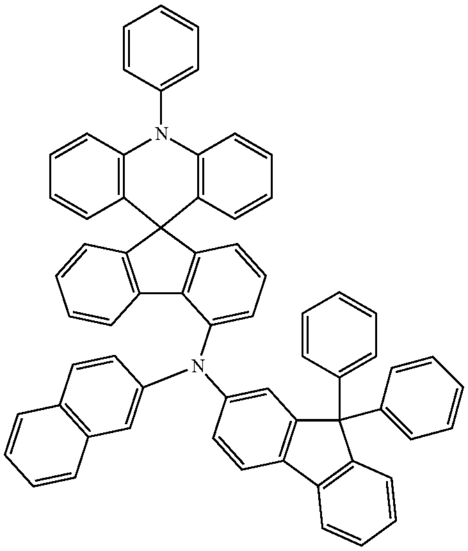
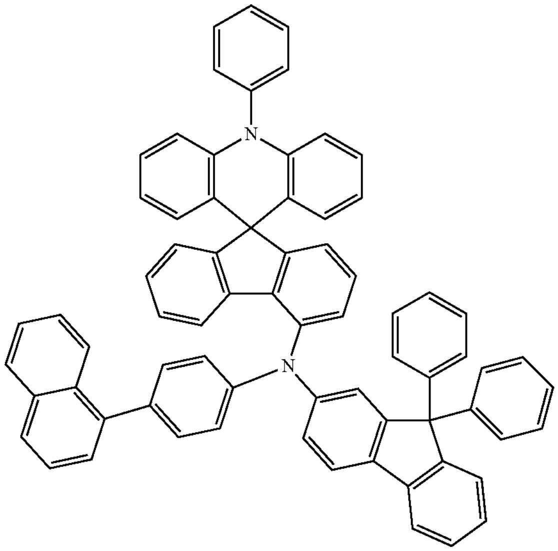
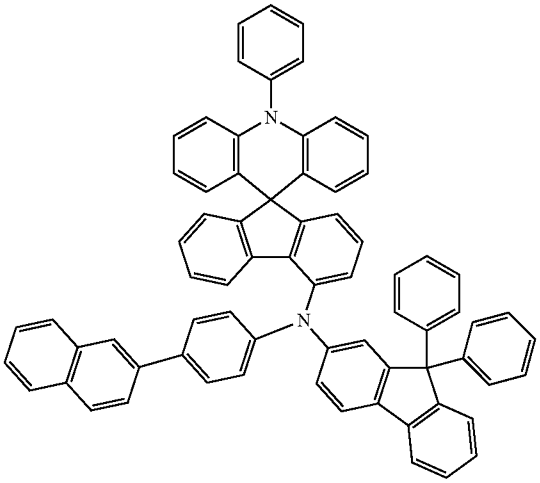

-continued
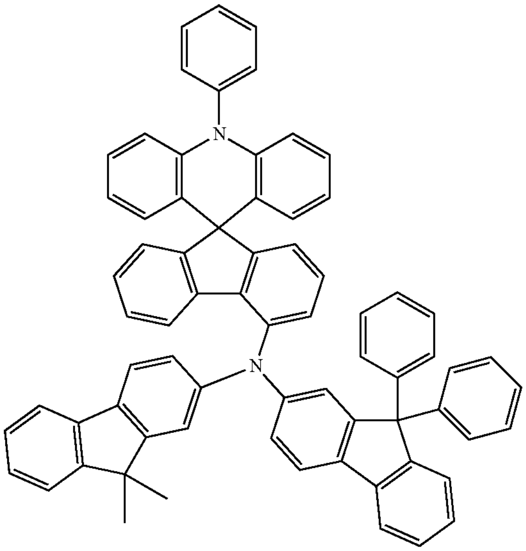
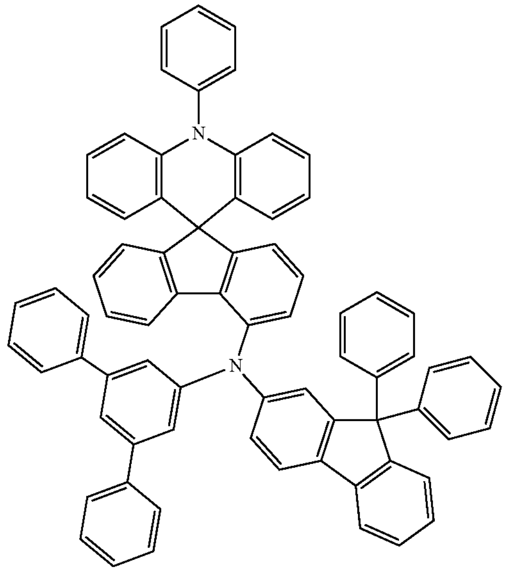
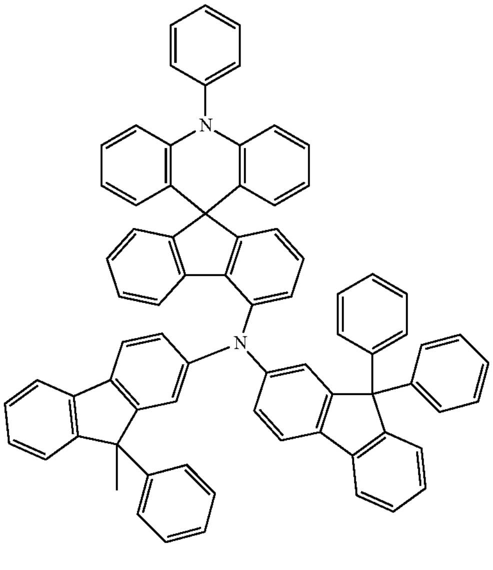
-continued
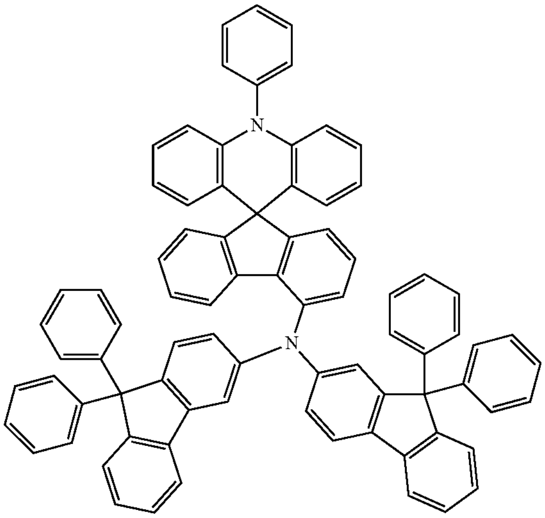
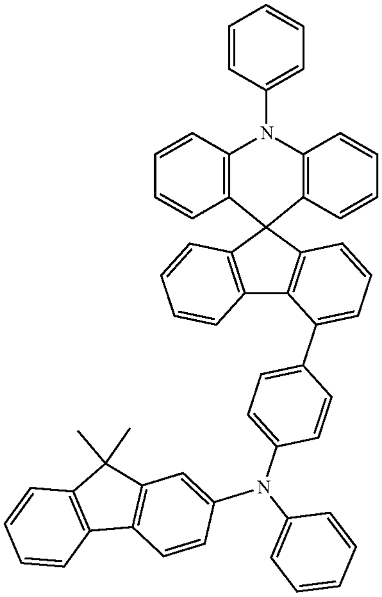
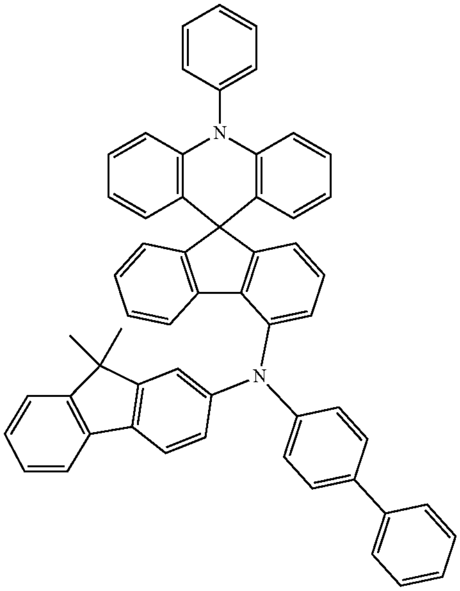

-continued
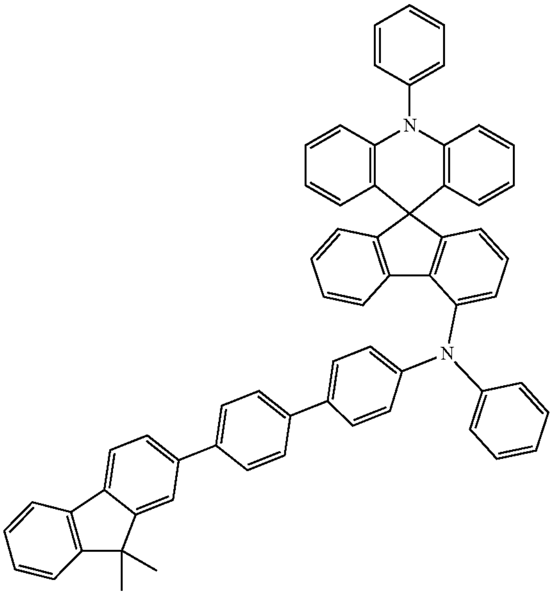
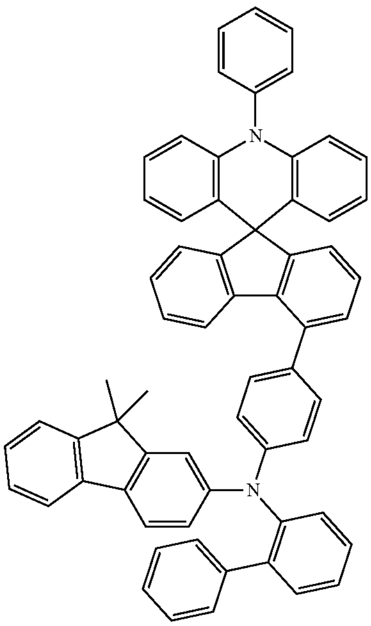
-continued
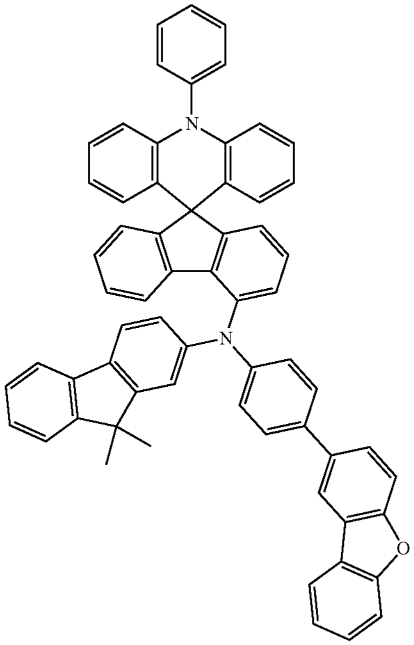
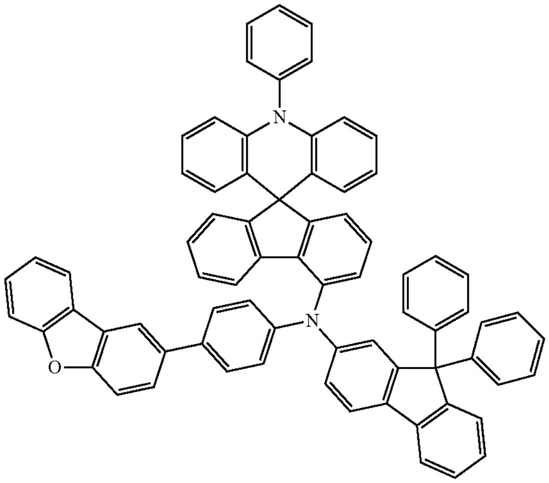

-continued
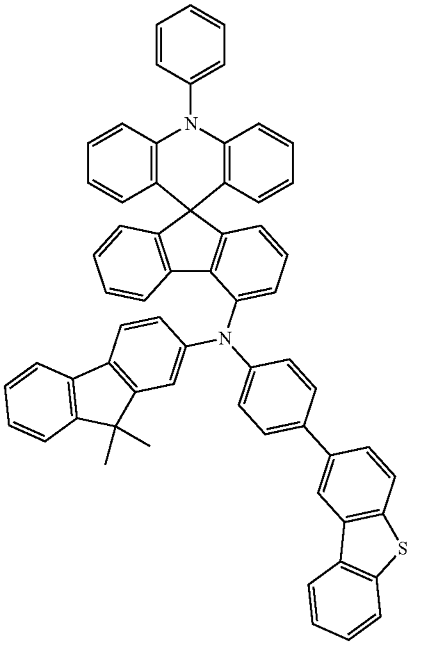
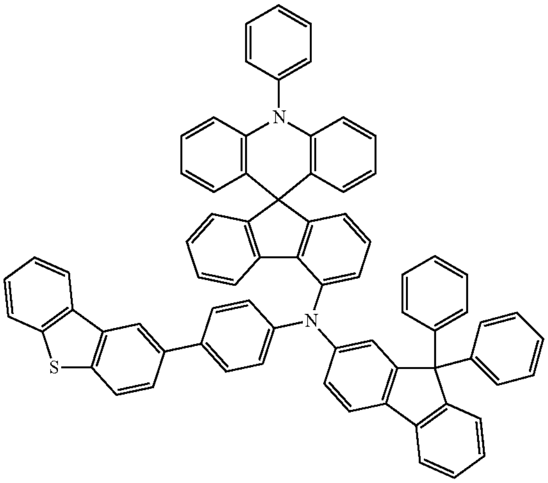
-continued
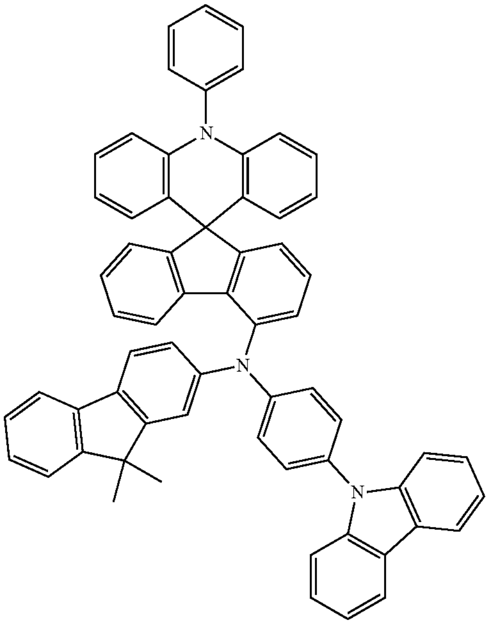
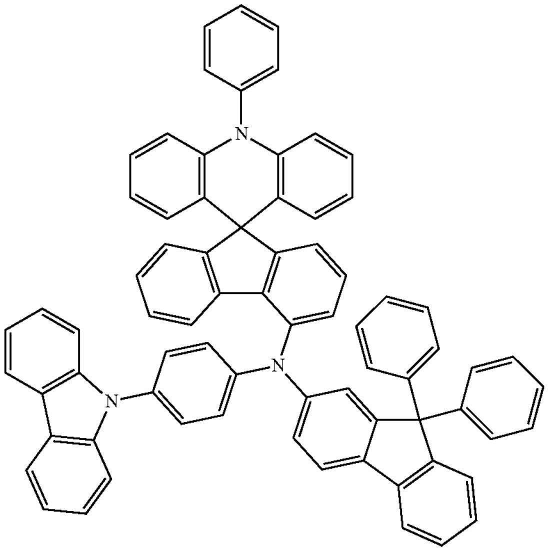

-continued
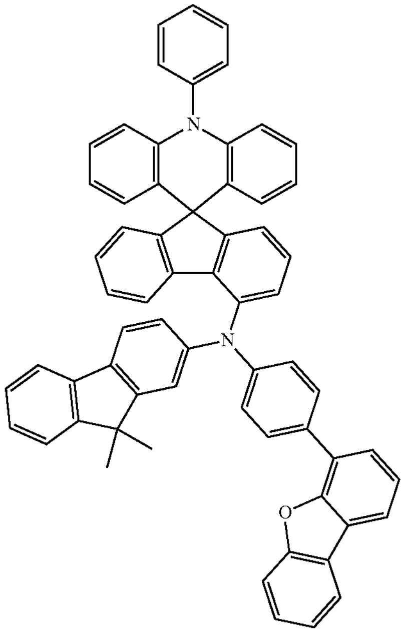
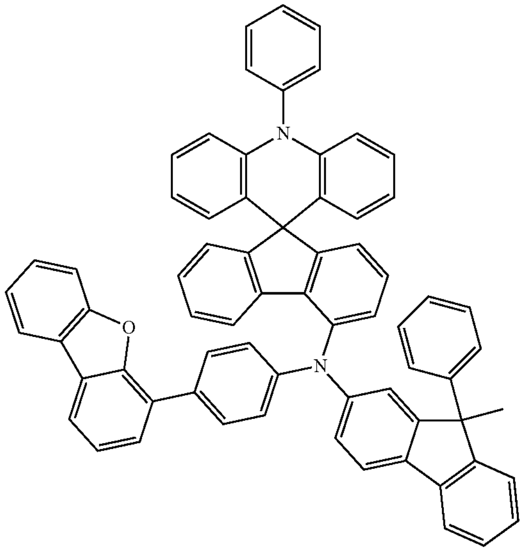
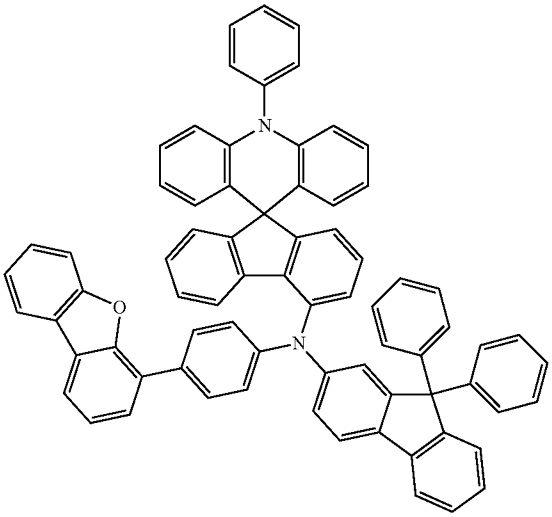
-continued
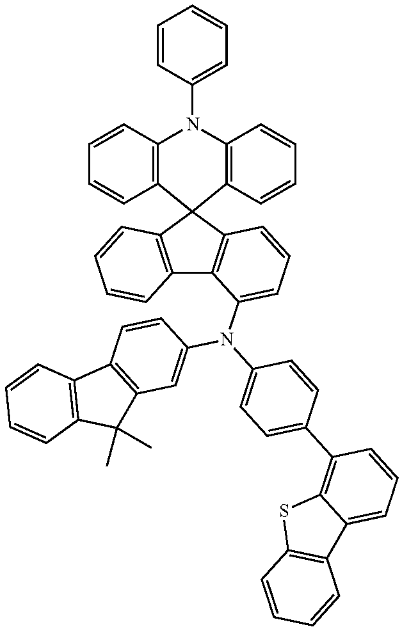
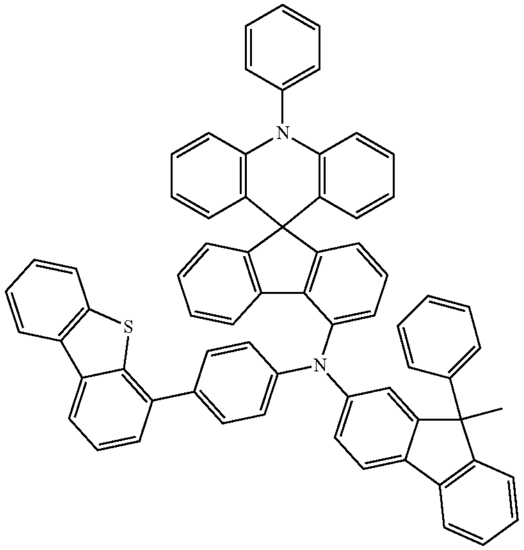
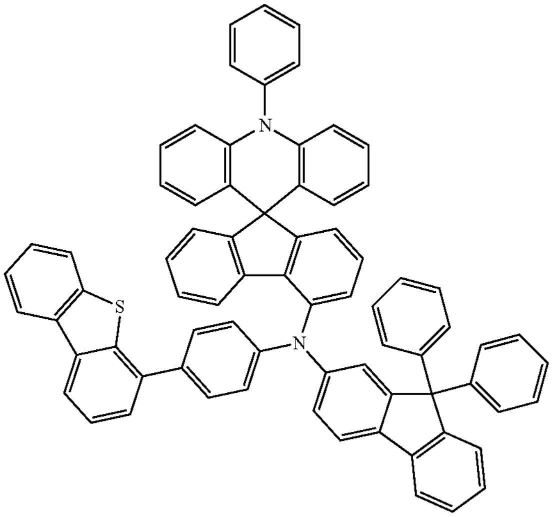

-continued
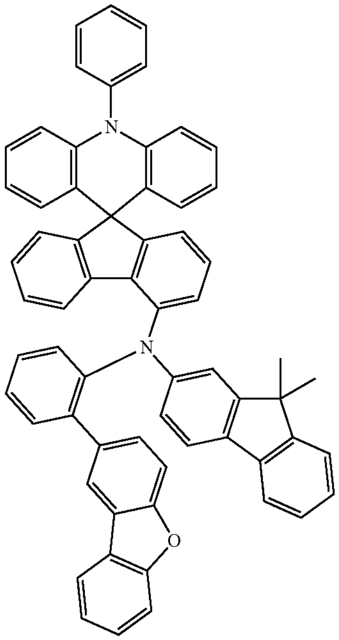
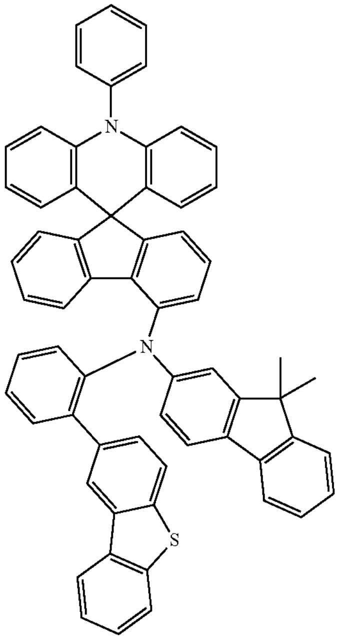
-continued
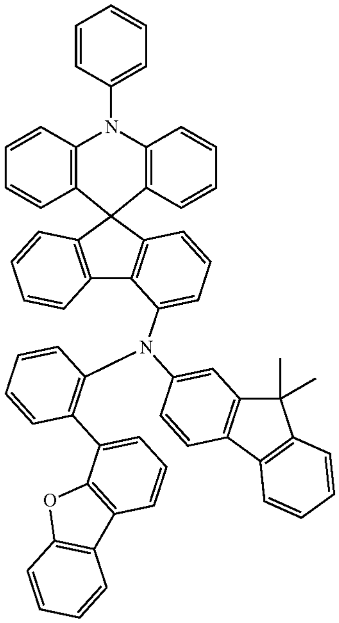
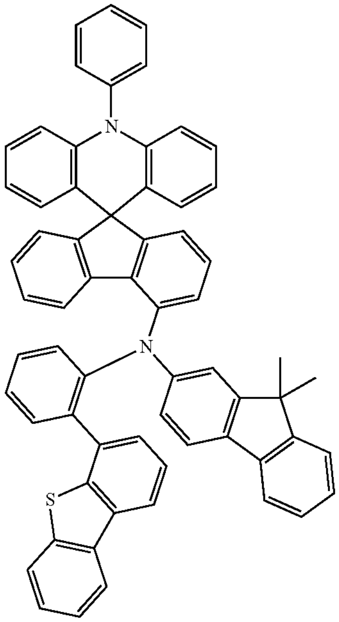

-continued
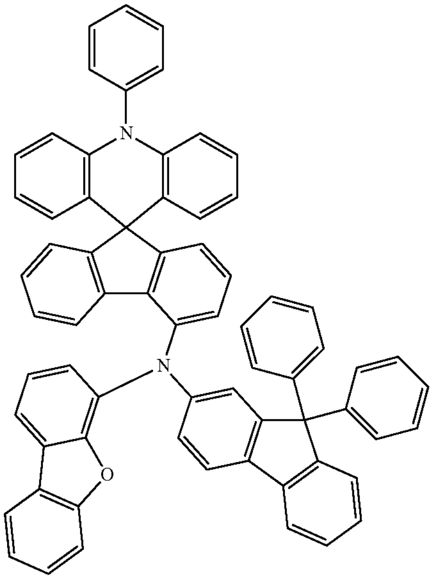
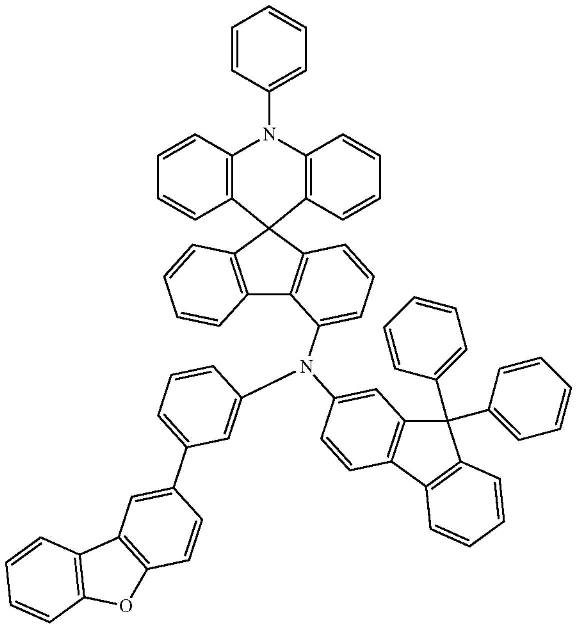
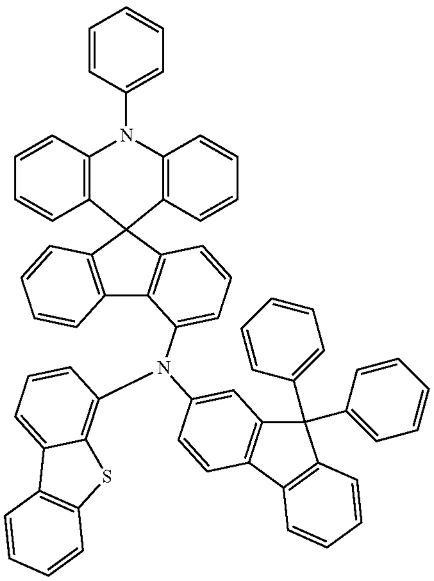
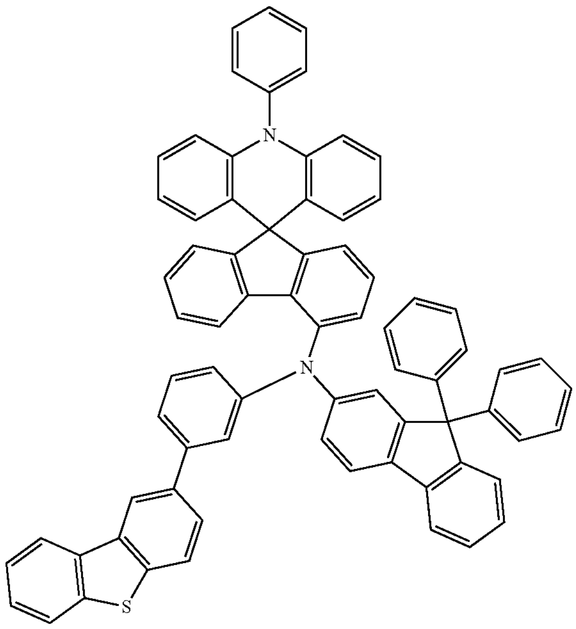
-continued

-continued
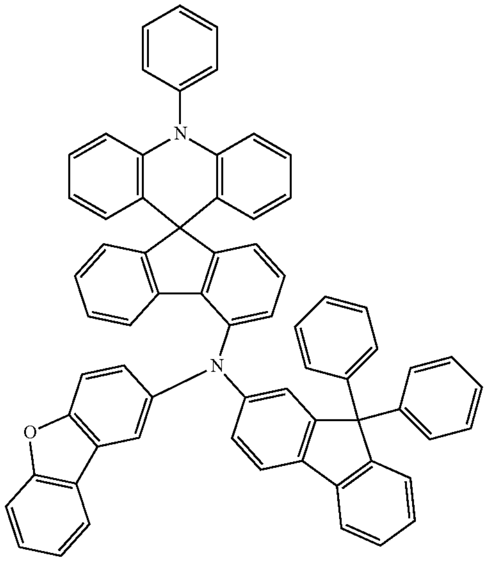
-continued
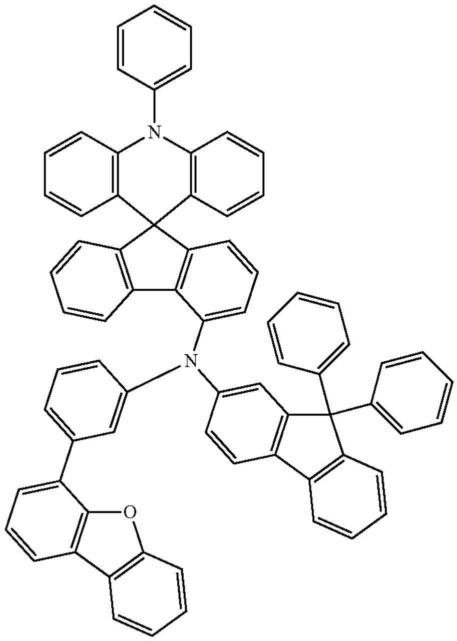
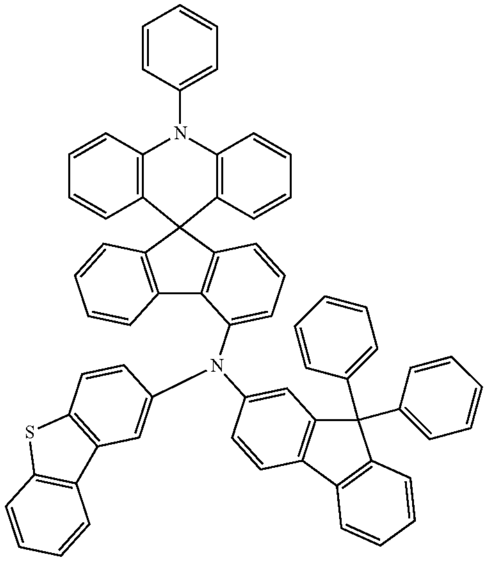
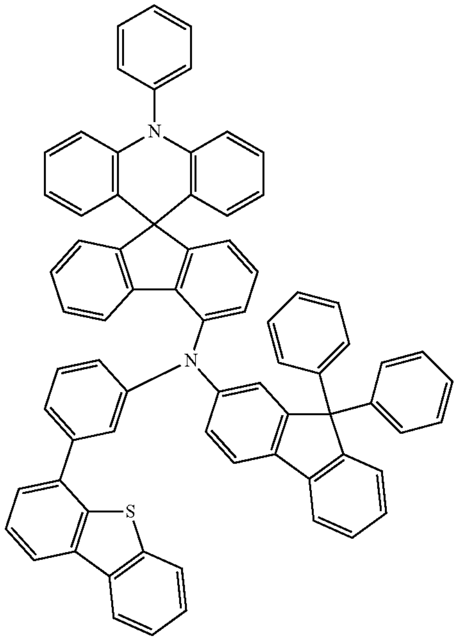

-continued
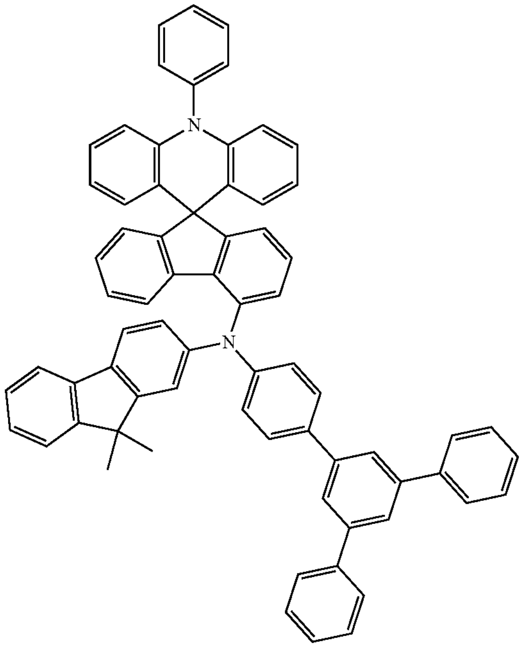
-continued
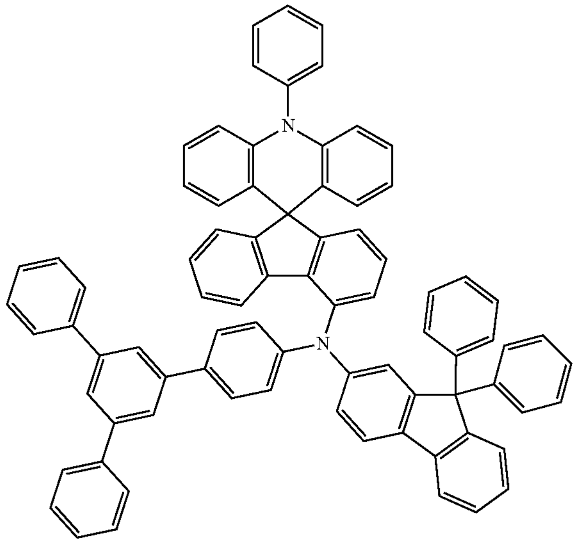
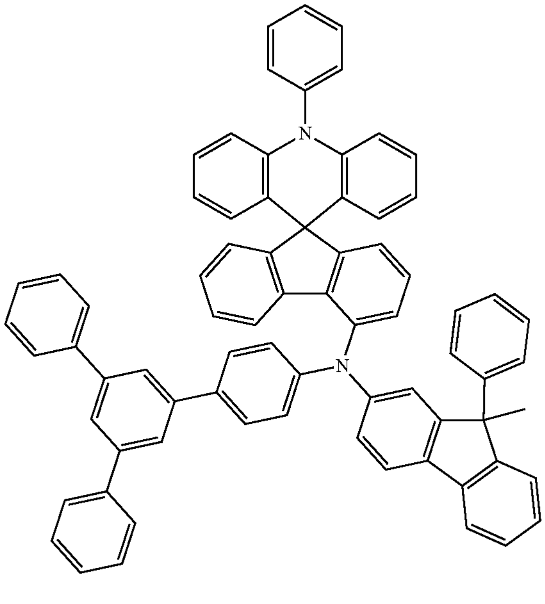
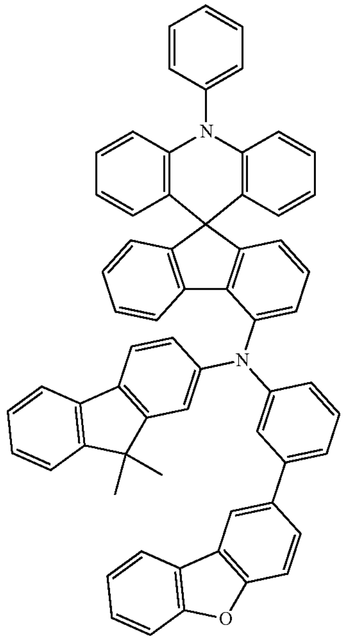

-continued
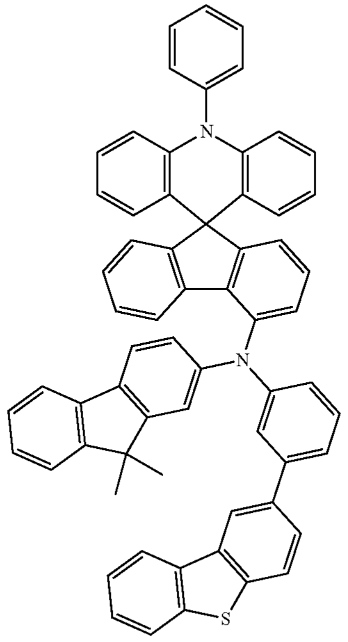
-continued
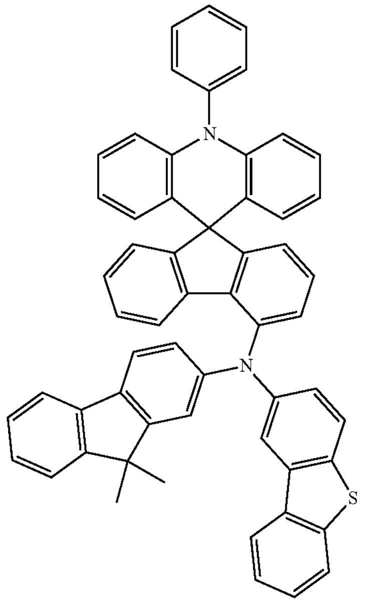
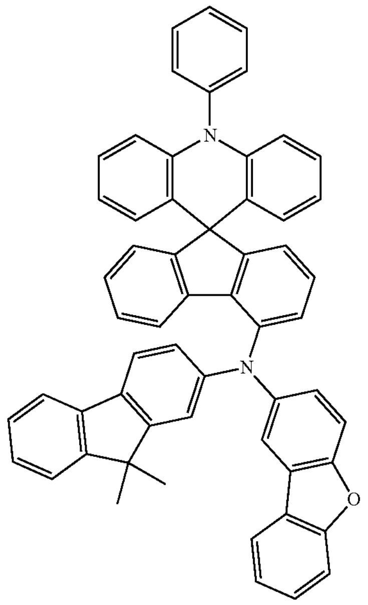
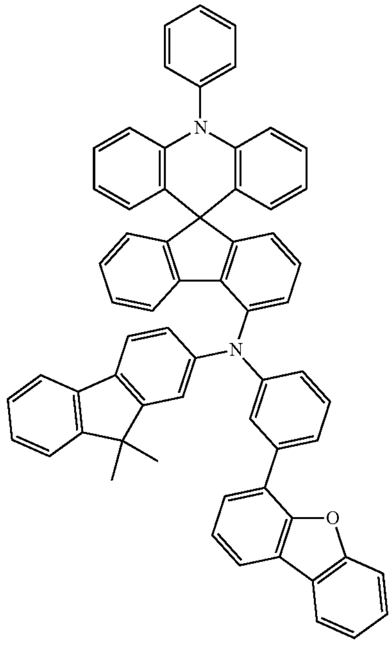

-continued
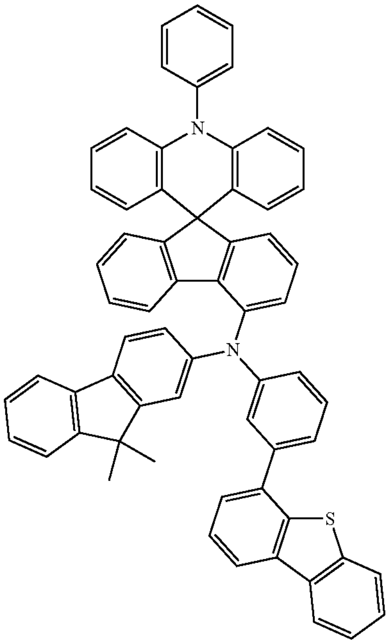
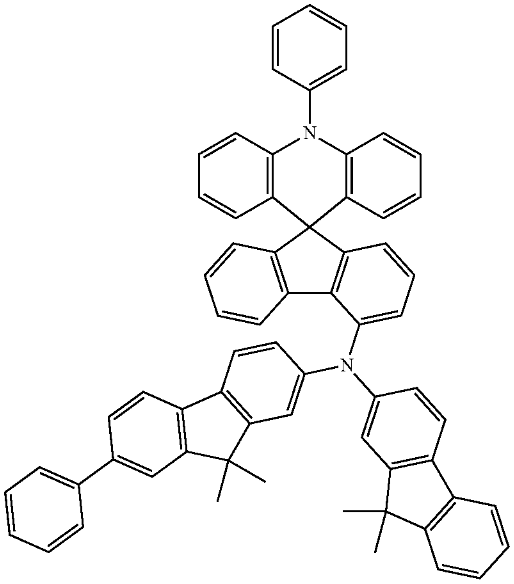
-continued
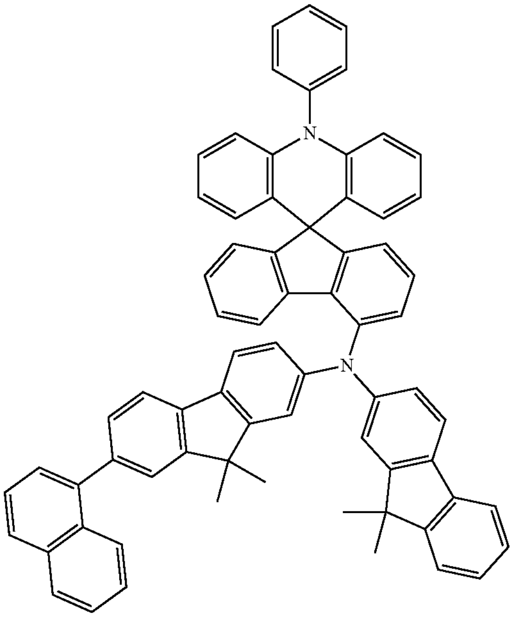
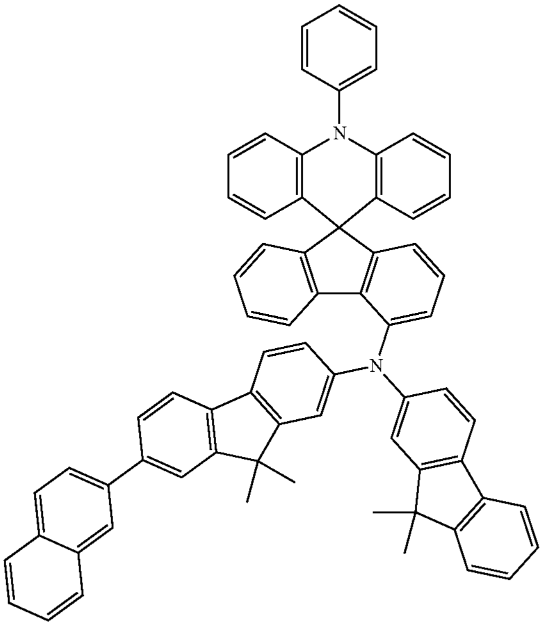

-continued
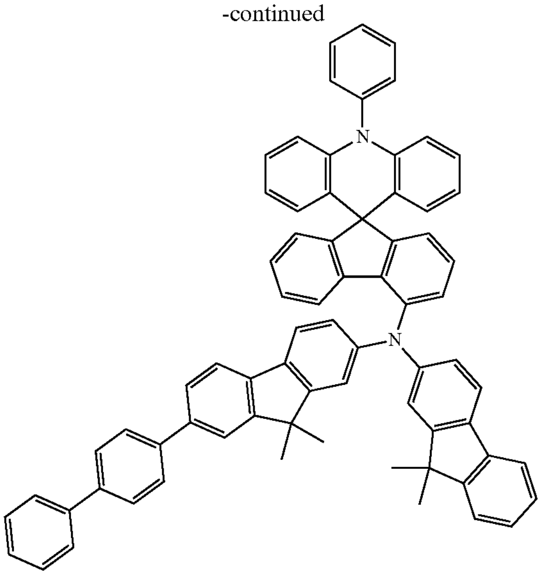
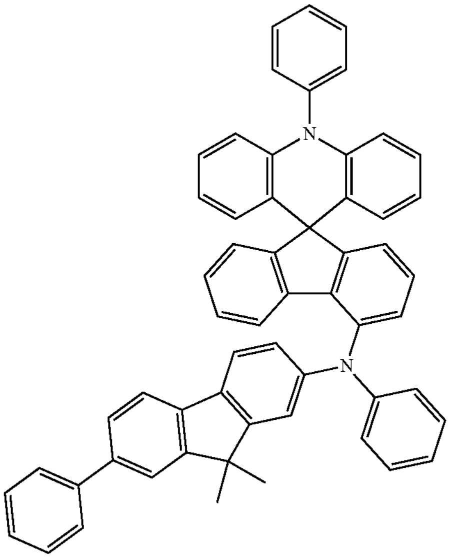
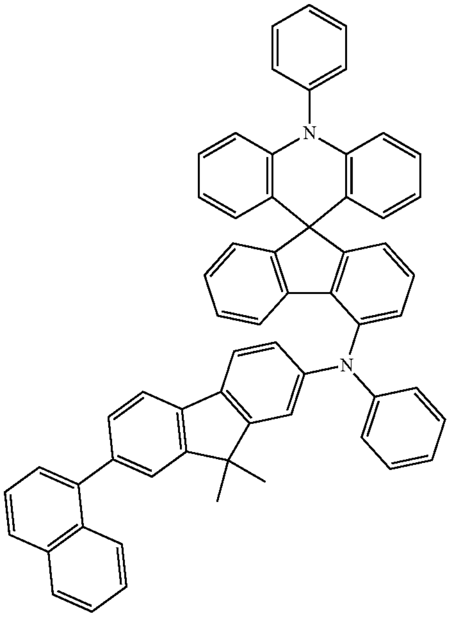
-continued
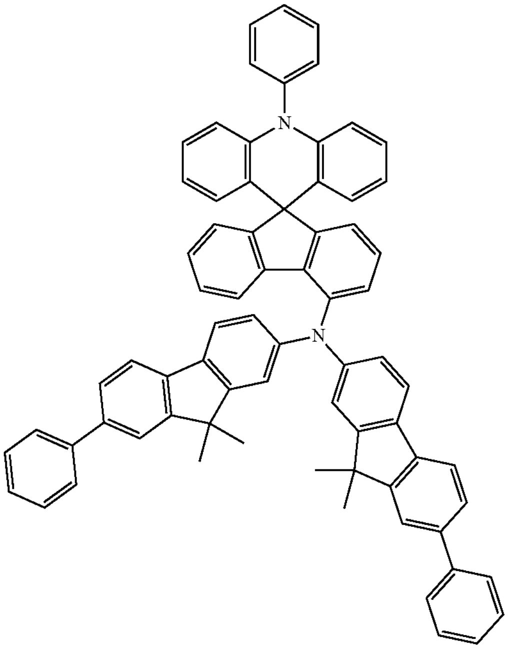
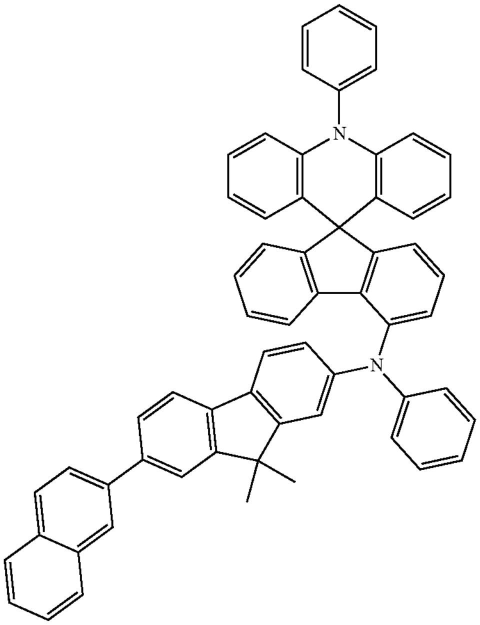

-continued
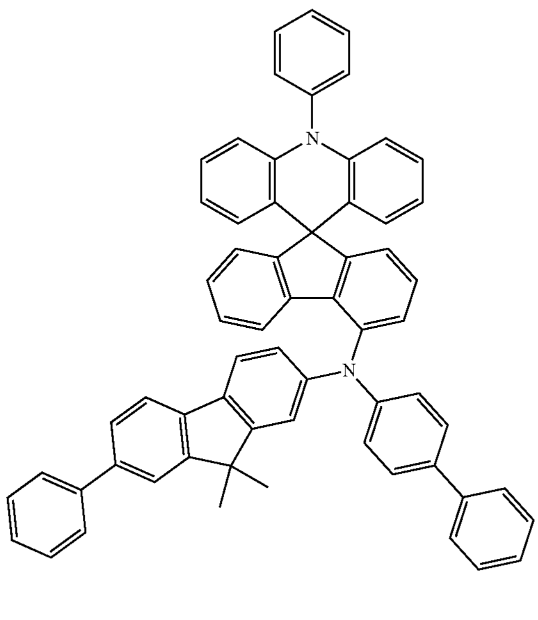
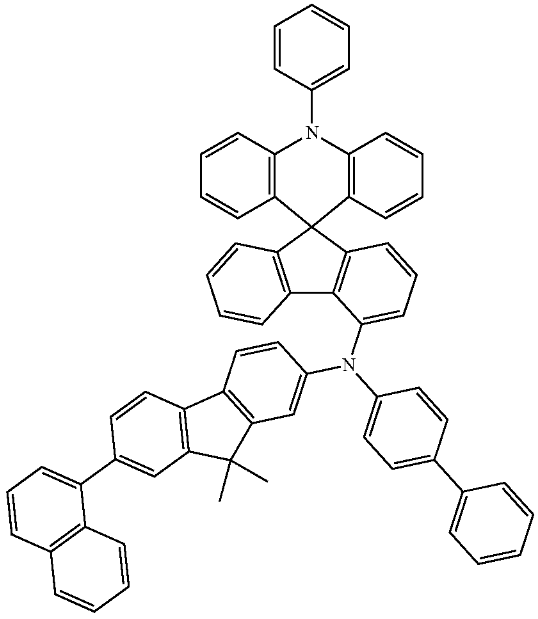
-continued
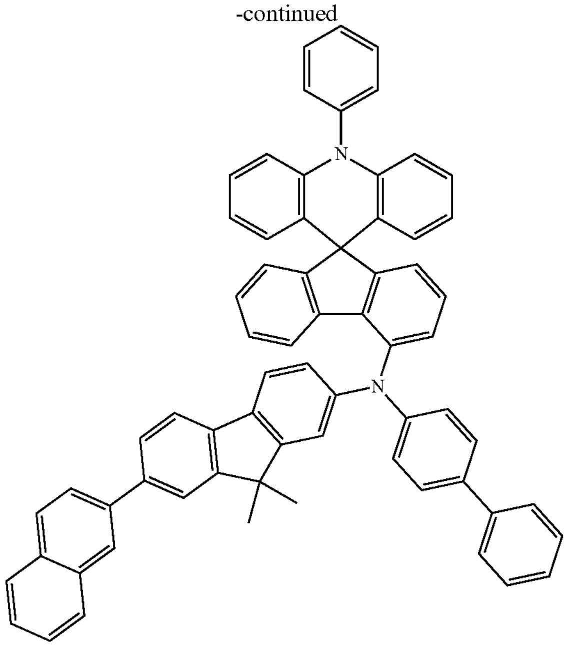
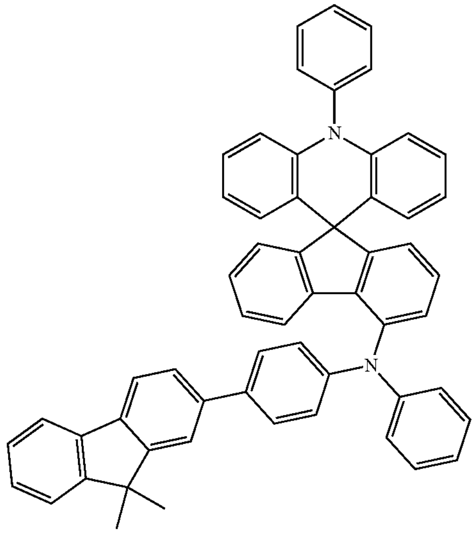
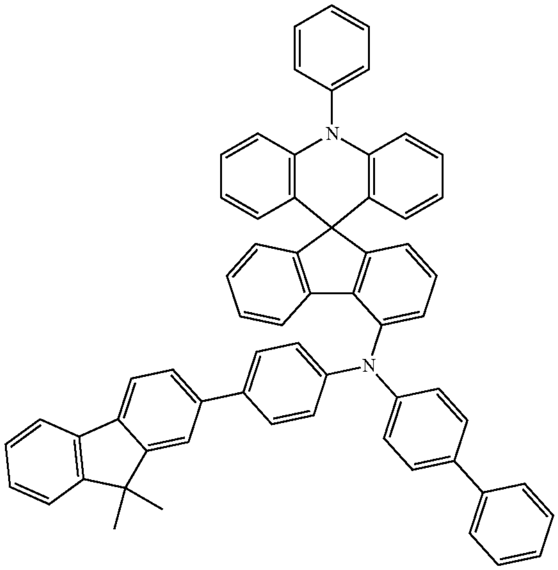

-continued
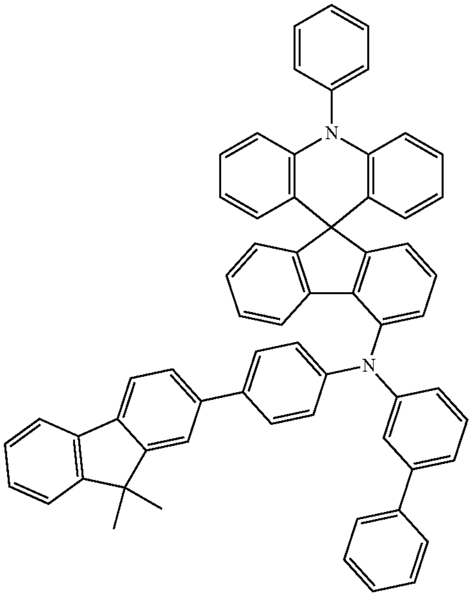
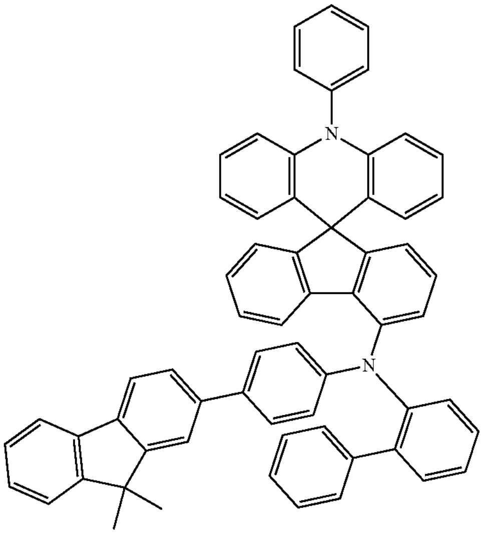
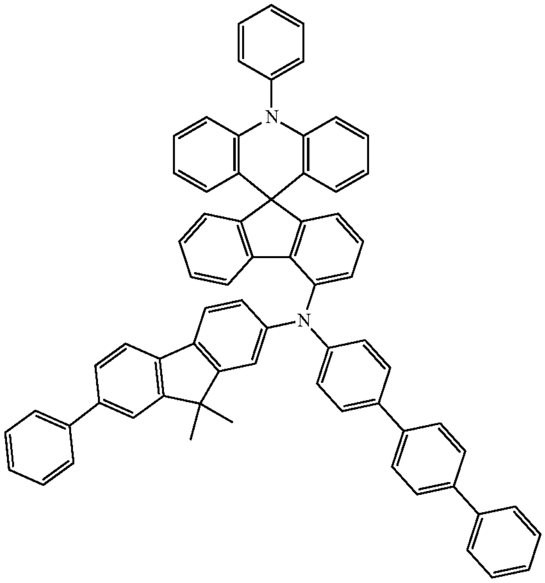
-continued
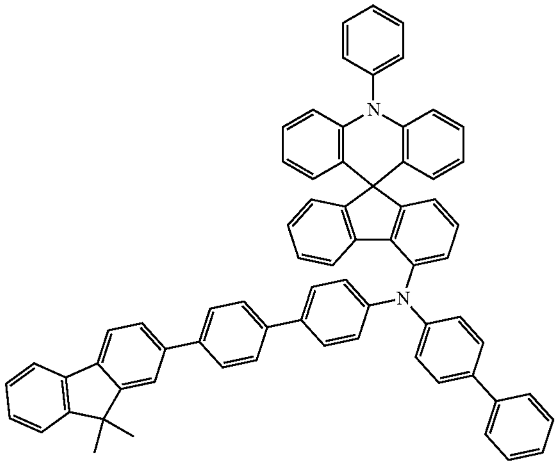
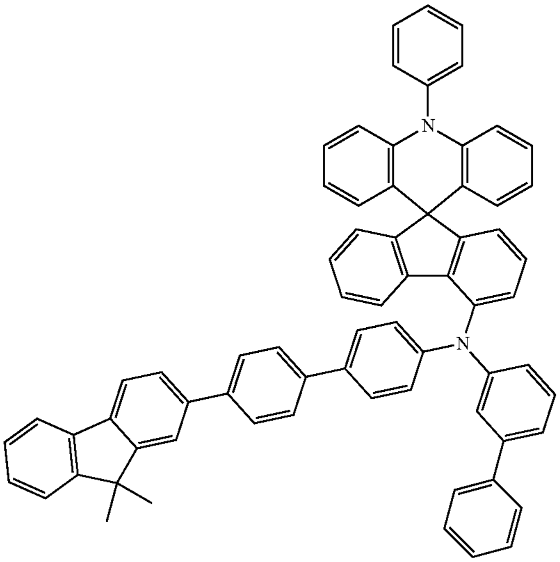
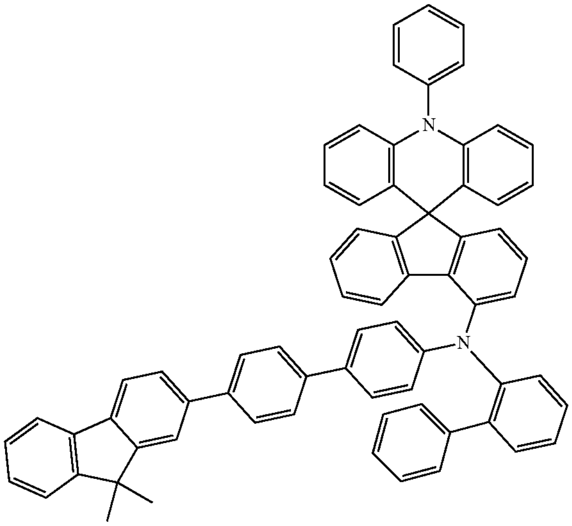

-continued
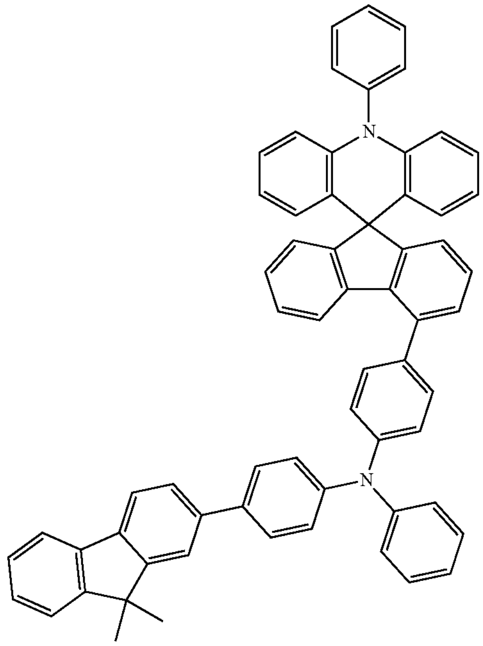
-continued
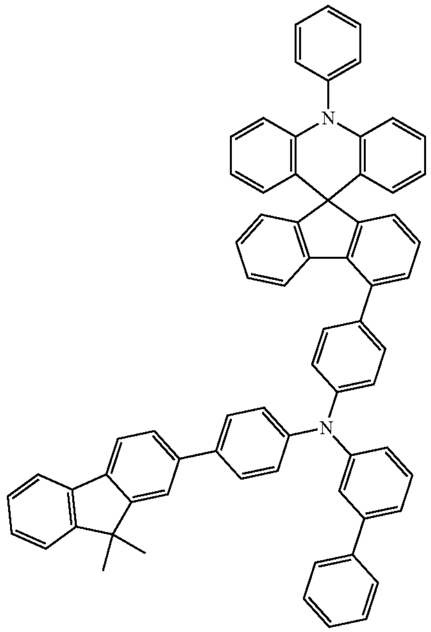
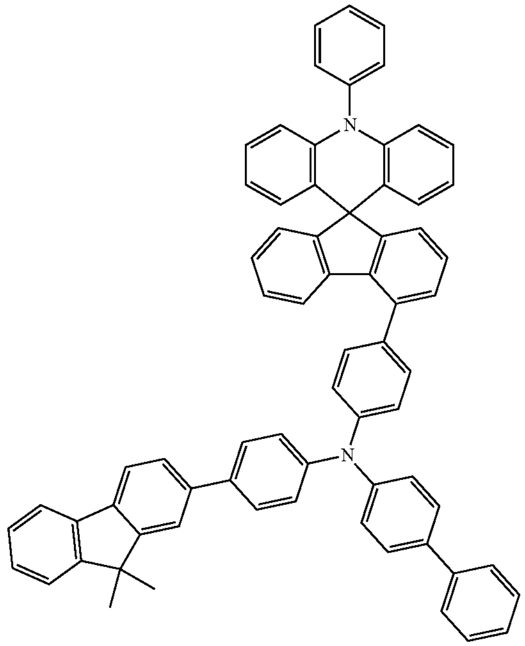
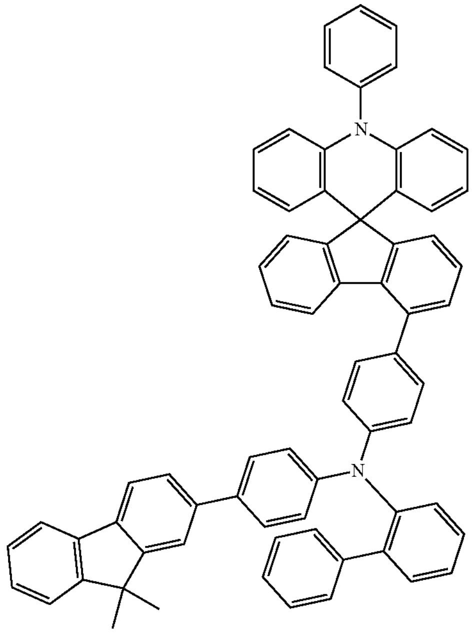

-continued
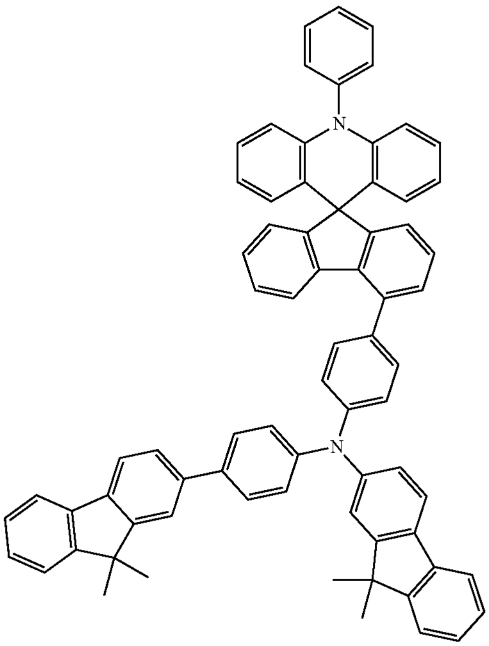
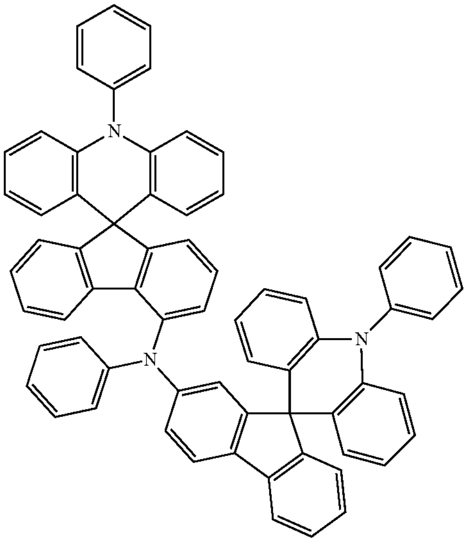
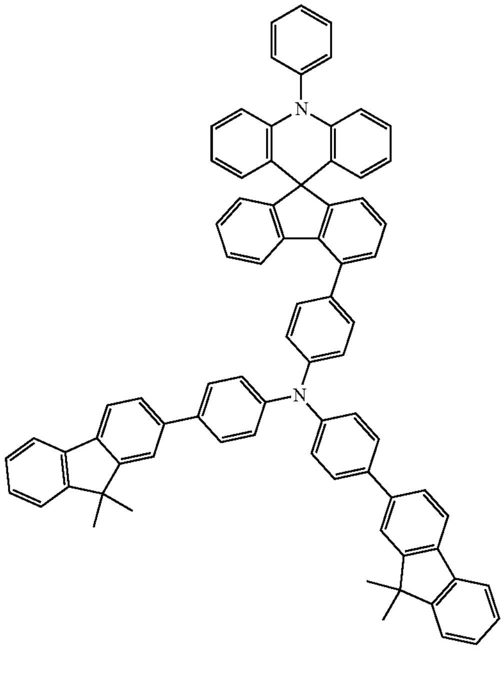
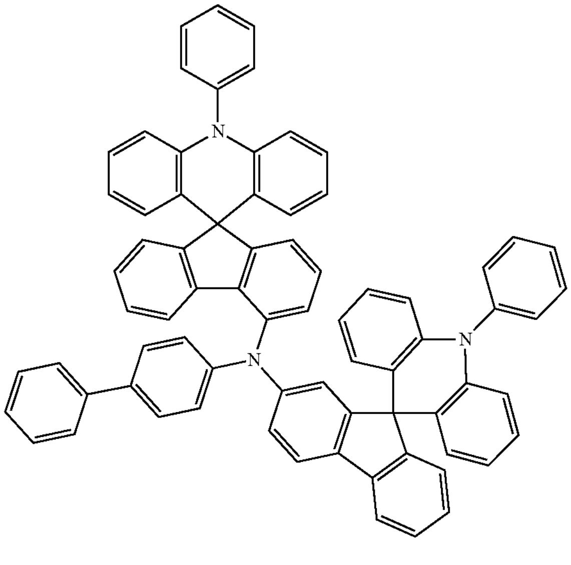
-continued
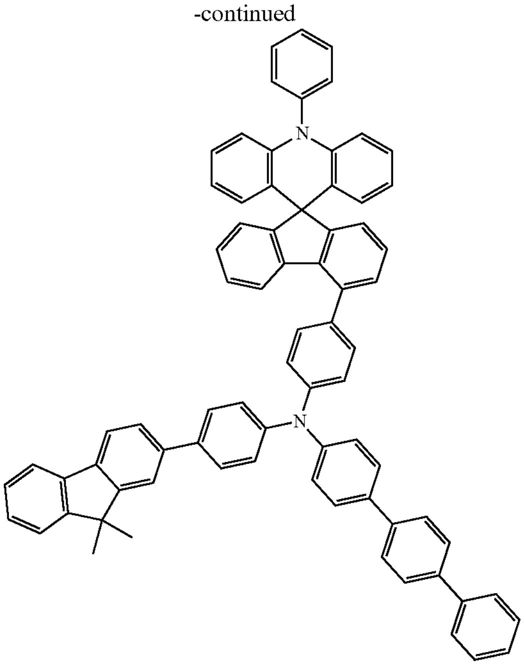

-continued
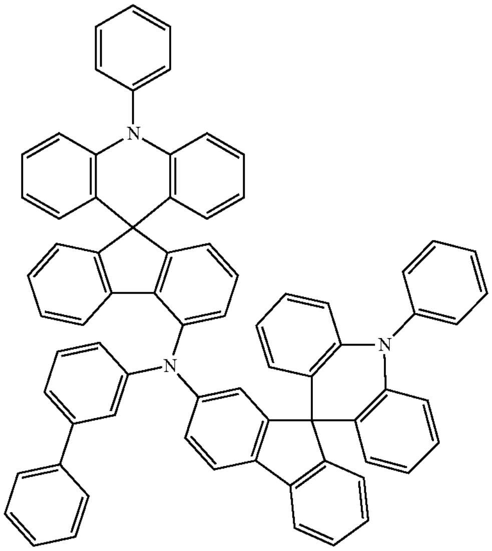
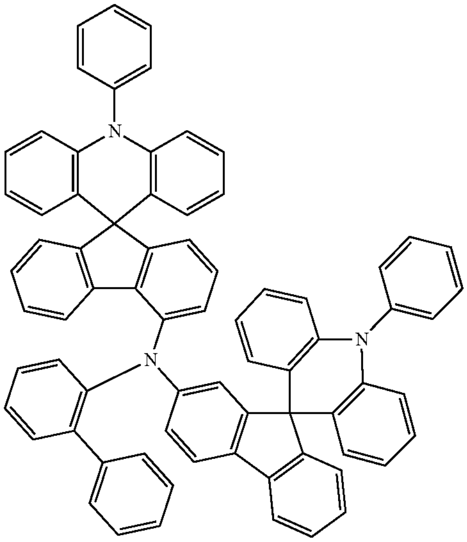
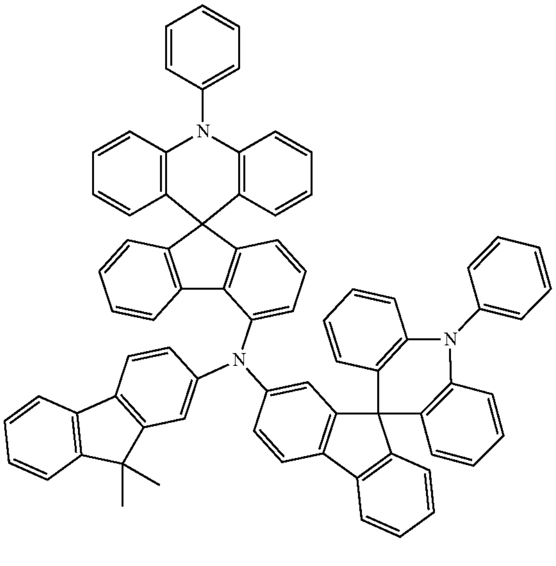
-continued
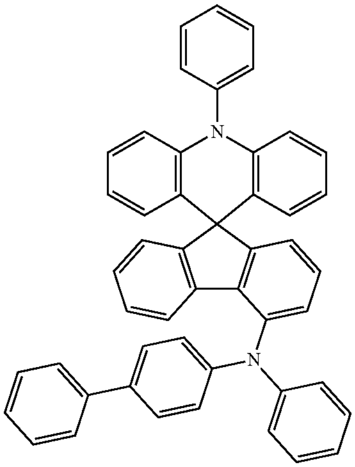
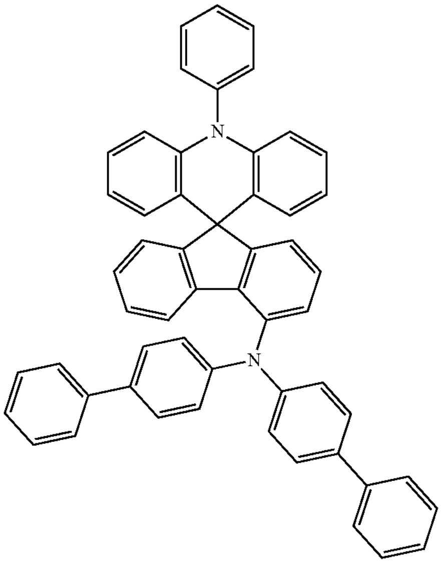
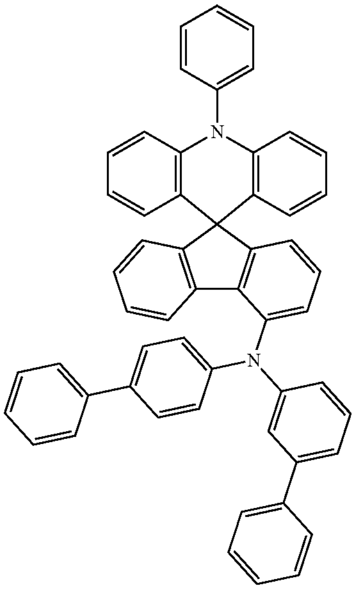

-continued
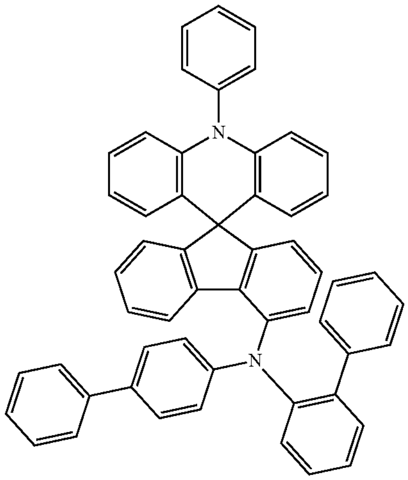
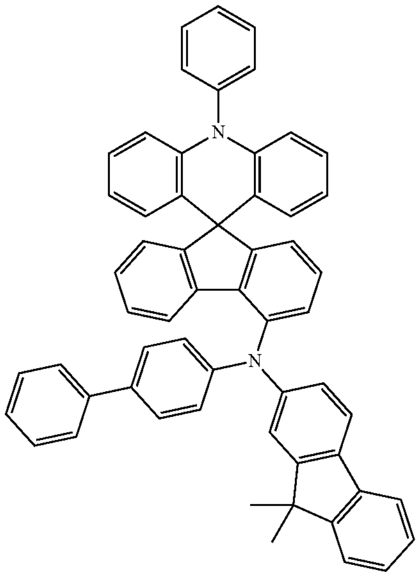
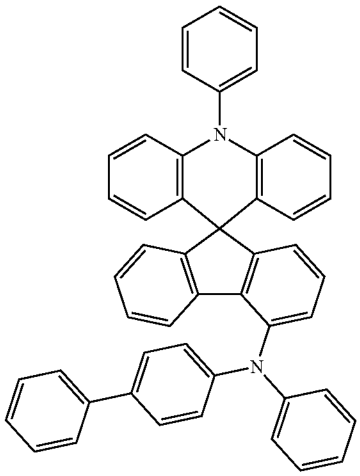
-continued
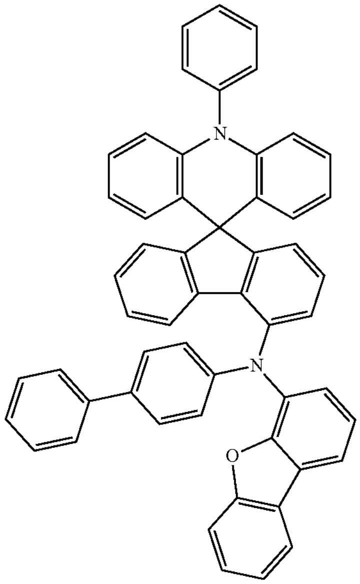
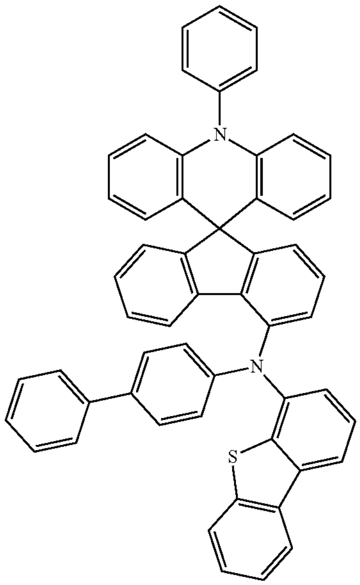

-continued
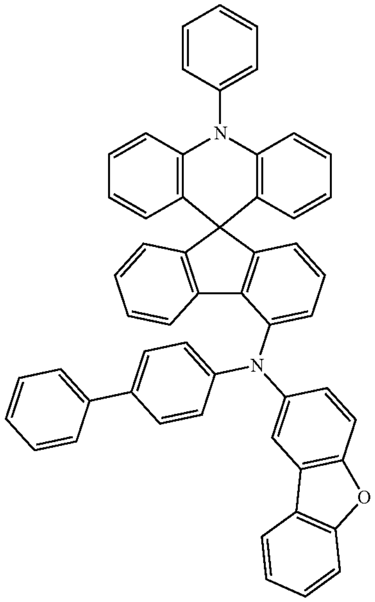
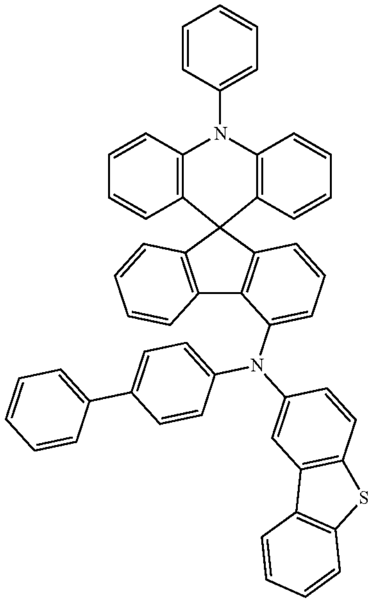
-continued
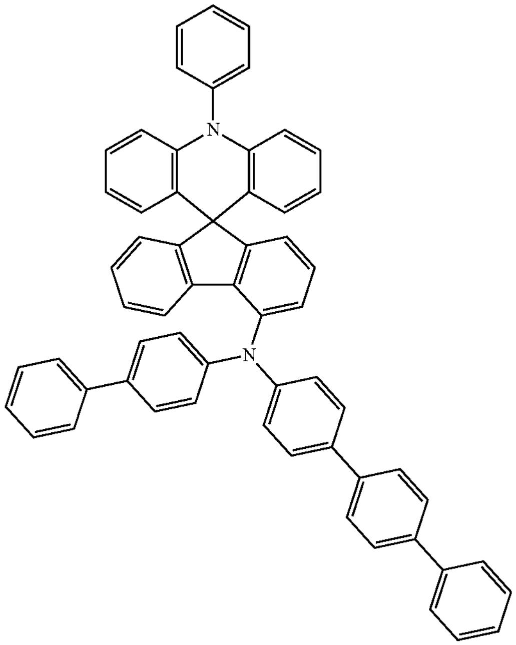
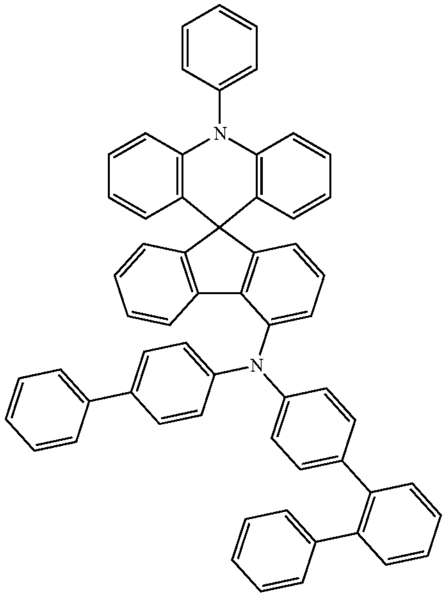

-continued
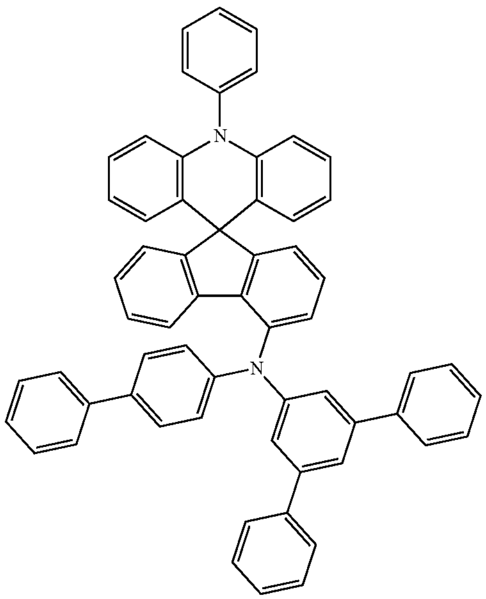
-continued
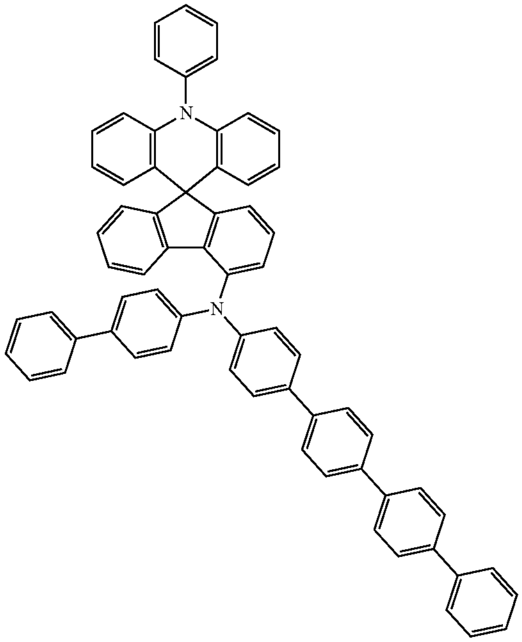
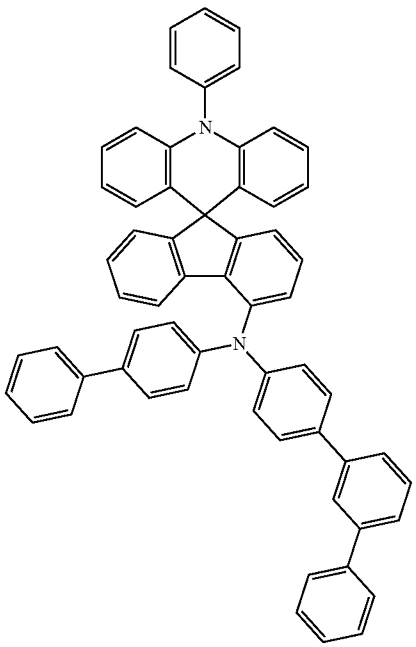
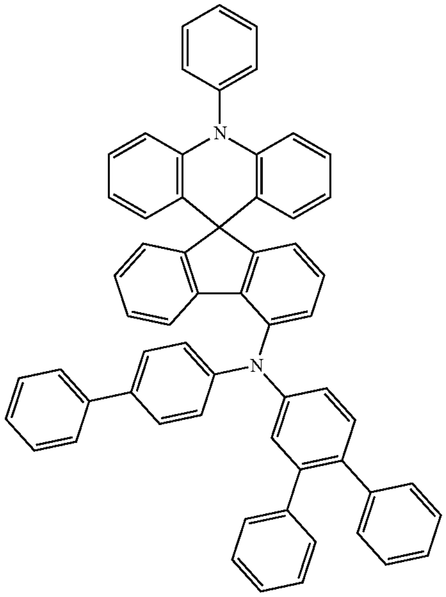

-continued
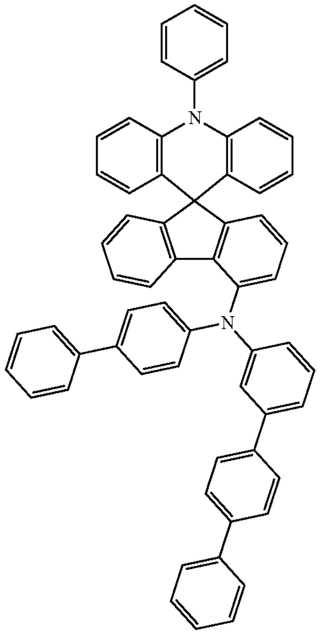
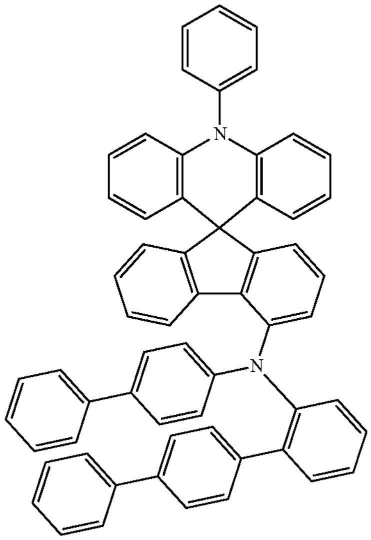
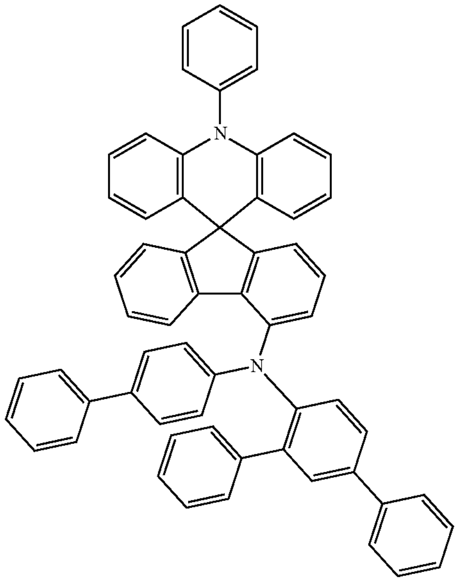
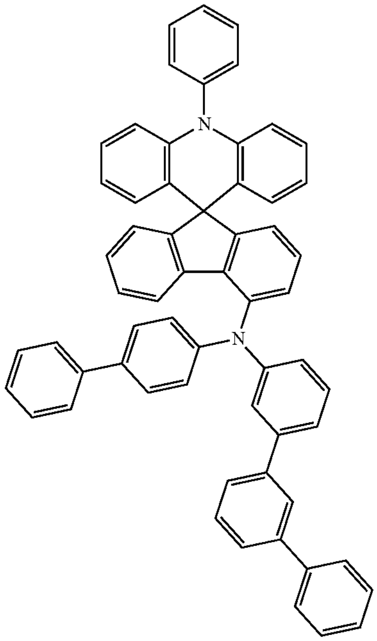

-continued
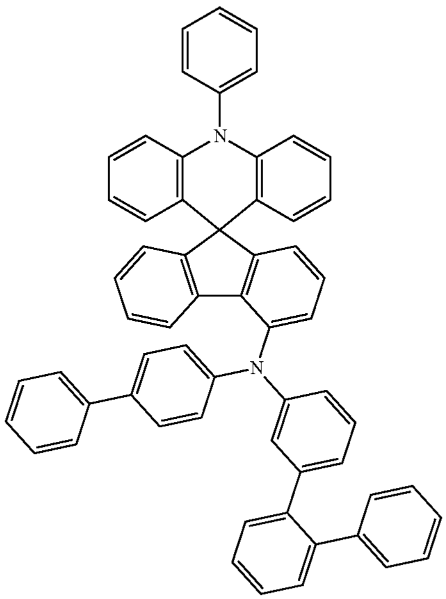
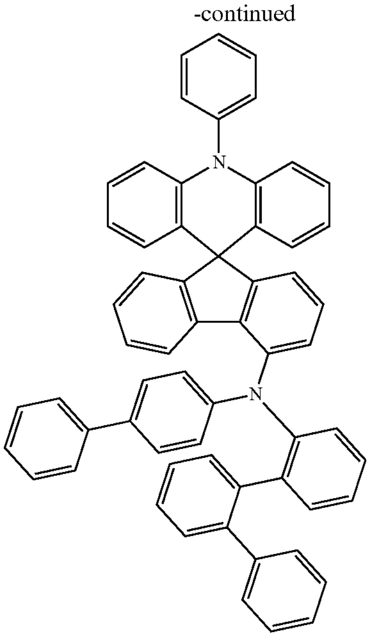
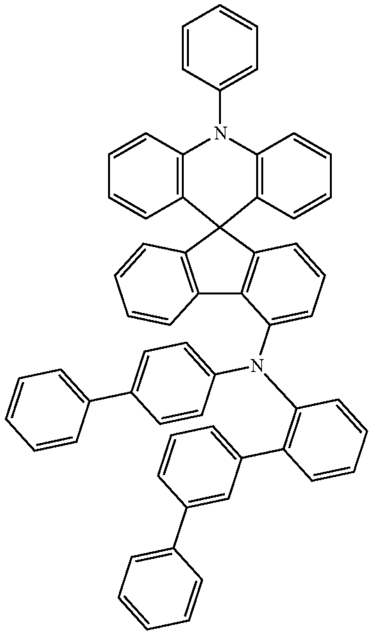
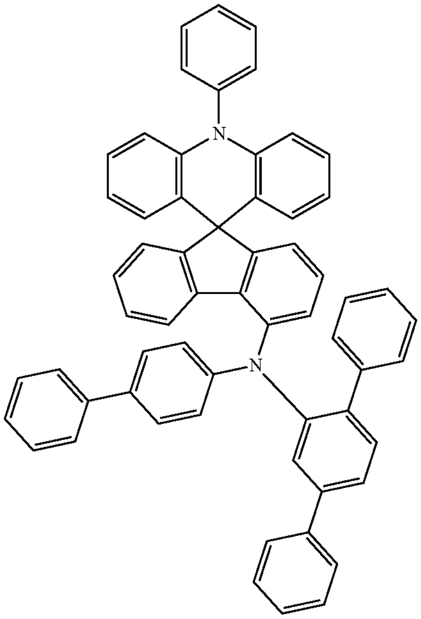

-continued
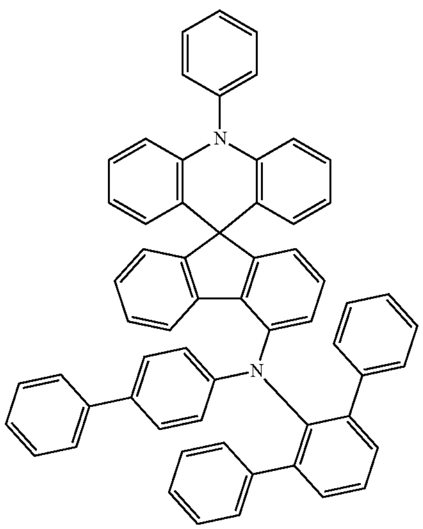
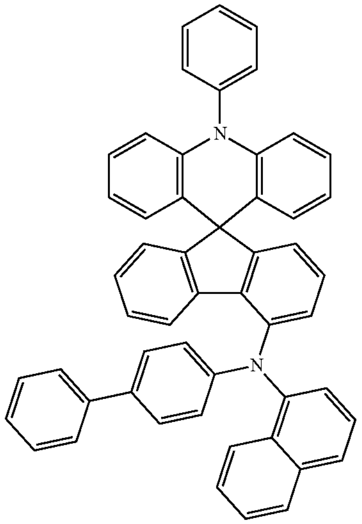
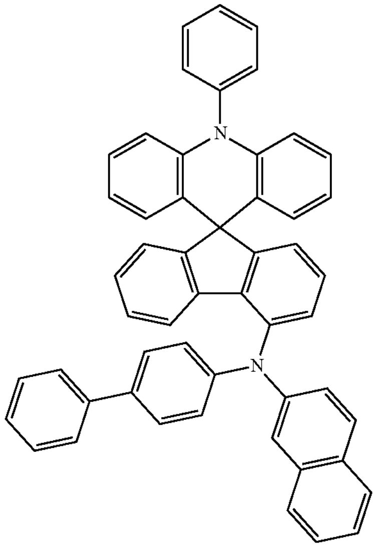
-continued
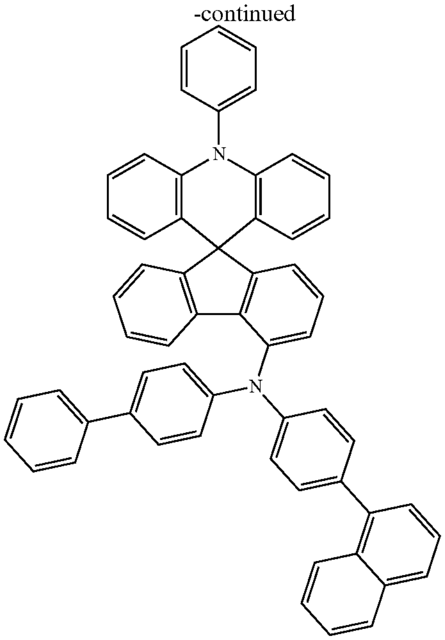
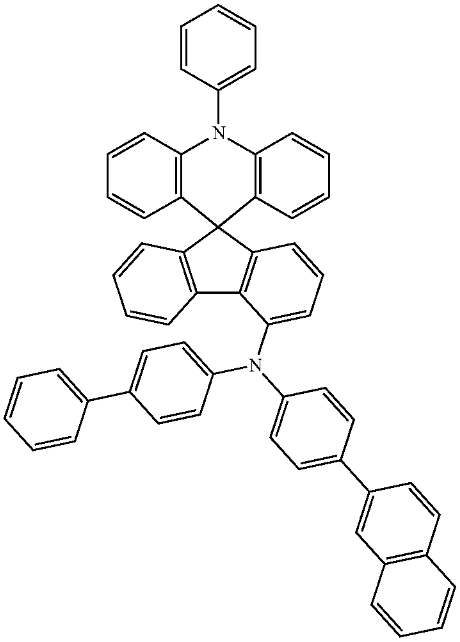

-continued
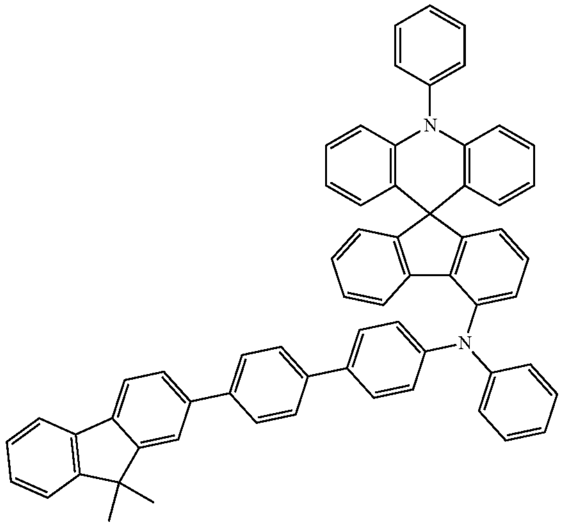
-continued
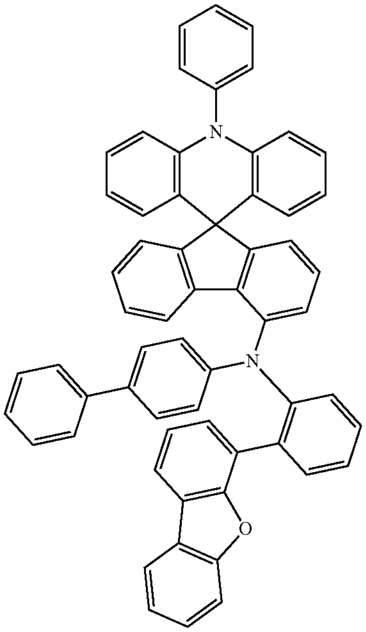
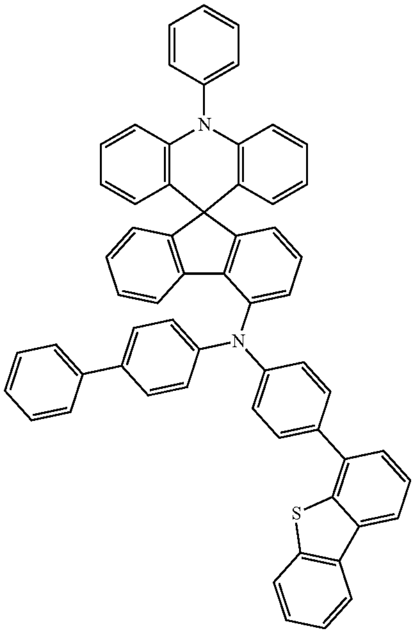
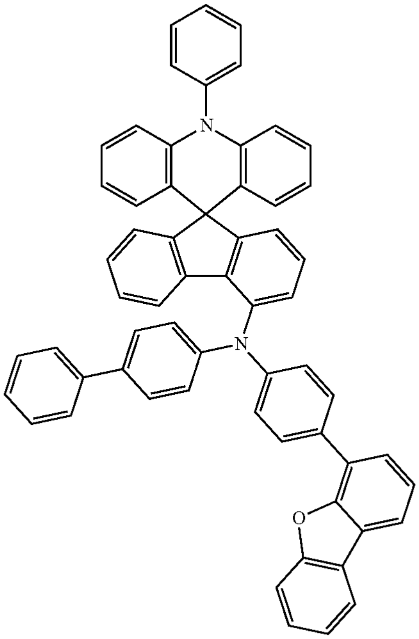

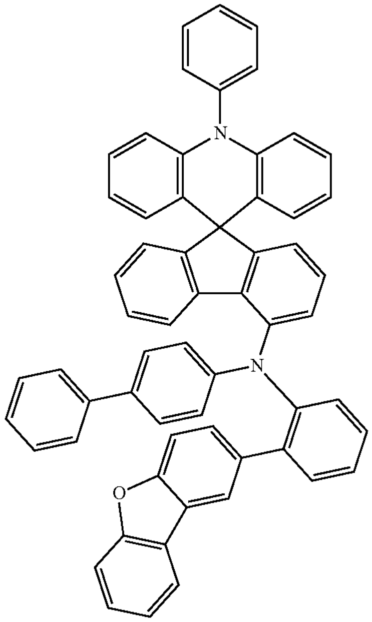
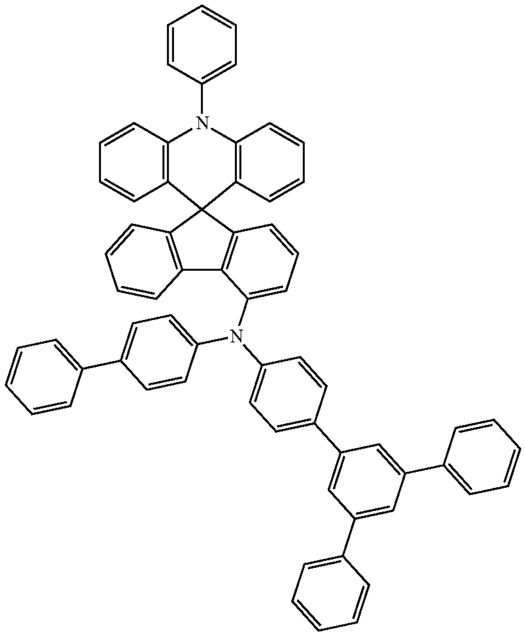
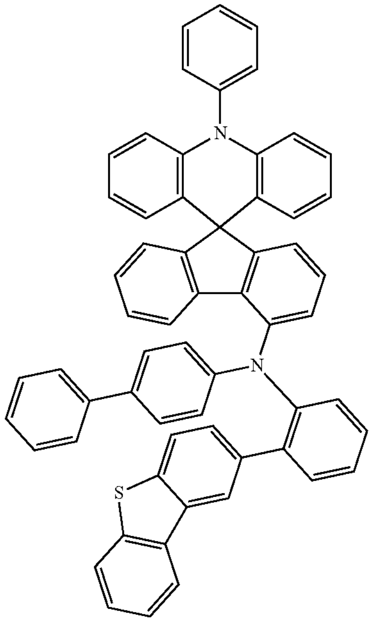
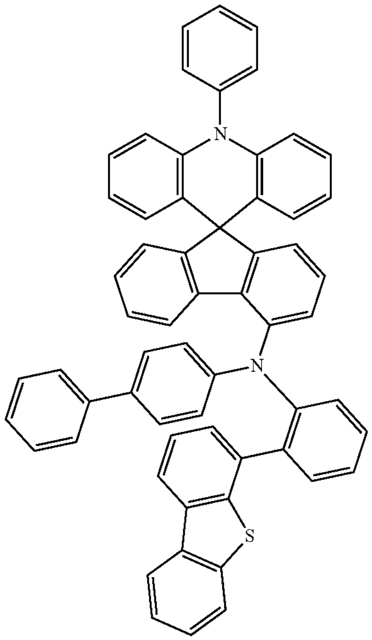

-continued
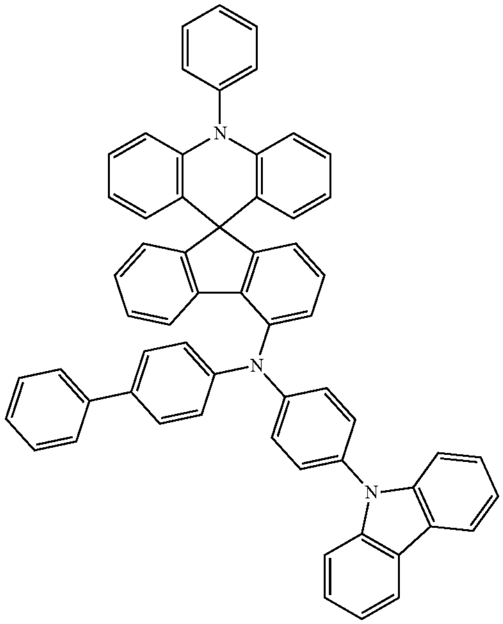
-continued
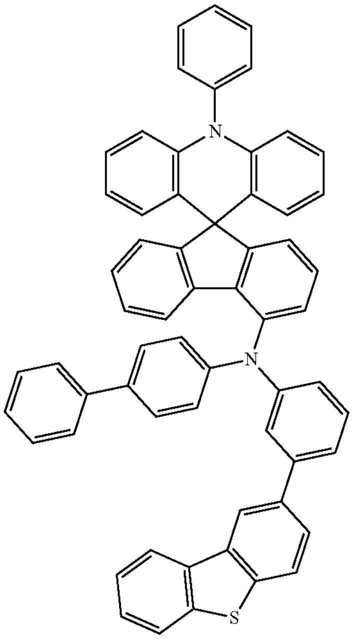
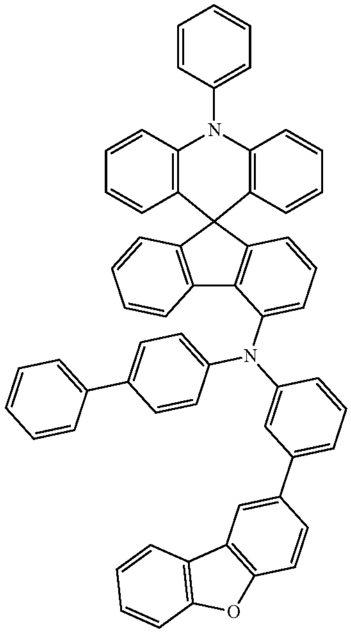
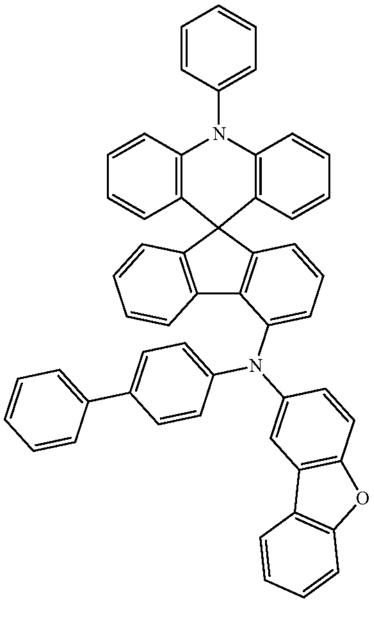

-continued
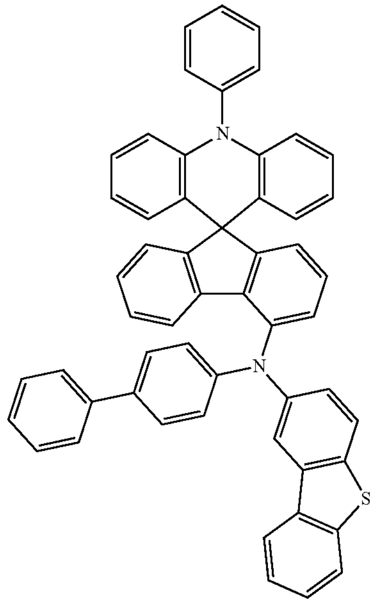
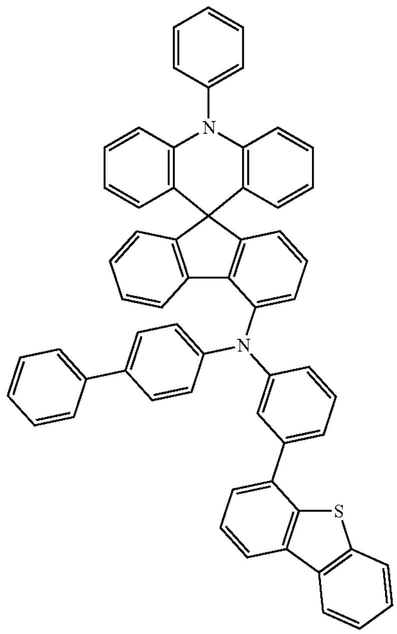
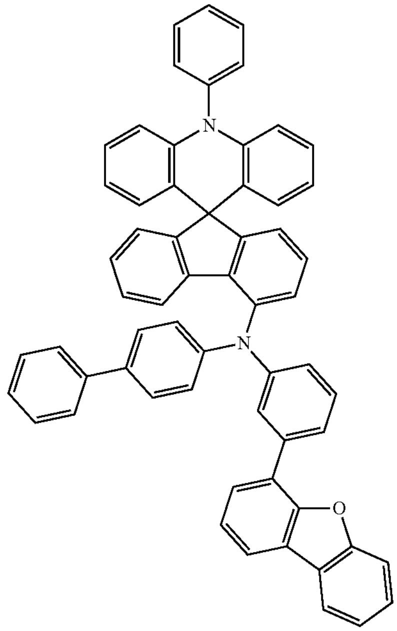
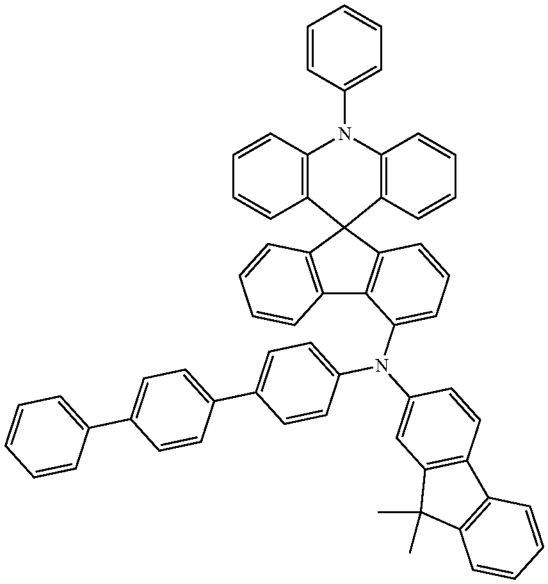

-continued
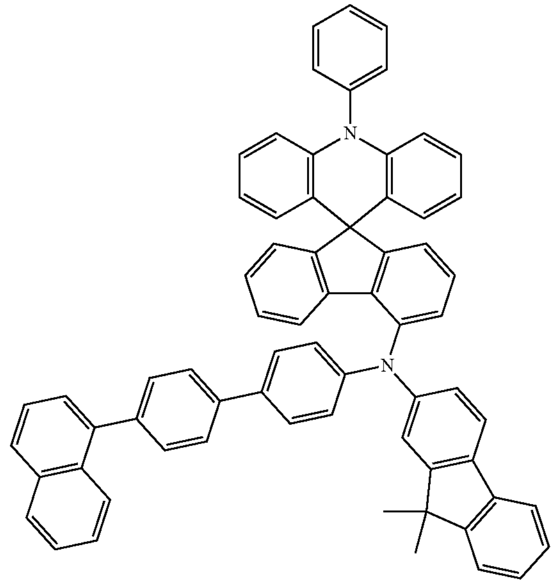
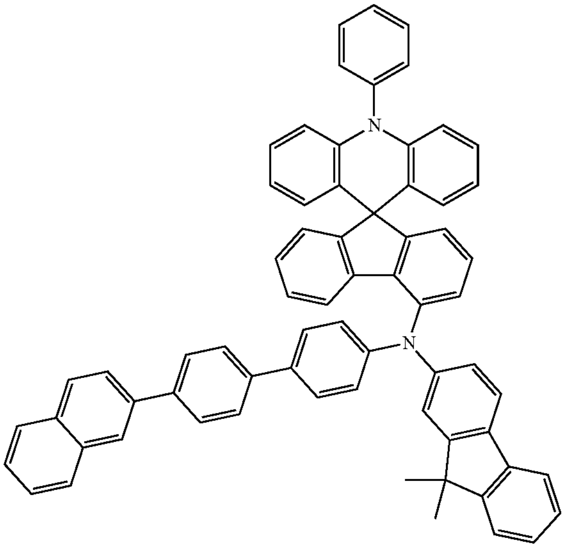
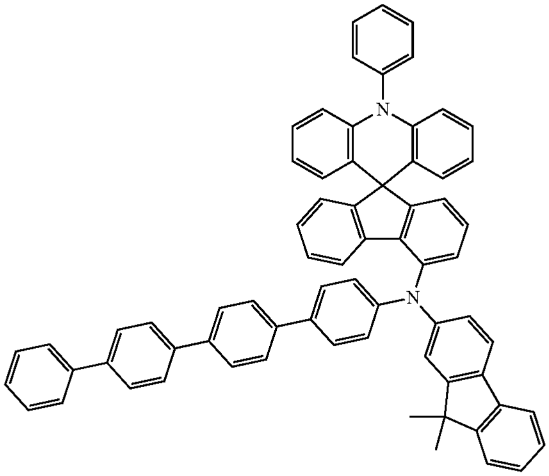
-continued
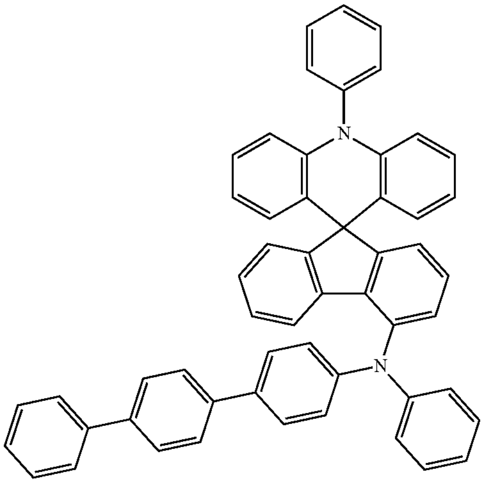
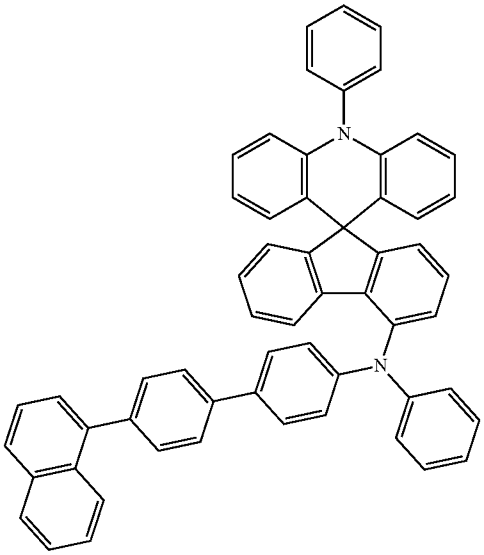
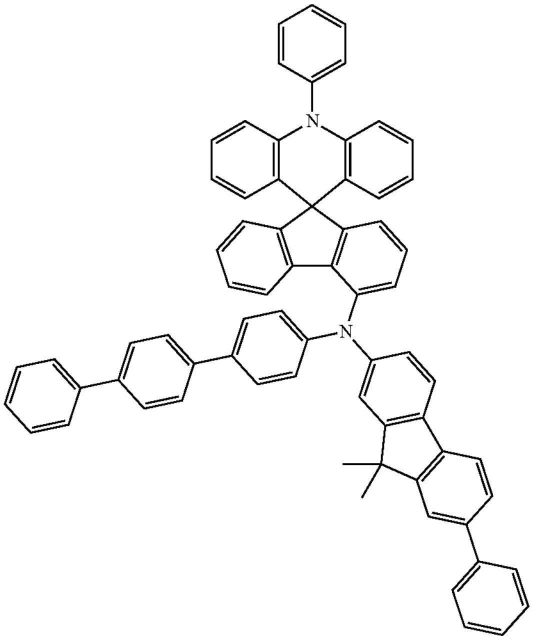

-continued
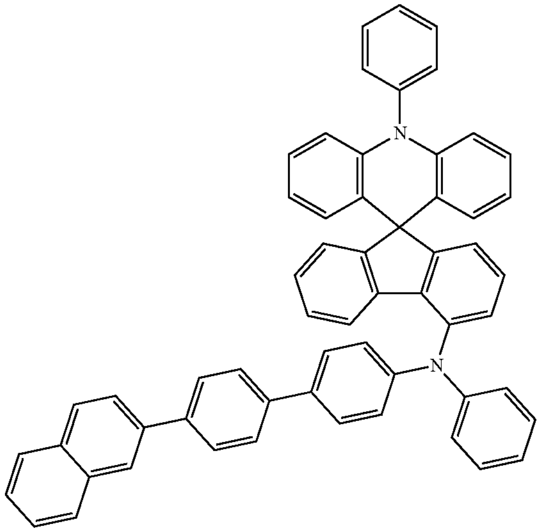
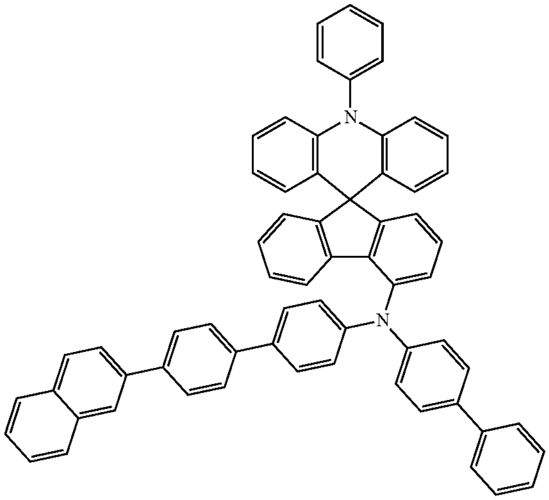
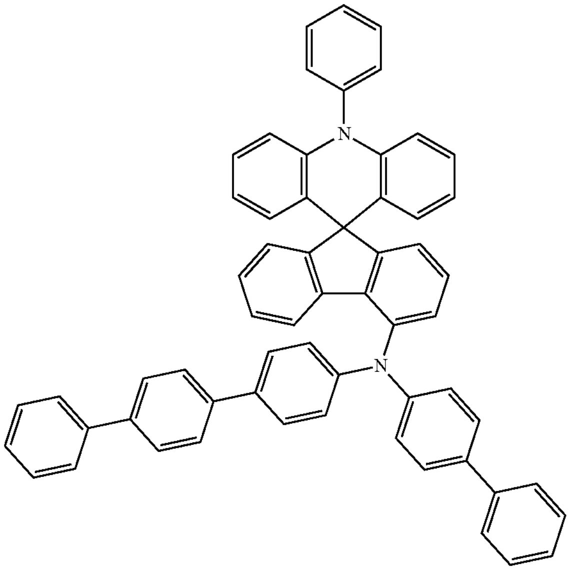
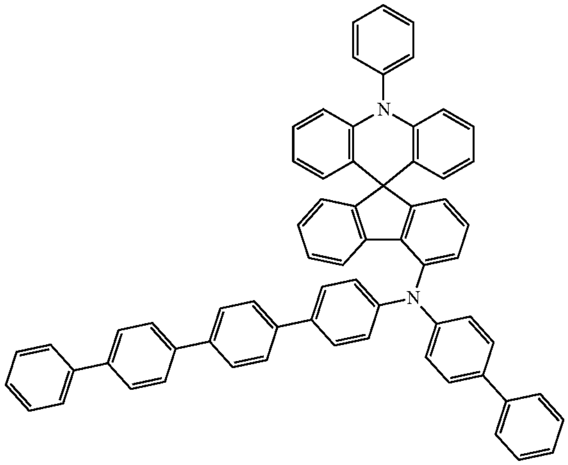
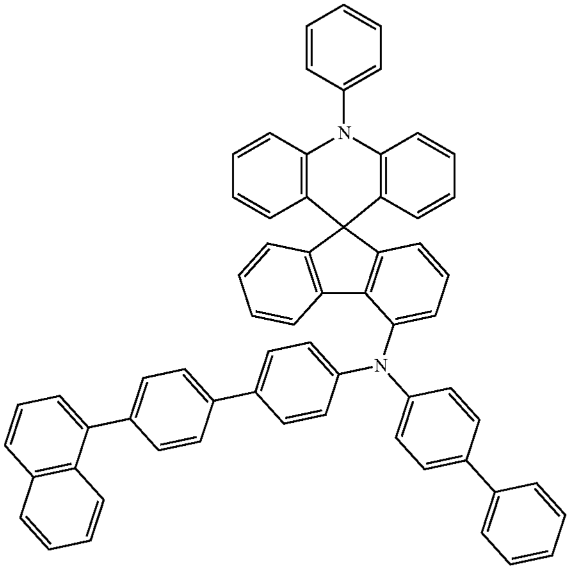
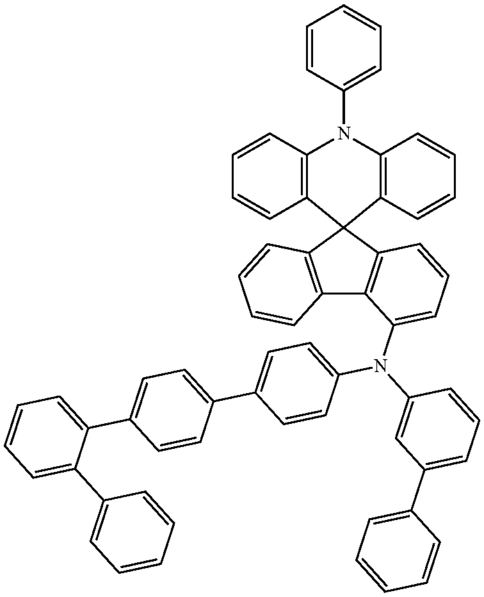
-continued -continued
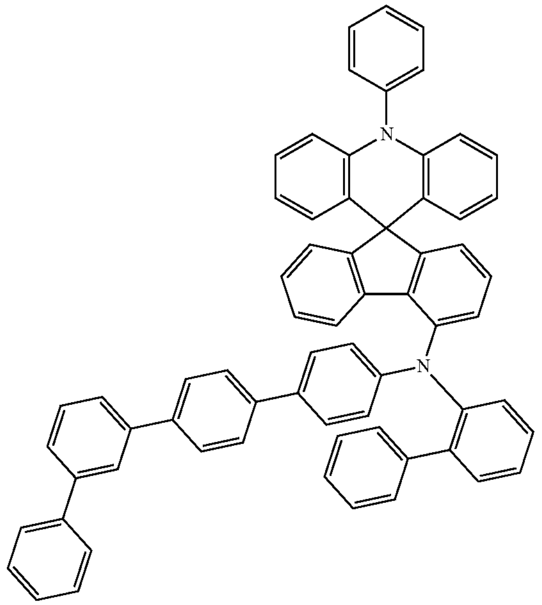
-continued
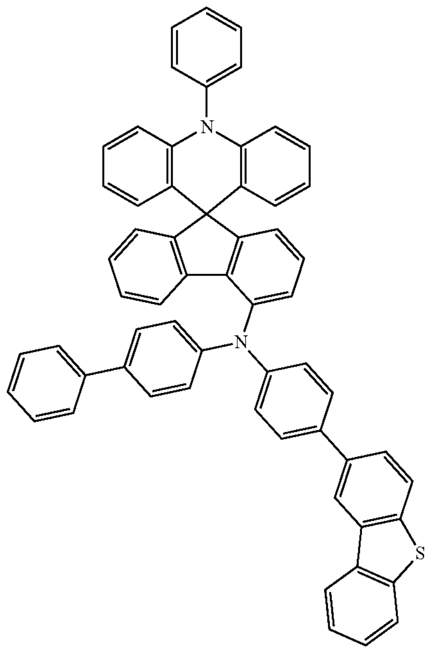
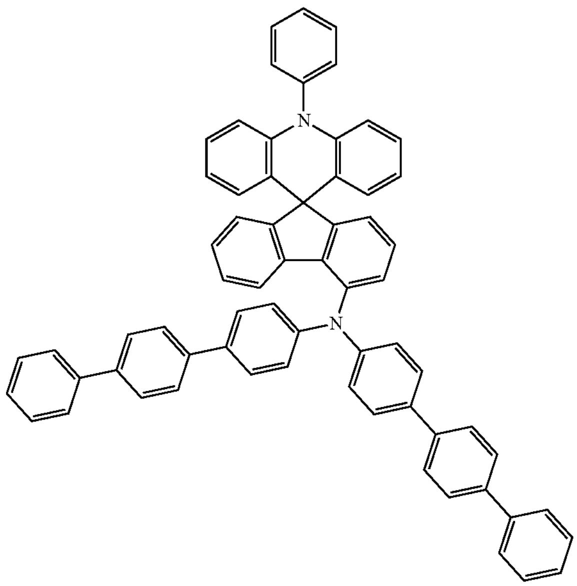
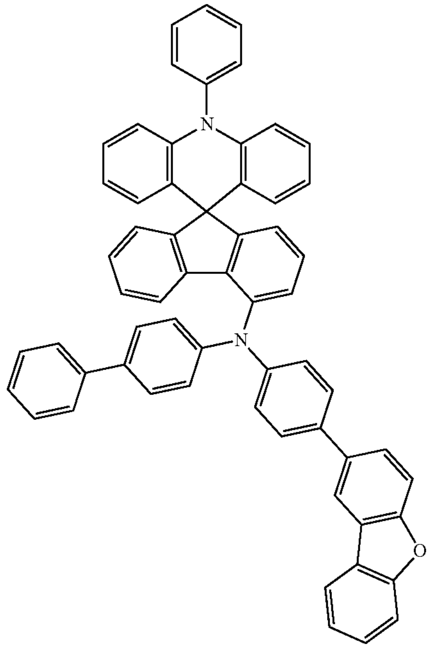

-continued
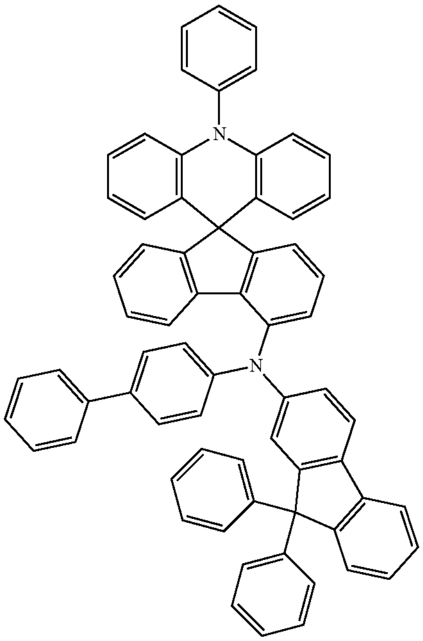
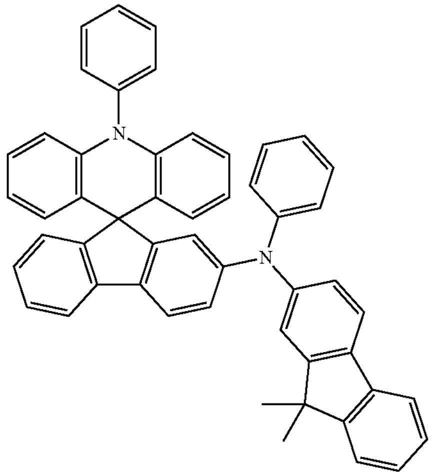
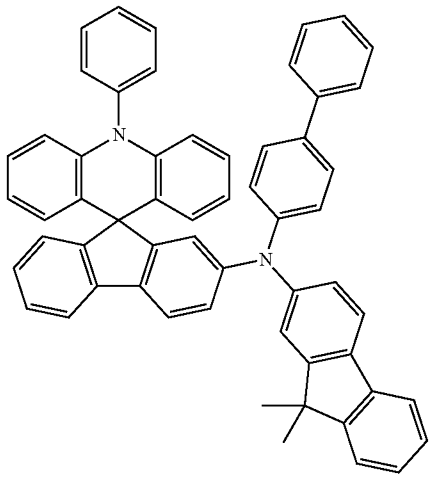
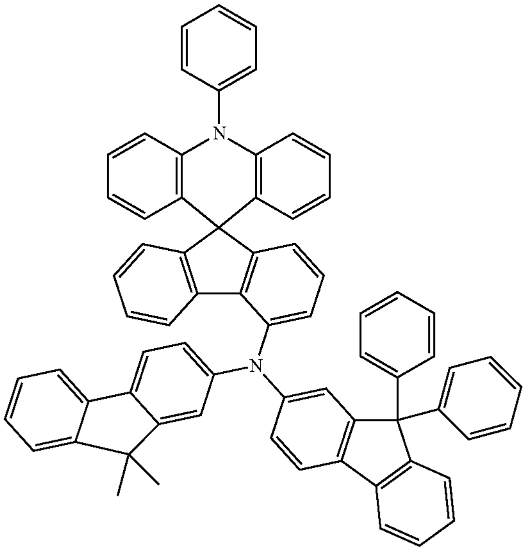
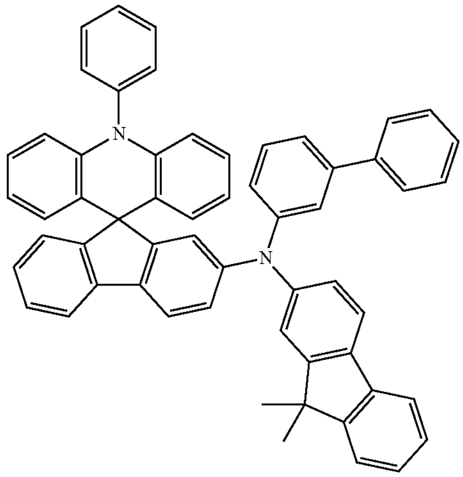

-continued
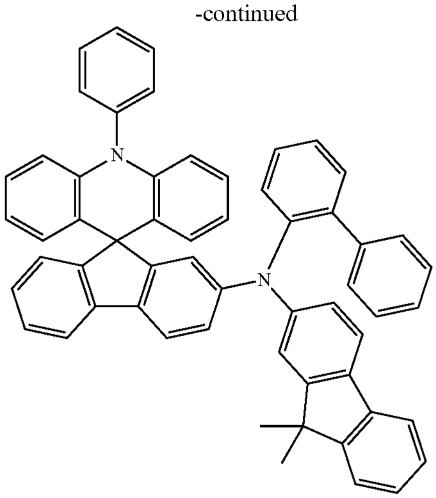
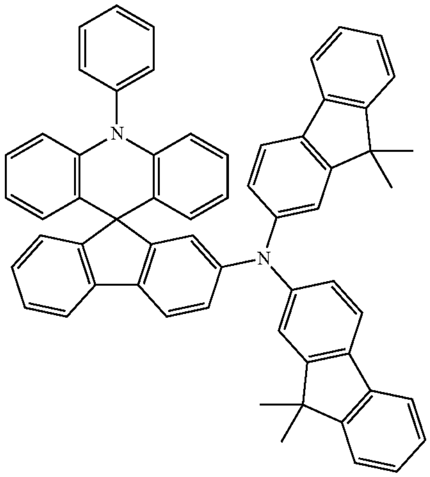
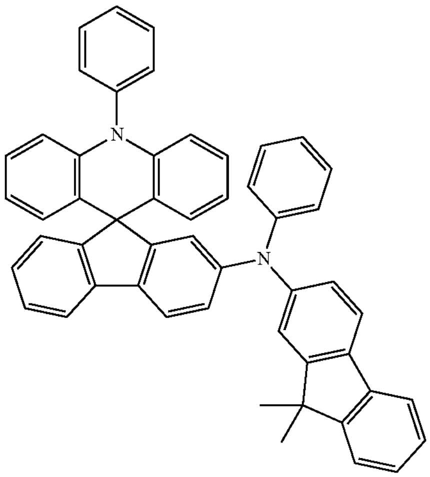
-continued
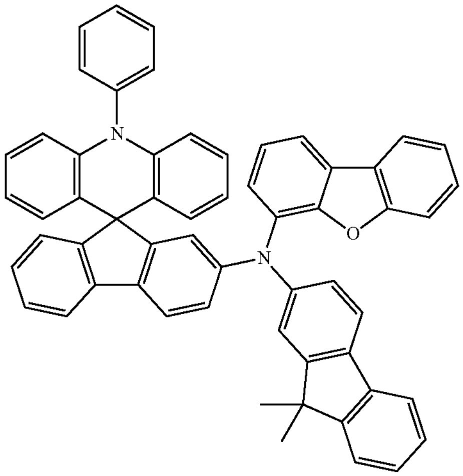
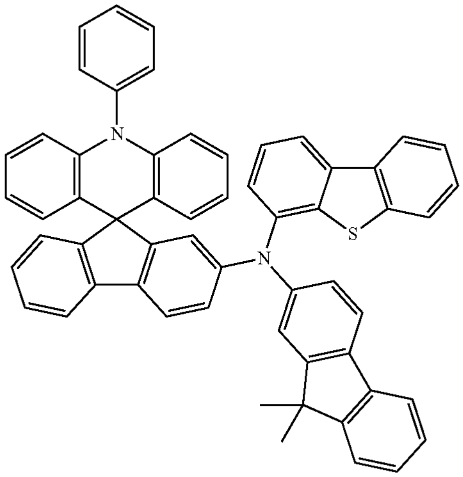
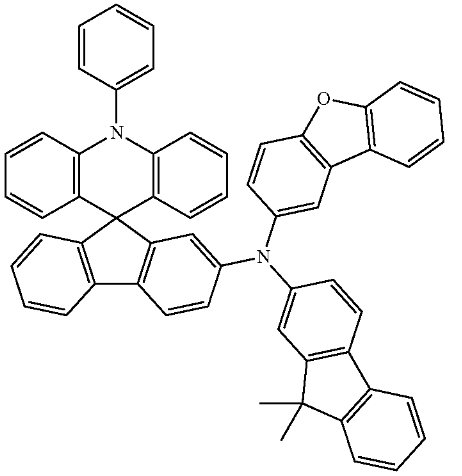

-continued
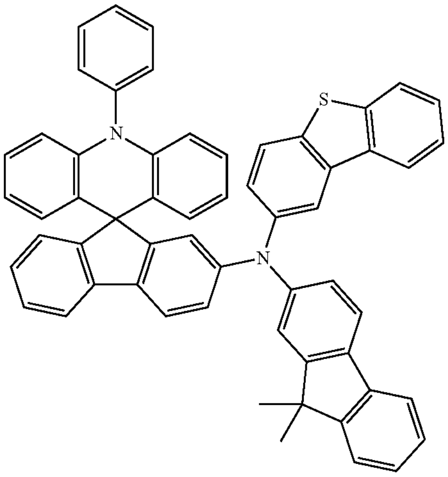
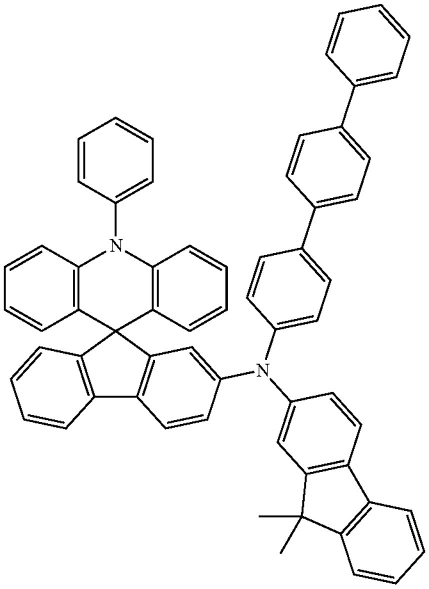
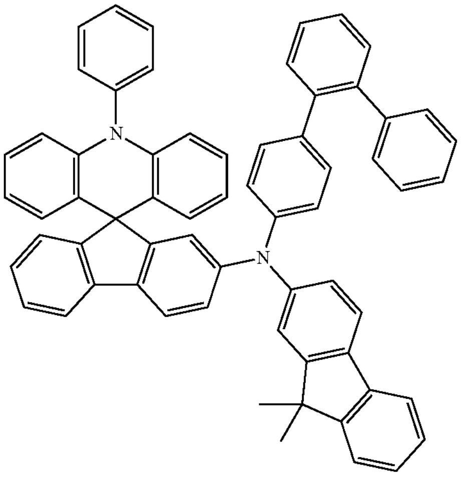
-continued
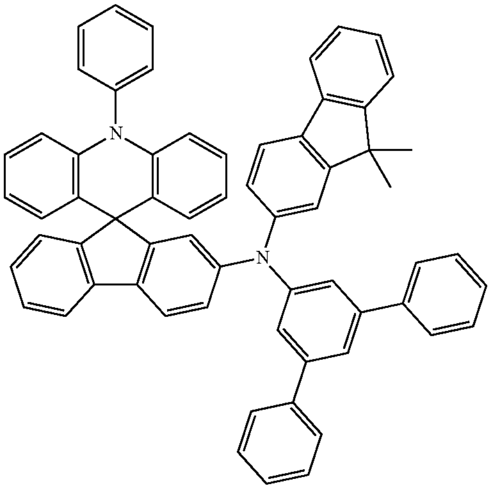
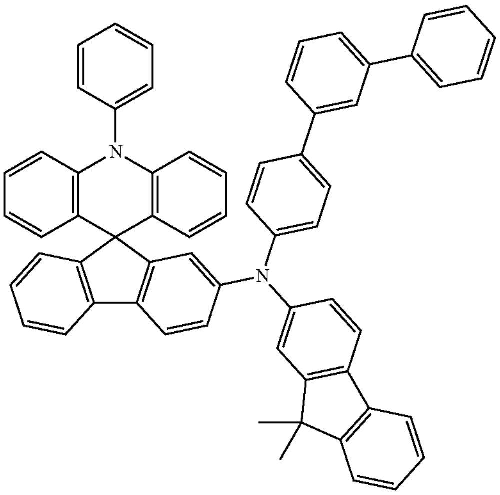
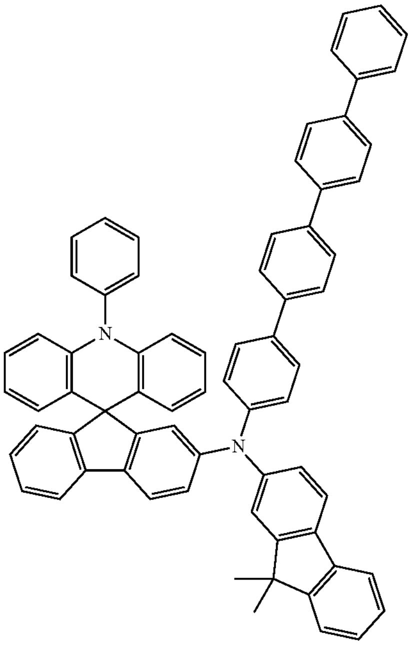

-continued
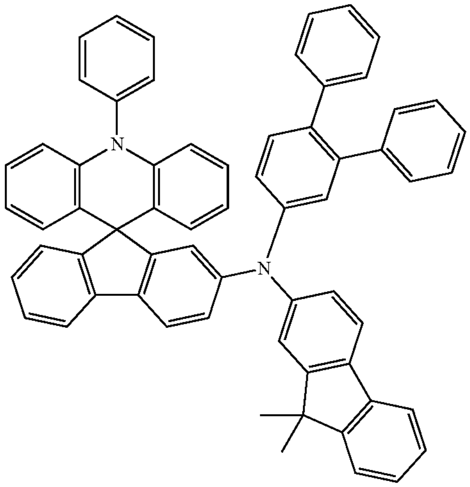 [SMILES: CC1(C)c2ccccc2-c2ccc(N(c3ccc(-c4ccccc4)c(-c4ccccc4)c3)c3ccc4c(c3)C3(c5ccccc5-4)c4ccccc4N(c4ccccc4)c4ccccc43)cc21]
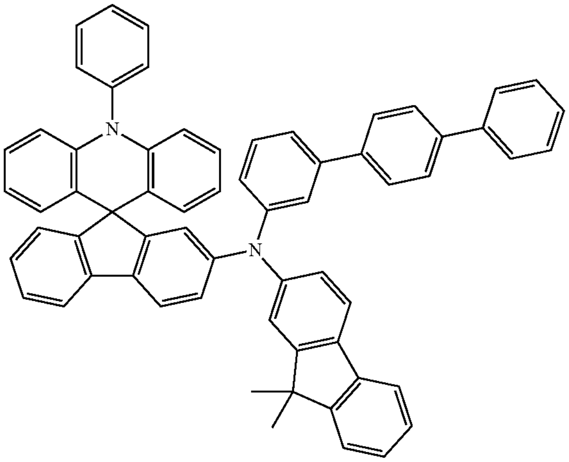
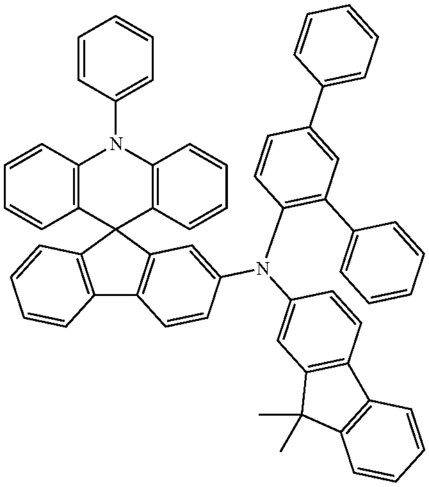
-continued
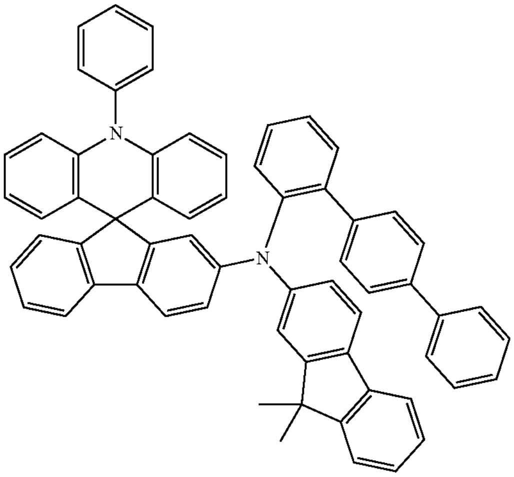
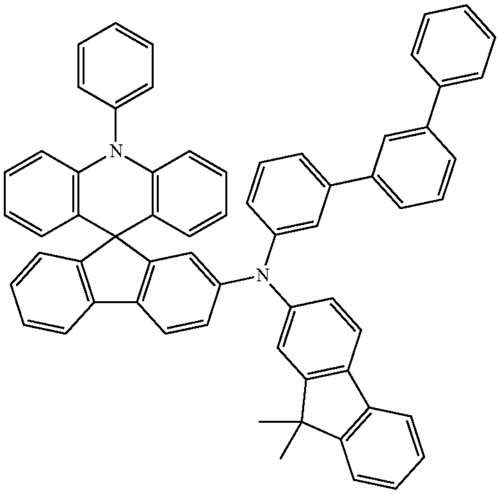
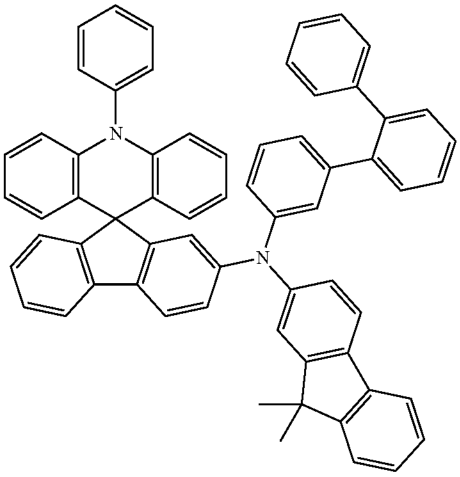

-continued
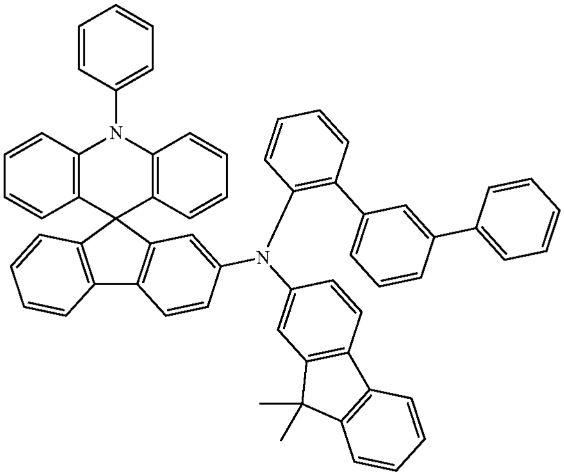
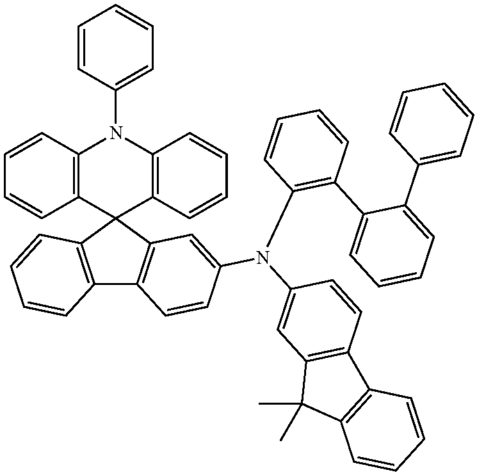
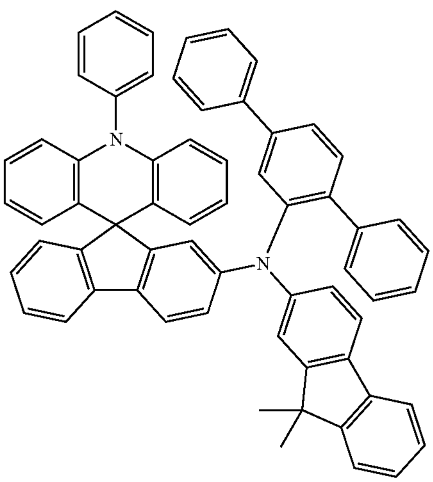
-continued
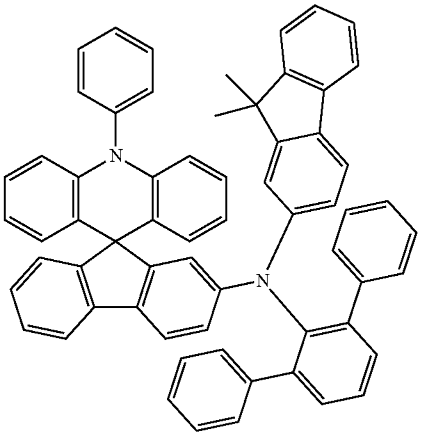
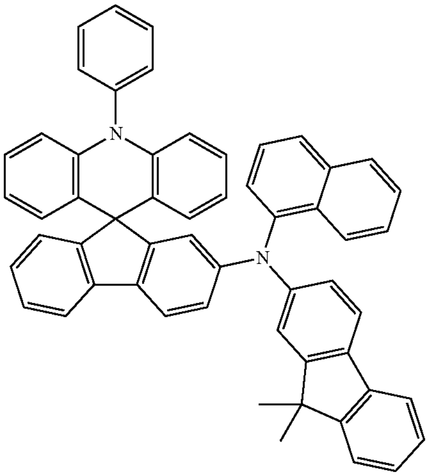
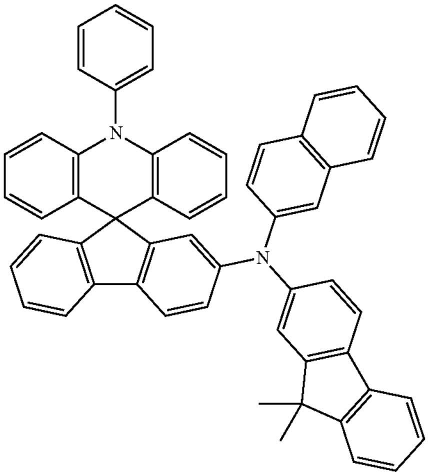

-continued
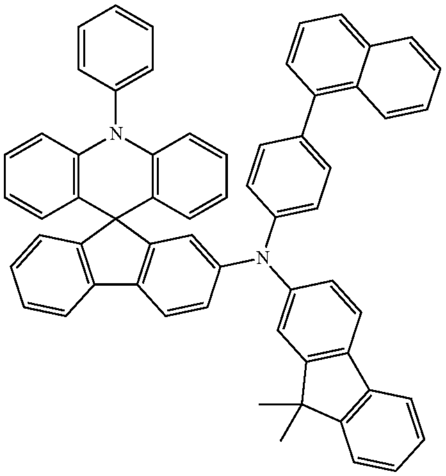
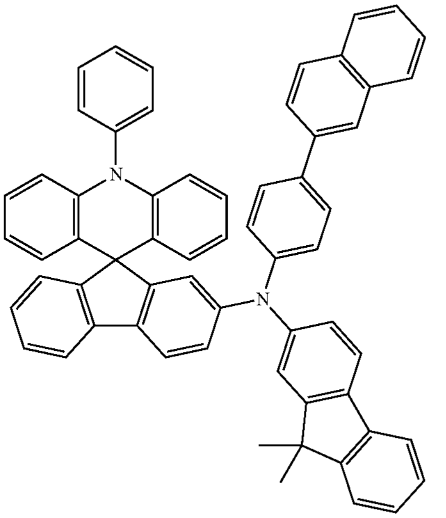
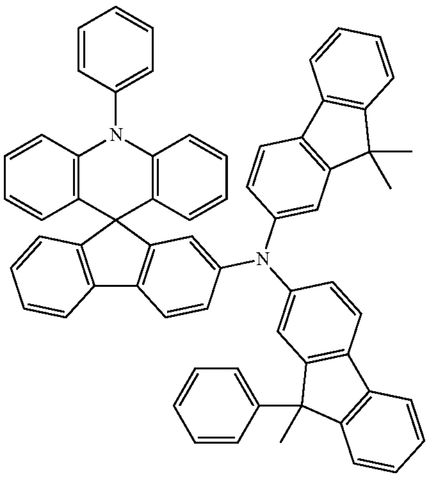
-continued
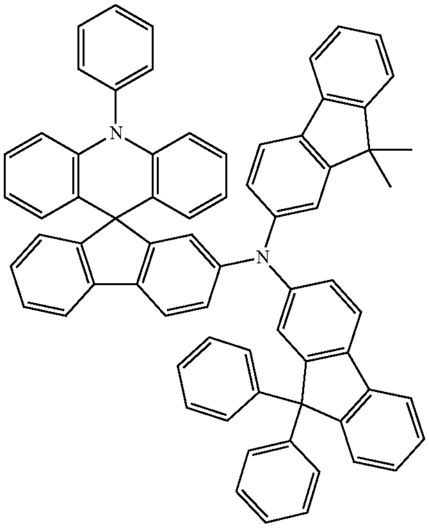
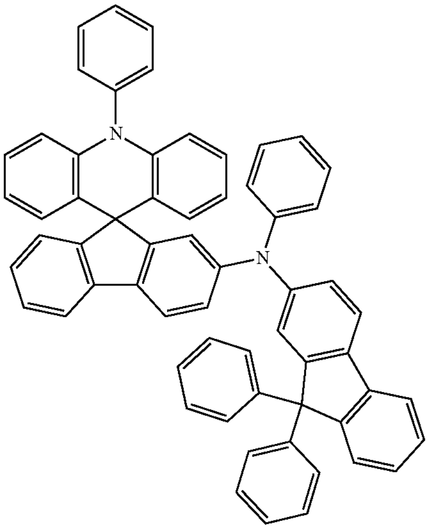
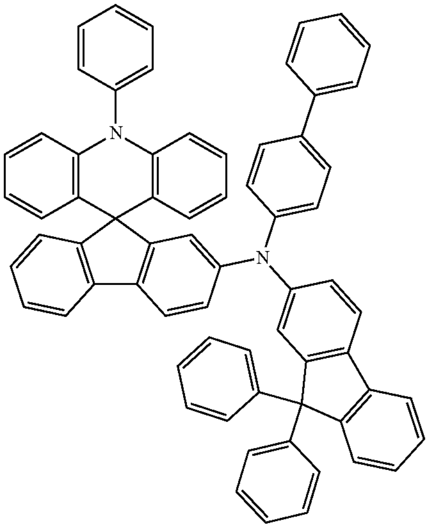

-continued
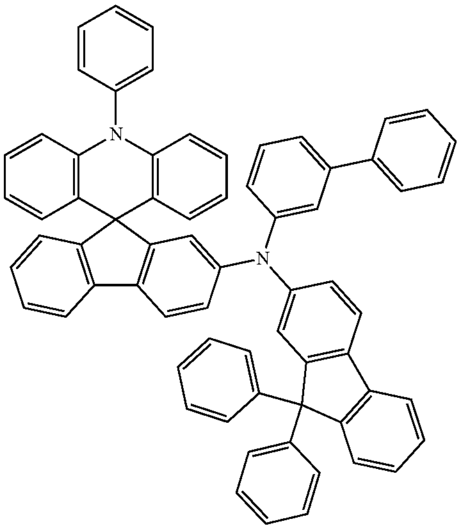
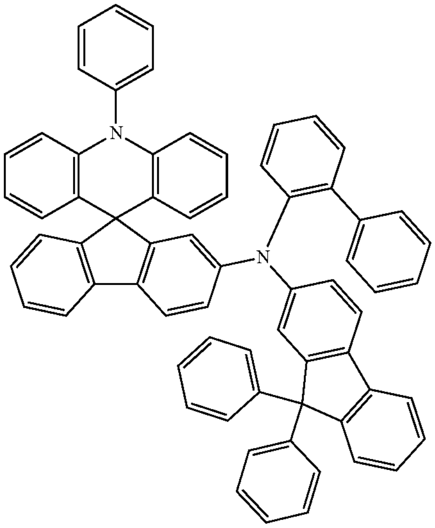
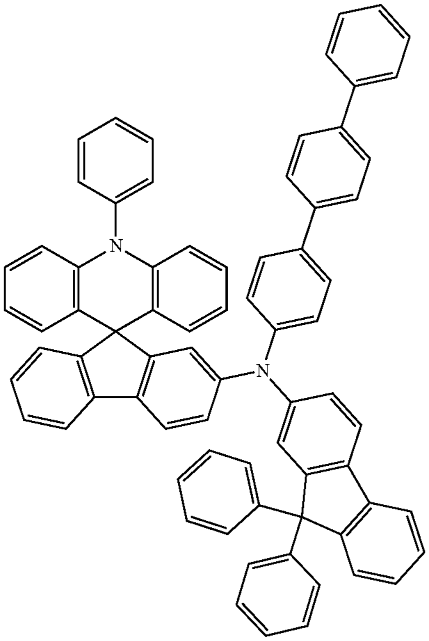
-continued
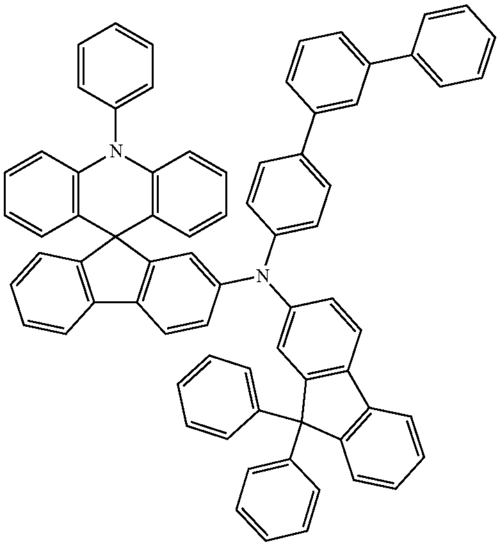
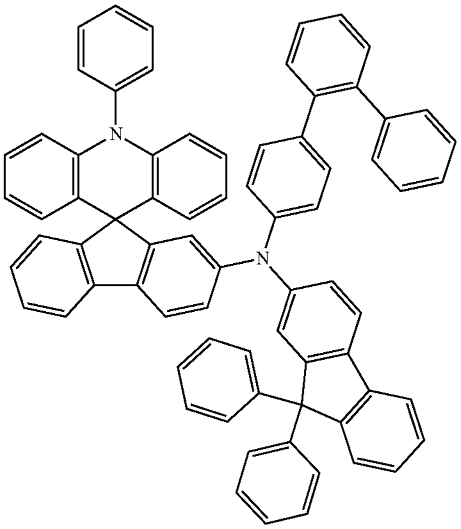
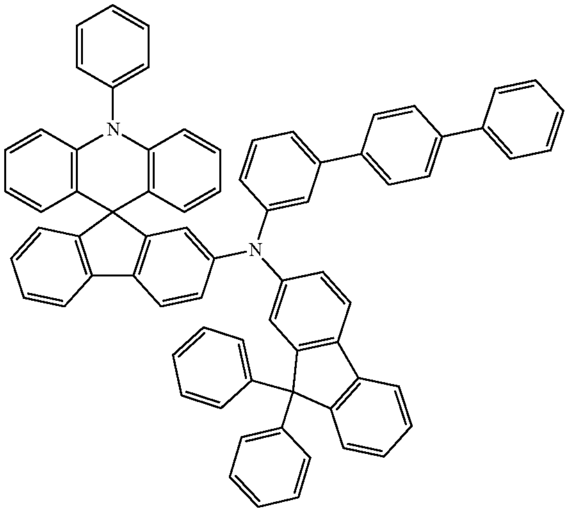

-continued
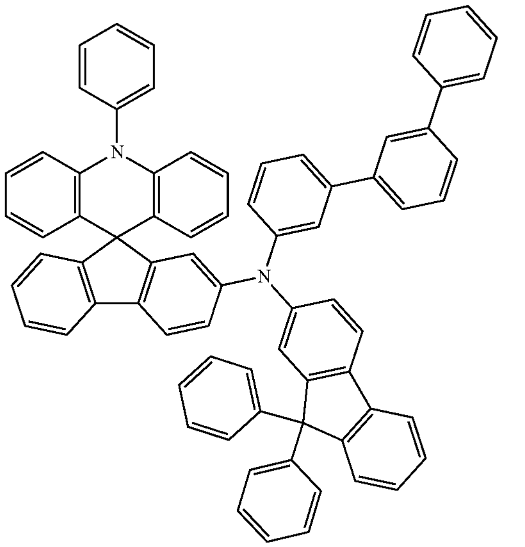
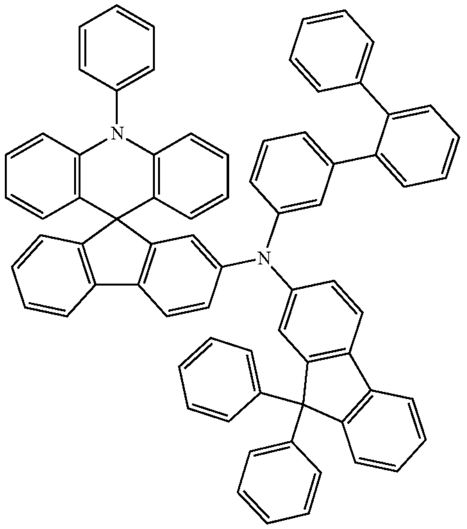
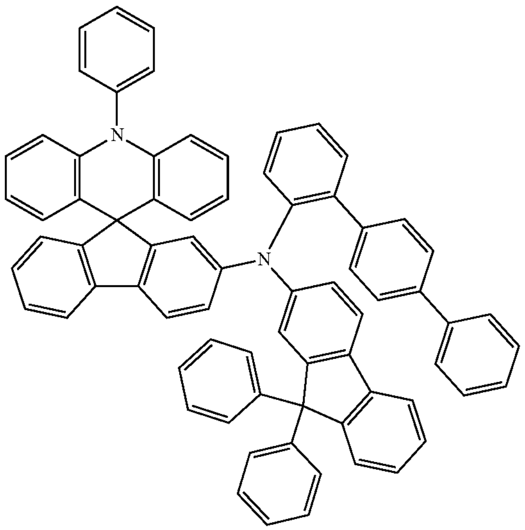
-continued
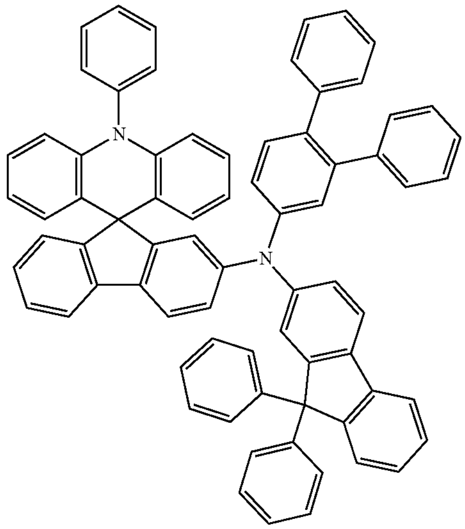
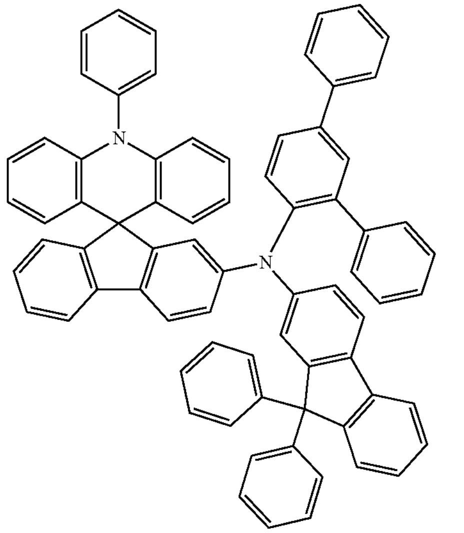
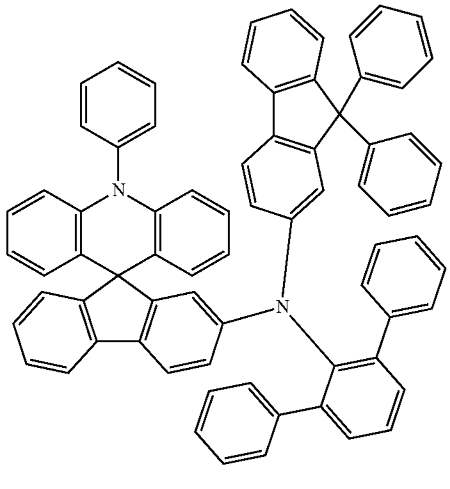

-continued
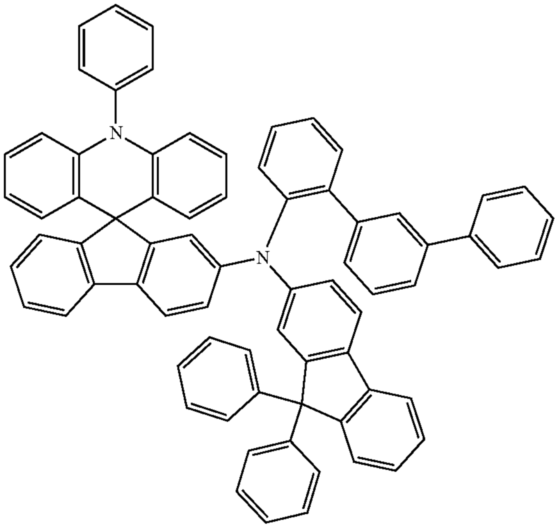
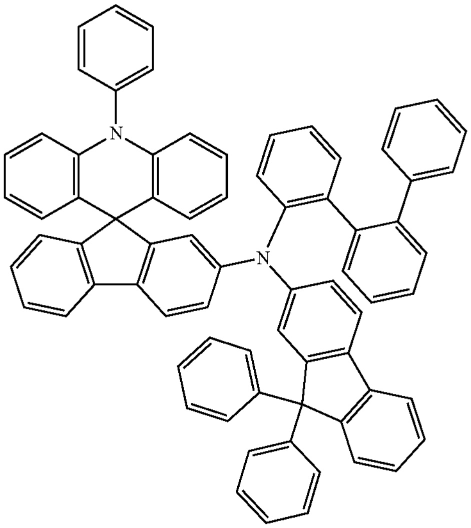
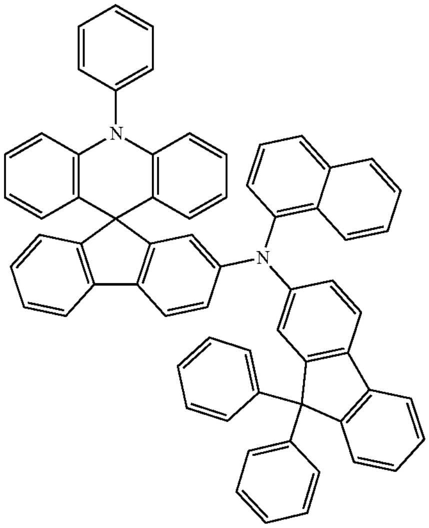
-continued
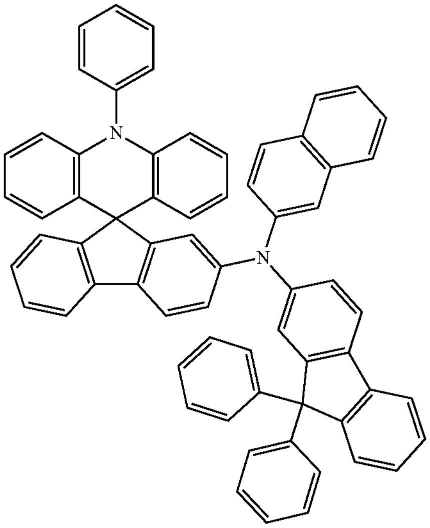
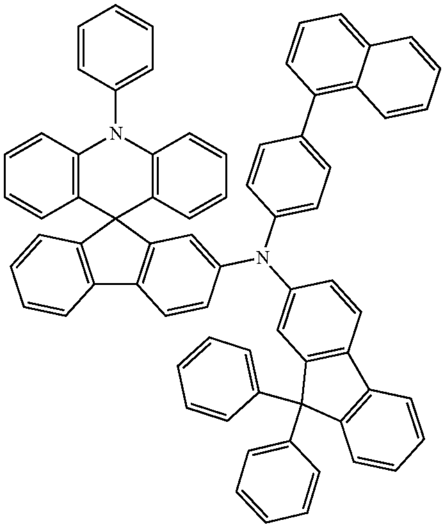
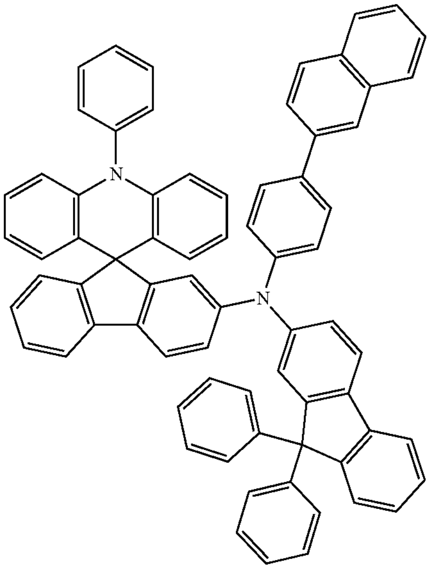

-continued
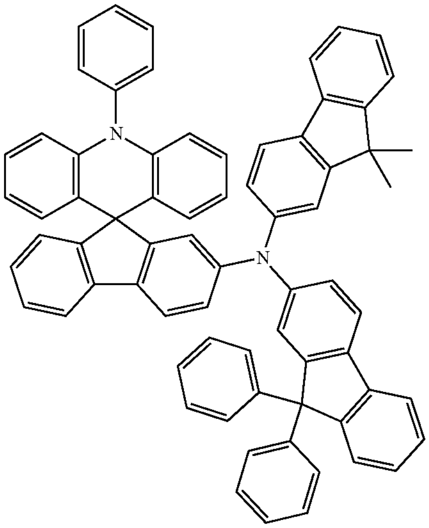
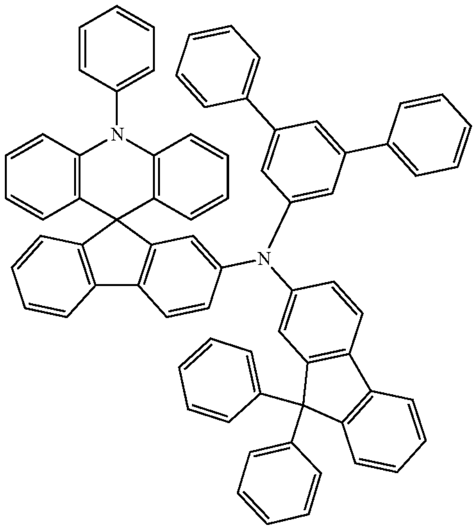
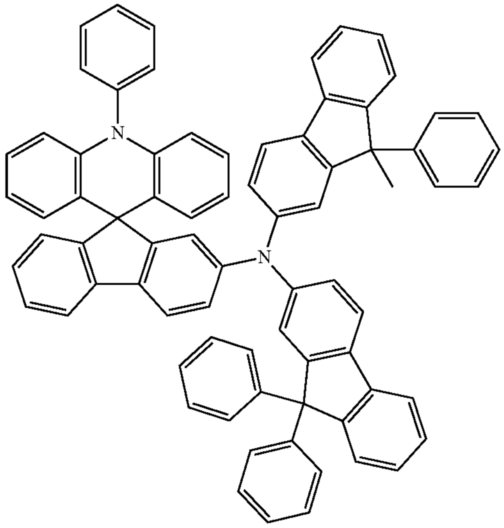
-continued
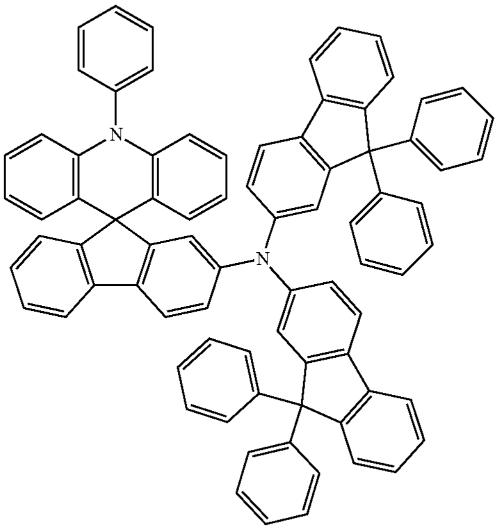
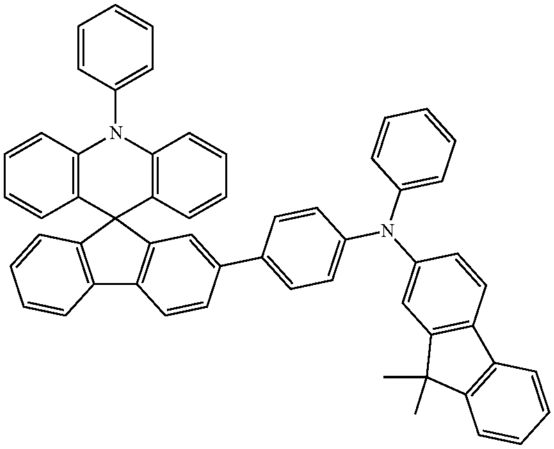
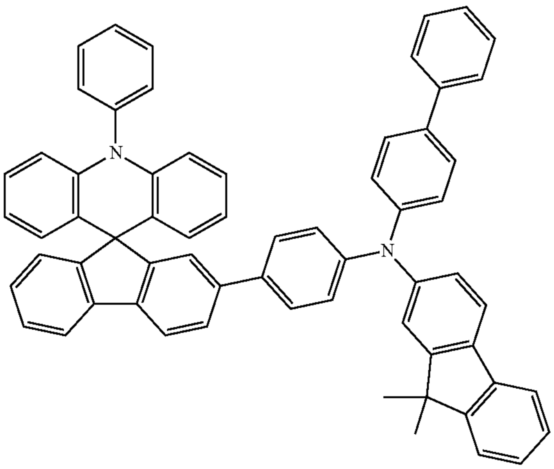

-continued
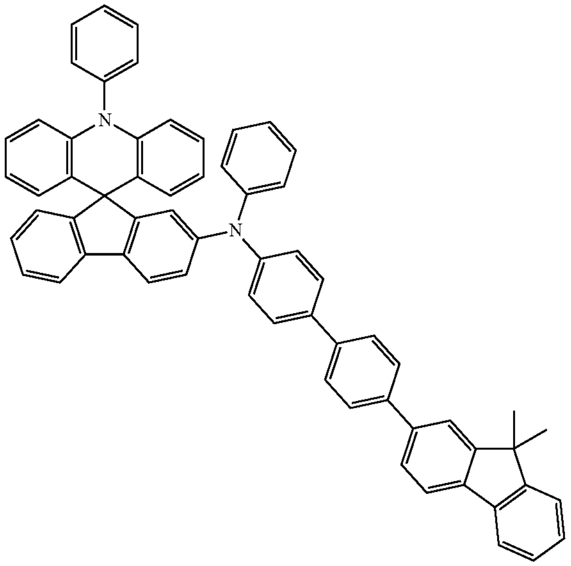
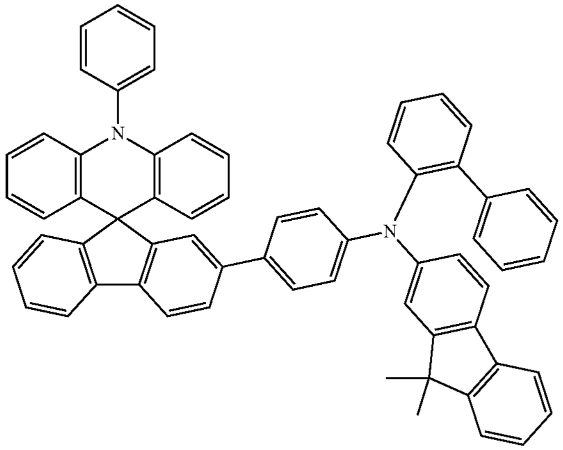
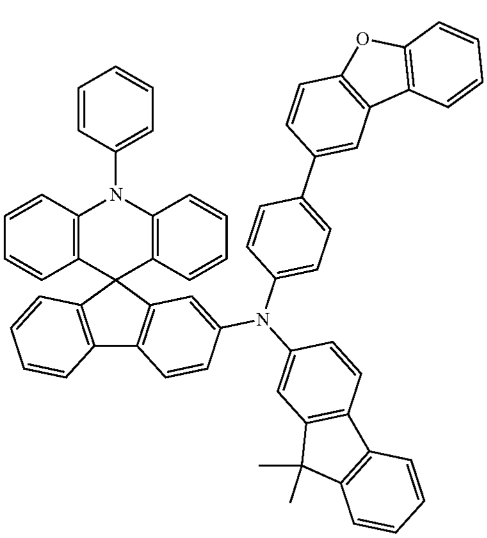
-continued
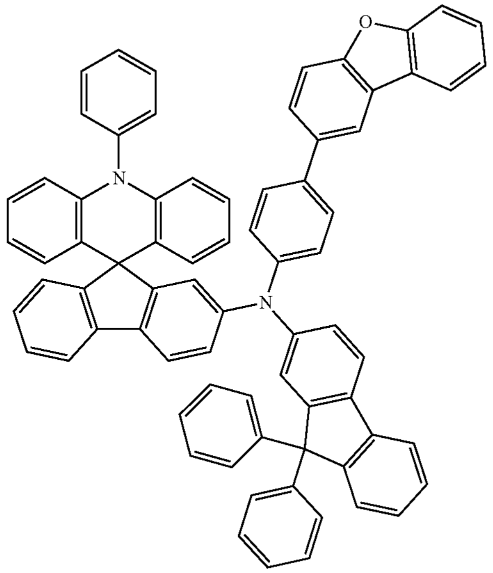
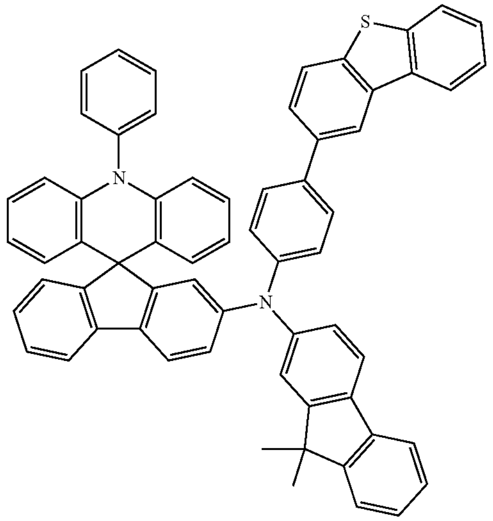
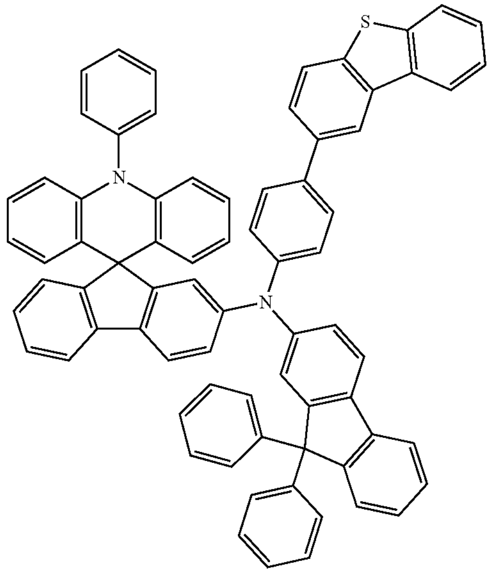

-continued
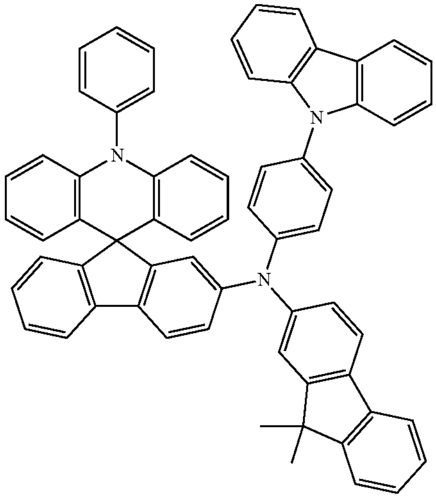
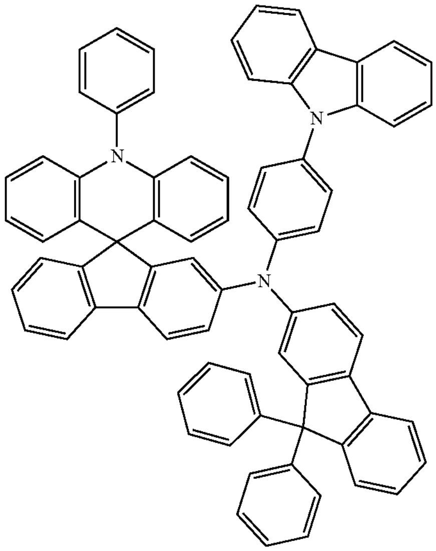
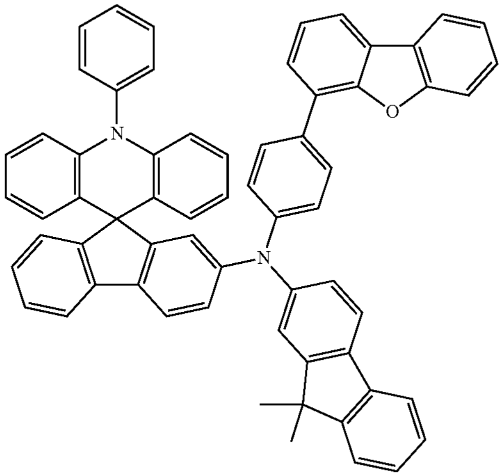
-continued
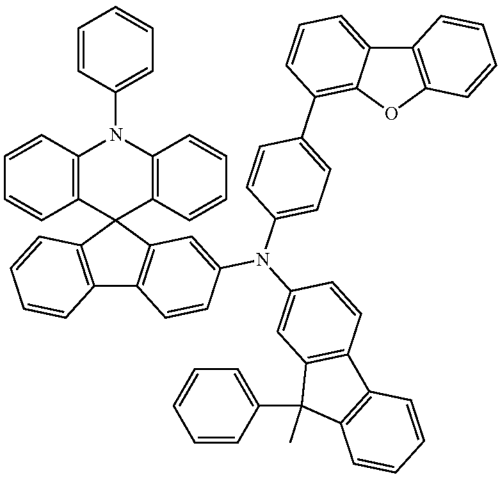
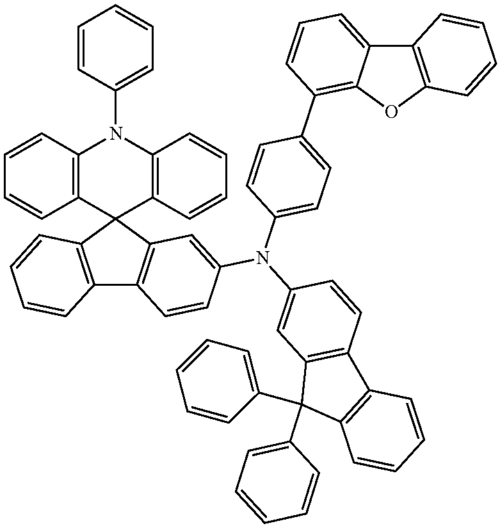
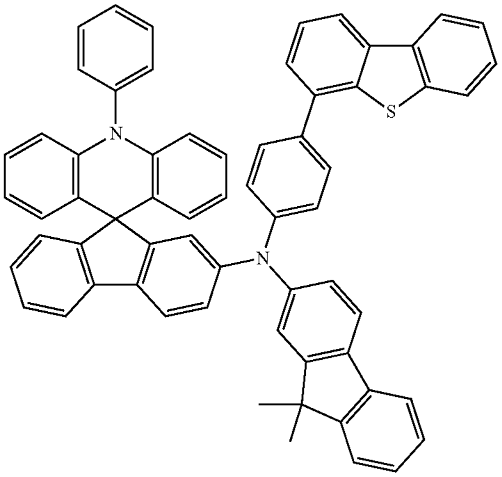

-continued
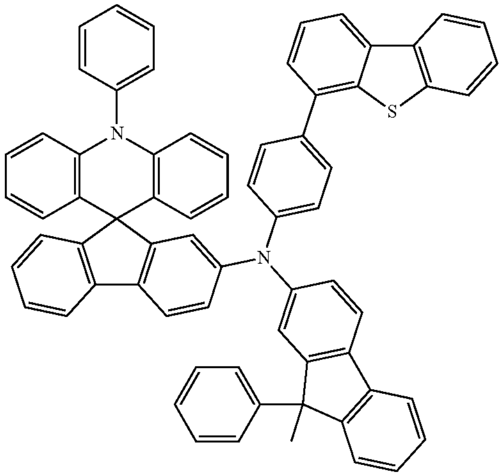
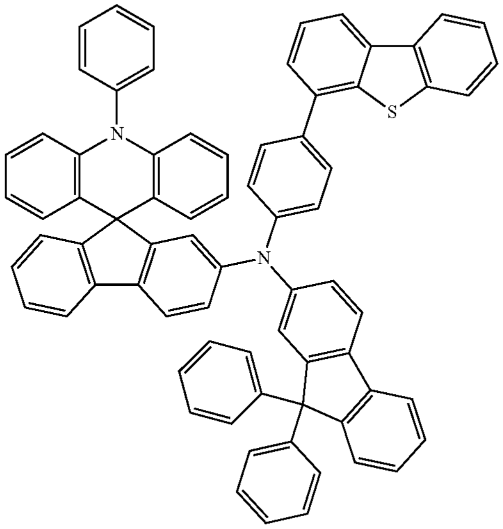
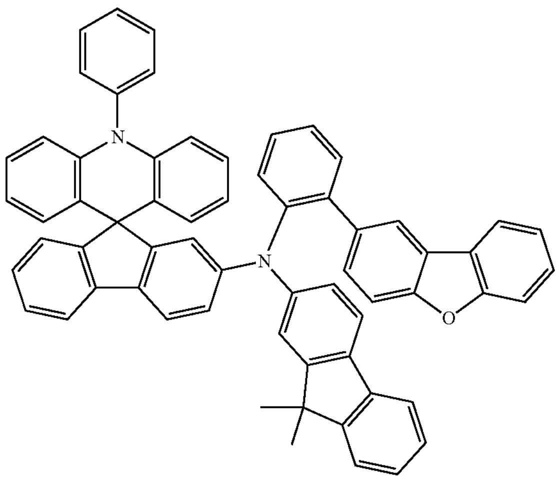
-continued
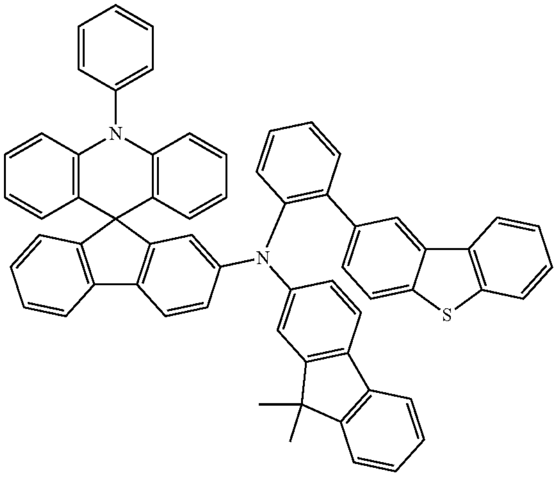
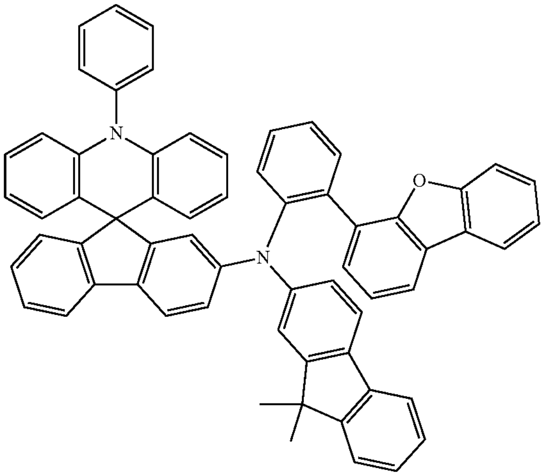
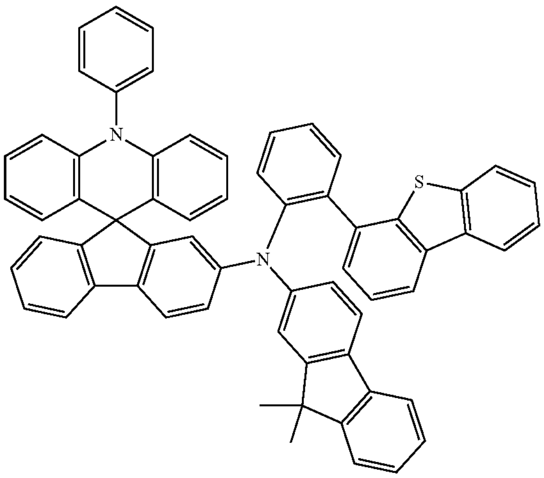

-continued
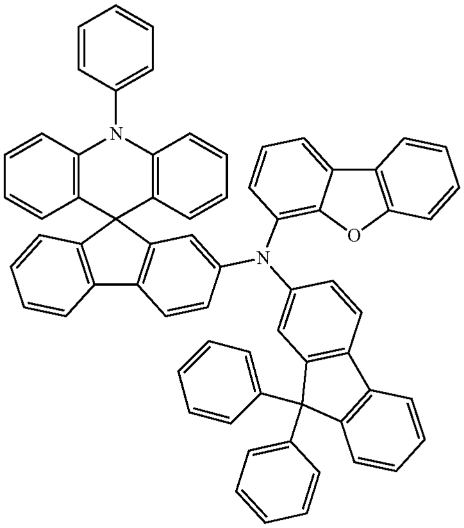
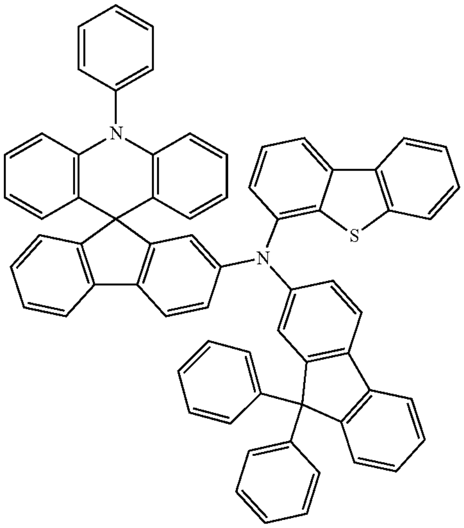
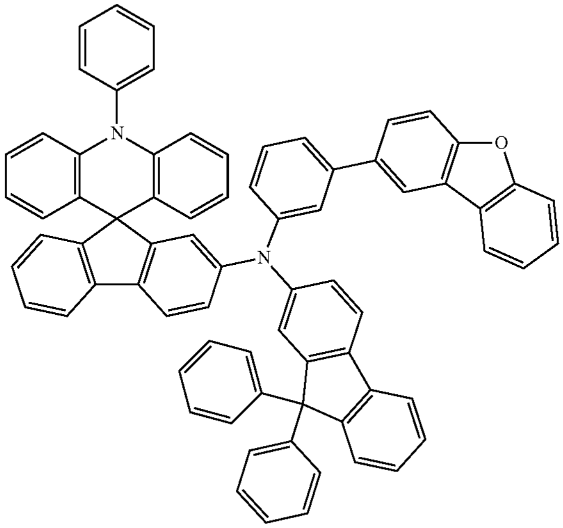
-continued
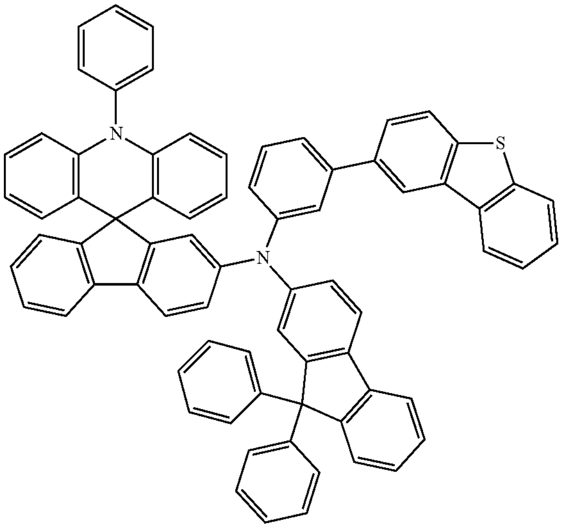
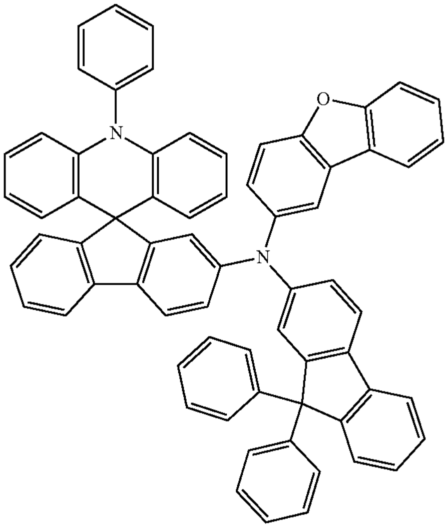
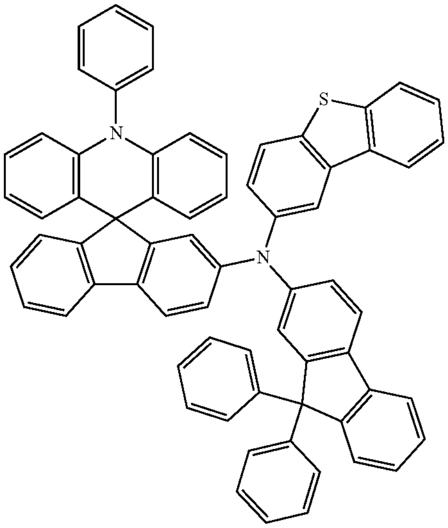

-continued
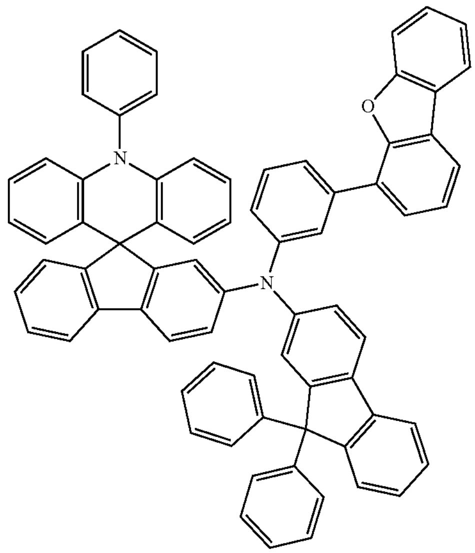
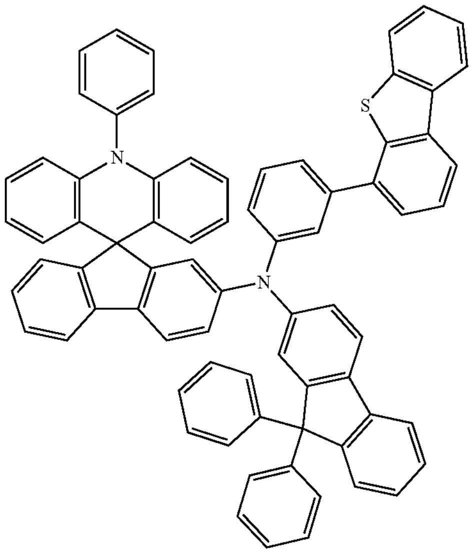
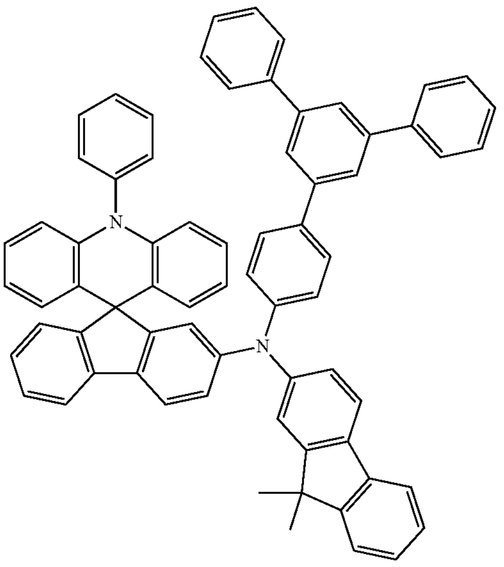
-continued
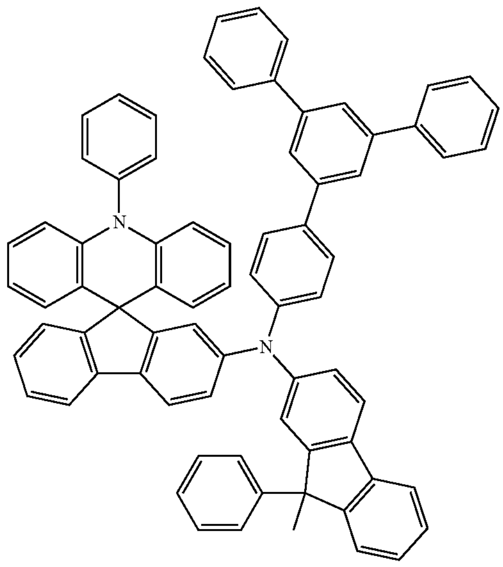
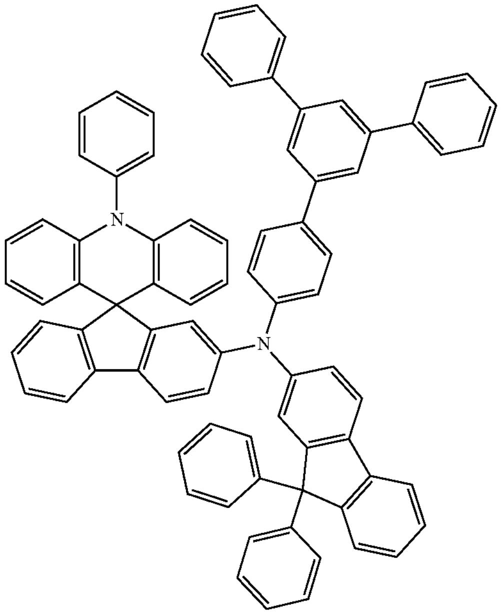
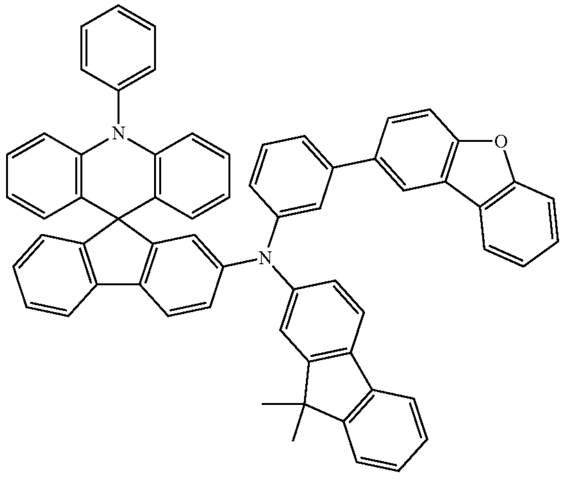

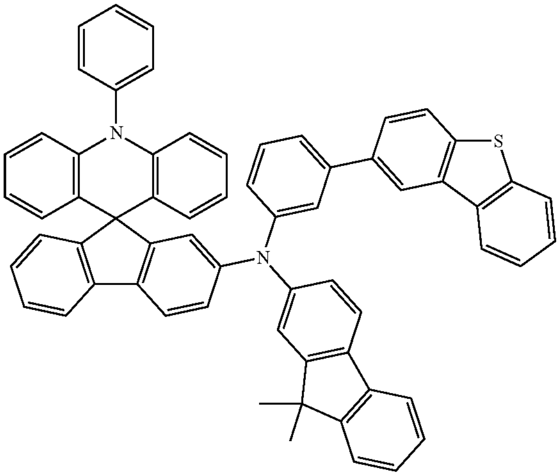
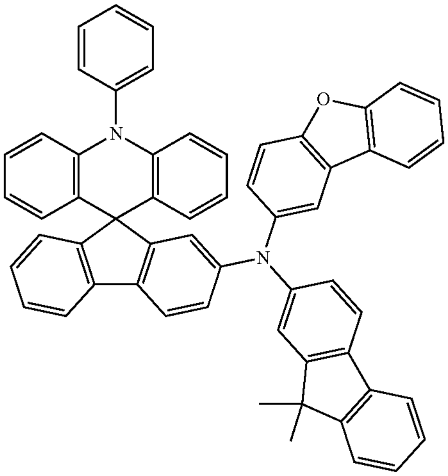
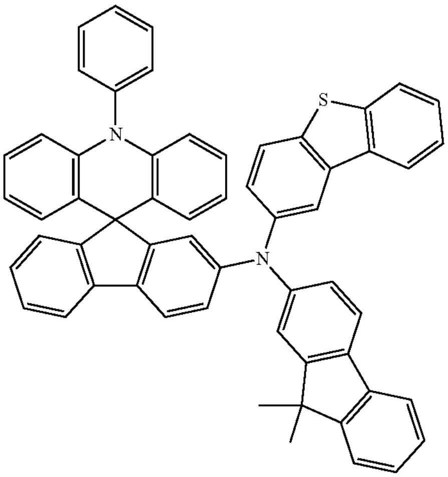
-continued
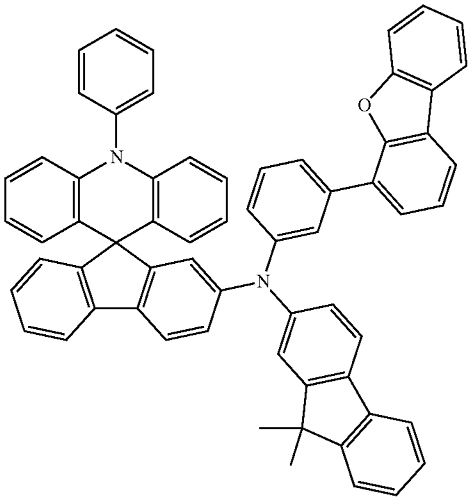
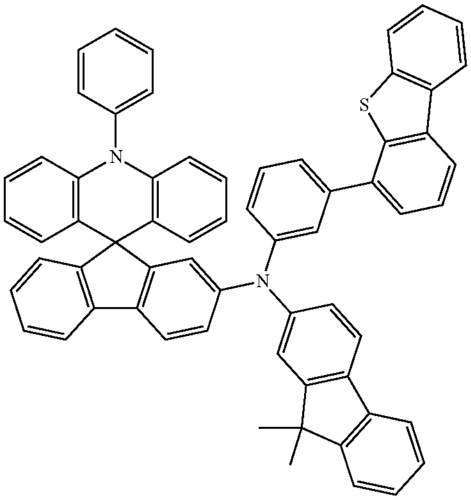
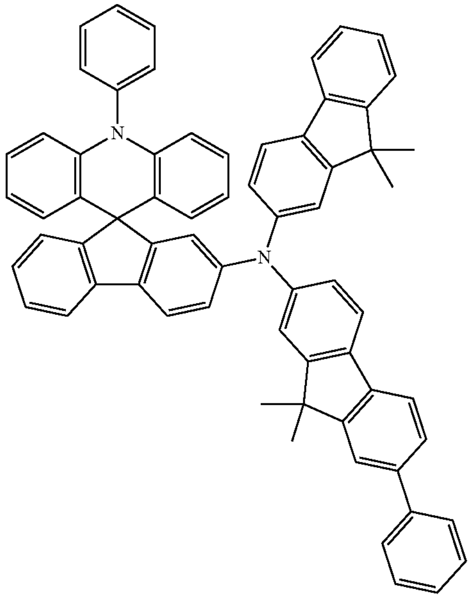

-continued
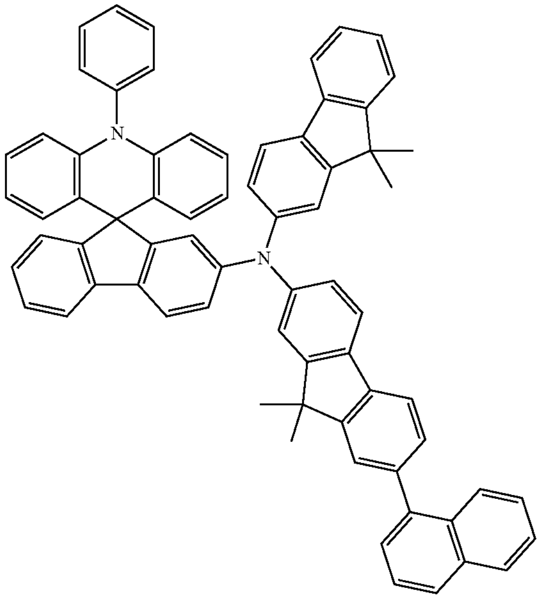
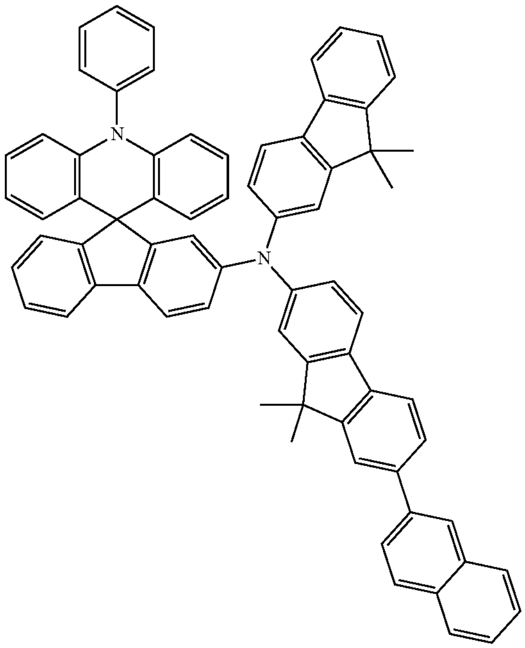
-continued
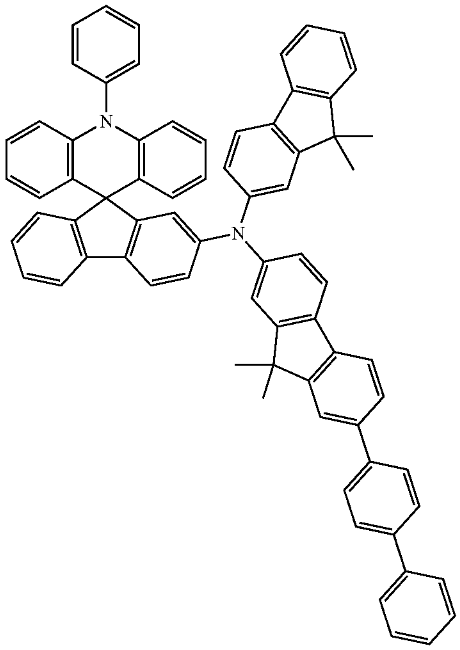
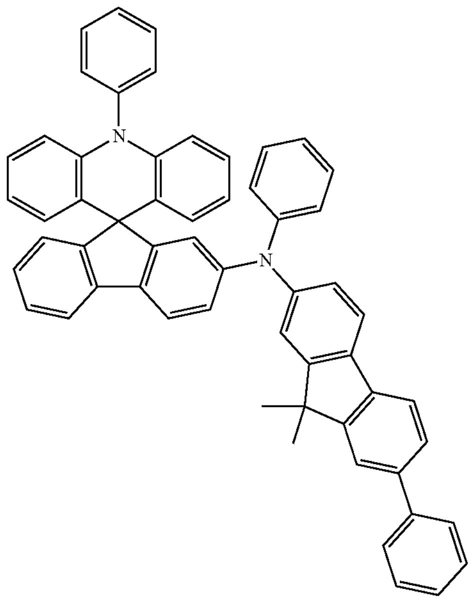

-continued
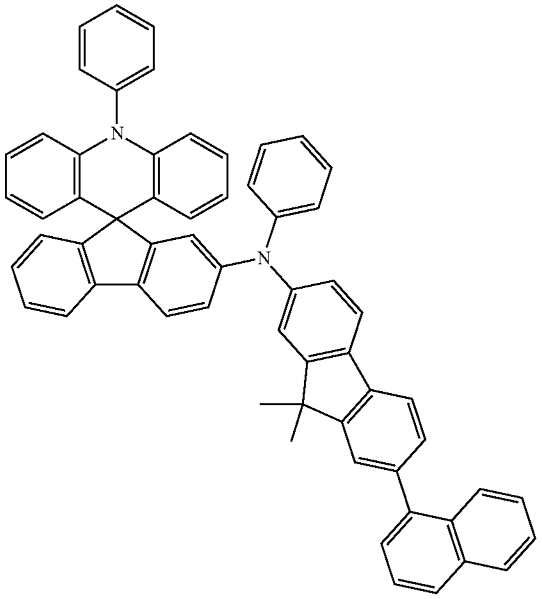
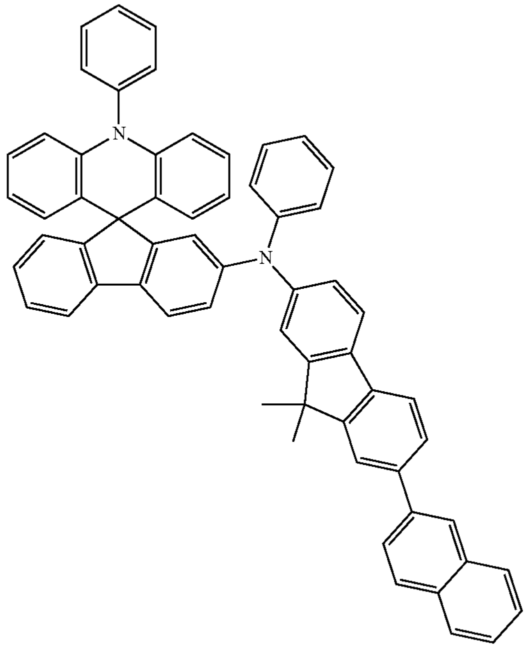
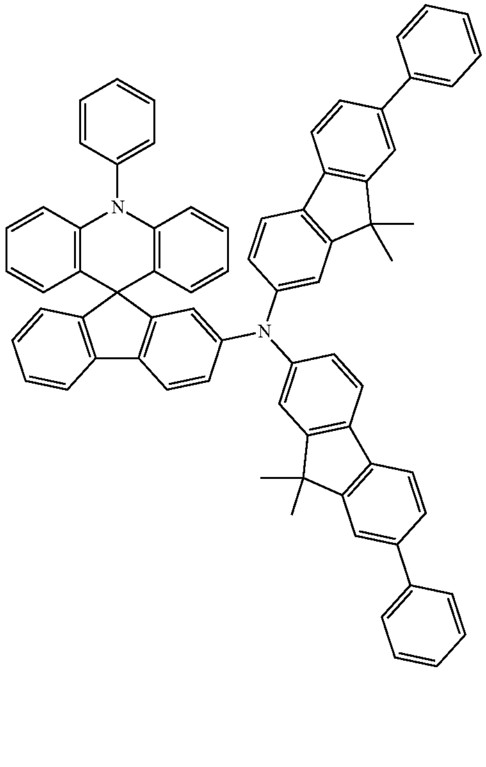
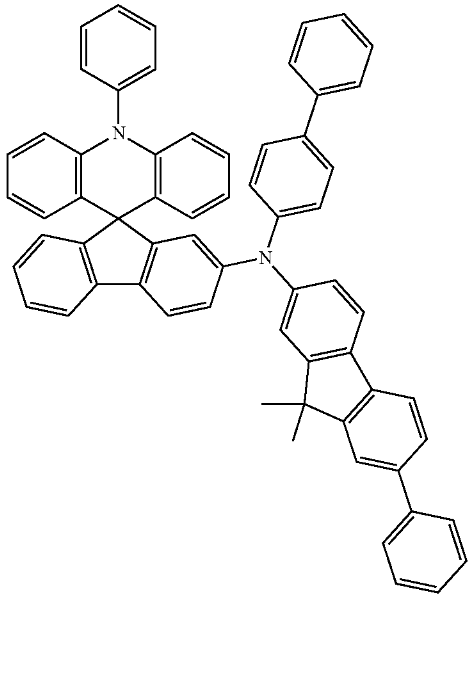
-continued

-continued
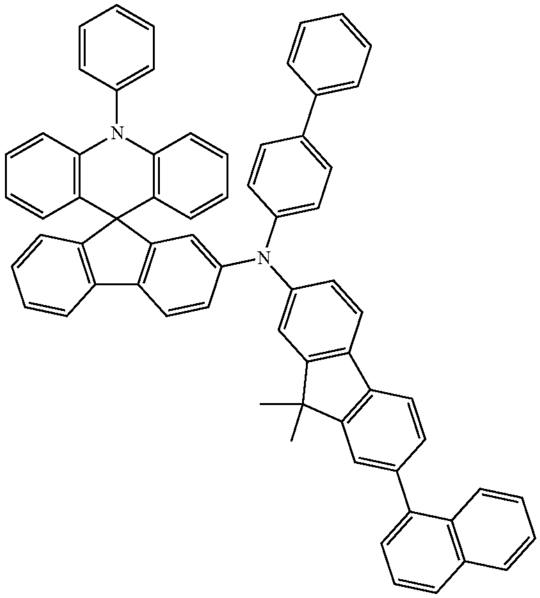
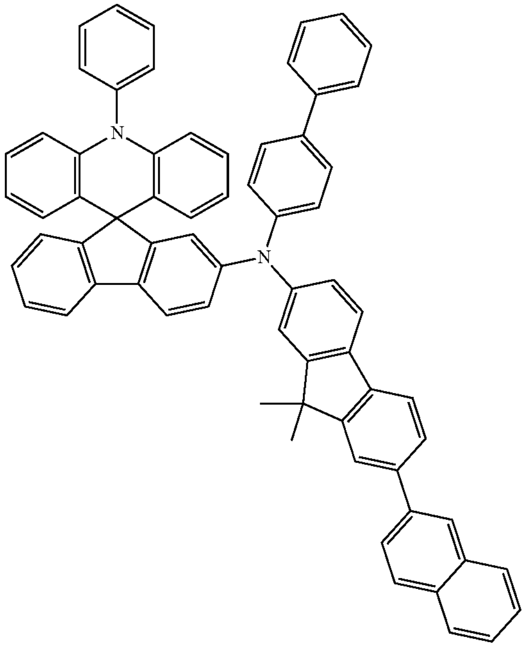
-continued
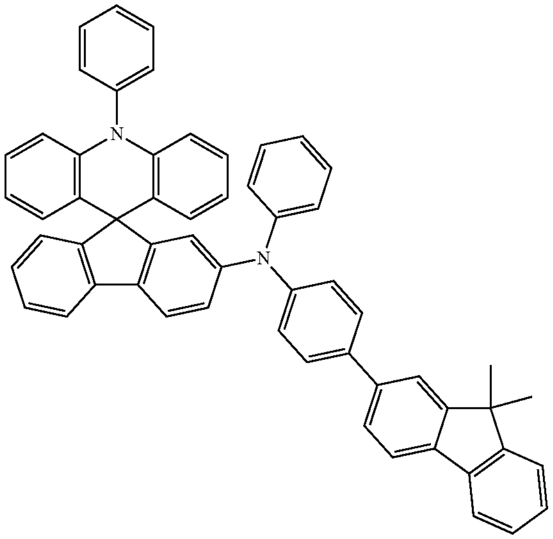
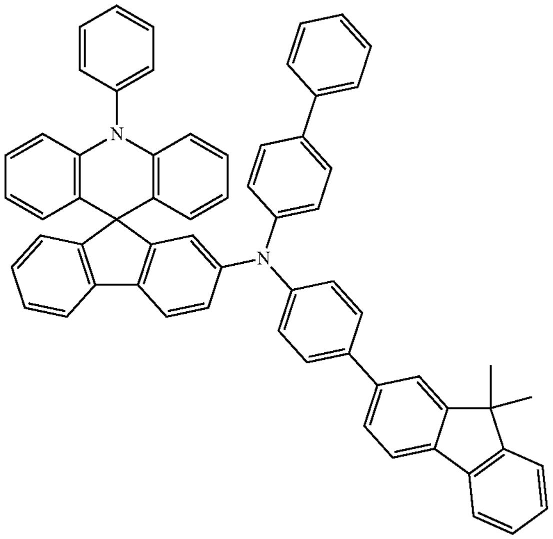
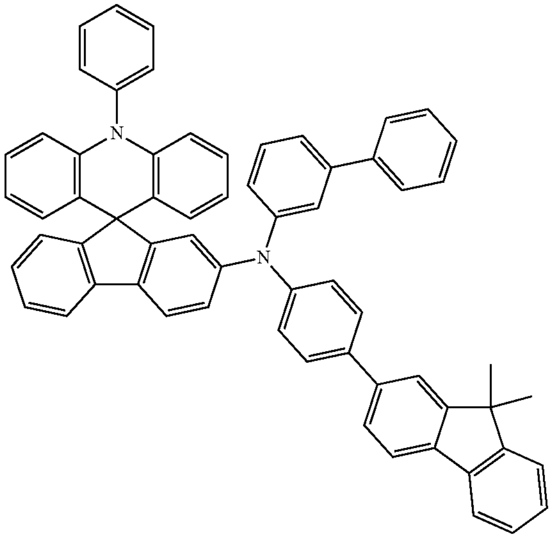

-continued
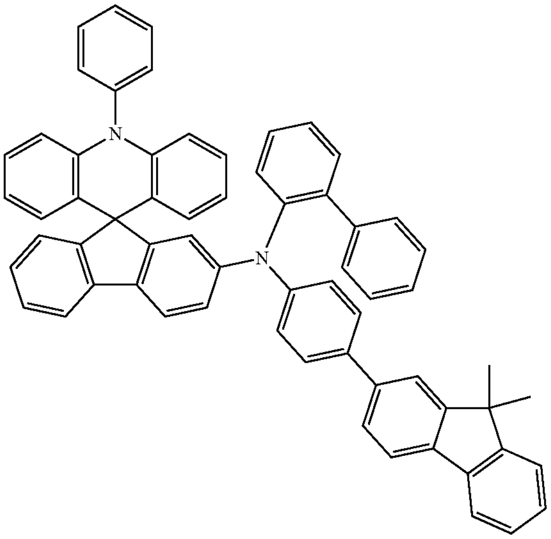
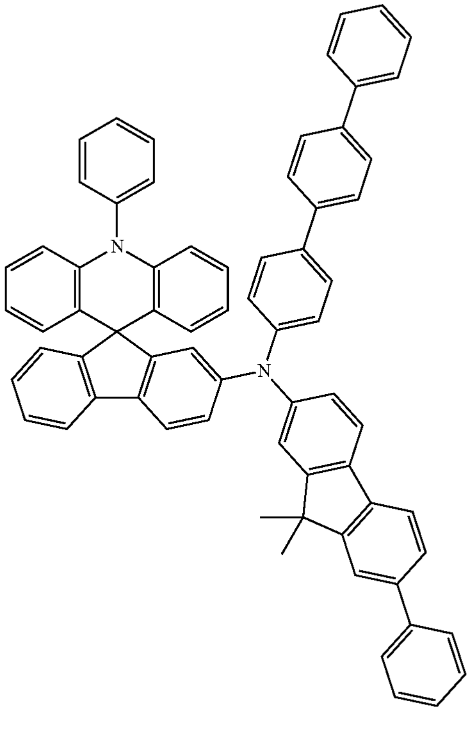
-continued
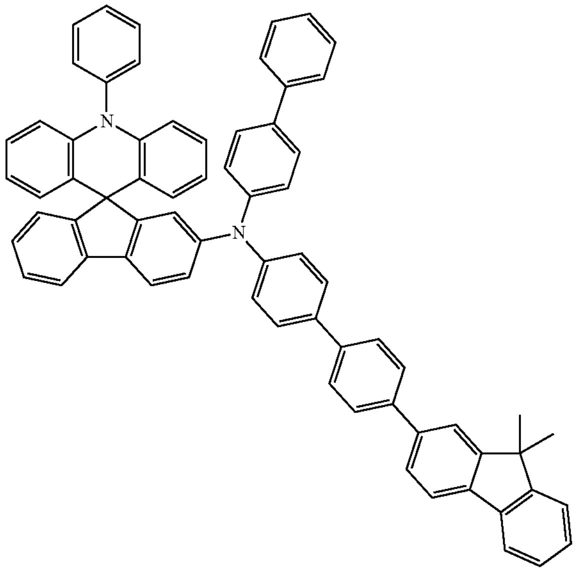
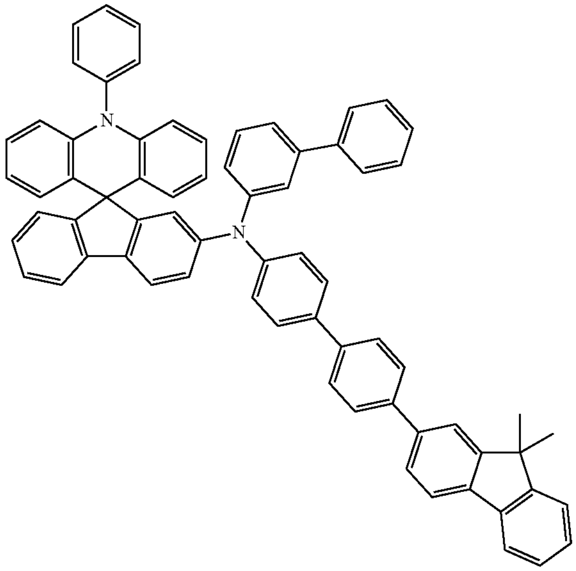
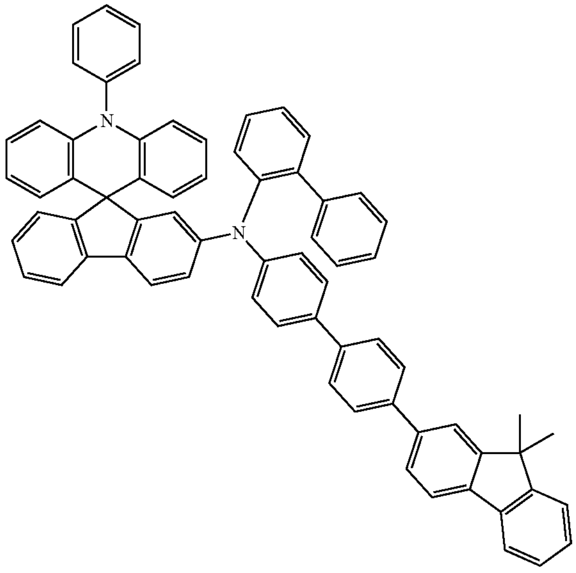

-continued
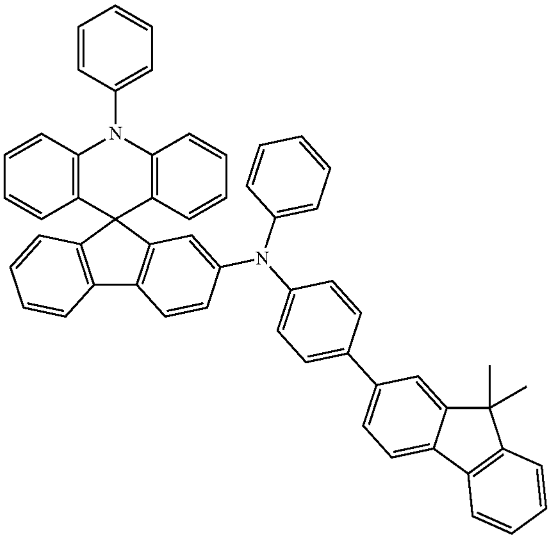
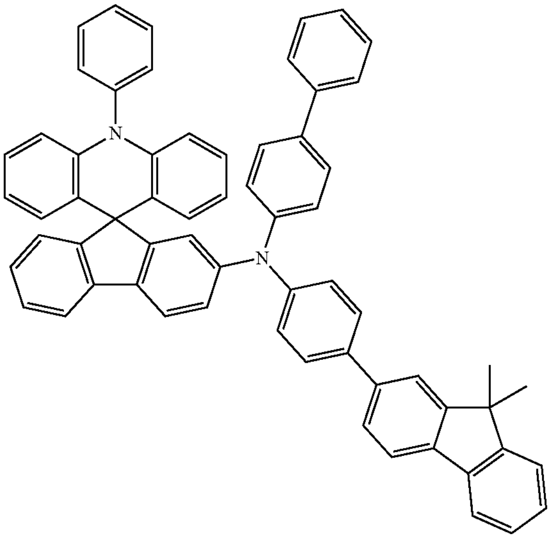
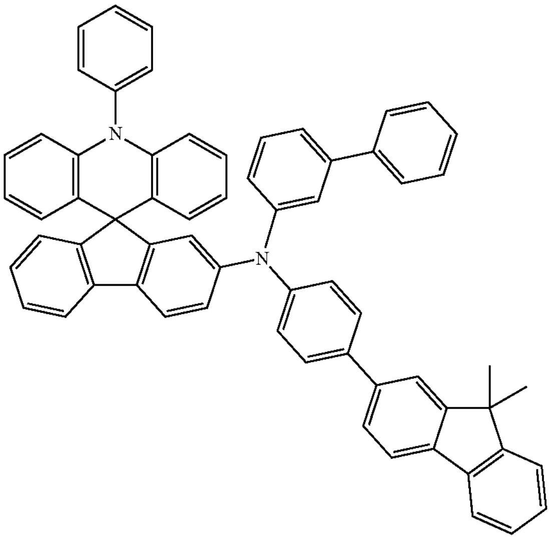
-continued
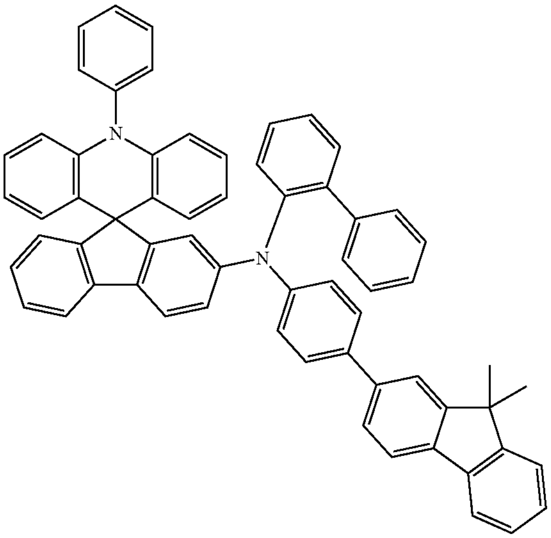 [SMILES: CC1(C)c2ccccc2-c2ccc(-c3ccc(N(c4ccc5c(c4)C4(c6ccccc6-5)c5ccccc5N(c5ccccc5)c5ccccc54)c4ccccc4-c4ccccc4)cc3)cc21]
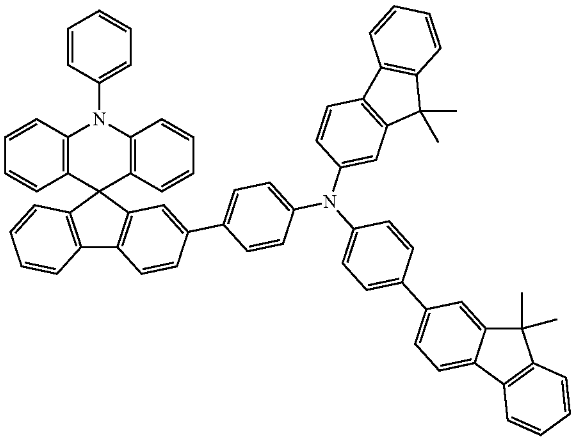
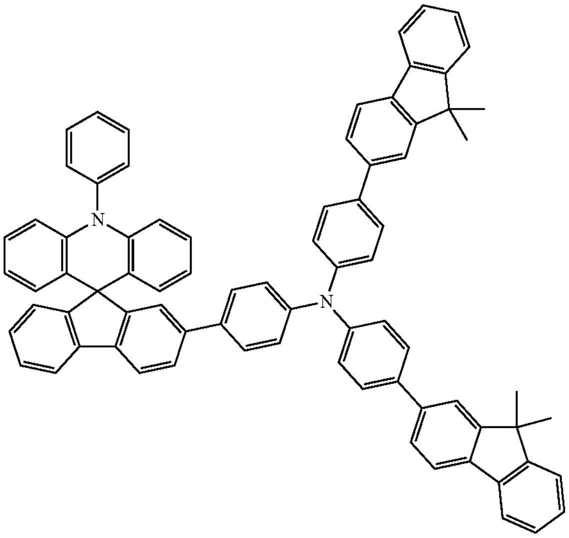

-continued
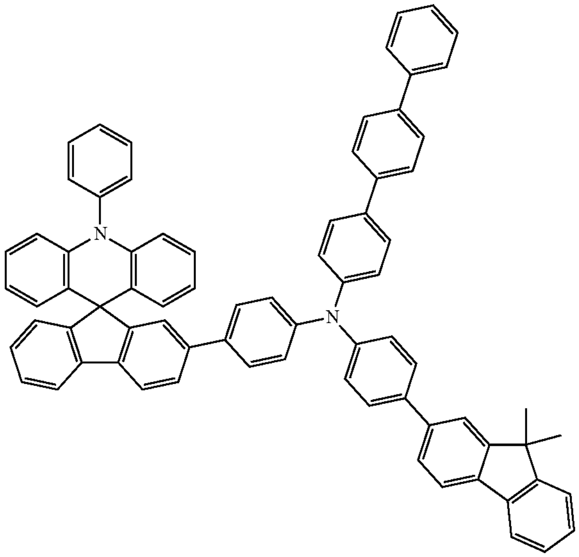
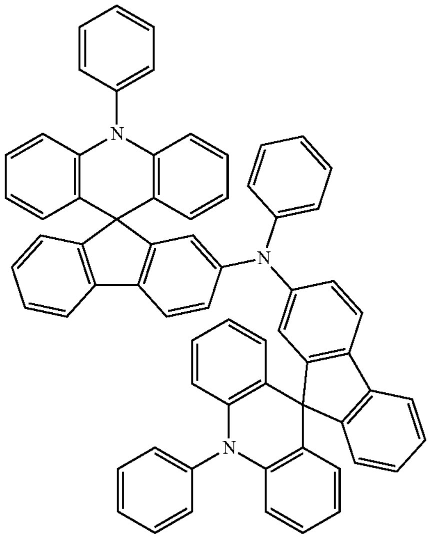
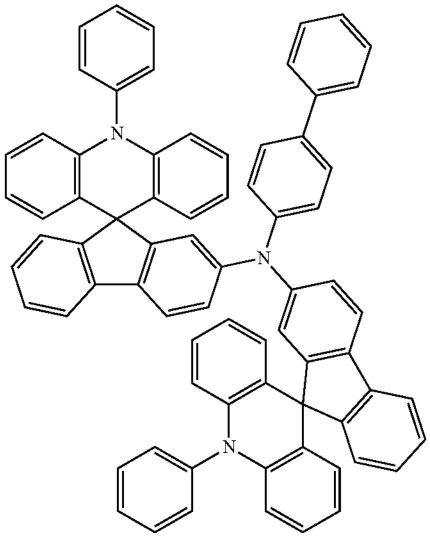
-continued
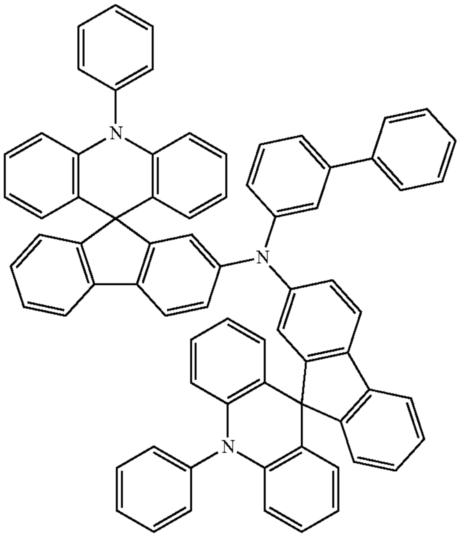
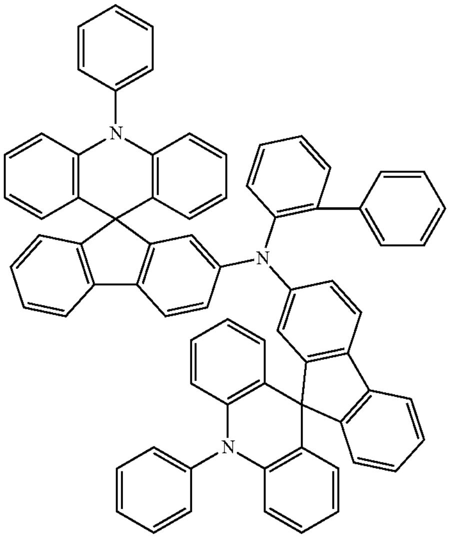
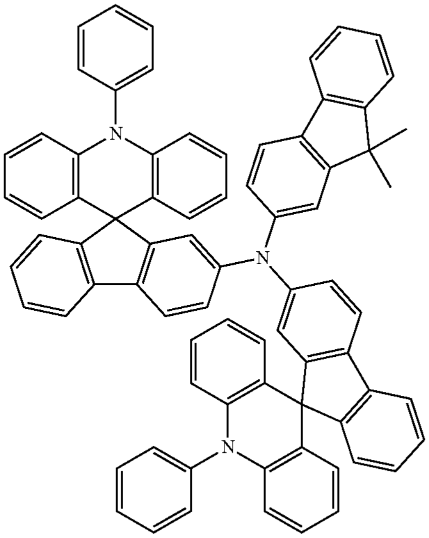

-continued
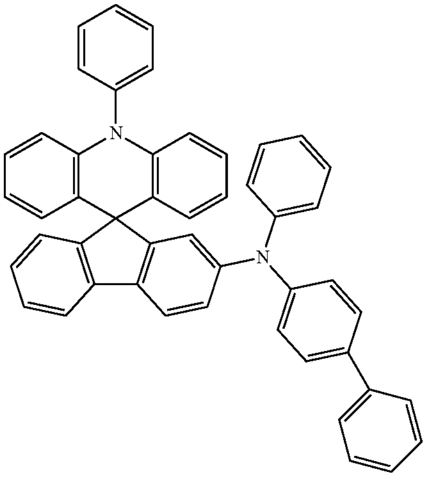
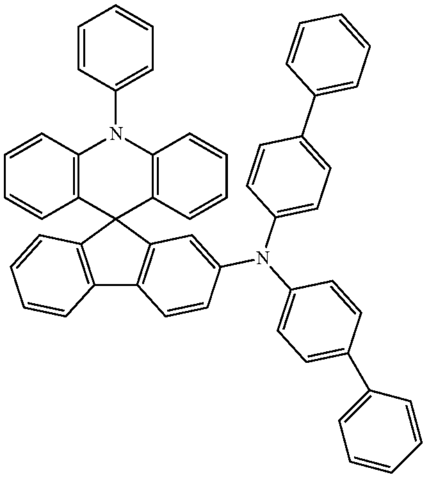
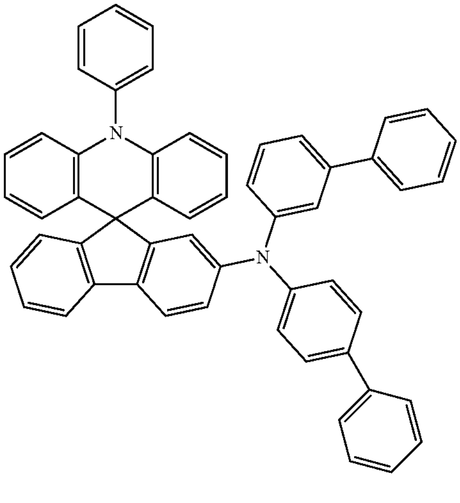
-continued
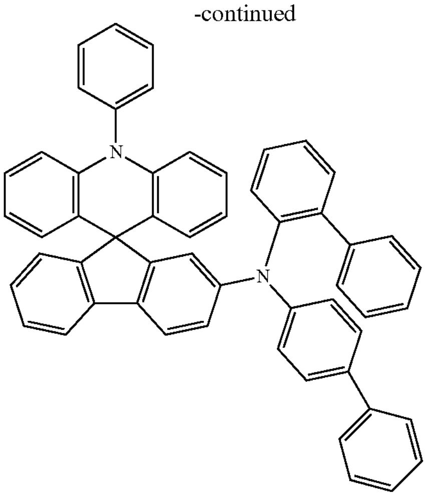
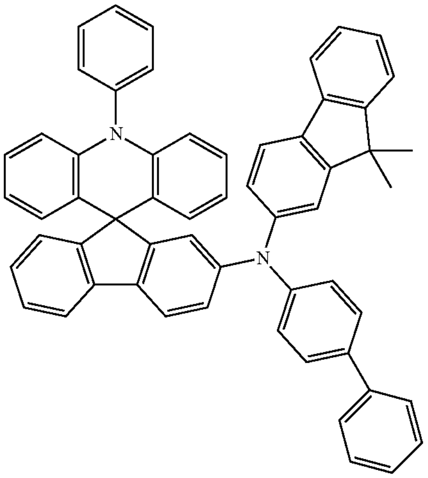
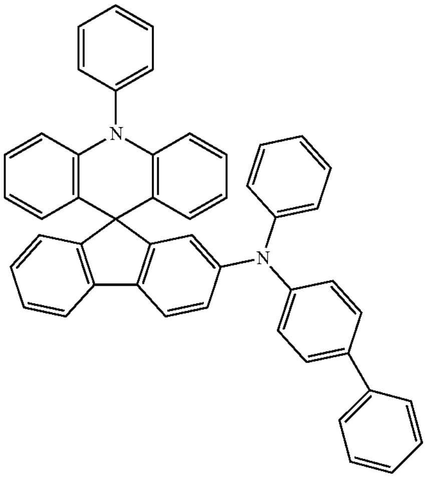

-continued
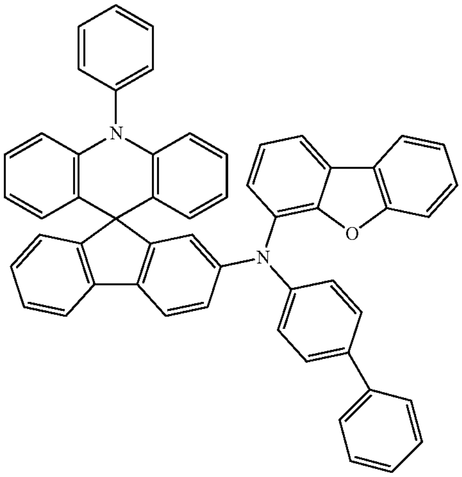
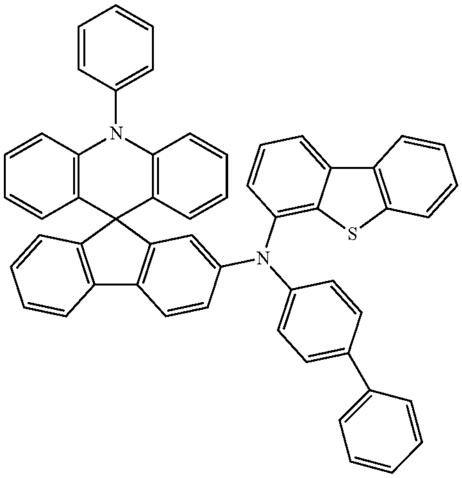
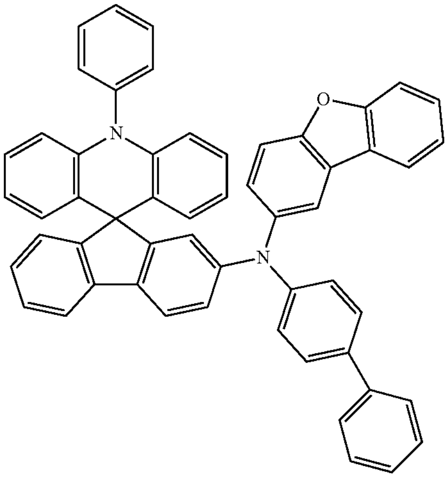
-continued
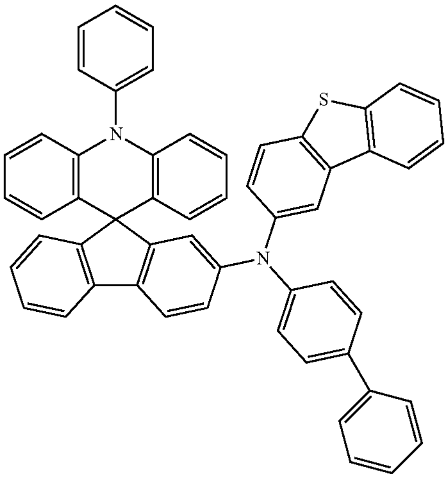
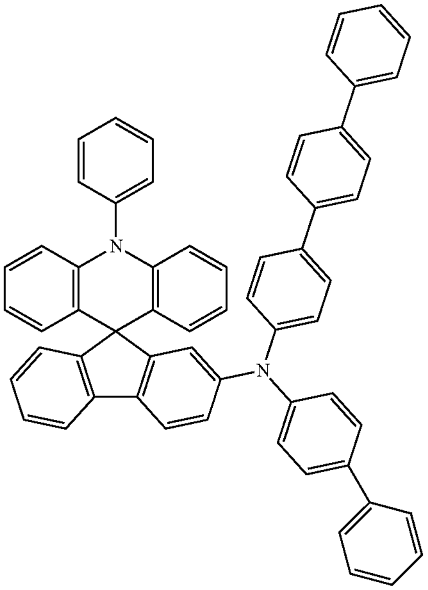
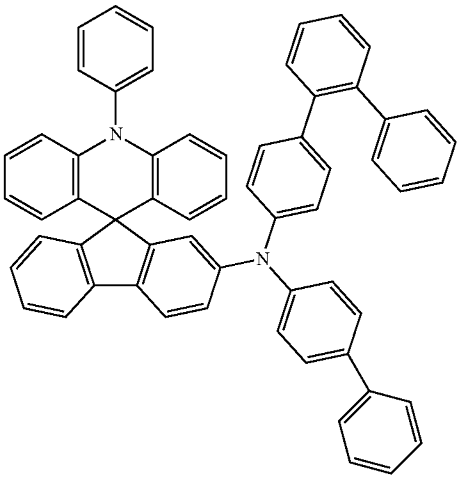

-continued
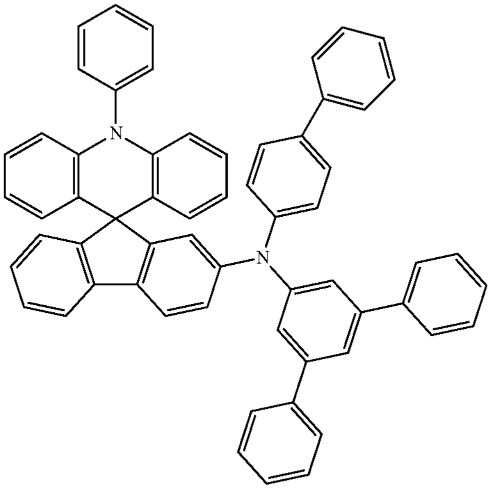
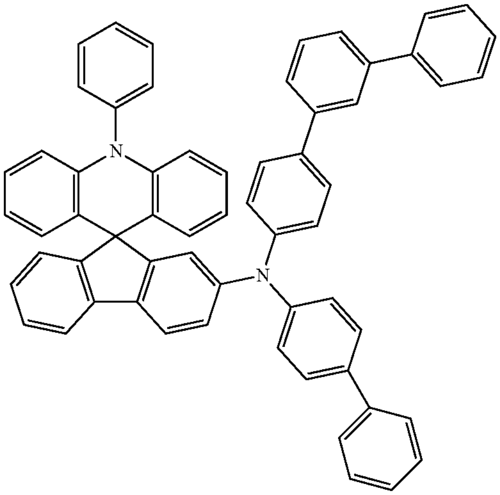
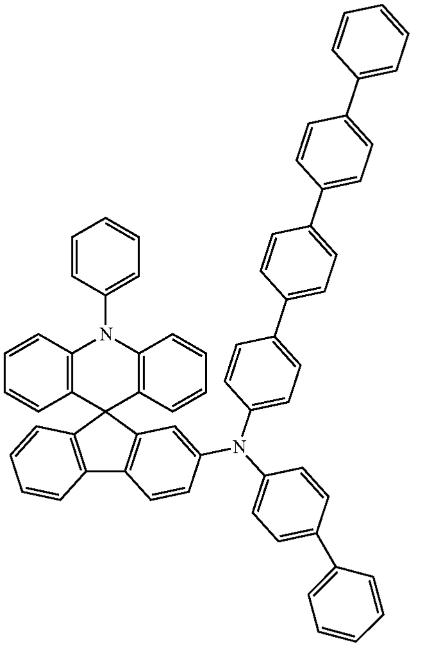
-continued
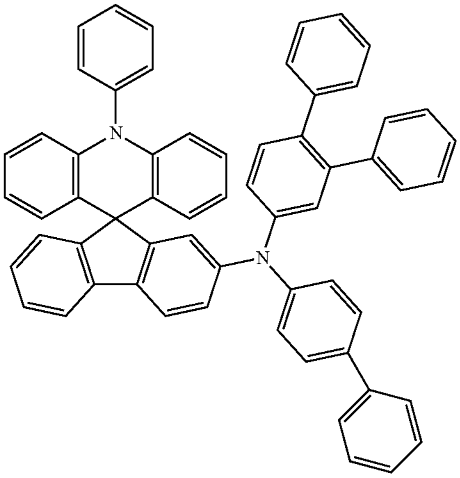
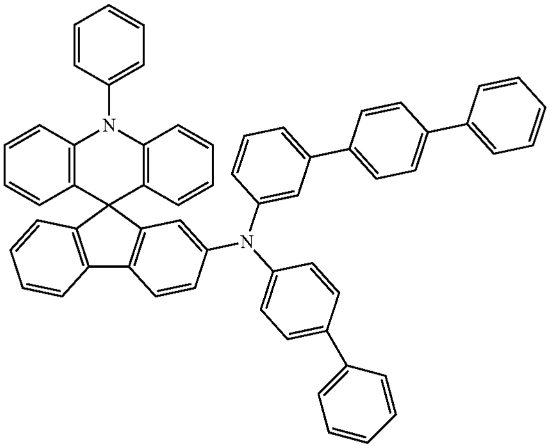
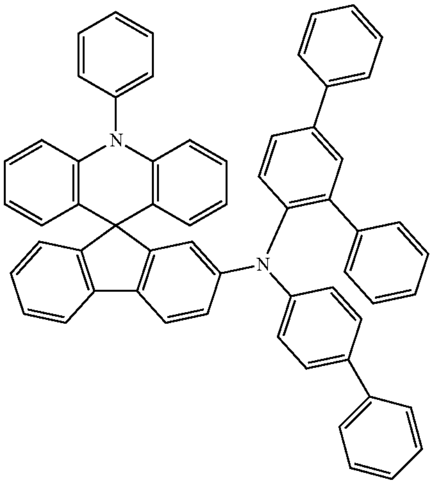

-continued
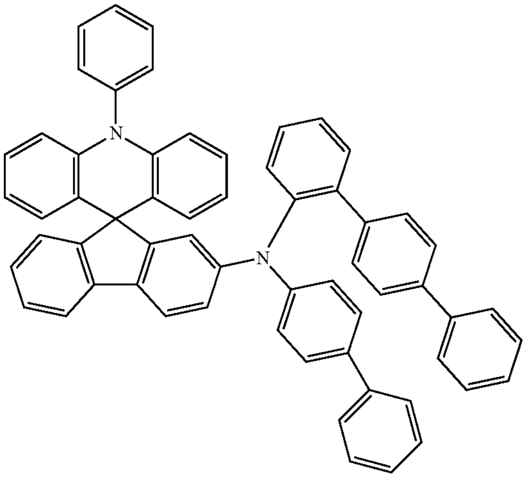
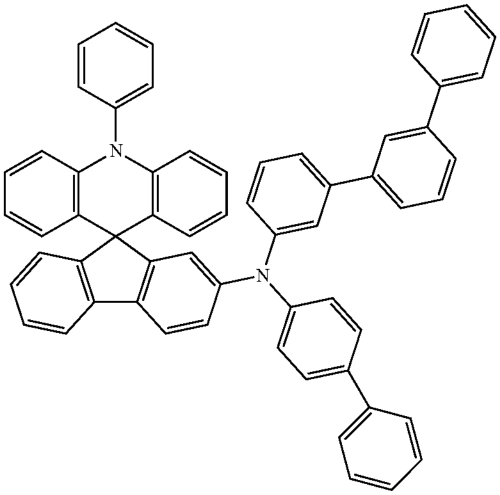
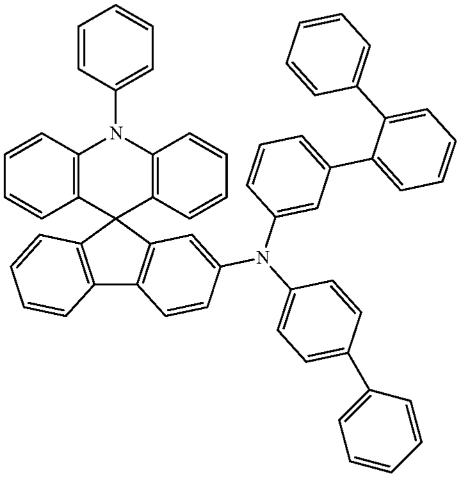
-continued
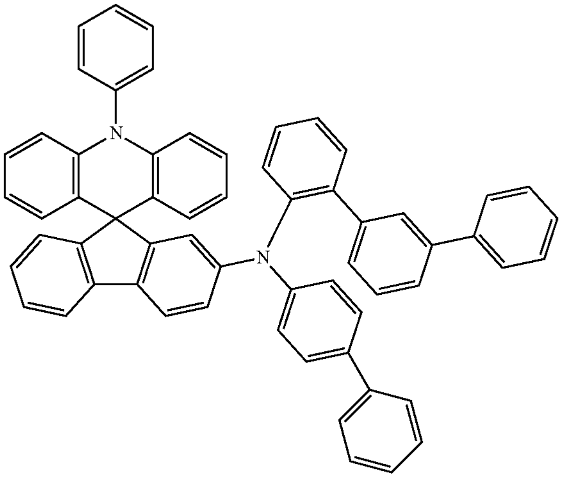
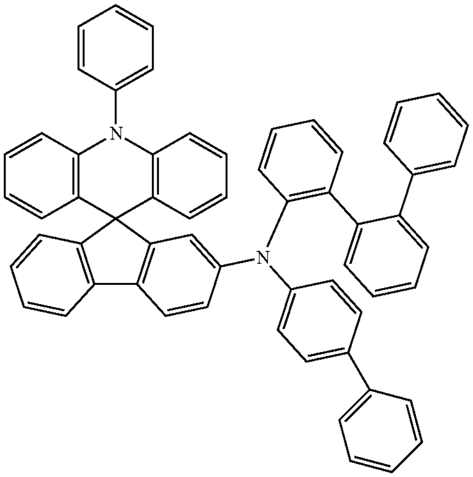
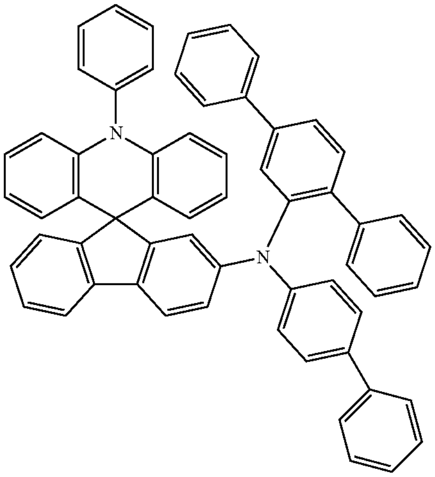

-continued
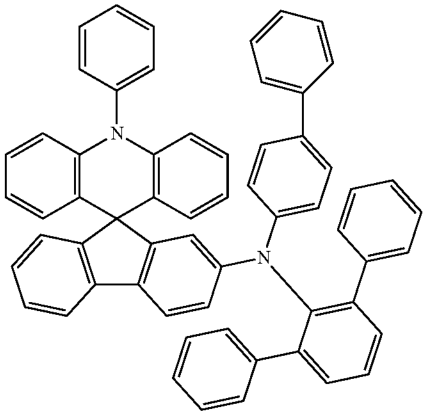
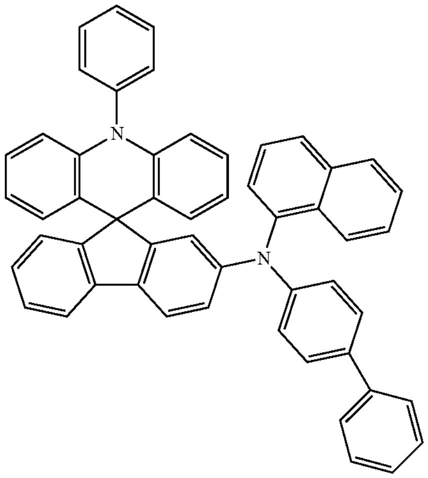
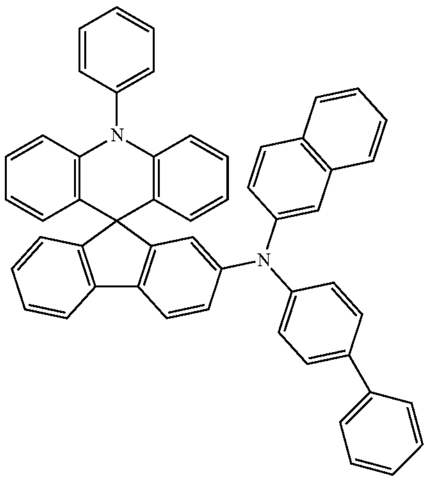
-continued
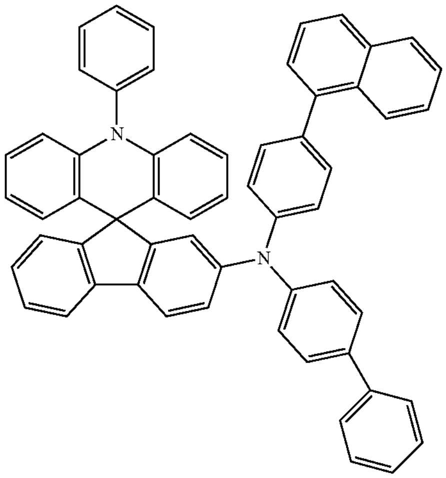
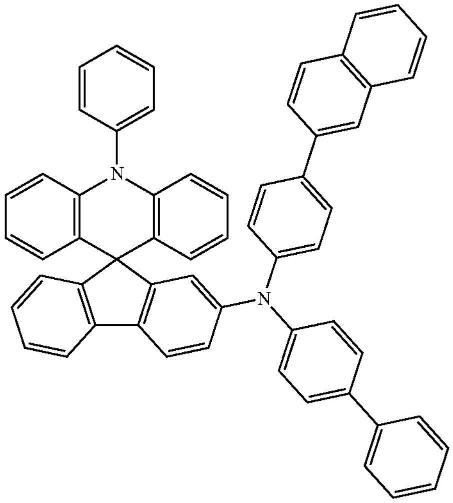
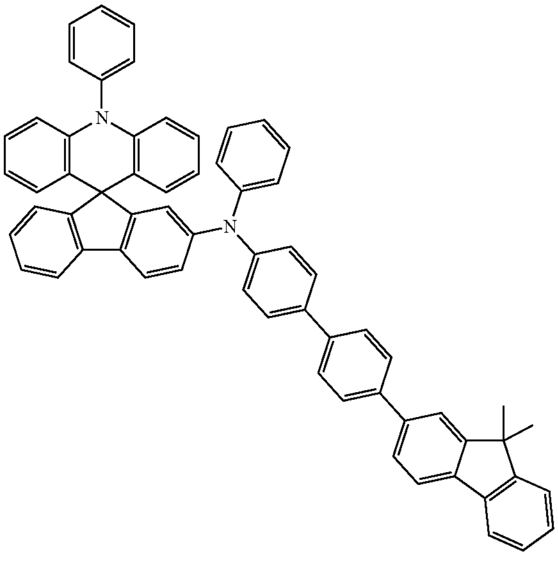

-continued
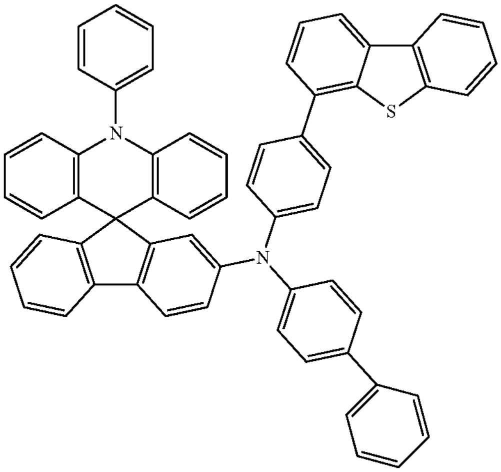
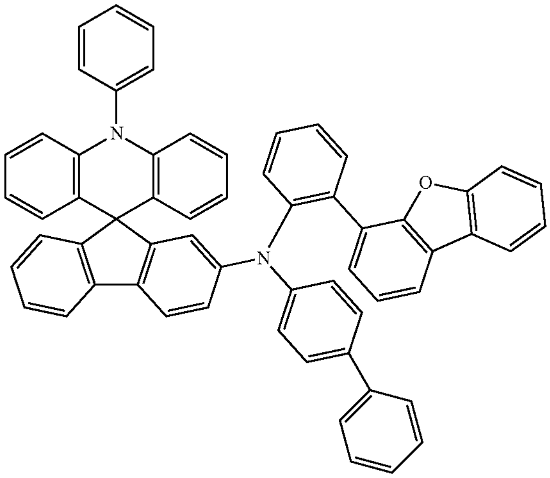
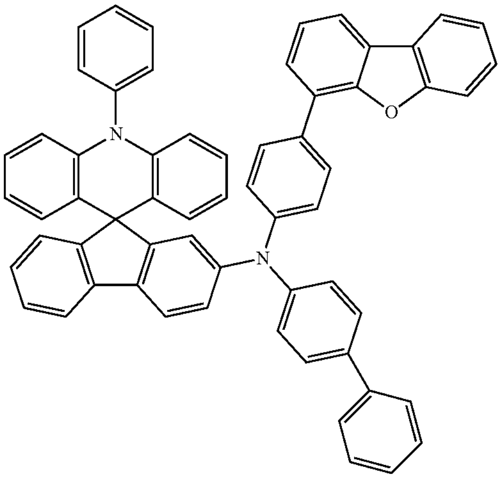
-continued
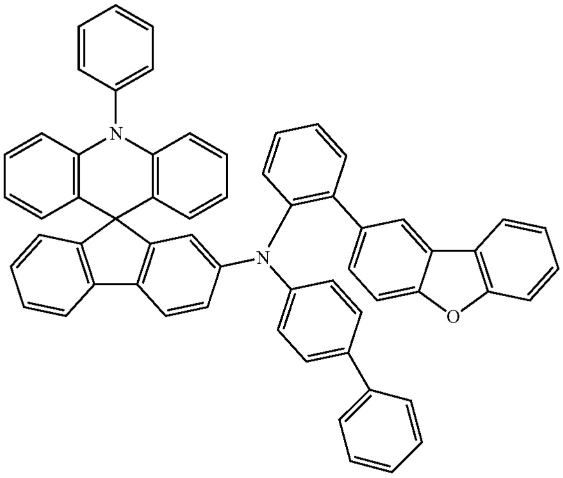
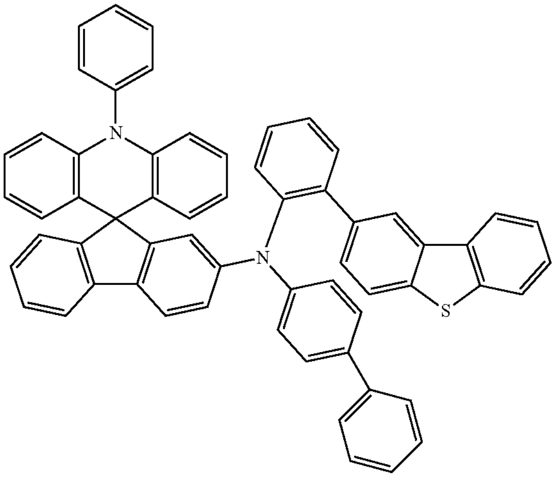
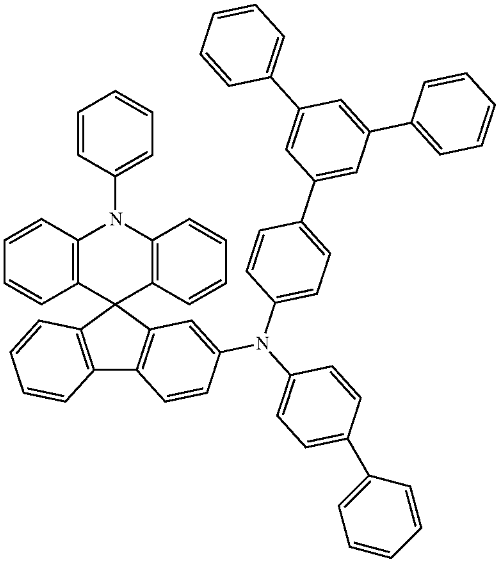

-continued
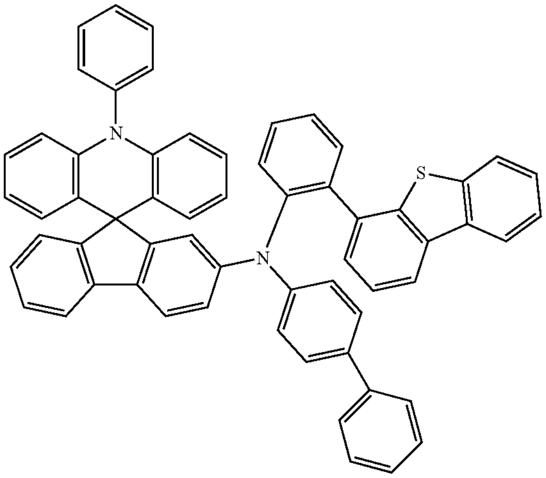
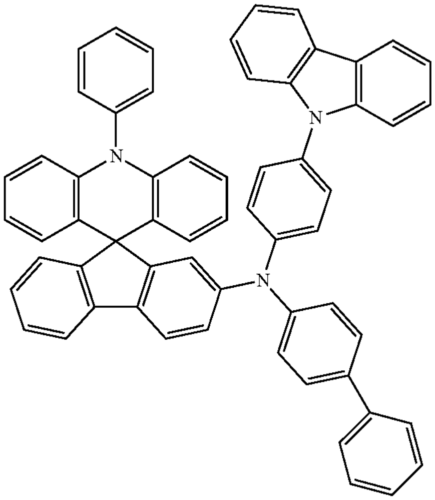
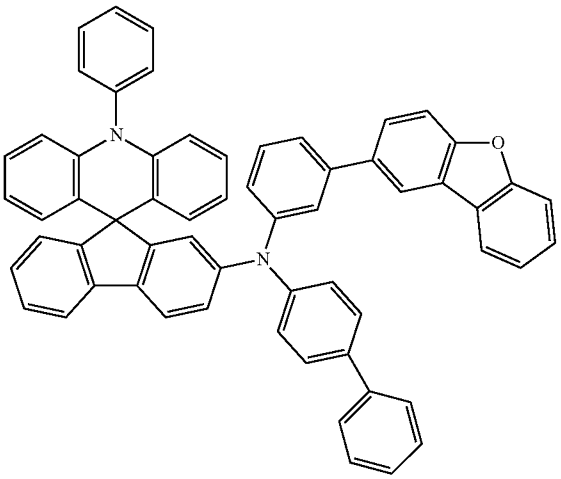
-continued
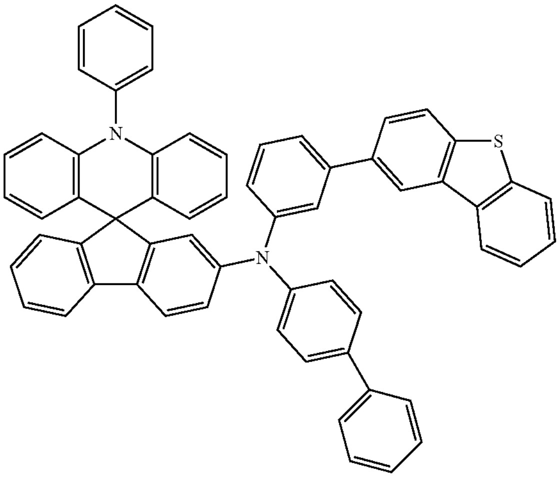
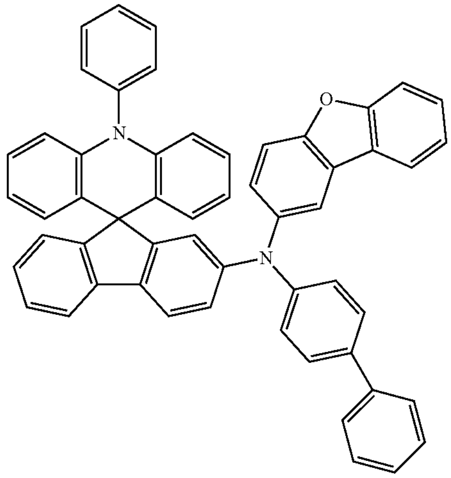
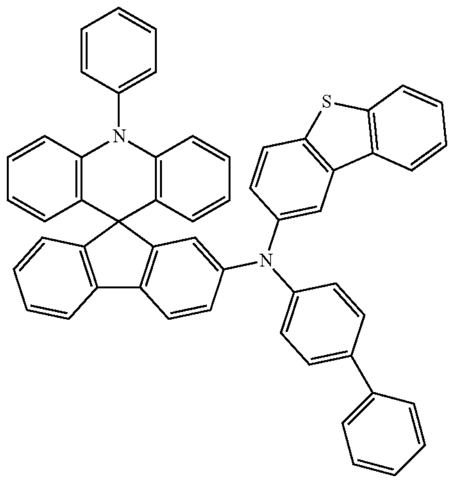

-continued
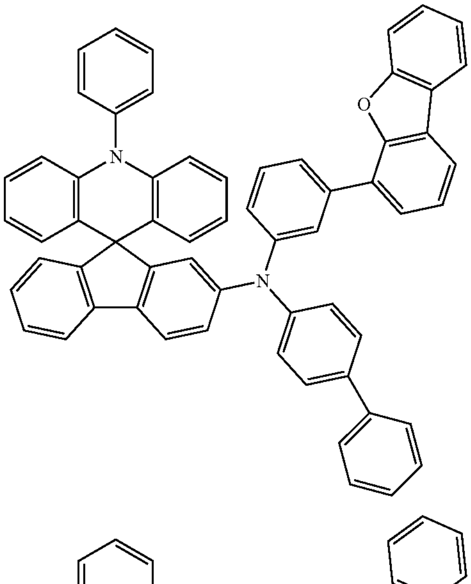
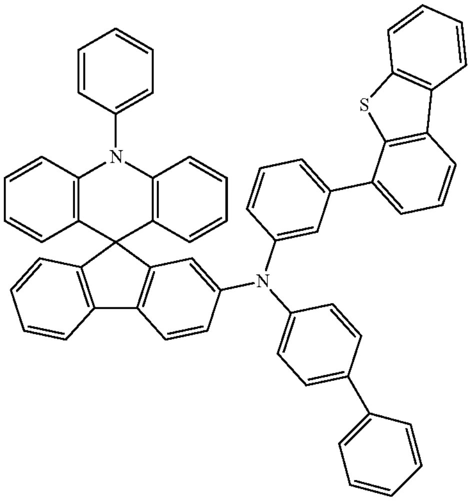
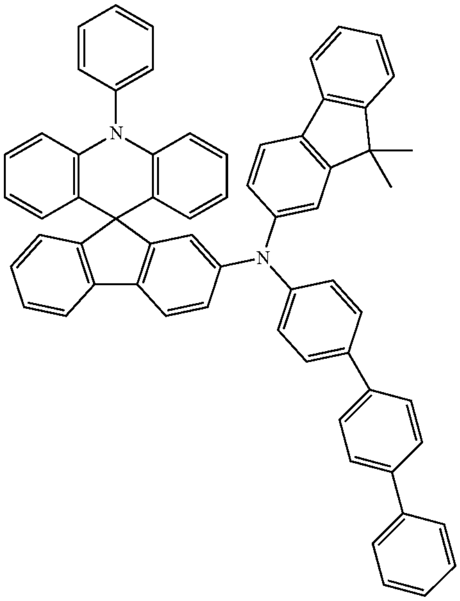
-continued
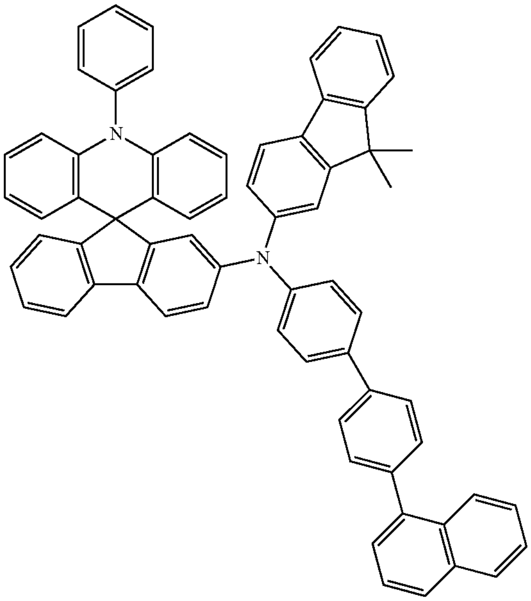
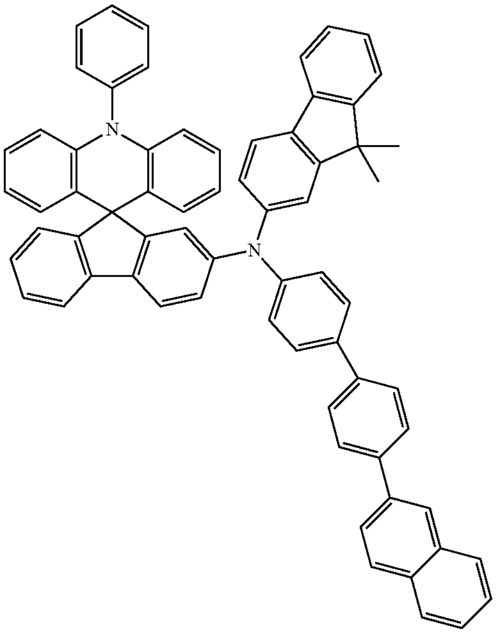

-continued
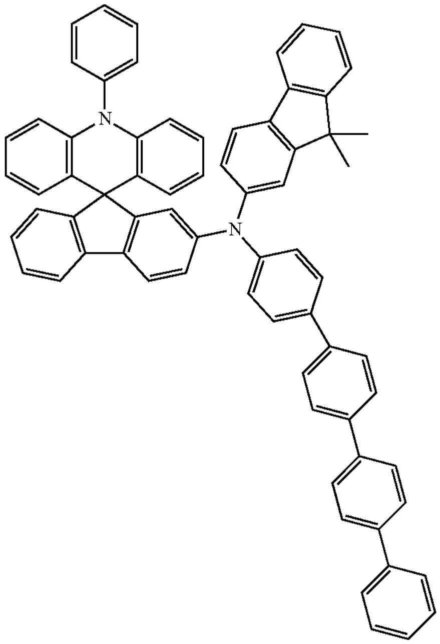
-continued
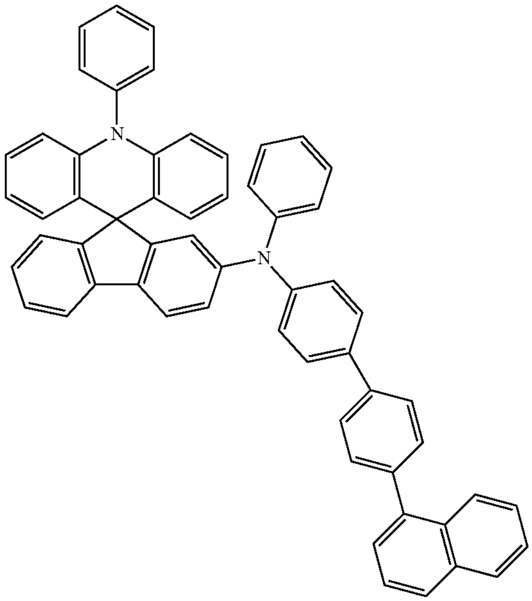
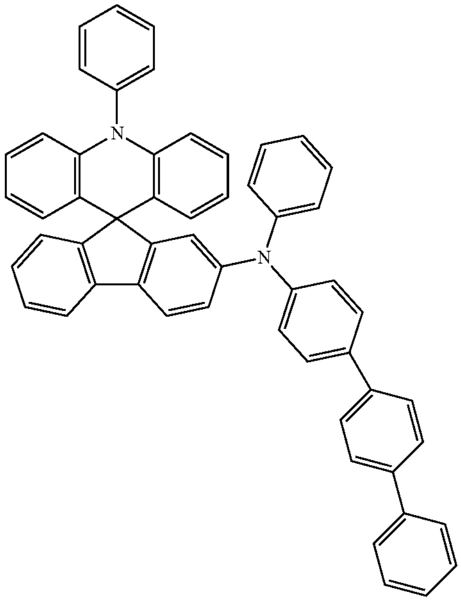
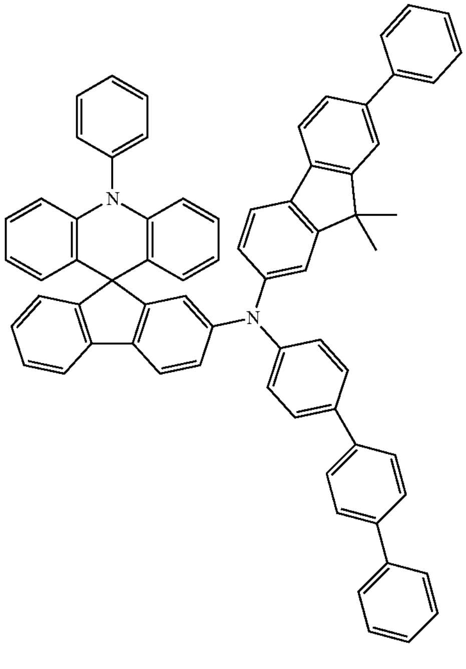

-continued
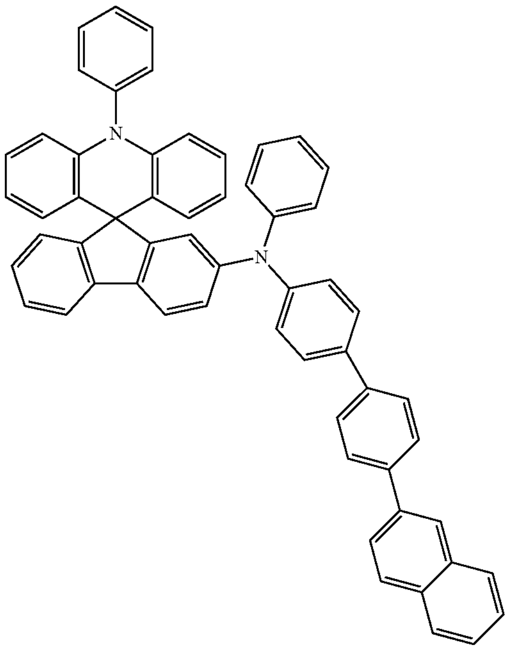
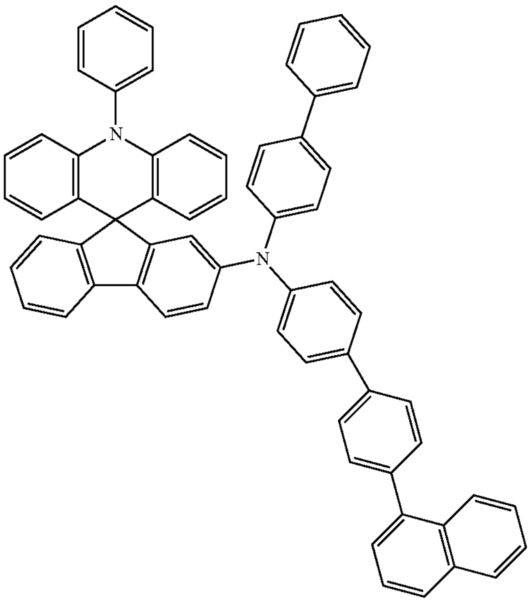
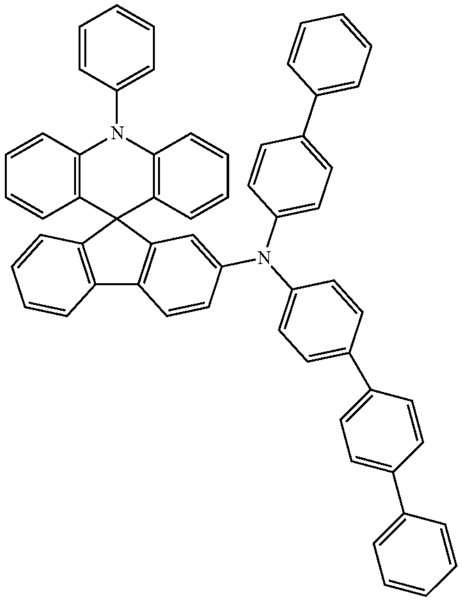
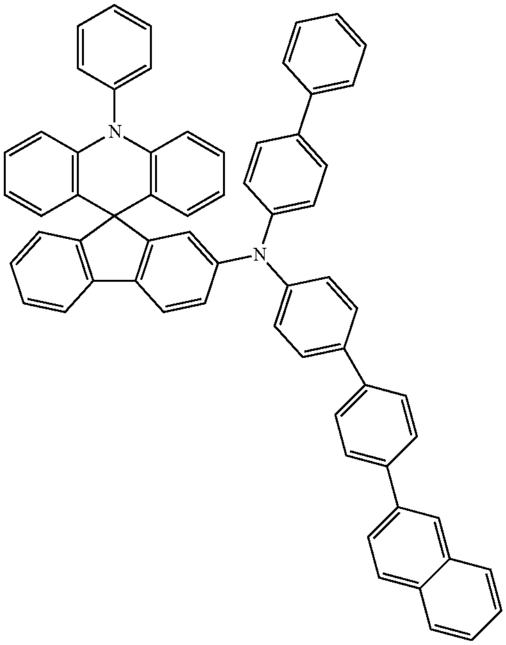

-continued
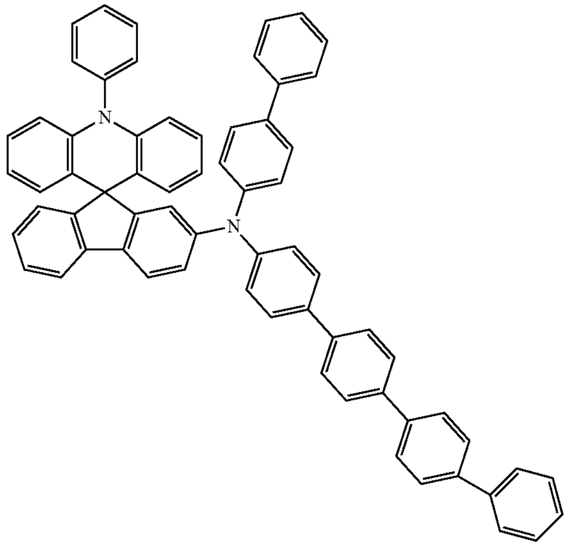
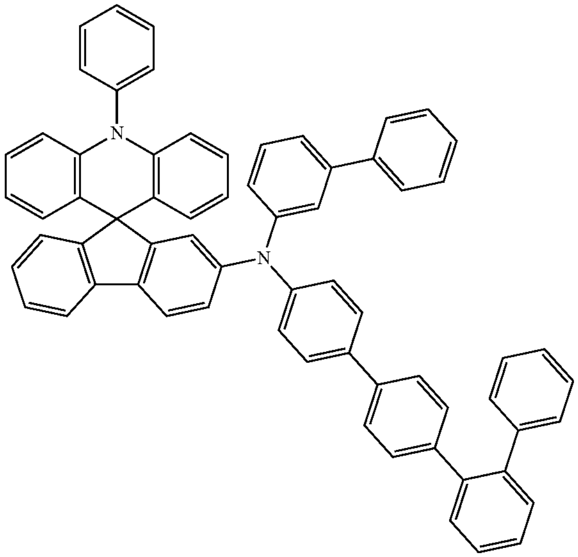
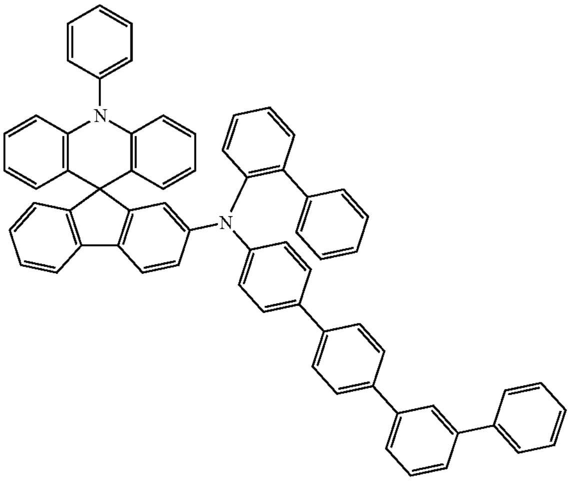
-continued
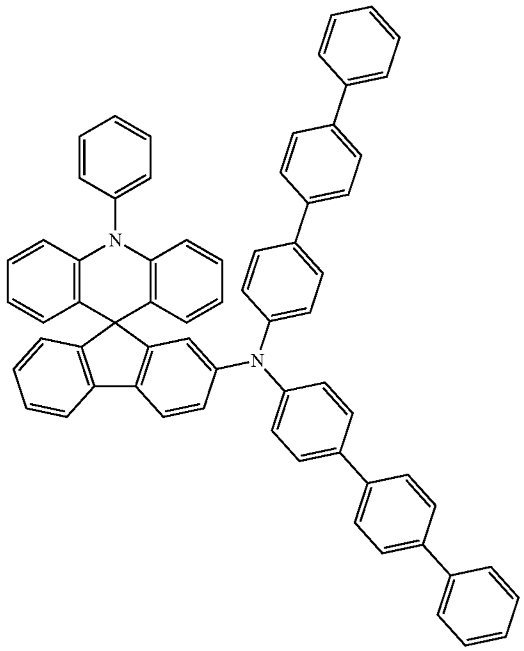
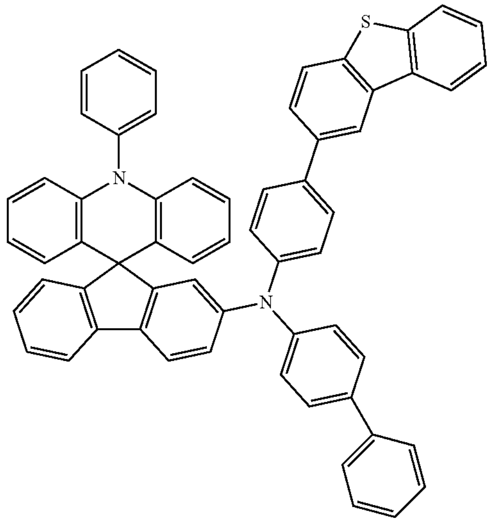
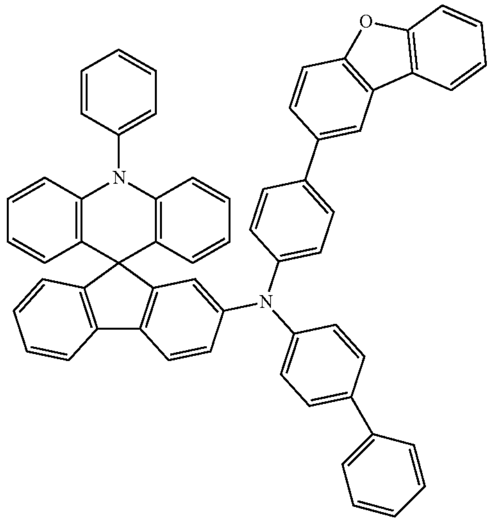

-continued
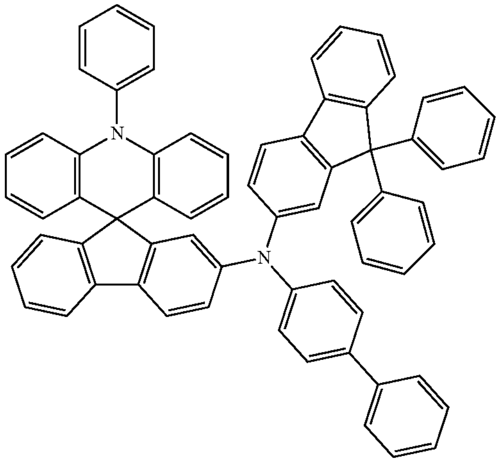
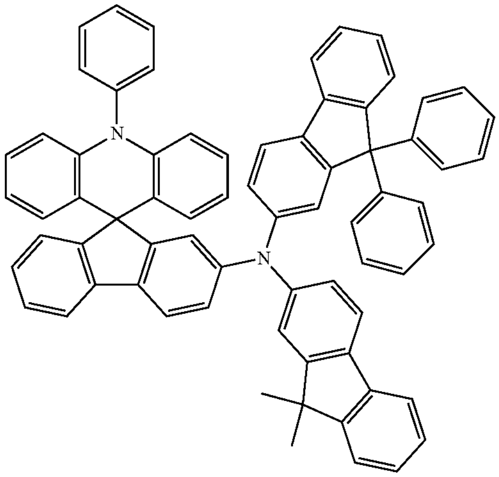
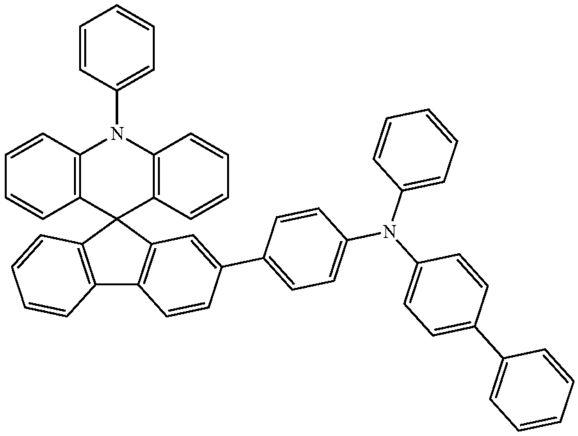
-continued
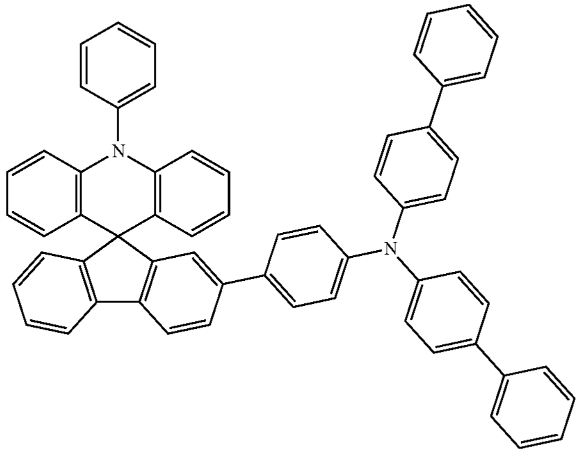
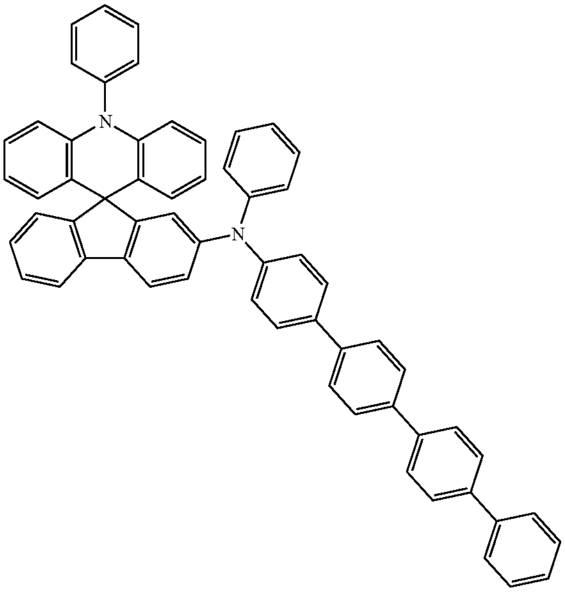
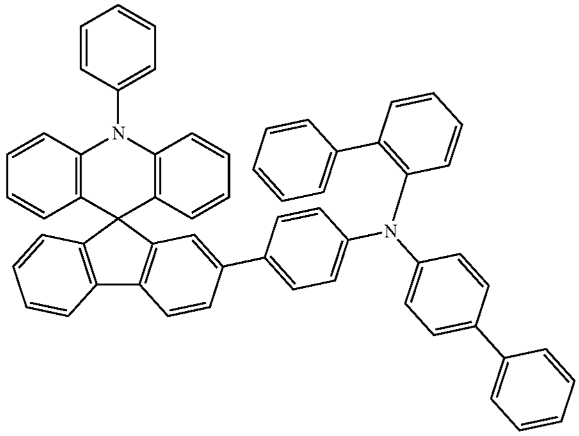

-continued
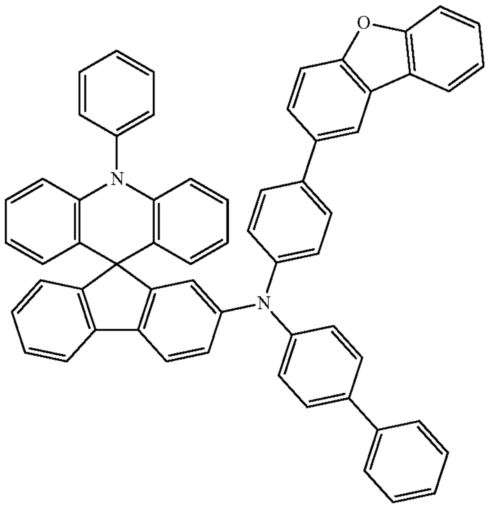
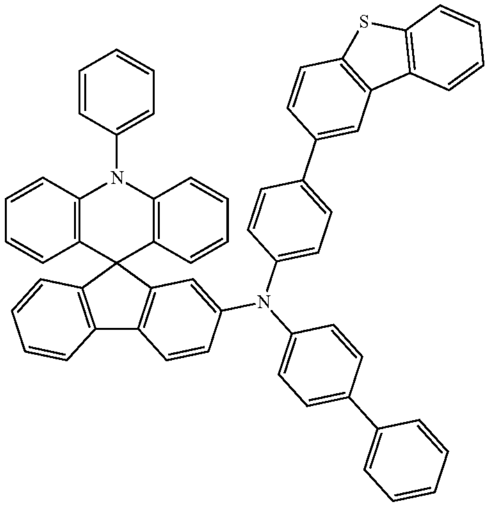
.
According to an exemplary embodiment of the present specification, Formula 3 is selected from among the following compounds:
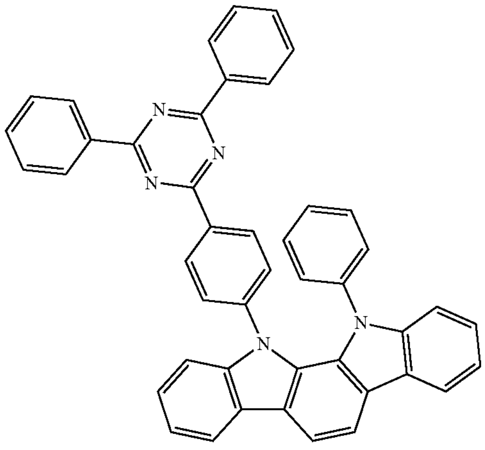
-continued
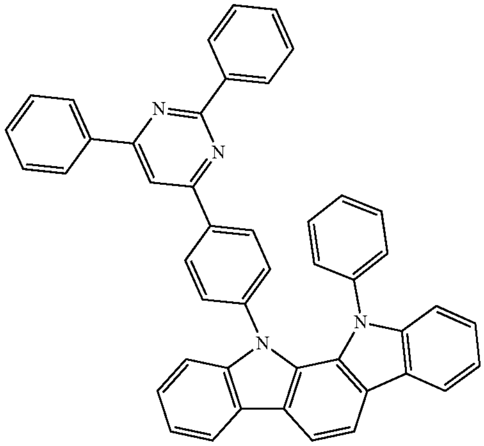
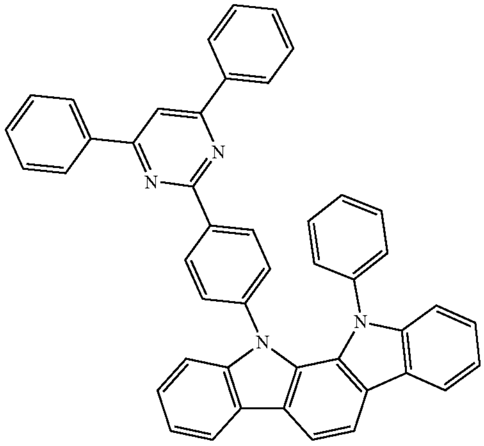
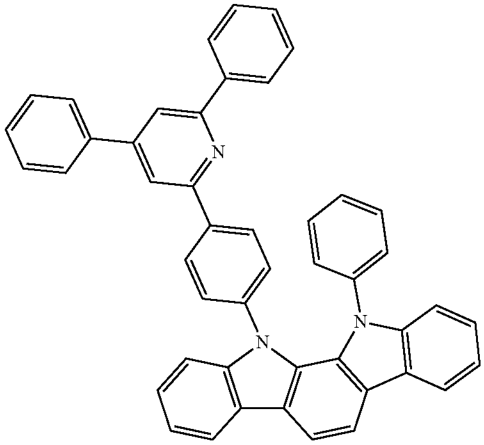

-continued
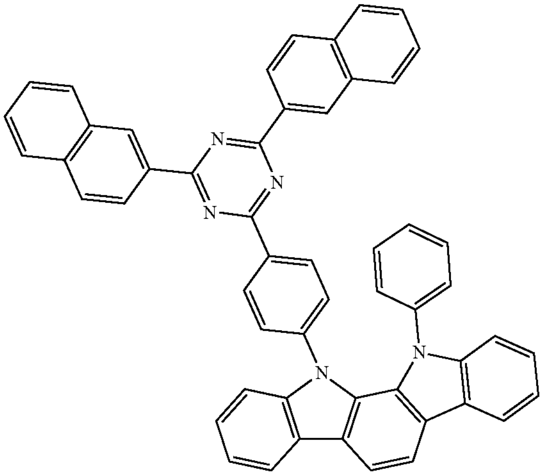
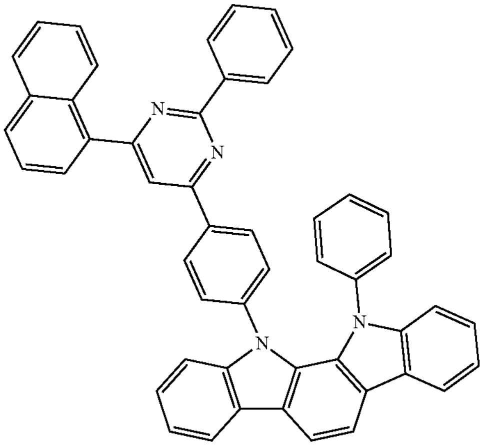
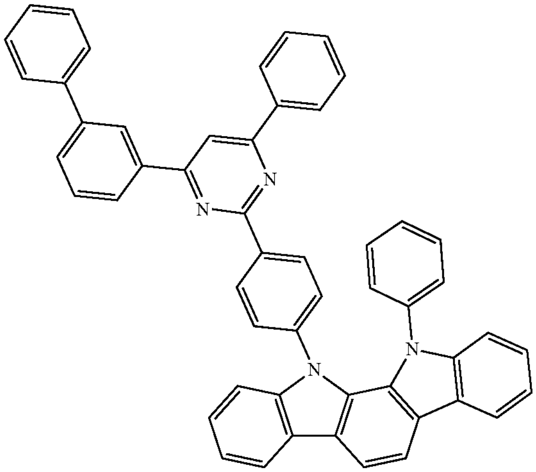
-continued
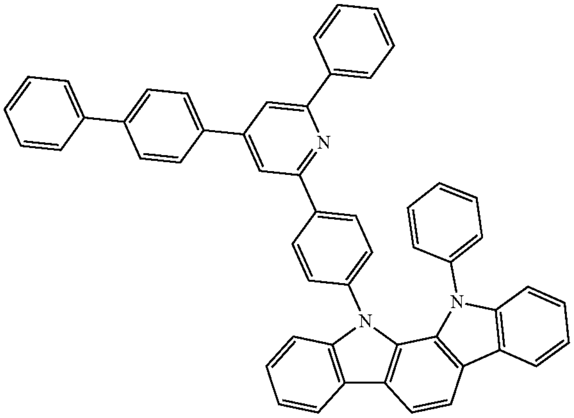
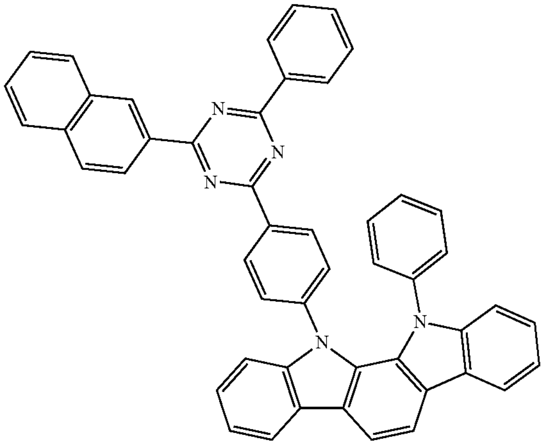
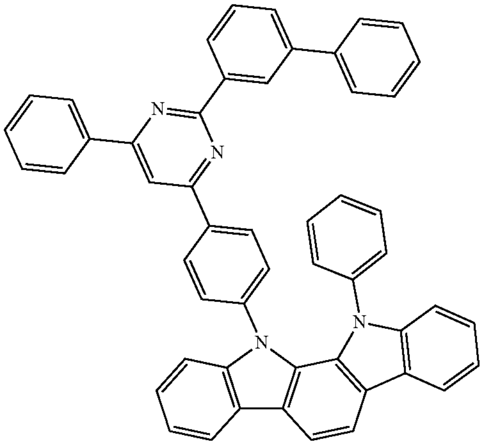

-continued
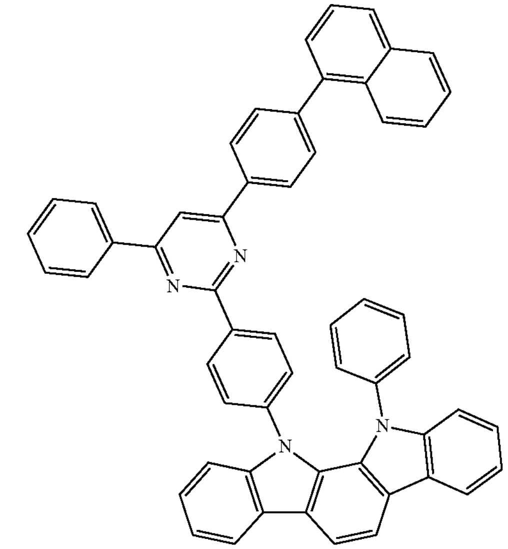
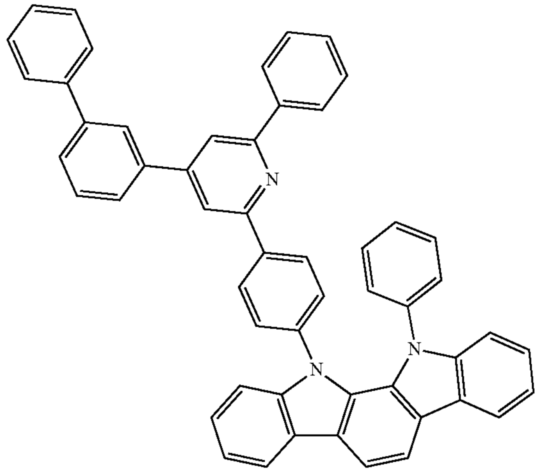
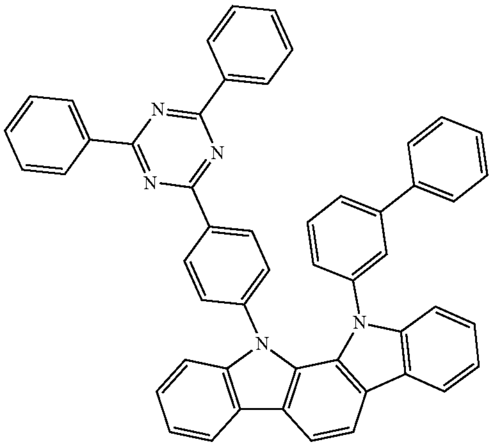
-continued
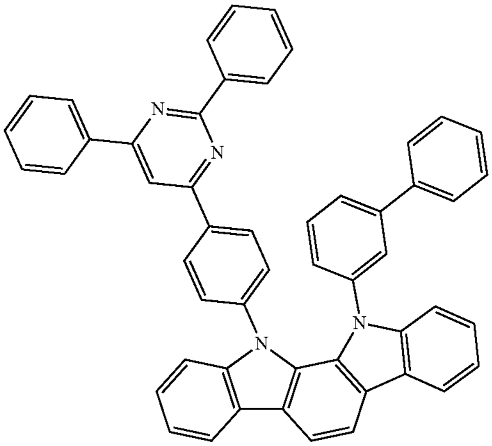
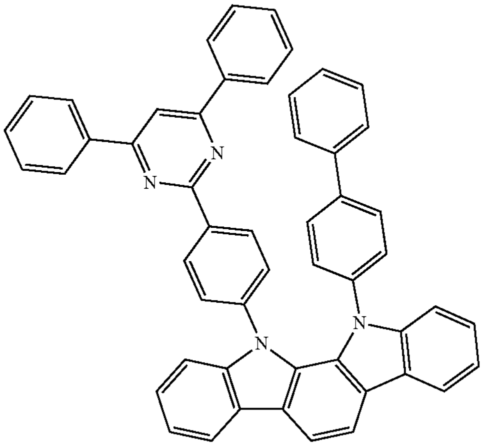
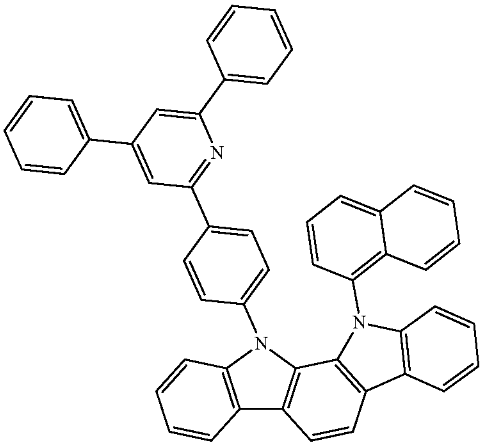

-continued
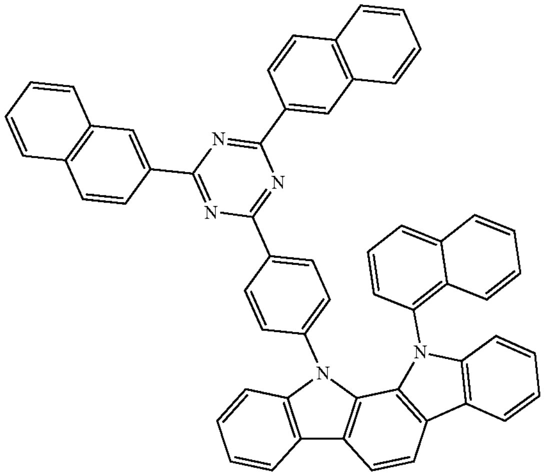
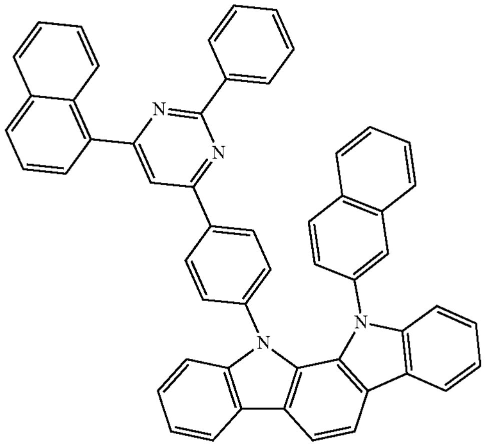
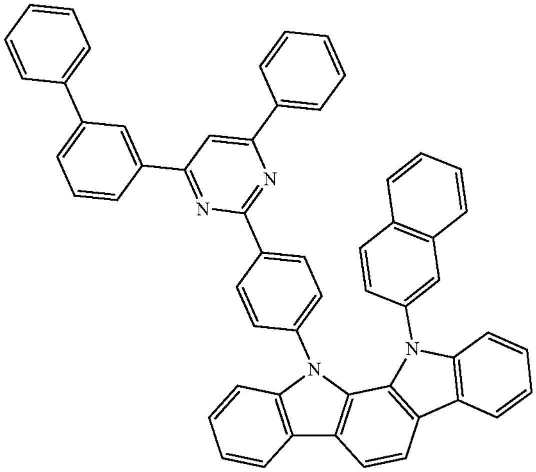
-continued
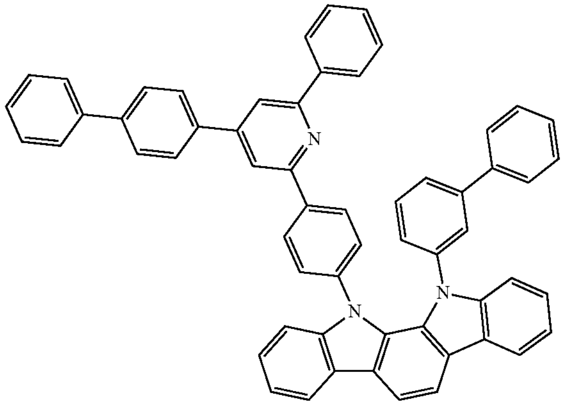
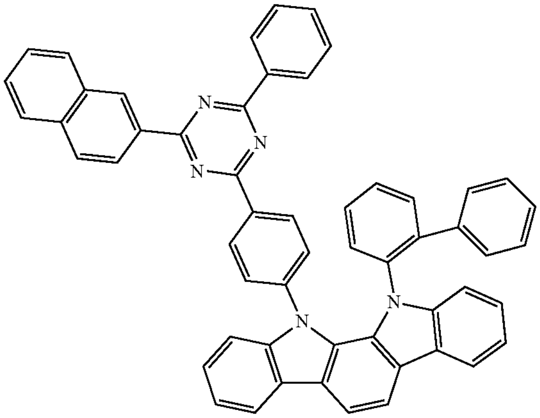
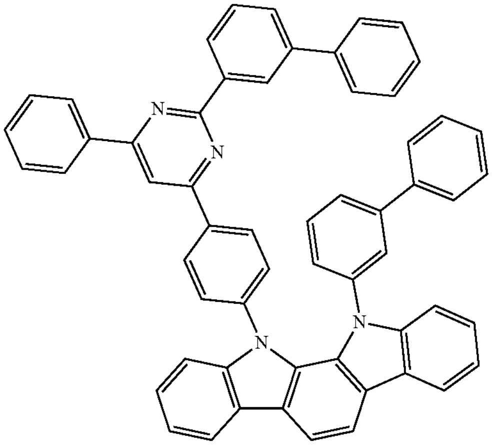

-continued
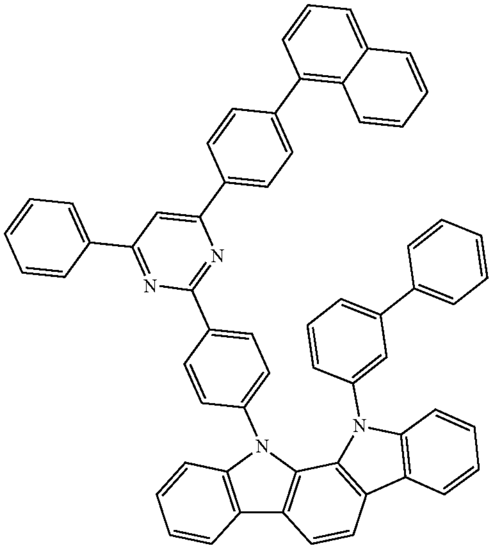
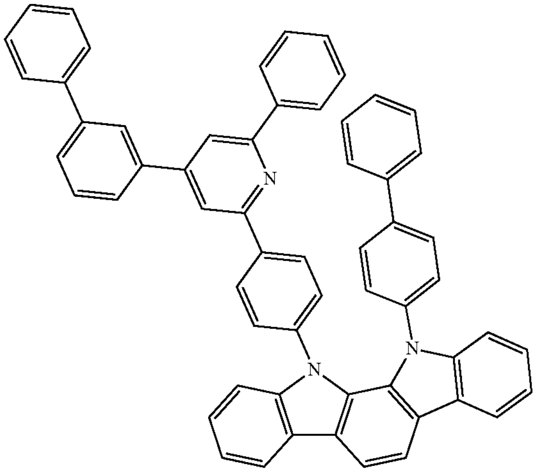
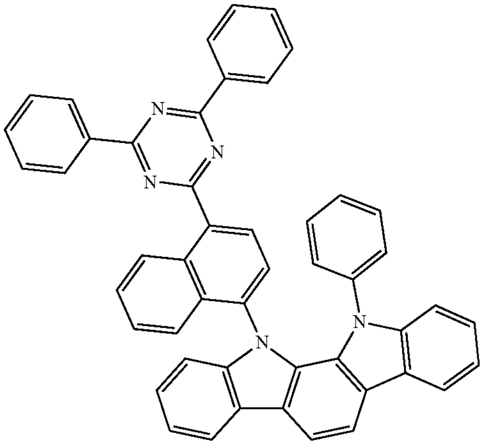
-continued
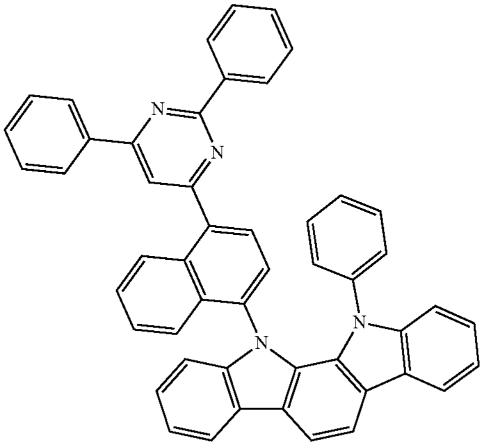
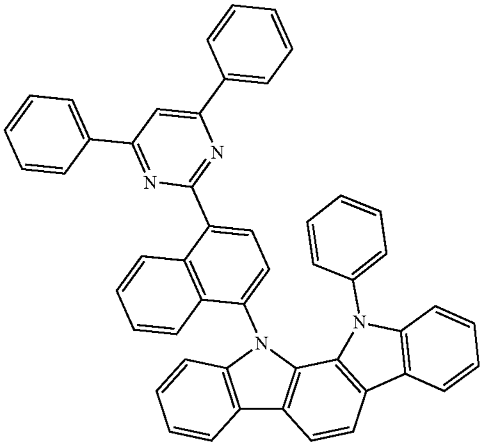
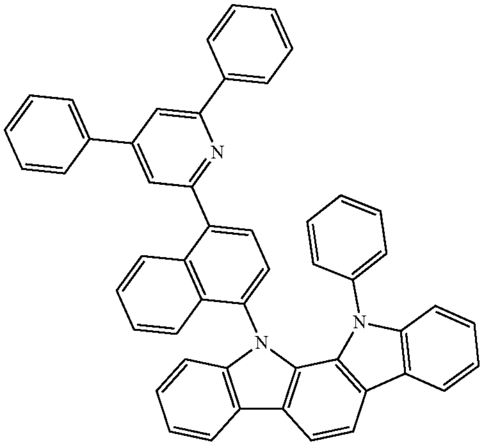

-continued
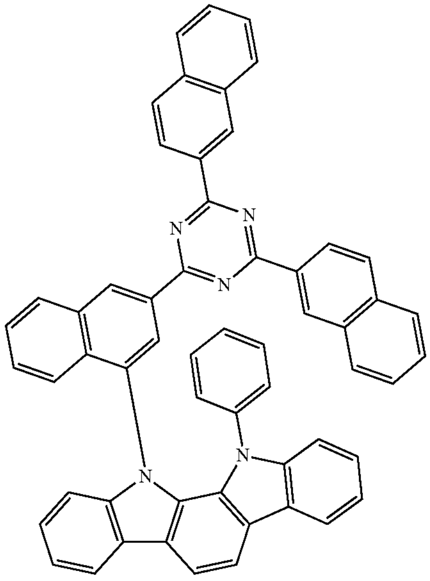
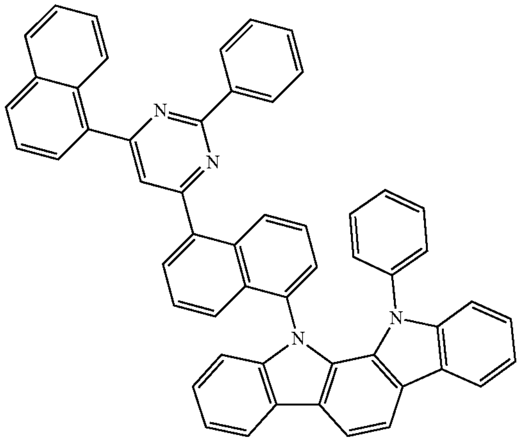
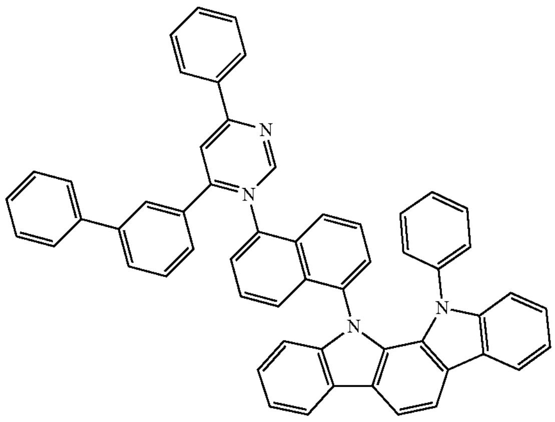
-continued
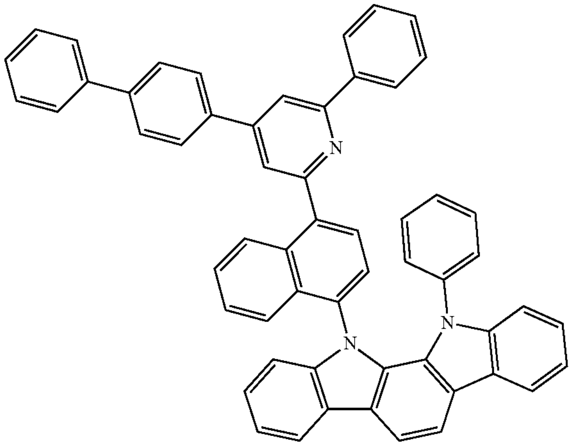
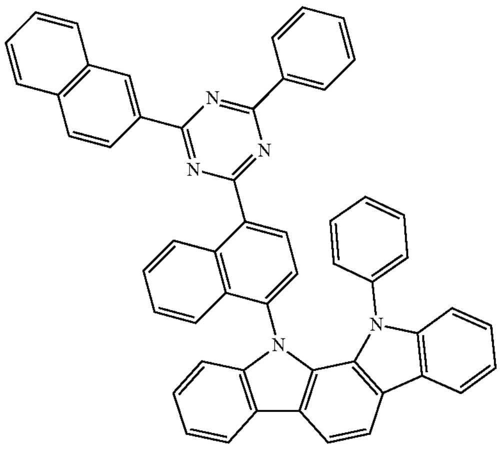
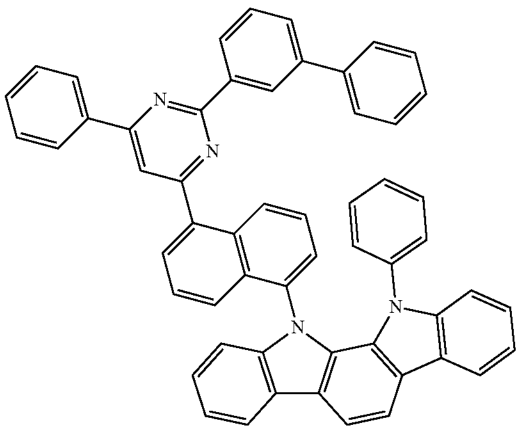

-continued
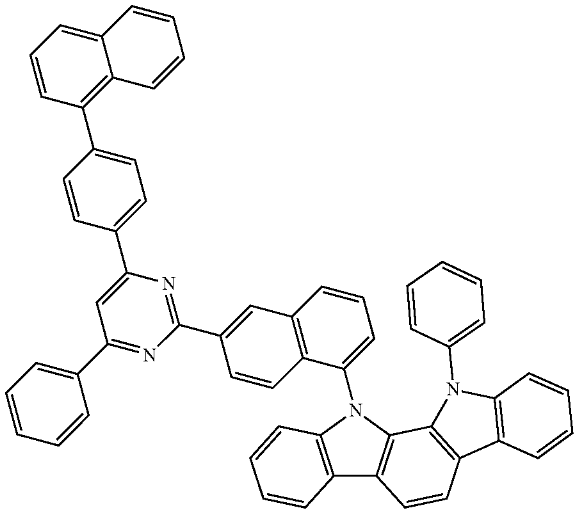
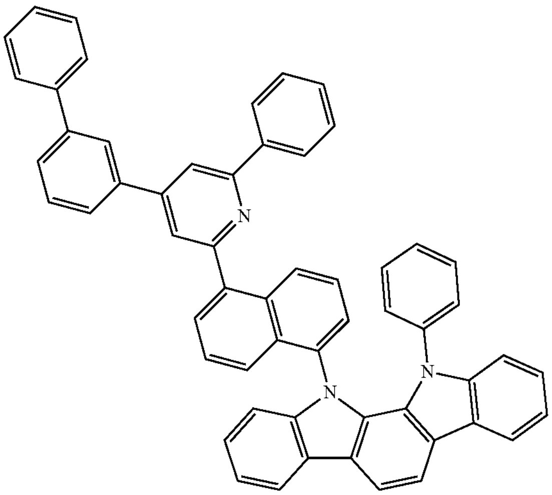
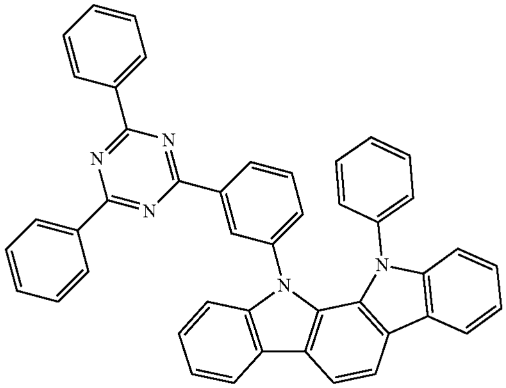
-continued
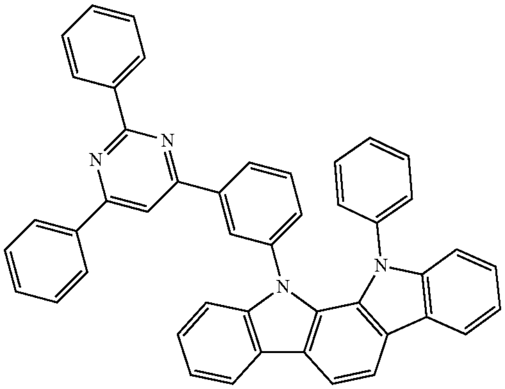
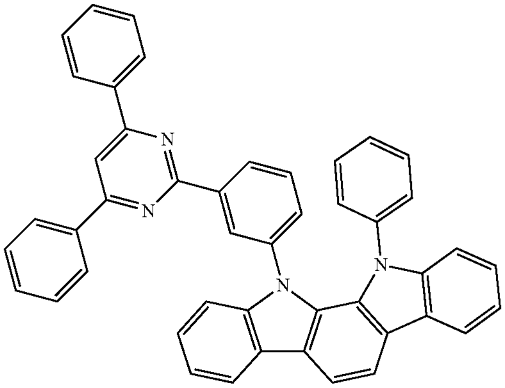
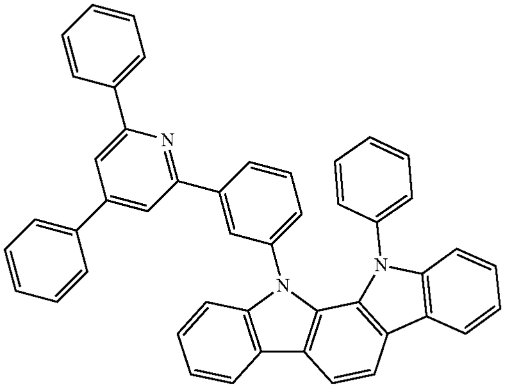
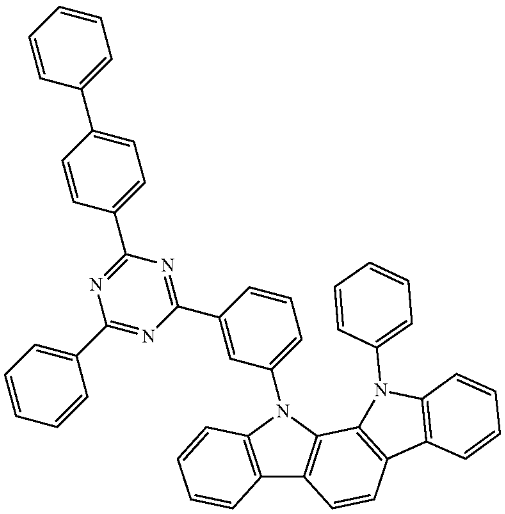

-continued
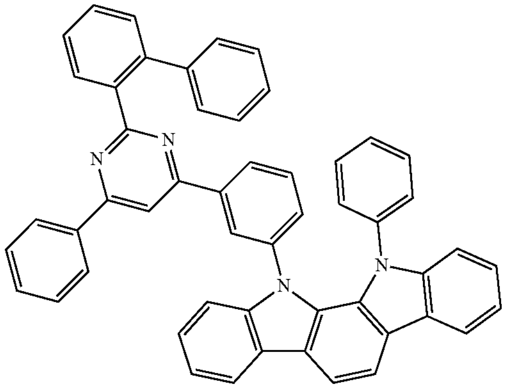
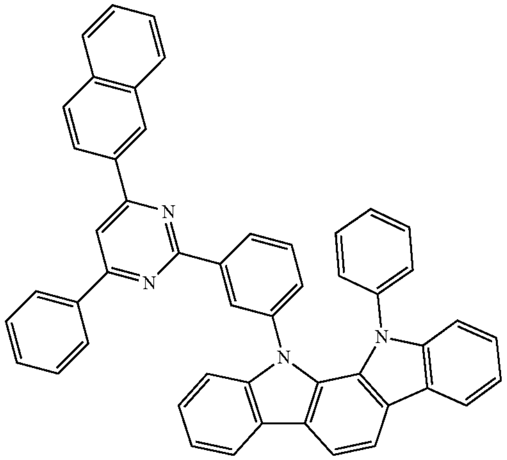
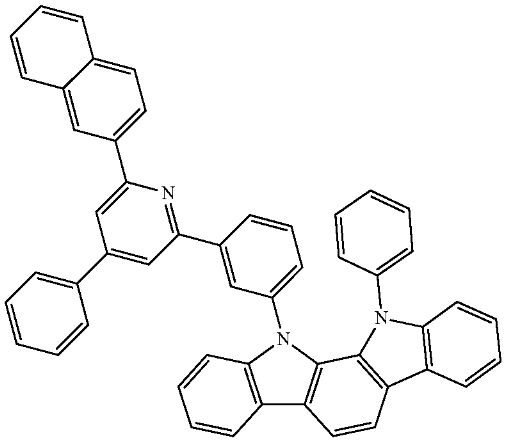
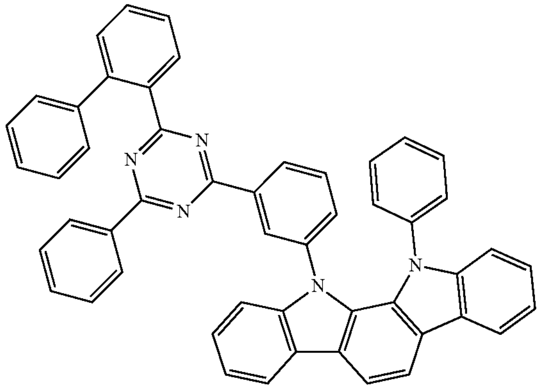
-continued
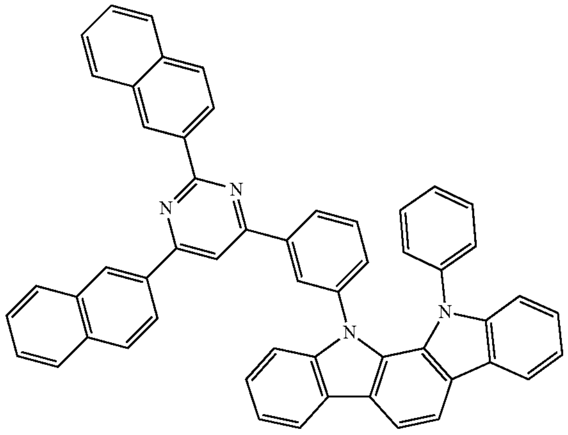
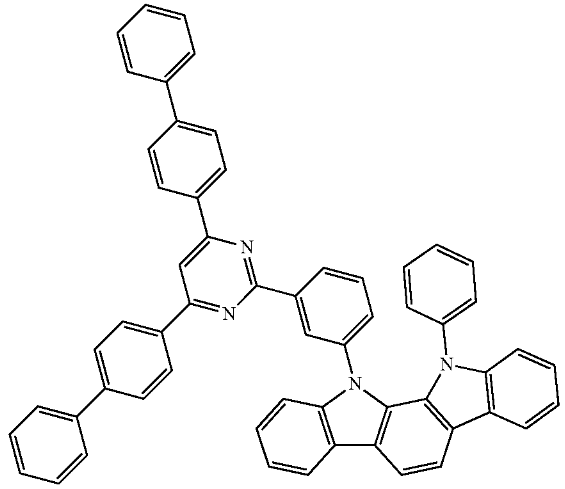
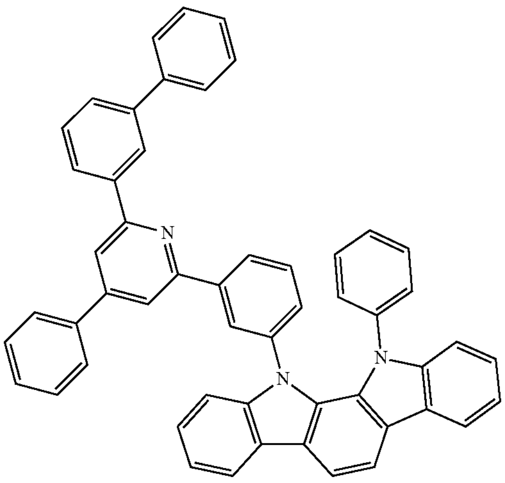

-continued
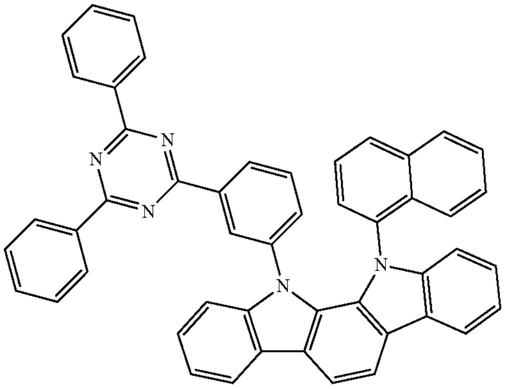
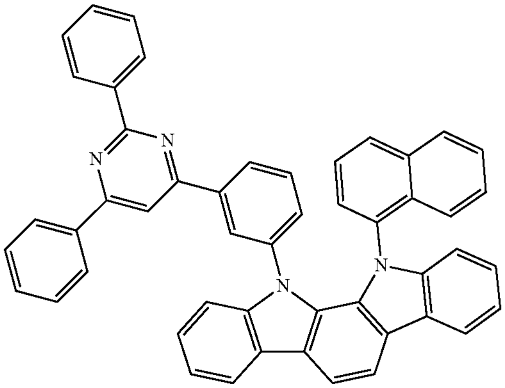
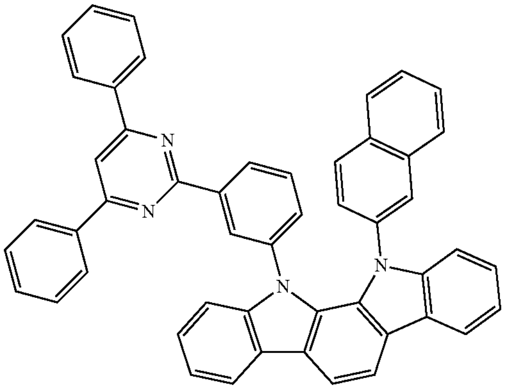
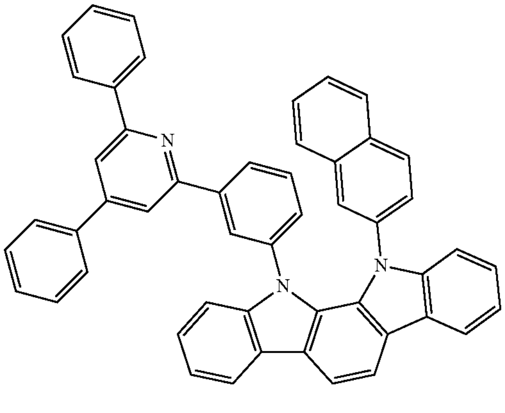
-continued
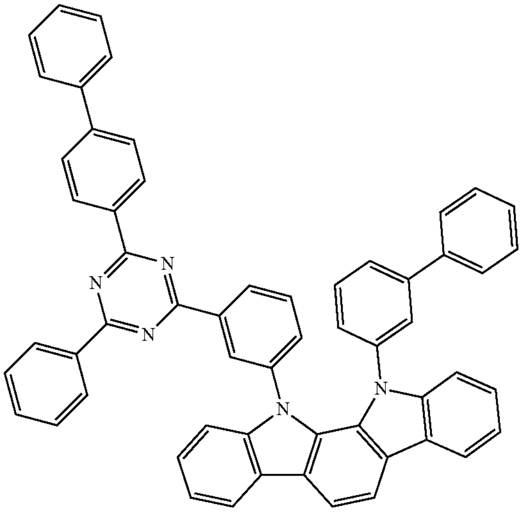
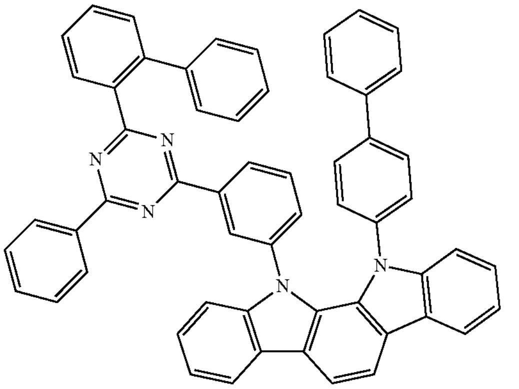
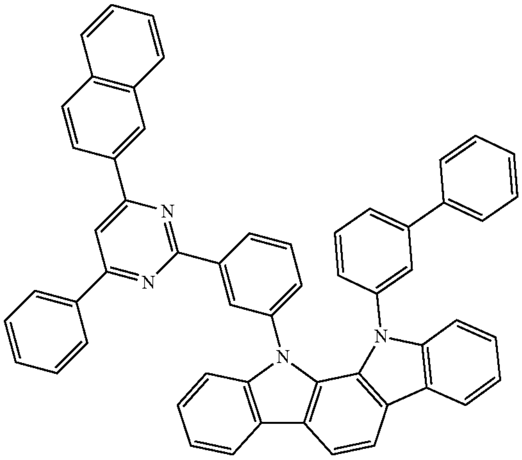

-continued
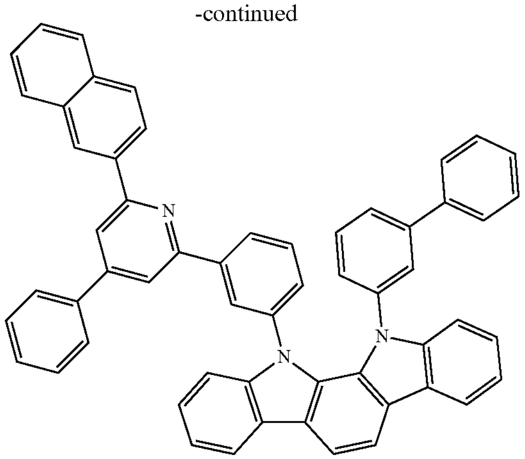
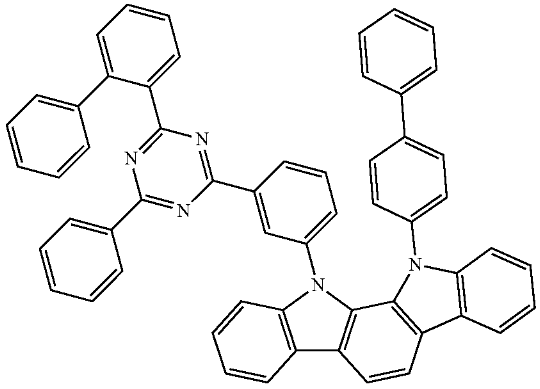
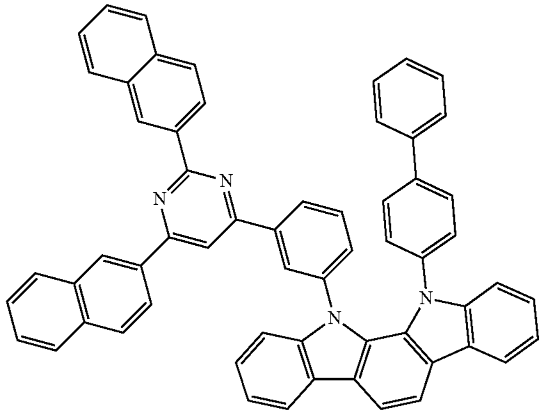
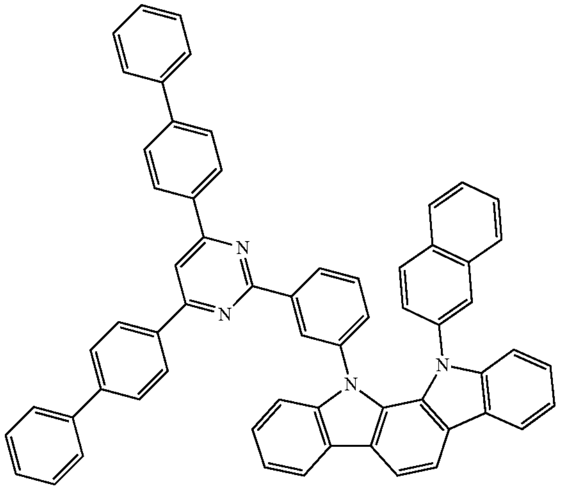
-continued
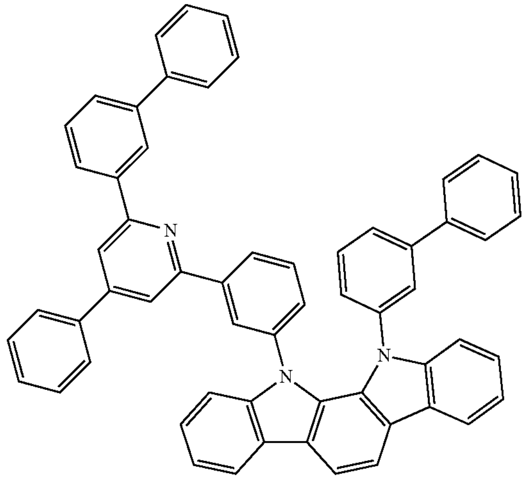
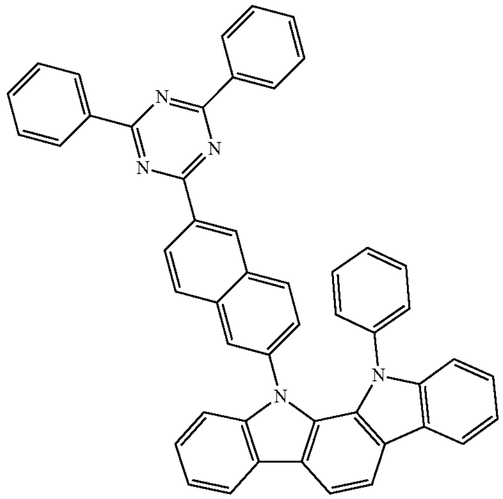
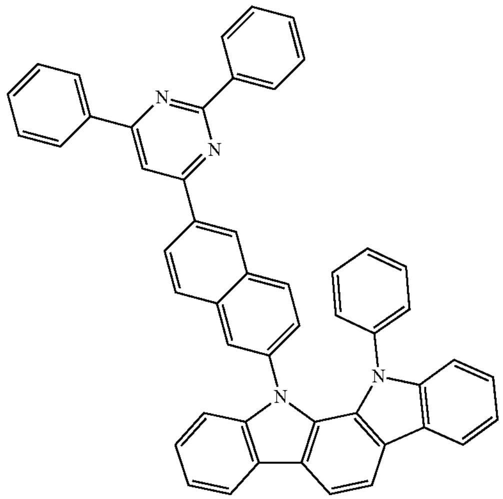

-continued
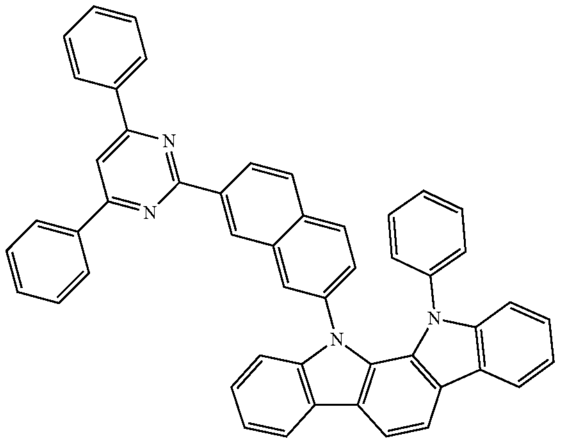
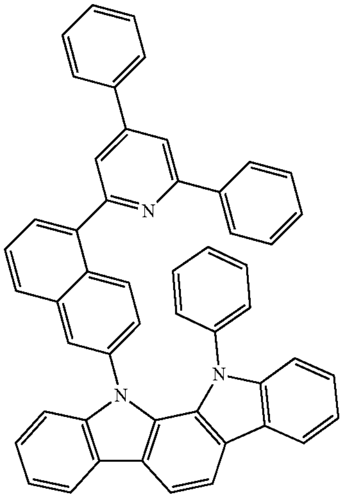
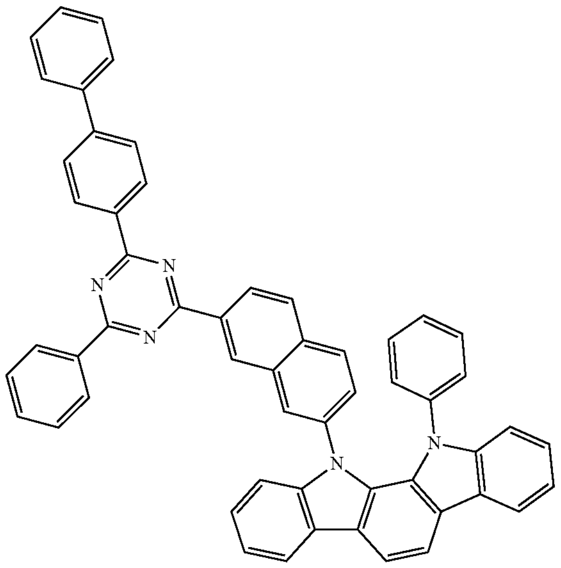
-continued
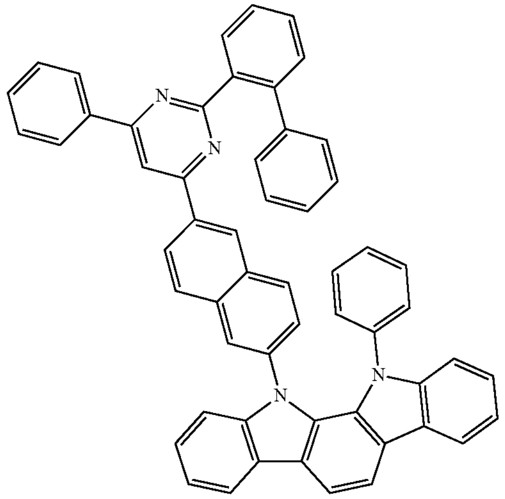
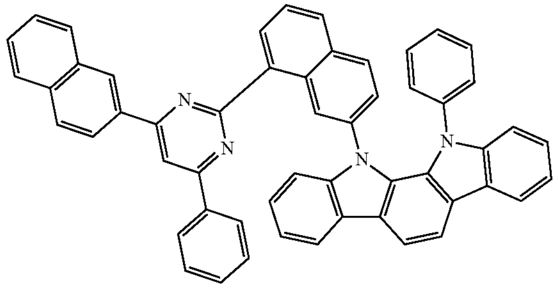
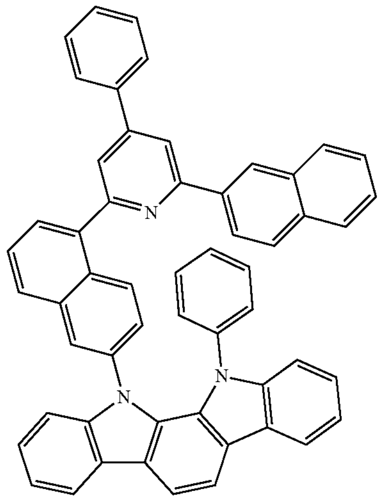

-continued
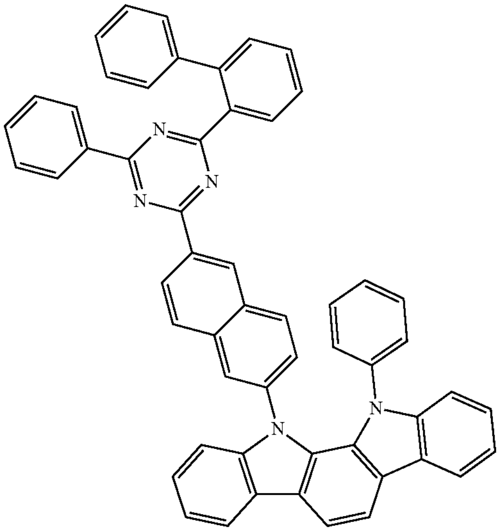
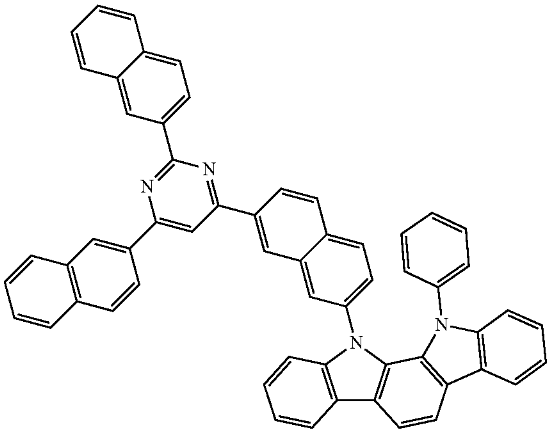
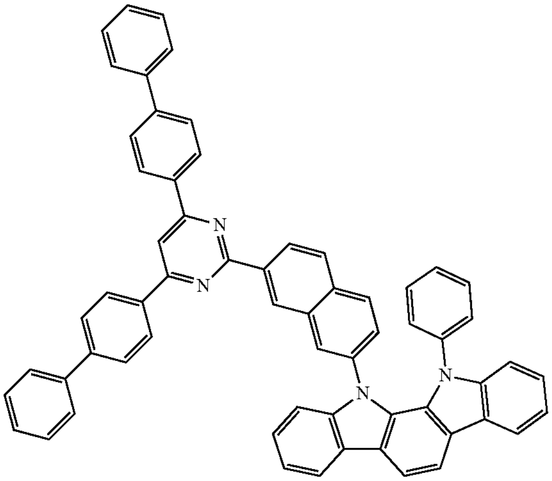
-continued
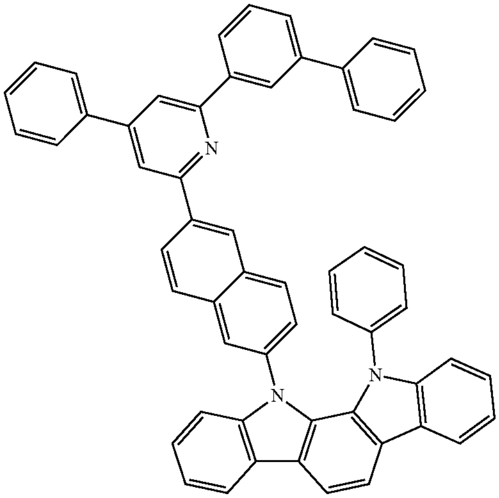
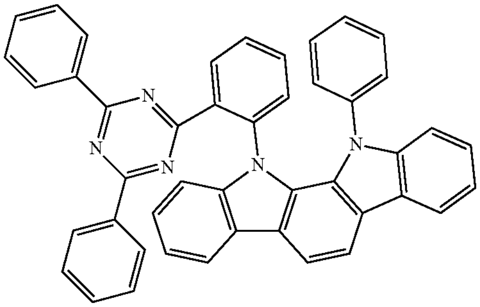
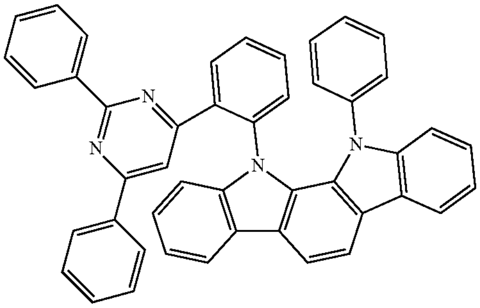
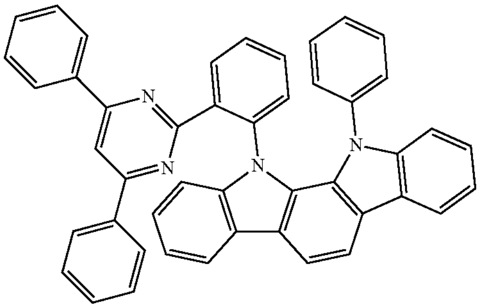
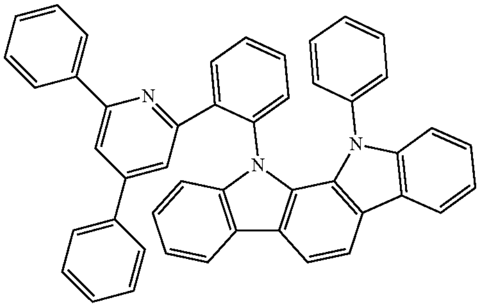

-continued
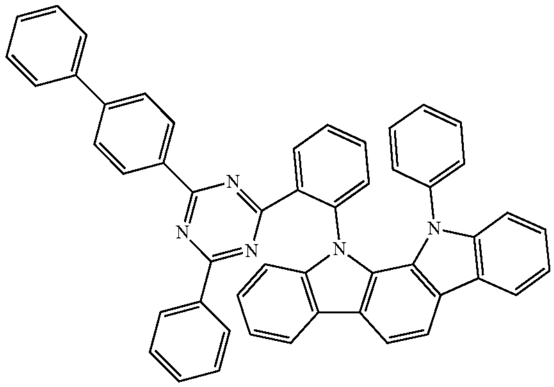
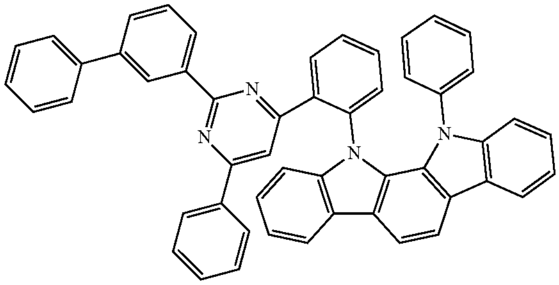
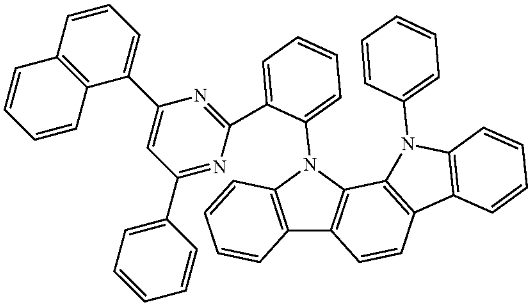
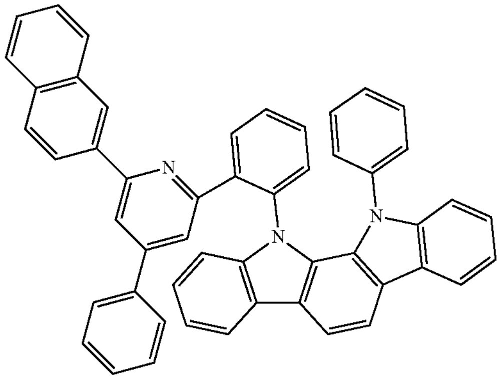
-continued
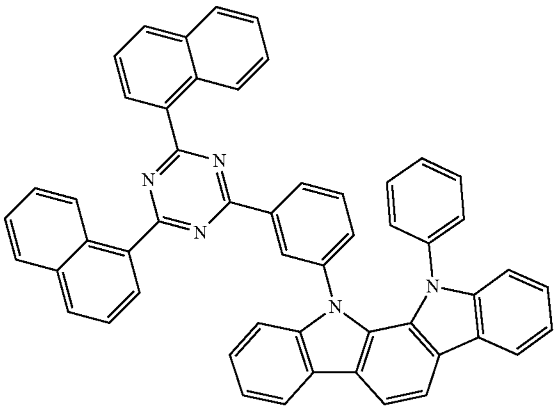
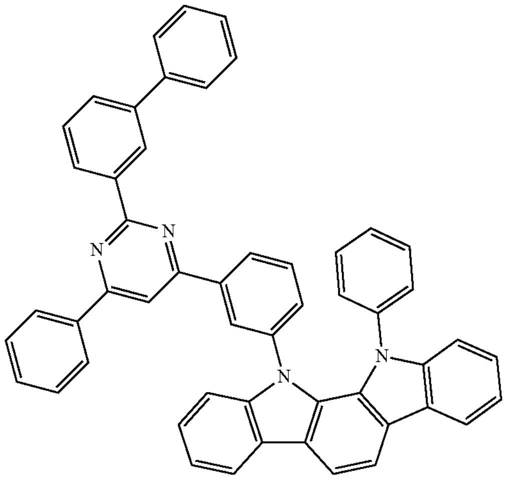
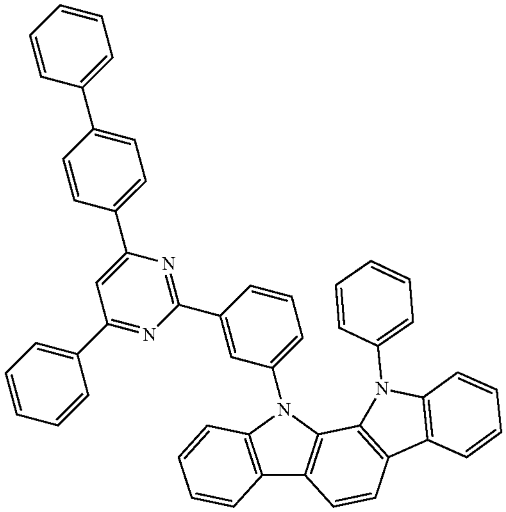

-continued
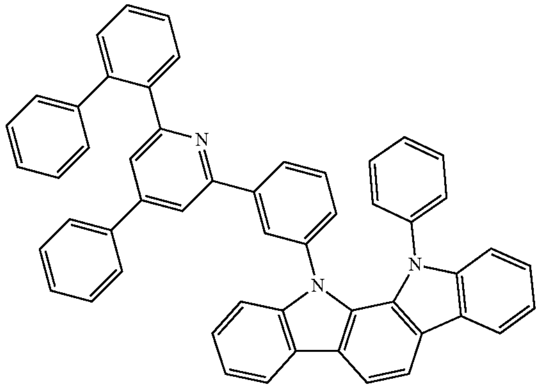
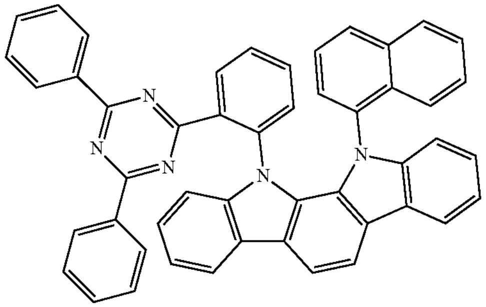
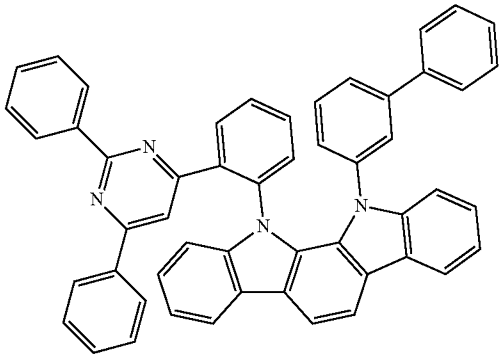
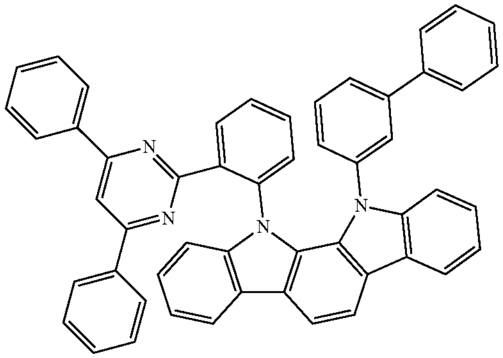
-continued
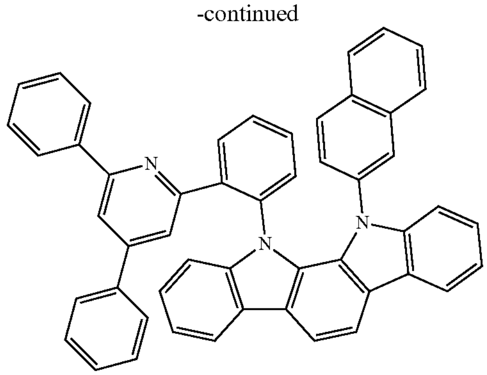
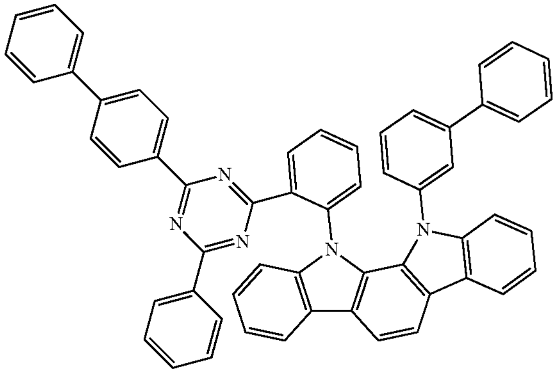
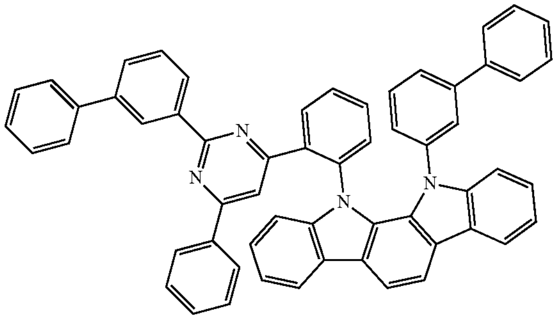
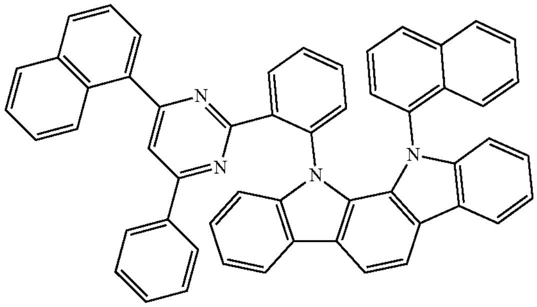
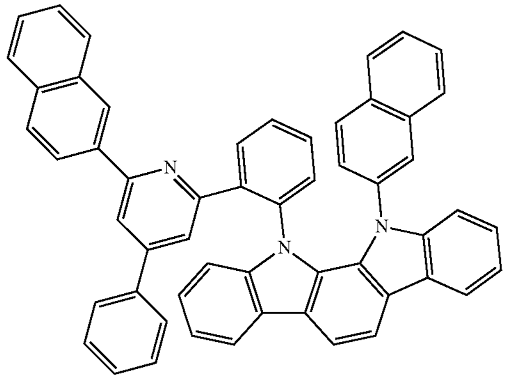

-continued
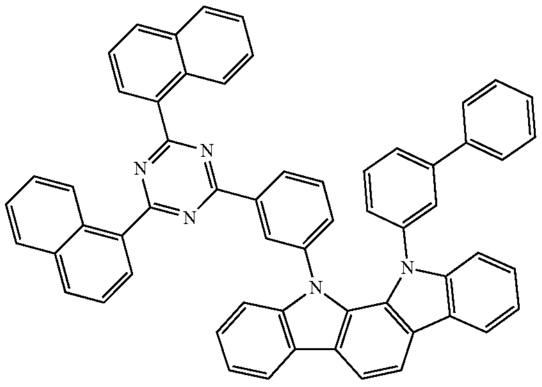
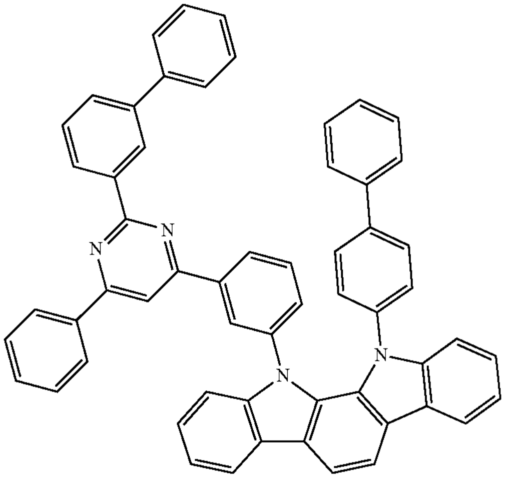
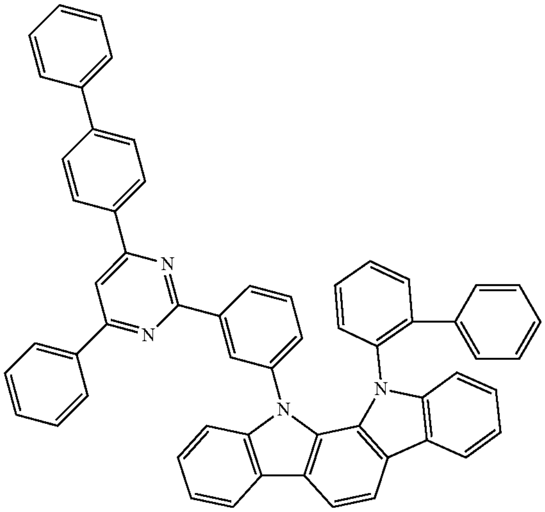
-continued
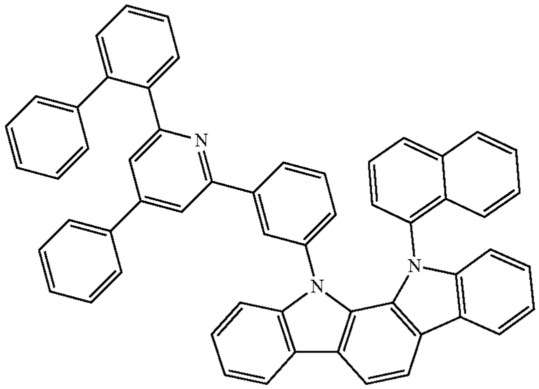
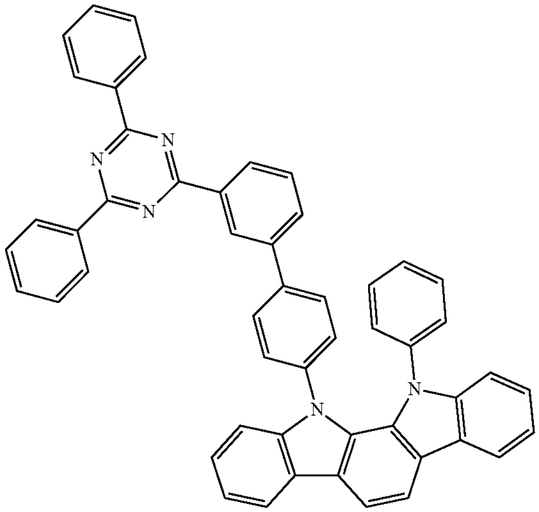
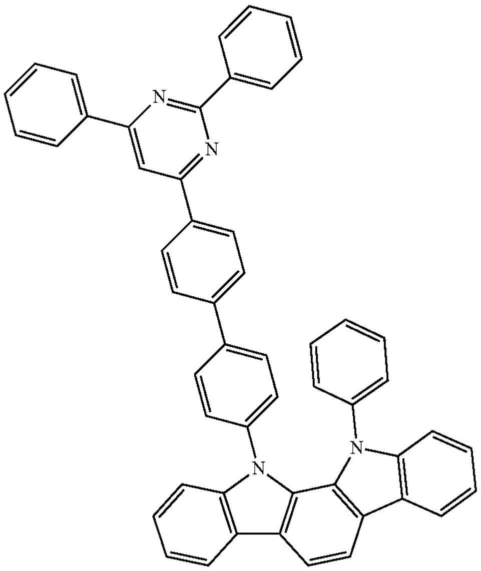

-continued
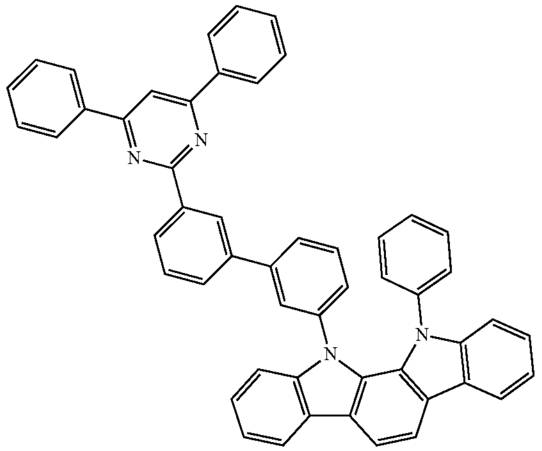
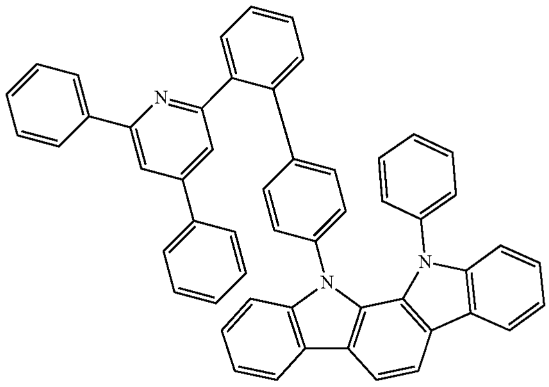
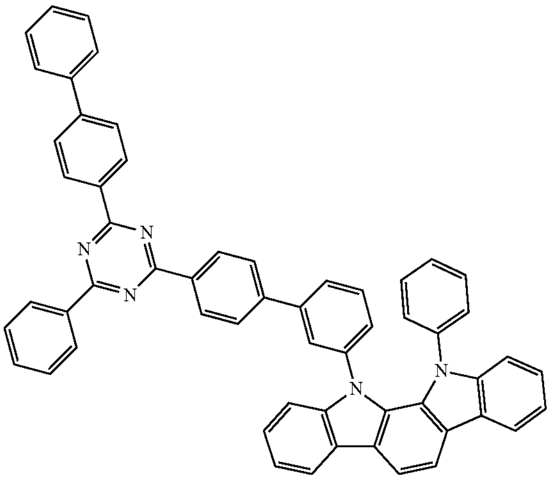
-continued
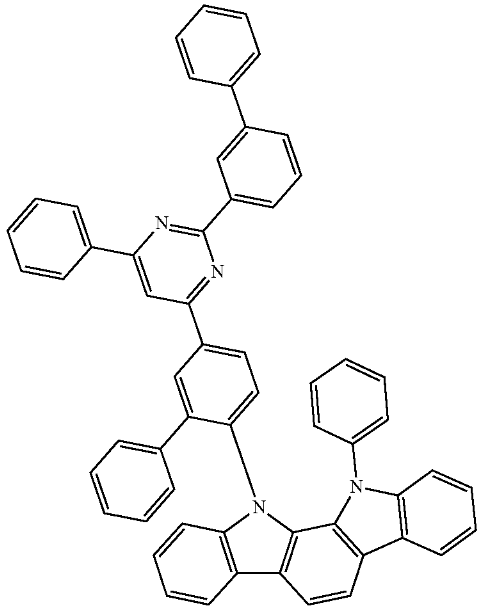
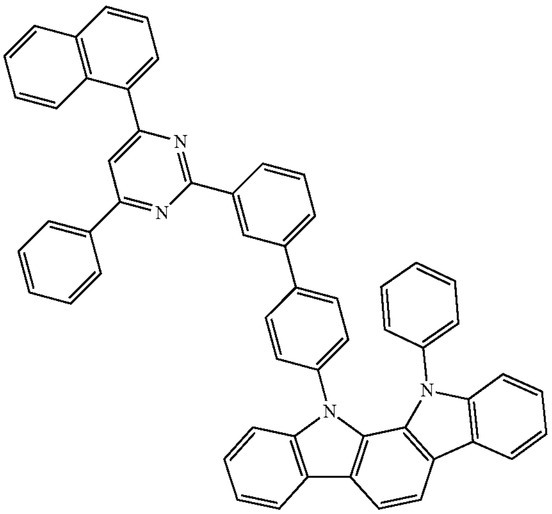
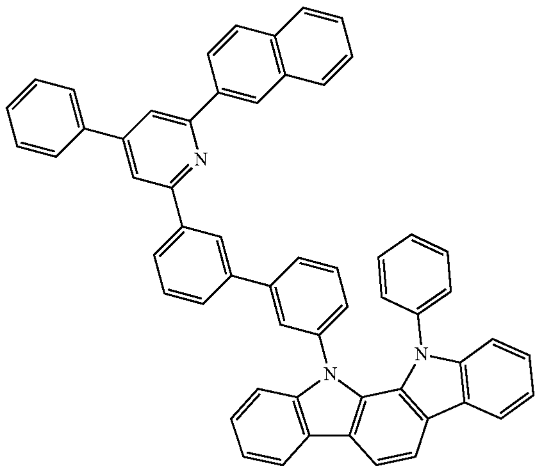

-continued
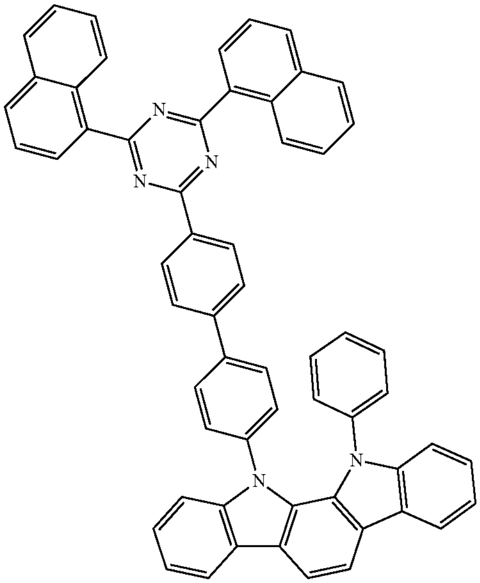
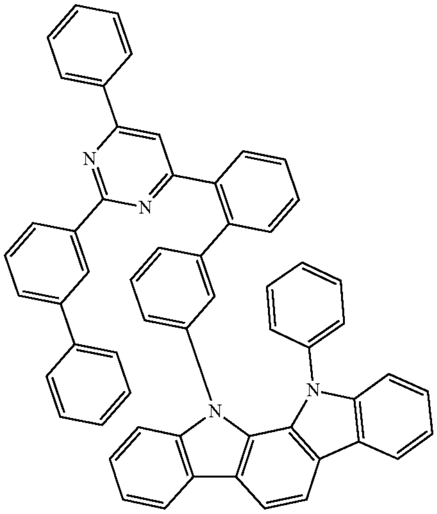
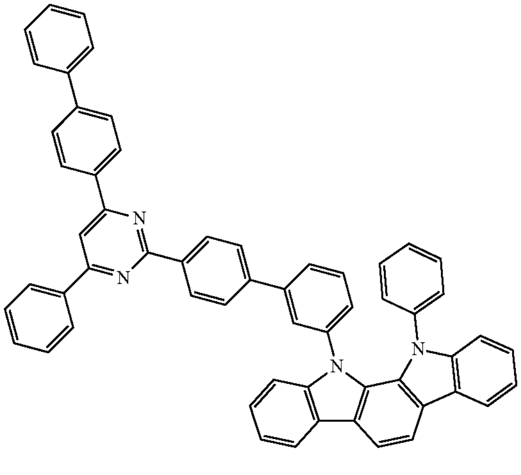
-continued
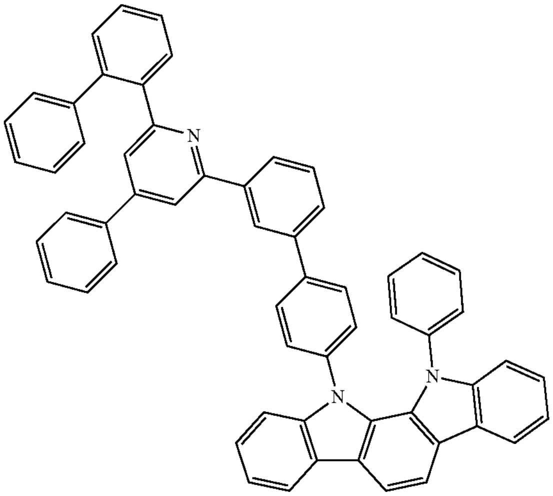
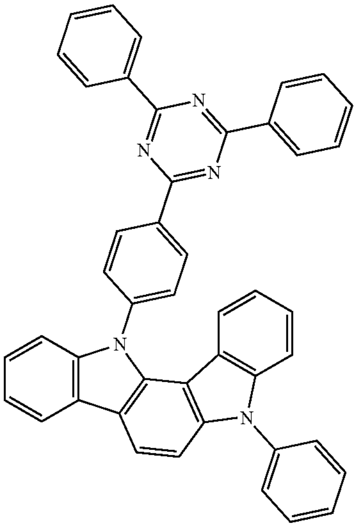
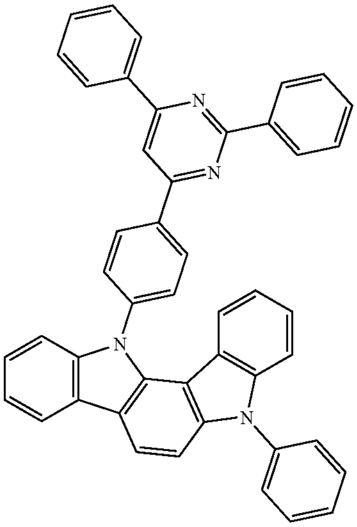

-continued
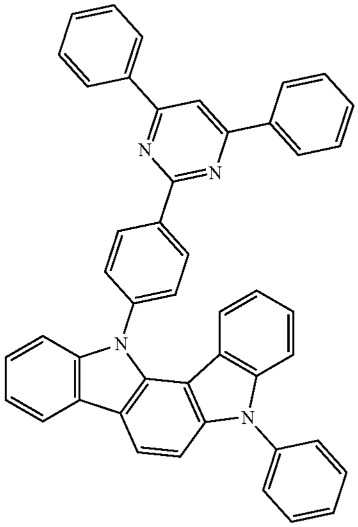
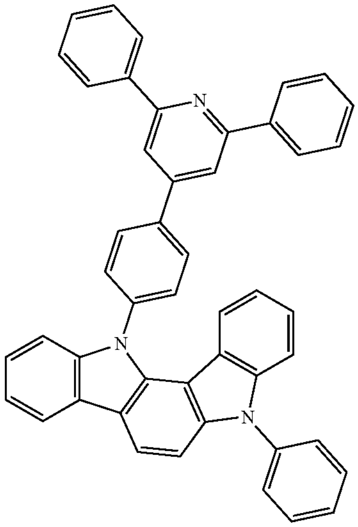
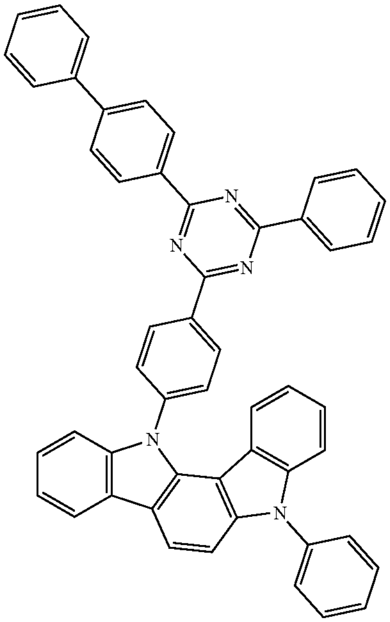
-continued
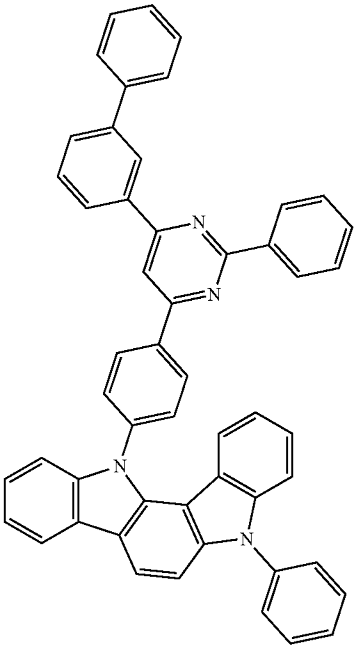
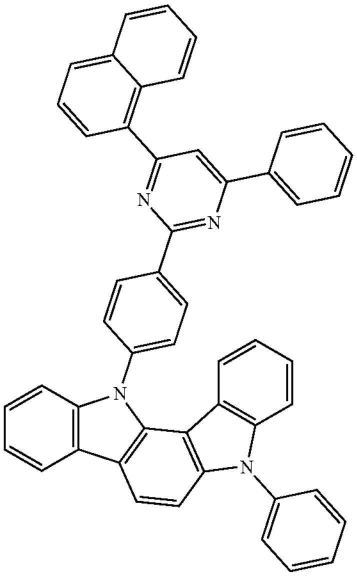

-continued
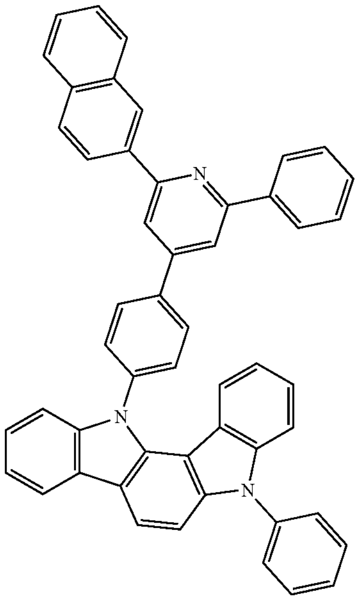
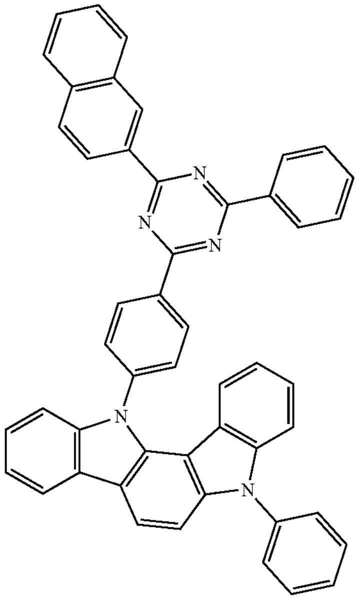
-continued
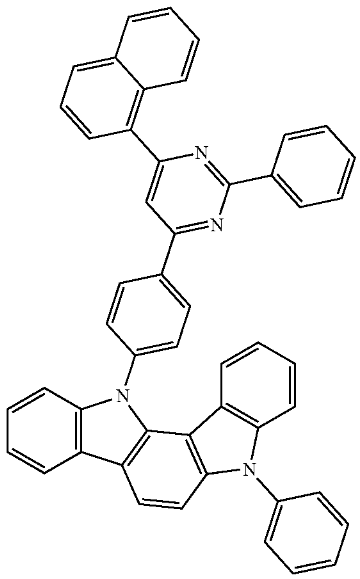
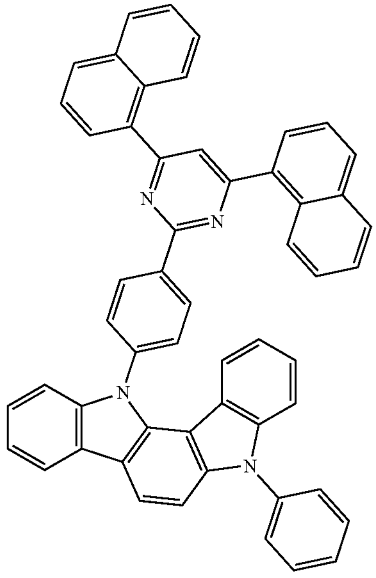

-continued
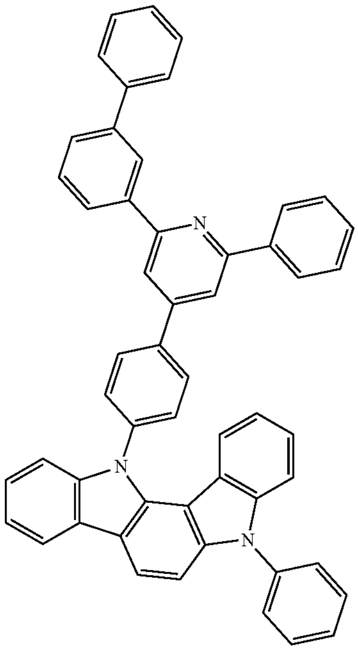
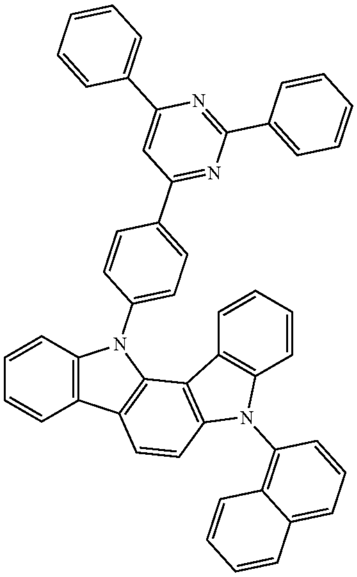
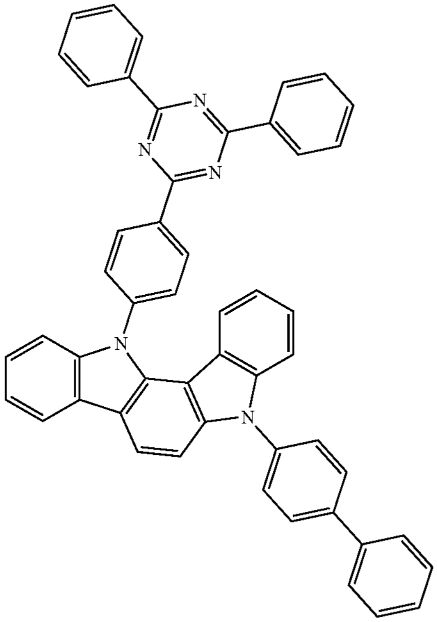
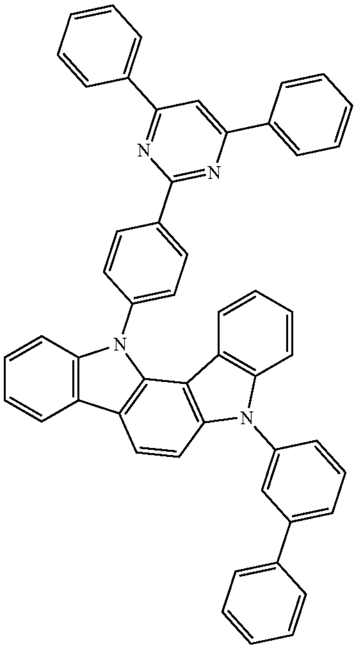
-continued

-continued
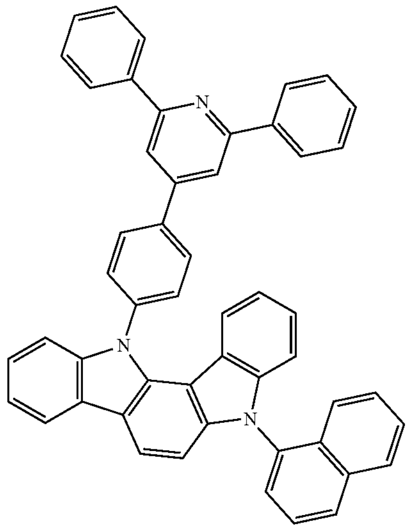
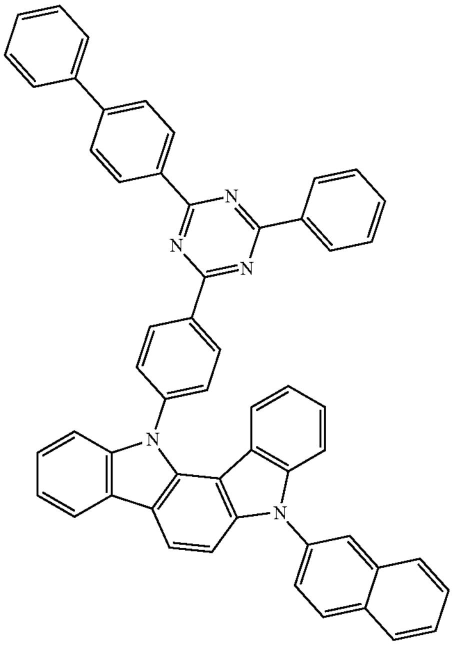
-continued
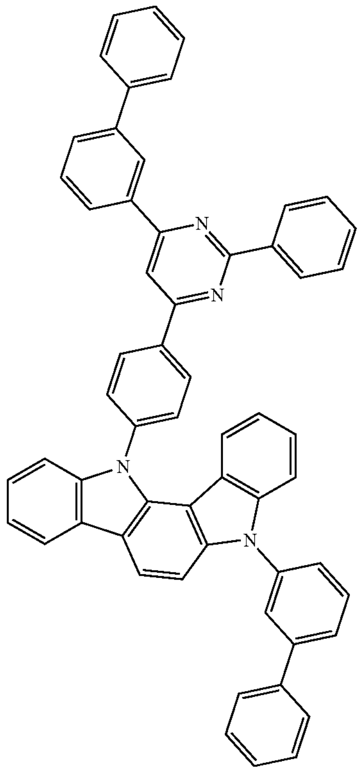
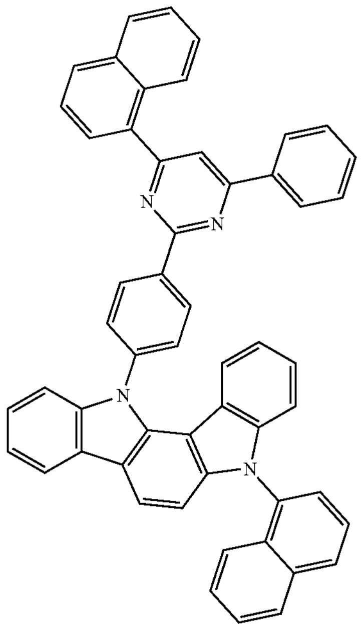

-continued
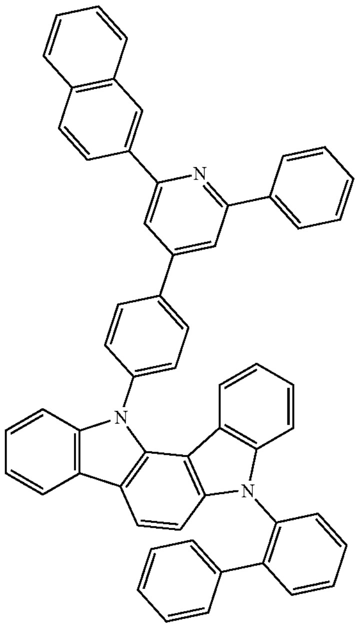
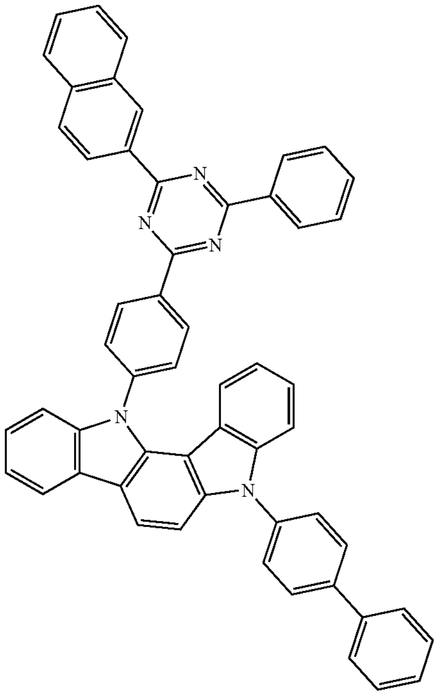
-continued
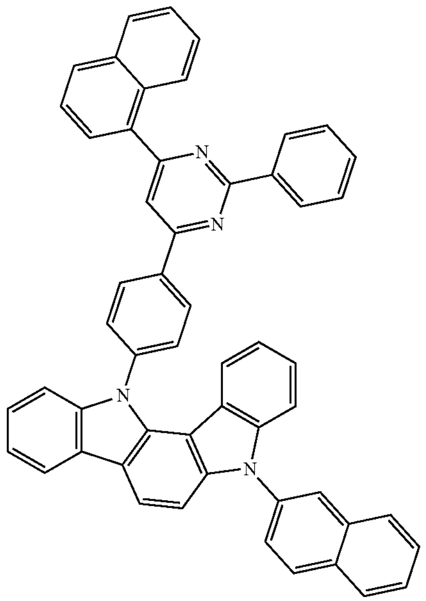
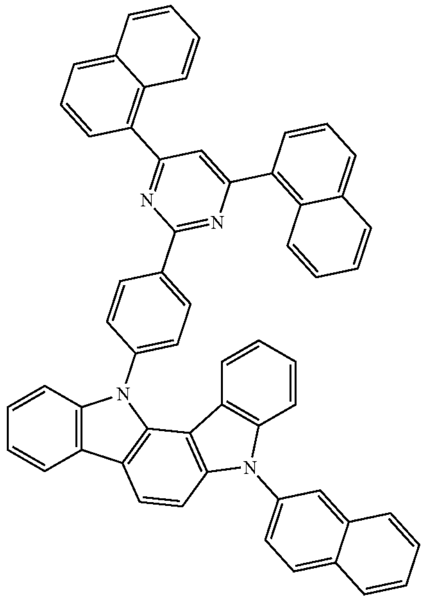

-continued
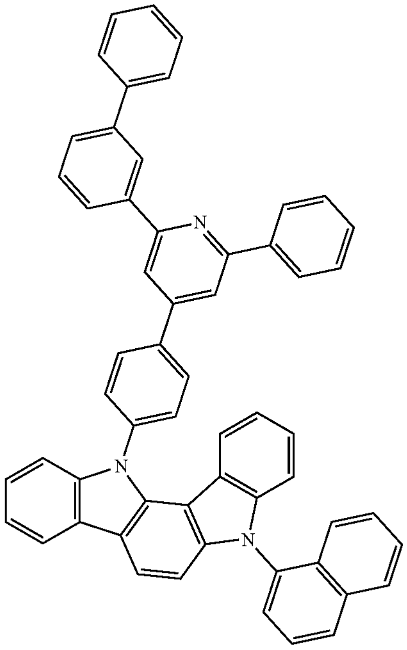
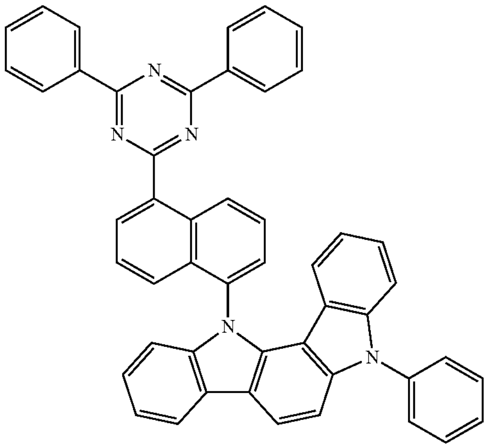
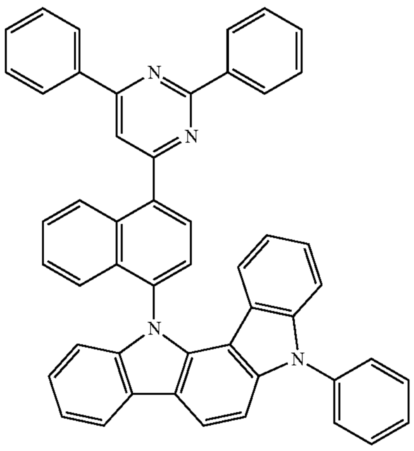
-continued
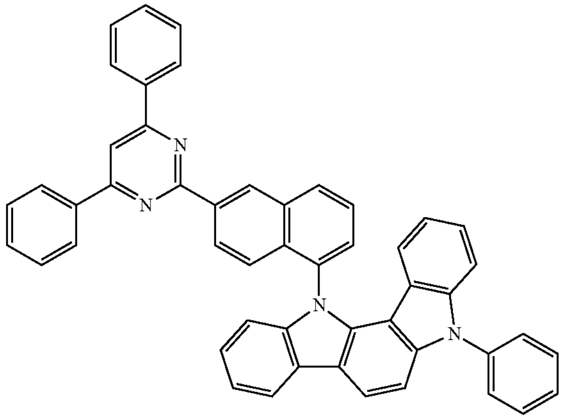
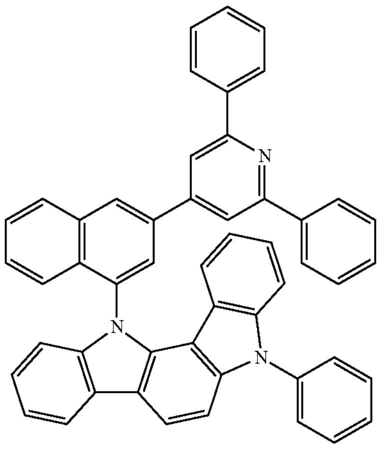
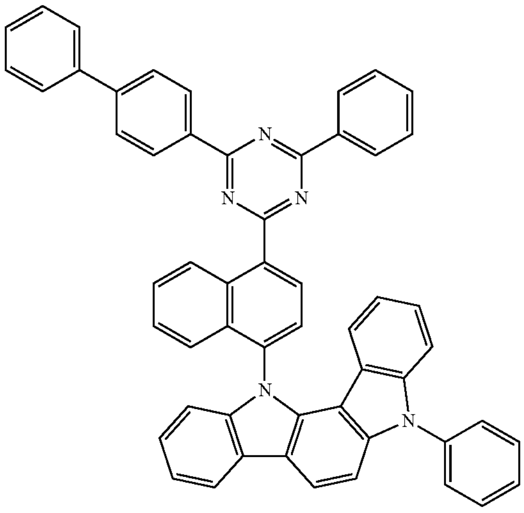

-continued
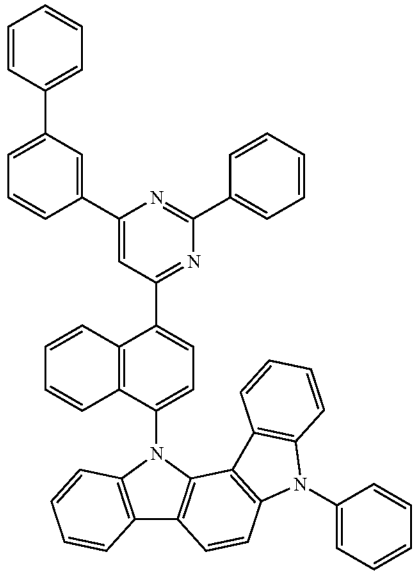
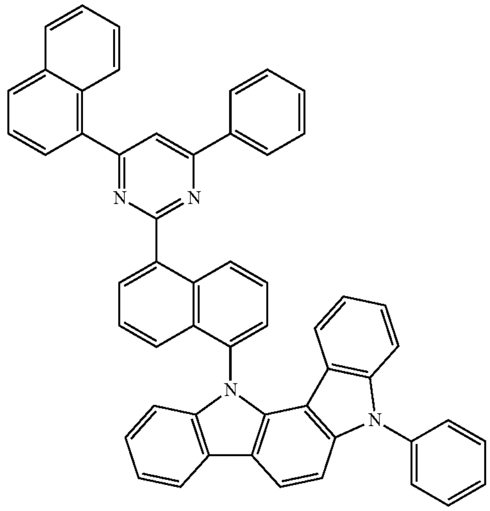
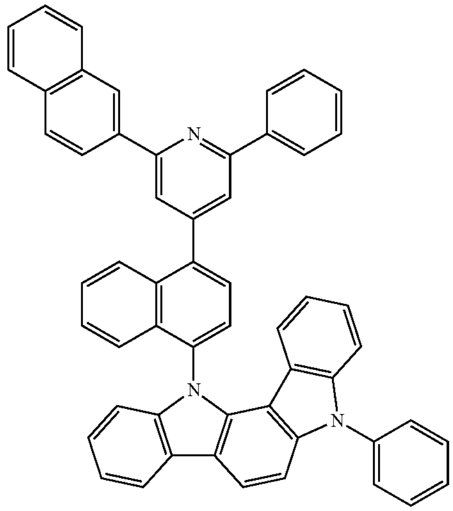
-continued
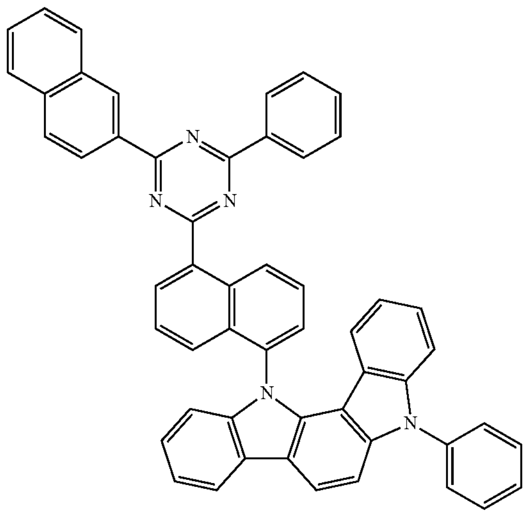
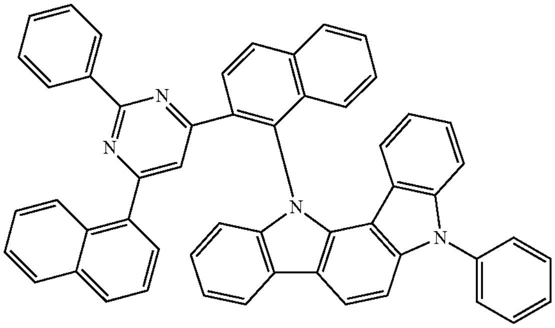
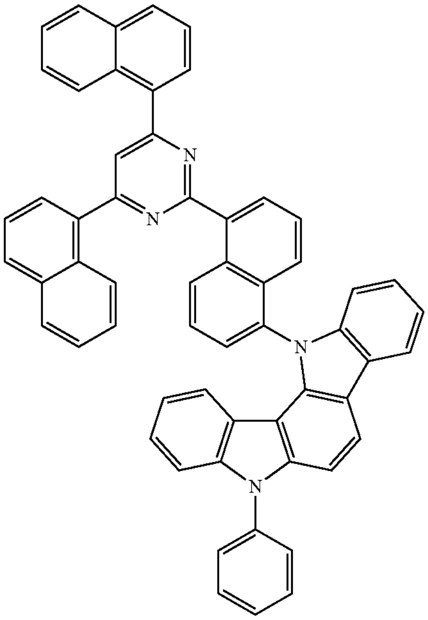

-continued
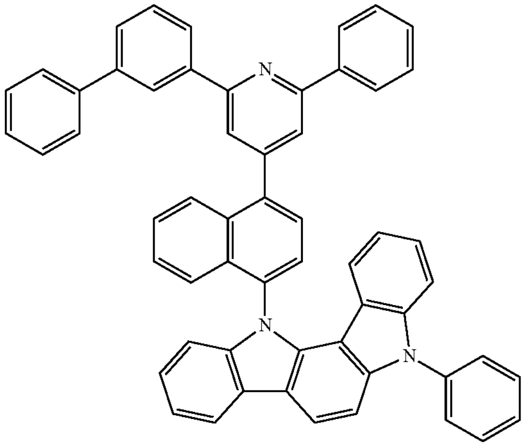
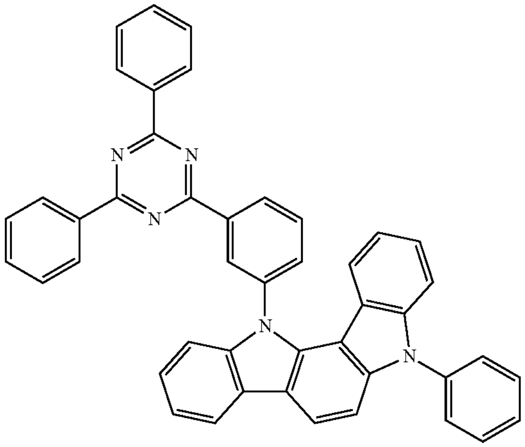
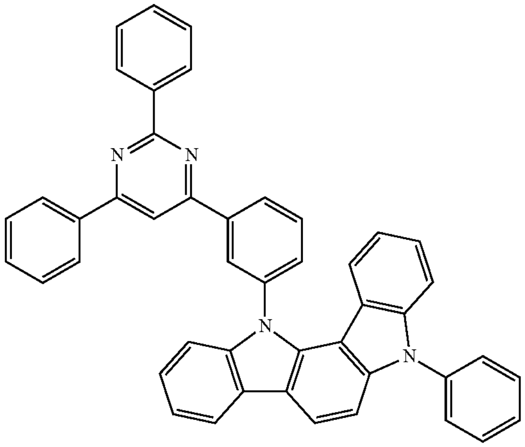
-continued
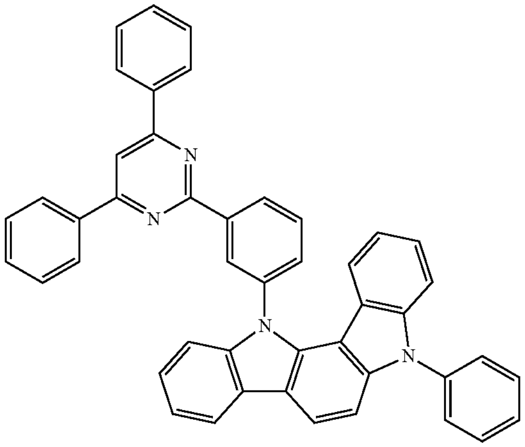
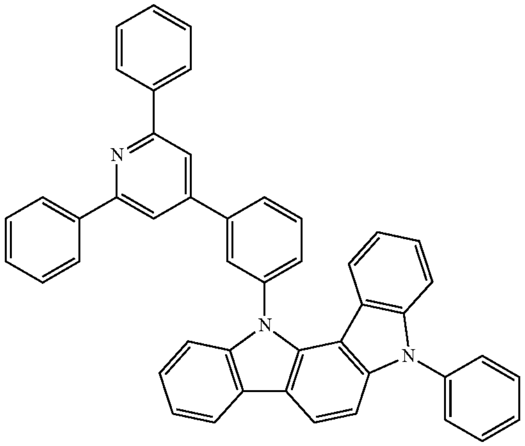
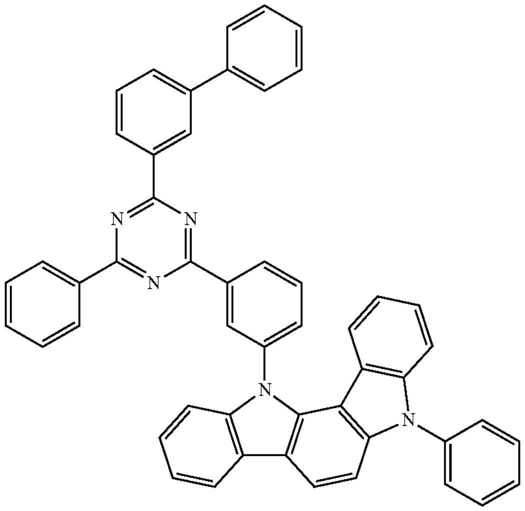

-continued
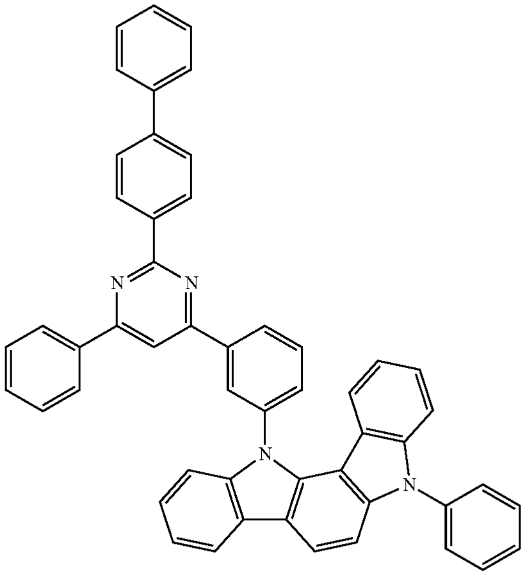
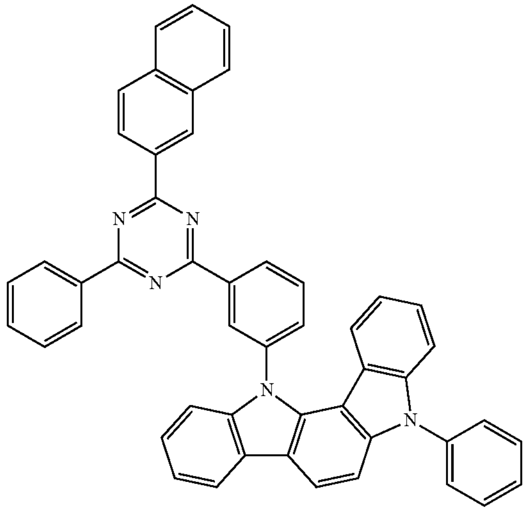
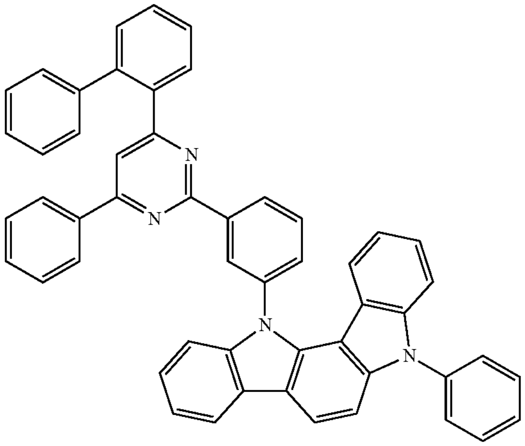
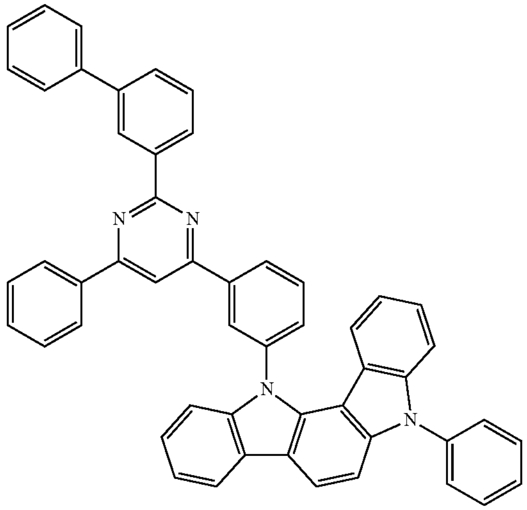
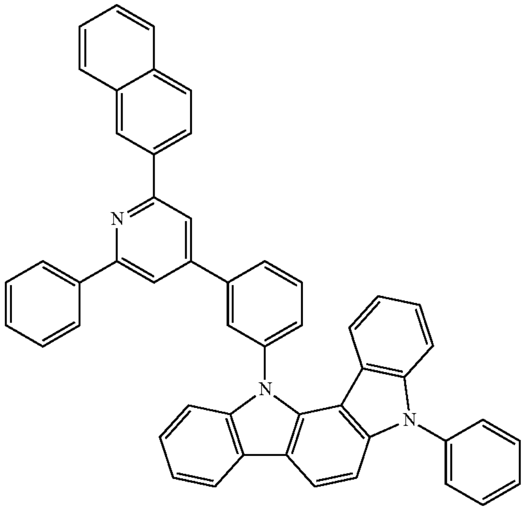
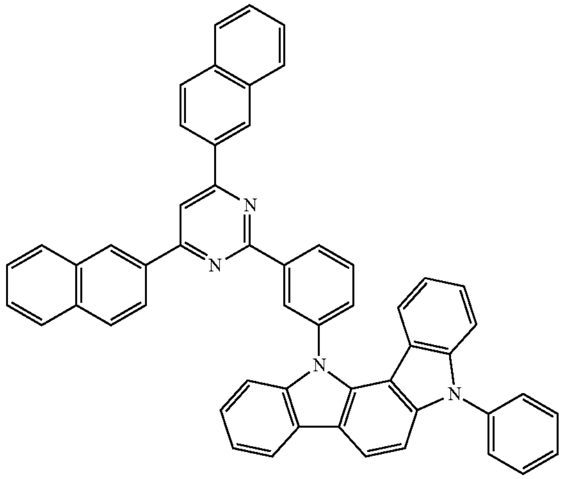
-continued -continued
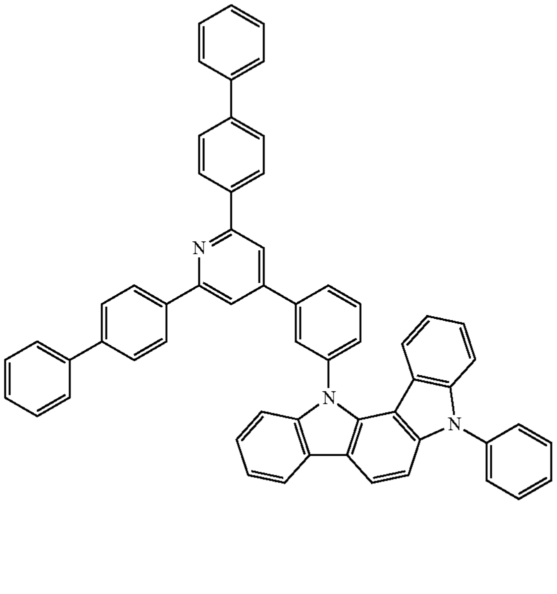
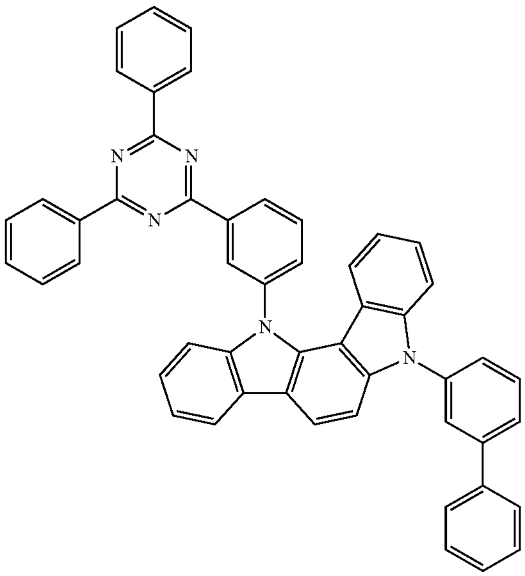
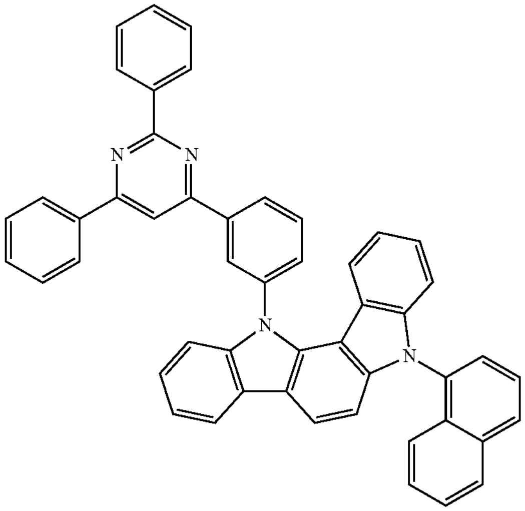
-continued
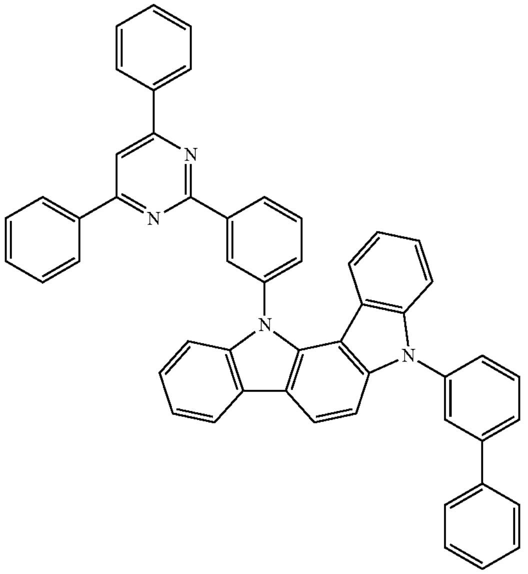
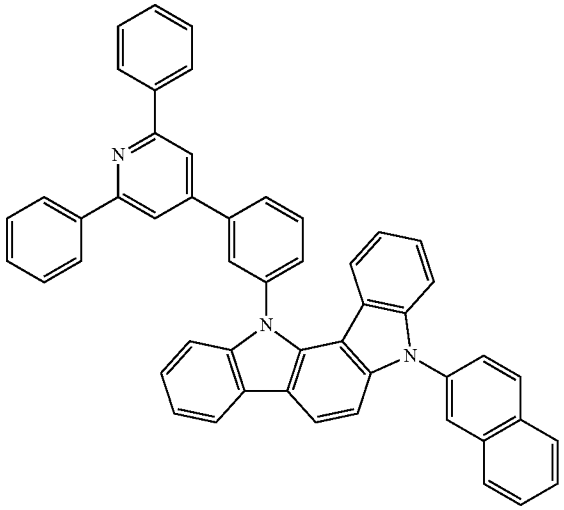
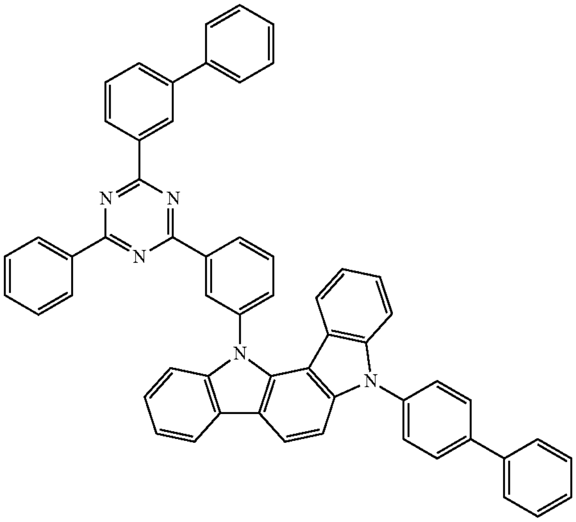

-continued
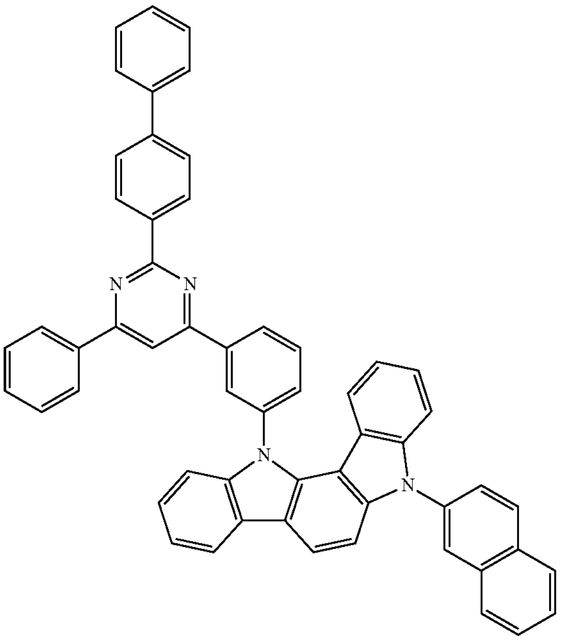
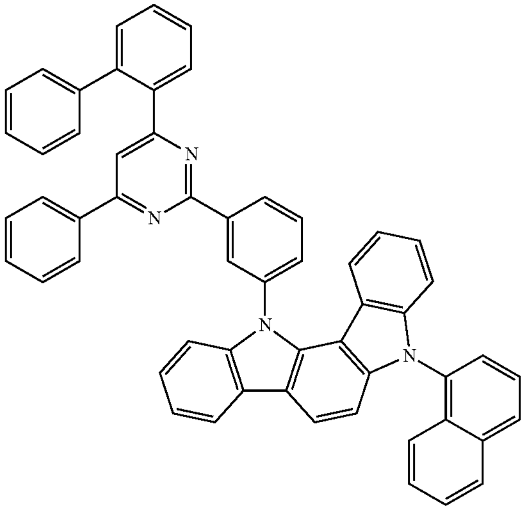
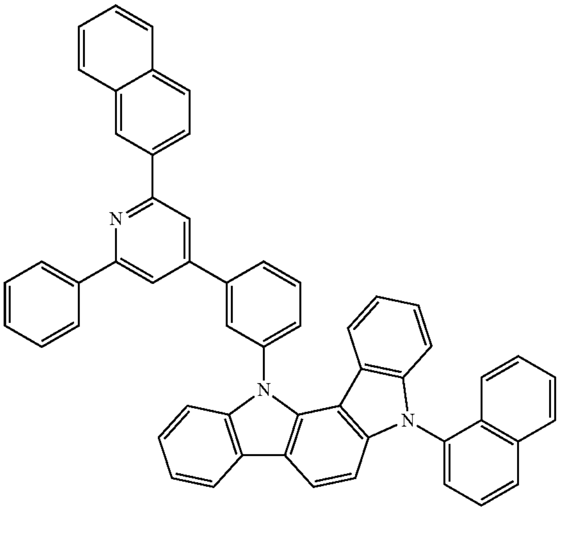
-continued
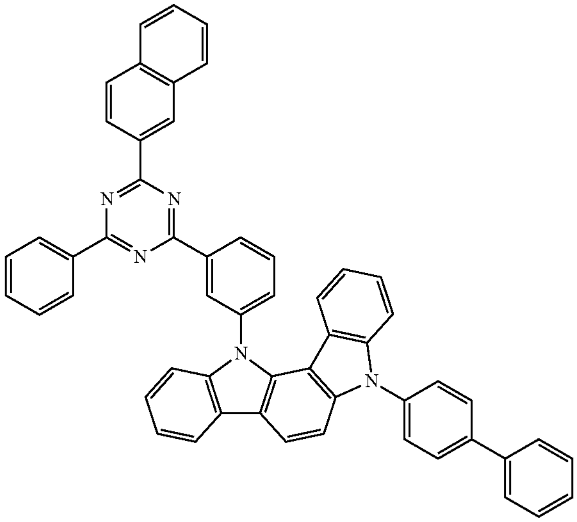
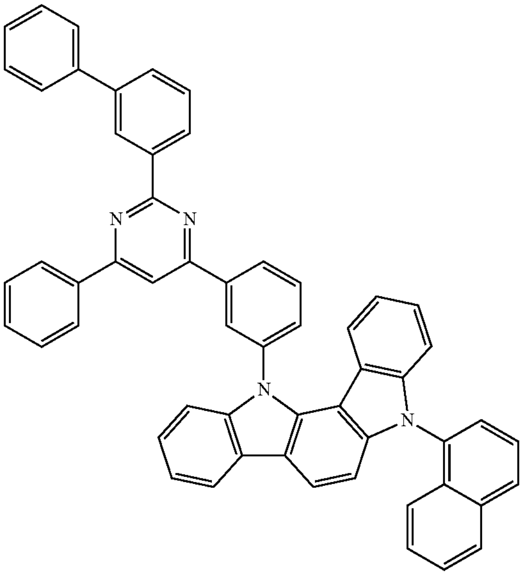
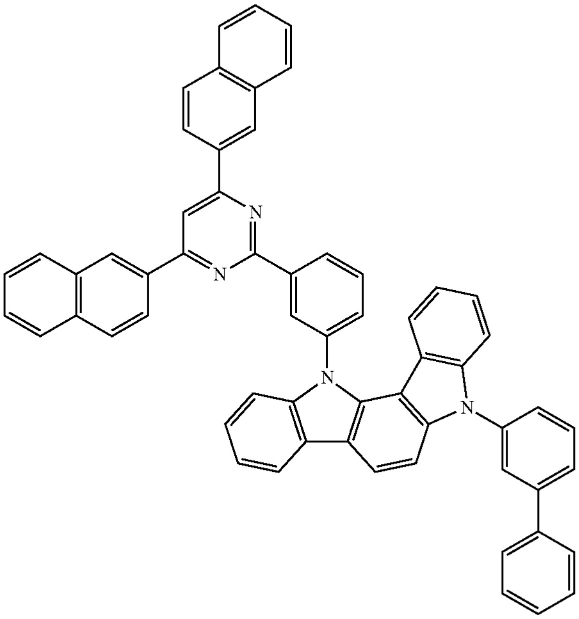

-continued
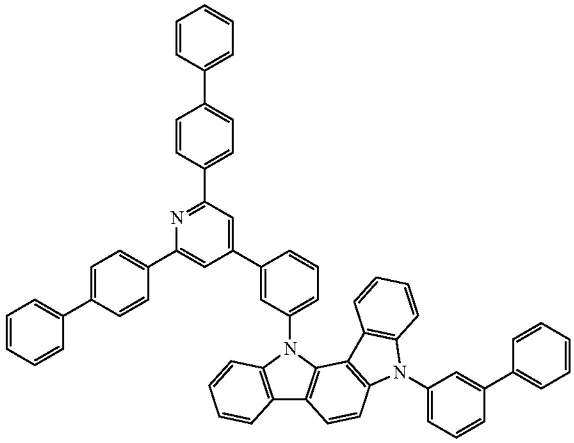
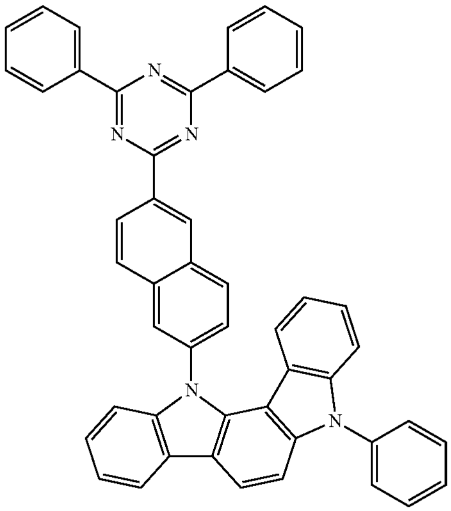
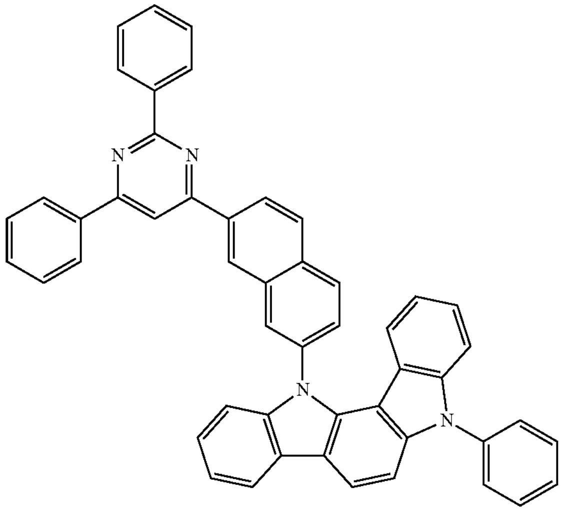
-continued
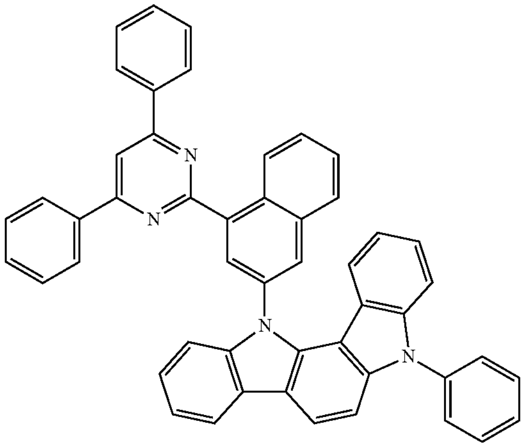
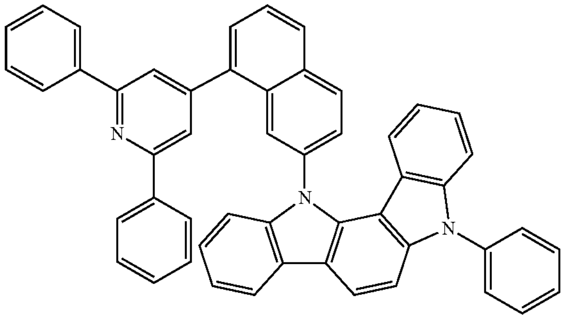
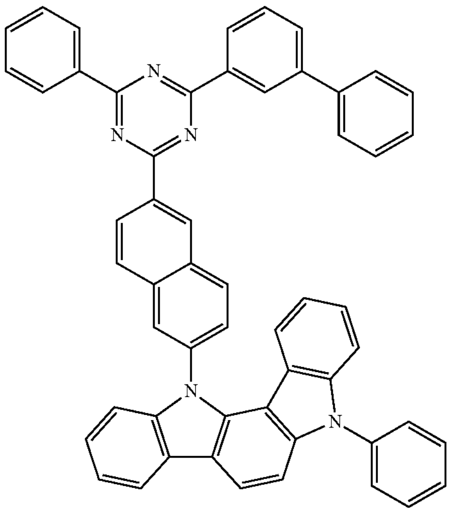

-continued
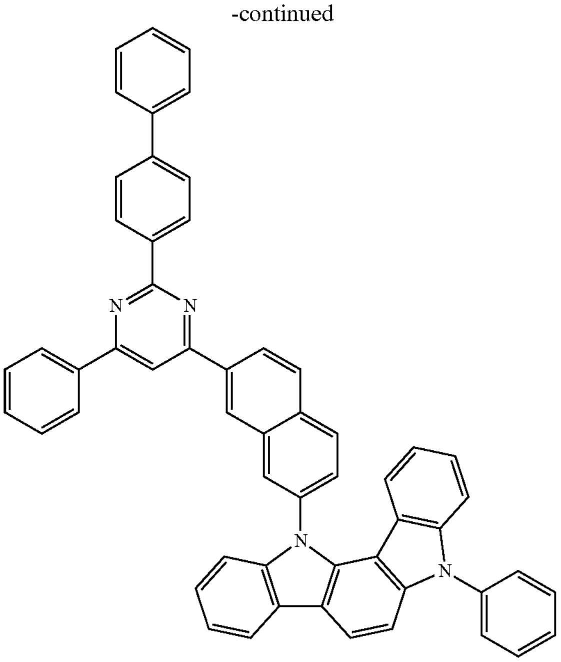
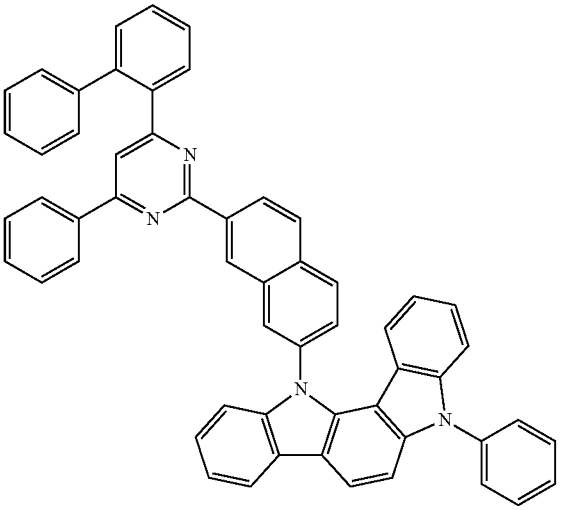
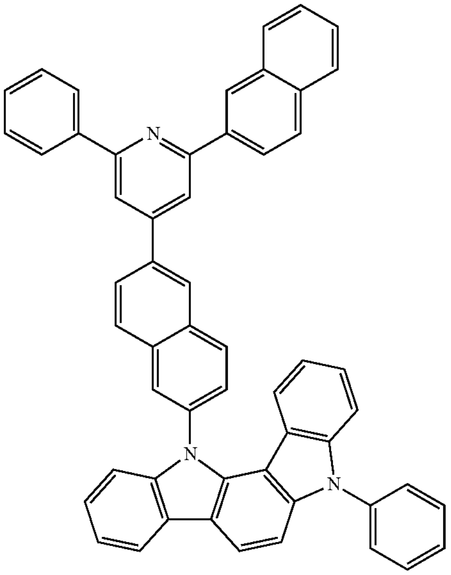
-continued
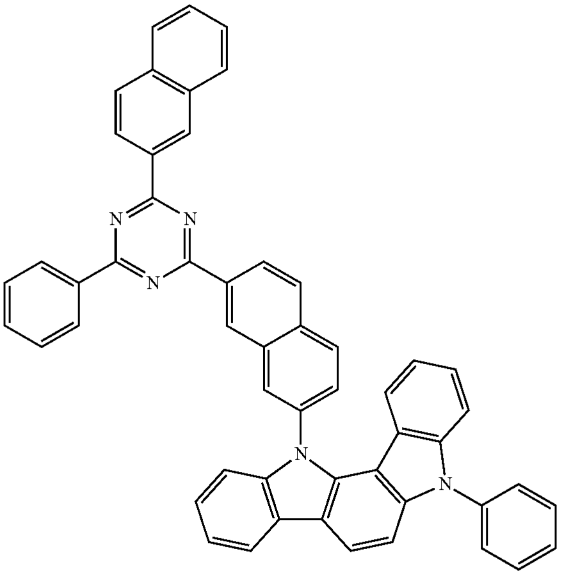
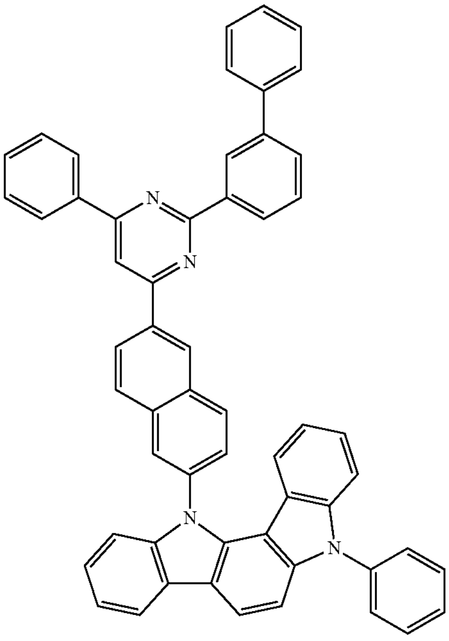
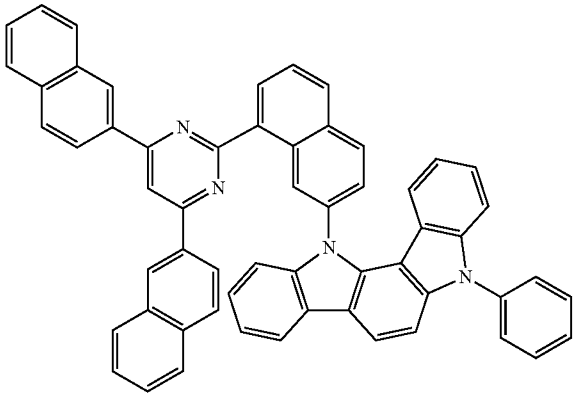

-continued
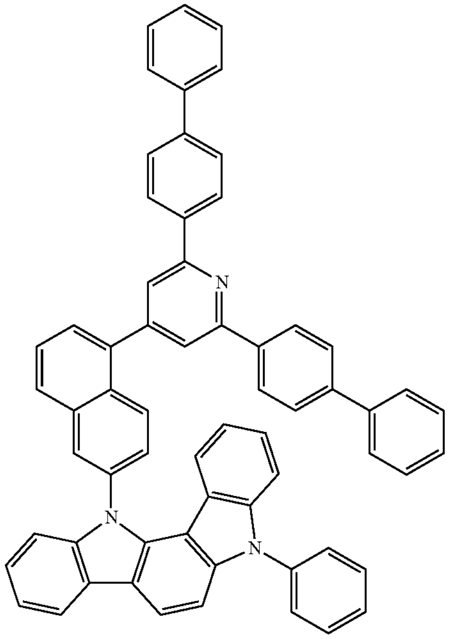
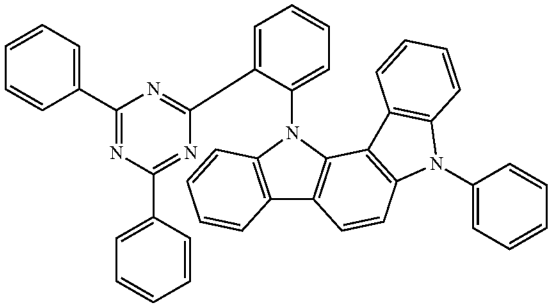
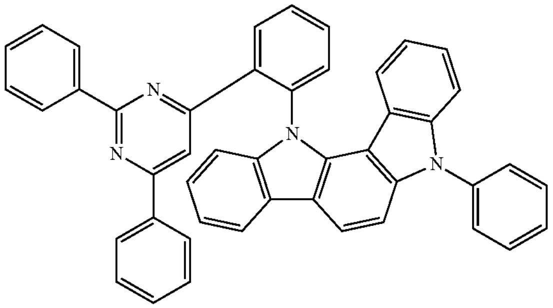
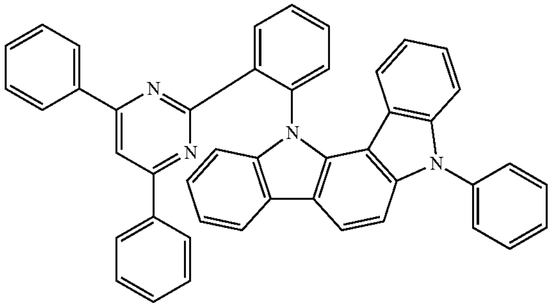
-continued
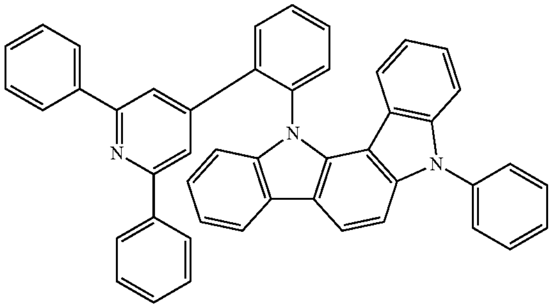
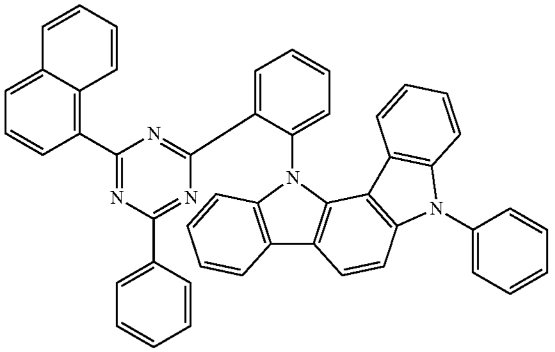
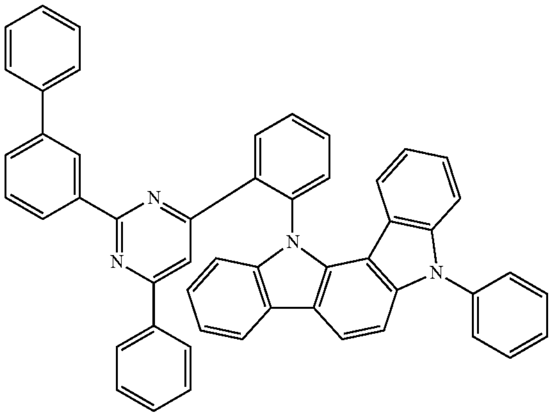
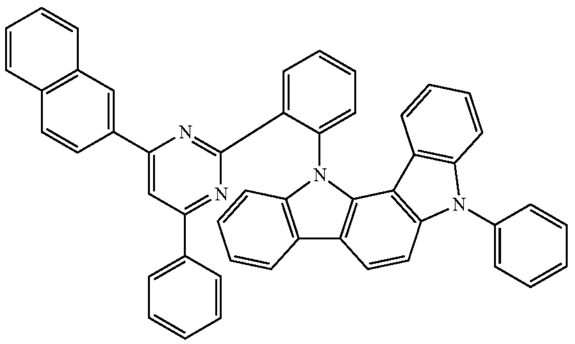

-continued
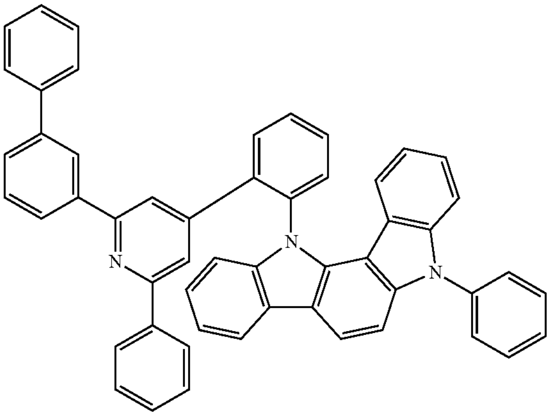
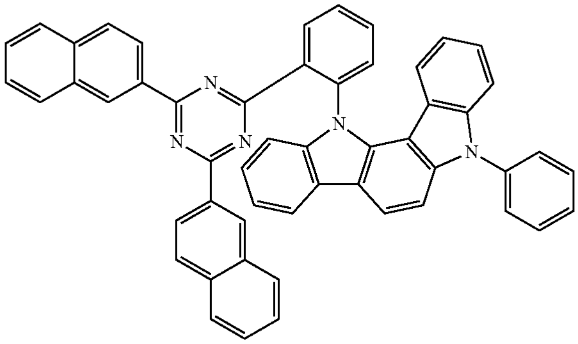
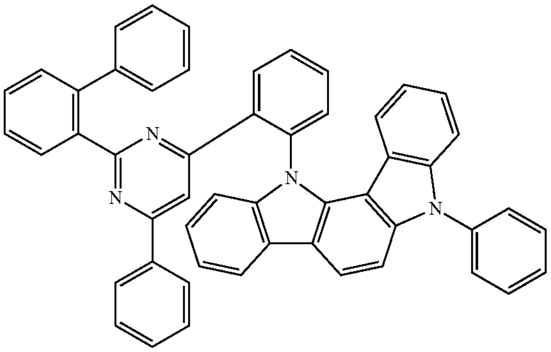
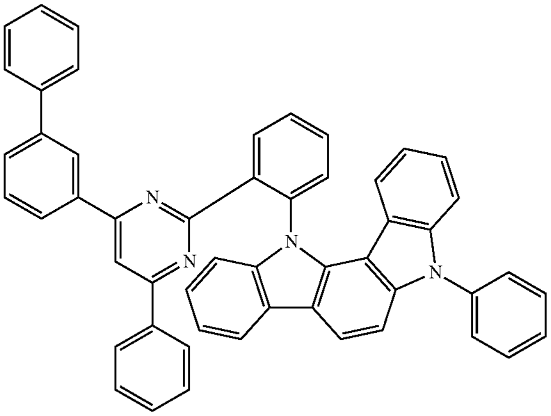
-continued
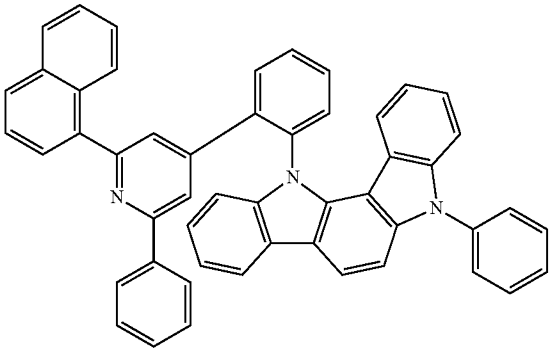
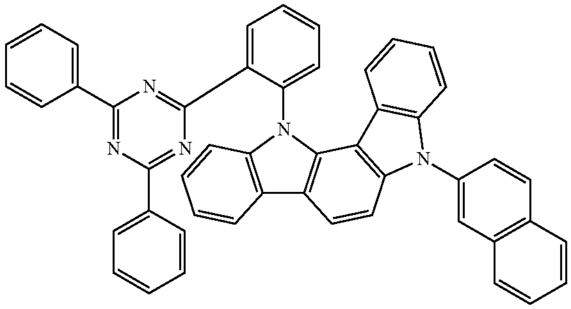
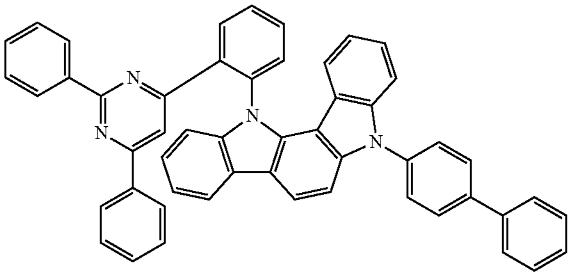
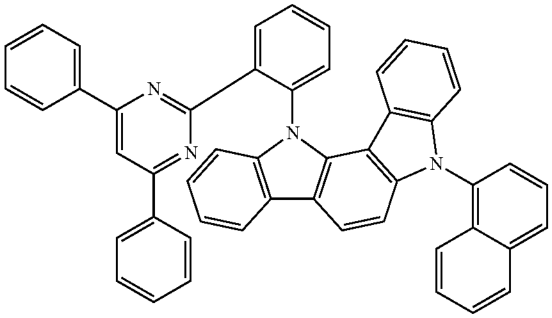
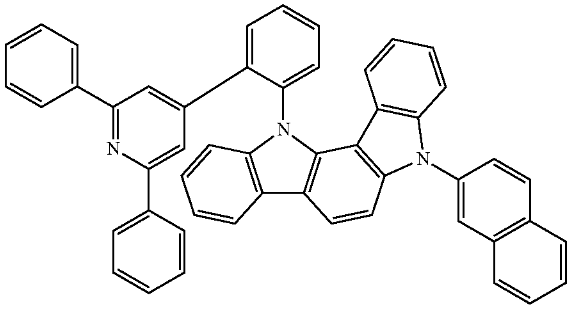

-continued
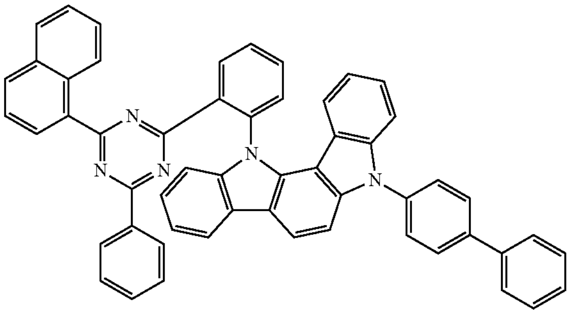
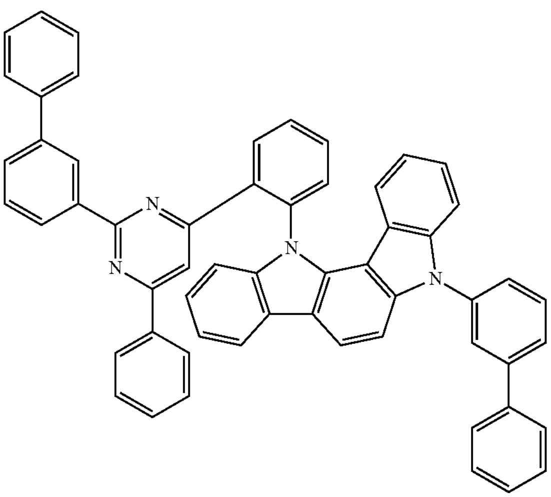
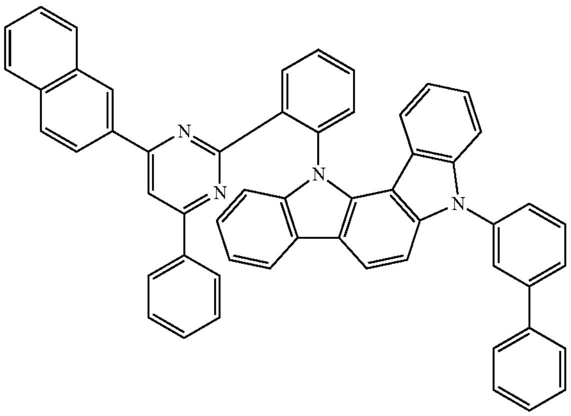
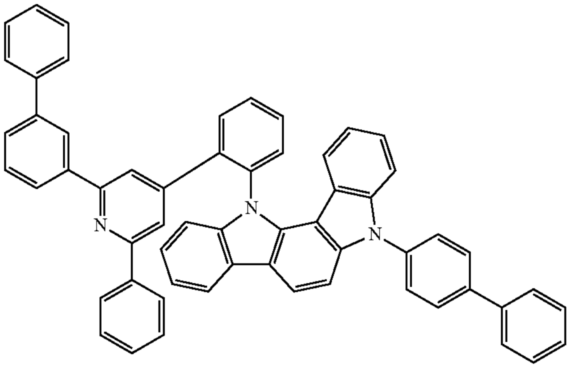
-continued
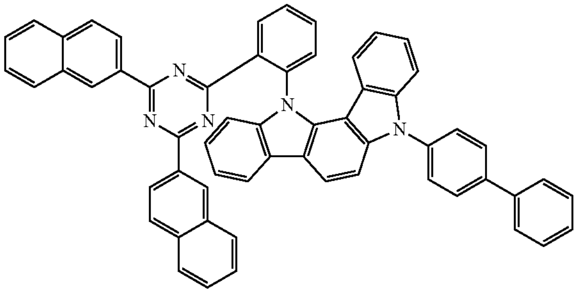
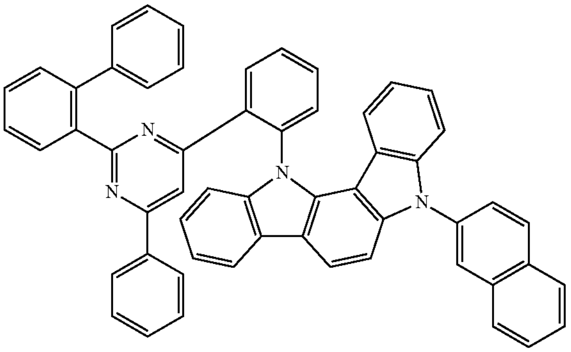
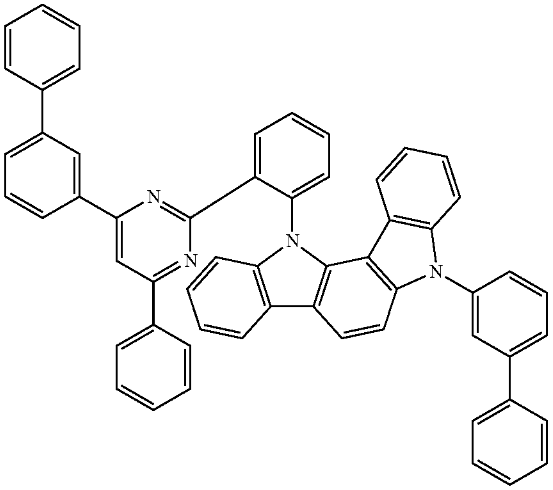
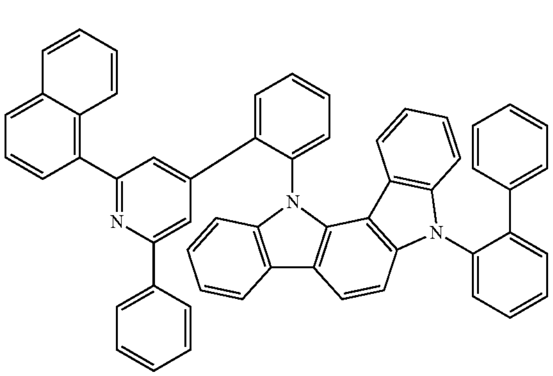

-continued
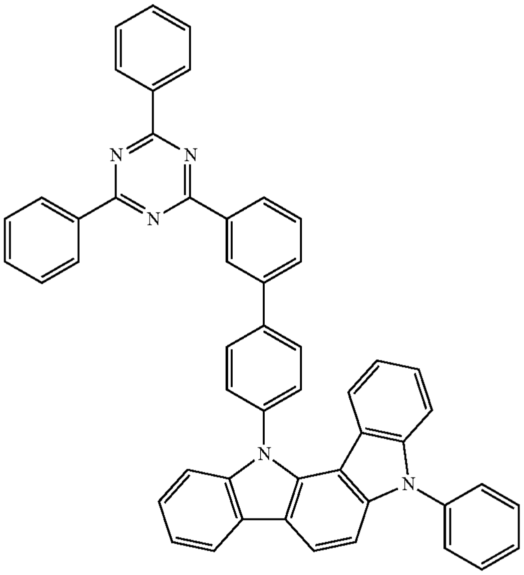
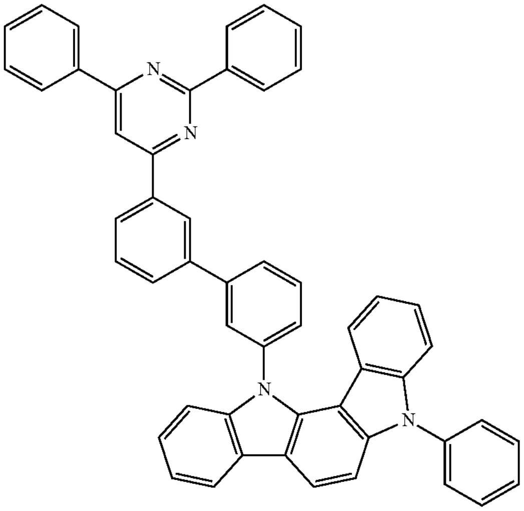
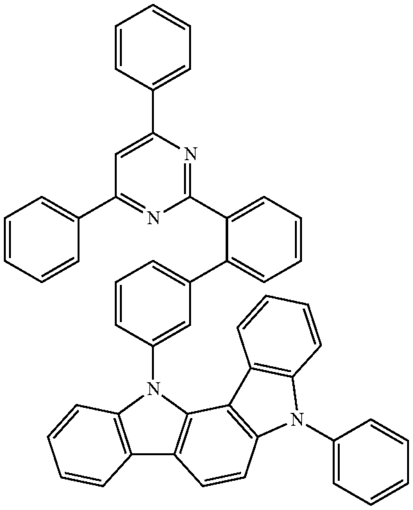
-continued
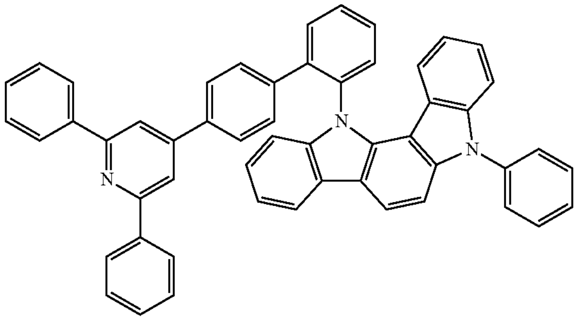
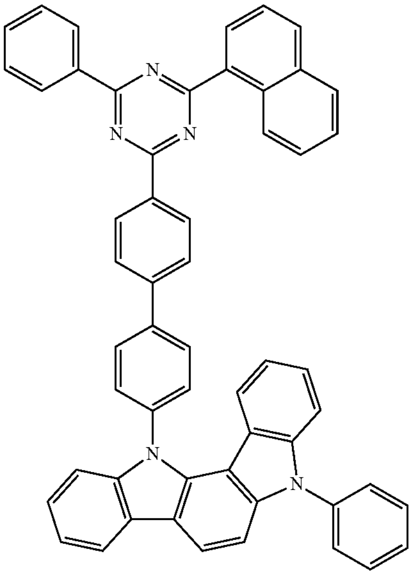
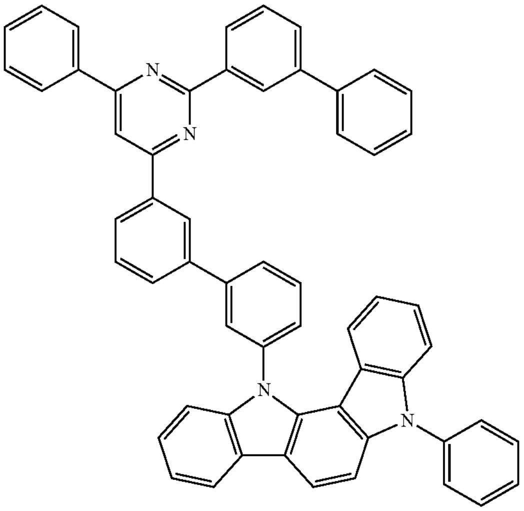

-continued
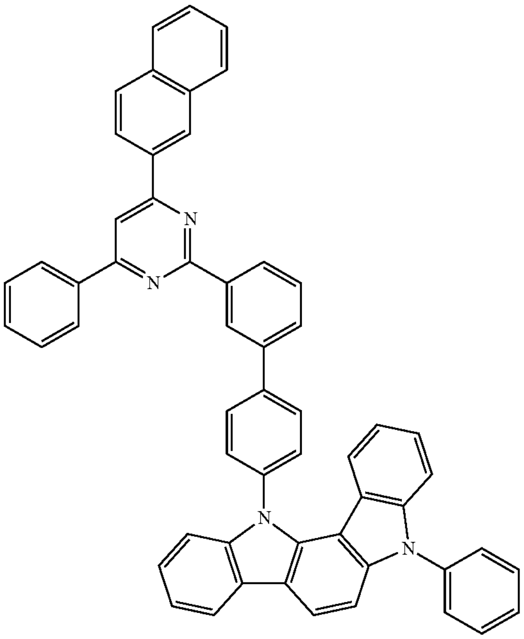
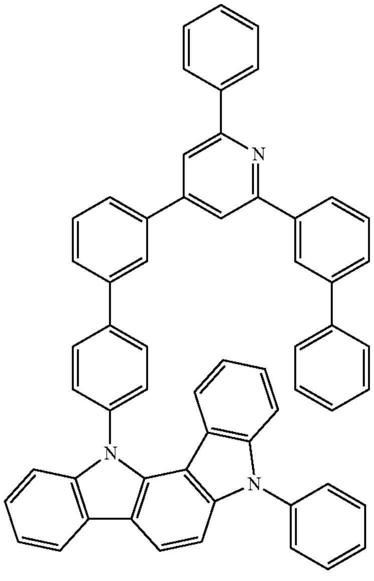
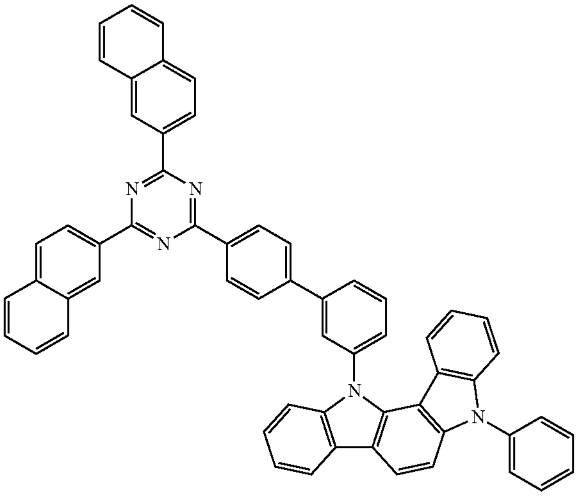
-continued
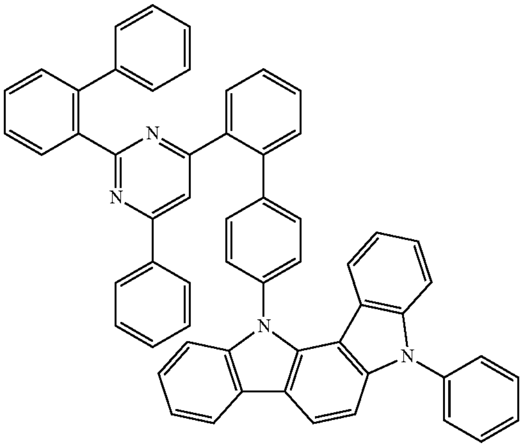
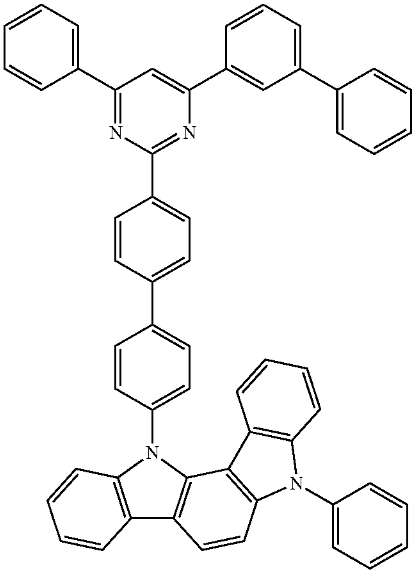
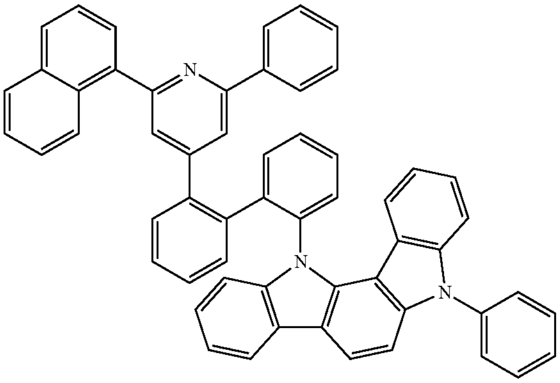

-continued
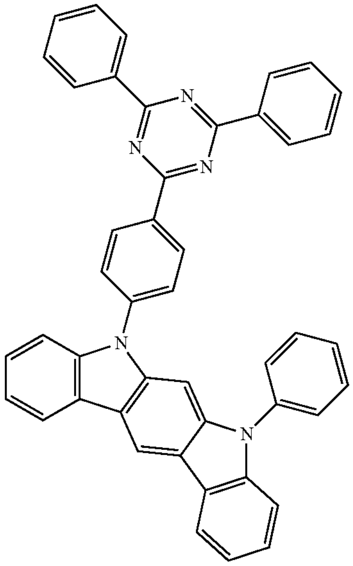
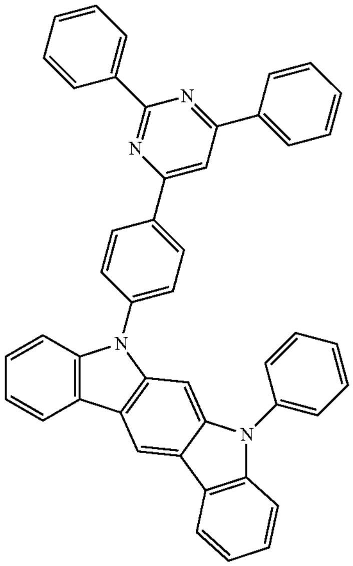
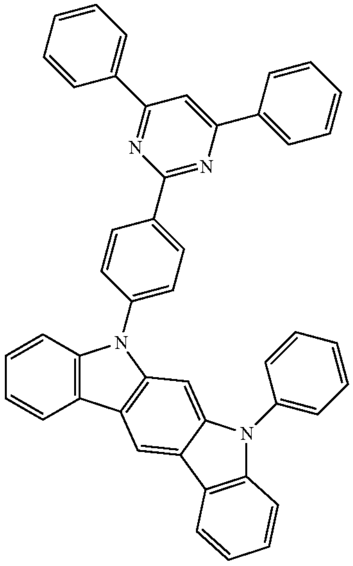
-continued
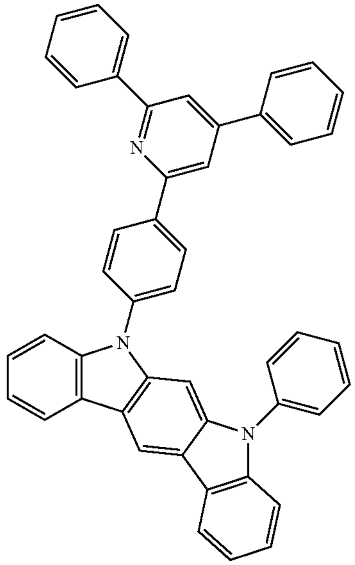
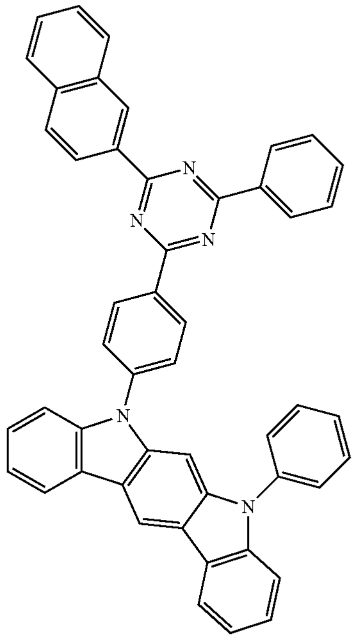

-continued
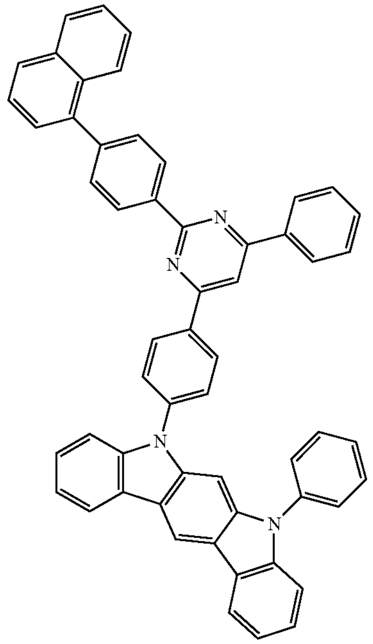
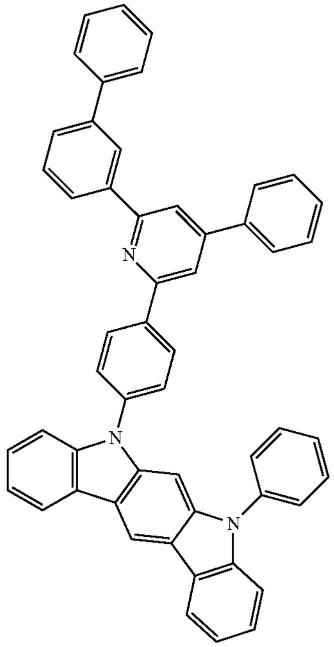
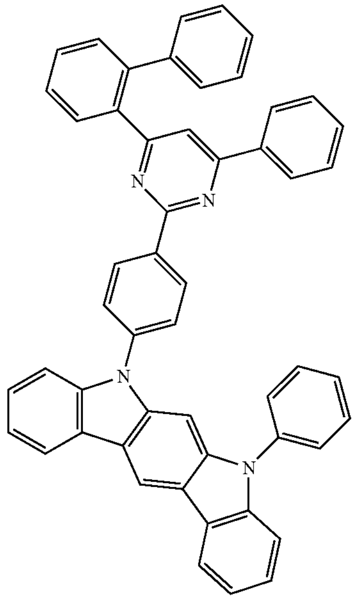
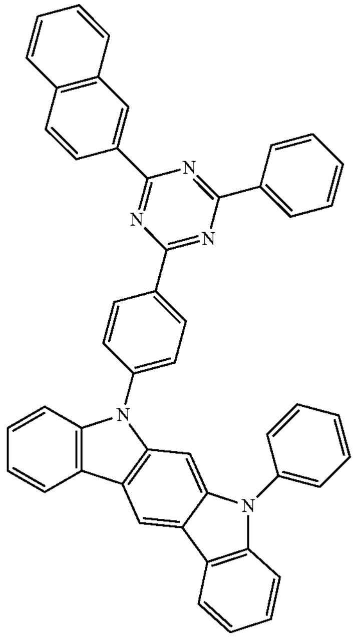
-continued

-continued
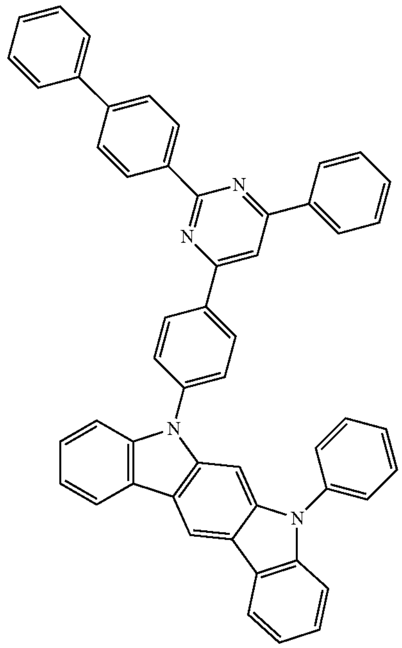
-continued
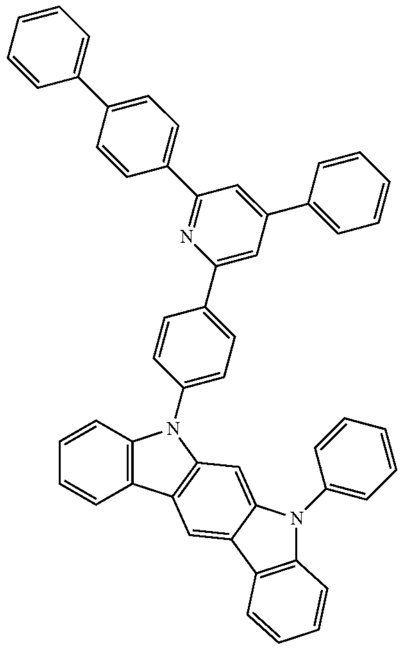
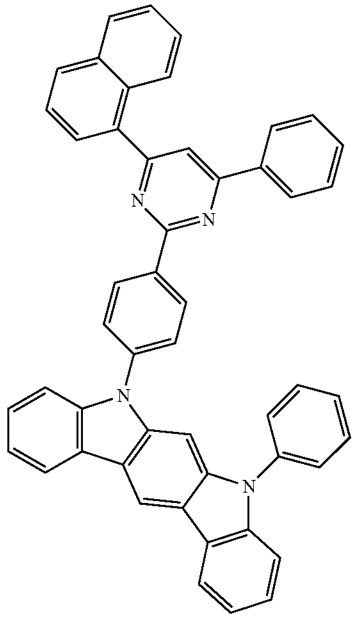
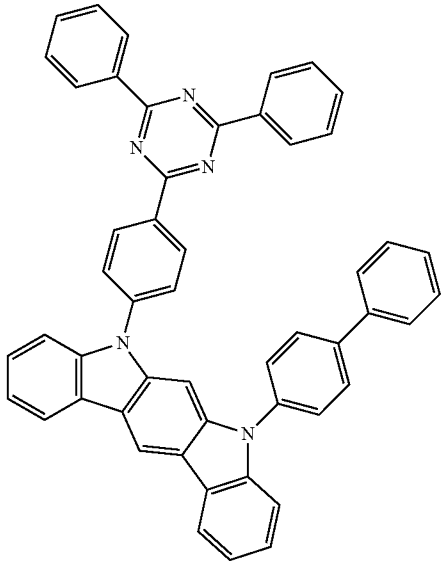

-continued
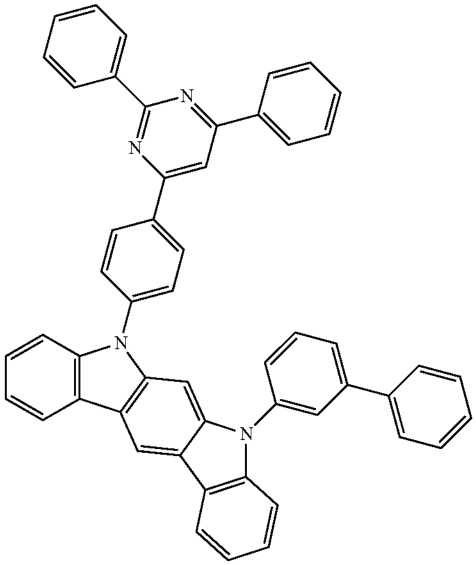
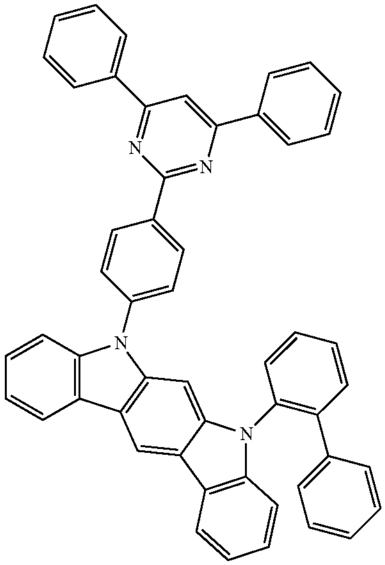
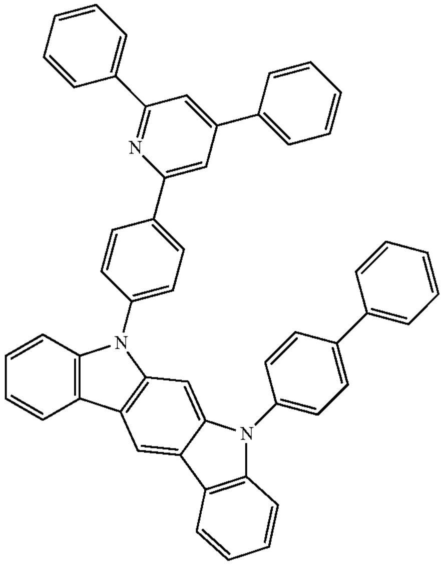
-continued
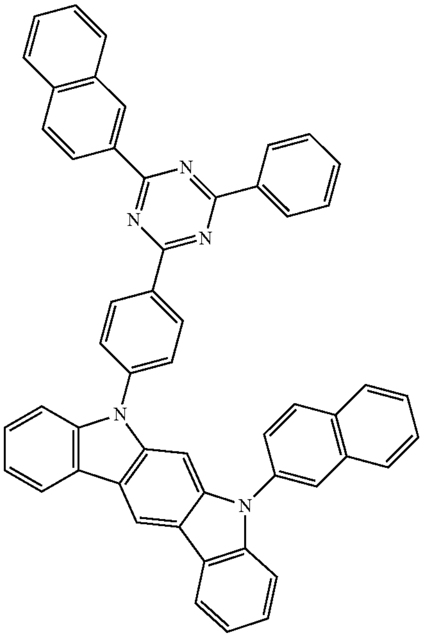
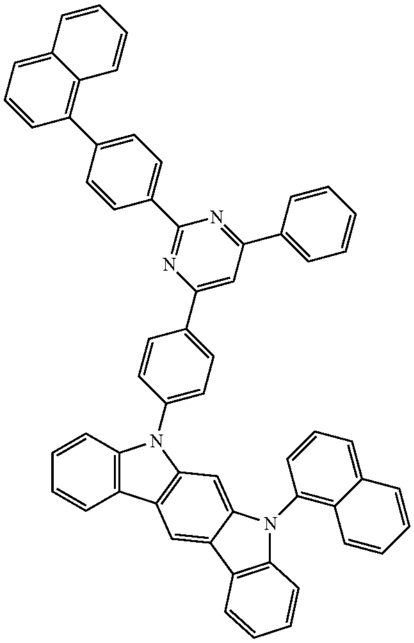

-continued
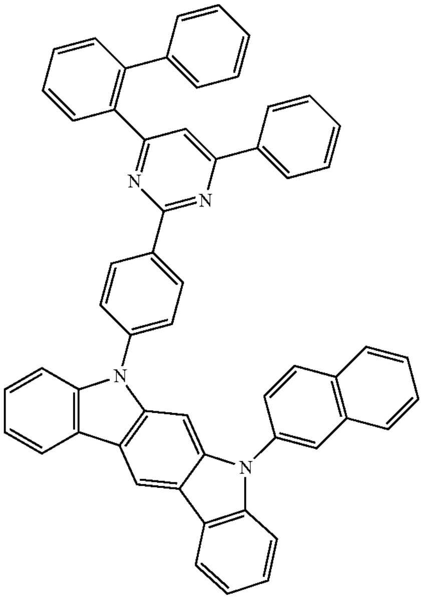
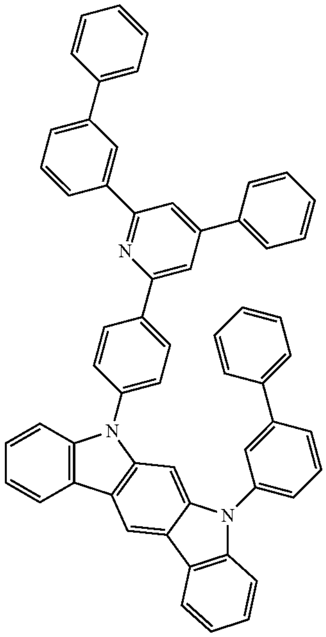
-continued
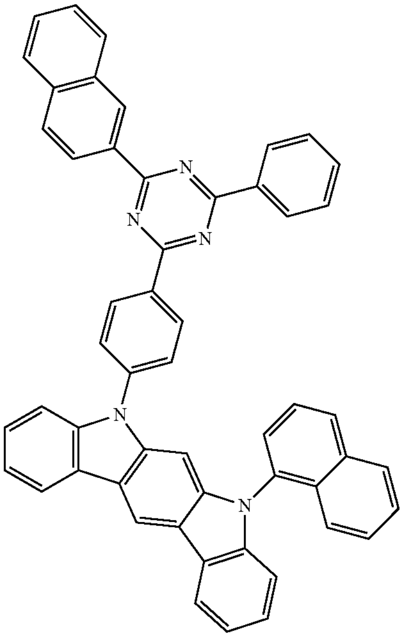
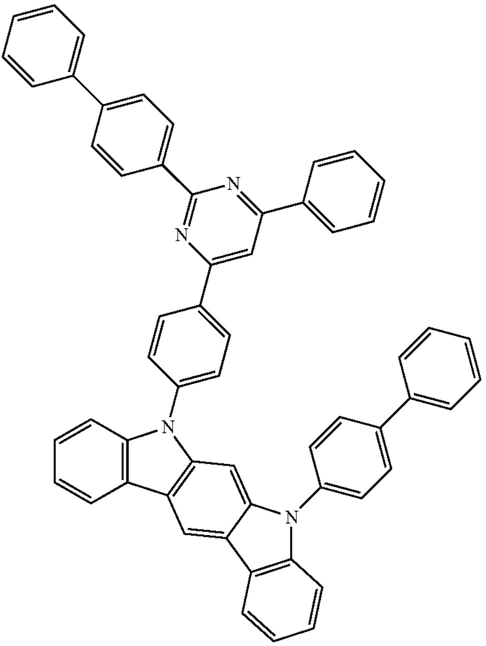

-continued
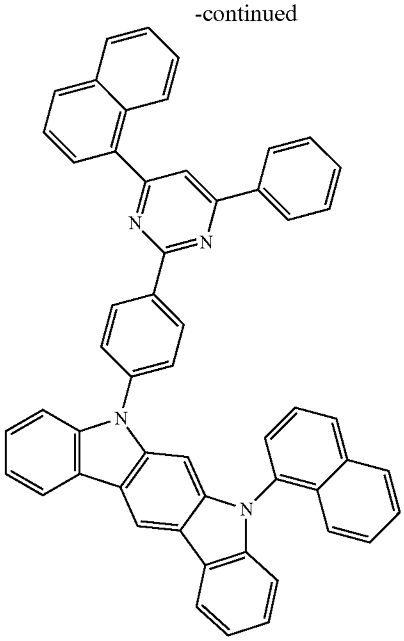
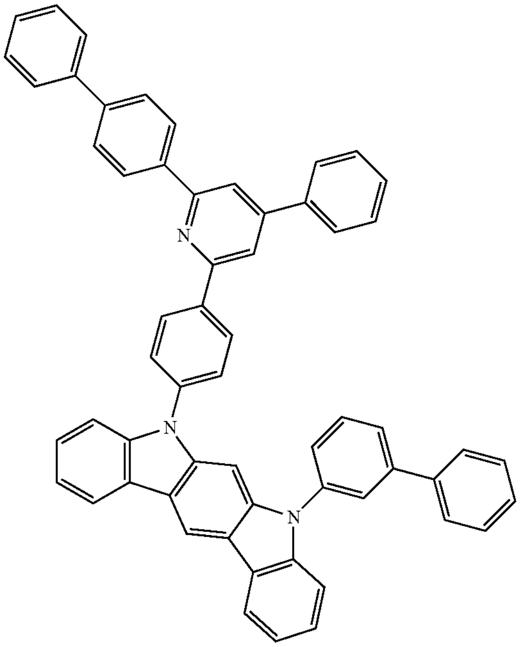
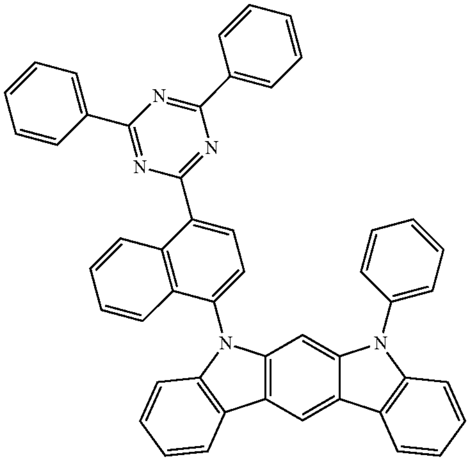
-continued
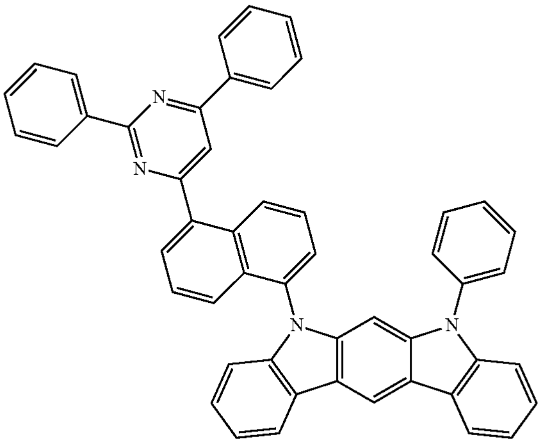
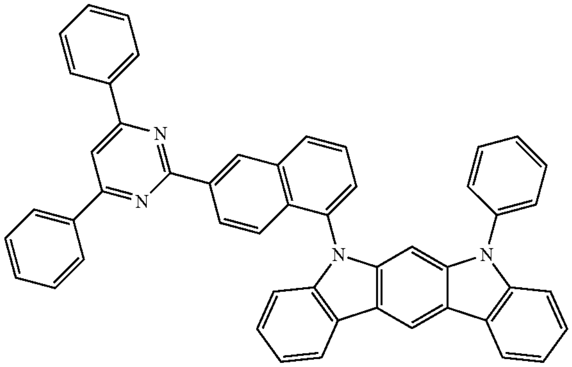
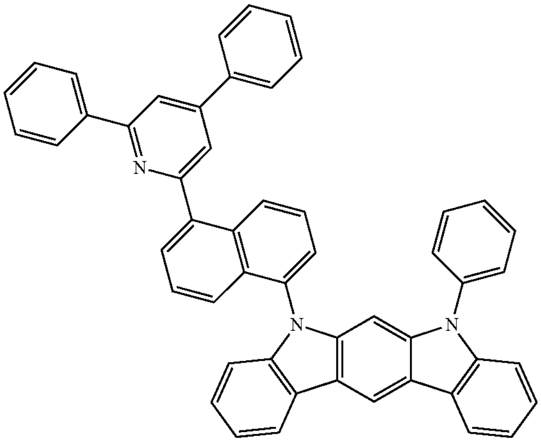
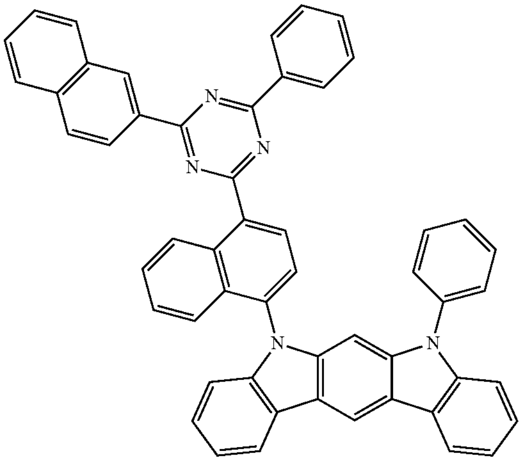

-continued
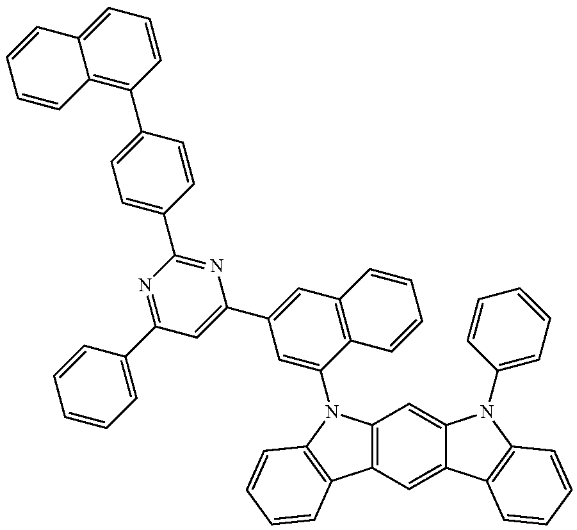
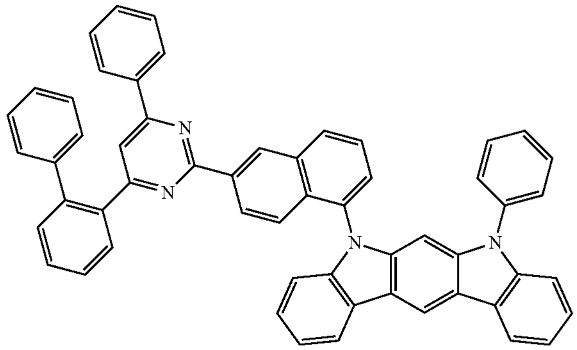
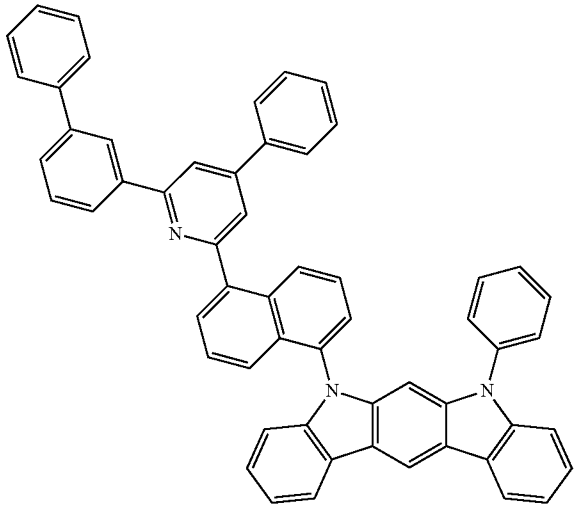
-continued
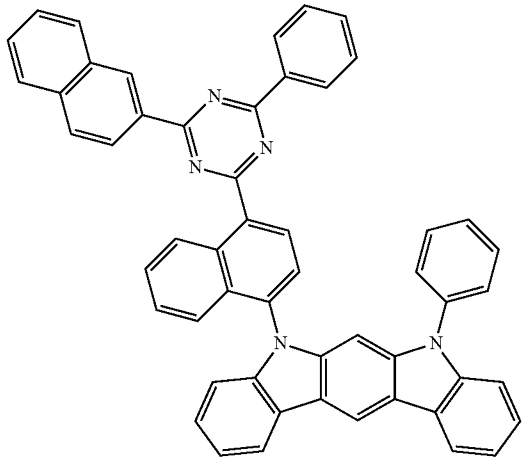
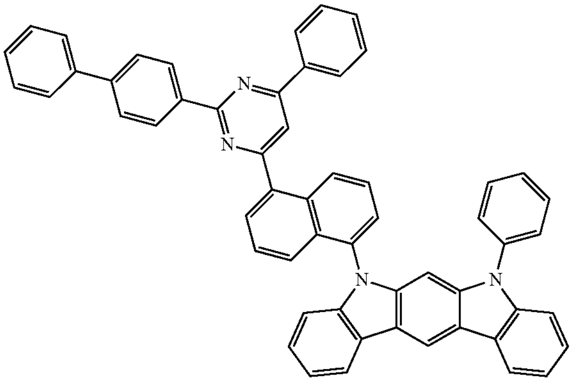
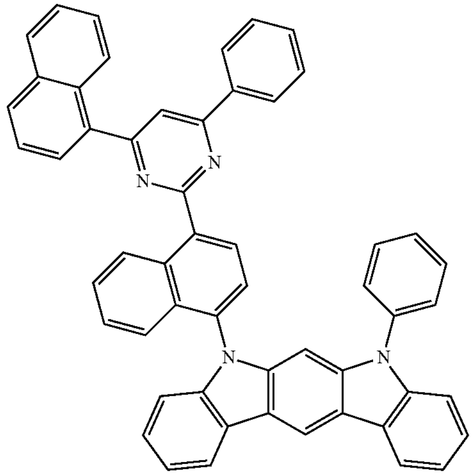
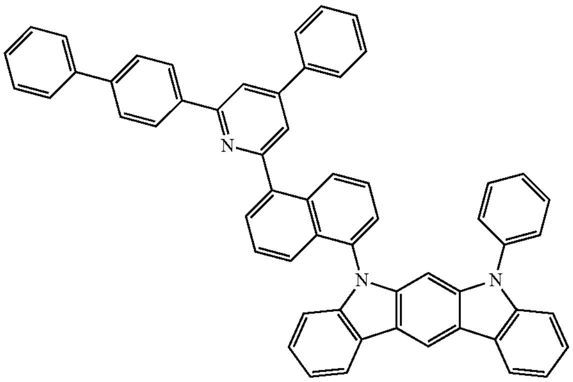

-continued
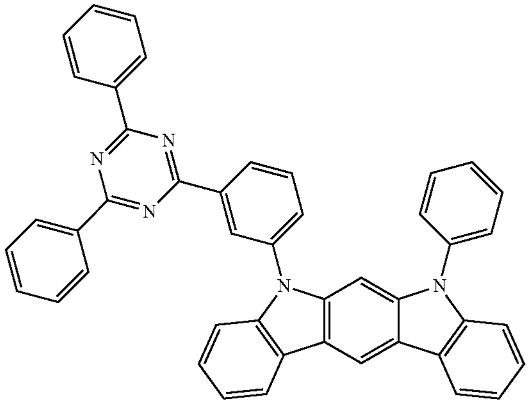
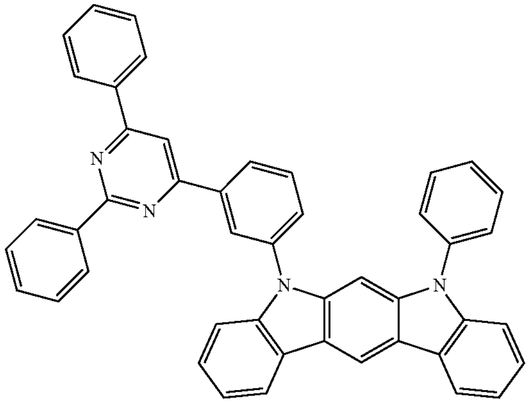
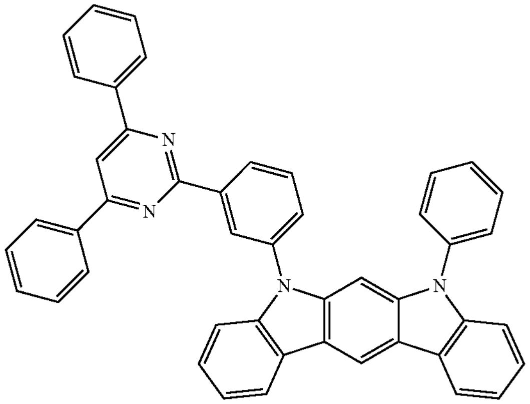
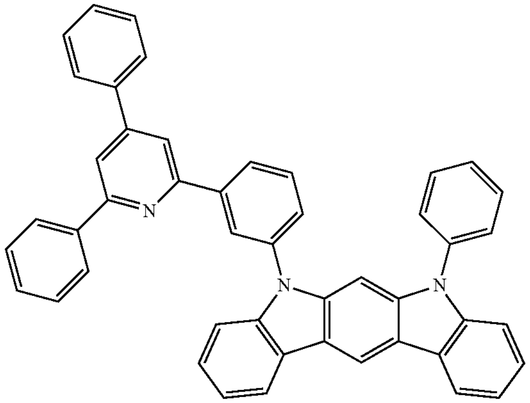
-continued
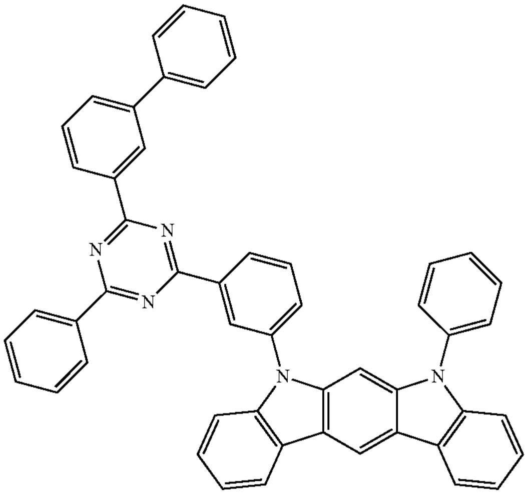
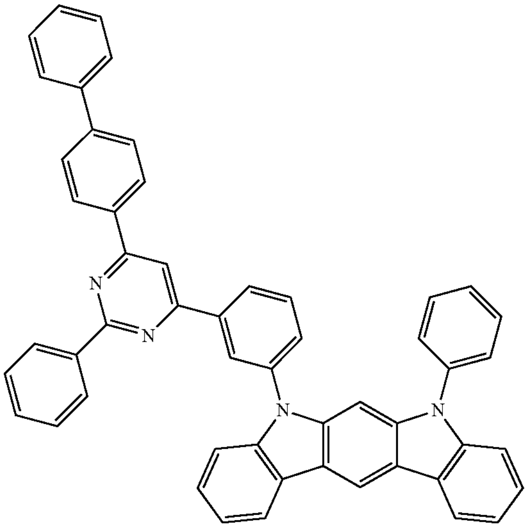
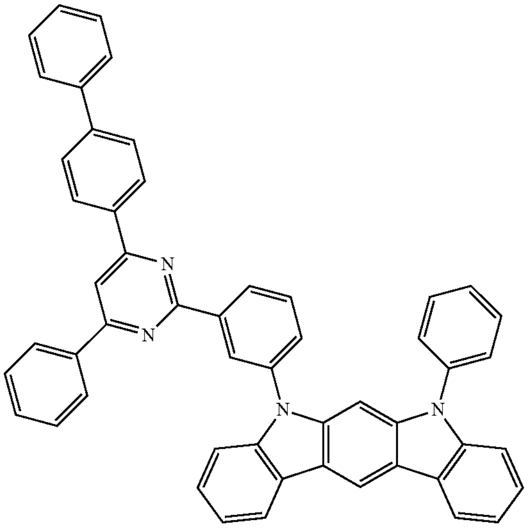

-continued
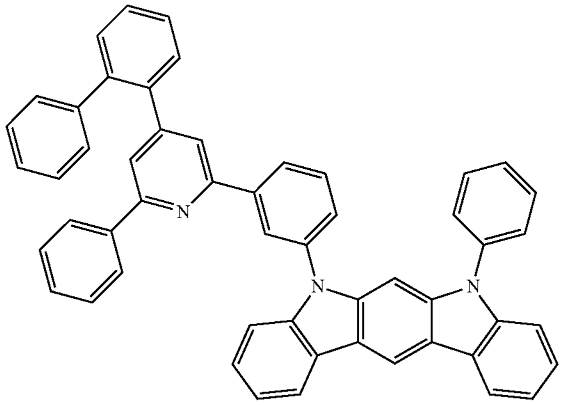
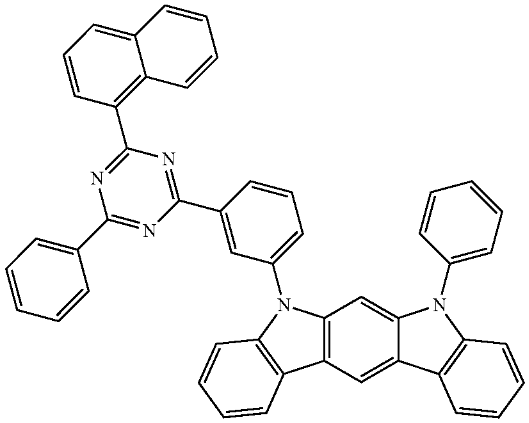
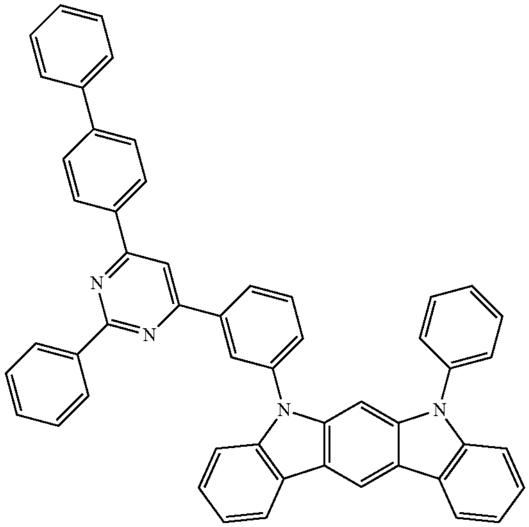
-continued
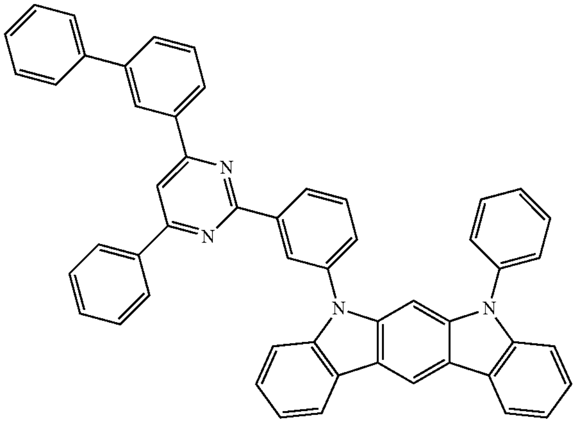
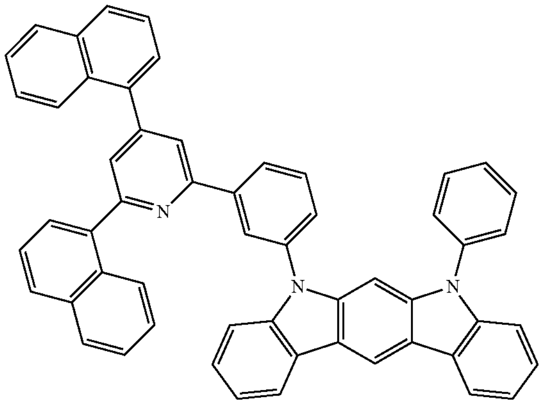
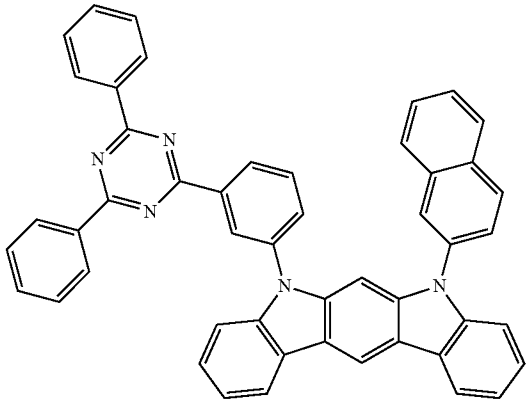
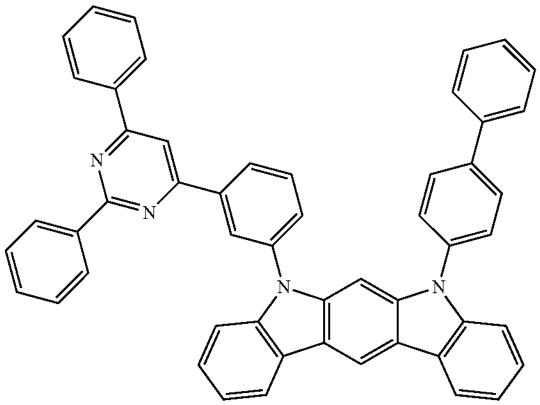

-continued
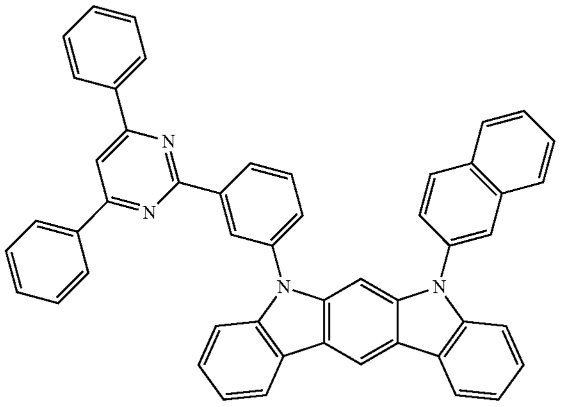
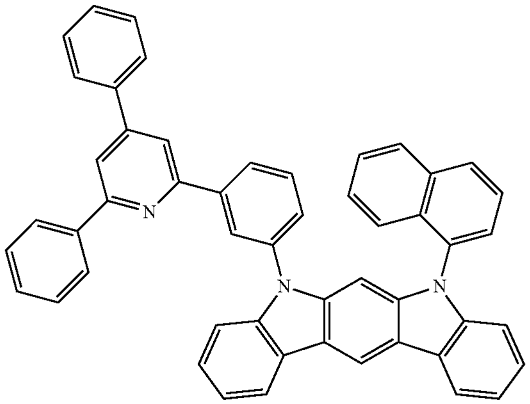
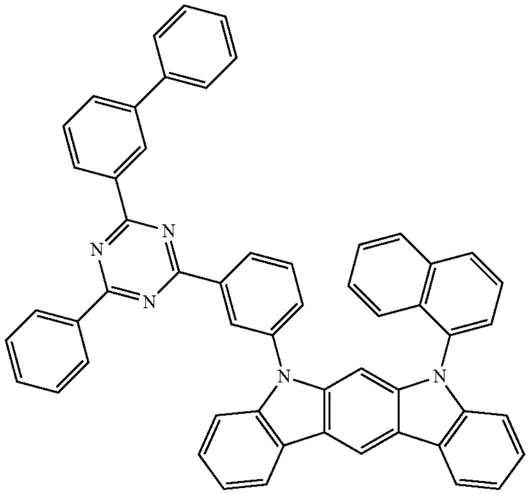
-continued
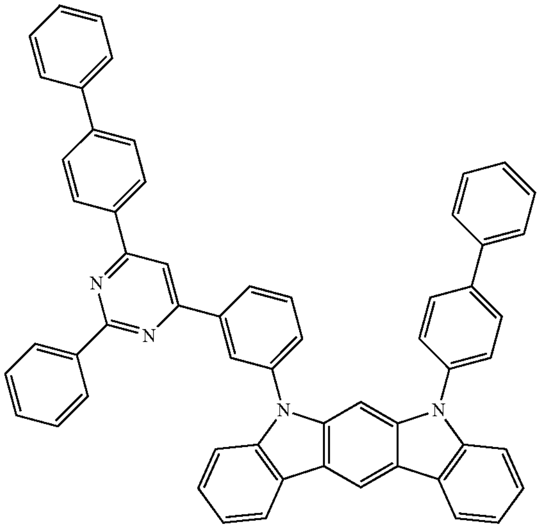
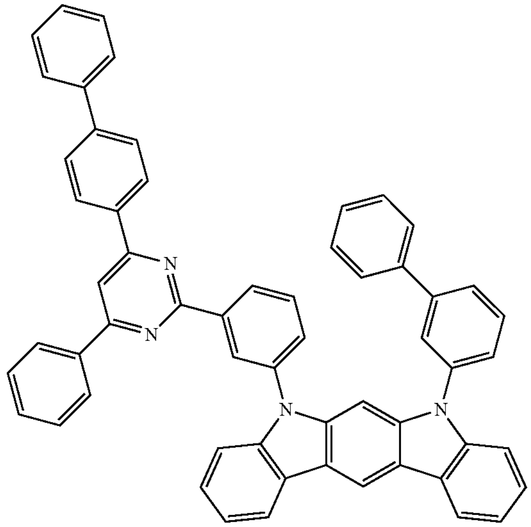
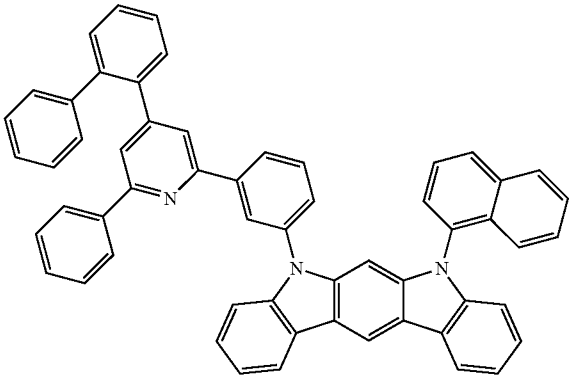

-continued
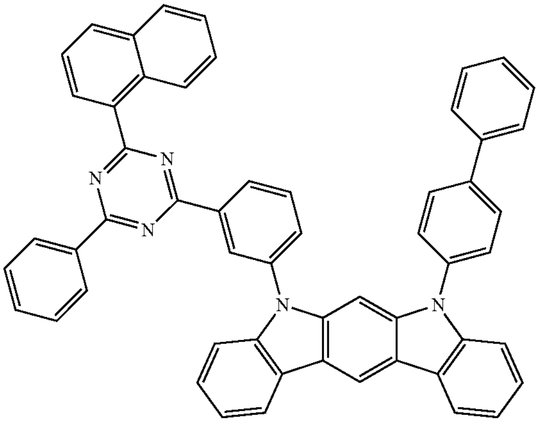
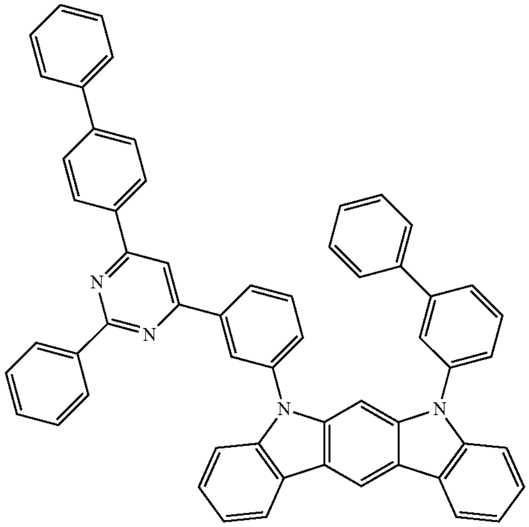
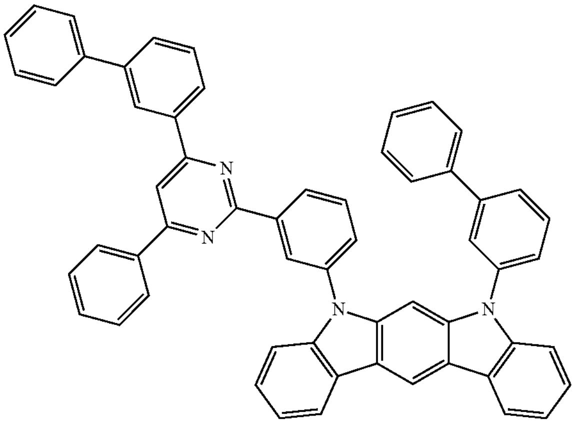
-continued
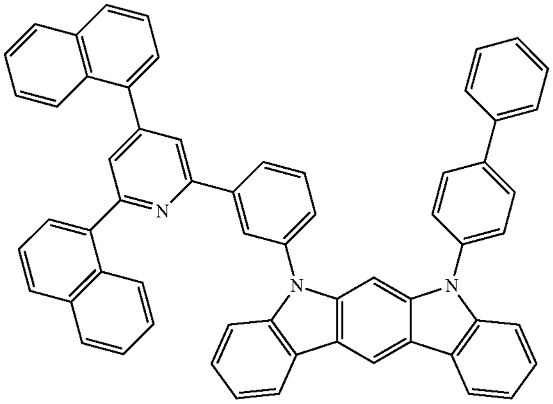
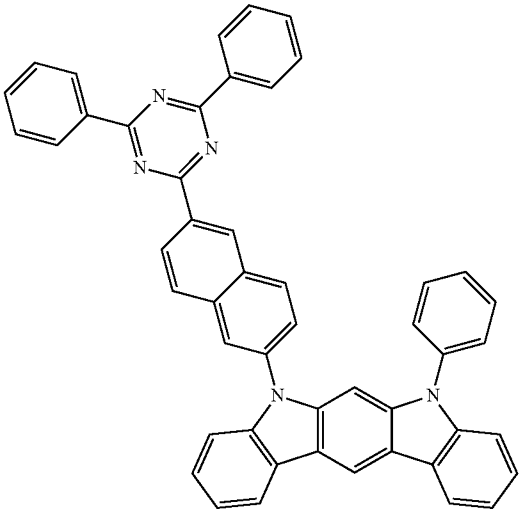
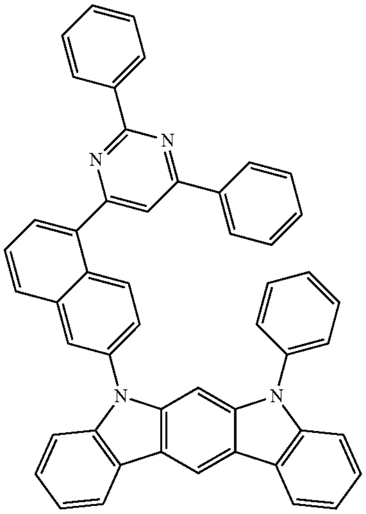

-continued
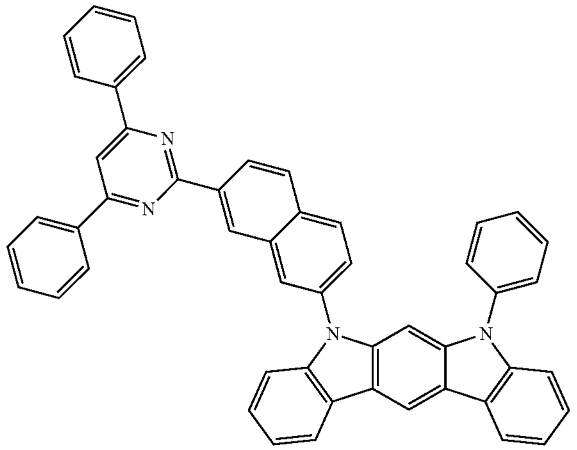
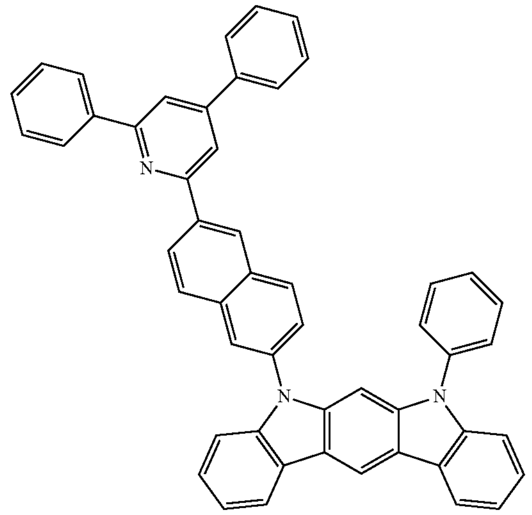
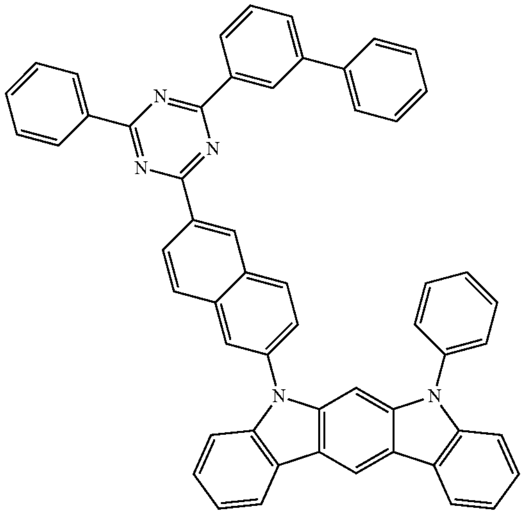
-continued
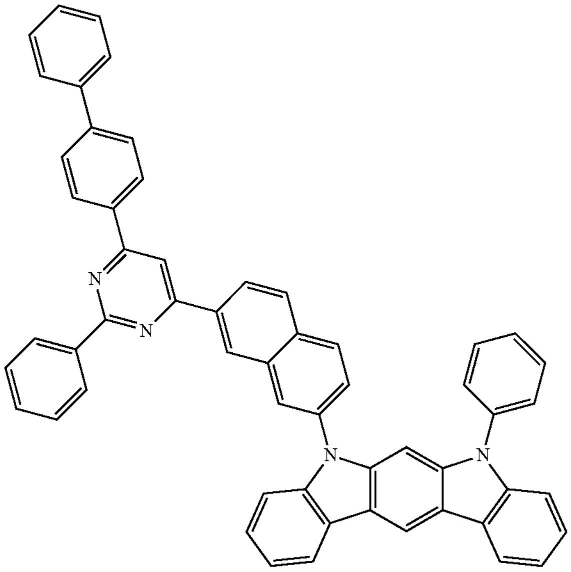
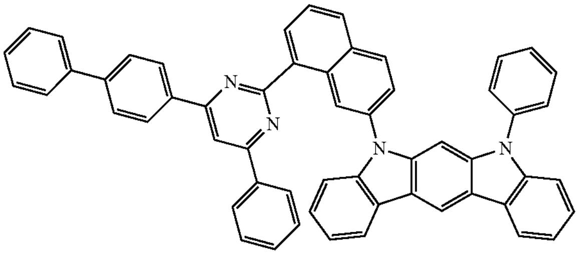
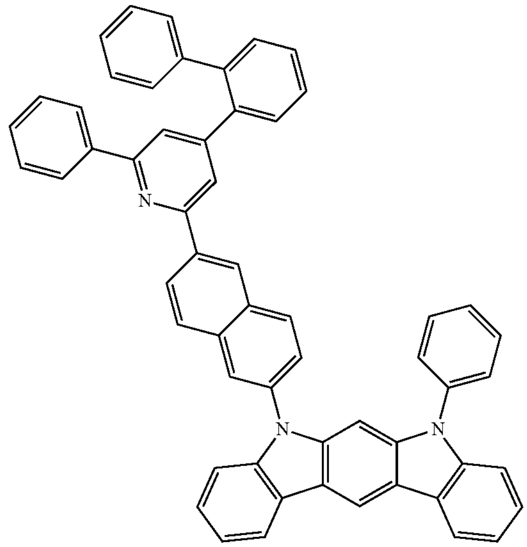

-continued
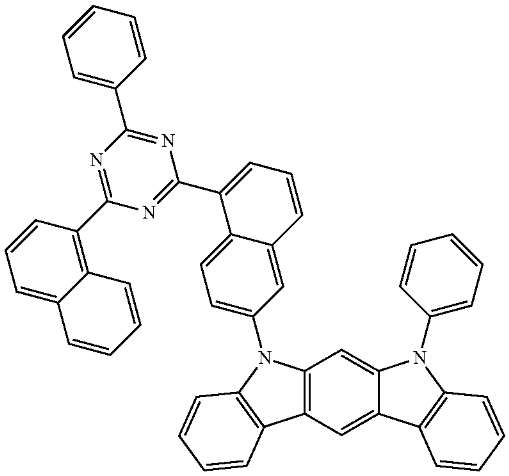
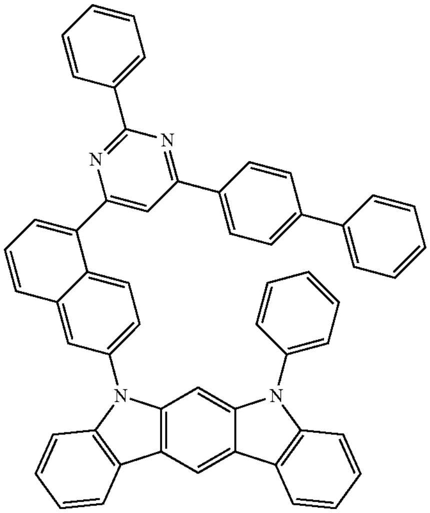
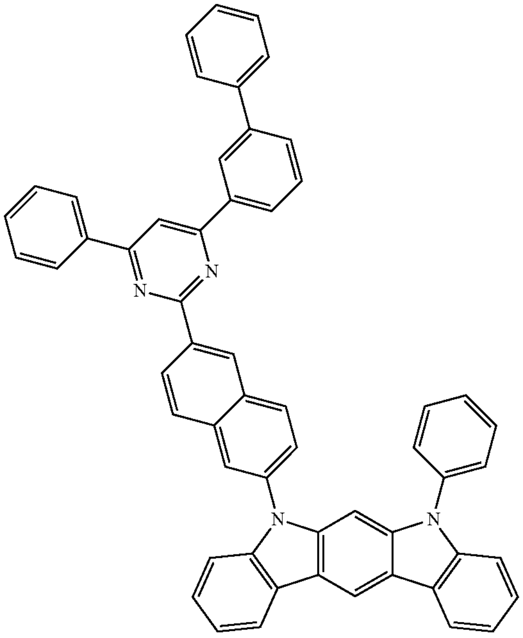
-continued
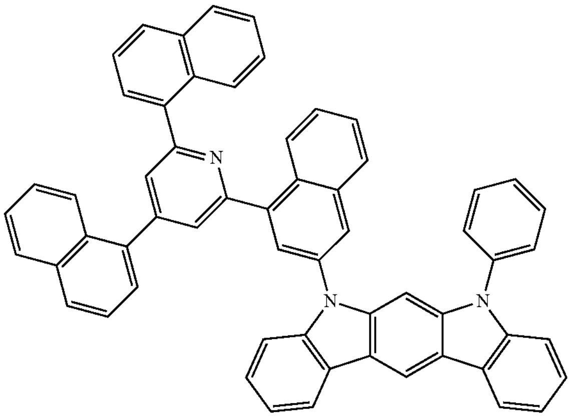
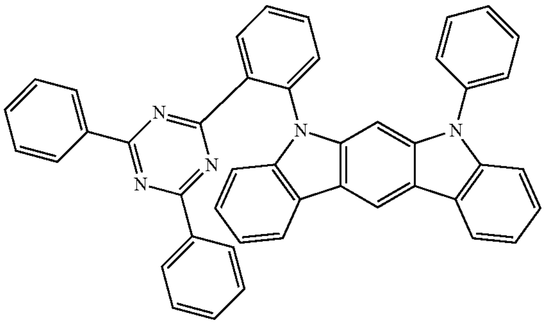
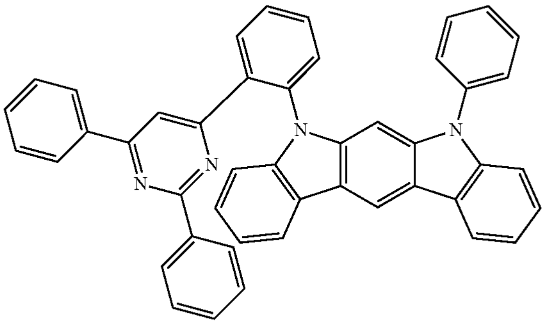
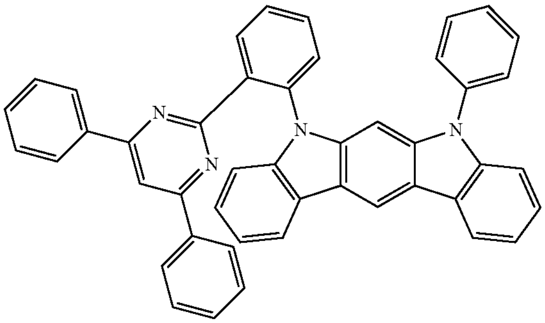
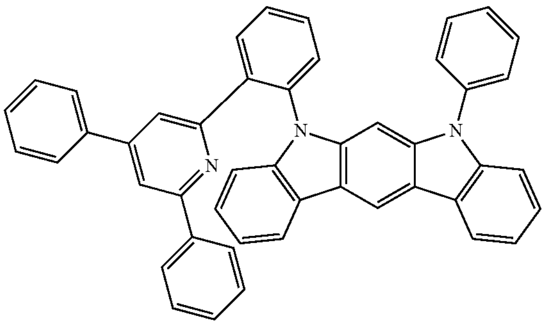

-continued
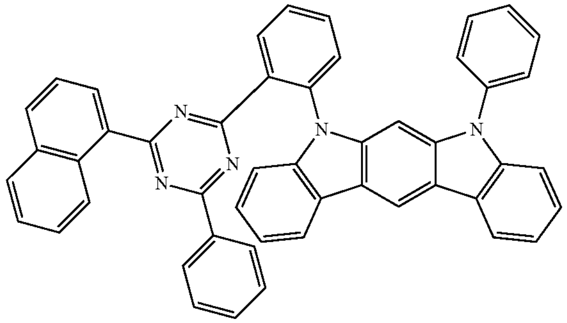
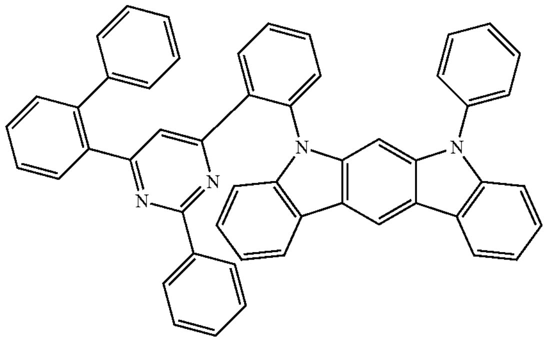
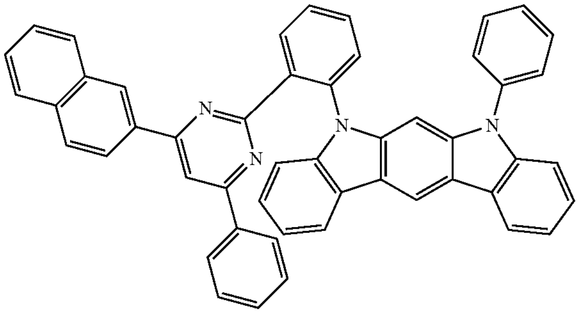
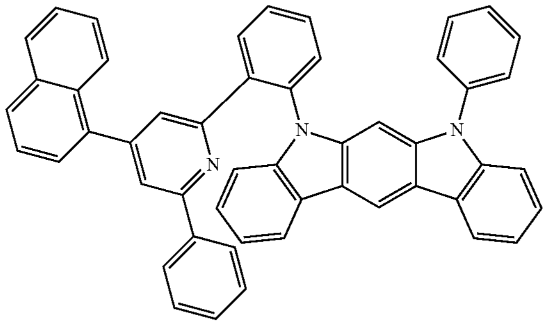
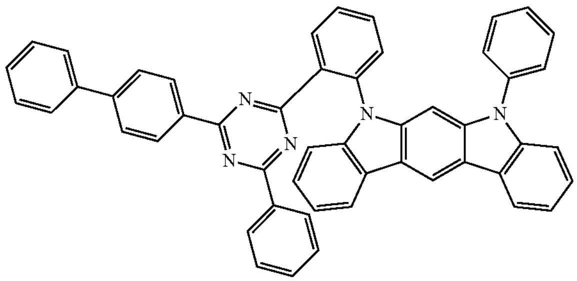
-continued
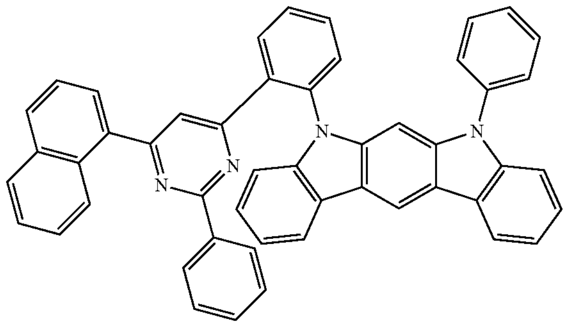
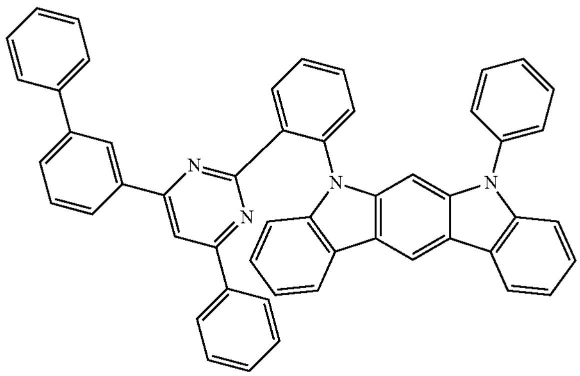
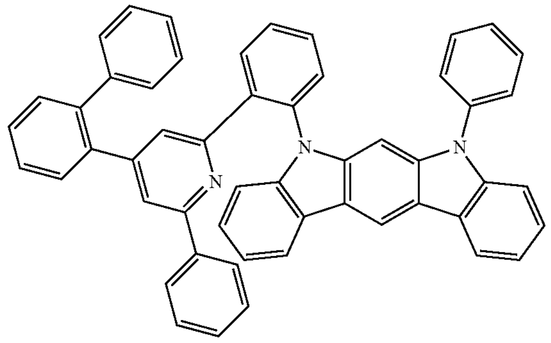
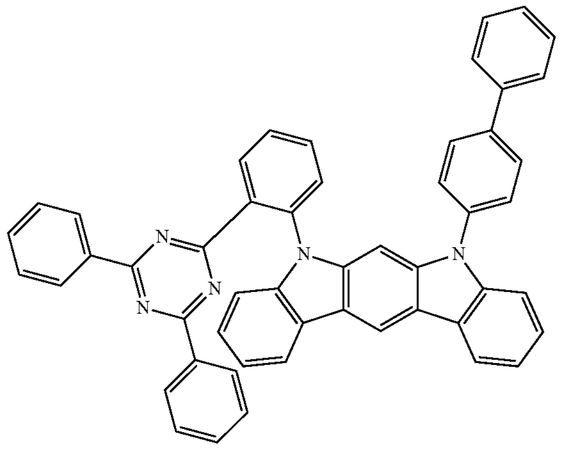

-continued
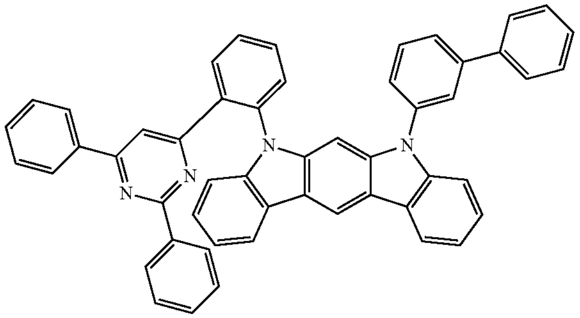
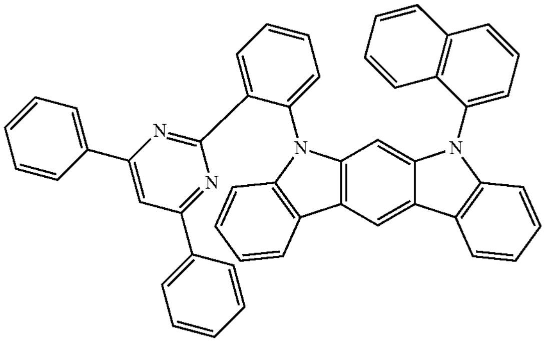
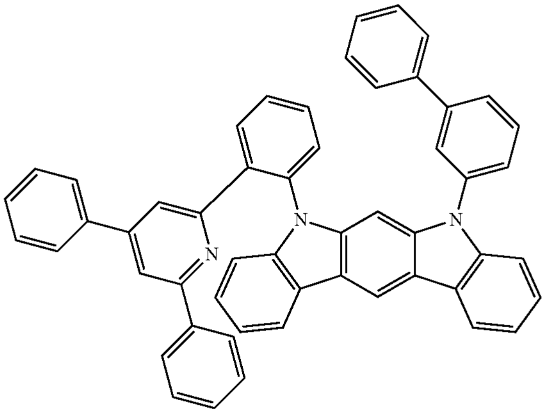
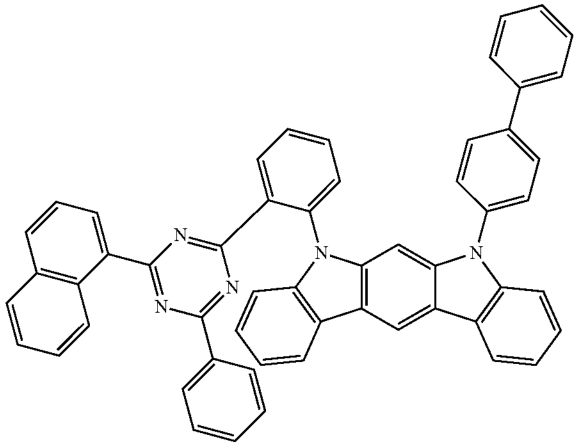
-continued
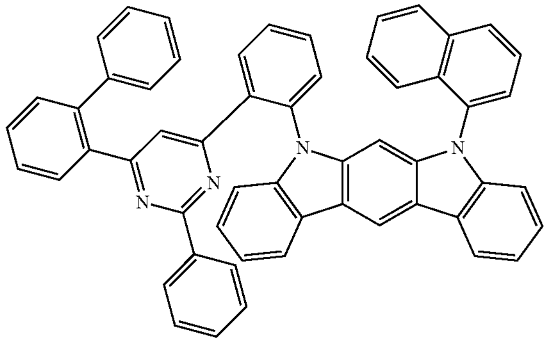
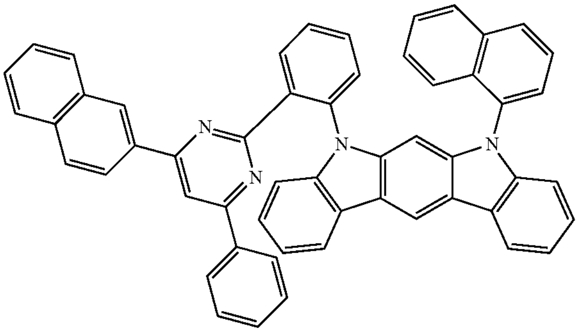
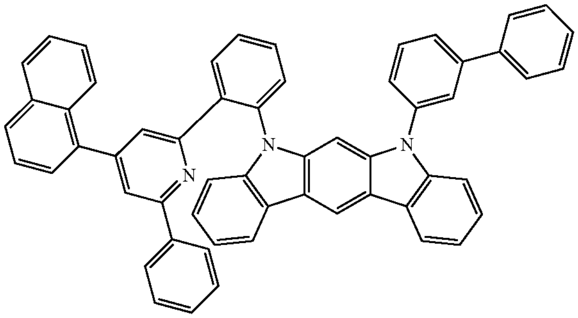
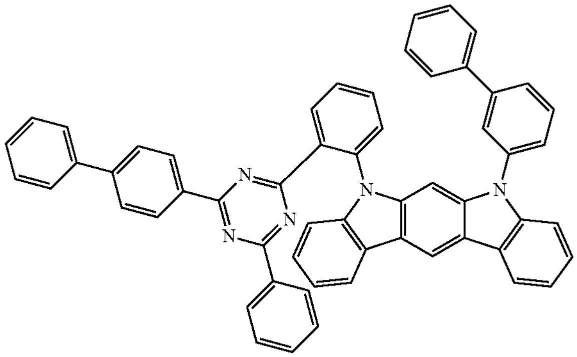

-continued
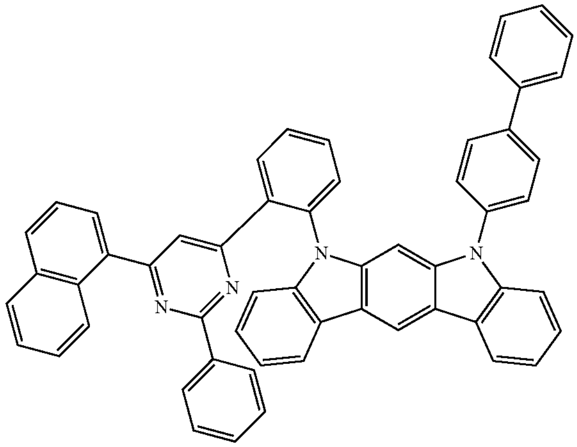
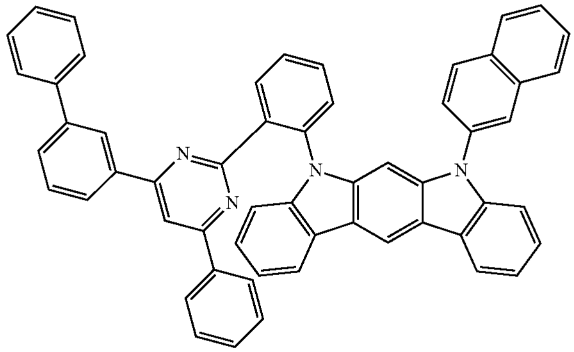
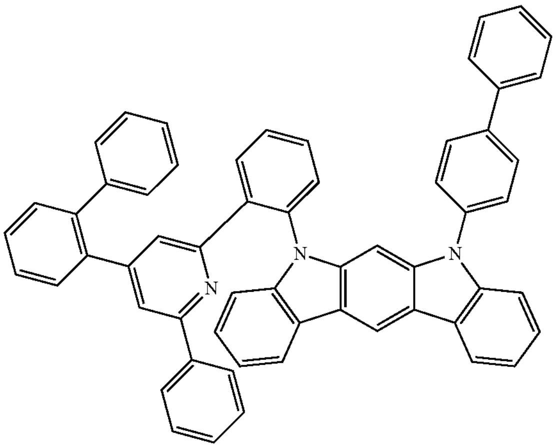
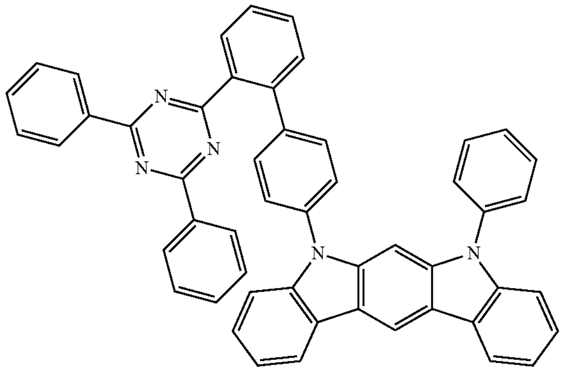
-continued
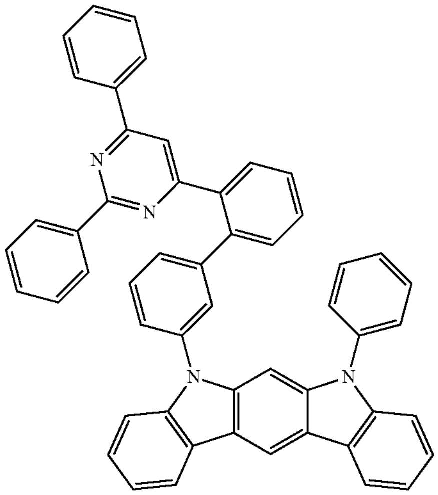
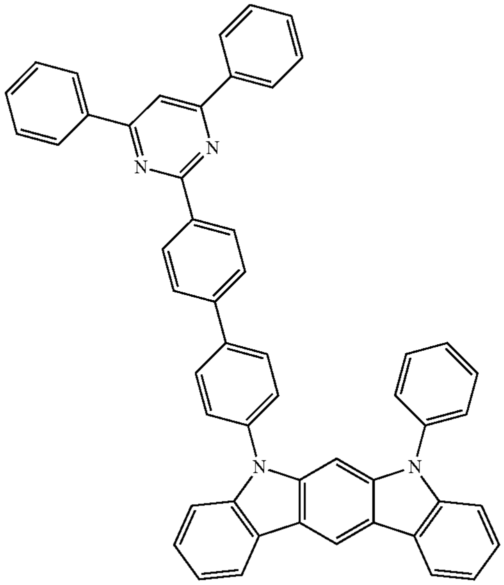
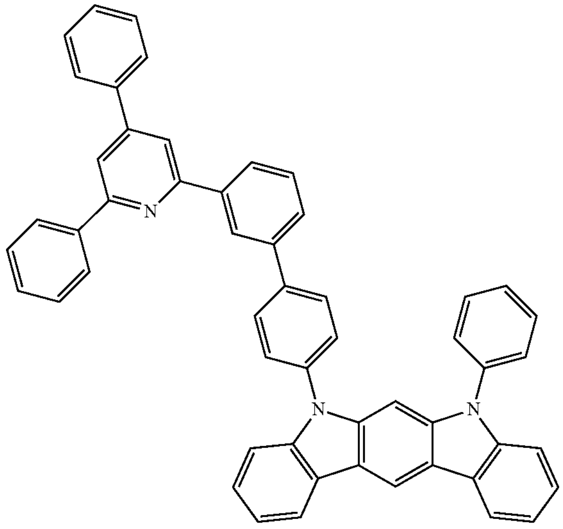

-continued
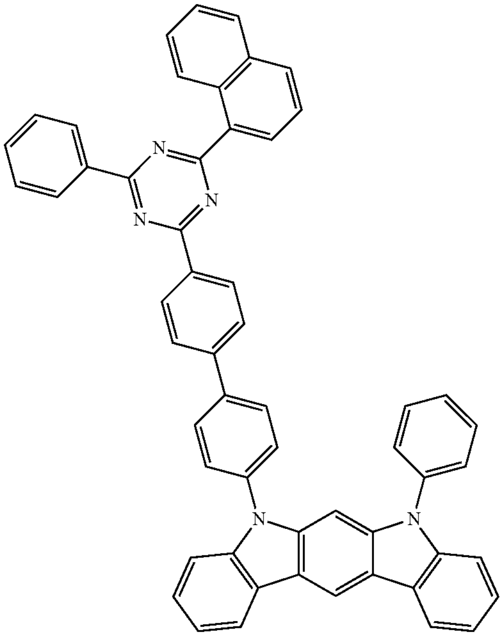
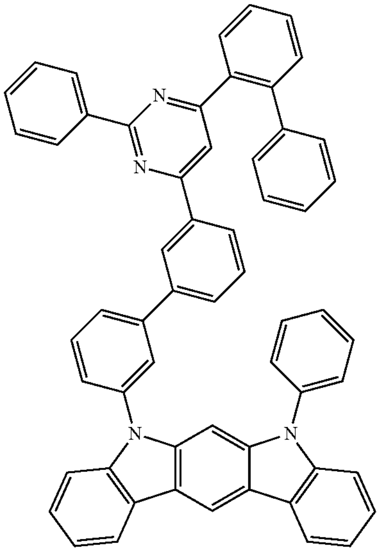
-continued
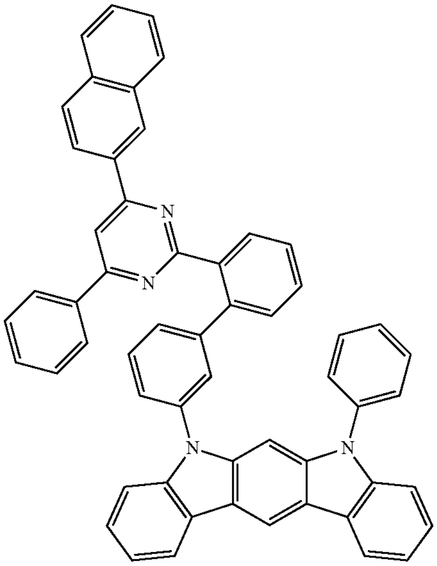
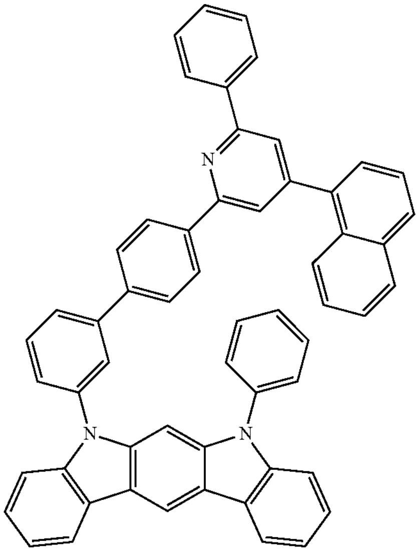

-continued
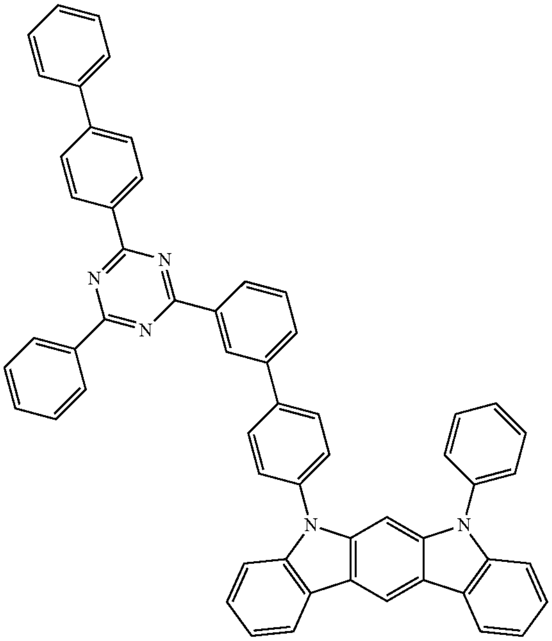
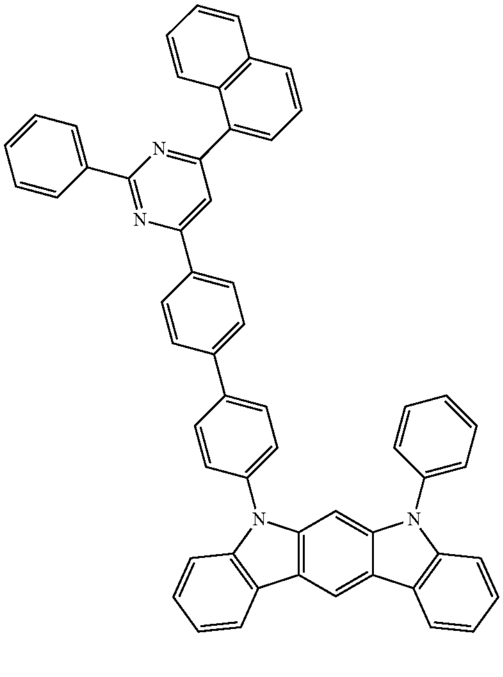
-continued
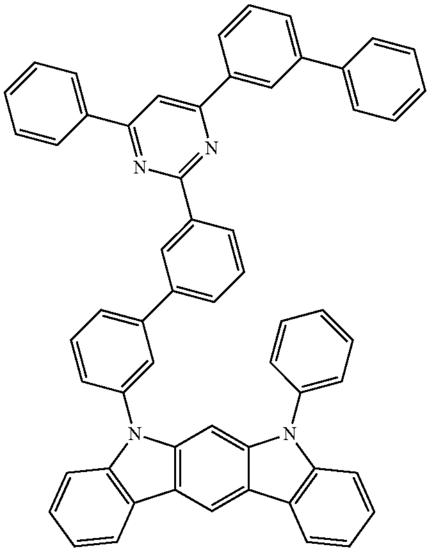
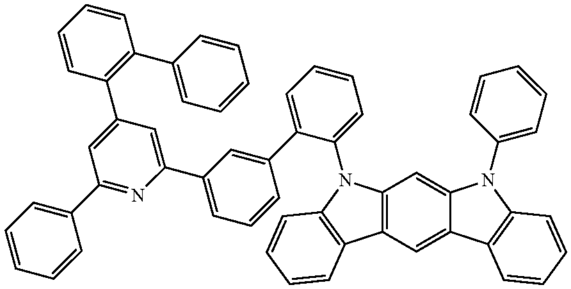
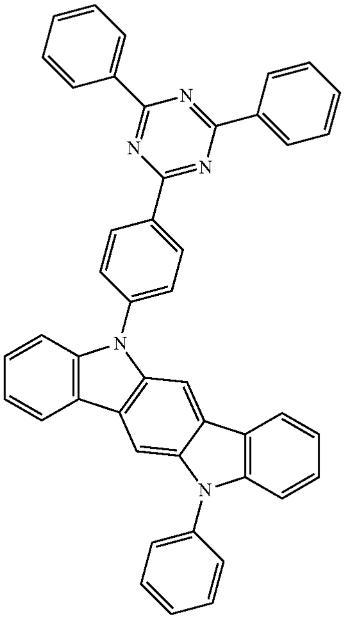

-continued
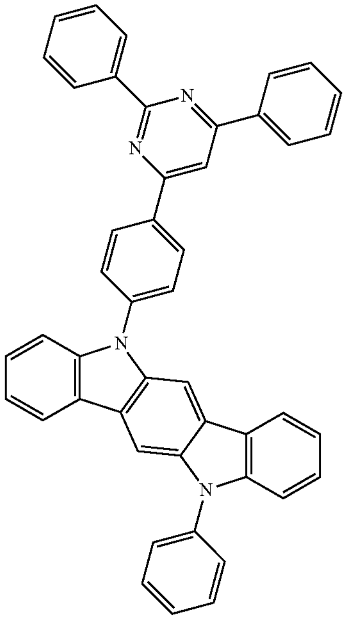
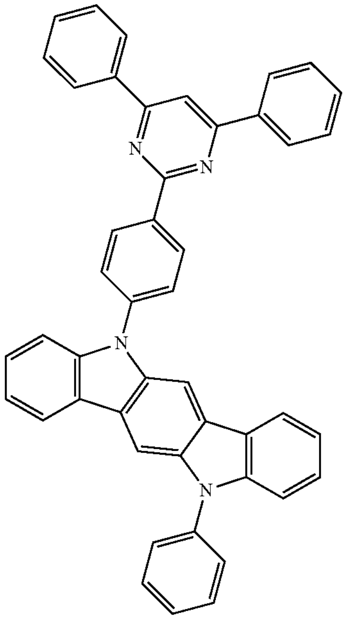
-continued
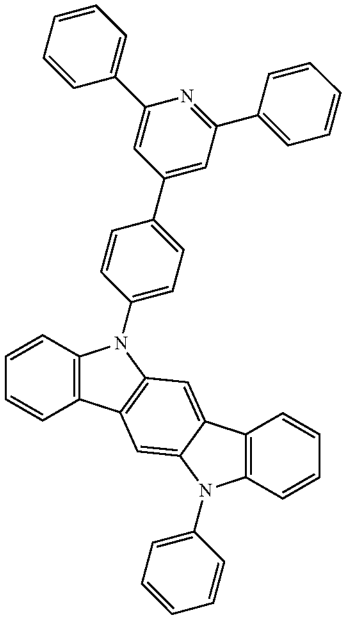
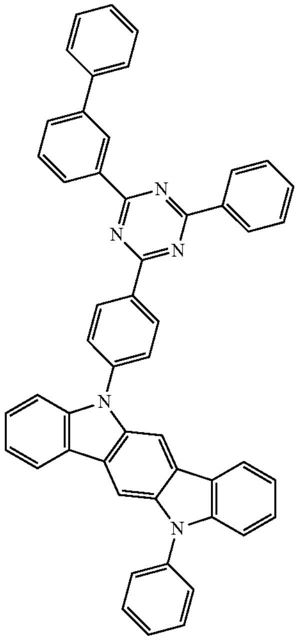

-continued
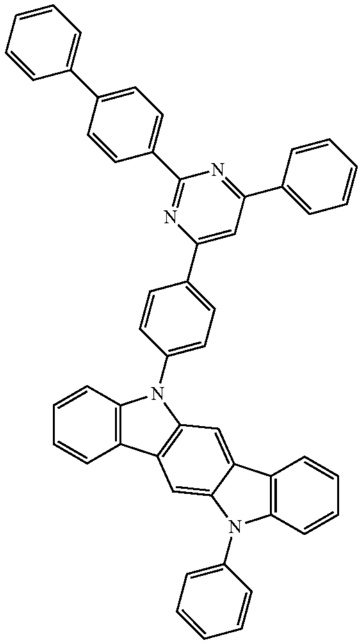
-continued
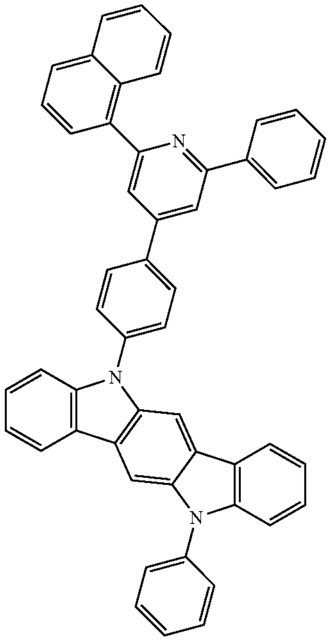
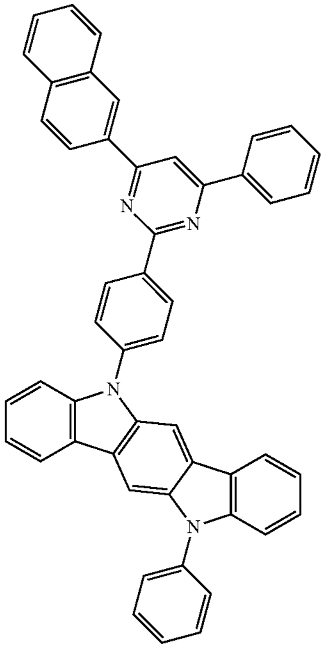
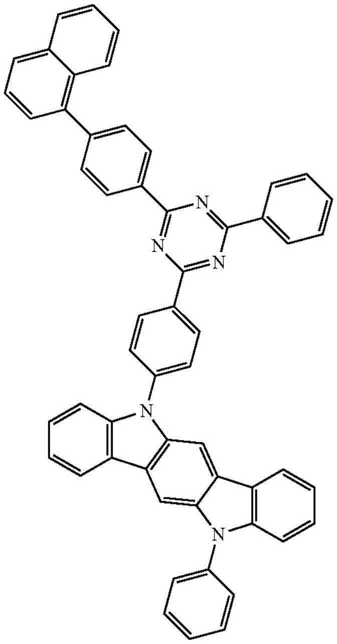

-continued
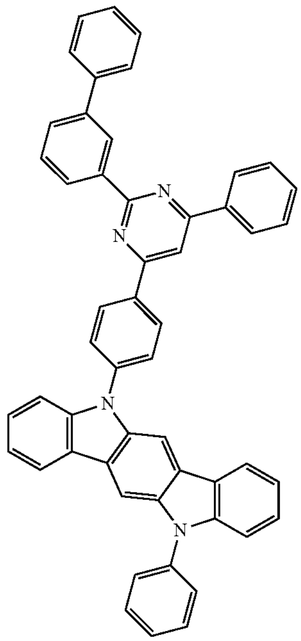
-continued
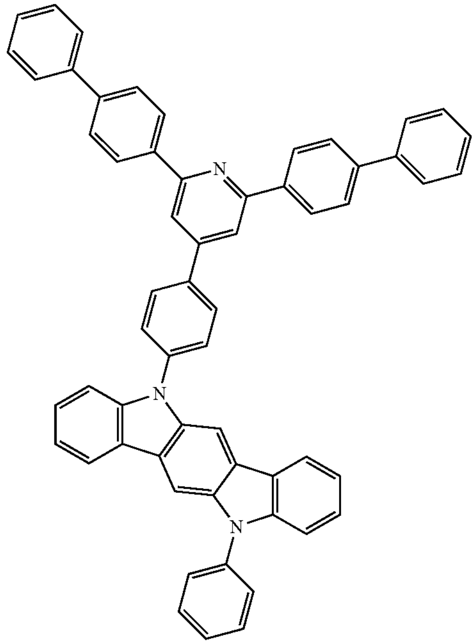
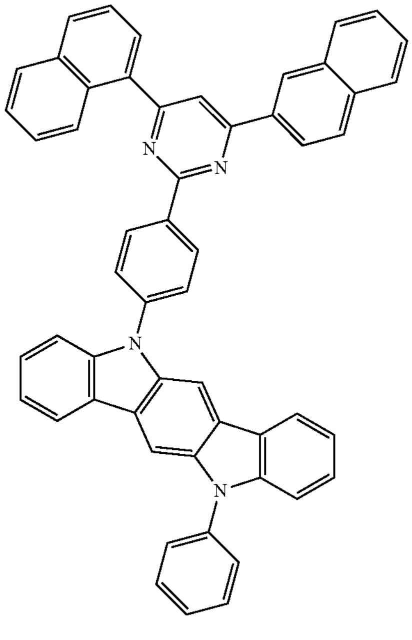
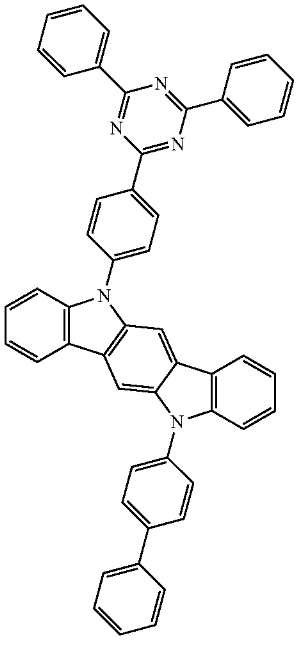

-continued
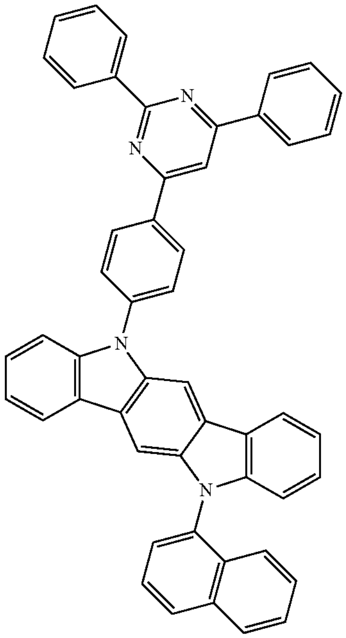
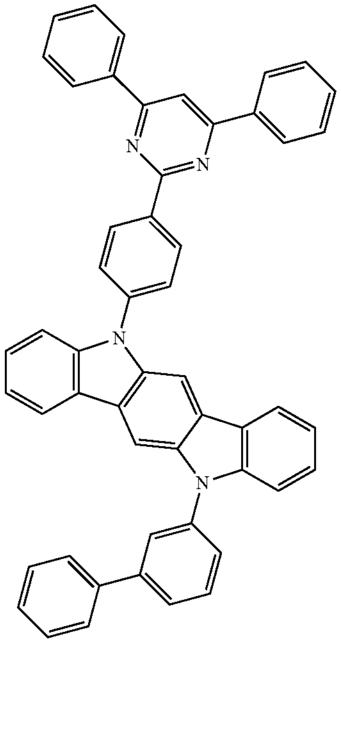
-continued
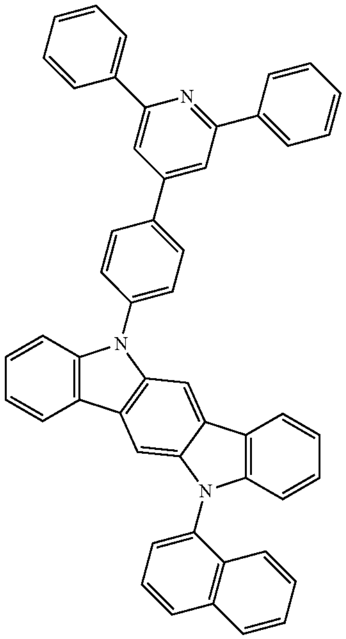
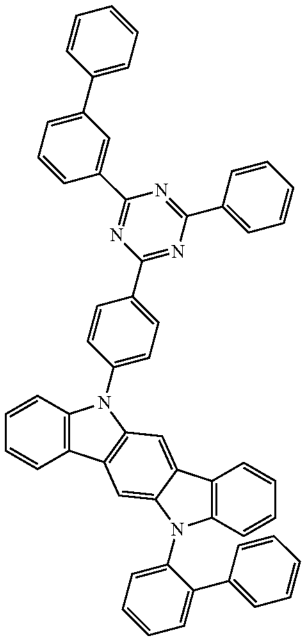

-continued
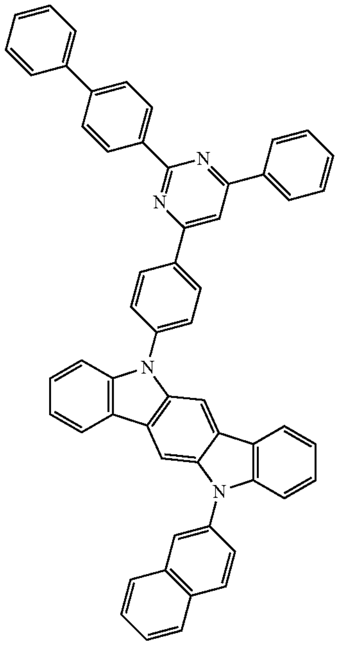
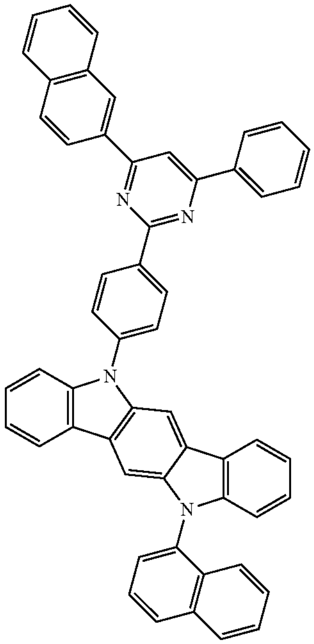
-continued
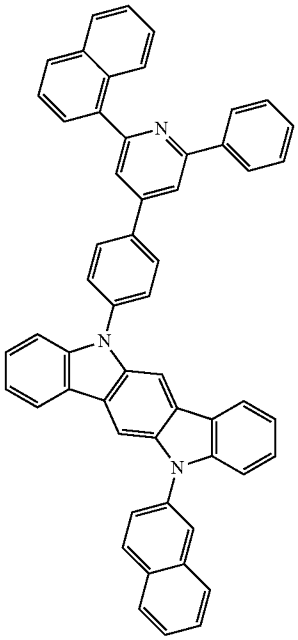
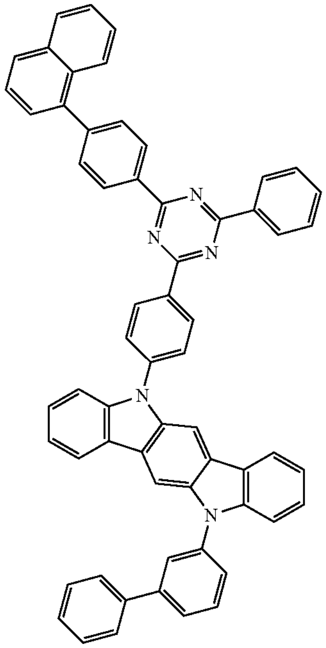

-continued
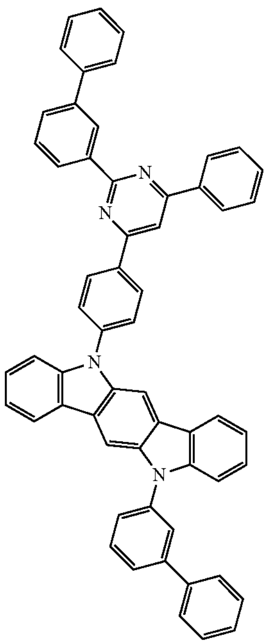
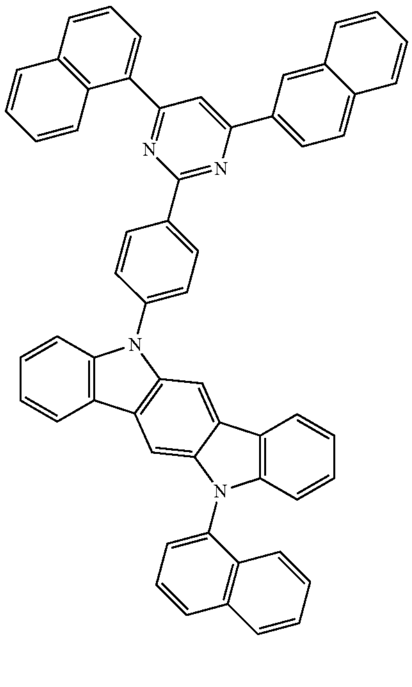
-continued
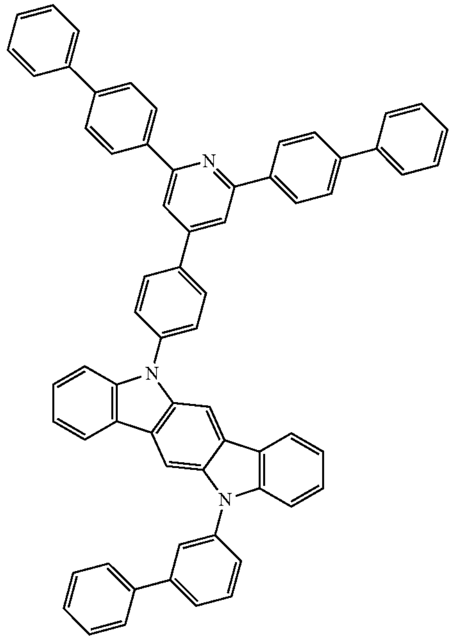
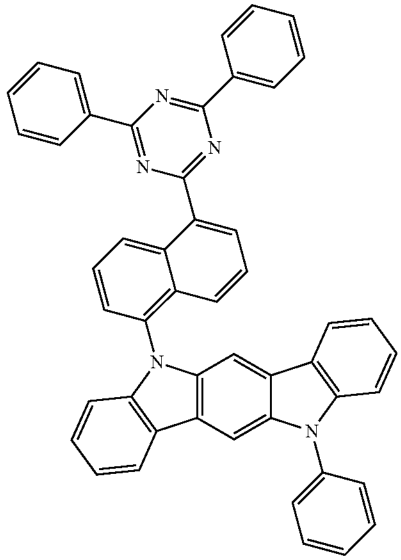
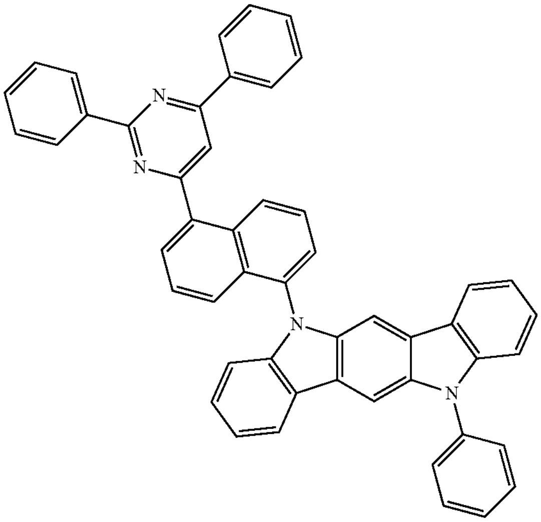

-continued
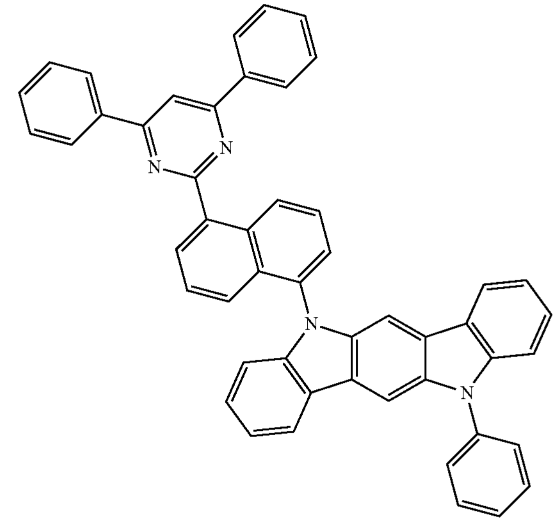
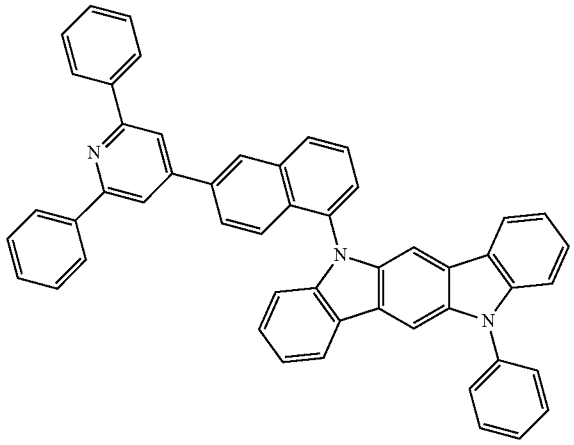
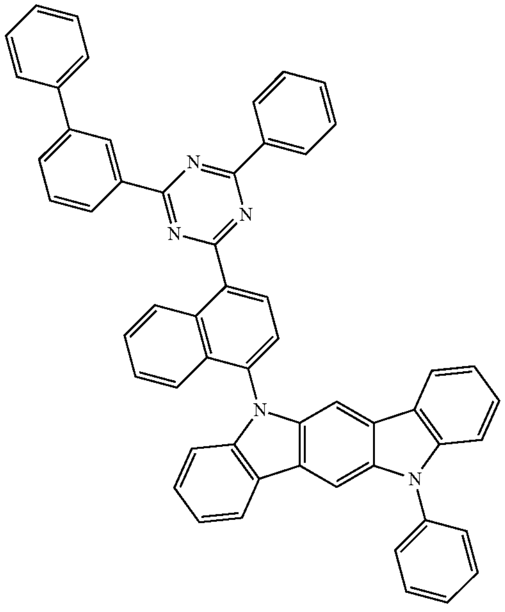
-continued
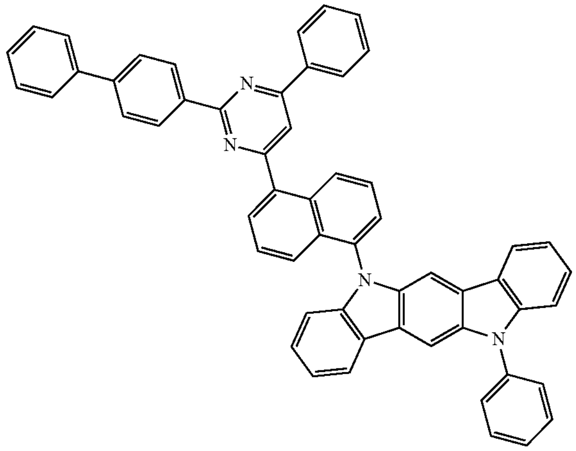
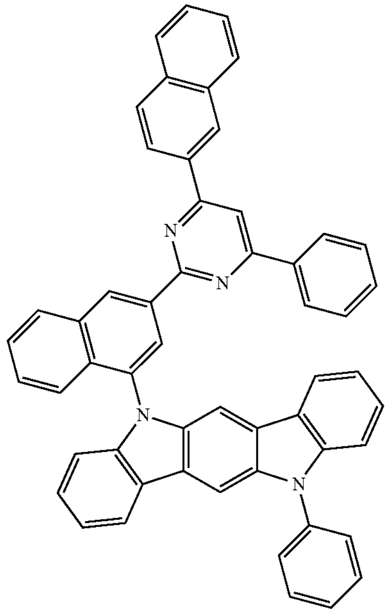
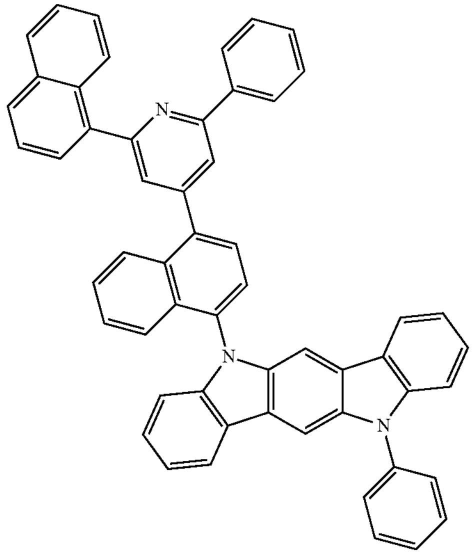

-continued
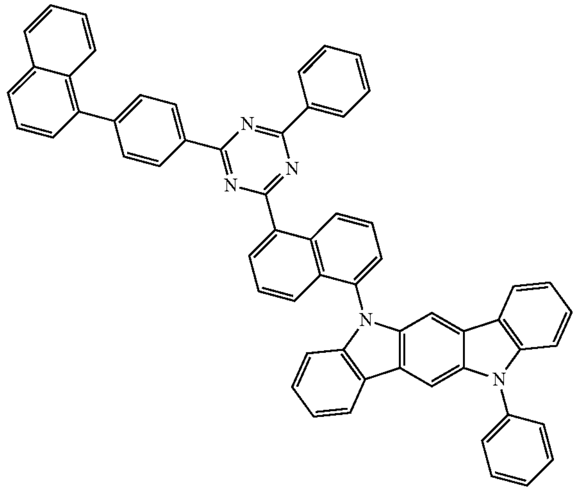
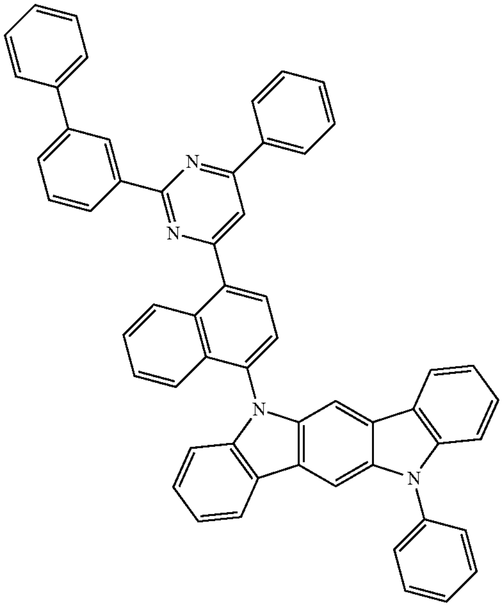
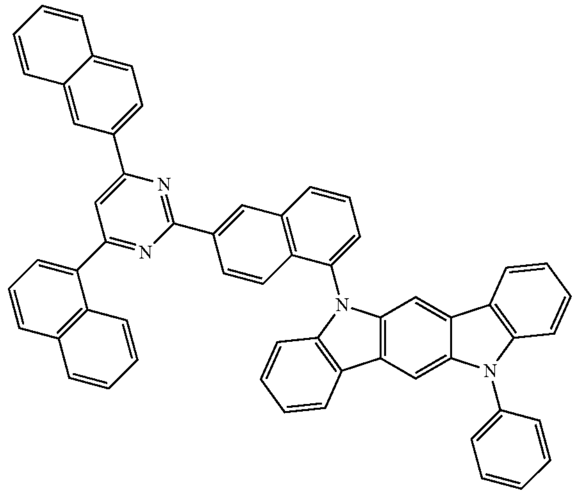
-continued
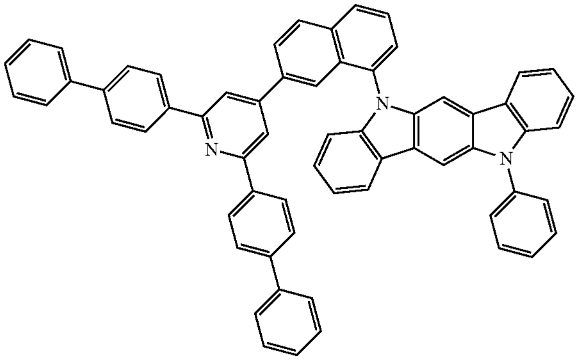
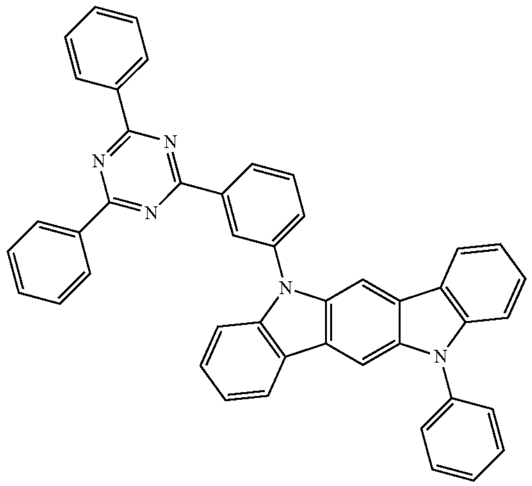
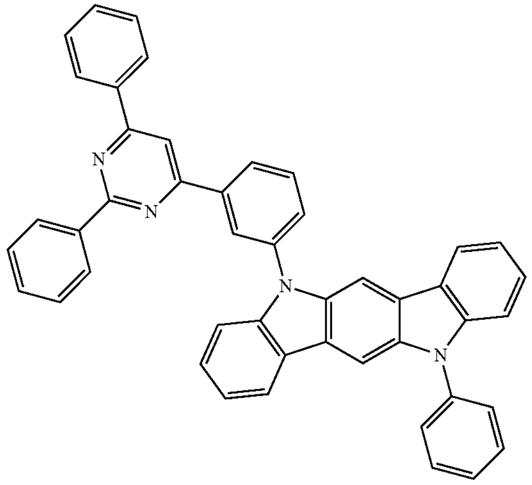

-continued
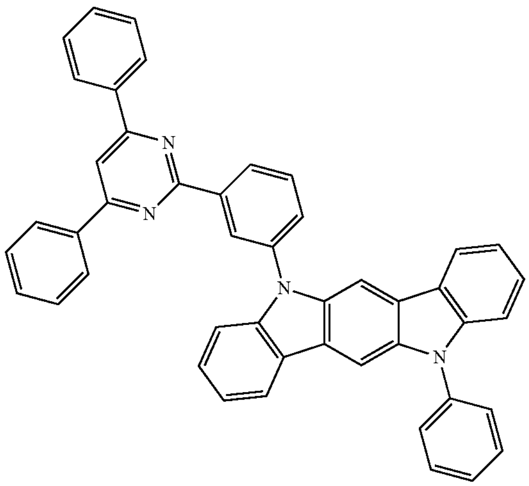
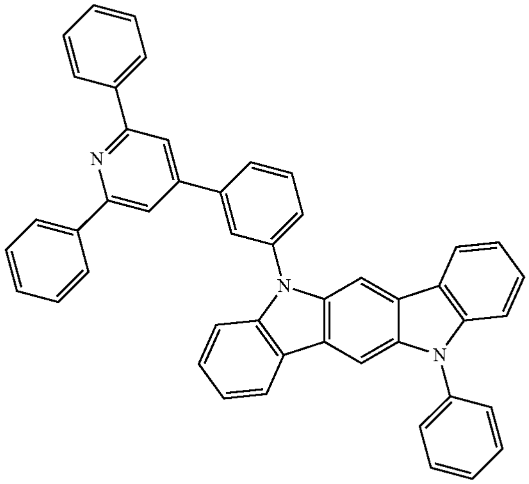
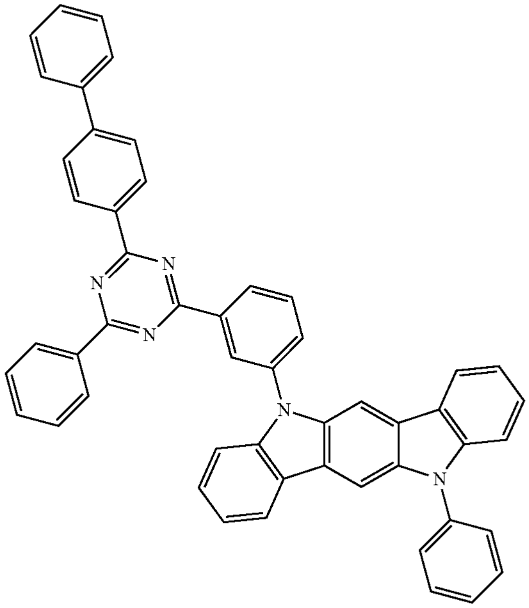
-continued
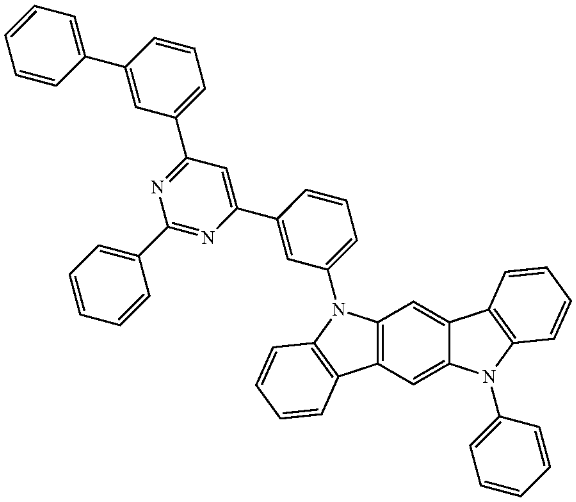
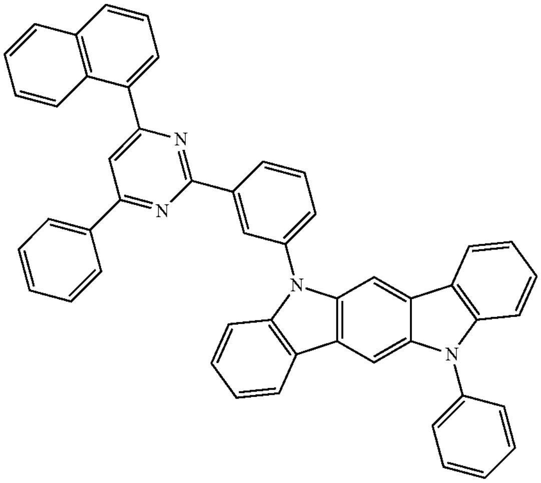
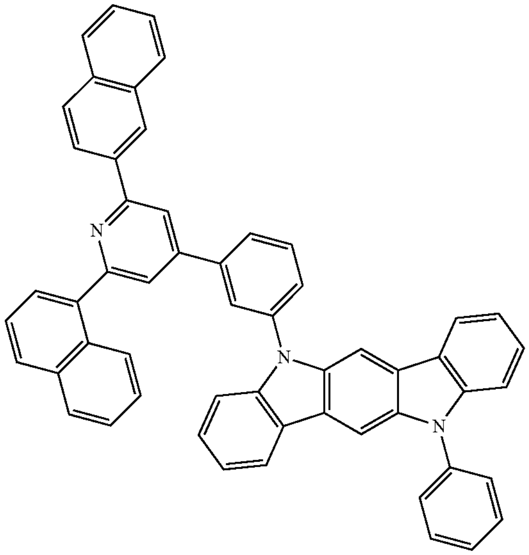

-continued
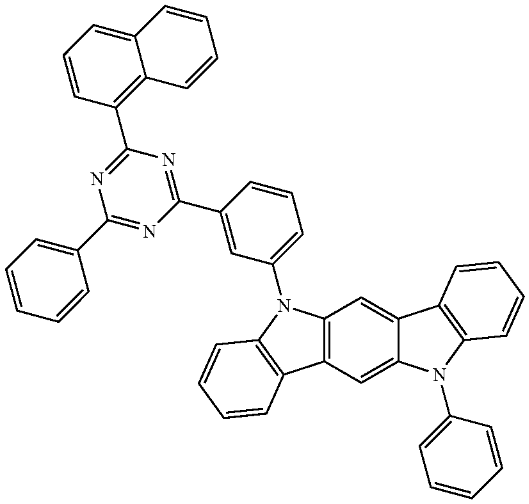
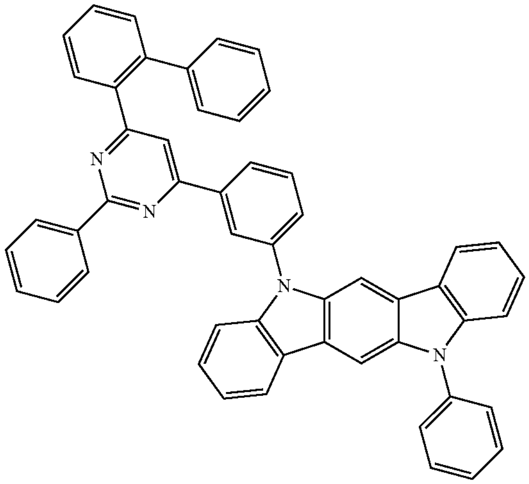
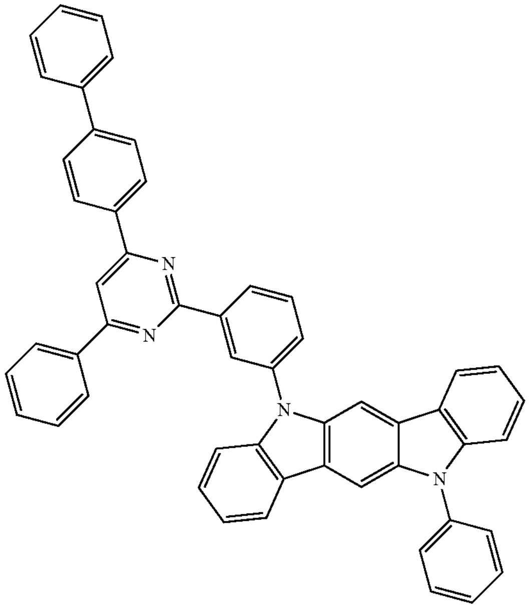
-continued
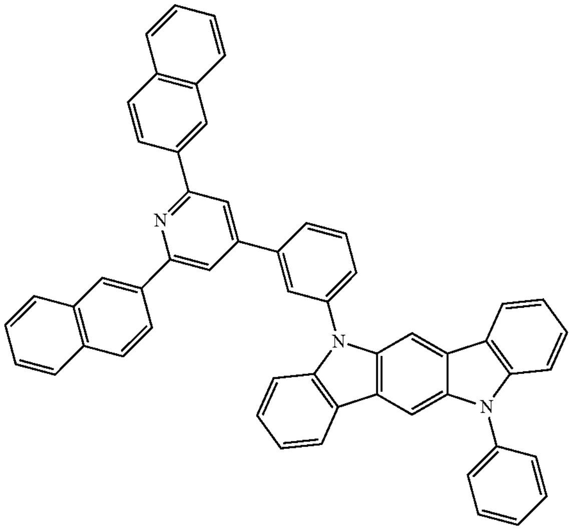
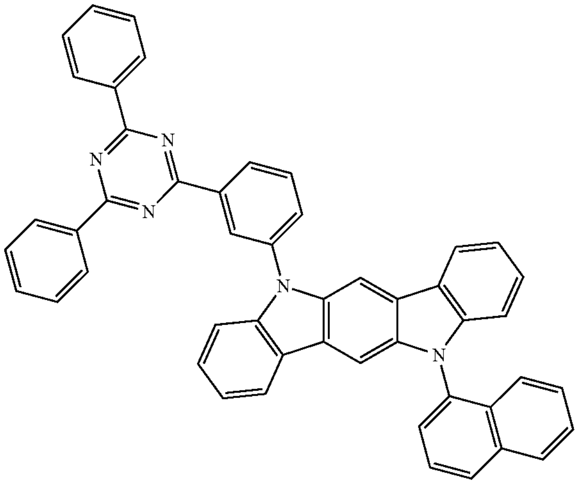
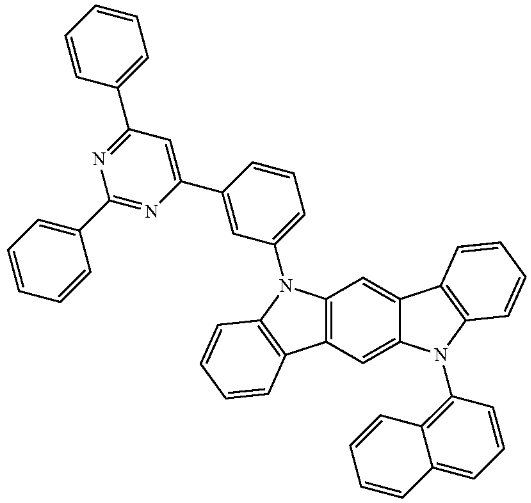

-continued
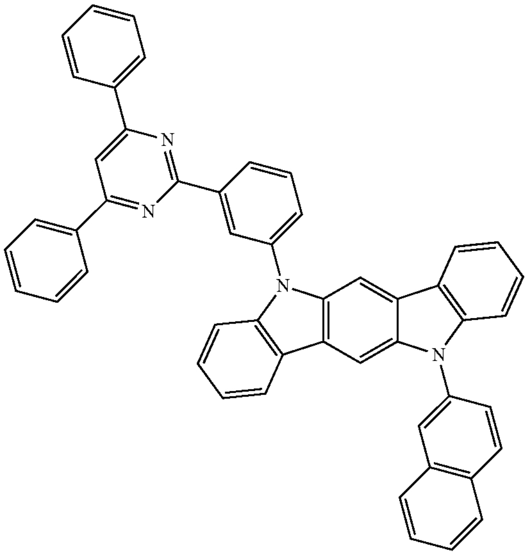
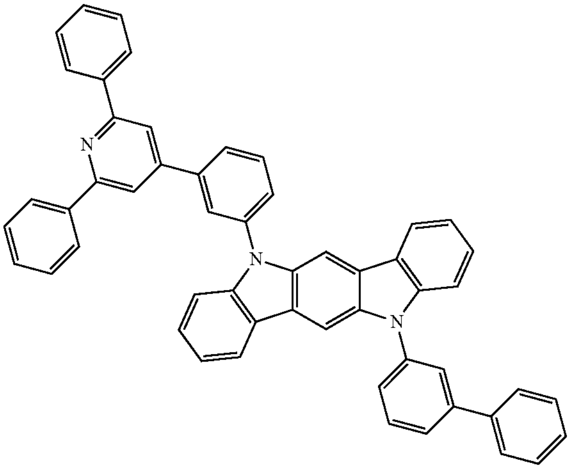
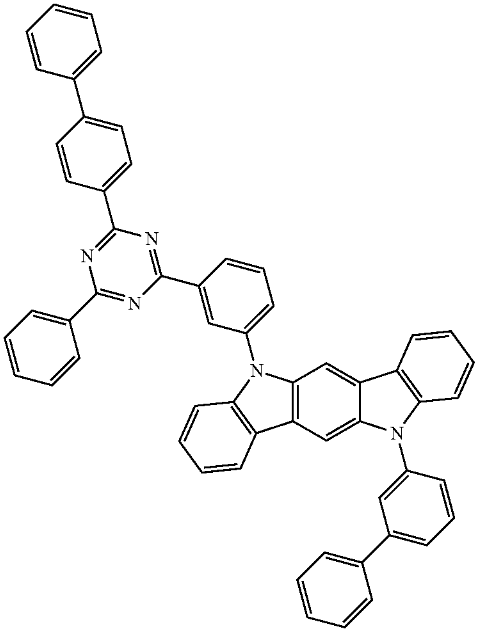
-continued
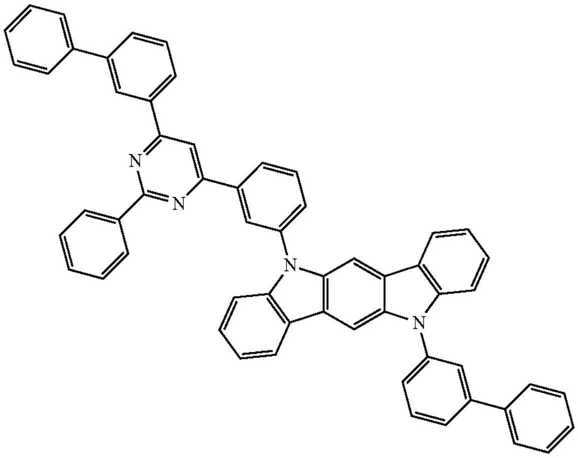
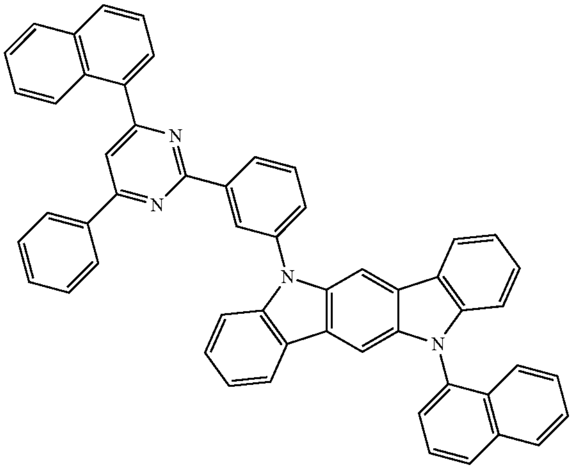
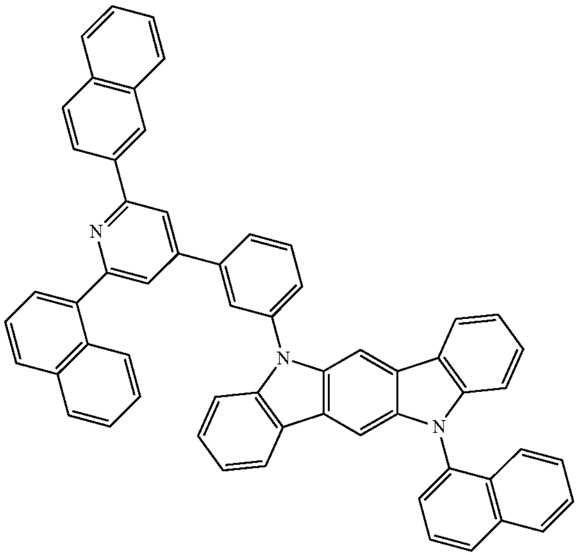

-continued
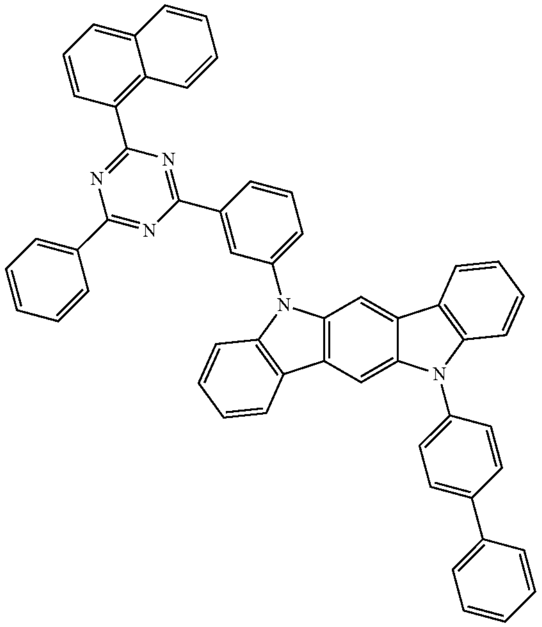
-continued
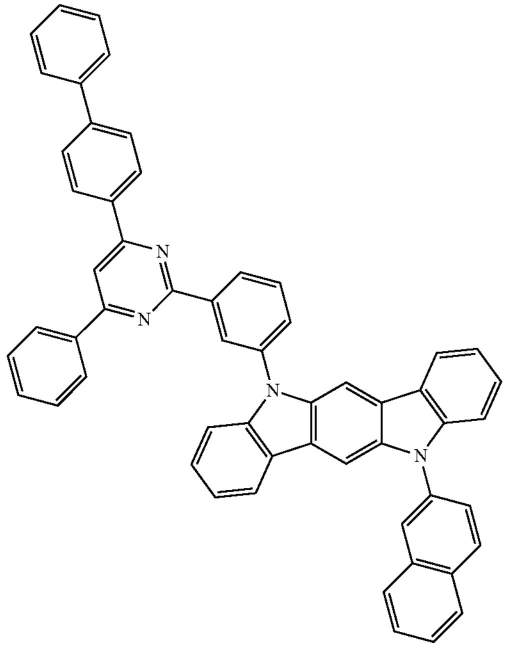
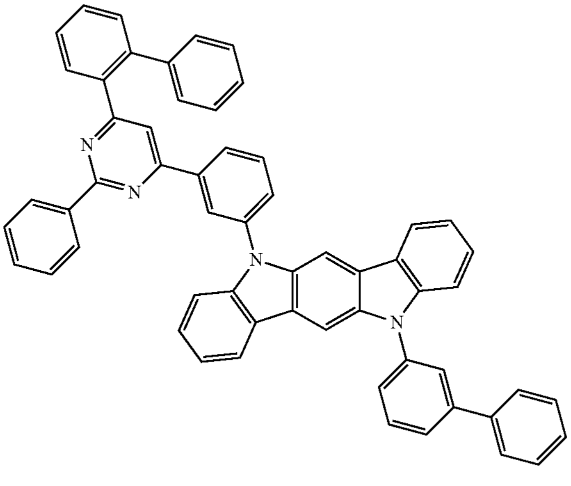
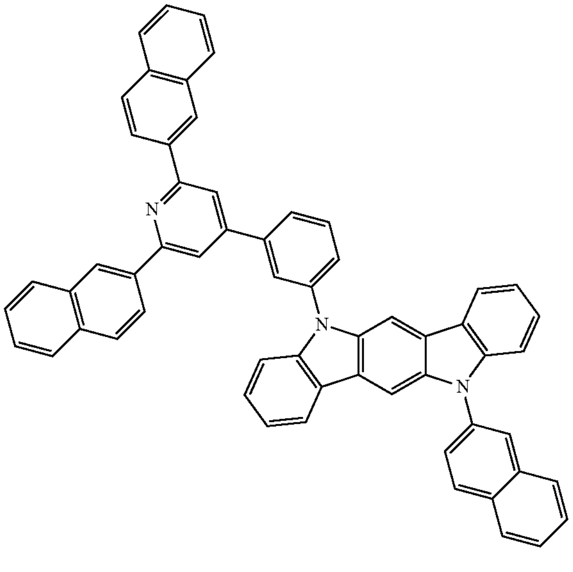

-continued
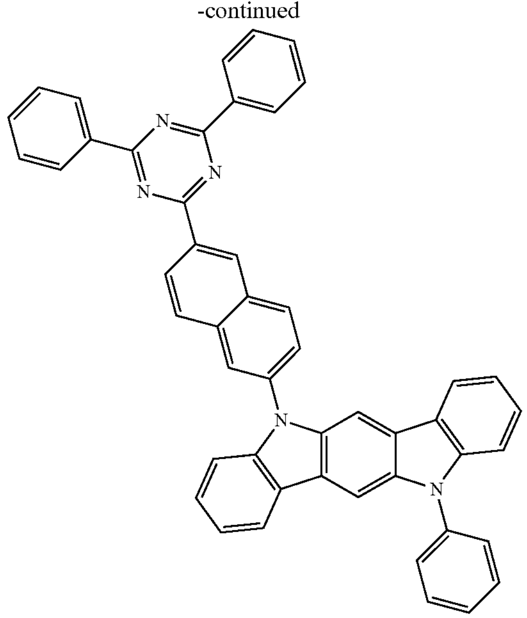
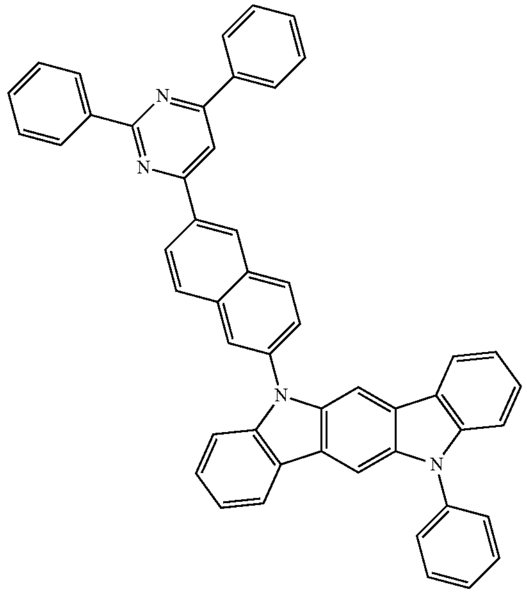
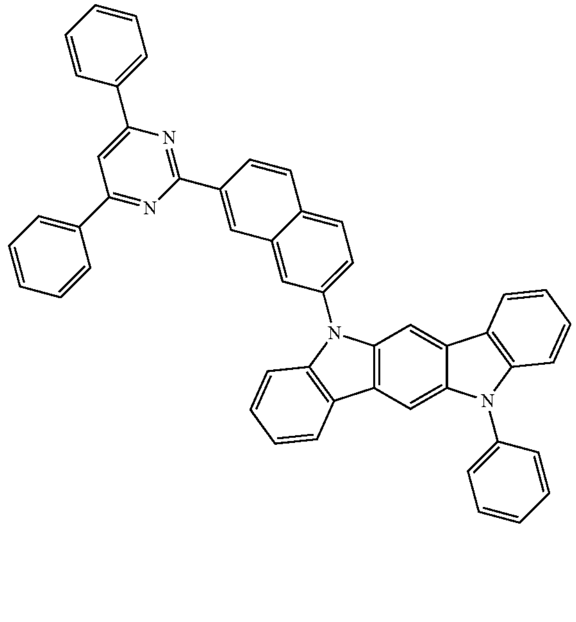
-continued
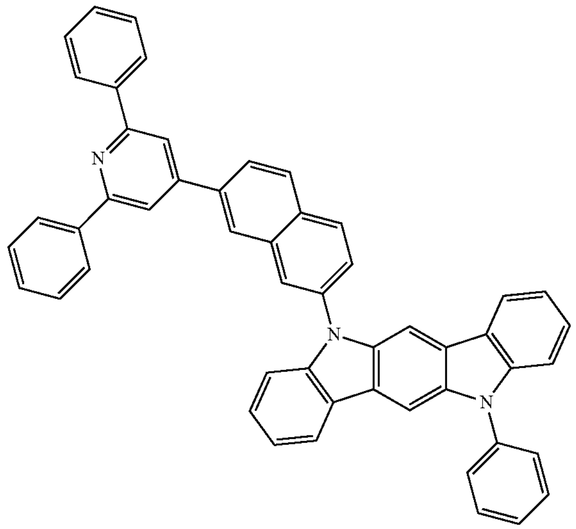
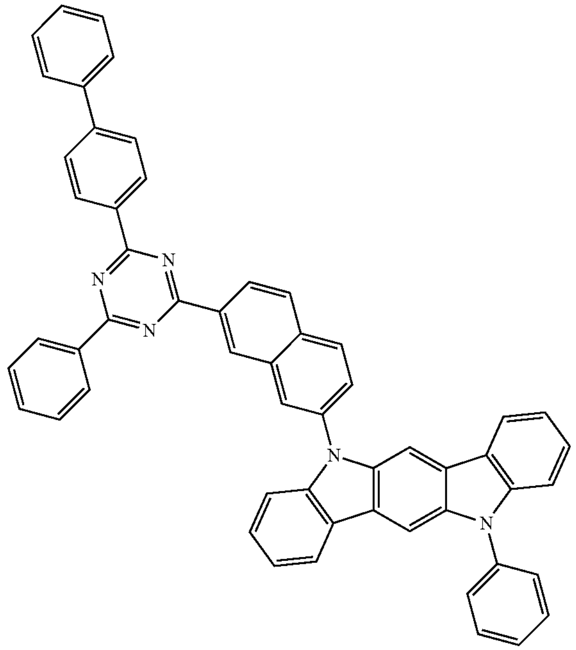

-continued
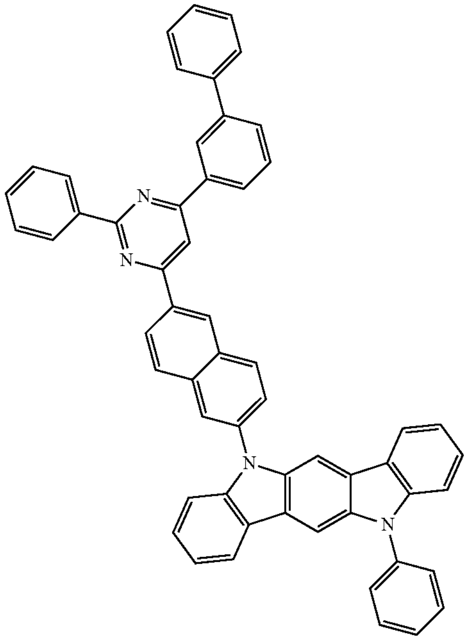
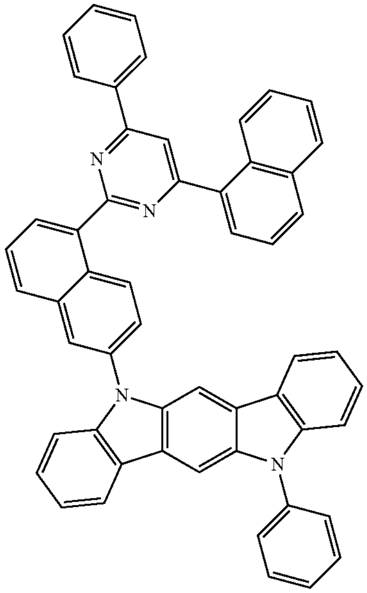
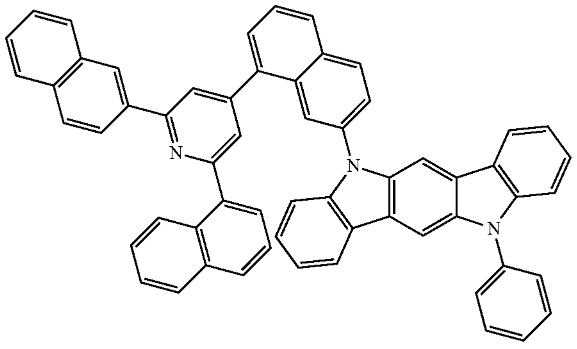
-continued
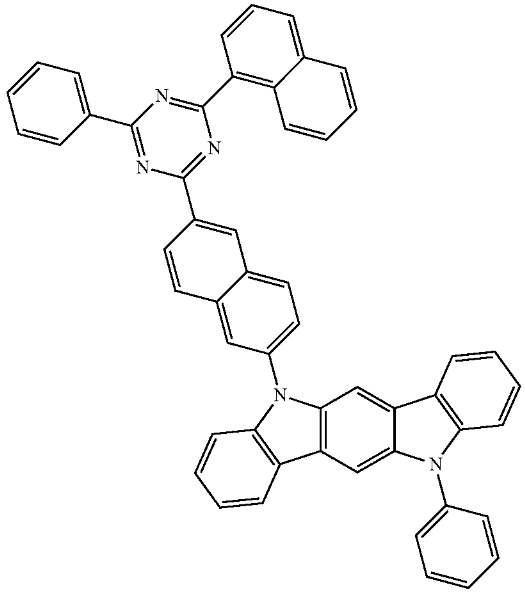
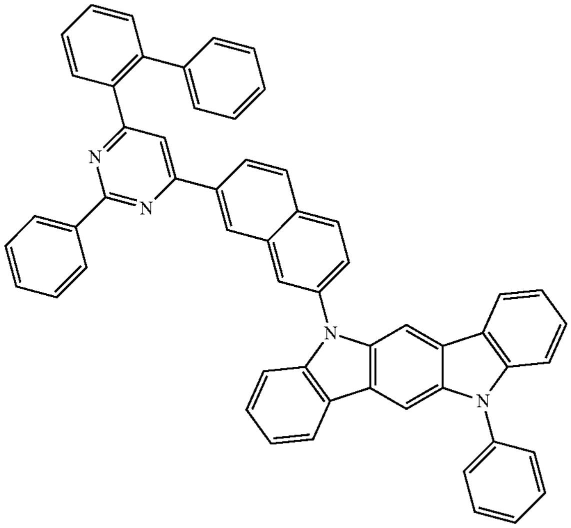
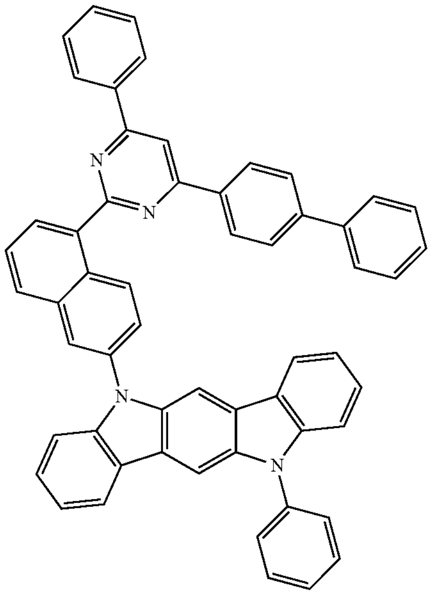

-continued
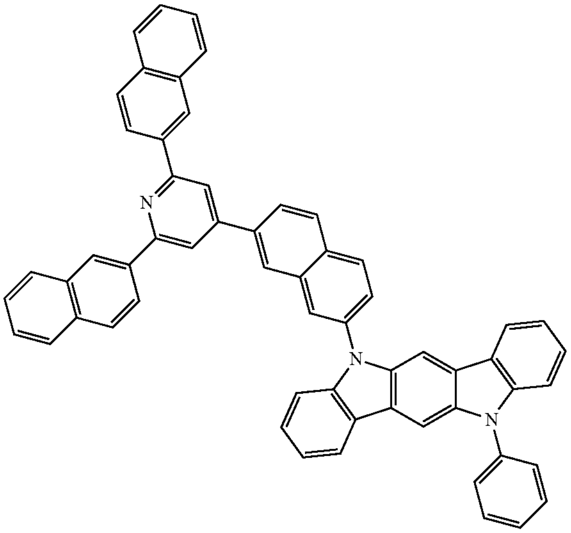
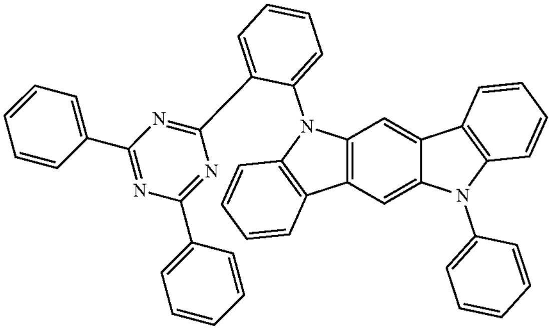
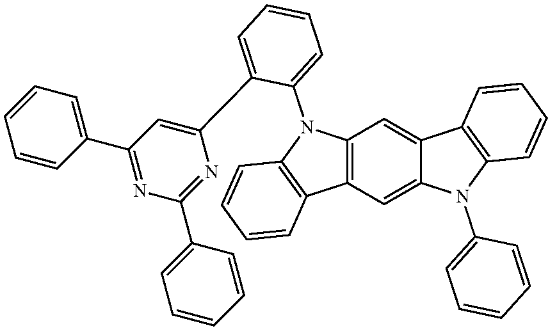
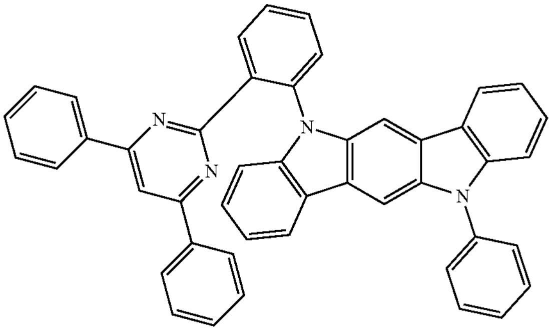
-continued
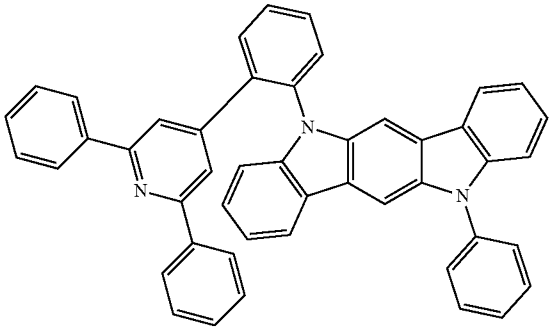
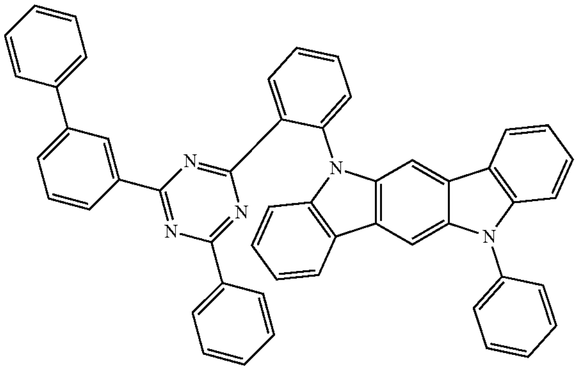
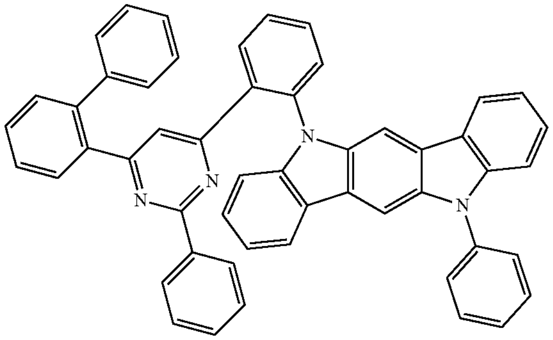
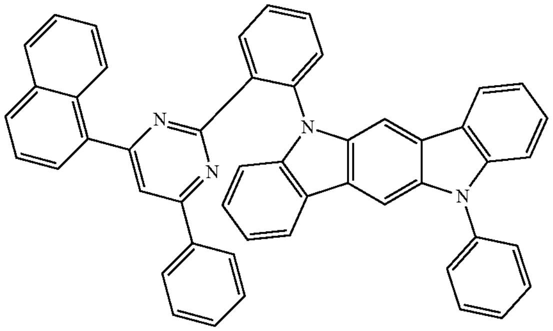
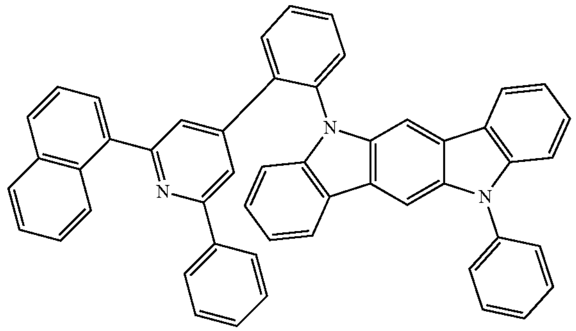

-continued
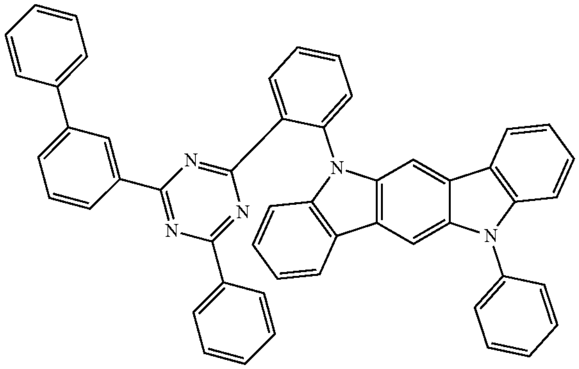
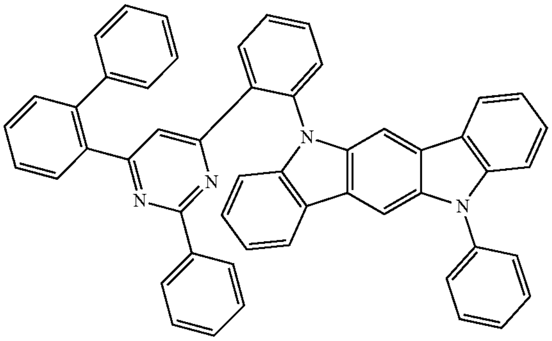
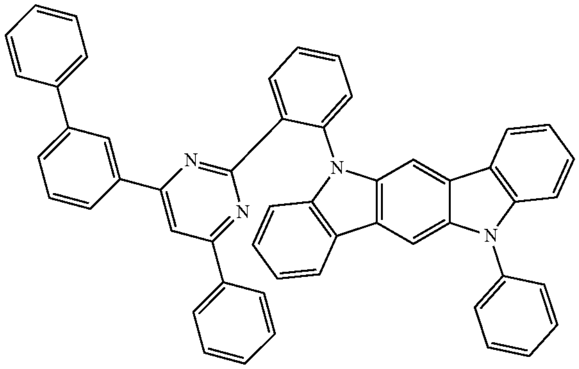
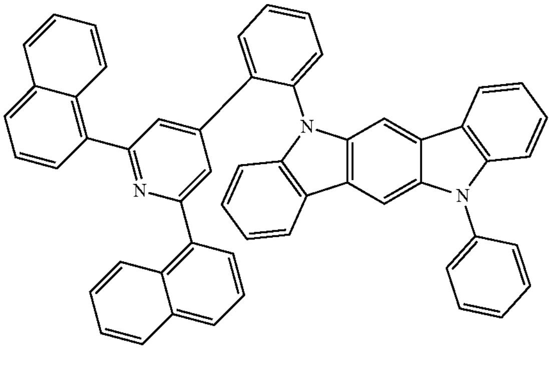
-continued
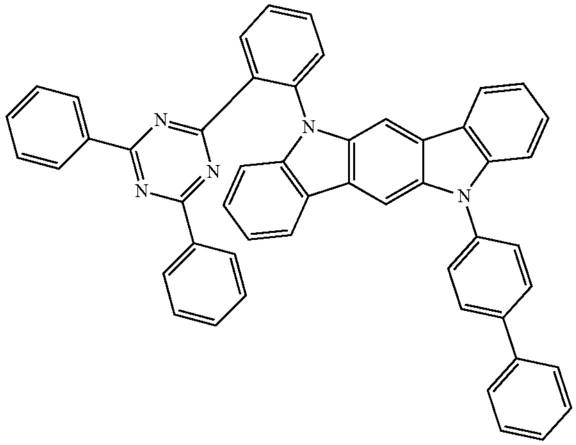
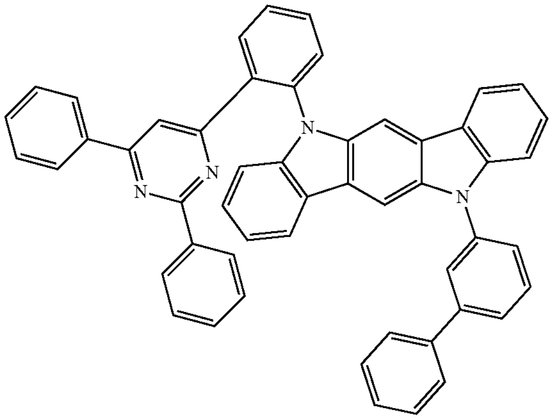
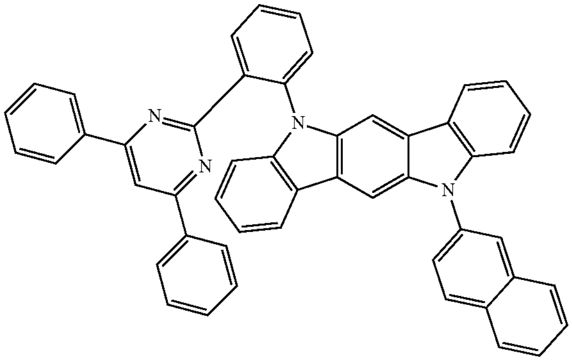
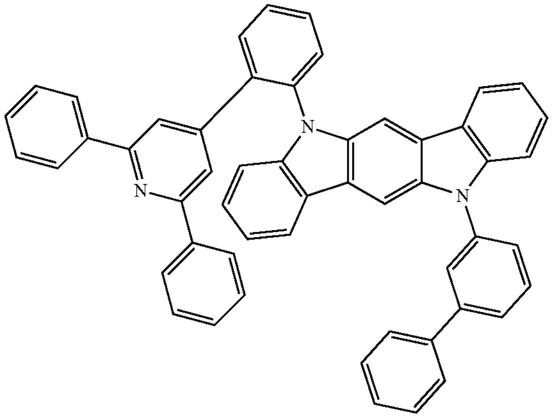

-continued
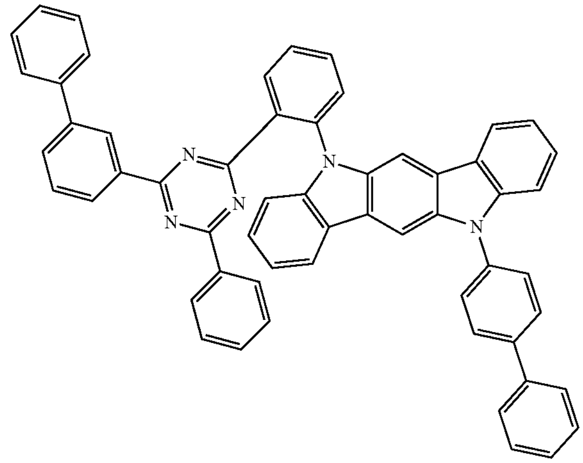
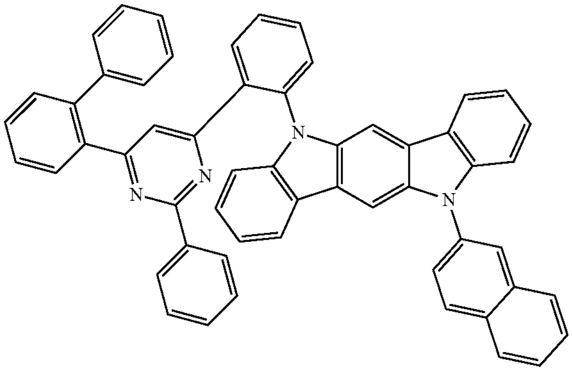
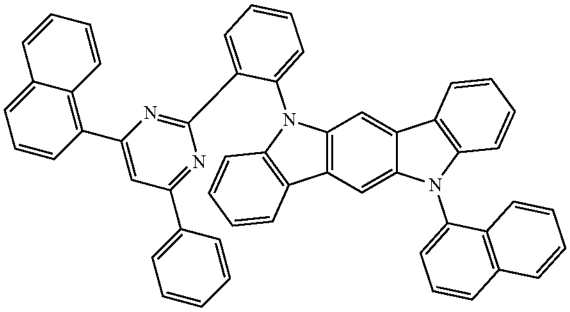
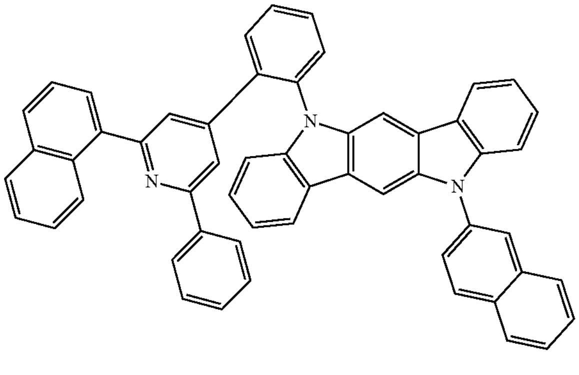
-continued
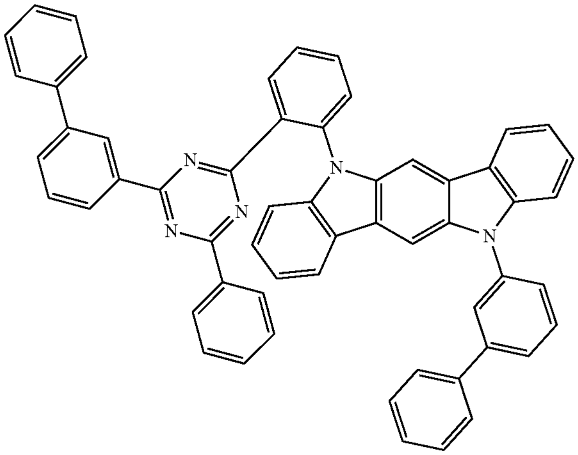
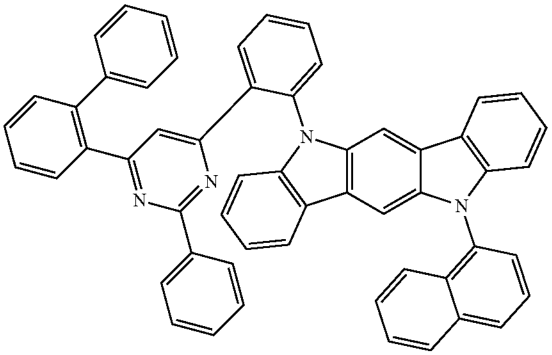
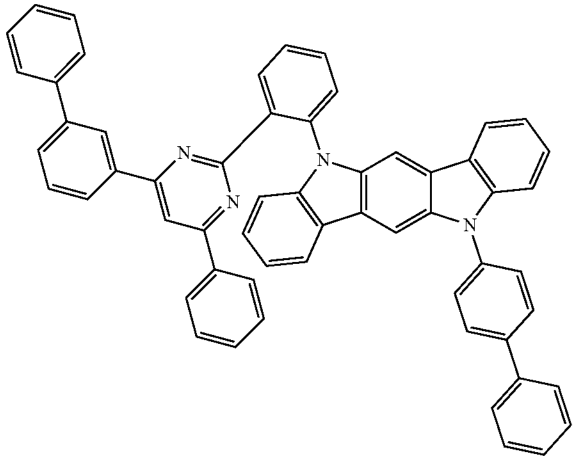
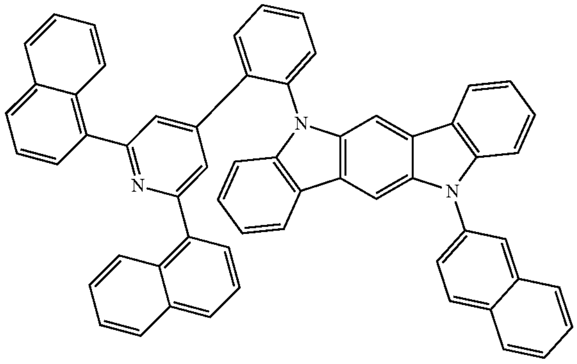

-continued
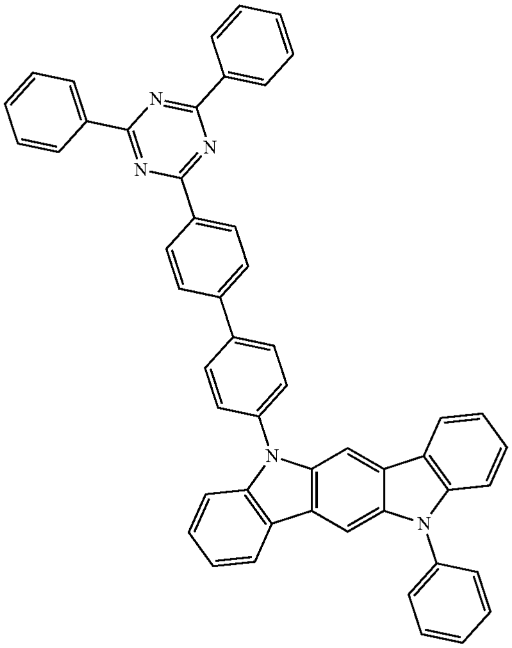
-continued
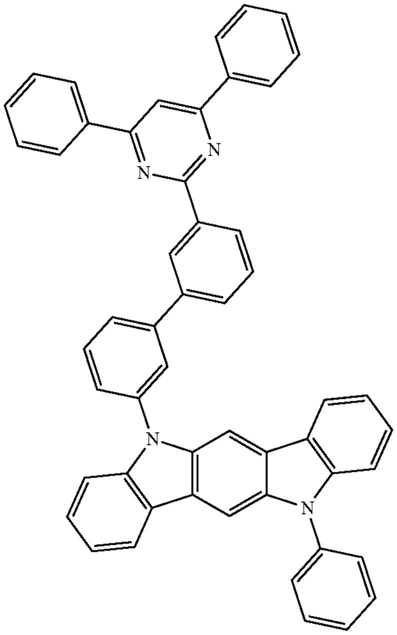
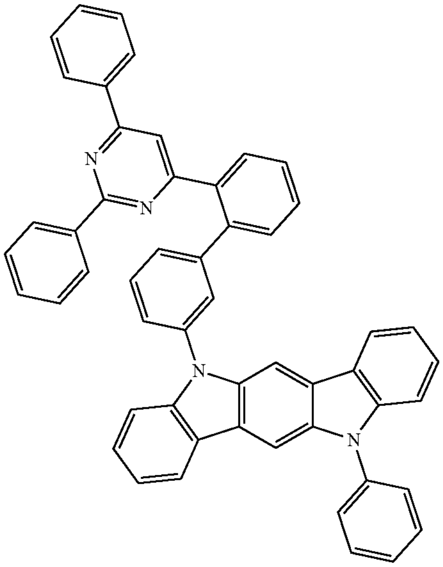
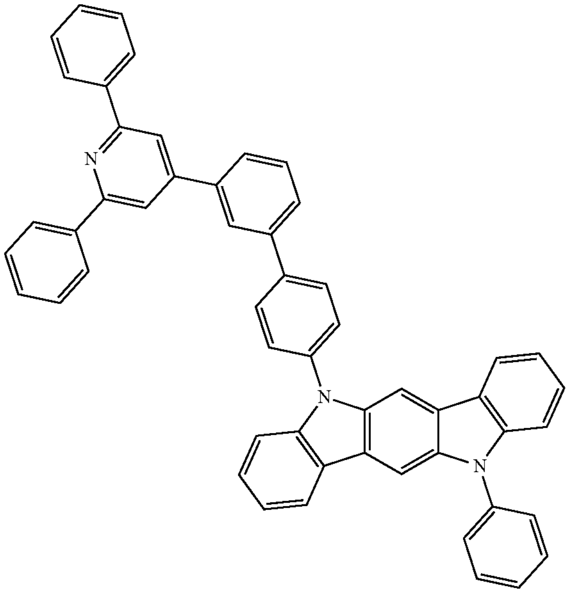

-continued
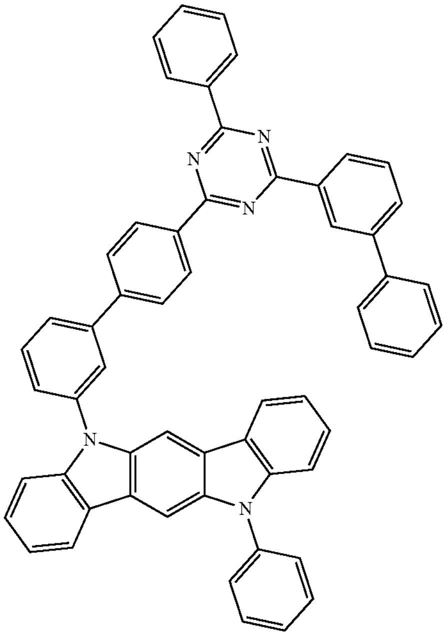
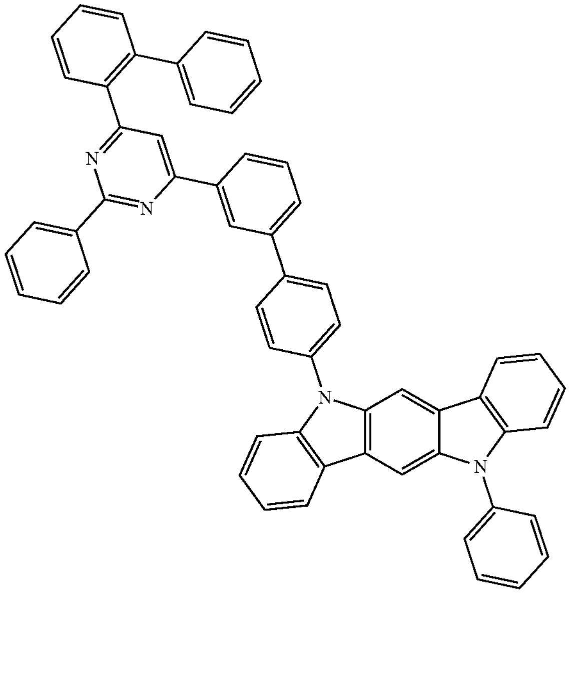
-continued
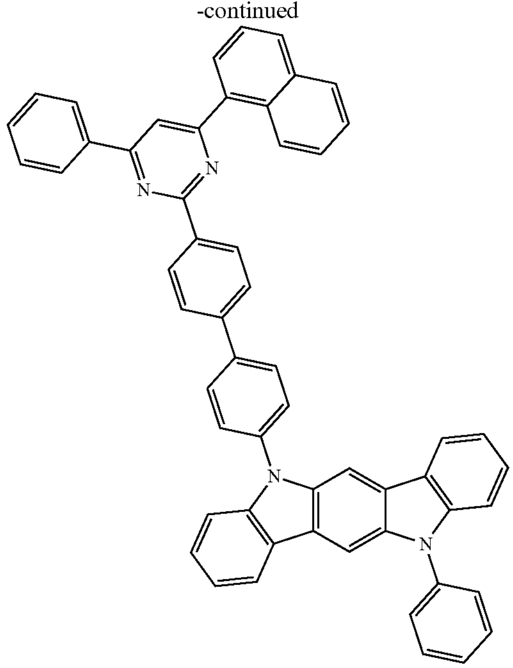
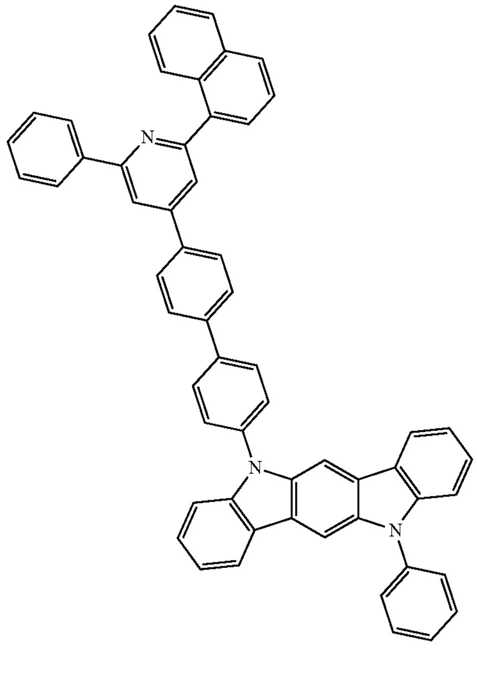

-continued
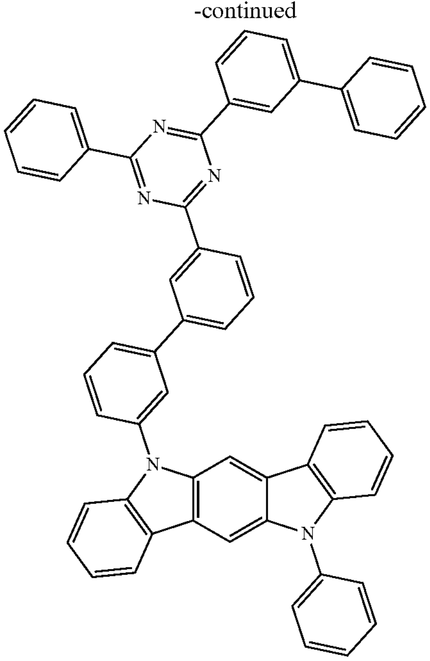
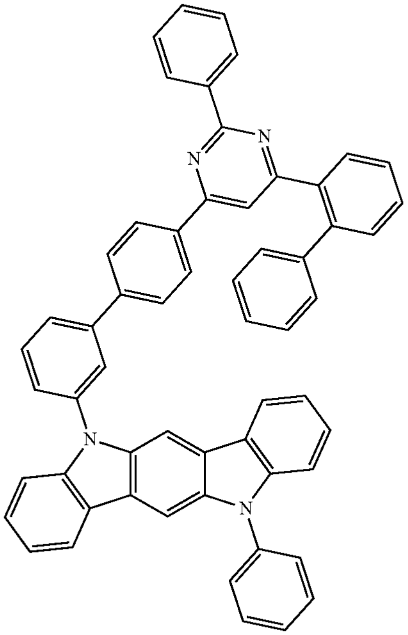
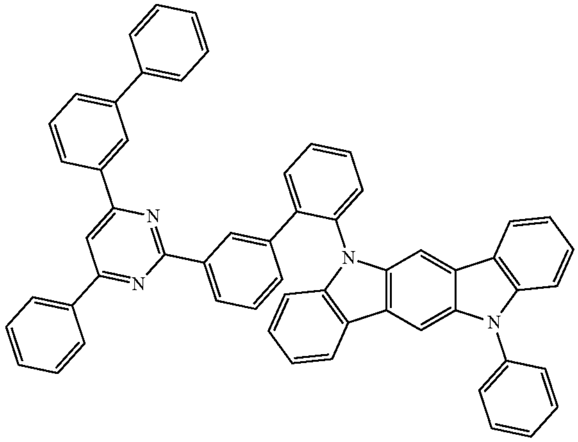
-continued
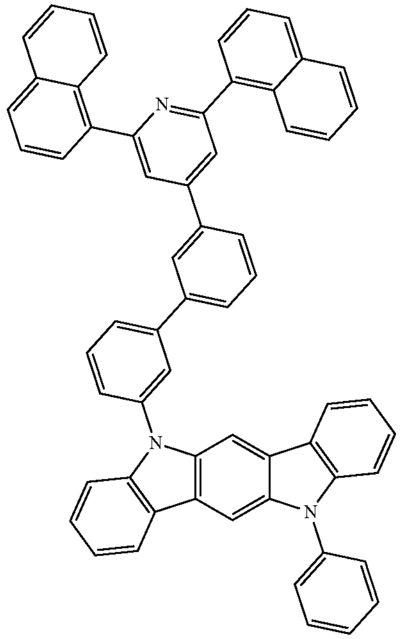
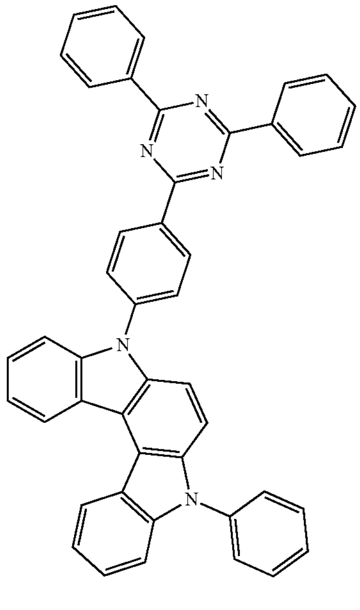

-continued
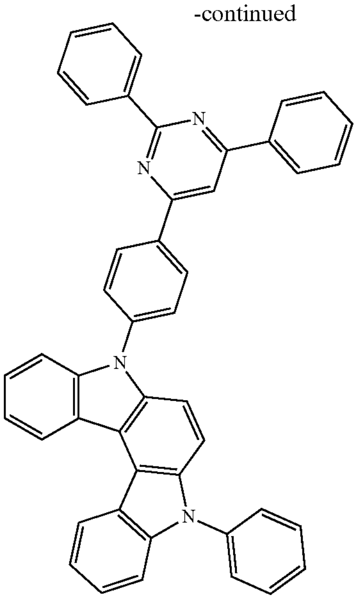
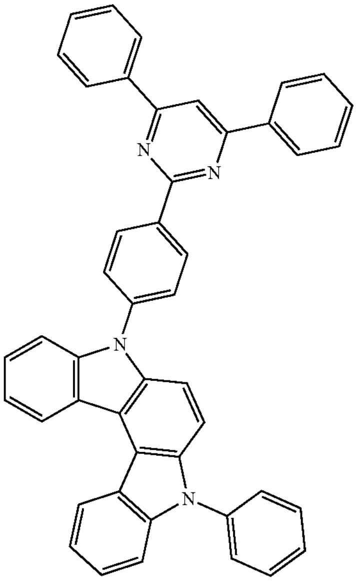
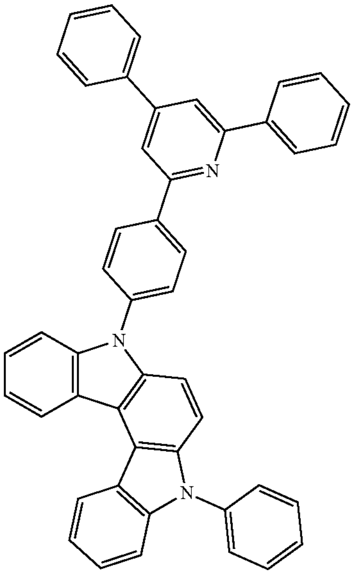
-continued
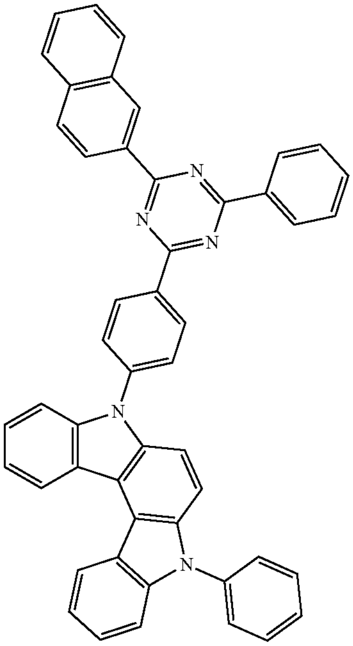
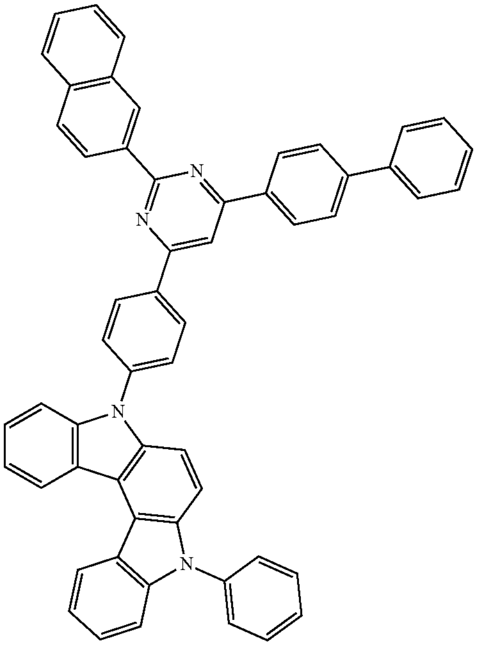

-continued
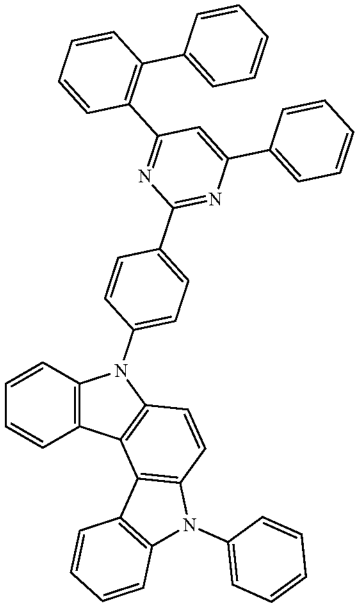
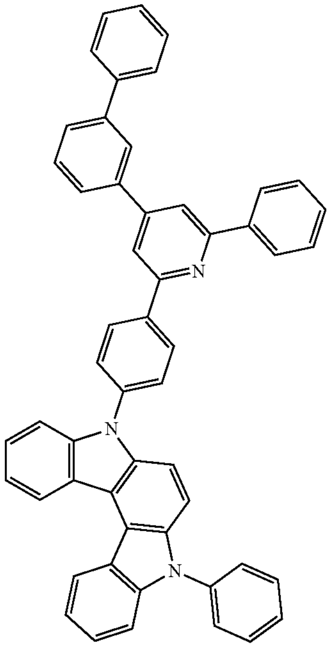
-continued
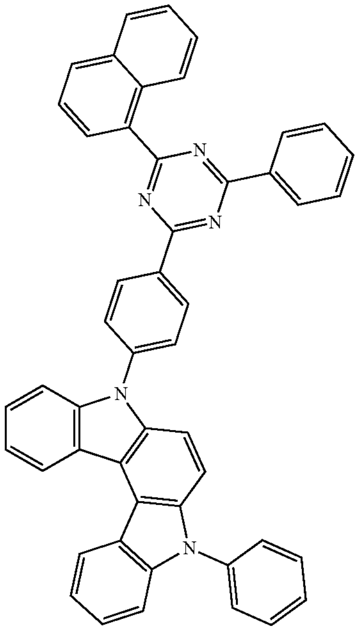
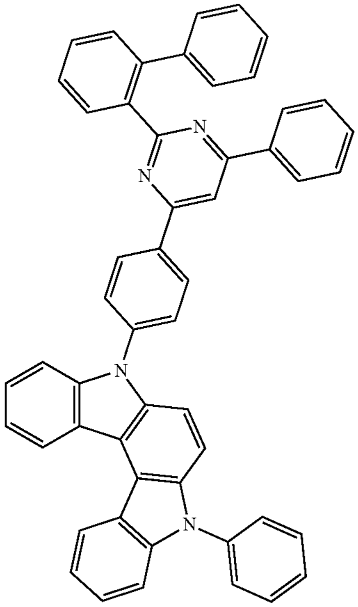

-continued
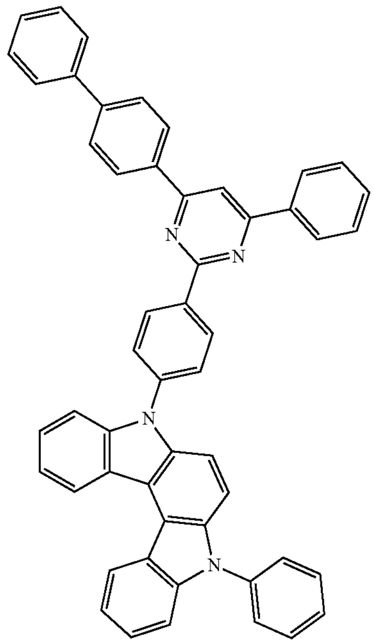
-continued
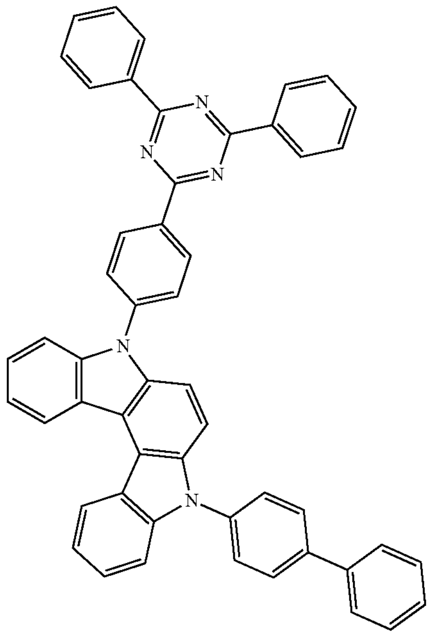
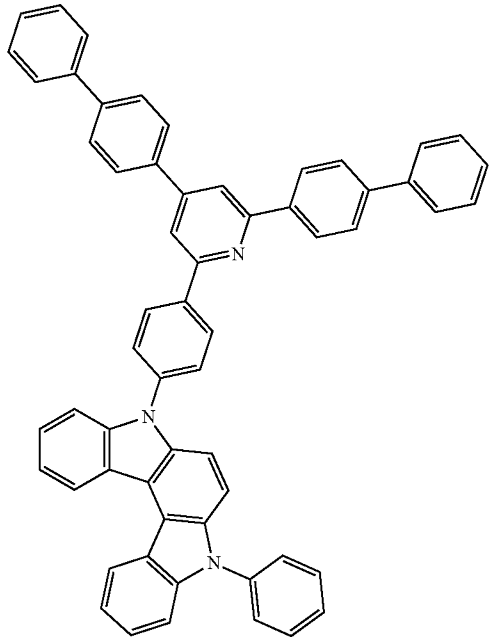 [SMILES: c1ccc(-c2ccc(-c3cc(-c4ccc(-c5ccccc5)cc4)nc(-c4ccc(-n5c6ccccc6c6c7c8ccccc8n(-c8ccccc8)c7ccc65)cc4)c3)cc2)cc1]
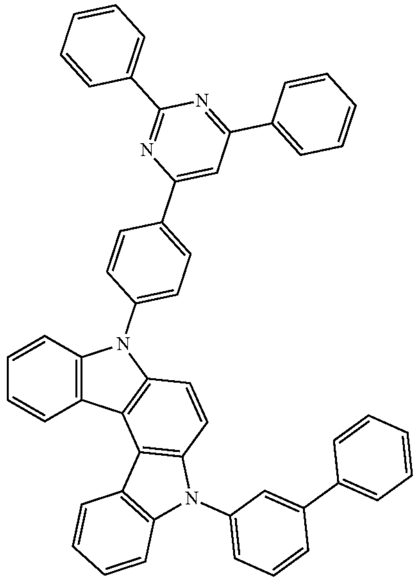

-continued
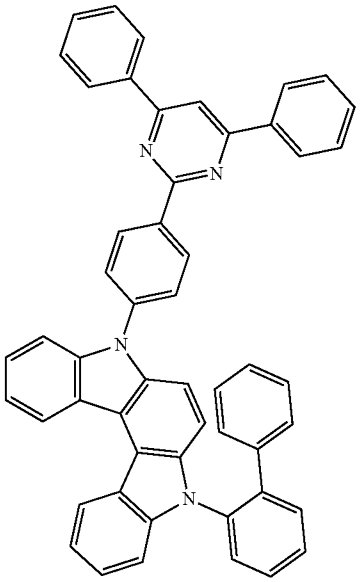
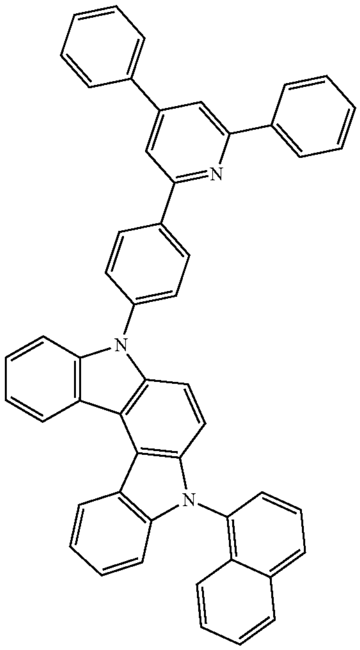
-continued
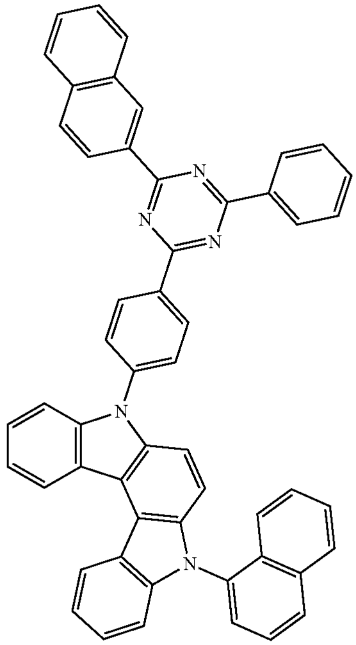
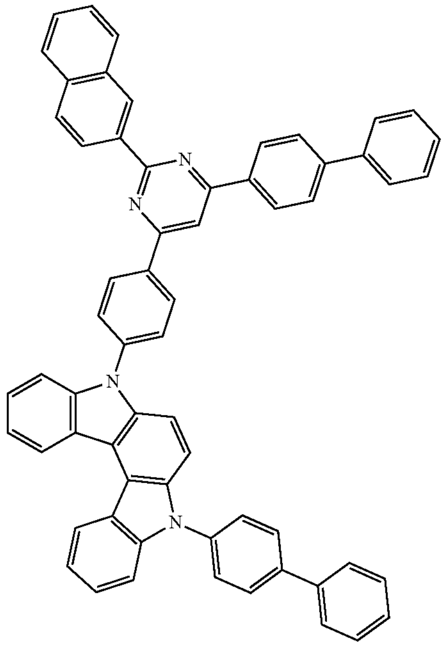

-continued
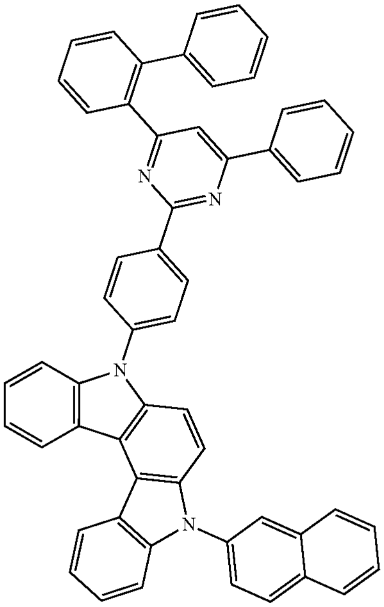
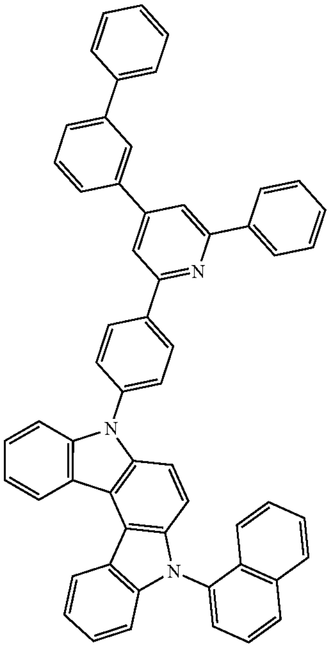
-continued
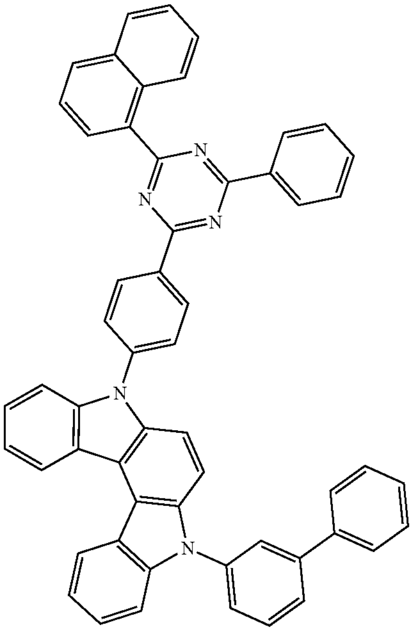
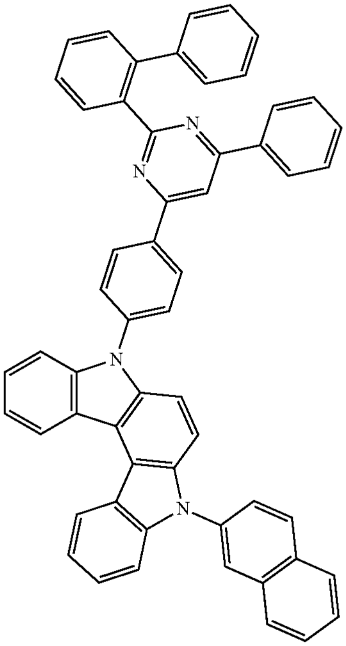

-continued
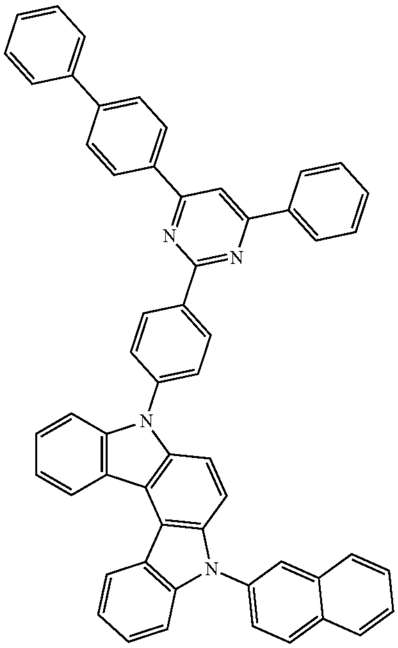
-continued
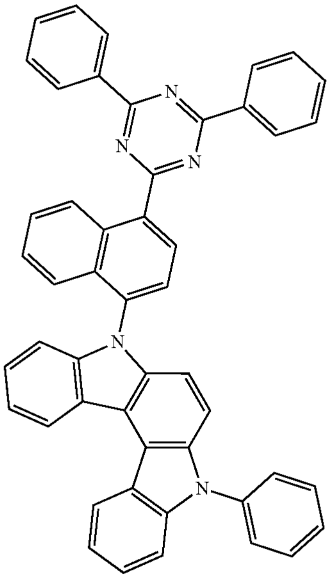
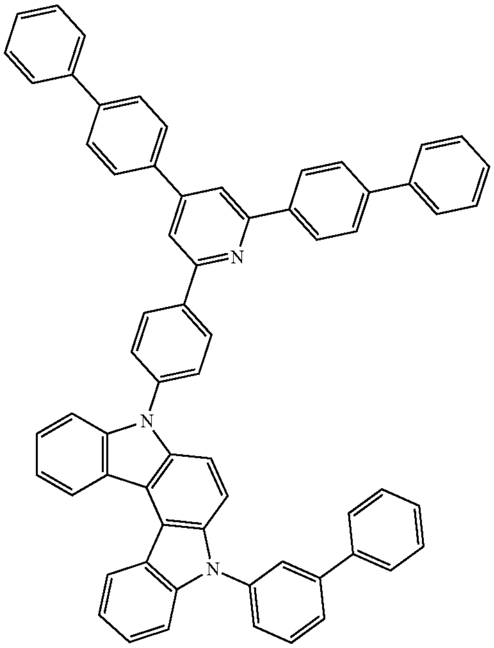
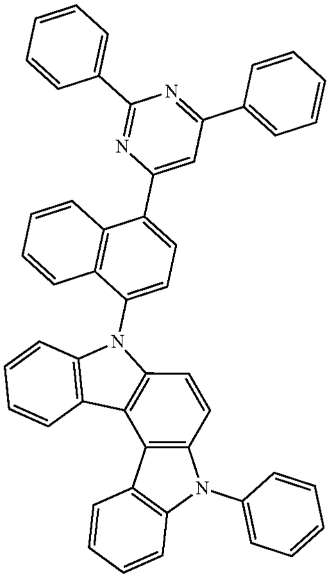

-continued
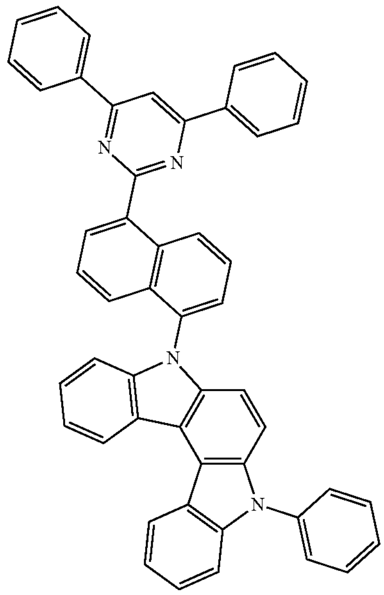
-continued
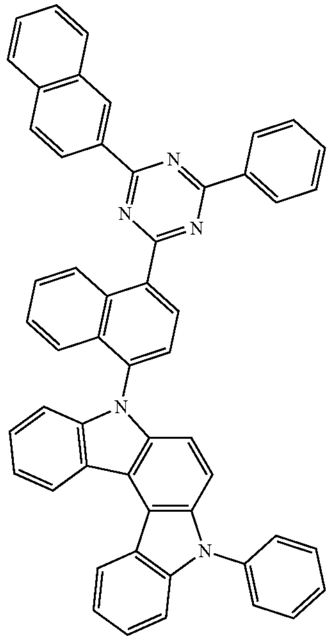
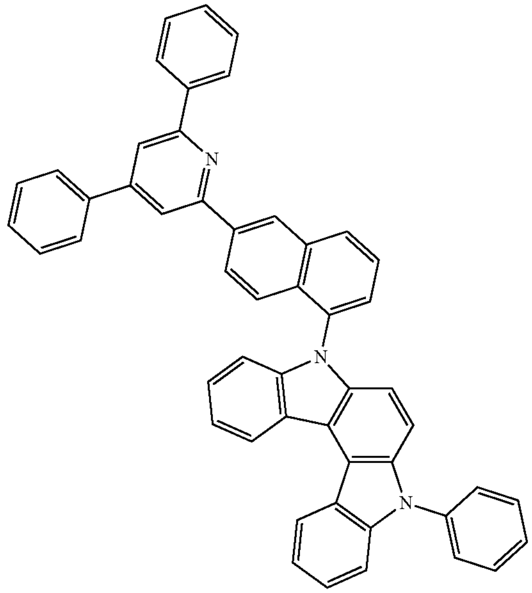
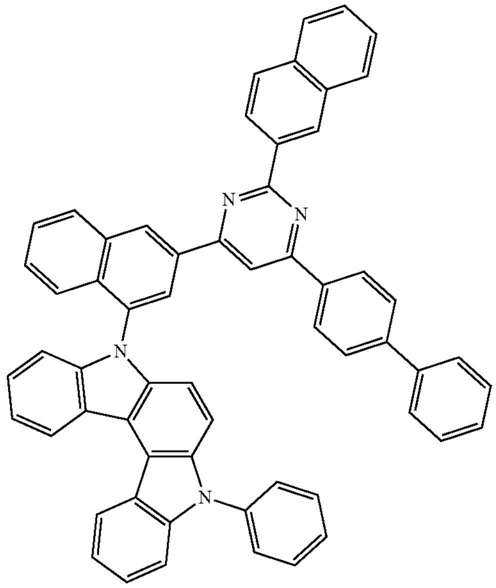

-continued
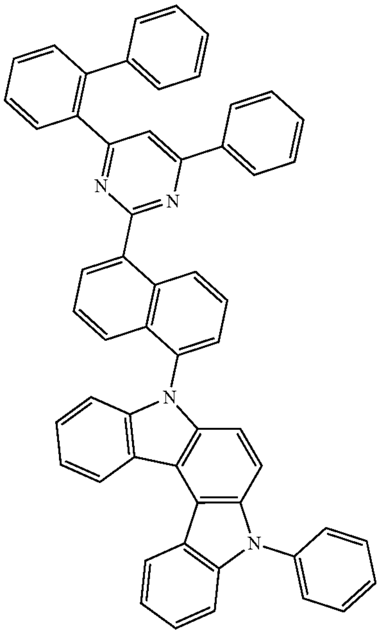
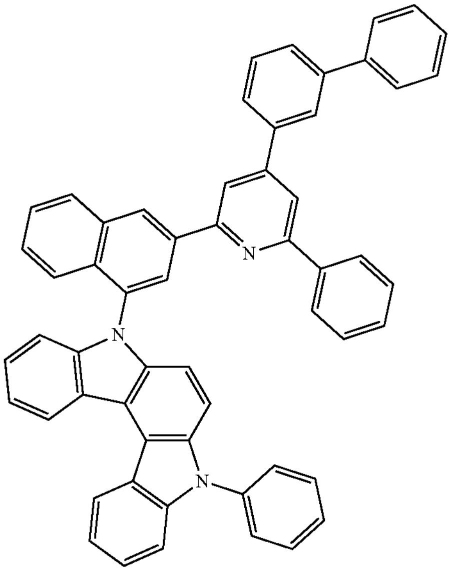
-continued
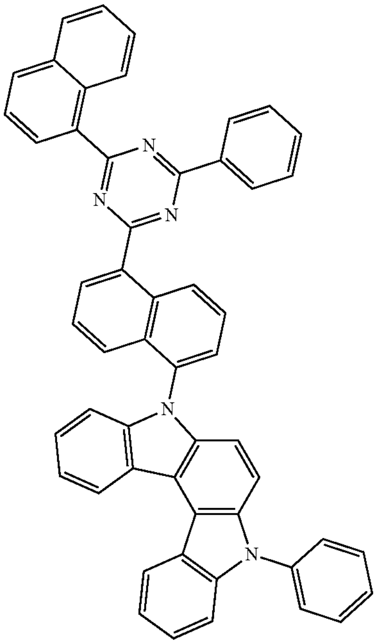
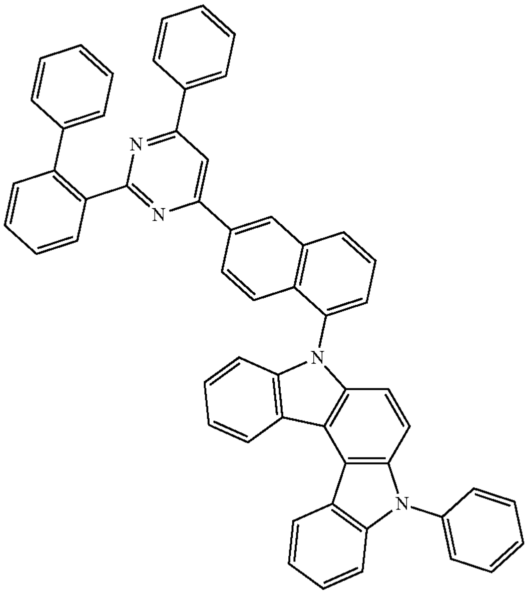
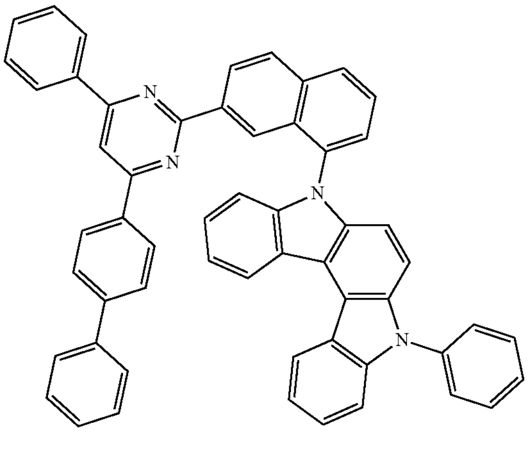

-continued
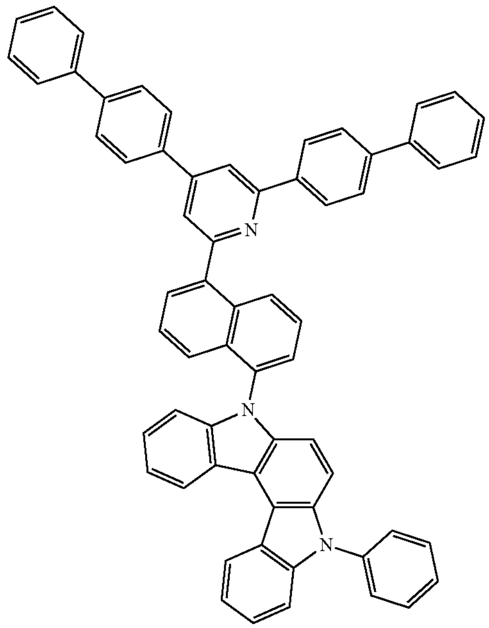
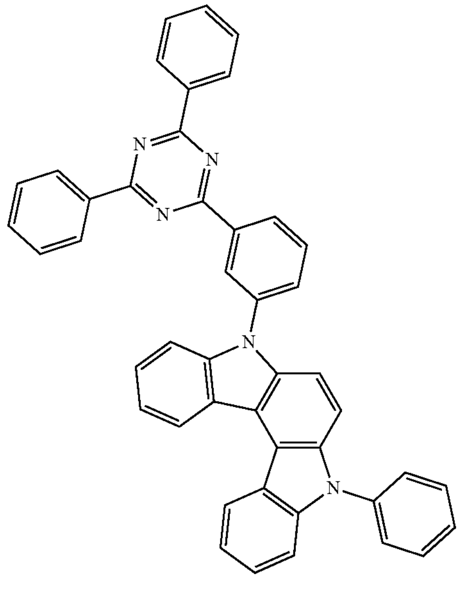
-continued
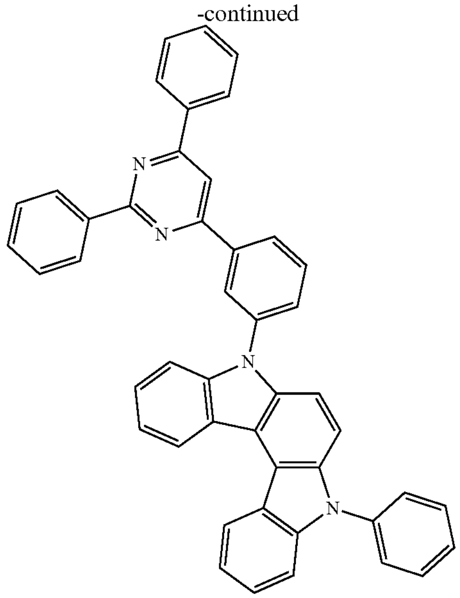
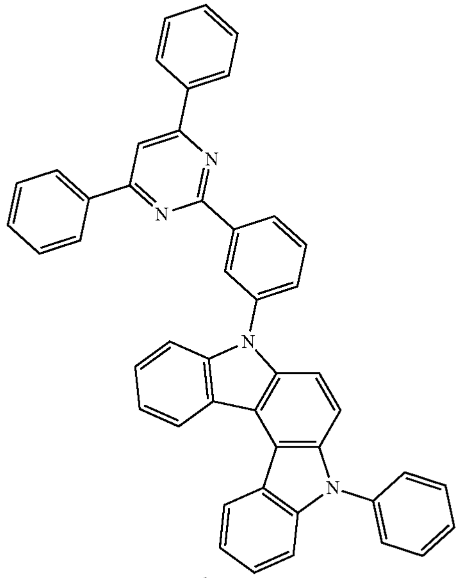
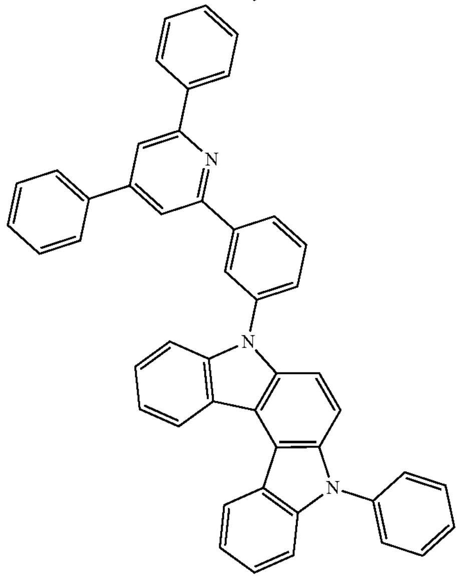

-continued
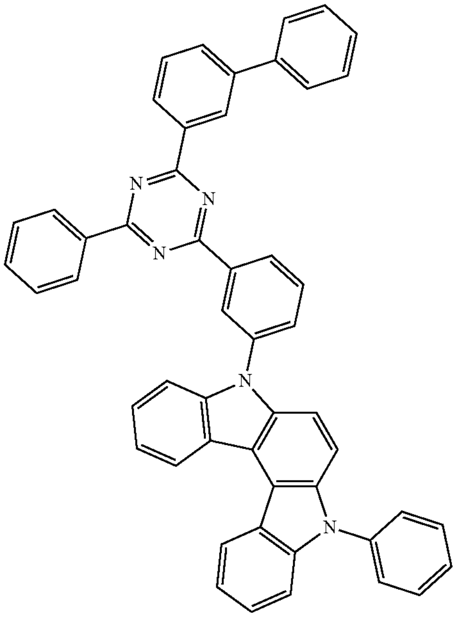
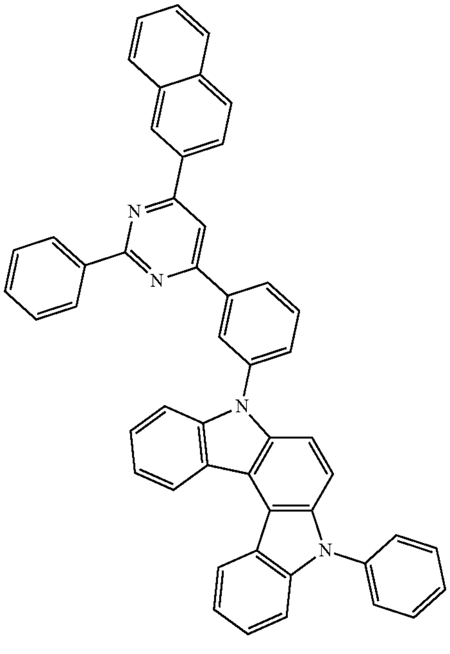
-continued
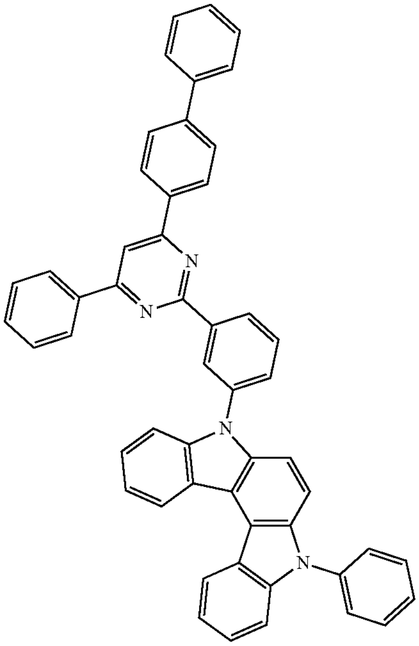
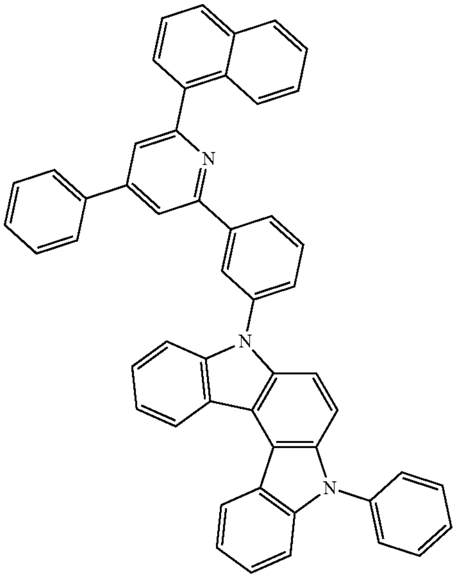

-continued
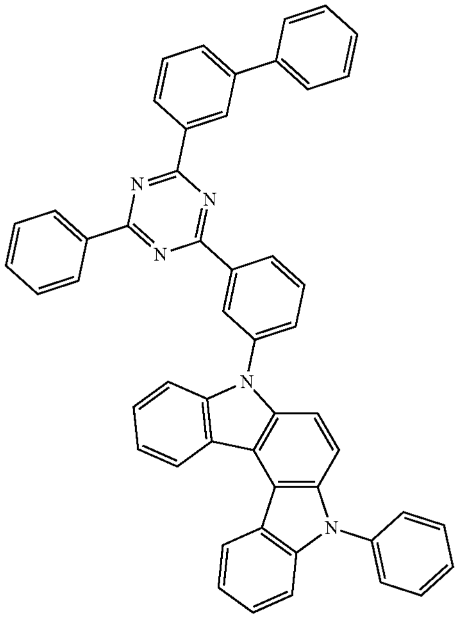
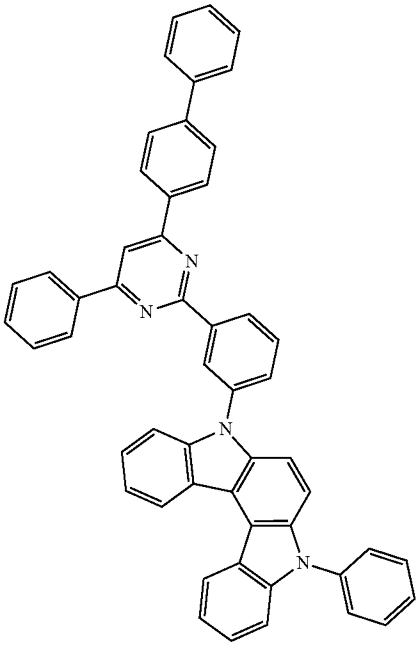
-continued
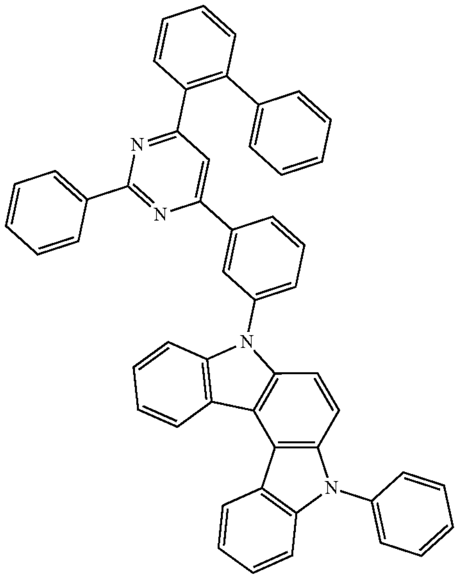
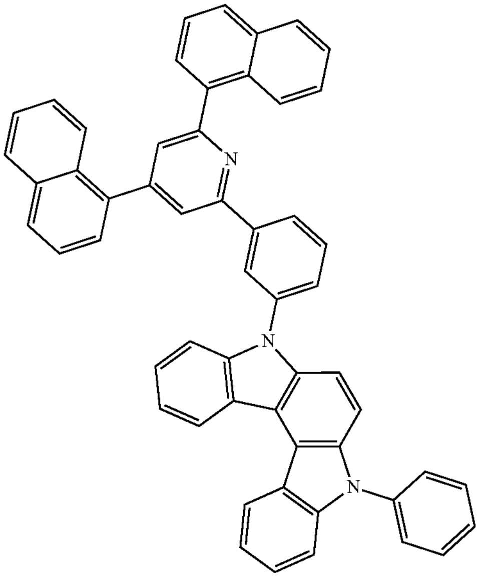

-continued
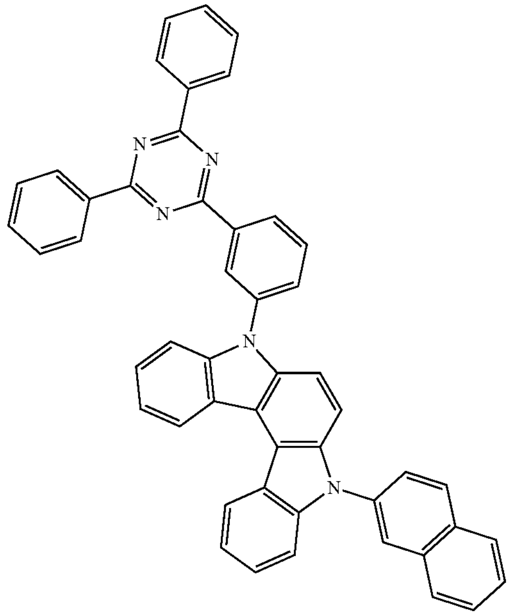
-continued
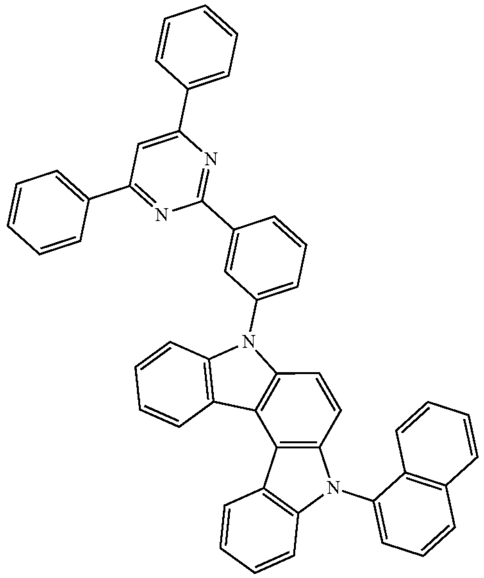
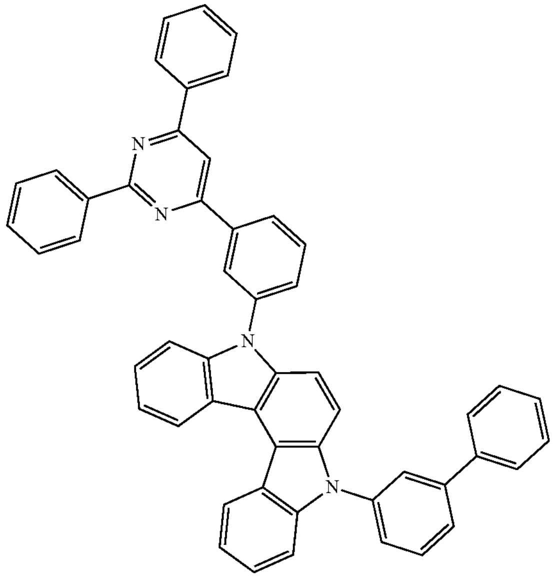
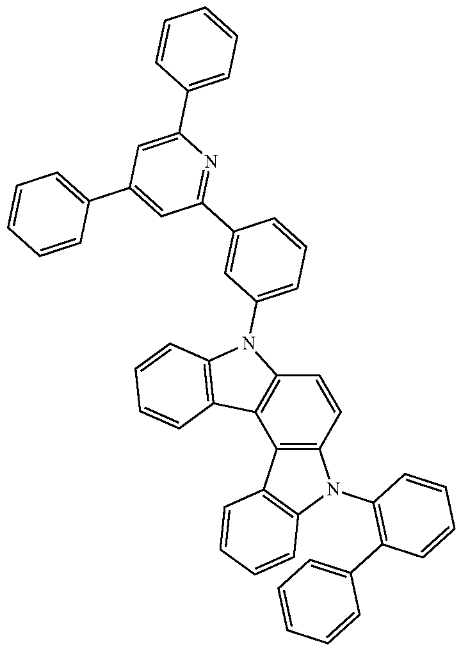

-continued
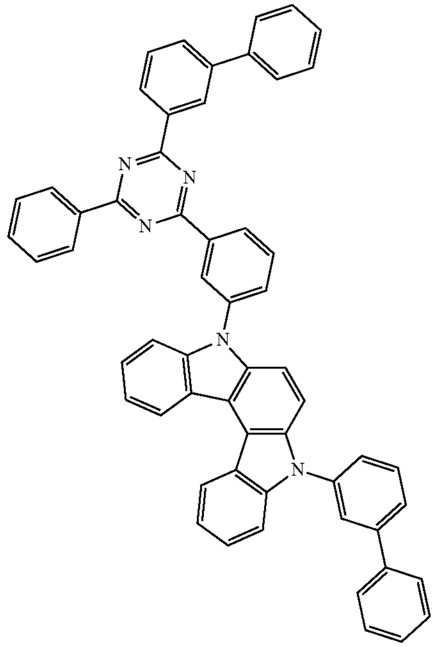
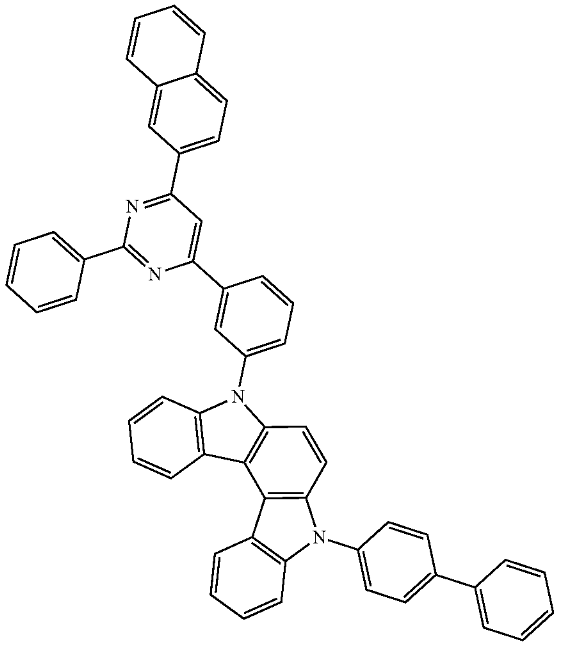
-continued
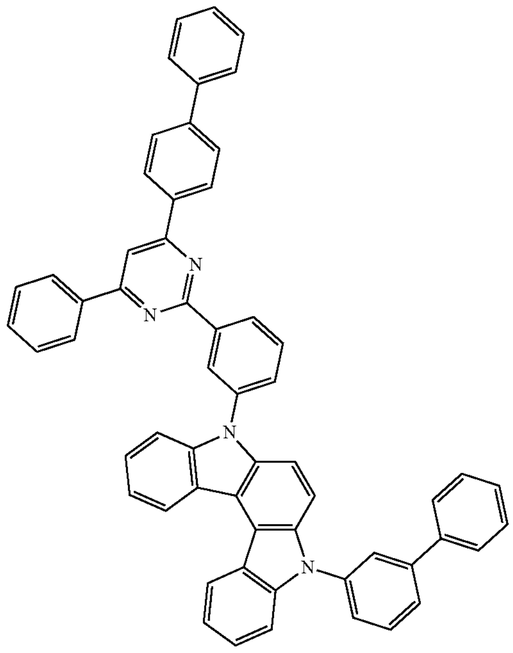
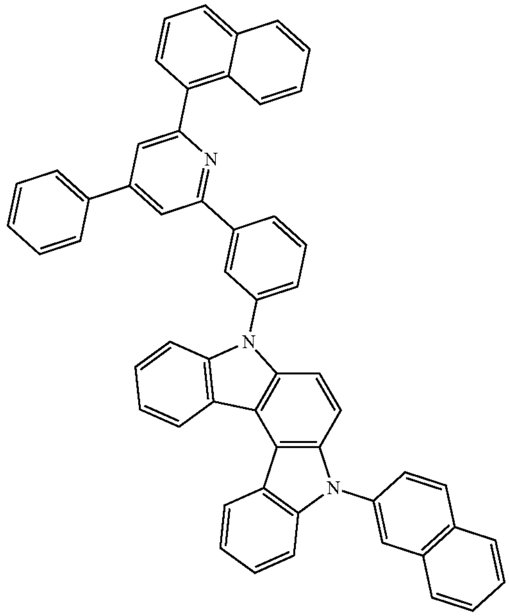

-continued
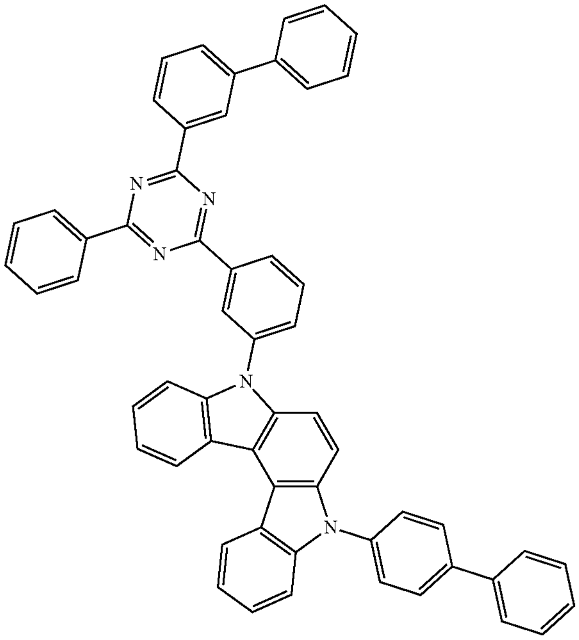
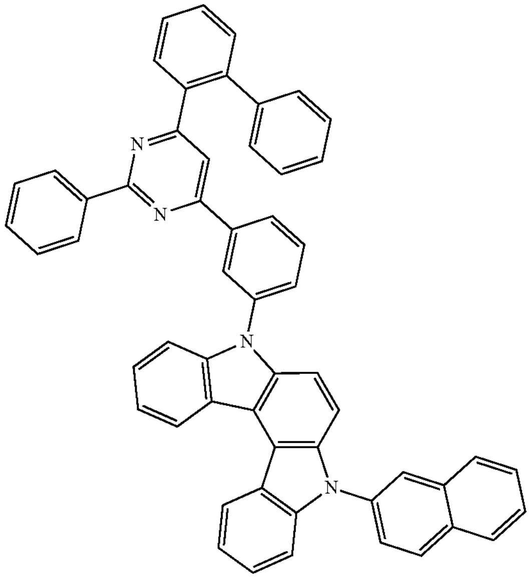
-continued
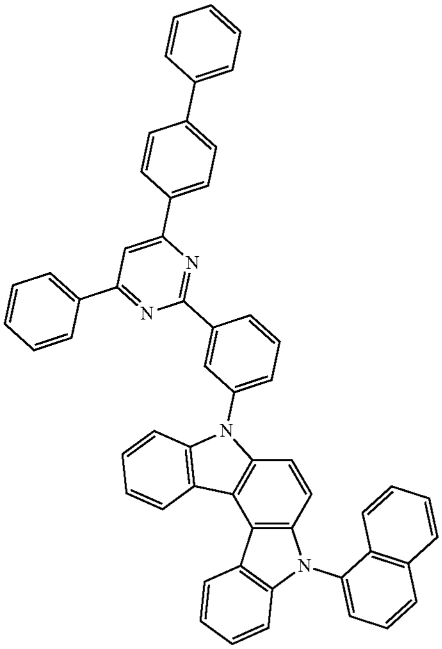
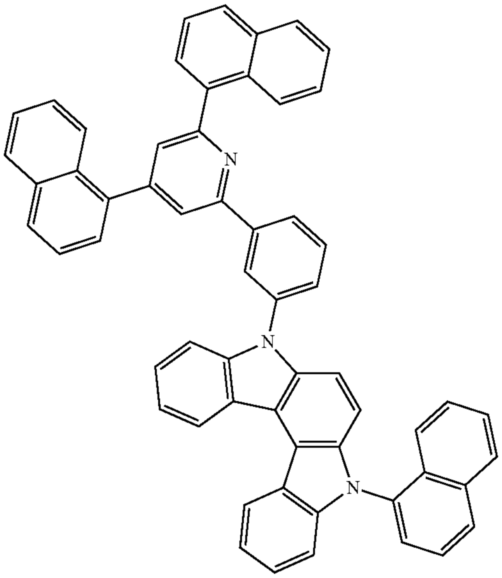

-continued
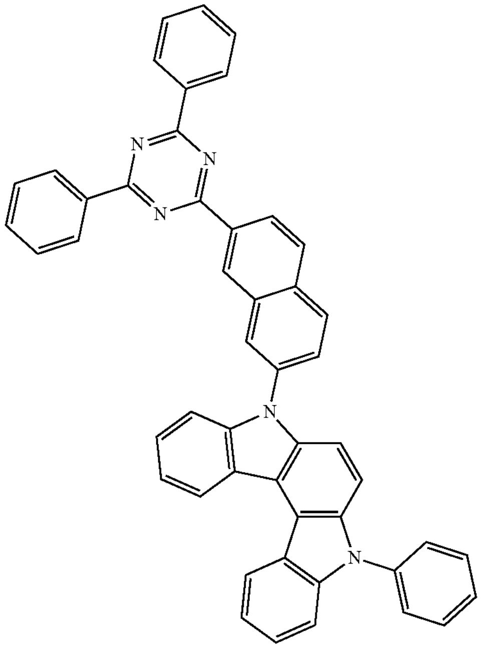
-continued
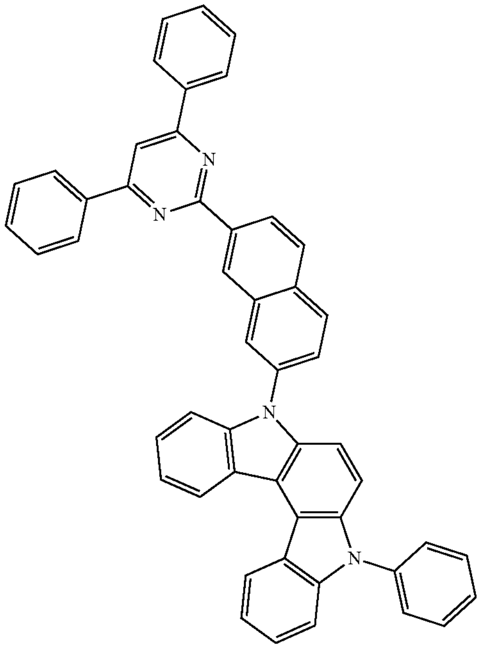
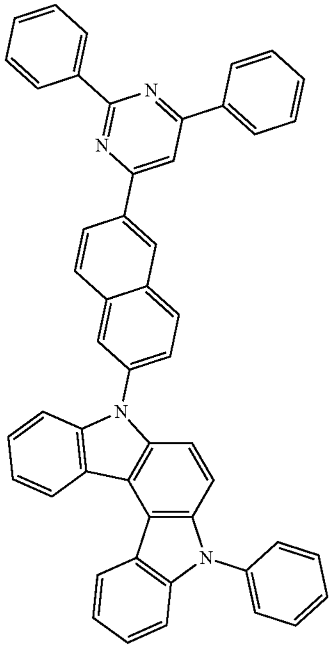
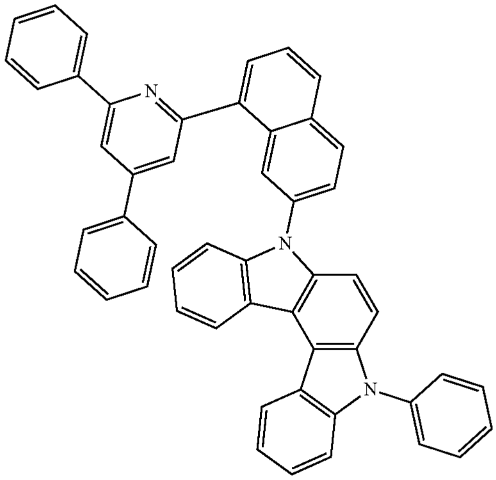

-continued
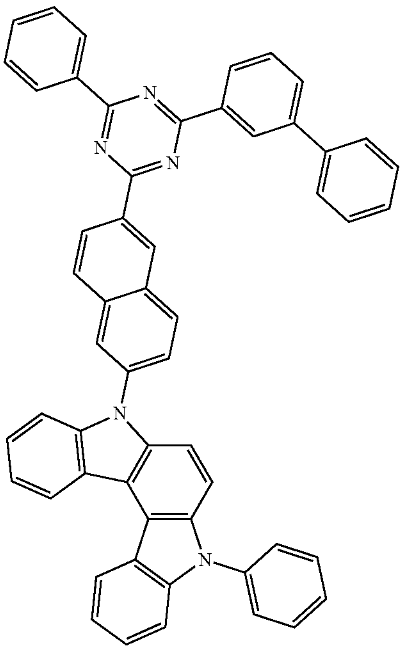
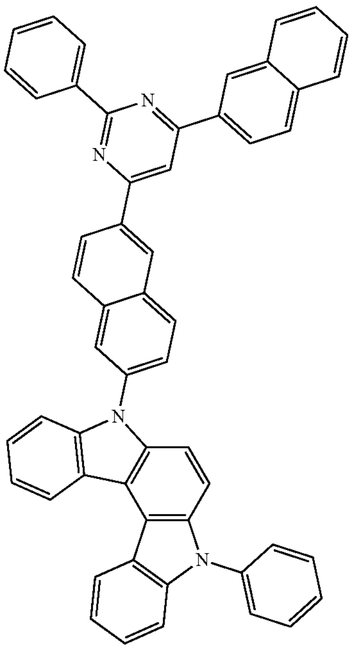
-continued
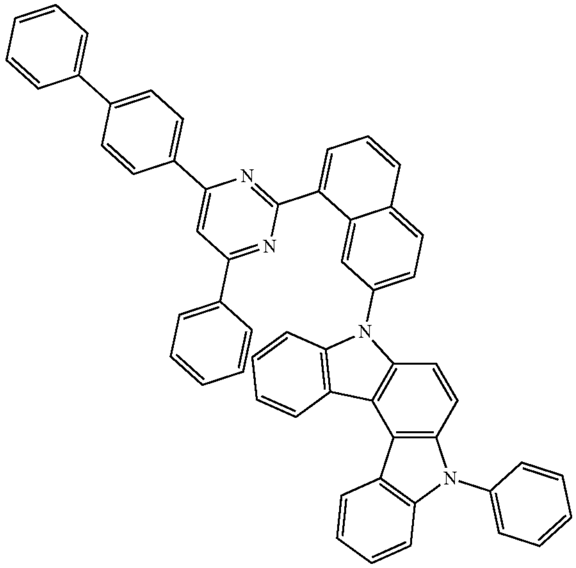
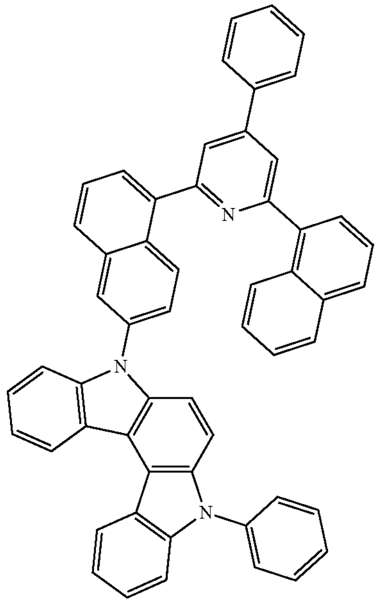

-continued
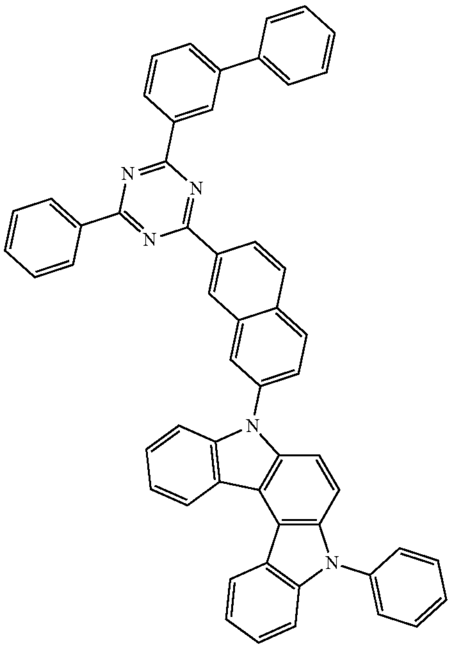
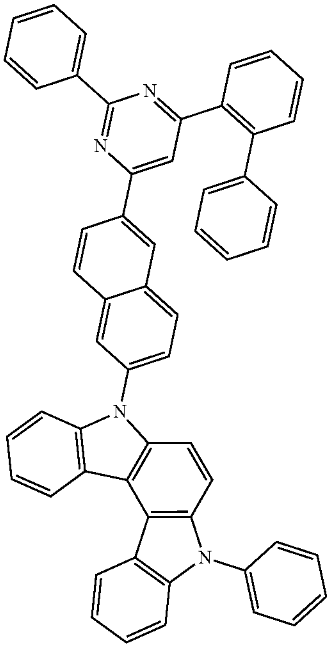
-continued
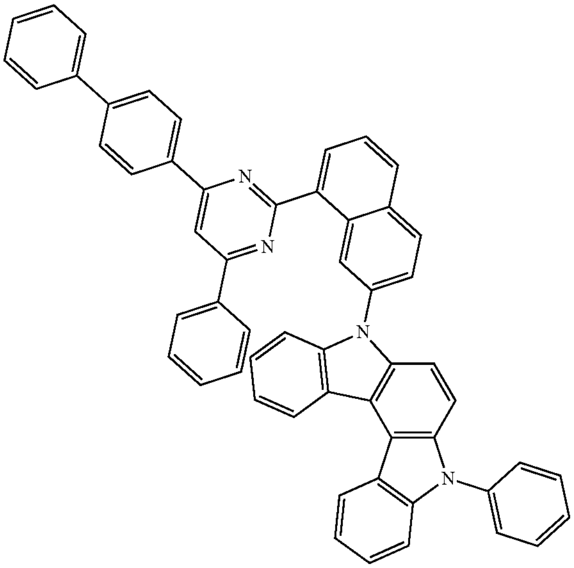
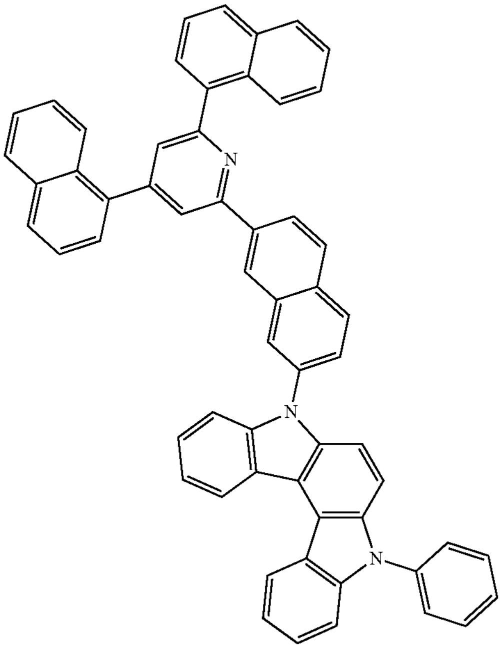
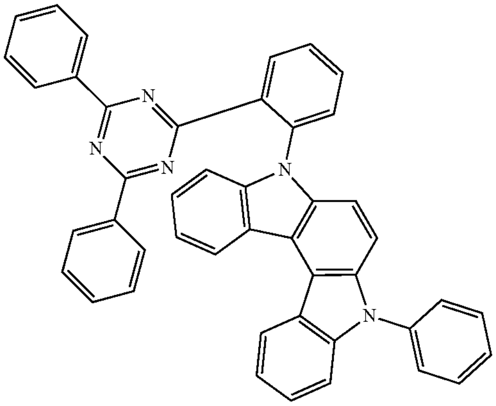

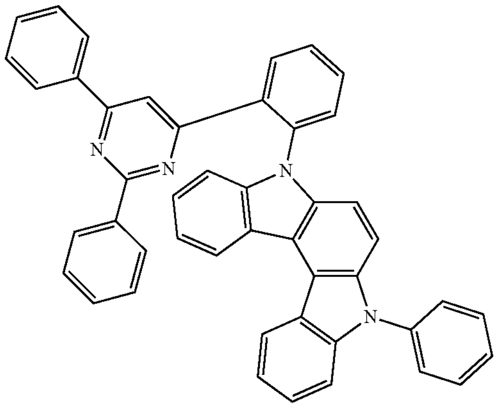
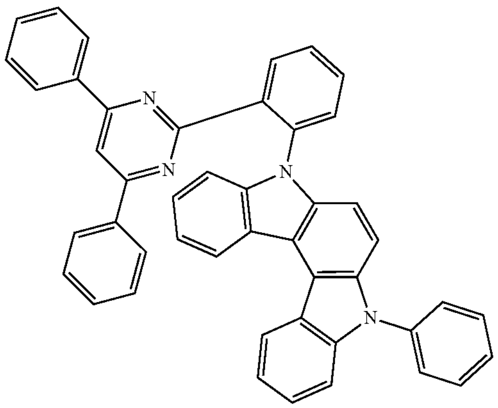
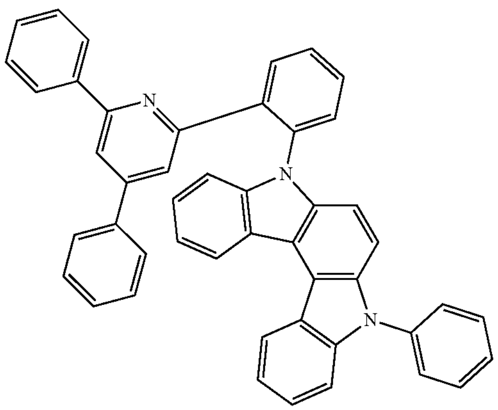
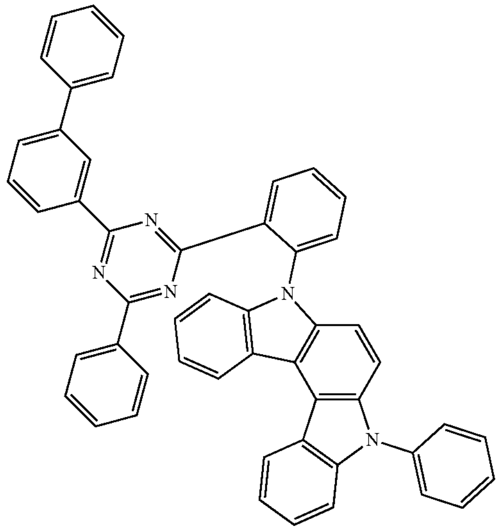
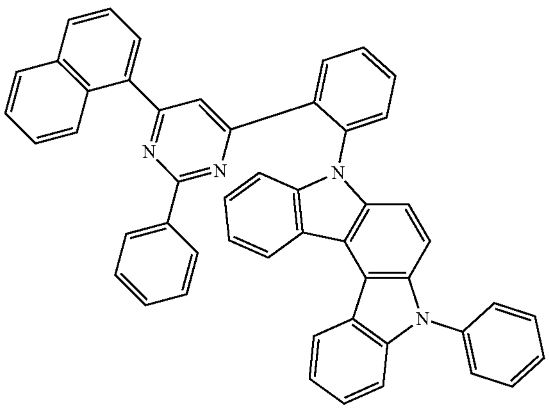
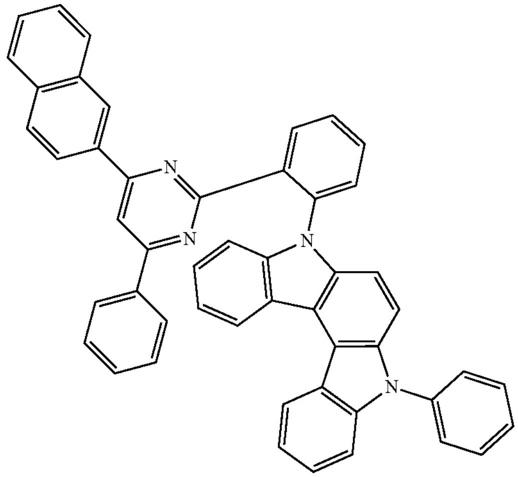

-continued
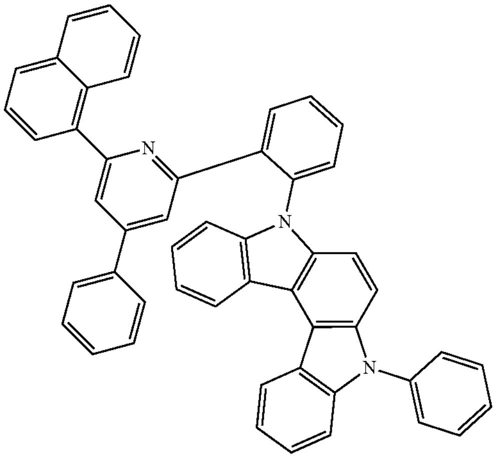
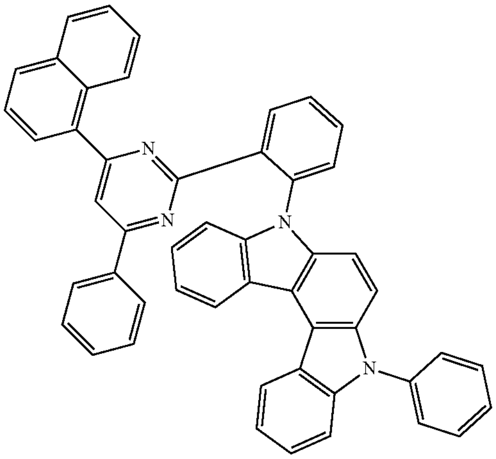
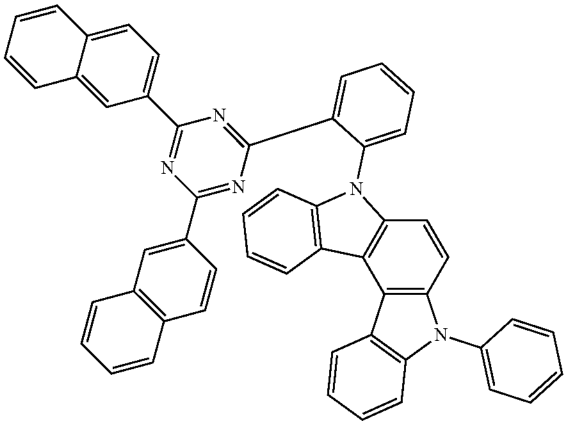
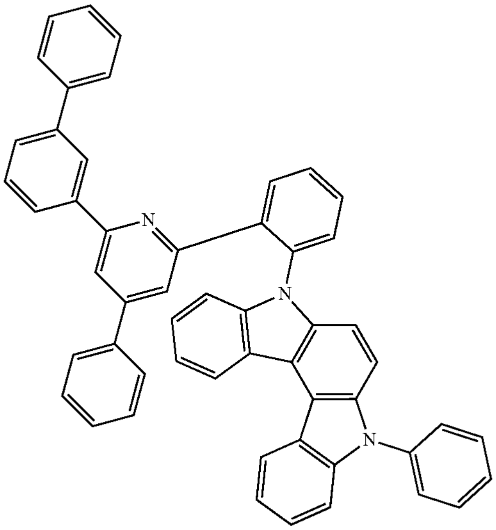
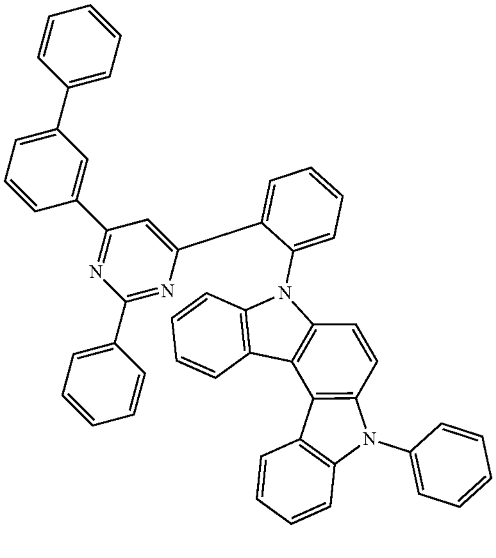
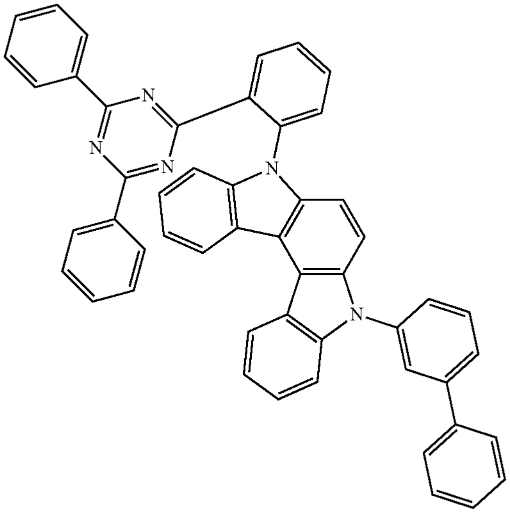
-continued -continued
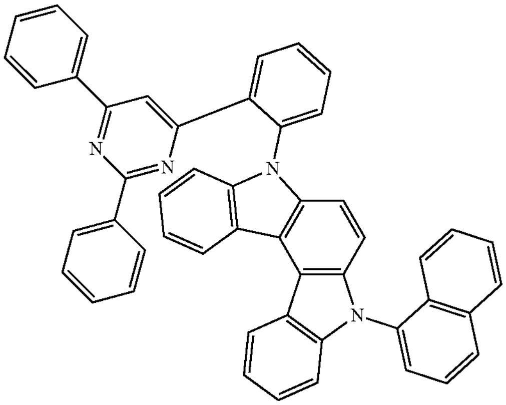
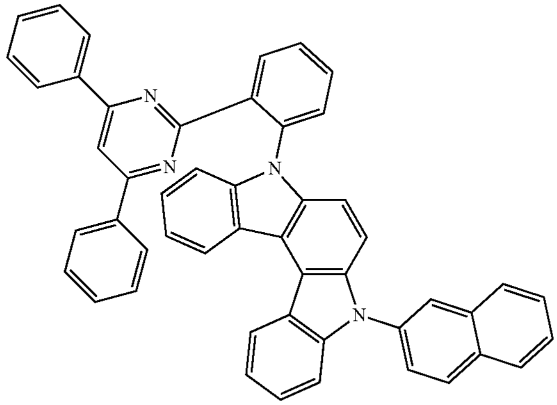
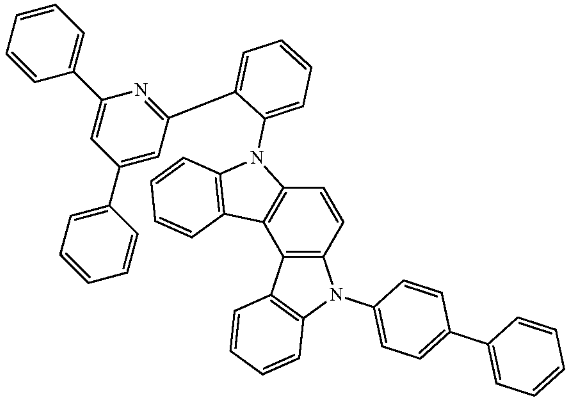
-continued
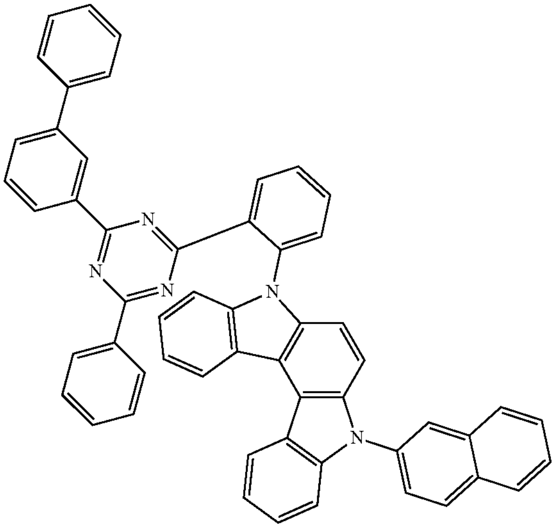
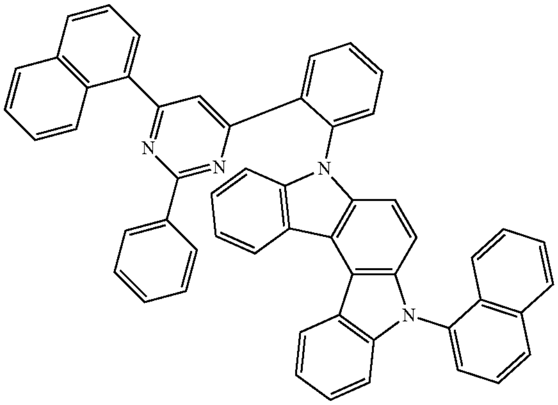
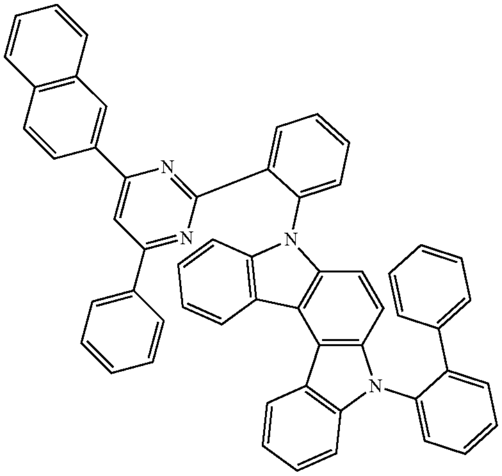

-continued
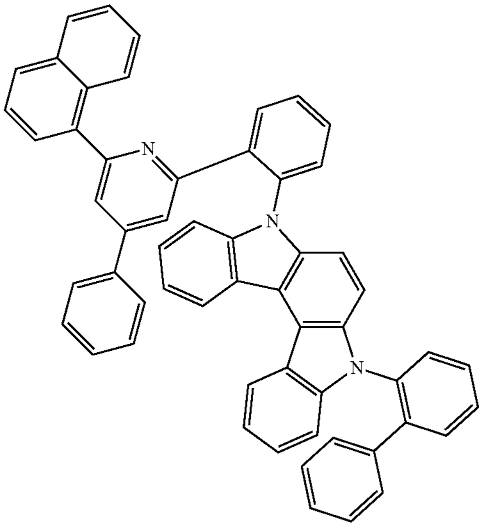
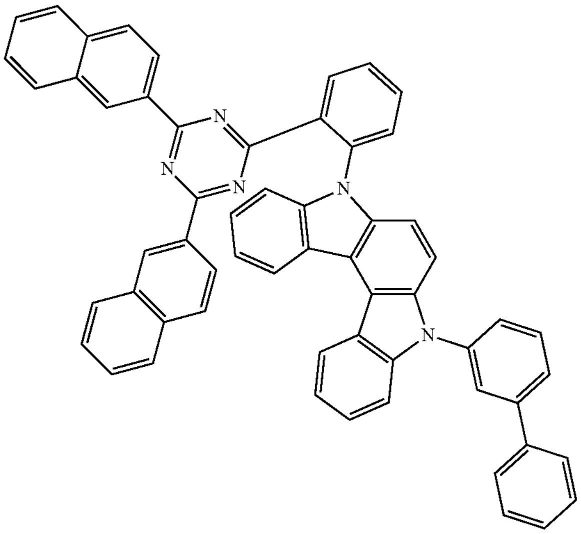
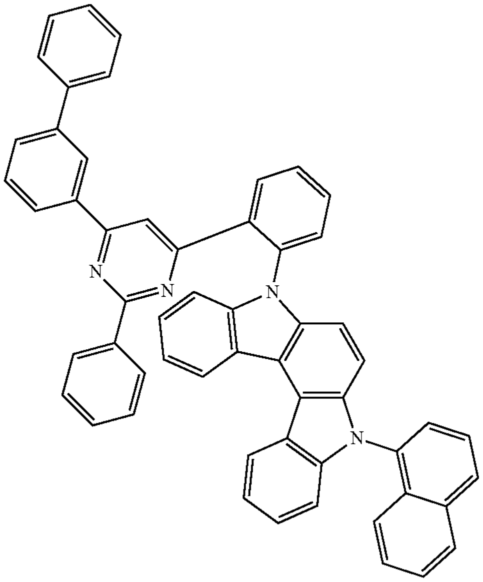
-continued
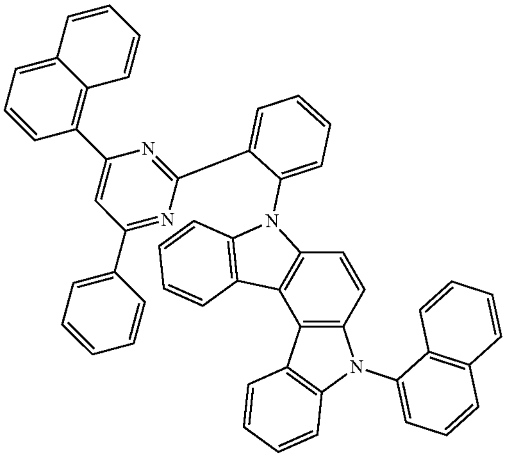
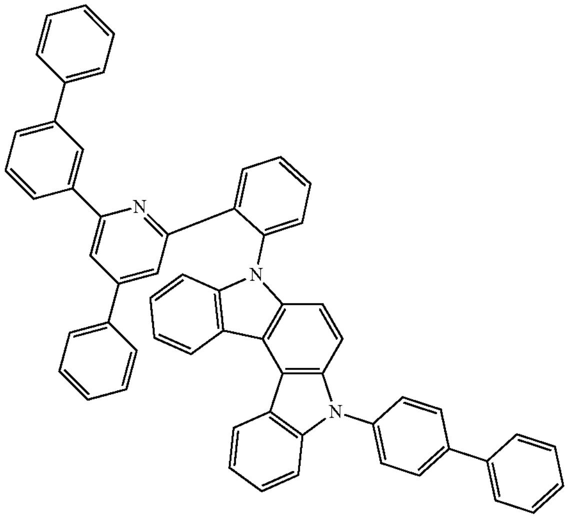
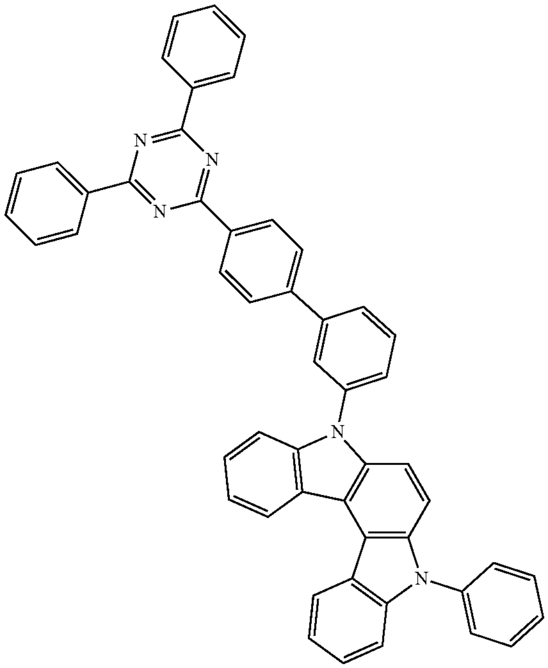

-continued
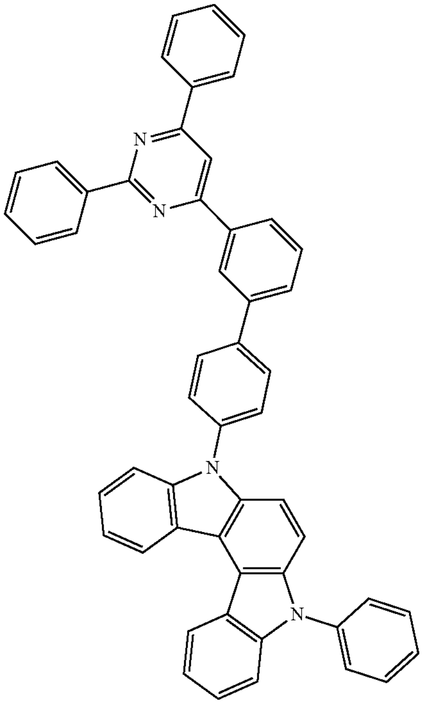
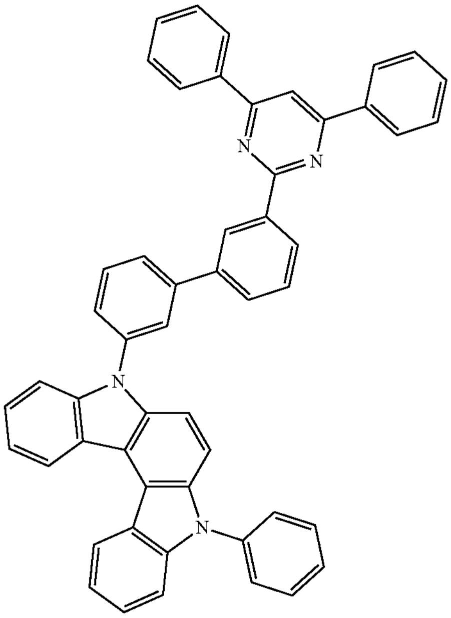
-continued
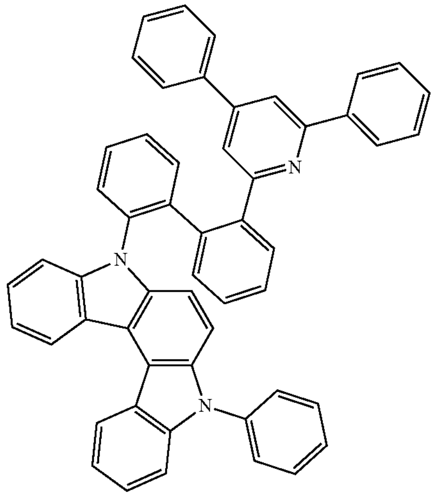
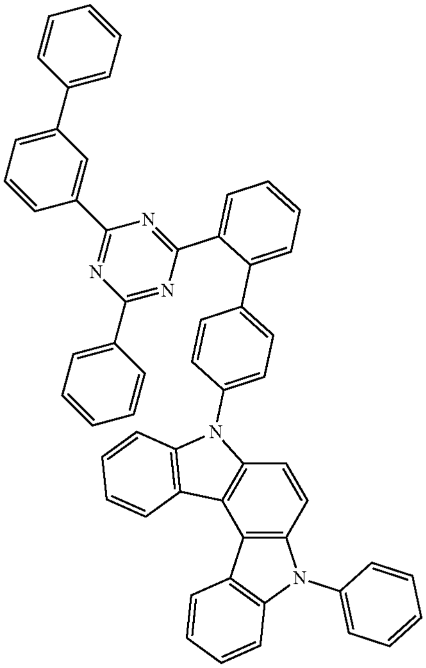

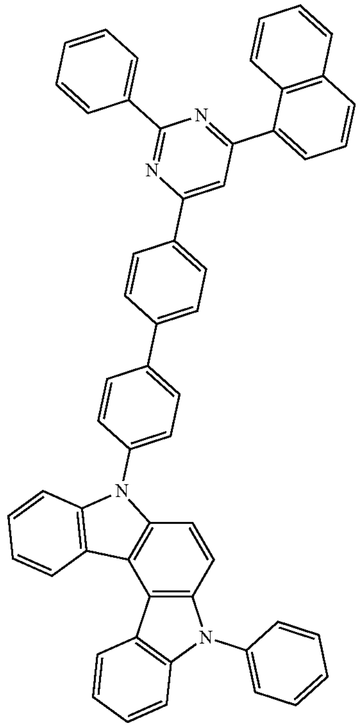
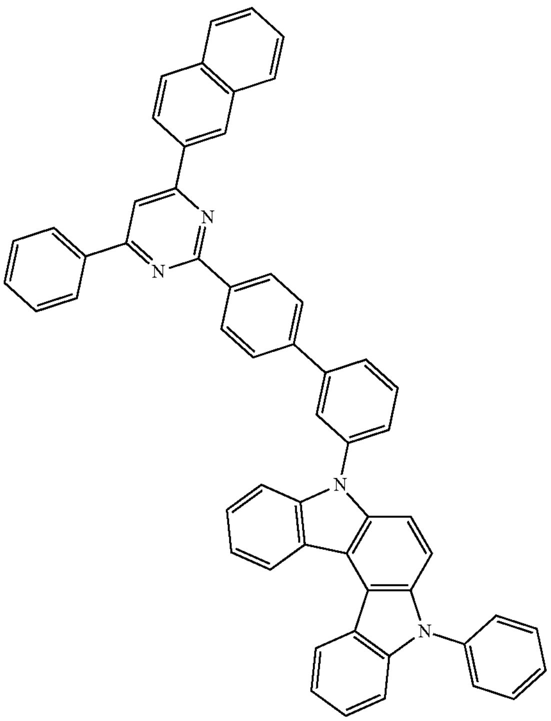
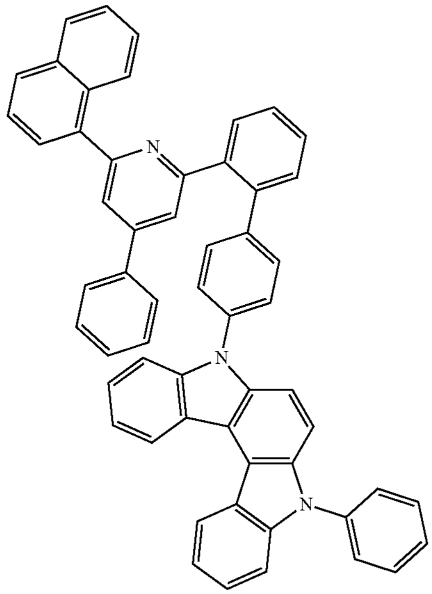
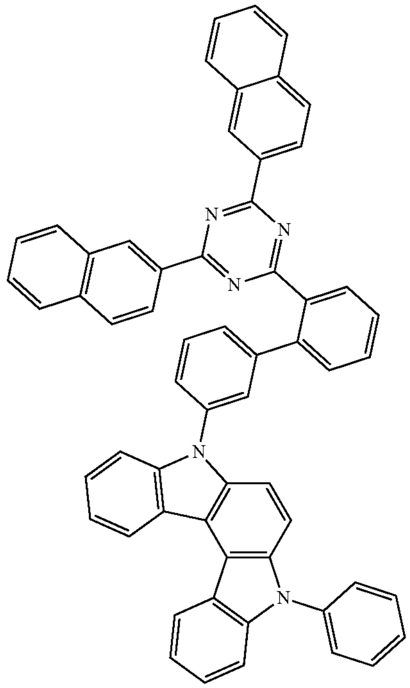

-continued
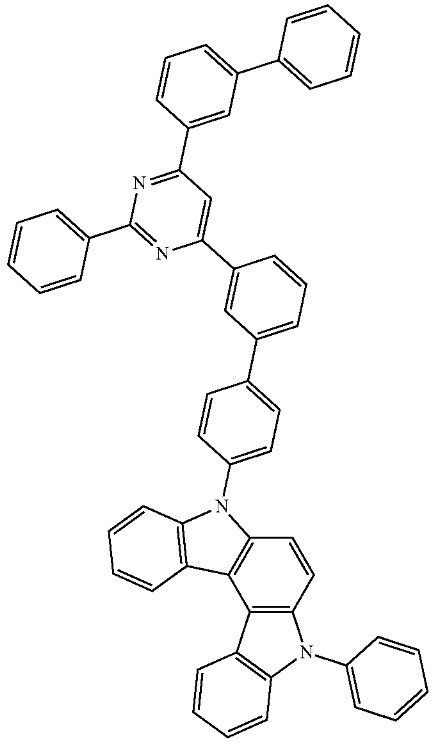
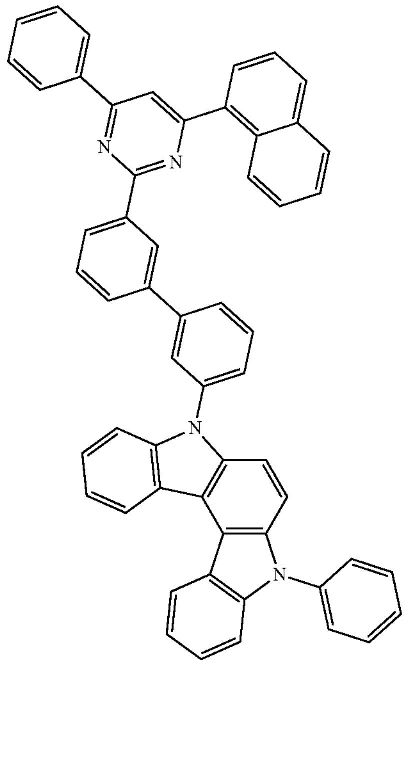
-continued
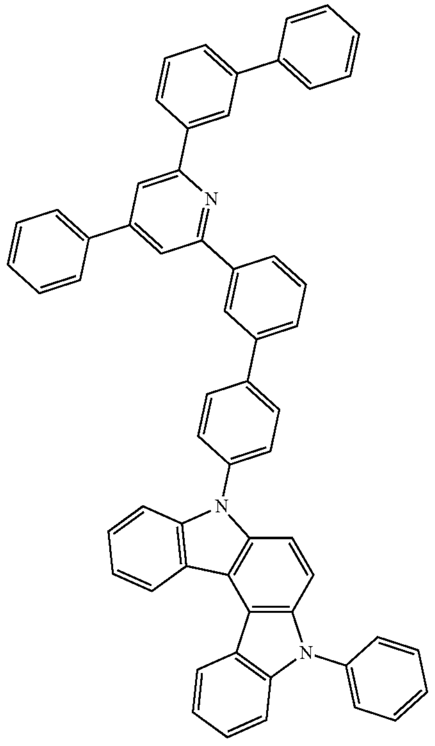
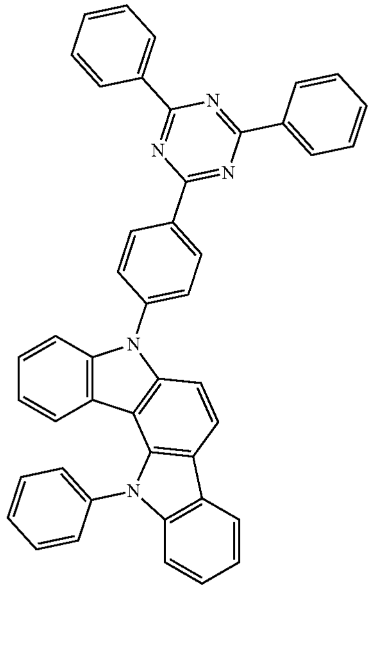

-continued
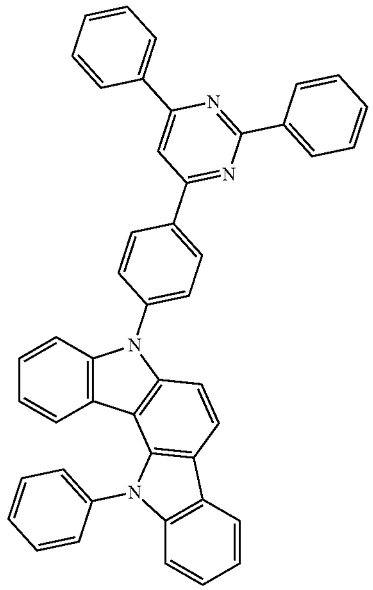
-continued
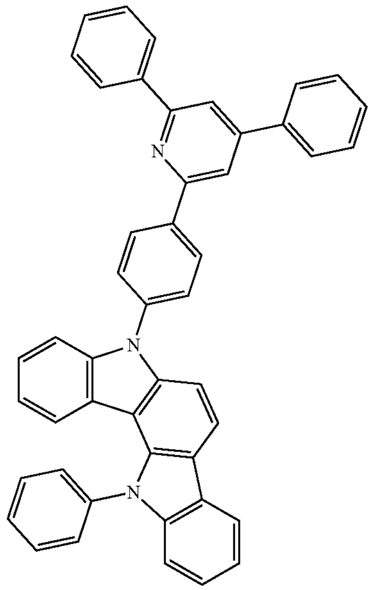
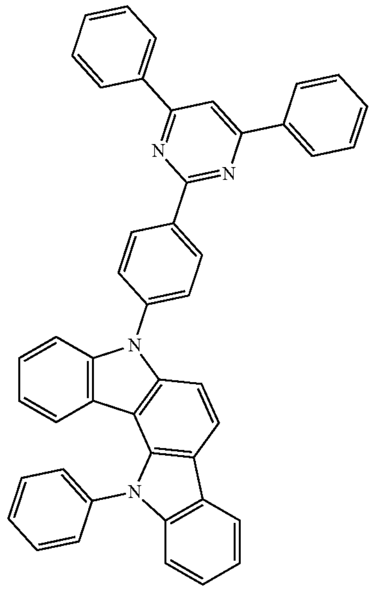
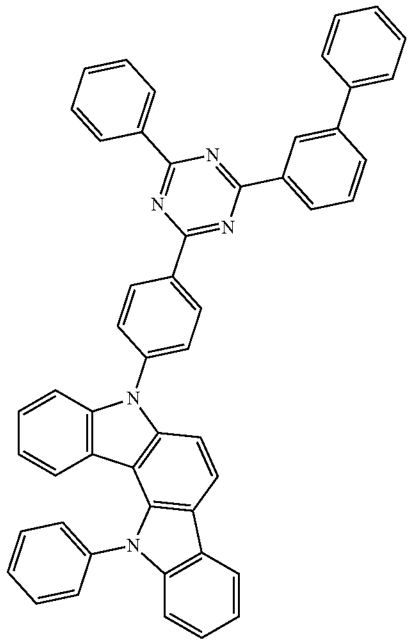

-continued
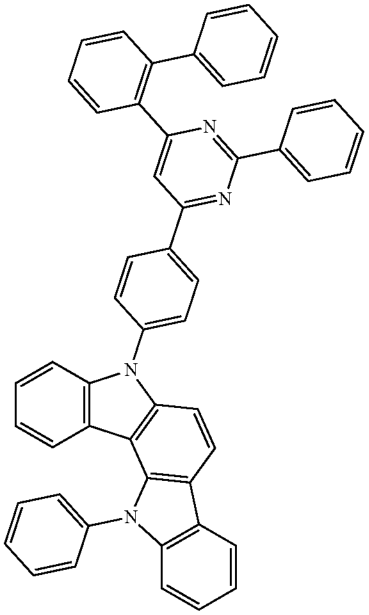
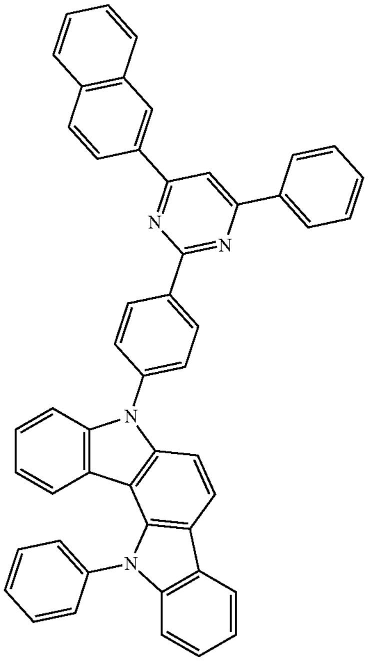
-continued
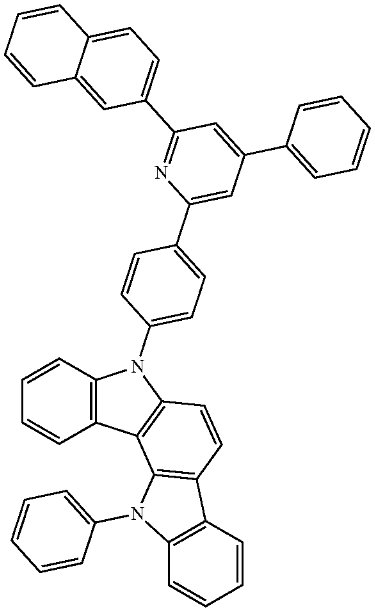
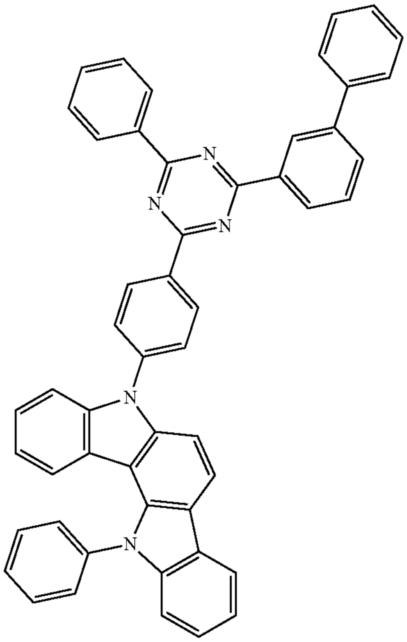

-continued
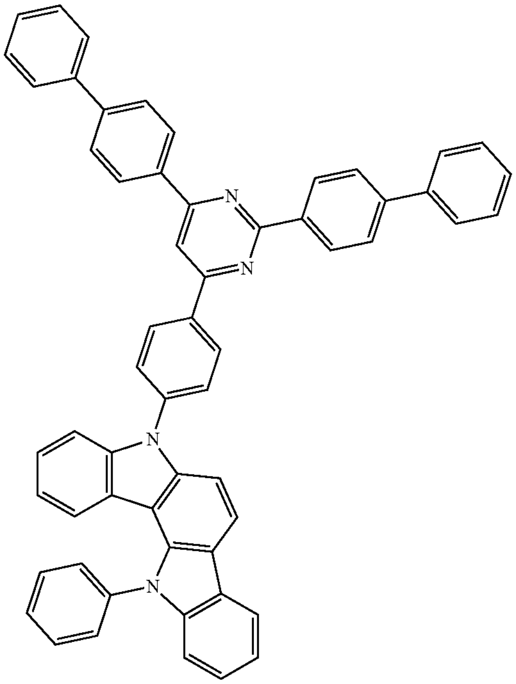
-continued
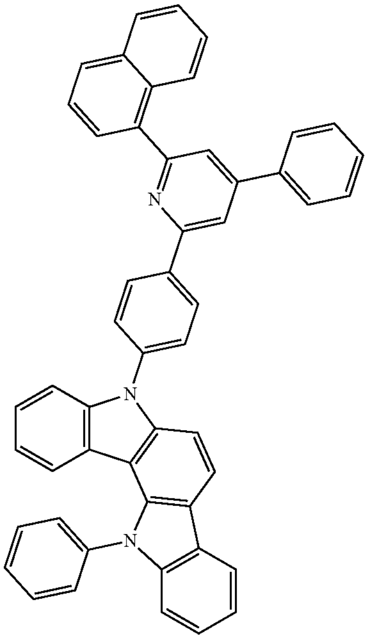
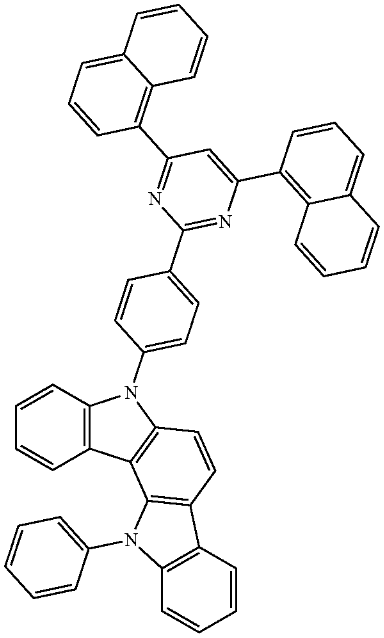
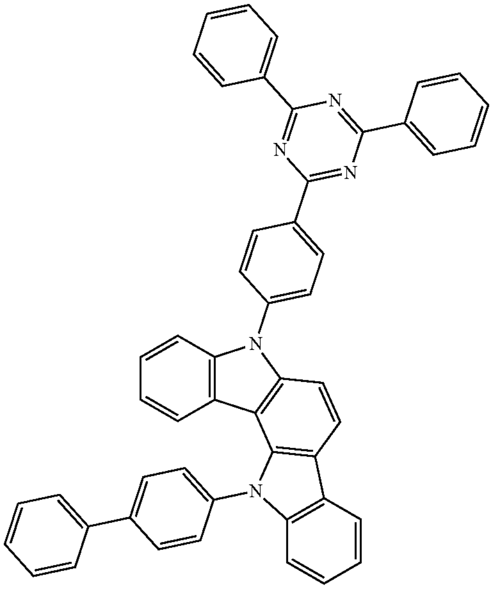

-continued
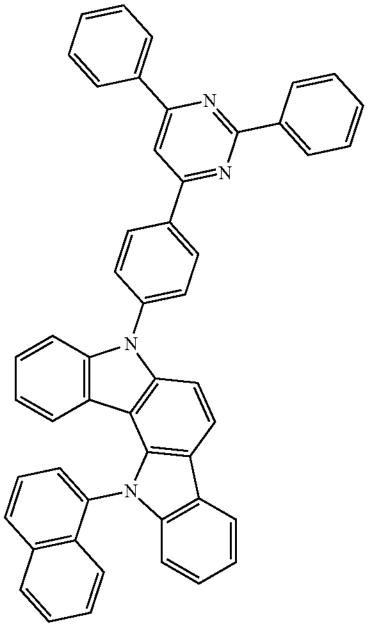
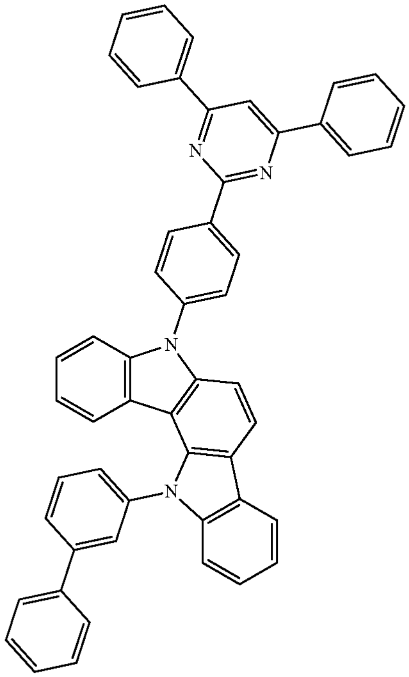
-continued
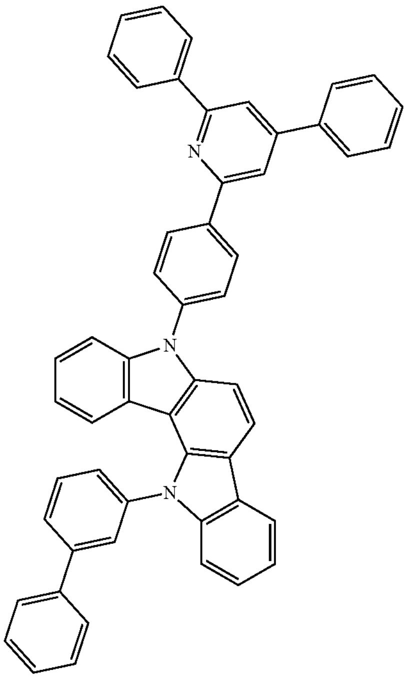
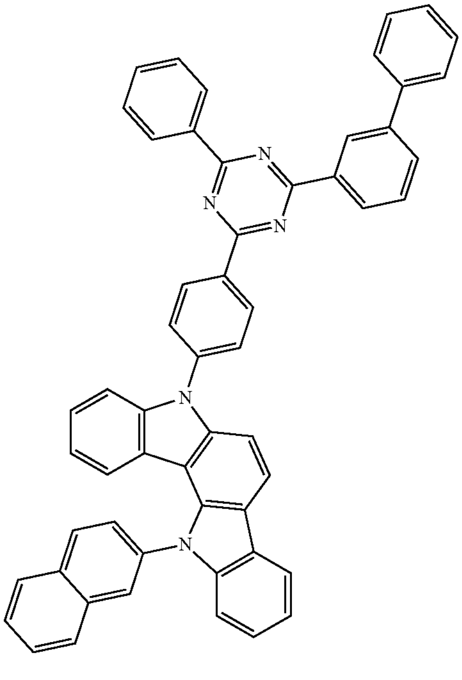

-continued
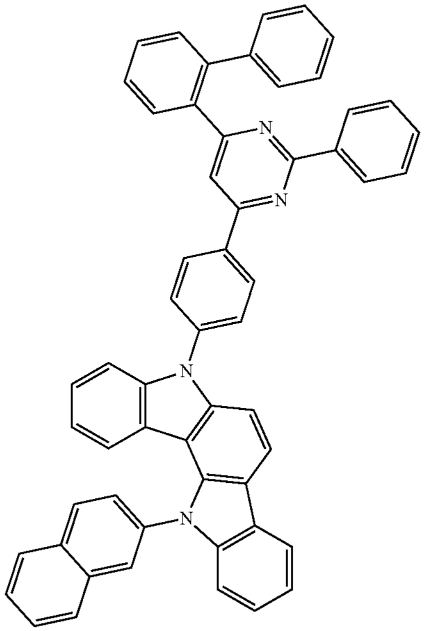
-continued
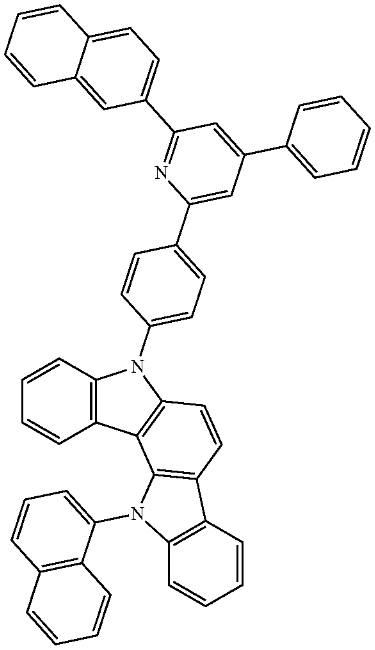
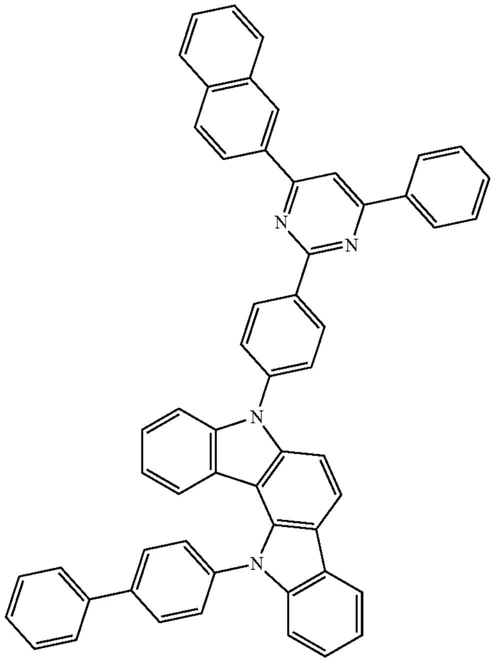
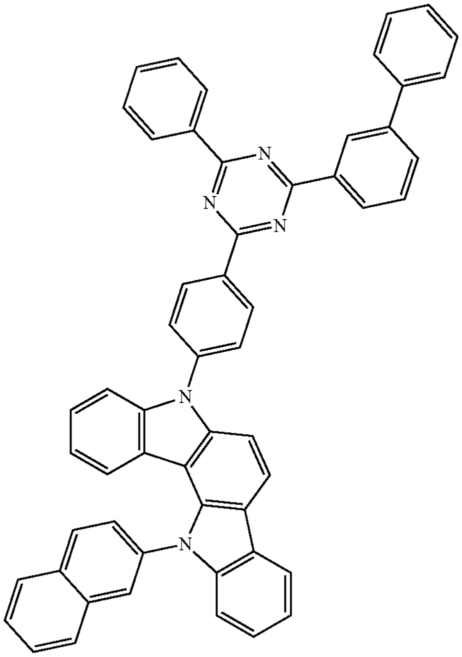

-continued
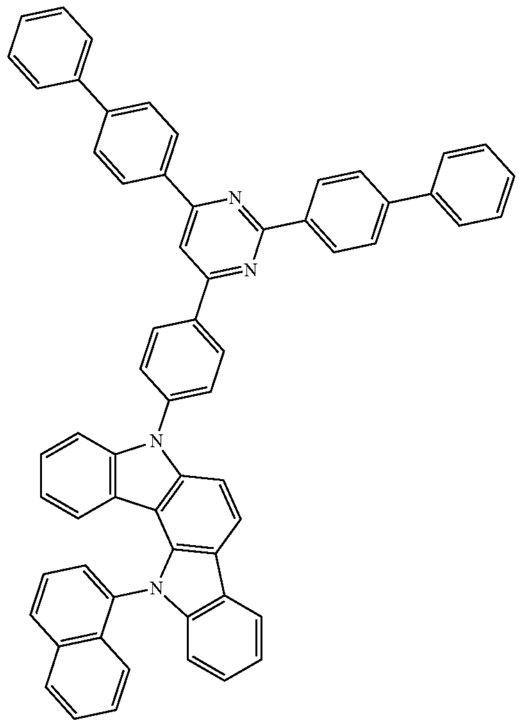
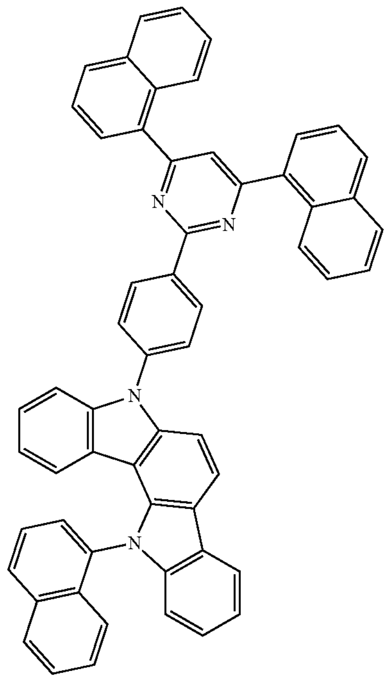
-continued
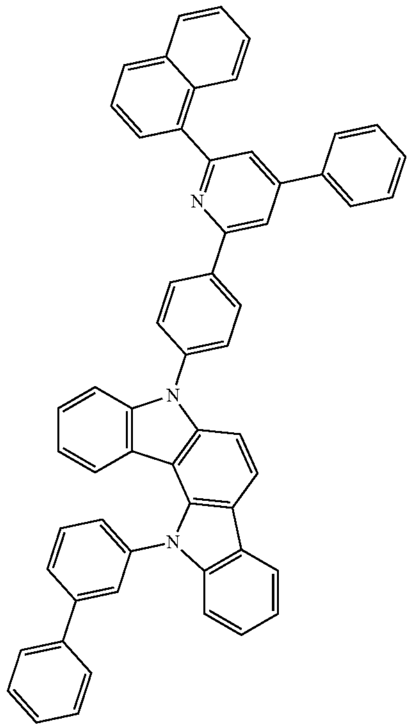
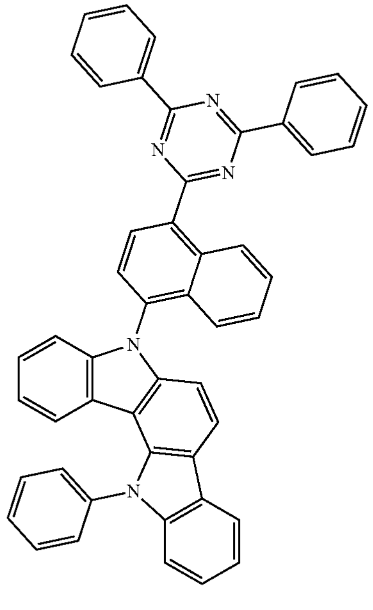

-continued
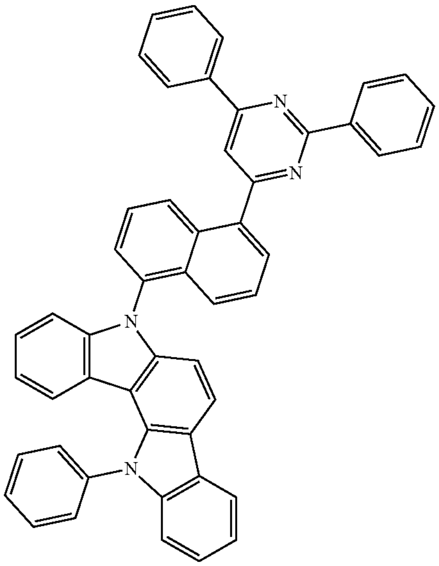
-continued
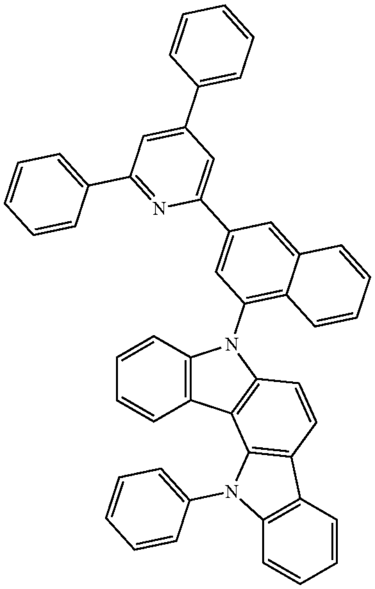
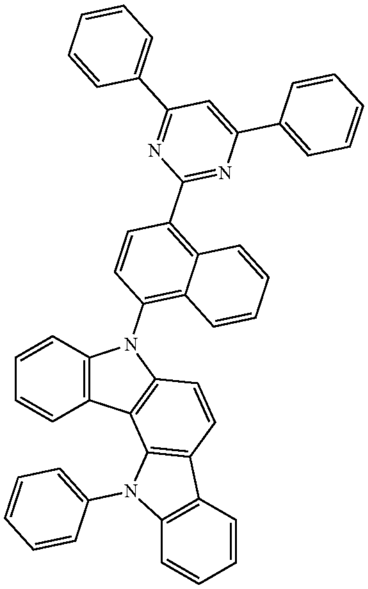
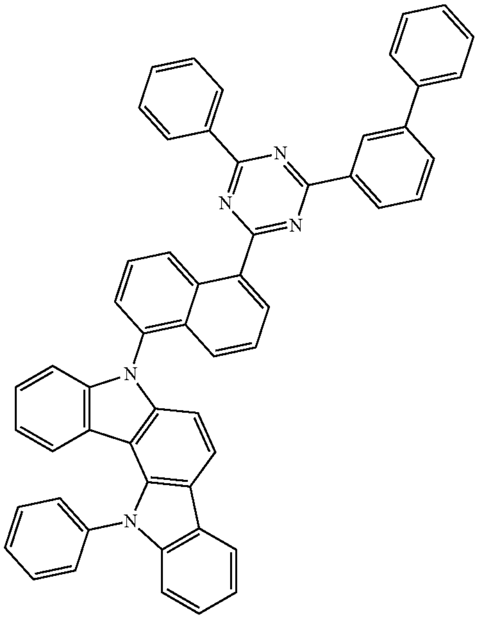

-continued
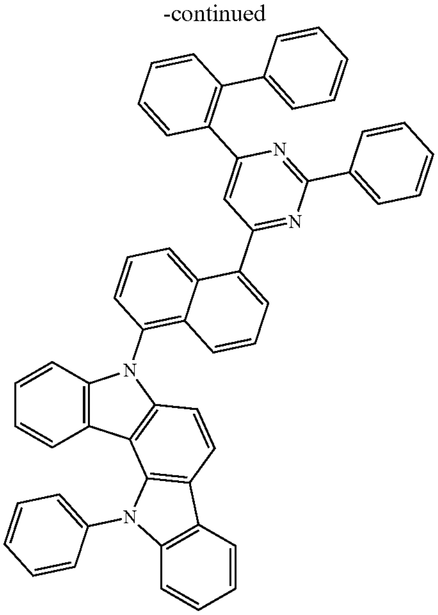
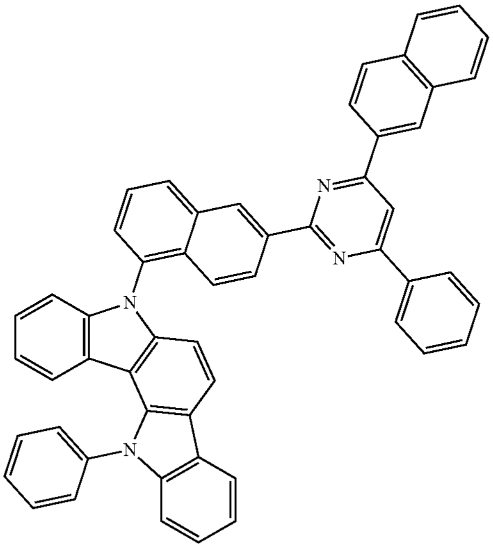
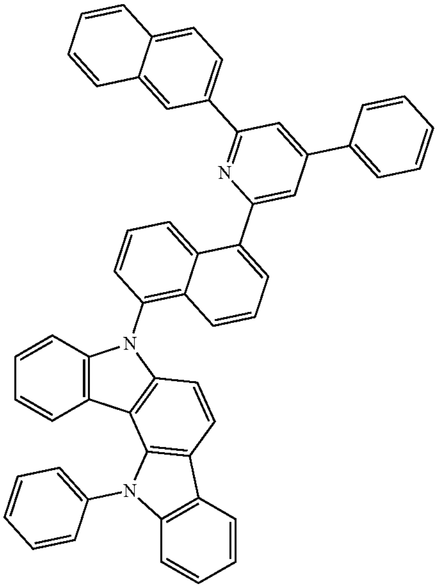
-continued
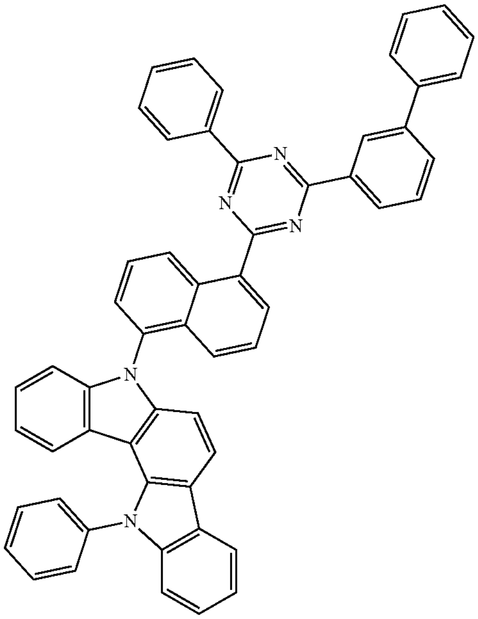
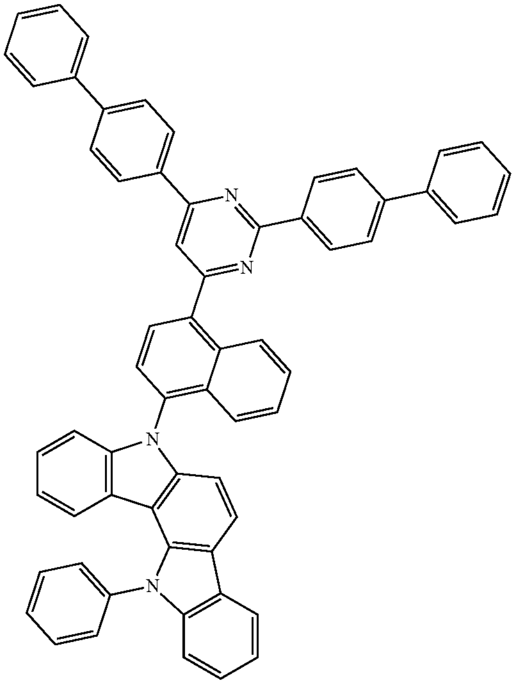

-continued
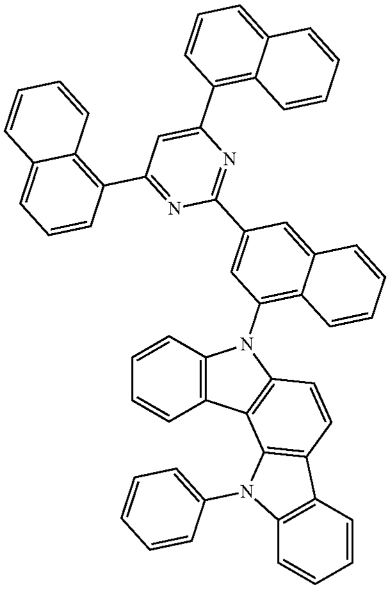
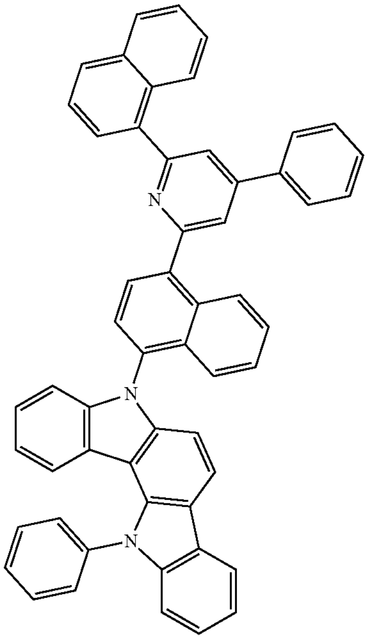
-continued
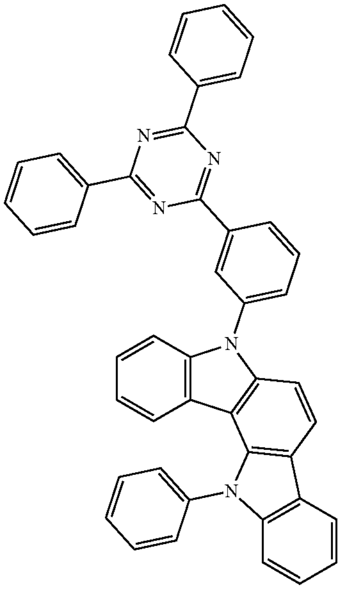
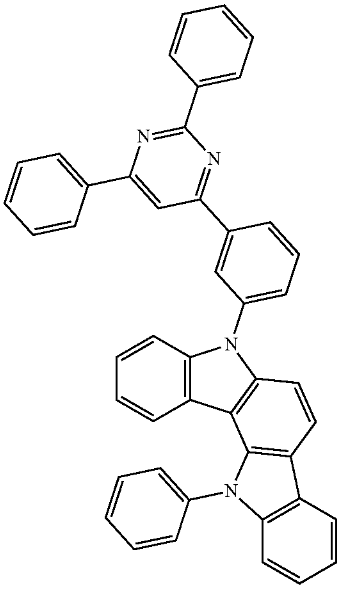

-continued
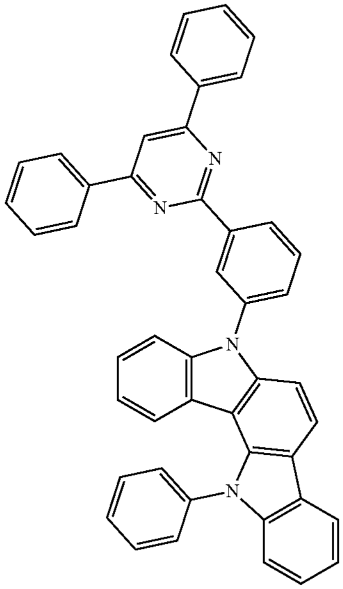
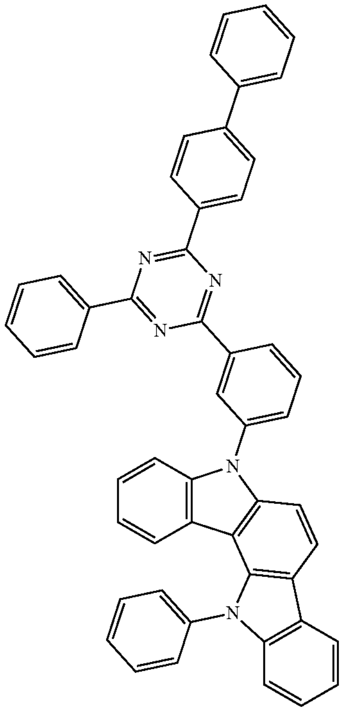
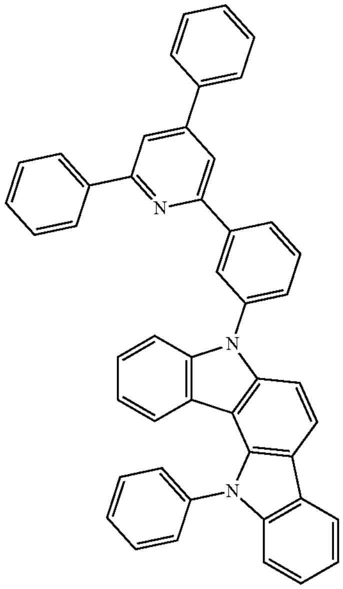
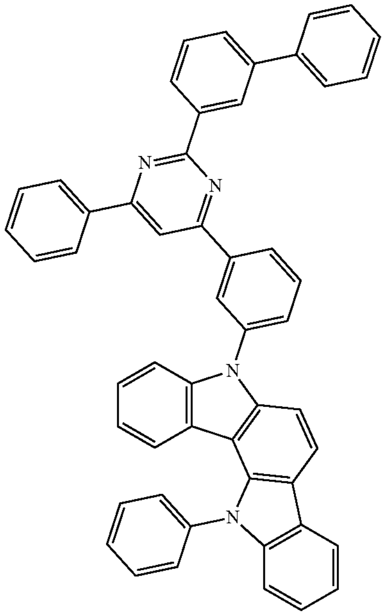

-continued
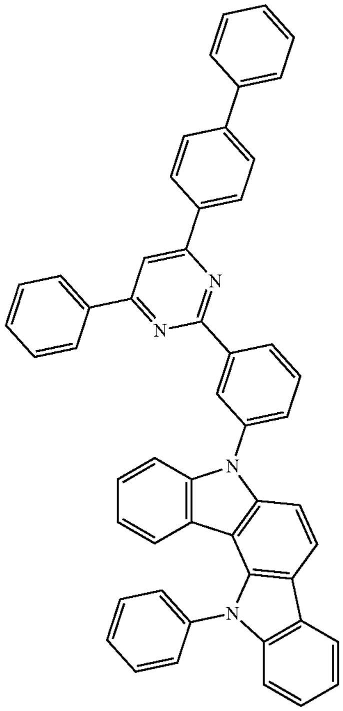
-continued
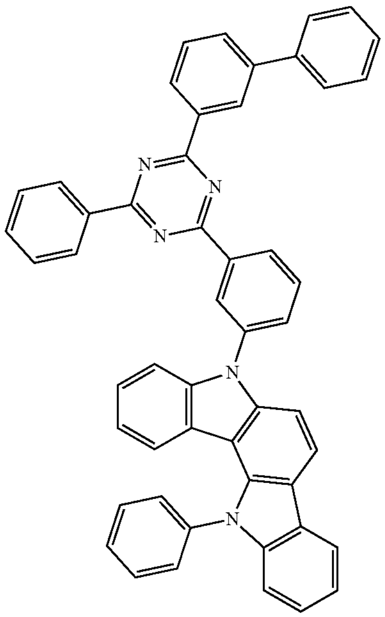
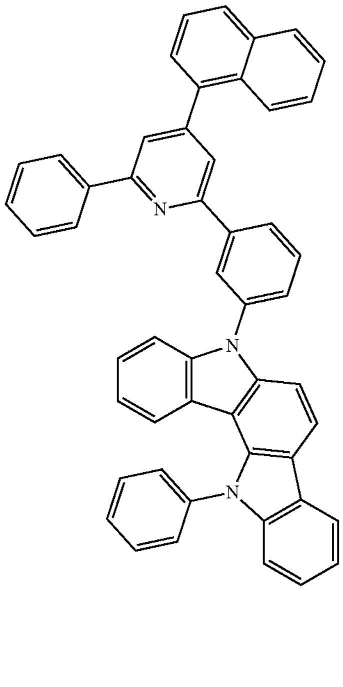
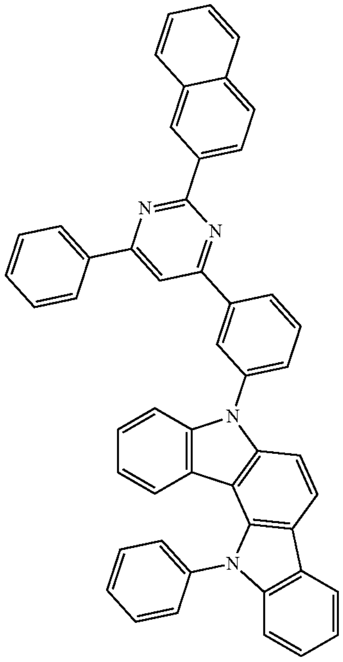

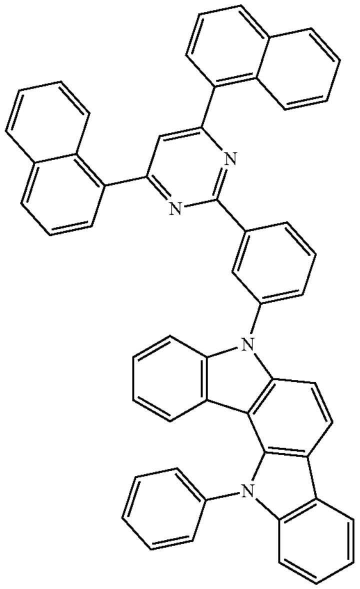
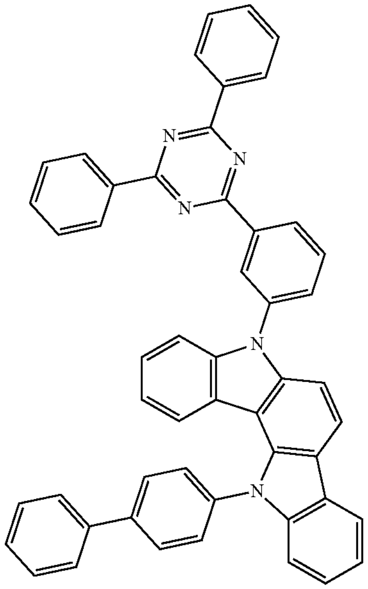
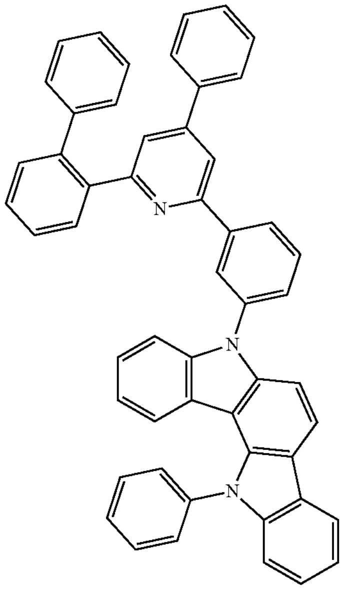
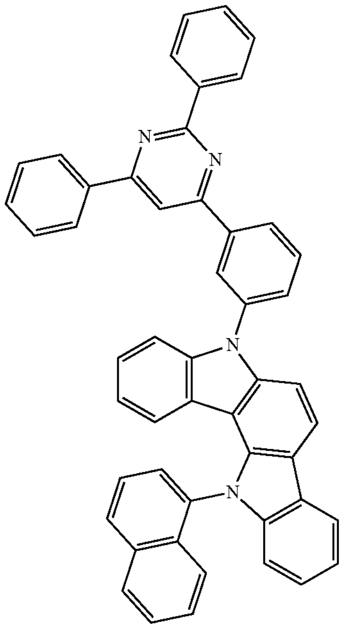

-continued
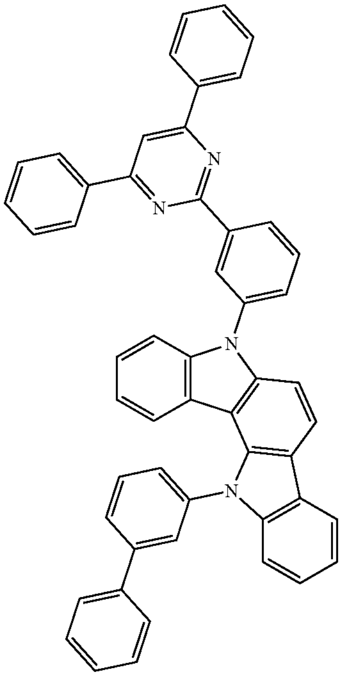
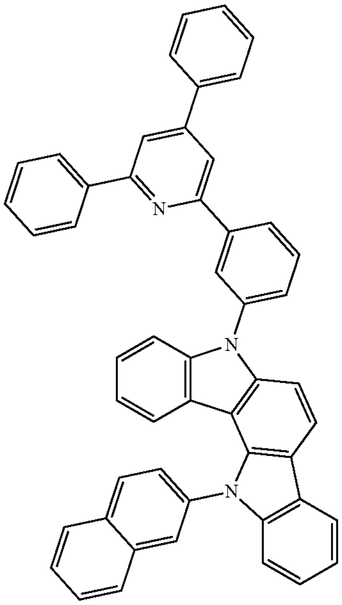
-continued
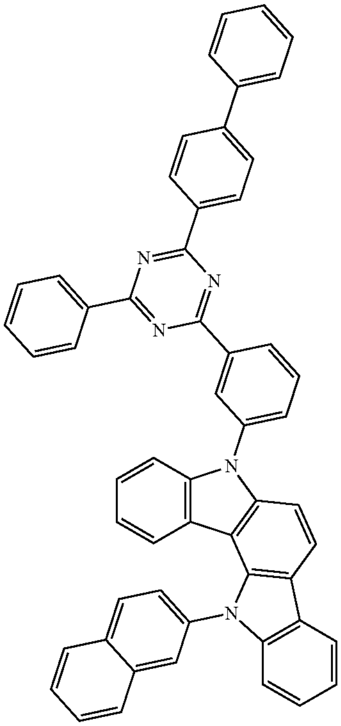
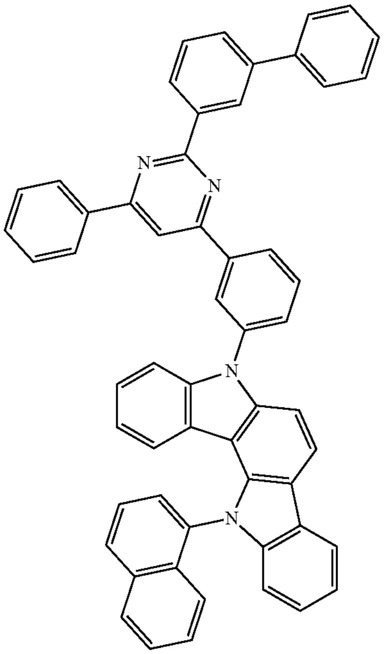

-continued
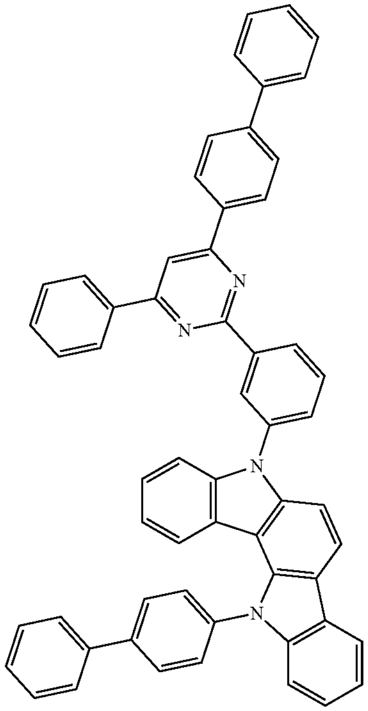
-continued
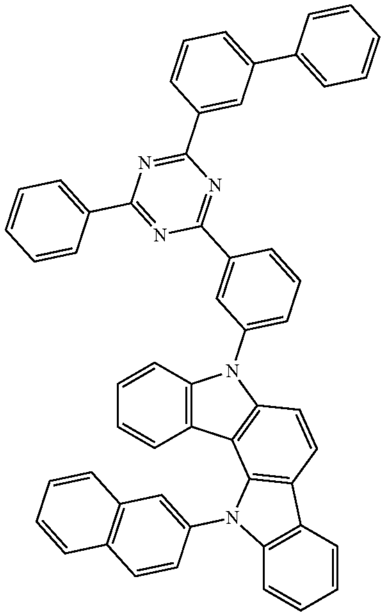
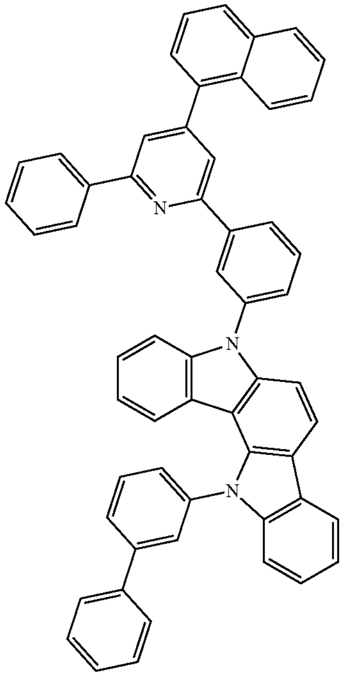
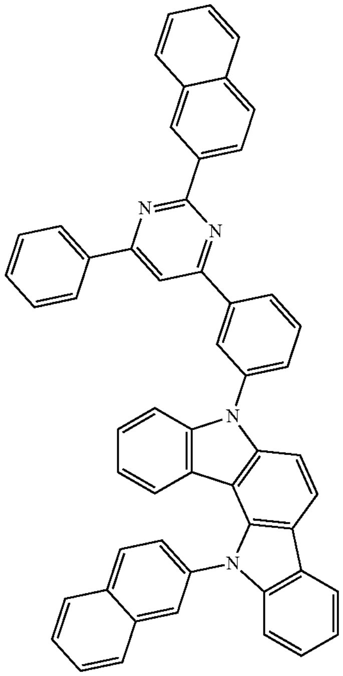

-continued
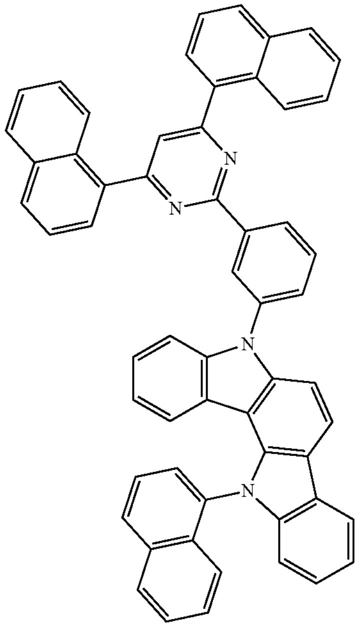
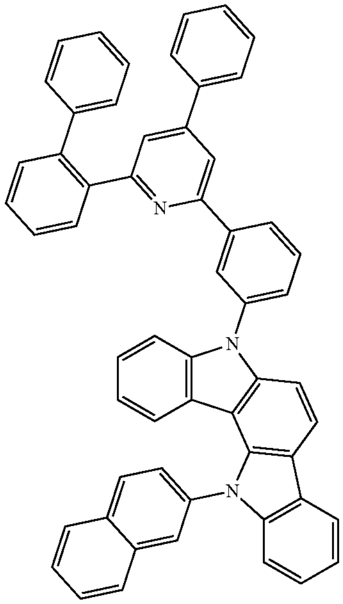
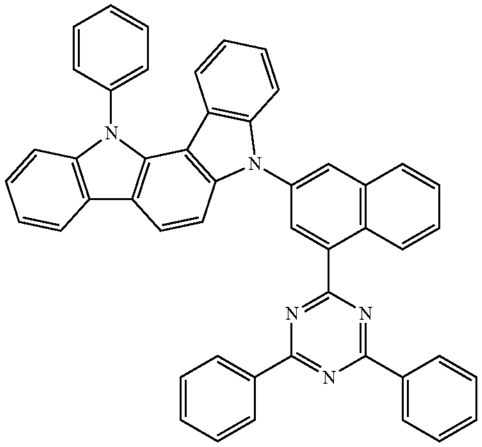
-continued
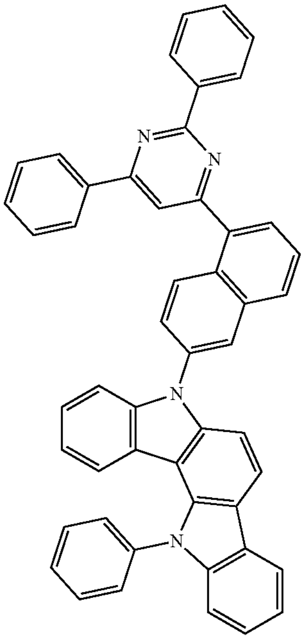
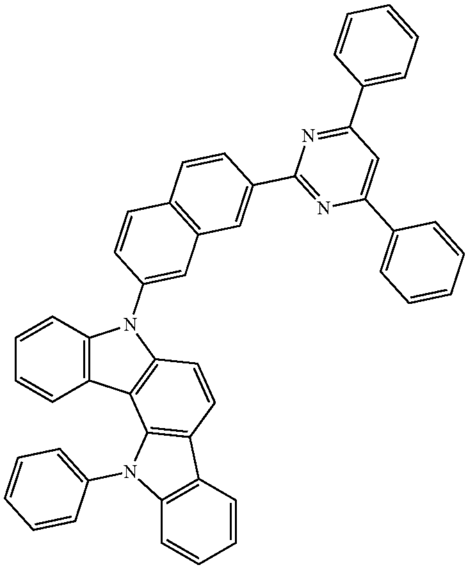

-continued
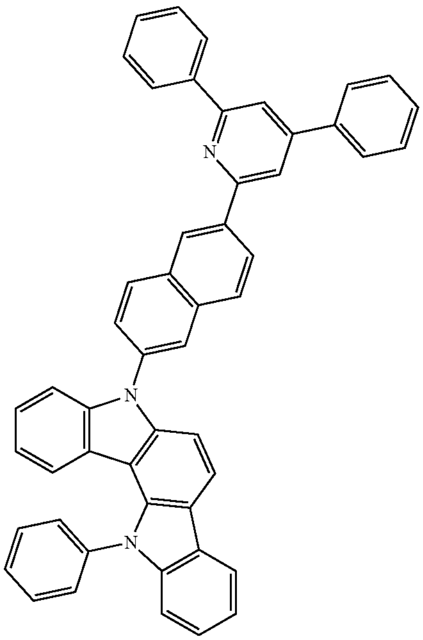
-continued
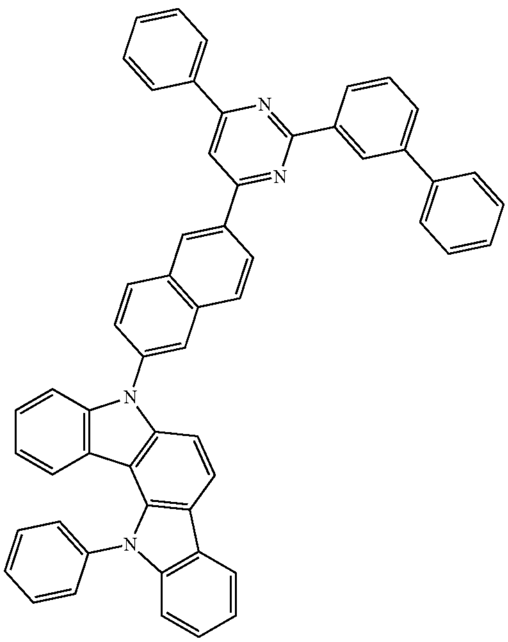
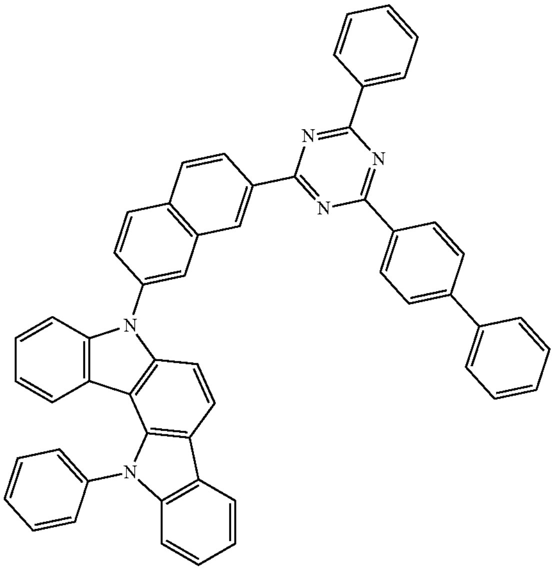
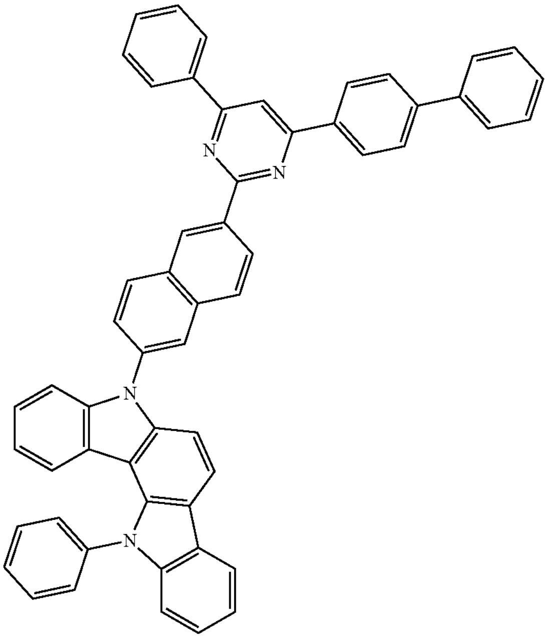

-continued
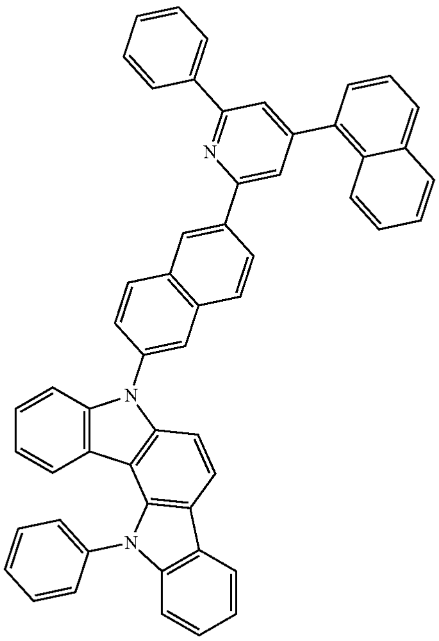
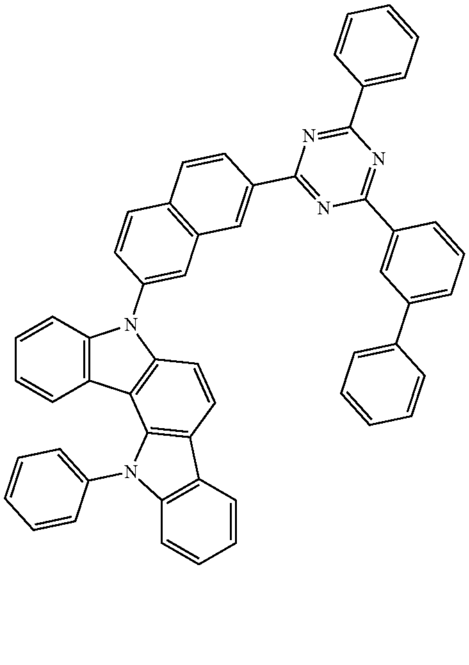
-continued
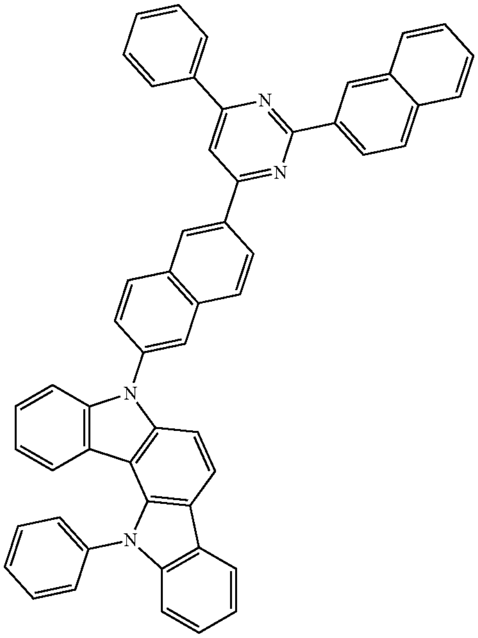
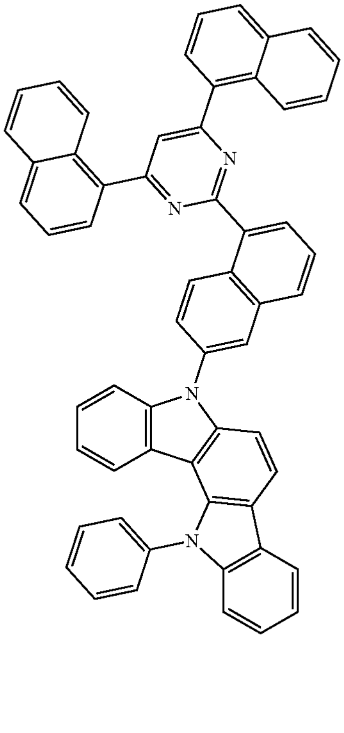

-continued
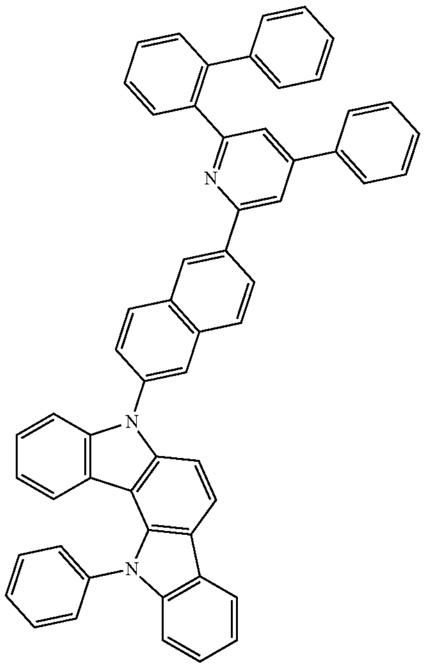
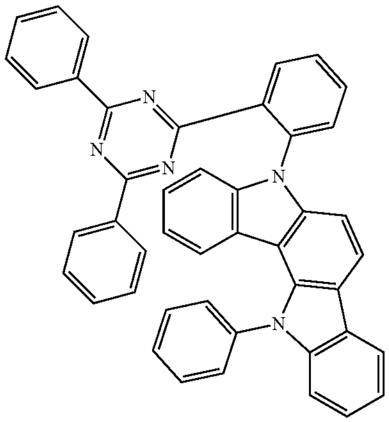
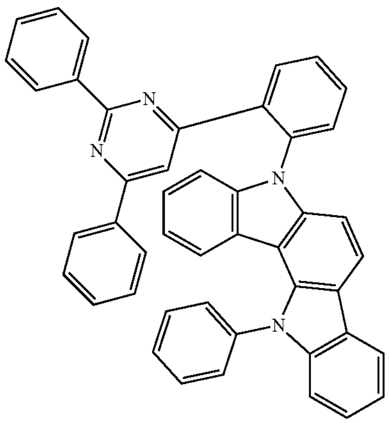
-continued
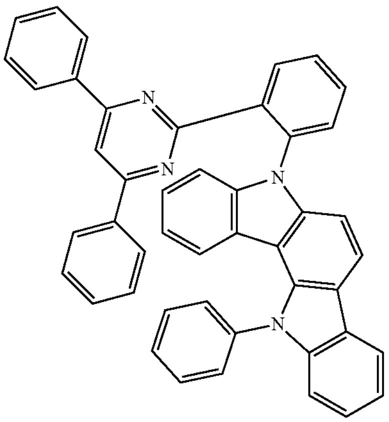
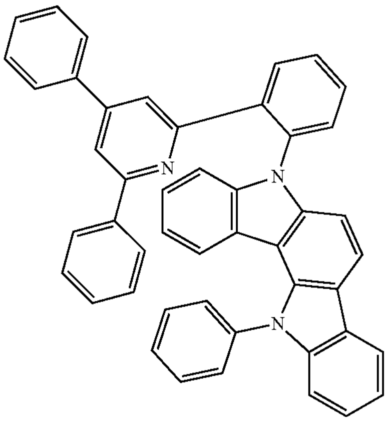
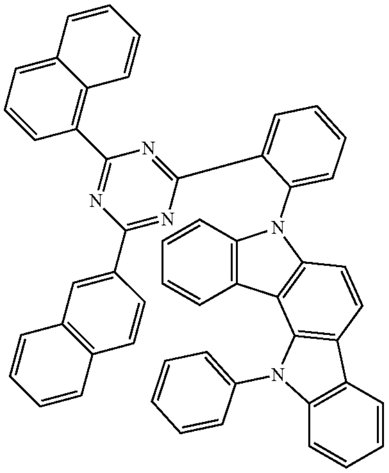

-continued
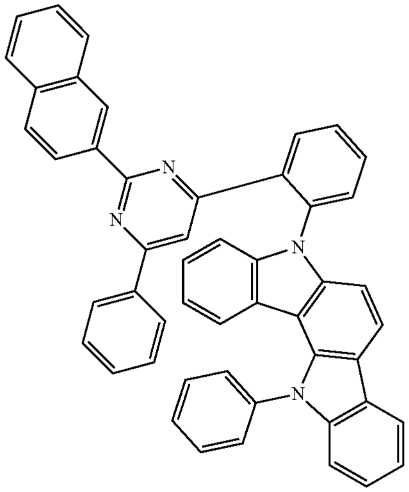
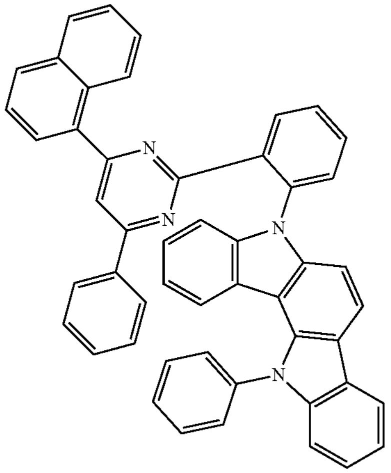
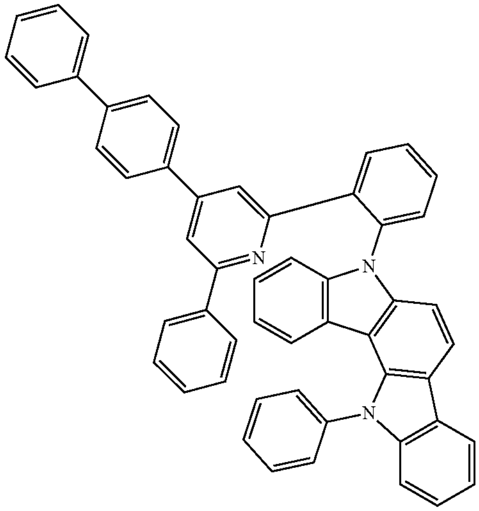
-continued
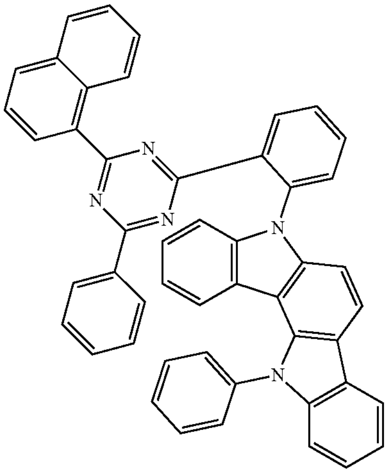
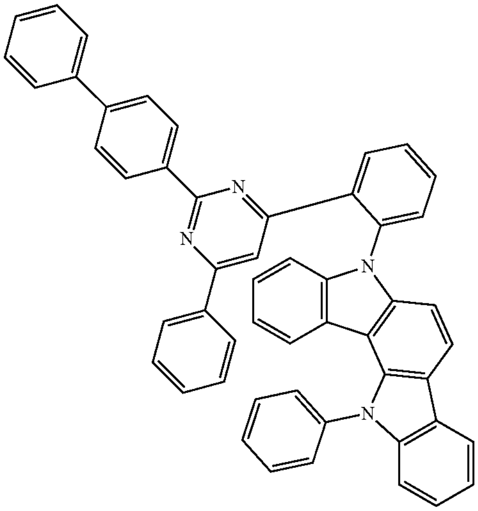
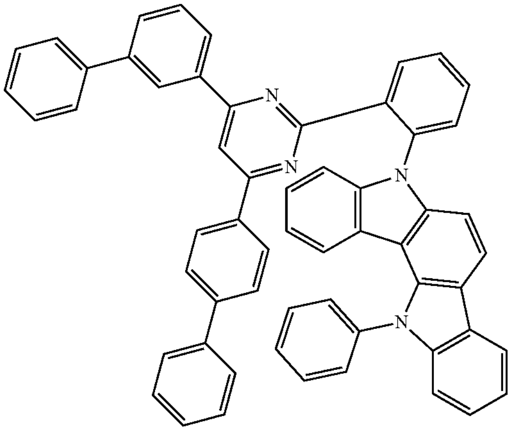

-continued
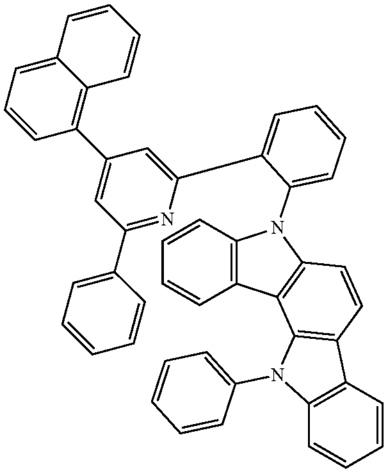
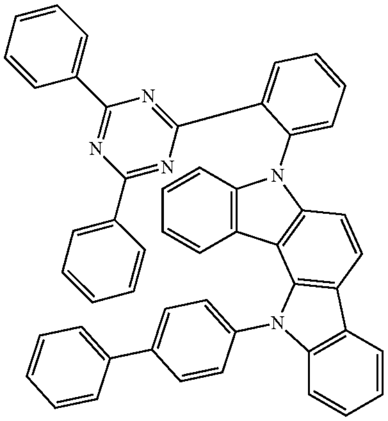
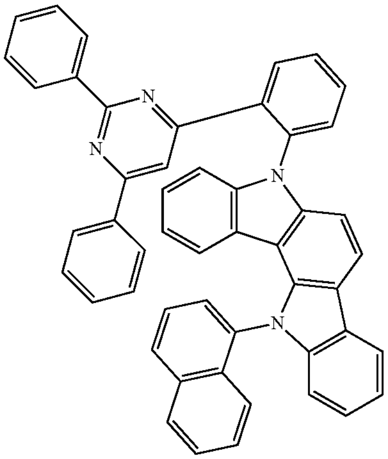
-continued
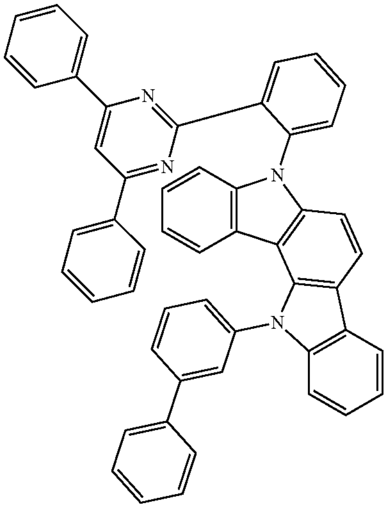
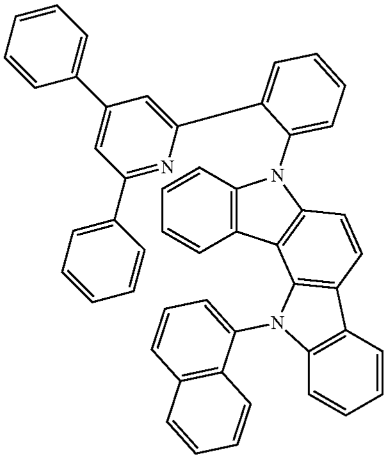
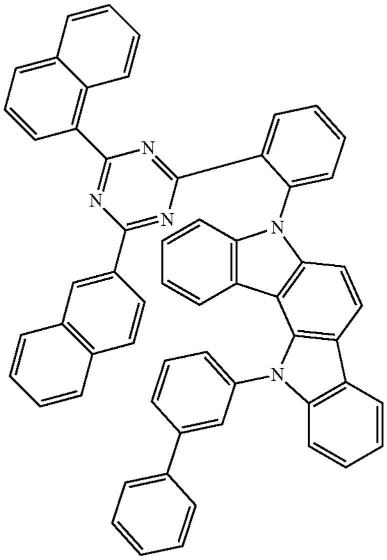

-continued
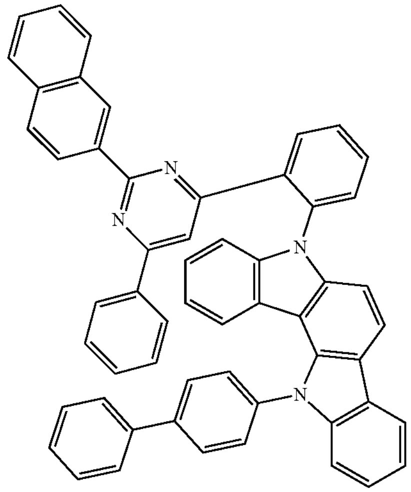
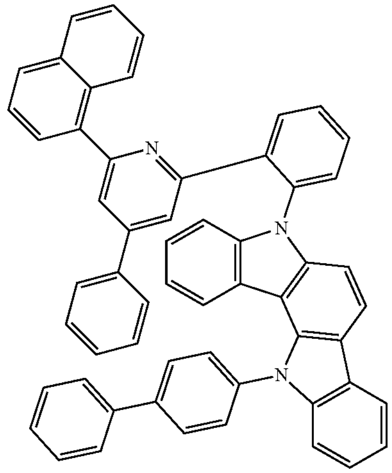
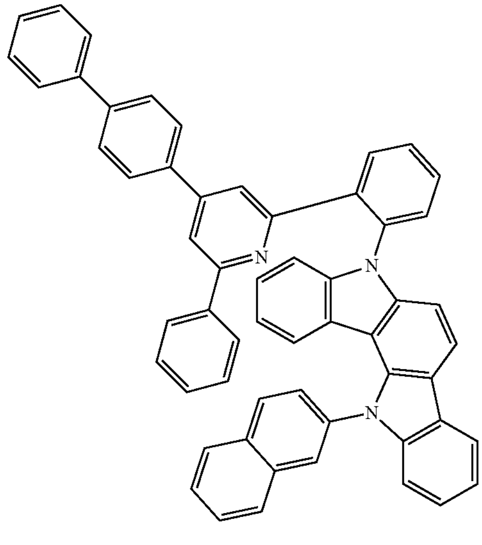
-continued
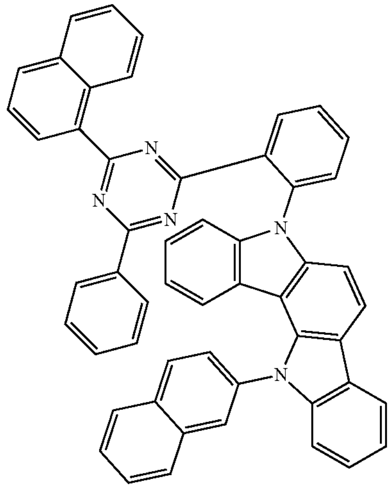
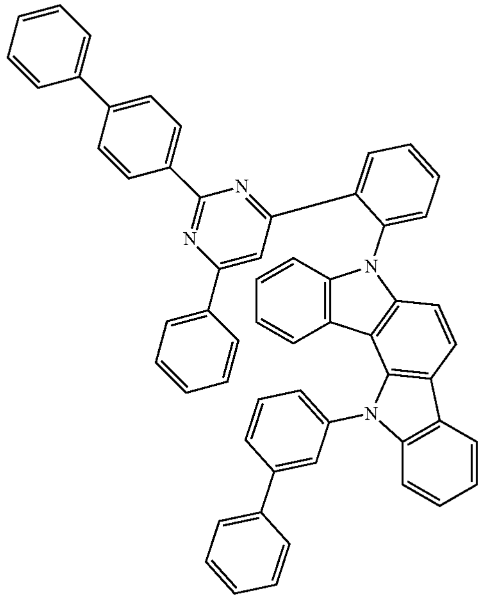
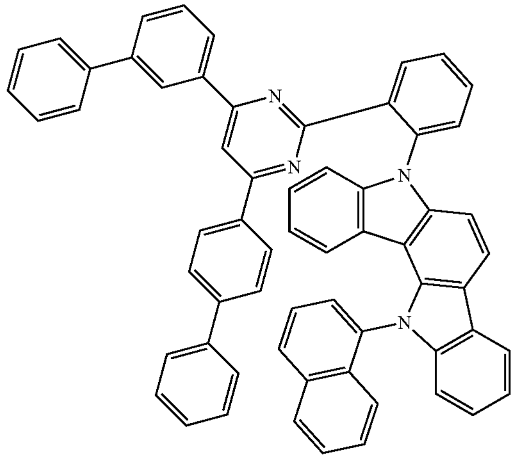

-continued
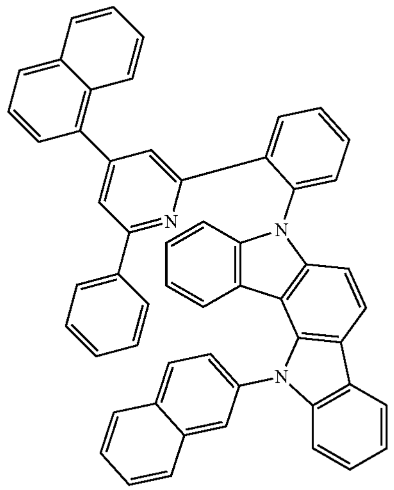
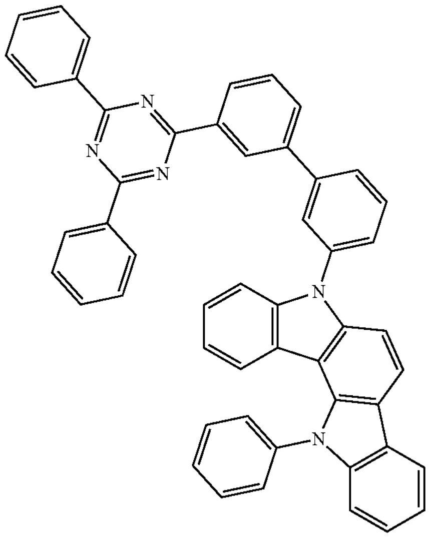
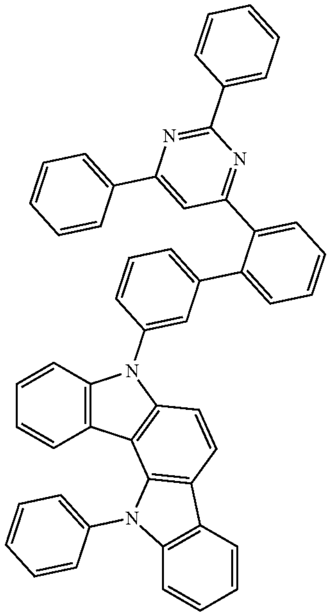
-continued
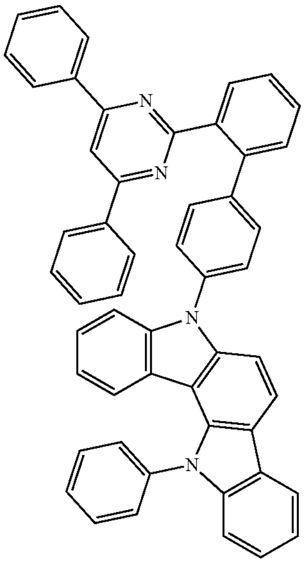
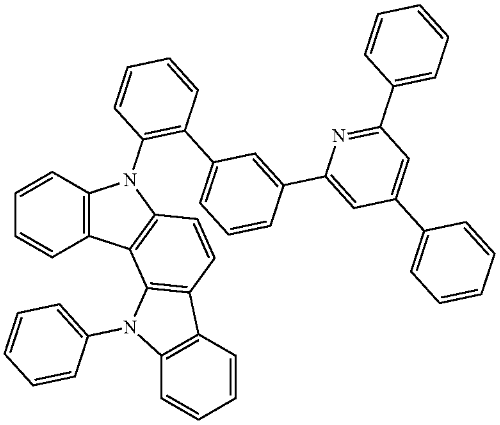
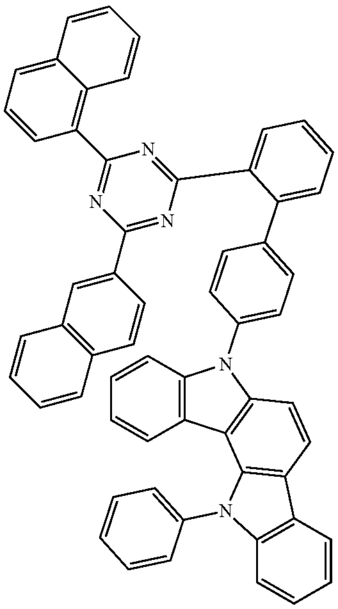

-continued
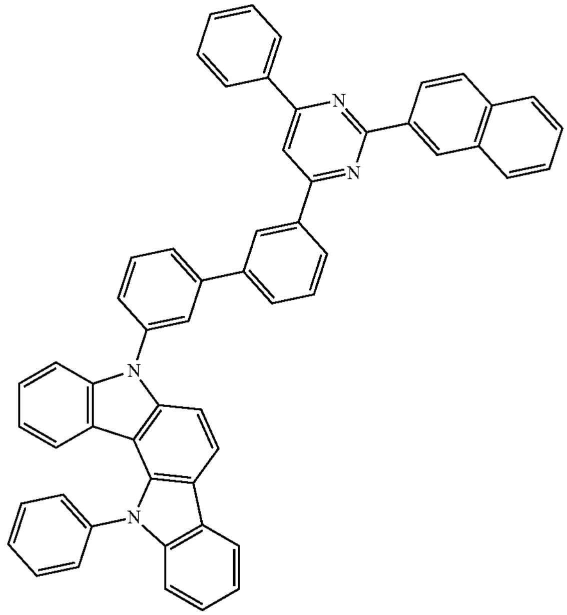
-continued
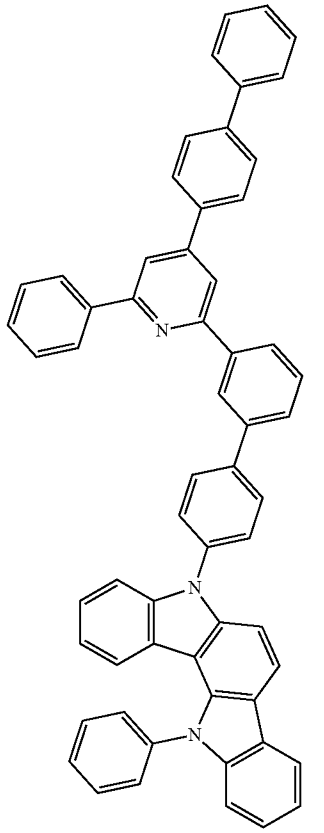
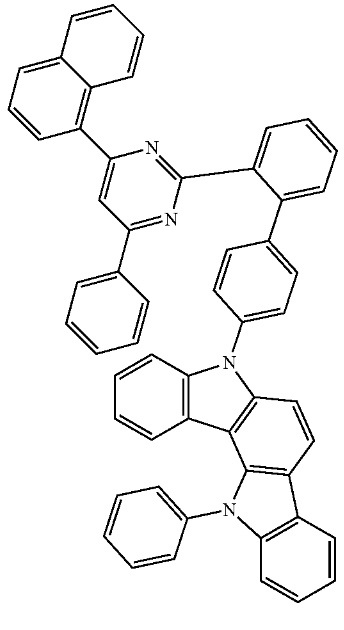
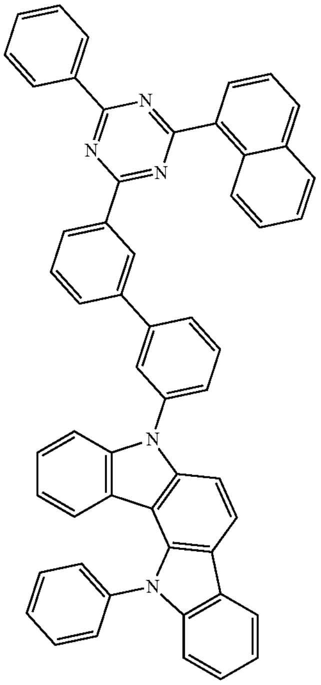

-continued

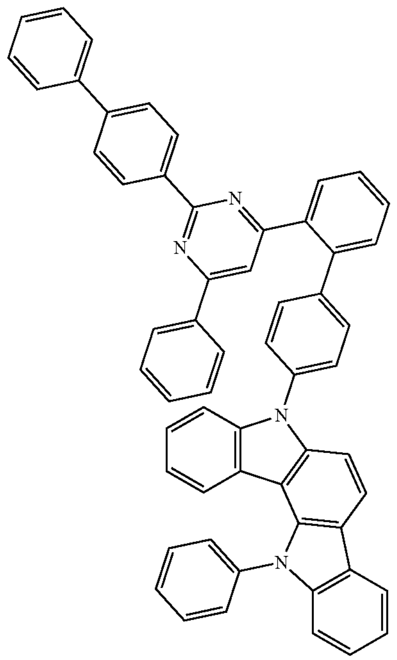

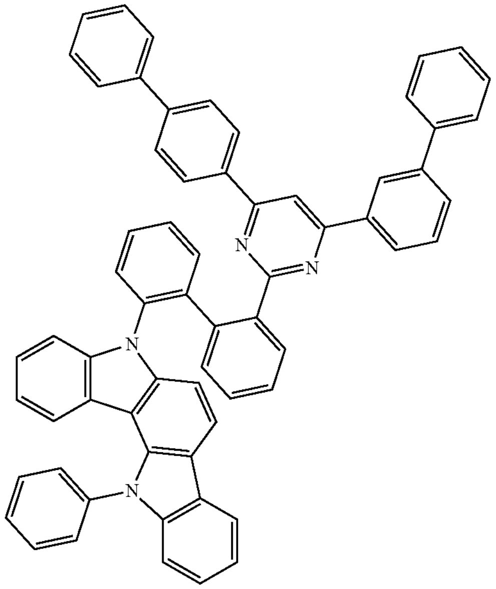

-continued

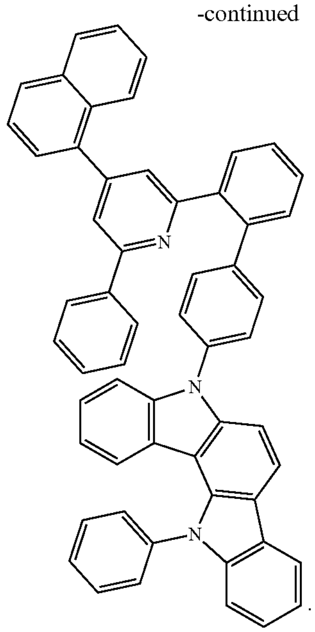

According to an exemplary embodiment of the present specification, the compounds of Formulae 1 to 3 can be prepared by using the starting materials and the reaction conditions known in the art. The type and number of substituents can be determined as a person skilled in the art appropriately selects a publicly-known starting material. Further, the compounds of Formulae 1 to 3 can be purchased from among those commercially available.

According to an exemplary embodiment of the present specification, the organic light emitting diode can include only the above-described hole adjusting layer and the above-described light emitting layer as organic material layers, but can further include an additional organic material layer. For example, the organic light emitting diode can further include an additional hole injection layer, hole transport layer, electron blocking layer, light emitting layer, hole blocking layer, electron transport layer, electron injection layer, and the like.

For example, the structure of the organic light emitting diode of the present specification can have a structure as illustrated in FIGS. 1 and 2, but is not limited thereto.

FIG. 1 exemplifies a structure of an organic light emitting diode 10 in which a positive electrode 30, a light emitting layer 40, and a negative electrode 50 are sequentially stacked on a substrate 20. FIG. 1 is an exemplified structure according to an exemplary embodiment of the present specification, and the structure can further include other organic material layers.

FIG. 2 exemplifies a structure of an organic light emitting diode in which a positive electrode 30, a hole injection layer 60, a hole transport layer 70, a hole adjusting layer 80, a light emitting layer 40, an electron transport layer 90, an electron injection layer 100, and a negative electrode 50 are sequentially stacked on a substrate 20. FIG. 2 is an exemplified structure according to an exemplary embodiment of the present specification, and can further include other organic material layers.

According to an exemplary embodiment of the present specification, the organic light emitting diode further includes a hole transport layer provided between the positive electrode and the hole adjusting layer, and the hole transport layer and the hole adjusting layer are provided to be brought into contact with each other.

According to an exemplary embodiment of the present specification, the hole adjusting layer and the light emitting layer are provided to be brought into contact with each other.

According to an exemplary embodiment of the present specification, the hole adjusting layer has one or more layers. FIG. 2 exemplifies a structure in which the hole adjusting layer has one layer, but is not limited thereto, and when the hole adjusting layer has a plurality of layers, an improved result can be exhibited due to more finely subdivided energy levels.

According to an exemplary embodiment of the present specification, the hole adjusting layer has one to three layers.

According to an exemplary embodiment of the present specification, the hole adjusting layer has one layer, that is, a single layer.

According to an exemplary embodiment of the present specification, when the hole adjusting layer has one layer, the hole adjusting layer includes a compound of Formula 1 or 2.

According to an exemplary embodiment of the present specification, when the hole adjusting layer has one layer, the hole adjusting layer includes a compound of Formula 1.

According to an exemplary embodiment of the present specification, when the hole adjusting layer has one layer, the hole adjusting layer includes a compound of Formula 2.

According to an exemplary embodiment of the present specification, the hole adjusting layer has two or three layers.

According to an exemplary embodiment of the present specification, when the hole adjusting layer has two or three layers, any one layer includes at least one compound of Formulae 1 or 2.

According to an exemplary embodiment of the present specification, when the hole adjusting layer has two or three layers, any one layer includes a compound of Formulae 1 and/or 2.

According to an exemplary embodiment of the present specification, when the hole adjusting layer has two or three layers, any one layer includes a compound of Formula 1.

According to an exemplary embodiment of the present specification, when the hole adjusting layer has two or three layers, any one layer includes a compound of Formula 2.

According to an exemplary embodiment of the present specification, the hole adjusting layer has two layers, that is, a double layer.

According to an exemplary embodiment of the present specification, when the hole adjusting layer has two layers, any one layer includes at least one compound of Formulae 1 or 2.

According to an exemplary embodiment of the present specification, when the hole adjusting layer has two layers, any one layer includes a compound of Formulae 1 and 2.

According to an exemplary embodiment of the present specification, when the hole adjusting layer has two layers, any one layer includes a compound of Formula 1.

According to an exemplary embodiment of the present specification, when the hole adjusting layer has two layers, any one layer includes a compound of Formula 2.

According to an exemplary embodiment of the present specification, the hole adjusting layer has three layers, that is, a triple layer.

According to an exemplary embodiment of the present specification, when the hole adjusting layer has three layers, any one layer includes at least one compound of Formulae 1 and/or 2.

According to an exemplary embodiment of the present specification, when the hole adjusting layer has three layers, any one layer includes compounds of Formulae 1 and 2.

According to an exemplary embodiment of the present specification, when the hole adjusting layer has three layers, any one layer includes a compound of Formula 1.

According to an exemplary embodiment of the present specification, when the hole adjusting layer has three layers, any one layer includes a compound of Formula 2.

According to an exemplary embodiment of the present specification, the hole adjusting layer has one layer, that is, a single layer. The single-layered hole adjusting layer is brought into contact with a light emitting layer.

According to an exemplary embodiment of the present specification, the hole adjusting layer has two layers, that is, a double layer. When the hole adjusting layer has two layers, the hole adjusting layer includes a first hole adjusting layer and a second hole adjusting layer.

According to an exemplary embodiment of the present specification, the hole adjusting layer includes a first hole adjusting layer and a second hole adjusting layer.

According to an exemplary embodiment of the present specification, the hole adjusting layer includes a first hole adjusting layer including one or more compounds of Formulae 1 and/or 2 and a second hole adjusting layer including one or more compounds of Formulae 1 and/or 2. According to one example, the first hole adjusting layer and the second hole adjusting layer are brought into contact with each other. According to another example, the second hole adjusting layer is brought into contact with a light emitting layer. According to still another example, the first hole adjusting layer is brought into contact with a hole transport layer.

According to one example, the compositions of the first hole adjusting layer and the second hole adjusting layer are different from each other. According to another example, the first hole adjusting layer and the second hole adjusting layer include different compounds.

According to one example, the first hole adjusting layer includes a compound of Formula 1, and the second hole adjusting layer includes a compound of Formula 1.

According to one example, the first hole adjusting layer includes a compound of Formula 1, and the second hole adjusting layer includes a compound of Formula 2.

According to one example, the first hole adjusting layer includes a compound of Formula 2, and the second hole adjusting layer includes a compound of Formula 1.

According to one example, the first hole adjusting layer includes a compound of Formula 2, and the second hole adjusting layer includes a compound of Formula 2.

According to one example, the first hole adjusting layer includes at least one compound of Formulae 1 and 2.

According to one example, the second hole adjusting layer includes at least one compound of Formulae 1 and 2.

According to one example, the first hole adjusting layer includes compounds of Formulae 1 and 2.

According to one example, the second hole adjusting layer includes compounds of Formulae 1 and 2.

According to one example, the first hole adjusting layer includes a compound of Formula 1.

According to one example, the second hole adjusting layer includes a compound of Formula 1.

According to one example, the first hole adjusting layer includes a compound of Formula 2.

According to one example, the second hole adjusting layer includes a compound of Formula 2.

According to one example, the first hole adjusting layer of the first hole adjusting layer and the second hole adjusting layer includes at least one compound of Formulae 1 and/or 2.

According to one example, the second hole adjusting layer of the first hole adjusting layer and the second hole adjusting layer includes at least one compound of Formulae 1 and/or 2.

According to one example, only the first hole adjusting layer of the first hole adjusting layer and the second hole adjusting layer includes at least one compound of Formulae 1 and/or 2.

According to one example, only the second hole adjusting layer of the first hole adjusting layer and the second hole adjusting layer includes at least one compound of Formulae 1 and/or 2.

According to one example, the first hole adjusting layer of the first hole adjusting layer and the second hole adjusting layer includes compounds of Formulae 1 and 2.

According to one example, the second hole adjusting layer of the first hole adjusting layer and the second hole adjusting layer includes compounds of Formulae 1 and 2.

According to one example, only the first hole adjusting layer of the first hole adjusting layer and the second hole adjusting layer includes compounds of Formulae 1 and 2.

According to one example, only the second hole adjusting layer of the first hole adjusting layer and the second hole adjusting layer includes compounds of Formulae 1 and 2.

According to one example, the first hole adjusting layer of the first hole adjusting layer and the second hole adjusting layer includes the compound of Formula 1.

According to one example, the second hole adjusting layer of the first hole adjusting layer and the second hole adjusting layer includes a compound of Formula 1.

According to one example, only the first hole adjusting layer of the first hole adjusting layer and the second hole adjusting layer includes a compound of Formula 1.

According to one example, only the second hole adjusting layer of the first hole adjusting layer and the second hole adjusting layer includes a compound of Formula 1.

According to one example, the first hole adjusting layer of the first hole adjusting layer and the second hole adjusting layer includes a compound of Formula 2.

According to one example, the second hole adjusting layer of the first hole adjusting layer and the second hole adjusting layer includes a compound of Formula 2.

According to one example, only the first hole adjusting layer of the first hole adjusting layer and the second hole adjusting layer includes a compound of Formula 2.

According to one example, only the second hole adjusting layer of the first hole adjusting layer and the second hole adjusting layer includes a compound of Formula 2.

According to an exemplary embodiment of the present specification, the first hole adjusting layer has a larger thickness than that of the second hole adjusting layer.

According to an exemplary embodiment of the present specification, the hole transport layer has a larger thickness than that of the hole adjusting layer.

According to an exemplary embodiment of the present specification, the sum of the thicknesses of the first hole adjusting layer and the second hole adjusting layer is smaller than the thickness of the hole transport layer.

According to an exemplary embodiment of the present specification, the thicknesses of the hole transport layer, the first hole adjusting layer, and the second hole adjusting layer satisfy the thickness of the hole transport layer>the thickness of the first hole adjusting layer>the thickness of the second hole adjusting layer.

The combination of the hole adjusting layer including at least one of the compounds of Formulae 1 and/or 2 of the present specification and the light emitting layer including a compound of Formula 3 of the present specification adjusts the HOMO of each layer and makes the balance of appropriate introduction of holes in a light emitting layer of a red light emitting device through the effective movement of holes of the mentioned chemical structure, thereby exhibiting a positive result to red light emission with low voltage and high efficiency.

According to an exemplary embodiment of the present specification, a compound of Formula 3 is included as a host of a light emitting layer.

According to an exemplary embodiment of the present specification, the light emitting layer includes a dopant. The dopant can include one or more selected from the following compounds, but is not limited thereto:

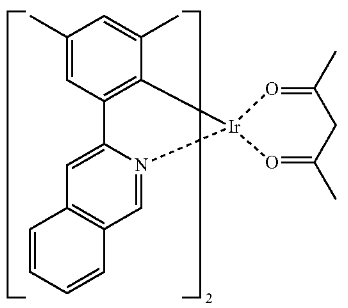

Dp-1

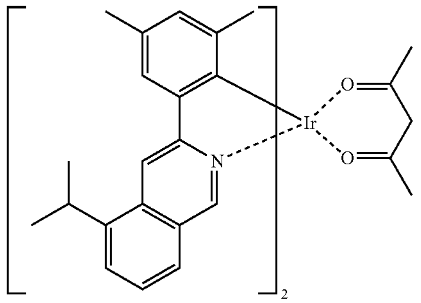

Dp-2

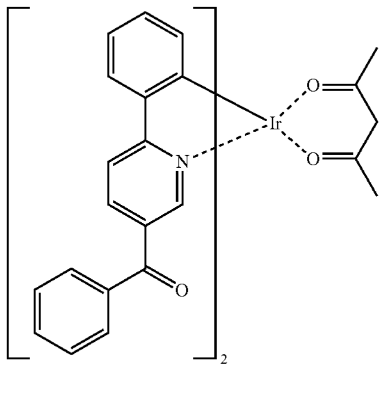

Dp-3

-continued
Dp-4
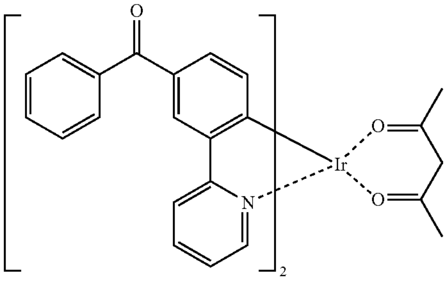
Dp-5
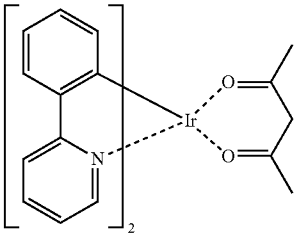
Dp-6
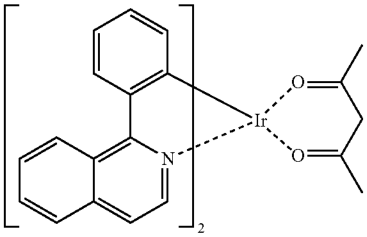
Dp-7
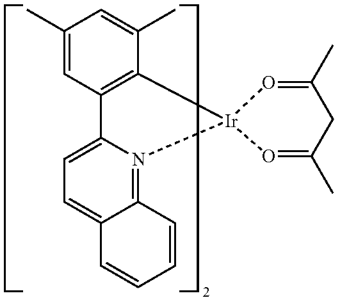
Dp-8
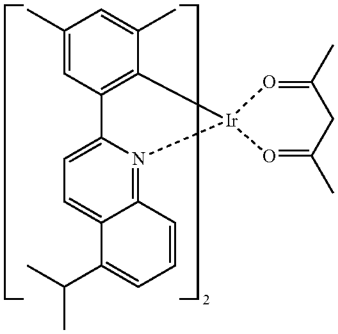
-continued
Dp-9
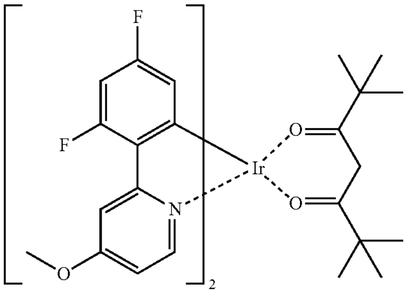
Dp-10
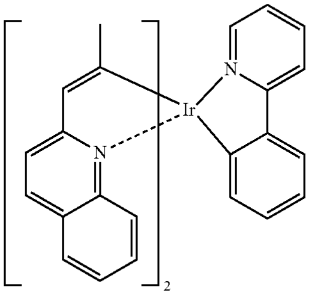
Dp-11
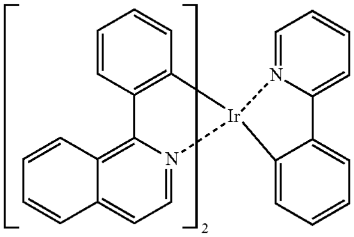
Dp-12
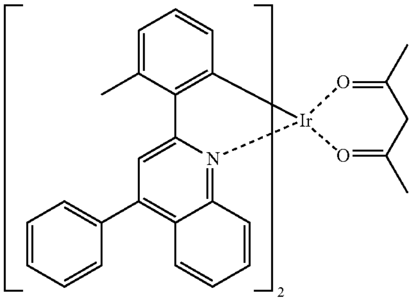
DP-13
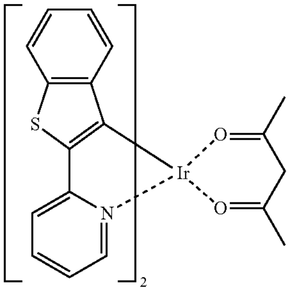

-continued
Dp-14
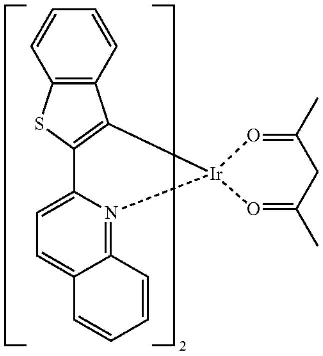
Dp-15
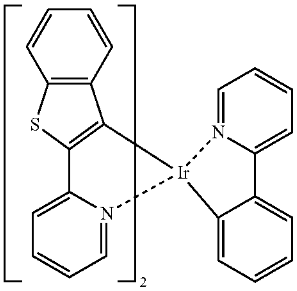
DP-16
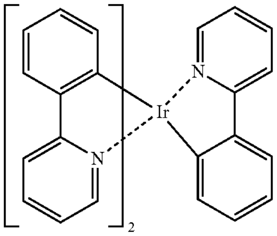
Dp-17
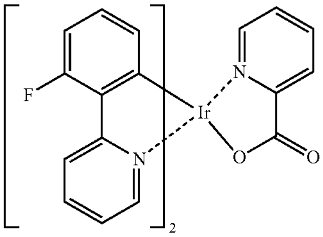
Dp-18
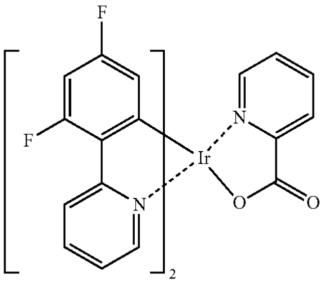
-continued
Dp-19
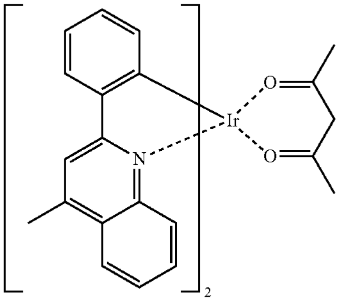
Dp-20
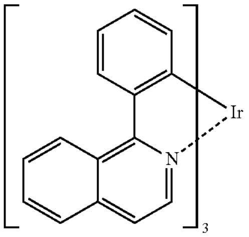
Dp-21
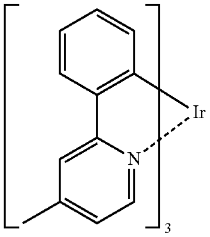
Dp-22
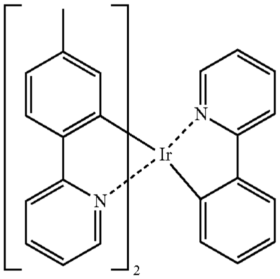
DP-23
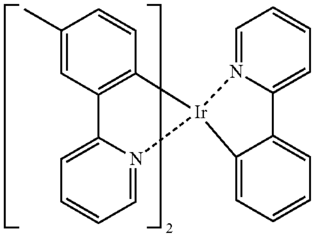

-continued
Dp-24
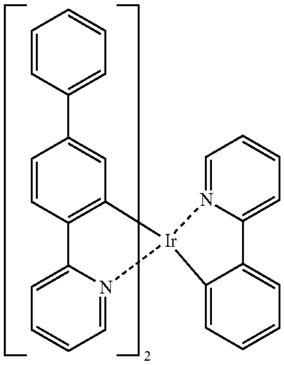
Dp-25
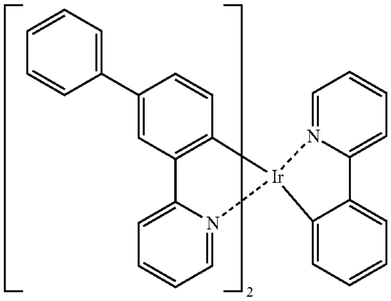
Dp-26
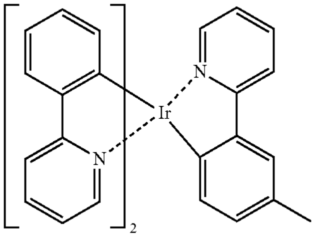
Dp-27
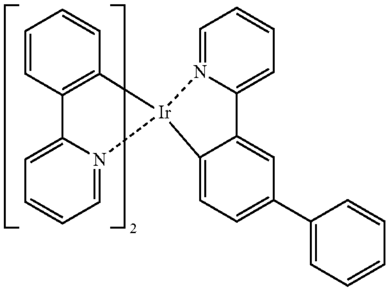
Dp-28
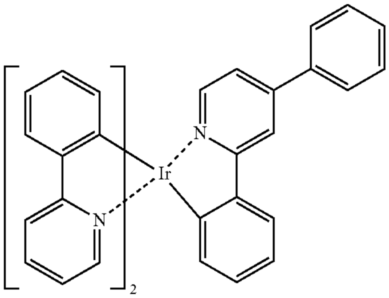
-continued
Dp-29
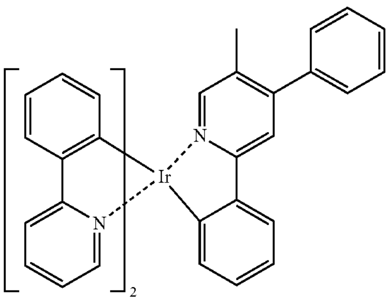
Dp-30
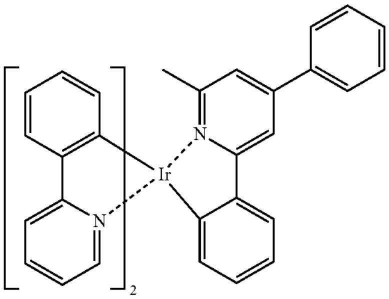
Dp-31
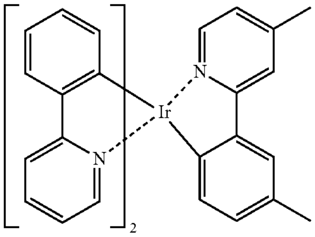
Dp-32
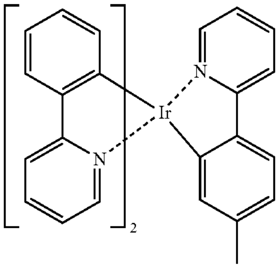
Dp-33
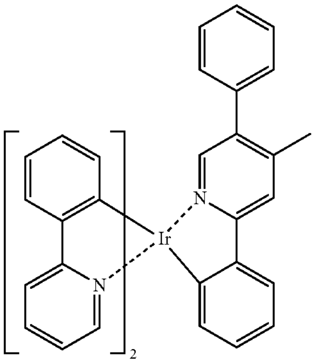

-continued

Dp-34

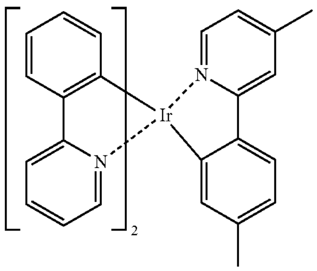

Dp-35

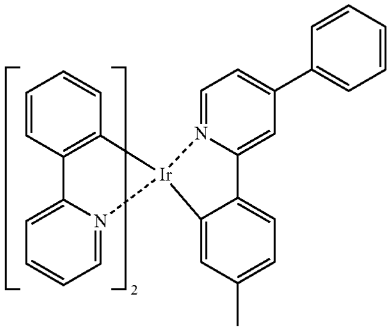

Dp-36

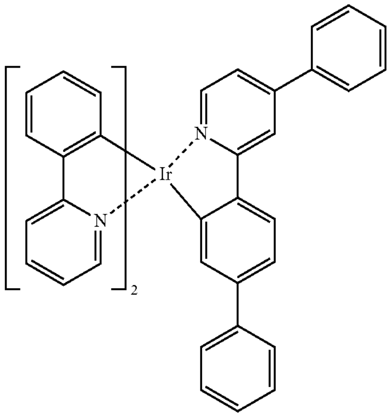

Dp-37

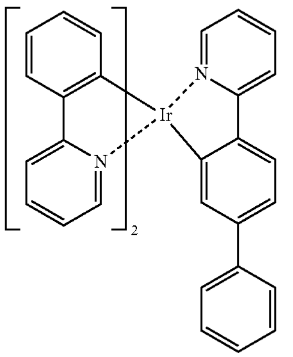

-continued

Dp-38

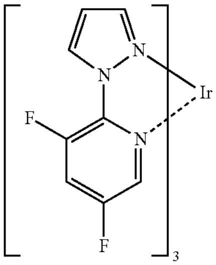

Dp 39 (RD-1)

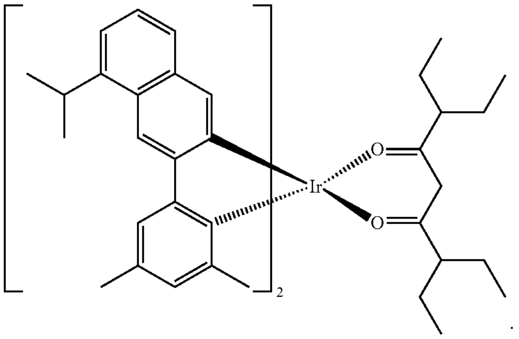

According to an exemplary embodiment of the present specification, the dopant is included in an amount of 1 wt % to 10 wt % in the light emitting layer.

In another exemplary embodiment, the organic light emitting diode can be an organic light emitting diode having a normal type structure in which a positive electrode, an organic material layer having one or more layers, and a negative electrode are sequentially stacked on a substrate.

In still another exemplary embodiment, the organic light emitting diode can be an organic light emitting diode having an inverted type structure in which a negative electrode, an organic material layer having one or more layers, and a positive electrode are sequentially stacked on a substrate.

When the organic light emitting diode includes a plurality of organic material layers, the organic material layers can be formed of the same material or different materials.

The organic light emitting diode of the present specification can be manufactured by materials and methods known in the art, except that the hole adjusting layer includes at least one of the compounds of Formulae 1 and/or 2, and the light emitting layer includes a compound of Formula 3.

For example, the organic light emitting diode of the present specification can be manufactured by sequentially stacking a positive electrode, an organic material layer, and a negative electrode on a substrate. In this case, the organic light emitting diode can be manufactured by depositing a metal or a metal oxide having conductivity, or an alloy thereof on a substrate to form a positive electrode, forming an organic material layer including a hole injection layer, a hole transport layer, a light emitting layer, and an electron transport layer thereon, and then depositing a material, which can be used as a negative electrode, thereon, by using a physical vapor deposition (PVD) method such as sputtering or e-beam evaporation. In addition to the method as described above, an organic light emitting diode can be made by sequentially depositing a negative electrode material, an organic material layer, and a positive electrode material on a substrate.

In addition to the method described above, an organic light emitting diode can also be made by sequentially depositing a negative electrode material, an organic material layer, and a positive electrode material on a substrate (International Publication No. WO2003/012890). However, the manufacturing method is not limited thereto.

As the positive electrode material, materials having a high work function are usually preferred so as to facilitate the injection of holes into an organic material layer. Specific examples of the positive electrode material which can be used in the present invention include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as ZnO:Al or $SnO_2$:Sb; a conductive polymer such as poly(3-methylthiophene), poly[3,4-(ethylene-1,2-dioxy)thiophene] (PEDOT), polypyrrole, and polyaniline; and the like, but are not limited thereto.

As the negative electrode material, materials having a low work function are usually preferred so as to facilitate the injection of electrons into an organic material layer. Specific examples of the negative electrode material include: a metal such as magnesium, calcium, sodium, potassium, titanium, indium, yttrium, lithium, gadolinium, aluminum, silver, tin, and lead, or an alloy thereof; a multi-layer structured material such as LiF/Al or $LiO_2$/Al and Mg/Ag; and the like, but are not limited thereto.

A capping layer for protecting electrodes can be additionally formed on the negative electrode, and as a material for the capping layer, a material used in the art can be appropriately used.

The hole injection layer is a layer which injects holes from an electrode, and a hole injection material is preferably a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. The highest occupied molecular orbital (HOMO) of the hole injection material is preferably a value between the work function of the positive electrode material and the HOMO of the neighboring organic material layer. Specific examples of the hole injection material include metal porphyrin, oligothiophene, arylamine-based organic materials, hexanitrile hexaazatriphenylene-based organic materials, quinacridone-based organic materials, perylene-based organic materials, anthraquinone, polyaniline-based and polythiophene-based conductive polymers, and the like, but are not limited thereto.

The hole transport layer is a layer which accepts holes from a hole injection layer and transports the holes to a light emitting layer, and a hole transport material is suitably a material having high hole mobility which can accept holes from a positive electrode or a hole injection layer and transfer the holes to a light emitting layer. Specific examples thereof include arylamine-based organic materials, conductive polymers, block copolymers having both conjugated portions and non-conjugated portions, and the like, but are not limited thereto.

The electron blocking layer is a layer which can improve the service life and efficiency of the device by preventing holes injected from a hole injection layer from passing through a light emitting layer and entering an electron injection layer, and can be formed at an appropriate portion between the light emitting layer and the electron injection layer using publicly-known materials.

The light emitting material for the light emitting layer is a material that can emit light in a visible light region by receiving and combining holes and electrons from a hole transport layer and an electron transport layer, respectively, and is preferably a material having good quantum efficiency to fluorescence or phosphorescence when the organic light emitting diode of the present specification includes an additional light emitting layer in addition to a light emitting layer including a compound of Formula 3. Specific examples thereof include: an 8-hydroxy-quinoline aluminum complex ($Alq_3$); a carbazole-based compound; a dimerized styryl compound; BAlq; a 10-hydroxybenzoquinoline-metal compound; a benzoxazole, benzothiazole and benzimidazole-based compound; a poly(p-phenylenevinylene) (PPV)-based polymer; a spiro compound; polyfluorene, rubrene, and the like, but are not limited thereto.

The light emitting layer can include a host material and a dopant material. Examples of the host material include fused aromatic ring derivatives, or hetero ring-containing compounds, and the like. Specific examples of the fused aromatic ring derivatives include anthracene derivatives, pyrene derivatives, naphthalene derivatives, pentacene derivatives, phenanthrene compounds, fluoranthene compounds, and the like, and examples of the hetero ring-containing compounds include carbazole derivatives, dibenzofuran derivatives, ladder-type furan compounds, pyrimidine derivatives, and the like, but the examples thereof are not limited thereto.

An electron adjusting layer can be additionally provided between the light emitting layer and the electron transport layer. As a material for the electron adjusting layer, materials used in the art can be appropriately used.

The electron transport layer is a layer which accepts electrons from an electron injection layer and transports the electrons to a light emitting layer, and an electron transport material is suitably a material having high electron mobility which can proficiently accept electrons from a negative electrode and transfer the electrons to a light emitting layer. Specific examples thereof include: an Al complex of 8-hydroxyquinoline; a complex including $Alq_3$; an organic radical compound; a hydroxyflavone-metal complex, and the like, but are not limited thereto. The electron transport layer can be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and an electron injection material is preferably a compound which has a capability of transporting electrons, an effect of injecting electrons from a negative electrode, and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, metal complex compounds, nitrogen-containing 5-membered ring derivatives, and the like, but are not limited thereto.

Examples of the metal complex compounds include 8-hydroxy-quinolinato lithium, bis(8-hydroxyquinolinato) zinc, bis(8-hydroxy-quinolinato) copper, bis(8-hydroxyquinolinato) manganese, tris(8-hydroxyquinolinato) aluminum, tris (2-methyl-8-hydroxy-quinolinato) aluminum, tris(8-hydroxyquinolinato) gallium, bis(10-hydroxybenzo[h]-quinolinato) beryllium, bis(10-hydroxybenzo[h]-quinolinato) zinc, bis(2-methyl-8-quinolinato) chlorogallium, bis(2-methyl-8-quinolinato)(o-cresolato) gallium, bis(2-methyl-8-quinolinato)(1-naphtholato) aluminum, bis(2-methyl-8-quinolinato)-(2-naphtholato) gallium, and the like, but are not limited thereto.

The hole blocking layer is a layer which blocks holes from reaching a negative electrode, and can be generally formed under the same conditions as those of the hole injection layer. Specific examples thereof include an oxadiazole derivative or a triazole derivative, a phenanthroline derivative, BCP, an aluminum complex, and the like, but are not limited thereto.

The organic light emitting diode according to the present specification can be a top emission type, a bottom emission type, or a dual emission type according to the materials to be used.

The structure according to an exemplary embodiment of the present specification can be operated by a principle which is similar to the principle applied to an organic light emitting diode, even in an organic electronic device including an organic solar cell, an organic photoconductor, an organic transistor, and the like.

EXAMPLES

The manufacture of the organic light emitting diode will be specifically described in the following Examples. However, the following Examples are provided for exemplifying the present specification, and the scope of the present specification is not limited thereby.

Synthesis Example 1-1. Synthesis of Compound 1-1

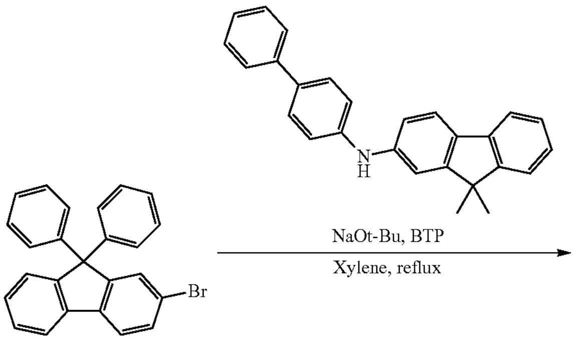

-continued

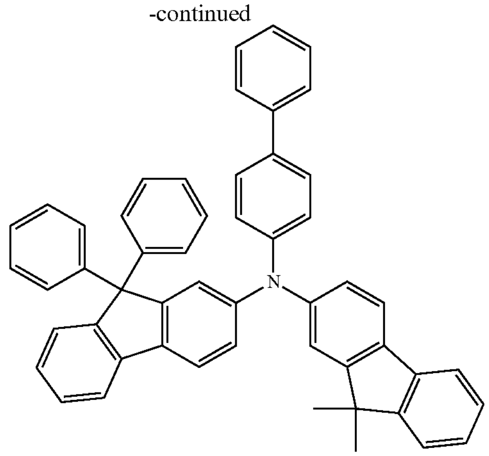

1-1

2-bromo-9,9-diphenyl-9H-fluorene (15 g, 37.7 mmol) and N-([1,1'-diphenyl]-4-yl)-9,9-dimethyl-9H-fluorene-2-amine (13.92 g, 38.5 mmol), and sodium-t-butoxide (5.07 g, 52.7 mol) were mixed with xylene, the resulting mixture was heated and stirred, and then refluxed, and [bis(tri-t-butylphosphine)]palladium (192 mg, 1 mol %) was added thereto. After the temperature was lowered to room temperature and the reaction was terminated, the resulting product was recrystallized by using tetrahydrofuran and ethyl acetate to prepare Compound 1-1 (19.16 g, 75%).

MS[M+H]$^+$=678.89

Synthesis Example 1-2. Synthesis of Compound 1-2

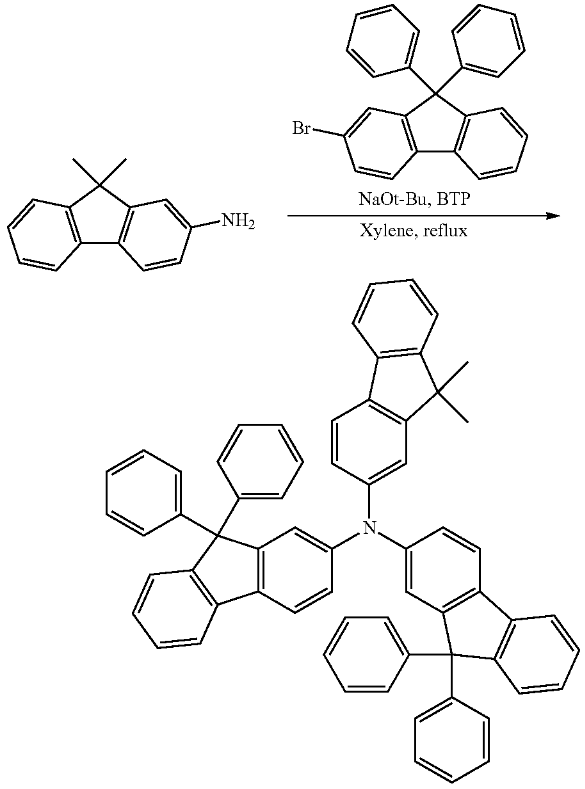

1-2

Compound 1-2 was prepared by performing the synthesis in the same manner as in the synthesis of Compound 1-1, except that 2 equivalents of 2-bromo-9,9-diphenyl-9H-fluorene were used and 9,9-dimethyl-9H-fluoren-2-amine was used instead of N-([1,1'-diphenyl]-4-yl)-9,9-dimethyl-9H-fluoren-2-amine.

MS[M+H]$^+$=843.10

Synthesis Examples 1-3 and 1-4. Preparation of Compounds 1-3 and 1-4

1) Synthesis of Int. 1-1 int. 1-1 was prepared by performing the synthesis in the same manner as in the synthesis of Compound 1-2, except that 1 equivalent of 2-bromo-9,9-diphenyl-9H-fluorene was used.

MS[M+H]$^+$=526.70

2) Synthesis of Compound 1-3

Compound 1-3 was prepared by performing the synthesis in the same manner as in the synthesis of Compound 1-1, except that 1-(4-chlorophenyl)naphthalene was used instead

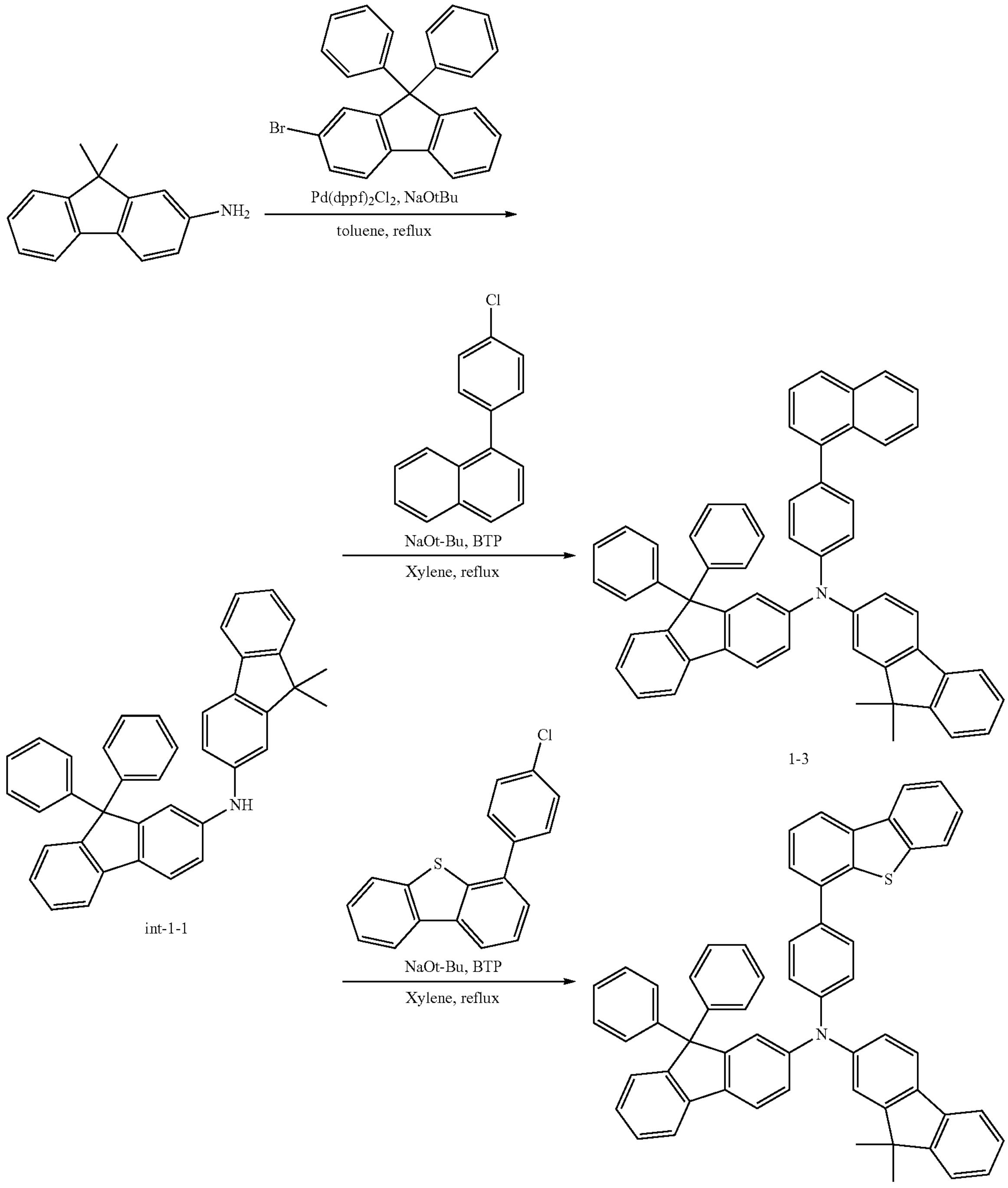

int-1-1

1-3

1-4 of 2-bromo-9,9-diphenyl-9H-fluorene and int. 1-1 was used instead of N-([1,1'-diphenyl]-4-yl)-9,9-dimethyl-9H-fluoren-2-amine.

MS[M+H]$^+$=728.95

3) Synthesis of Compound 1-4

Compound 1-4 was prepared by performing the synthesis in the same manner as in the synthesis of Compound 1-1, except that 4-(4-chlorophenyl)dibenzo[b,d]thiophene was used instead of 2-bromo-9,9-diphenyl-9H-fluorene and int. 1-1 was used instead of N-([1,1'-diphenyl]-4-yl)-9,9-dimethyl-9H-fluoren-2-amine.

MS[M+H]$^+$=785.03

Synthesis Example 1-5. Synthesis of Compound 1-5

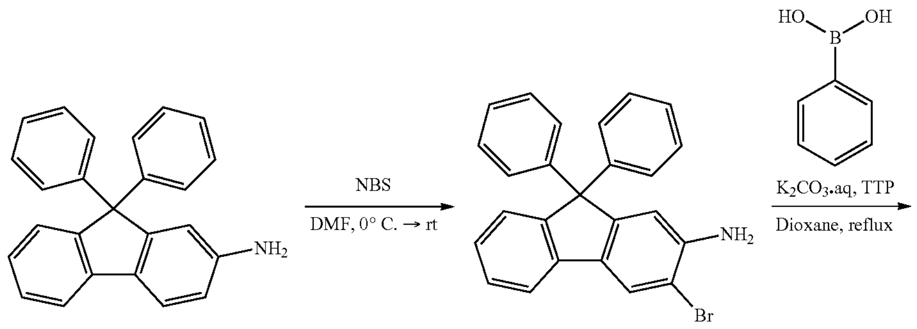

int 2-1

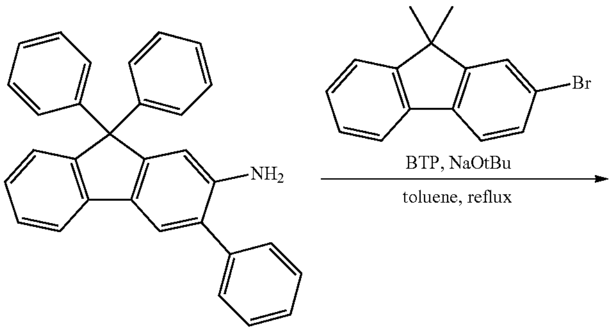

int 2-2

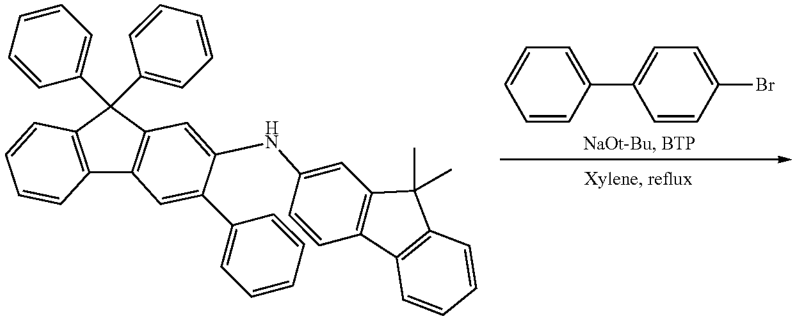

int 2-3

-continued

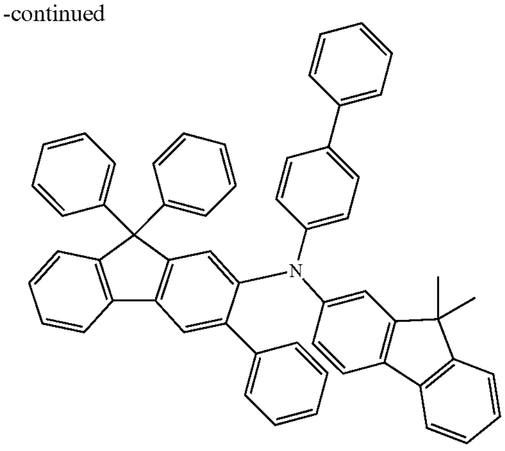

1-5

1) Synthesis of Int. 2-1

After dimethylformamide (DMF, 400 ml) was added to and dissolved in 9,9-diphenyl-9H-fluoren-2-amine (150 g, 449.8 mmol), bromosuccinimide (NBS)(56.25 g, 449.8 mmol) was slowly added dropwise to the solution at 0° C., and the resulting mixture was stirred at room temperature for 3 hours. After extraction was performed with water and chloroform at room temperature, a white solid was recrystallized with hexane to prepare the compound int. 2-1 (167.32 g, yield, 90%).

MS[M+H]$^+$=413.33

2) Synthesis of Int. 2-2

After int. 2-1 (50 g, 120.9 mmol) and phenylboronic acid (15.48 g, 127.0 mmol) were added to dioxane (300 ml), a 2M aqueous potassium carbonate solution (100 ml) was added thereto, tetrakistriphenyl-phosphinopalladium (2.79 g, 2 mol %) was added thereto, and then the resulting mixture was heated and stirred for 10 hours. After the temperature was lowered to normal temperature and the reaction was terminated, the aqueous potassium carbonate solution was removed to separate the layers. After the solvent was removed, a white solid was recrystallized with hexane to prepare int. 2-2 (42.18 g, yield 85%).

MS[M+H]$^+$=410.53

3) Synthesis of Int. 2-3

2-bromo-9,9-dimethyl-9H-fluorene (15 g, 54.9 mmol), int. 2-2 (22.71 g, 55.45 mmol), and sodium-t-butoxide (7.38 g, 76.8 mol) were added to toluene and heated and stirred and then the resulting mixture was refluxed, and [bis(tri-t-butylphosphine)]palladium (140 mg, 0.05 mol %) was added thereto. After the temperature was lowered to normal temperature and the reaction was terminated, the resulting product was recrystallized by using tetrahydrofuran (THF) and ethyl acetate to prepare int. 2-3 (24.8 g, 75%).

MS[M+H]$^+$=602.79

4) Synthesis of Compound 1-5

Compound 1-5 was prepared by performing the synthesis in the same manner as in the synthesis of Compound 1-1, except that 4-bromo-biphenyl was used instead of 2-bromo-9,9-diphenyl-9H-fluorene and int. 2-3 was used instead of N-([1,1'-diphenyl]-4-yl)-9,9-dimethyl-9H-fluoren-2-amine.

MS[M+H]$^+$=754.99

Synthesis Example 1-6. Synthesis of Compound 1-6

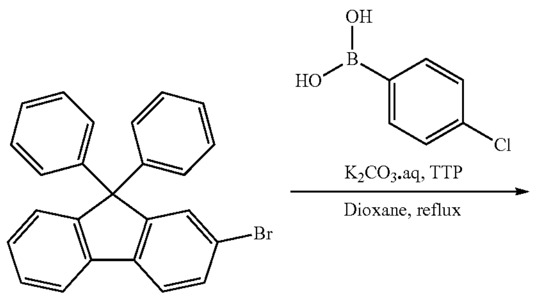

-continued
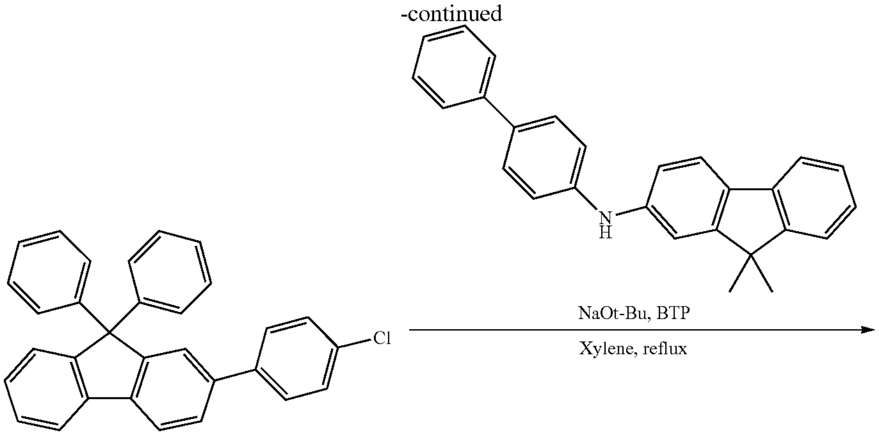
int 3-1
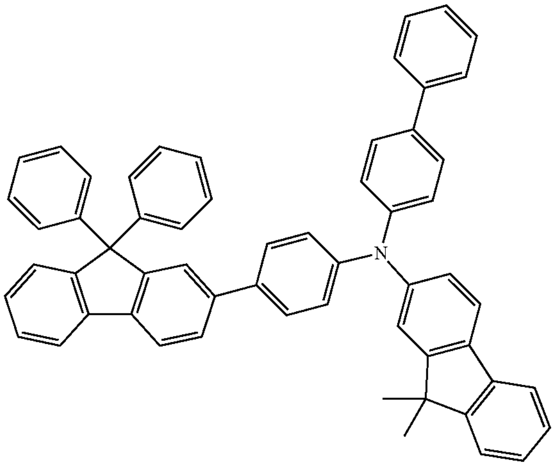
1-6
Compound 1-6 was prepared by performing the synthesis in the same manner as in Synthesis Example 1-5, except that 4-chlorophenyl-boronic acid was used instead of phenylboronic acid in the synthesis of int. 2-2 in 2) of Synthesis Example 1-5.
MS$[M+H]^+$=754.99

Synthesis Example 2-a. Synthesis of Int. 4-1 and 4-2

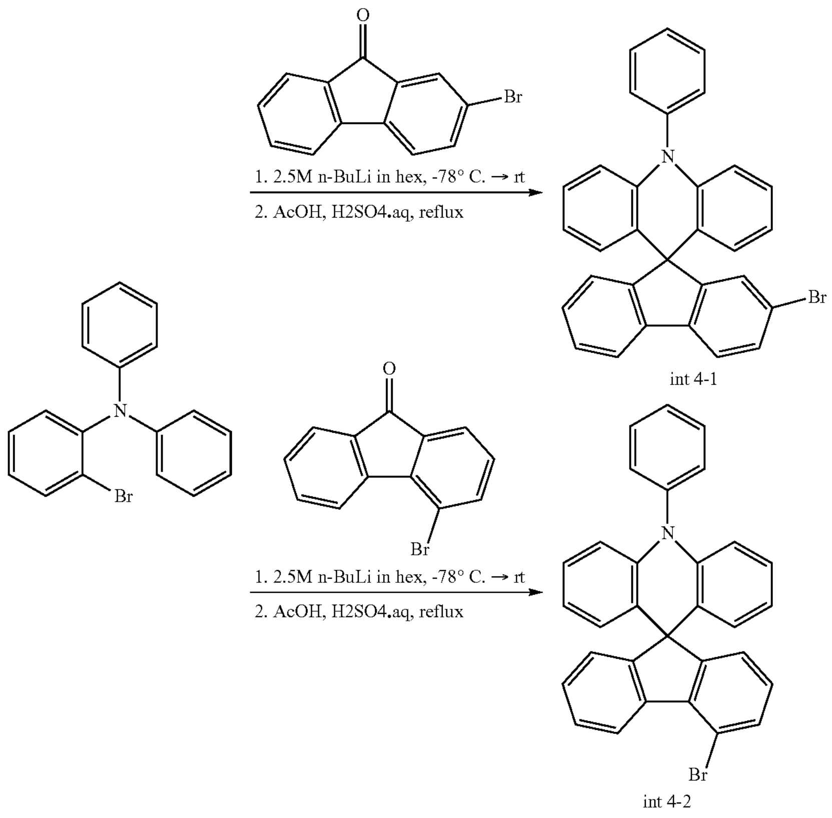

1) Synthesis of Int. 4-1

After 2-bromo-N,N-diphenylaniline (14 g, 43.1 mmol) was dissolved in THF (250 ml), the temperature was lowered to −78° C., and 30 minutes after 2.5 M n-BuLi (24.2 ml) was added dropwise thereto, 2-bromo-9H-fluoren-9-one (11.16 g, 43.1 mmol) was added thereto, the temperature was increased to room temperature, and then the resulting mixture was stirred for 1 hour. After 1 N HCl (300 ml) was added thereto, the resulting mixture was stirred for 30 minutes. The solvent was removed by separating the layers, and then the residue was purified with ethyl acetate. An obtained solid was added to acetic acid (250 ml), and then 1 ml of sulfuric acid was added dropwise thereto, and the resulting mixture was stirred and refluxed. The temperature was lowered to room temperature, the resulting product was neutralized with water, and then the filtered solid was recrystallized with tetrahydrofuran and ethyl acetate to prepare Compound int. 4-1 (18.86 g, 90%).

$MS[M+H]^+=487.41$

2) Synthesis of Int. 4-2 int. 4-2 was prepared by performing the synthesis in the same manner as in the synthesis of int. 4-1, except that 4-bromo-9H-fluoren-9-one was used instead of 2-bromo-9H-fluoren-9-one.

$MS[M+H]^+=487.41$

Synthesis Example 2-1 to 2-6. Synthesis of Compounds 2-1 to 2-6
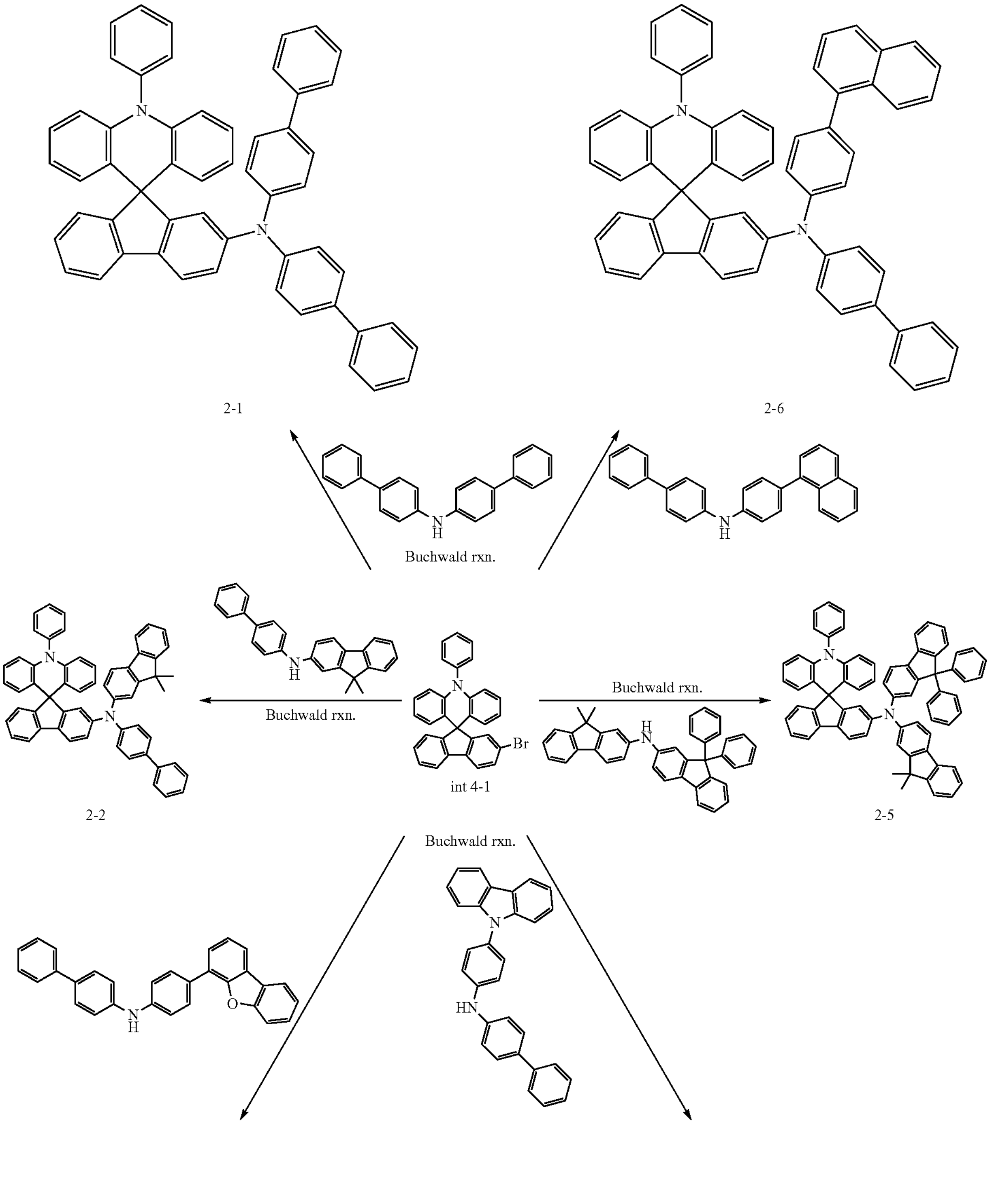
2-1
2-6
2-2
int 4-1
2-5

-continued

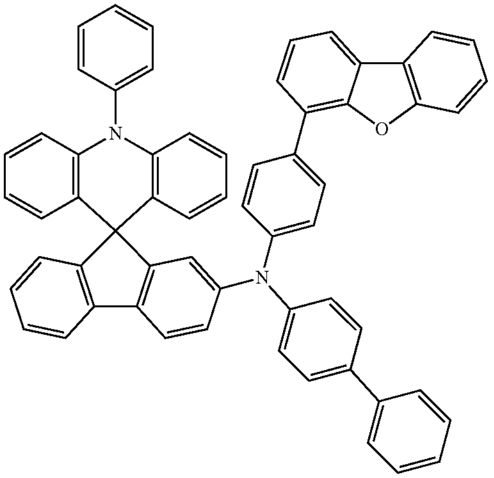

2-3

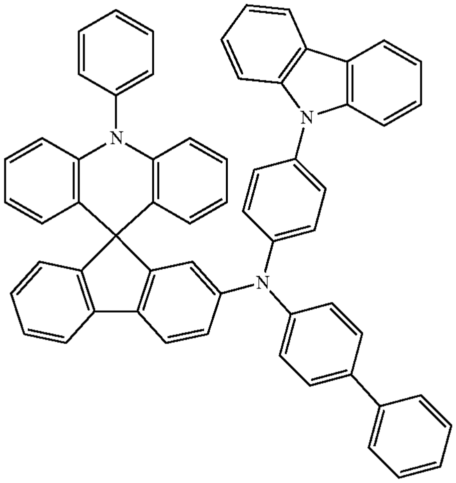

2-4

1) Synthesis of Compound 2-1

Compound 2-1 was prepared by performing the synthesis in the same manner as in the synthesis of Compound 1-1, except that int. 4-1 was used instead of 2-bromo-9,9-diphenyl-9H-fluorene and di([1,1'-biphenyl]-4-yl)amine was used instead of N-([1,1'-diphenyl]-4-yl)-9,9-dimethyl-9H-fluoren-2-amine.

MS[M+H]$^+$=727.92

2) Synthesis of Compound 2-2

Compound 2-2 was prepared by performing the synthesis in the same manner as in the synthesis of Compound 2-1, except that N-([1.1'-diphenyl]-4-yl)-9,9-dimethyl-9H-fluoren-2-amine was used instead of di([1.1'-biphenyl]-4-yl) amine.

MS[M+H]$^+$=767.99

3) Synthesis of Compound 2-3

Compound 2-3 was prepared by performing the synthesis in the same manner as in the synthesis of Compound 2-1, except that N-(4-dibenzo[b,d]furan-4yl)phenyl)-[1,1'-biphenyl]-4-amine was used instead of di([1.1'-biphenyl]-4-yl) amine.

MS[M+H]$^+$=818.00

4) Synthesis of Compound 2-4

Compound 2-4 was prepared by performing the synthesis in the same manner as in the synthesis of Compound 2-1, except that N-(4-9H-carbazol-9-yl)phenyl)-[1,1'-biphenyl]-4-amine was used instead of di([1,1'-biphenyl]-4-yl)amine.

MS[M+H]$^+$=817.02

5) Synthesis of Compound 2-5

Compound 2-5 was prepared by performing the synthesis in the same manner as in the synthesis of Compound 2-1, except that int. 1-1 was used instead of di([1,1'-biphenyl]-4-yl)amine.

MS[M+H]$^+$=932.20

6) Synthesis of Compound 2-6

Compound 2-6 was prepared by performing the synthesis in the same manner as in the synthesis of Compound 2-1, except that N-(4-(naphthalen-1-yl)phenyl-[1,1'-biphenyl]-4-amine was used instead of di([1,1'-biphenyl]-4-yl)amine.

MS[M+H]$^+$=777.98

Synthesis Example 2-7. Synthesis of Compound 2-7

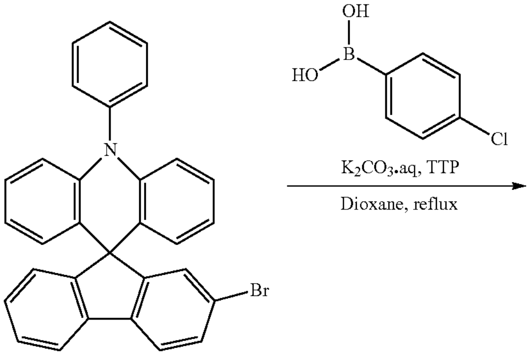

int 4-1

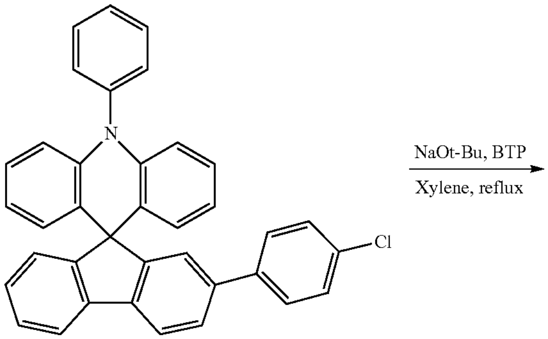

int 5-1

-continued

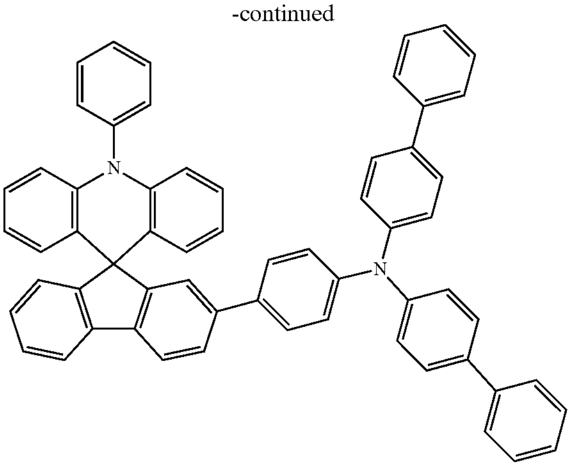

2-7

1) Synthesis of Int. 5-1 int. 5-1 was prepared by performing the synthesis in the same manner as in the synthesis of int. 3-1, except that int. 4-1 was used instead of 2-bromo-9,9-diphenyl-9H-fluorene.

MS[M+H]$^+$=519.06

2) Synthesis of Compound 2-7

Compound 2-7 was prepared by performing the synthesis in the same manner as in the synthesis of Compound 2-1, except that int.

5-1 was used instead of int. 4-1.

MS[M+H]$^+$=804.02

Synthesis Example 2-8. Synthesis of Compound 2-8

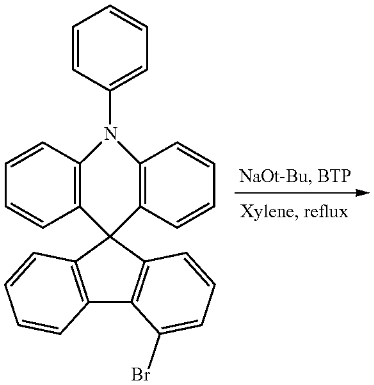

int 4-2

-continued

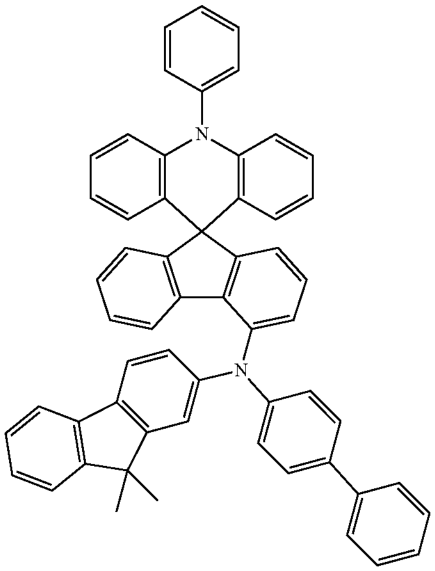

2-8

Compound 2-8 was prepared by performing the synthesis in the same manner as in the synthesis of Compound 2-2, except that int. 4-2 was used instead of int. 4-1.

MS[M+H]$^+$=767.99

Synthesis Example 3-1. Synthesis of Compound 3-1

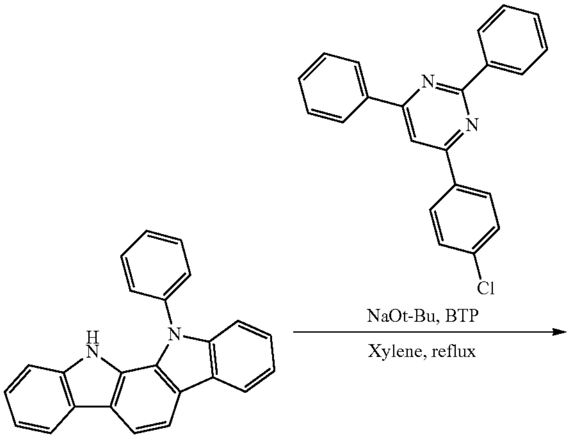

-continued

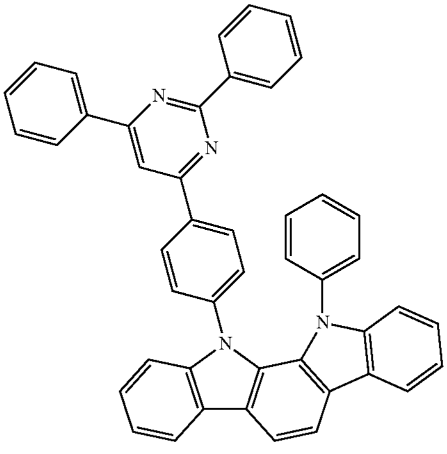

3-1

11-phenyl-11,12-dihydroindolo[2,3-a]carbazole (15 g, 45.1 mmol), 4-(4-chlorophenyl)-2,6-diphenylpyrimidine (15.62 g, 45.57 mmol), and sodium-t-butoxide (6.06 g, 63.1 mol) were mixed with xylene, the resulting mixture was heated and stirred, and then refluxed, and [bis(tri-t-butylphosphine)]palladium (230 mg, 1 mol %) was added thereto. After the temperature was lowered to room temperature and the reaction was terminated, the resulting product was recrystallized by using tetrahydrofuran and ethyl acetate to prepare Compound 3-1 (20.19 g, 70%).

$MS[M+H]^+=639.77$

Synthesis Example 3-2. Synthesis of Compound 3-2

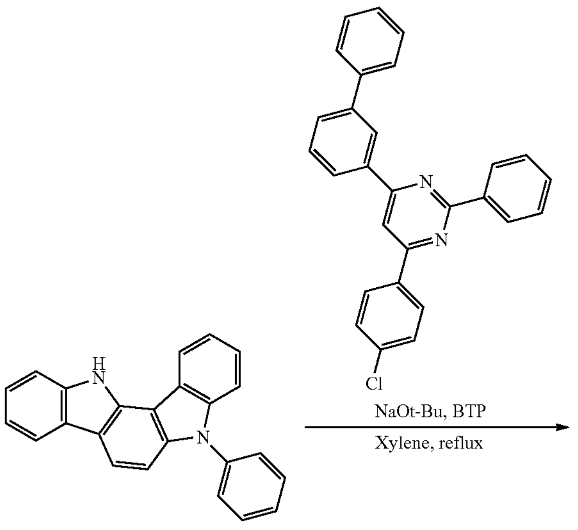

-continued

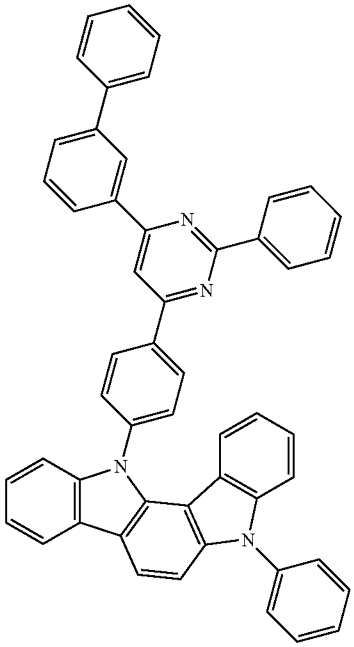

3-3

Compound 3-2 was prepared by performing the synthesis in the same manner as in the synthesis of Compound 3-1, except that 5-phenyl-5,12-dihydroindolo[3,2-a]carbazole was used instead of 11-phenyl-11,12-dihydroindolo[2,3-a]carbazole and 4-([1,1'-biphenyl]-3-yl)-6-(4-chlorophenyl)-2-phenylpyrimidine was used instead of 4-(4-chlorophenyl)-2,6-diphenylpyrimidine.

$MS[M+H]^+=715.87$

Synthesis Example 3-3. Synthesis of Compound 3-3

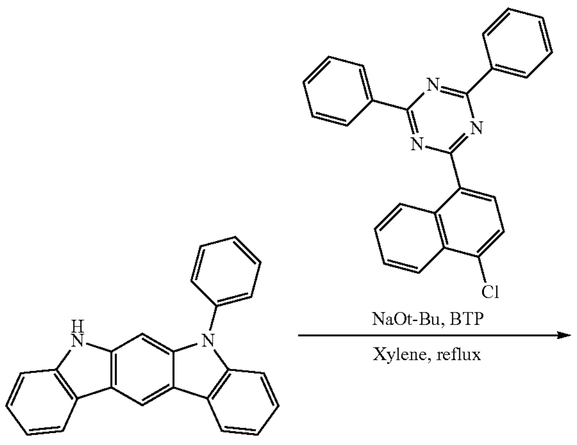

-continued

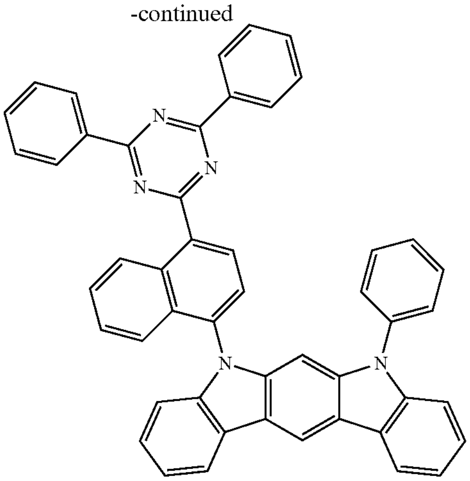

3-3

Compound 3-3 was prepared by performing the synthesis in the same manner as in the synthesis of Compound 3-1, except that 5-phenyl-5,7-dihydroindolo[2,3-b]carbazole was used instead of 11-phenyl-11,12-dihydroindolo[2,3-a]carbazole and 2-(4-chloronaphthalen-1-yl)-4,6-diphenyl-1,3,5-triazine was used instead of 4-(4-chlorophenyl)-2,6-diphenylpyrimidine.

MS[M+H]$^+$=690.82

Synthesis Example 3-4. Synthesis of Compound 3-4

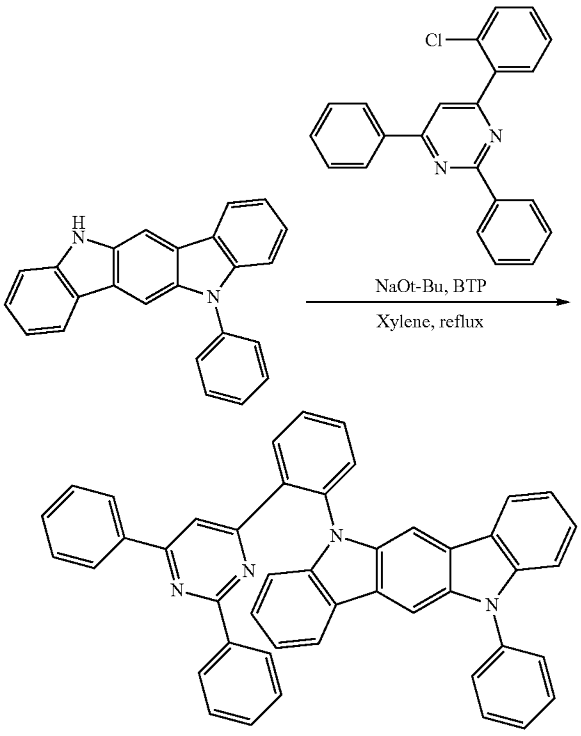

3-4

Compound 3-4 was prepared by performing the synthesis in the same manner as in the synthesis of Compound 3-1, except that 5-phenyl-5,11-dihydroindolo[3,2-b]carbazole was used instead of 11-phenyl-11,12-dihydroindolo[2,3-a]carbazole and 4-(2-chlorophenyl)-2,6-diphenylpyrimidine was used instead of 4-(4-chlorophenyl)-2,6-diphenylpyrimidine.

MS[M+H]$^+$=639.77

Synthesis Example 3-5. Synthesis of Compound 3-5

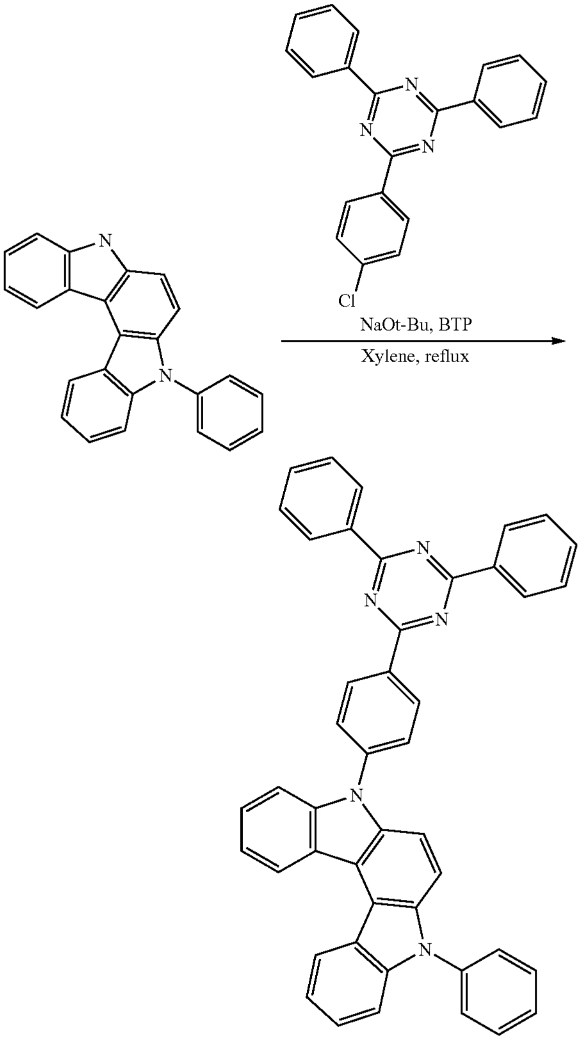

3-5

Compound 3-5 was prepared by performing the synthesis in the same manner as in the synthesis of Compound 3-1, except that 5-phenyl-5,8-dihydroindolo[2,3-c]carbazole was used instead of 11-phenyl-11,12-dihydroindolo[2,3-a]carbazole and 2-(4-chlorophenyl)-4,6-diphenyl-1,3,5-triazine was used instead of 4-(4-chlorophenyl)-2,6-diphenylpyrimidine.

MS[M+H]$^+$=640.76

Synthesis Example 3-6. Synthesis of Compound 3-6

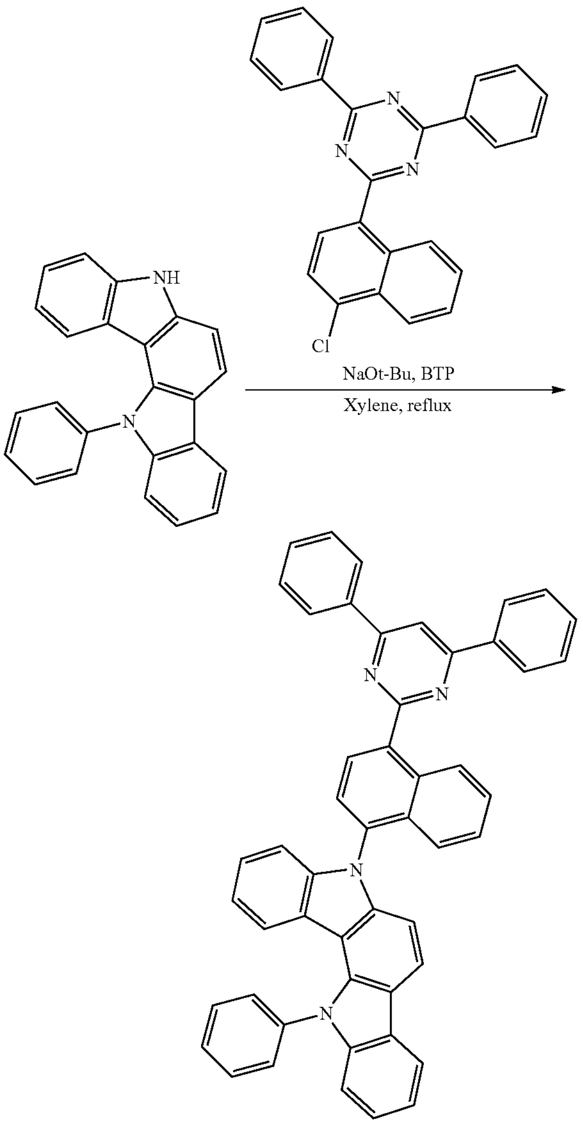

3-6

Compound 3-6 was prepared by performing the synthesis in the same manner as in the synthesis of Compound 3-1, except that 12-phenyl-5,12-dihydroindolo[3,2-c]carbazole was used instead of 11-phenyl-11,12-dihydroindolo[2,3-a] carbazole and 2-(4-chloronaphthalen-1-yl)-4,6-diphenylpyrimidine was used instead of 4-(4-chlorophenyl)-2,6-diphenylpyrimidine.

$MS[M+H]^+=689.83$

Example 1. Manufacture of Organic Light Emitting Diode

A glass substrate (Corning 7059 glass) thinly coated with indium tin oxide (ITO) to have a thickness of 1,000 Å was put into distilled water in which a detergent was dissolved, and ultrasonically washed. A product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents in this order, and drying was then conducted.

Hexanitrile hexaazatriphenylene (HI-1) was thermally vacuum deposited to have a thickness of 500 Å on a transparent ITO electrode, which was thus prepared, thereby forming a hole injection layer. HT-1 (1100 Å), shown below, which is a material for transporting holes, was vacuum deposited thereon, and then Compound 1-1 synthesized in Synthesis Example 1-1 was sequentially vacuum deposited to have a film thickness of 500 Å on the hole transport layer, thereby forming a hole adjusting layer. Compound 3-1 synthesized in Preparation Example 3-1 as a host of a light emitting layer and Dopant RD-1, shown below, were together vacuum deposited at a ratio of 50:1 to have a thickness of 300 Å. Next, after an electron adjusting layer was formed of ET-1 Compound (100 Å), shown below, an electron transport layer was sequentially formed by thermally vacuum depositing ET-2, shown below, and LiQ at a ratio of 1:1. On the electron transport layer, lithium fluoride (LiF) having a thickness of 12 Å and a negative electrode having a thickness of 150 Å were sequentially formed at a ratio of Mg and Ag of 10:1, and a capping layer was formed by HT-5 (600 Å), shown below, thereby manufacturing an organic light emitting diode.

In the aforementioned procedure, the deposition rates of the organic material, lithium fluoride, and Mg and Ag were maintained at 1 Å/sec, 0.2 Å/sec, and 3 to 7 Å/sec, respectively.

HI-1

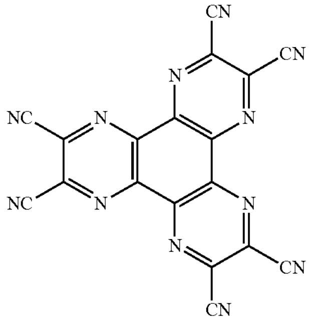

HT-1

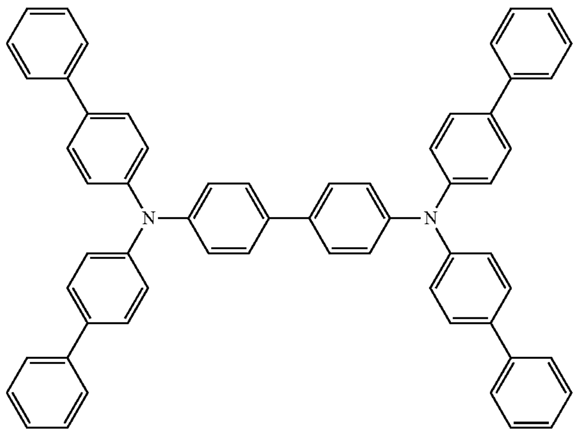

-continued
HT-2
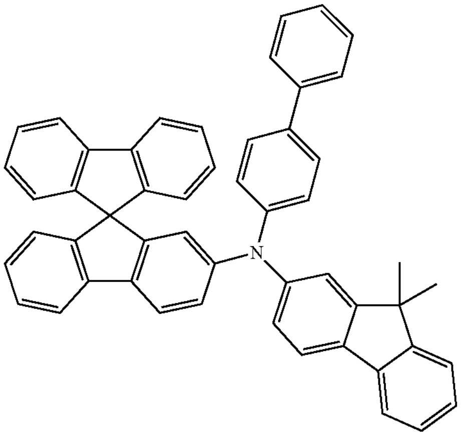
HT-3
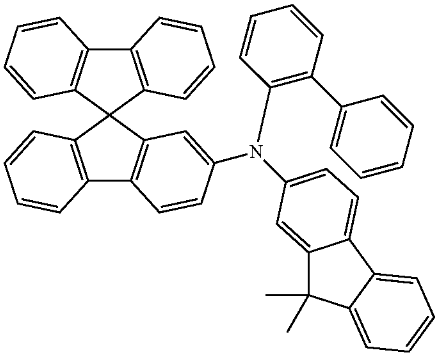
HT-4
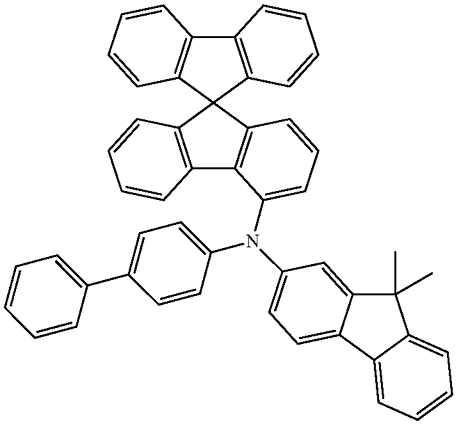
-continued
HT-5
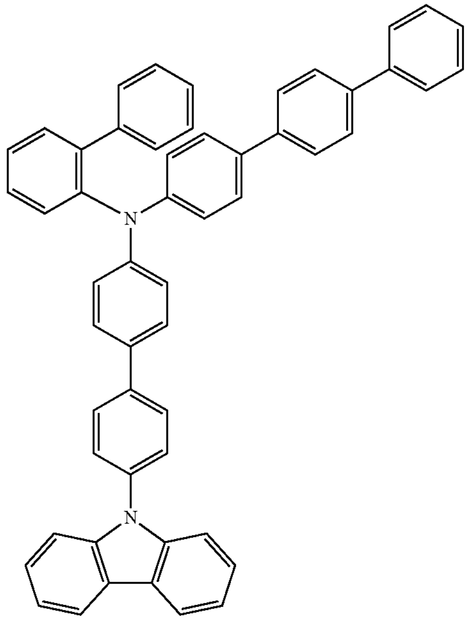
RH-1
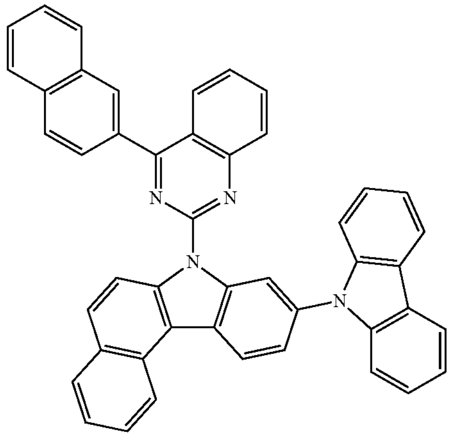
RH-2
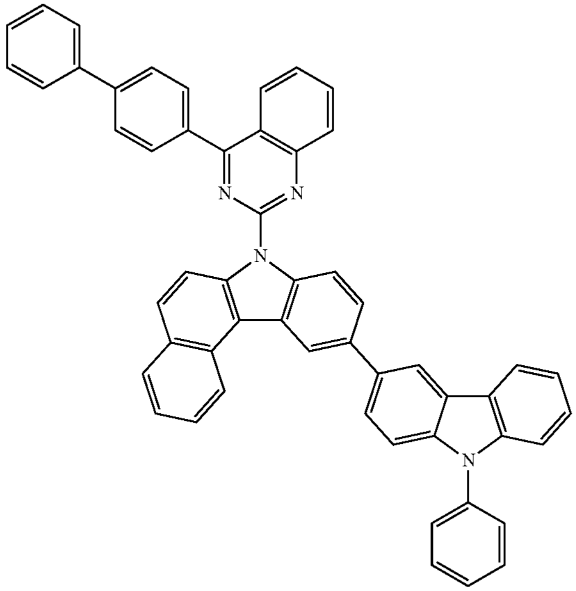

-continued

RD-1

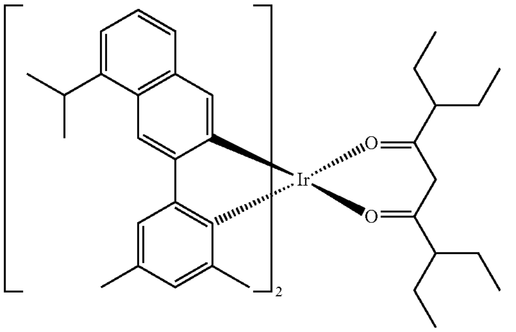

ET-1

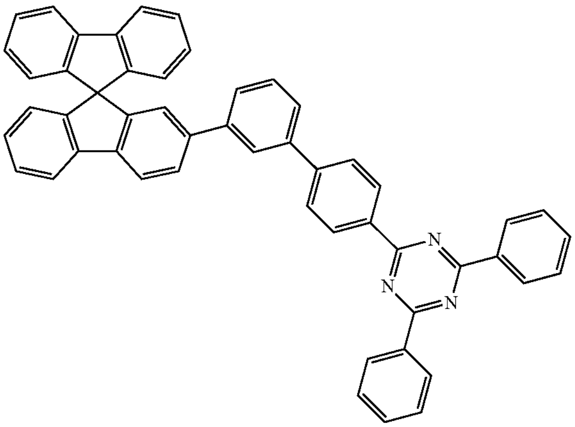

-continued

ET-2

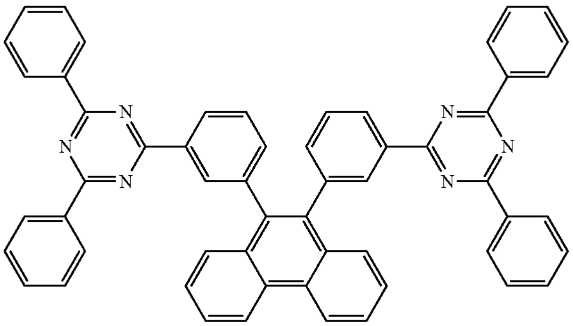

Examples 2 to 70 and Comparative Examples 1 to 13. Manufacture of Organic Light Emitting Diode Organic light emitting diodes were manufactured in the same manner as in Example 1, except that the compounds shown in the following Table 1 were used.

Device Evaluation

The driving voltage, efficiency, service life, and light emitting color were measured by applying electric current to the organic light emitting diodes manufactured in Examples 1 to 70 and Comparative Examples 1 to 13, and the results are shown in the following Table 1. The service life in the following Table 1 indicates time taken until the initial light current value becomes 95%.

TABLE 1

| No | hole adjusting layer | Host:Dopant (thickness, Å)Dopant Content | Voltage (V) (@20mA/cm$^2$) | Cd/A (%) (@20mA/cm$^2$) | Color Coordinate (x, y) | Service life (T95, h) (@20mA/cm$^2$) |
|---|---|---|---|---|---|---|
| Example 1 | Compound 1-1 | Compound3-1:RD-1 (350:2%) | 4.34 | 43.6 | (0.688, 0.312) | 689 |
| Example 2 | Compound 1-1 | Compound3-2:RD-1 (350:2%) | 4.12 | 39.1 | (0.688, 0.313) | 702 |
| Example 3 | Compound 1-1 | Compound3-4:RD-1 (350:2%) | 4.22 | 37.9 | (0.688, 0.312) | 699 |
| Example 4 | Compound 1-1 | Compound3-5:RD-1 (350:2%) | 4.26 | 42.0 | (0.689, 0.313) | 649 |
| Example 5 | Compound 1-1 | Compound3-6:RD-1 (350:2%) | 4.31 | 40.3 | (0.687, 0.312) | 705 |
| Example 6 | Compound 1-2 | Compound3-3:RD-1 (350:2%) | 4.34 | 43.1 | (0.687, 0.312) | 652 |
| Example 7 | Compound 1-2 | Compound3-4:RD-1 (350:2%) | 4.12 | 38.1 | (0.689, 0.313) | 678 |
| Example 8 | Compound 1-2 | Compound3-5:RD-1 (350:2%) | 4.22 | 42.5 | (0.667, 0.311) | 699 |
| Example 9 | Compound 1-2 | Compound3-6:RD-1 (350:2%) | 4.28 | 41.4 | (0.687, 0.312) | 703 |
| Example 10 | Compound 1-2 | Compound3-1:RD-1 (350:2%) | 4.31 | 37.5 | (0.689, 0.313) | 698 |
| Example 11 | Compound 1-3 | Compound3-1:RD-1 (350:2%) | 4.18 | 42.2 | (0.687, 0.312) | 682 |
| Example 12 | Compound 1-3 | Compound3-3:RD-1 (350:2%) | 4.25 | 45.1 | (0.687, 0.312) | 677 |
| Example 13 | Compound 1-3 | Compound3-4:RD-1 (350:2%) | 4.22 | 36.4 | (0.689, 0.313) | 676 |
| Example 14 | Compound 1-3 | Compound3-6:RD-1 (350:2%) | 4.28 | 39.1 | (0.688, 0.312) | 679 |
| Example 15 | Compound 1-3 | Compound3-1:RD-1 (350:2%) | 4.31 | 42.0 | (0.687, 0.311) | 678 |
| Example 16 | Compound 1-4 | Compound3-2:RD-1 (350:2%) | 4.42 | 36.8 | (0.687, 0.312) | 649 |

TABLE 1-continued

| No | hole adjusting layer | Host:Dopant (thickness, Å)Dopant Content | Voltage (V) (@20mA/ cm$^2$) | Cd/A (%) (@20mA/ cm$^2$) | Color Coordinate (x, y) | Service life (T95, h) (@20mA/cm$^2$) |
|---|---|---|---|---|---|---|
| Example 17 | Compound 1-4 | Compound3-3:RD-1 (350:2%) | 4.30 | 41.5 | (0.689, 0.313) | 701 |
| Example 18 | Compound 1-4 | Compound3-4:RD-1 (350:2%) | 4.37 | 41.7 | (0.687, 0.312) | 711 |
| Example 19 | Compound 1-4 | Compound3-5:RD-1 (350:2%) | 4.67 | 37.9 | (0.687, 0.312) | 679 |
| Example 20 | Compound 1-4 | Compound3-6:RD-1 (350:2%) | 4.65 | 42.6 | (0.689, 0.313) | 666 |
| Example 21 | Compound 1-5 | Compound3-2:RD-1 (350:2%) | 4.12 | 43.8 | (0.687, 0.312) | 685 |
| Example 22 | Compound 1-5 | Compound3-5:RD-1 (350:2%) | 4.23 | 44.5 | (0.687, 0.312) | 688 |
| Example 23 | Compound 1-5 | Compound3-4:RD-1 (350:2%) | 4.53 | 42.7 | (0.687, 0.312) | 645 |
| Example 24 | Compound 1-5 | Compound3-3:RD-1 (350:2%) | 4.34 | 43.4 | (0.689, 0.313) | 654 |
| Example 25 | Compound 1-5 | Compound3-1:RD-1 (350:2%) | 4.12 | 45.8 | (0.688, 0.312) | 662 |
| Example 26 | Compound 1-6 | Compound3-6:RD-1 (350:2%) | 4.22 | 29.1 | (0.687, 0.311) | 638 |
| Example 27 | Compound 1-6 | Compound3-3:RD-1 (350:2%) | 4.23 | 41.2 | (0.687, 0.312) | 699 |
| Example 28 | Compound 1-6 | Compound3-4:RD-1 (350:2%) | 4.31 | 42.8 | (0.688, 0.313) | 708 |
| Example 29 | Compound 1-6 | Compound3-1:RD-1 (350:2%) | 4.13 | 42.5 | (0.688, 0.312) | 702 |
| Example 30 | Compound 1-6 | Compound3-2:RD-1 (350:2%) | 4.25 | 41.8 | (0.689, 0.313) | 700 |
| Example 31 | Compound 2-1 | Compound3-2:RD-1 (350:2%) | 4.23 | 45.9 | (0.687, 0.312) | 712 |
| Example 32 | Compound 2-1 | Compound3-1:RD-1 (350:2%) | 4.28 | 44.7 | (0.687, 0.312) | 698 |
| Example 33 | Compound 2-1 | Compound3-4:RD-1 (350:2%) | 4.31 | 46.2 | (0.689, 0.313) | 698 |
| Example 34 | Compound 2-1 | Compound3-3:RD-1 (350:2%) | 4.32 | 43.5 | (0.687, 0.211) | 682 |
| Example 35 | Compound 2-1 | Compound3-5:RD-1 (350:2%) | 4.21 | 44.7 | (0.689, 0.313) | 677 |
| Example 36 | Compound 2-2 | Compound3-6:RD-1 (350:2%) | 4.18 | 48.5 | (0.689, 0.312) | 676 |
| Example 37 | Compound 2-2 | Compound3-4:RD-1 (350:2%) | 4.11 | 44.2 | (0.689, 0.313) | 702 |
| Example 38 | Compound 2-2 | Compound3-5:RD-1 (350:2%) | 4.21 | 41.2 | (0.687, 0.312) | 698 |
| Example 39 | Compound 2-2 | Compound3-1:RD-1 (350:2%) | 4.28 | 43.6 | (0.687, 0.312) | 666 |
| Example 40 | Compound 2-2 | Compound3-2:RD-1 (350:2%) | 4.30 | 44.7 | (0.689, 0.312) | 687 |
| Example 41 | Compound 2-3 | Compound3-5:RD-1 (350:2%) | 4.37 | 41.5 | (0.688, 0.312) | 659 |
| Example 42 | Compound 2-3 | Compound3-1:RD-1 (350:2%) | 4.38 | 46.5 | (0.687, 0.311) | 698 |
| Example 43 | Compound 2-3 | Compound3-4:RD-1 (350:2%) | 4.22 | 29.1 | (0.687, 0.312) | 702 |
| Example 44 | Compound 2-3 | Compound3-3:RD-1 (350:2%) | 4.28 | 41.2 | (0.689, 0.313) | 698 |
| Example 45 | Compound 2-3 | Compound3-1:RD-1 (350:2%) | 4.31 | 42.8 | (0.687, 0.311) | 666 |
| Example 46 | Compound 2-4 | Compound3-2:RD-1 (350:2%) | 4.18 | 42.5 | (0.689, 0.313) | 687 |
| Example 47 | Compound 2-4 | Compound3-5:RD-1 (350:2%) | 4.25 | 41.8 | (0.688, 0.312) | 662 |
| Example 48 | Compound 2-4 | Compound3-1:RD-1 (350:2%) | 4.23 | 45.9 | (0.669, 0.312) | 638 |
| Example 49 | Compound 2-4 | Compound3-4:RD-1 (350:2%) | 4.23 | 45.9 | (0.667, 0.312) | 699 |
| Example 50 | Compound 2-4 | Compound2-3:RD-1 (350:2%) | 4.27 | 38.1 | (0.667, 0.312) | 708 |
| Example 51 | Compound 2-5 | Compound3-4:RD-1 (350:2%) | 4.48 | 42.5 | (0.680, 0.313) | 702 |
| Example 52 | Compound 2-5 | Compound3-1:RD-1 (350:2%) | 4.40 | 41.4 | (0.687, 0.311) | 676 |

TABLE 1-continued

| No | hole adjusting layer | Host:Dopant (thickness, Å)Dopant Content | Voltage (V) (@20mA/cm$^2$) | Cd/A (%) (@20mA/cm$^2$) | Color Coordinate (x, y) | Service life (T95, h) (@20mA/cm$^2$) |
|---|---|---|---|---|---|---|
| Example 53 | Compound 2-5 | Compound3-6:RD-1 (350:2%) | 4.47 | 37.5 | (0.687, 0.312) | 679 |
| Example 54 | Compound 2-5 | Compound3-2:RD-1 (350:2%) | 4.67 | 42.2 | (0.687, 0.312) | 678 |
| Example 55 | Compound 2-5 | Compound3-5:RD-1 (350:2%) | 4.51 | 45.1 | (0.680, 0.313) | 699 |
| Example 56 | Compound 2-6 | Compound3-3:RD-1 (350:2%) | 4.42 | 36.4 | (0.688, 0.312) | 649 |
| Example 57 | Compound 2-6 | Compound3-2:RD-1 (350:2%) | 4.30 | 44.7 | (0.687, 0.311) | 705 |
| Example 58 | Compound 2-6 | Compound3-1:RD-1 (350:2%) | 4.37 | 41.5 | (0.687, 0.312) | 652 |
| Example 59 | Compound 2-6 | Compound3-5:RD-1 (350:2%) | 4.67 | 37.9 | (0.688, 0.313) | 678 |
| Example 60 | Compound 2-6 | Compound3-6:RD-1 (350:2%) | 4.65 | 42.0 | (0.689, 0.313) | 699 |
| Example 61 | Compound 2-7 | Compound3-4:RD-1 (350:2%) | 4.51 | 40.3 | (0.688, 0.312) | 703 |
| Example 62 | Compound 2-7 | Compound3-6:RD-1 (350:2%) | 4.54 | 43.1 | (0.689, 0.313) | 702 |
| Example 63 | Compound 2-7 | Compound3-1:RD-1 (350:2%) | 4.44 | 42.5 | (0.687, 0.312) | 698 |
| Example 64 | Compound 2-7 | Compound3-2:RD-1 (350:2%) | 4.23 | 42.0 | (0.689, 0.313) | 702 |
| Example 65 | Compound 2-7 | Compound3-3:RD-1 (350:2%) | 4.51 | 45.1 | (0.688, 0.312) | 676 |
| Example 66 | Compound 2-8 | Compound3-1:RD-1 (350:2%) | 4.42 | 36.4 | (0.687, 0.311) | 679 |
| Example 67 | Compound 2-8 | Compound3-2:RD-1 (350:2%) | 4.30 | 44.7 | (0.687, 0.312) | 678 |
| Example 68 | Compound 2-8 | Compound3-4:RD-1 (350:2%) | 4.28 | 43.2 | (0.688, 0.313) | 699 |
| Example 69 | Compound 2-8 | Compound3-5:RD-1 (350:2%) | 4.31 | 45.1 | (0.689, 0.313) | 649 |
| Example 70 | Compound 2-8 | Compound3-6:RD-1 (350:2%) | 4.18 | 36.4 | (0.688, 0.312) | 678 |
| Comparative Example 1 | HT-2 | RH-1:RD-1 (350:2%) | 4.79 | 30.2 | (0.687, 0.312) | 528 |
| Comparative Example 2 | HT-2 | RH-2:RD-1 (350:2%) | 4.88 | 31.1 | (0.688, 0.313) | 533 |
| Comparative Example 3 | HT-3 | RH-1:RD-1 (350:2%) | 4.69 | 35.2 | (0.688, 0.312) | 514 |
| Comparative Example 4 | HT-3 | RH-2:RD-1 (350:2%) | 4.87 | 33.3 | (0.689, 0.313) | 600 |
| Comparative Example 5 | HT-4 | RH-1:RD-1 (350:2%) | 4.71 | 29.8 | (0.687, 0.312) | 612 |
| Comparative Example 6 | HT-4 | RH-2:RD-1 (350:2%) | 4.73 | 31.5 | (0.687, 0.312) | 589 |
| Comparative Example 7 | HT-2 | RH-2:RD-1 (350:2%) | 4.81 | 30.8 | (0.689, 0.313) | 577 |
| Comparative Example 8 | HT-3 | RH-1:RD-1 (350:2%) | 4.92 | 34.2 | (0.687, 0.312) | 578 |
| Comparative Example 9 | HT-4 | RH-2:RD-1 (350:2%) | 4.81 | 32.8 | (0.689, 0.312) | 598 |
| Comparative Example 10 | HT-2 | Compound3-6:RD-1 (350:2%) | 4.94 | 31.5 | (0.688, 0.312) | 588 |
| Comparative Example 11 | HT-4 | Compound3-2:RD-1 (350:2%) | 4.87 | 23.1 | (0.687, 0.311) | 578 |
| Comparative Example 12 | Compound1-4 | RH-1:RD-1 (350:2%) | 4.88 | 32.1 | (0.687, 0.312) | 568 |
| Comparative Example 13 | Compound 2-5 | RH-2:RD-1 (350:2%) | 4.98 | 33.3 | (0.688, 0.313) | 542 |

In Table 1, the organic light emitting diodes in Examples 1 to 70 and Comparative Examples 1 to 13 are organic light emitting diodes including a single-layered hole adjusting layer, and the organic light emitting diodes in Examples 1 to 70 are organic light emitting diodes in which a compound of Formula 1 or 2 of the present invention is used as a material for a hole adjusting layer and a compound of Formula 3 of the present invention is used as a host material of the light emitting layer.

Further, Comparative Examples 1 to 9 are organic light emitting diodes in which a hole adjusting material in the related art and a host material of a light emitting layer in the related art are used, Comparative Examples 10 and 11 are organic light emitting diodes in which a hole adjusting material in the related art is used and a compound of Formula 3 of the present invention is used as a host material of the light emitting layer, and Comparative Examples 12 and 13 are organic light emitting diodes in which a compound of Formula 1 or 2 of the present invention is used as a material for a hole adjusting layer and a host material for a light emitting layer in the related art is used.

Since the organic light emitting diodes in Examples 1 to 70 include at least one of the compounds of Formulae 1 and/or 2 of the present invention, which are excellent in ability to adjust holes and include, as a host of a light emitting layer, a compound of Formula 3 of the present invention in which the conjugation of N unshared electron pairs with indolocarbazole and a monocyclic hetero ring is appropriately maintained, the organic light emitting diodes in Examples 1 to 70 have low driving voltage, excellent efficiency, long service life, and stability of the device as compared to the organic light emitting diodes in Comparative Examples 1 to 13.

Example 71. Manufacture of Organic Light Emitting Diode

A glass substrate (Corning 7059 glass) thinly coated with indium tin oxide (ITO) to have a thickness of 1,000 Å was put into distilled water in which a detergent was dissolved, and ultrasonically washed. A product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents in this order, and drying was then conducted.

Hexanitrile hexaazatriphenylene (HI-1) was thermally vacuum deposited to have a thickness of 500 Å on a transparent ITO electrode, which was thus prepared, thereby forming a hole injection layer. HT-1 (1100 Å), which is a material for transporting holes, was vacuum deposited thereon, and then Compound 1-1 synthesized in Synthesis Example 1-1 was sequentially vacuum deposited to have a thickness of 500 Å on the hole transport layer, thereby forming a first hole adjusting layer, and the following HT-4 was vacuum deposited to have a thickness of 200 Å to form a second hole adjusting layer. Compound 3-1 synthesized in Synthesis Example 3-1 as a host of a light emitting layer and Dopant RD-1 were together vacuum deposited at a ratio of 50:1 to have a thickness of 300 Å. Next, after an electron adjusting layer was formed of ET-1 Compound (100 Å), an electron transport layer was sequentially formed by thermally vacuum depositing ET-2 and LiQ at a ratio of 1:1. On the electron transport layer, lithium fluoride (LiF) having a thickness of 12 Å and a negative electrode having a thickness of 150 Å were sequentially formed at a ratio of Mg and Ag of 10:1, and a capping layer was formed by HT-5 (600 Å), thereby manufacturing an organic light emitting diode.

In the aforementioned procedure, the deposition rates of the organic material, lithium fluoride, and Mg and Ag were maintained at 1 Å/sec, 0.2 Å/sec, and 3 to 7 Å/sec, respectively.

HI-1

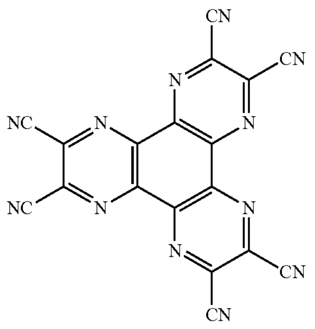

HT-1

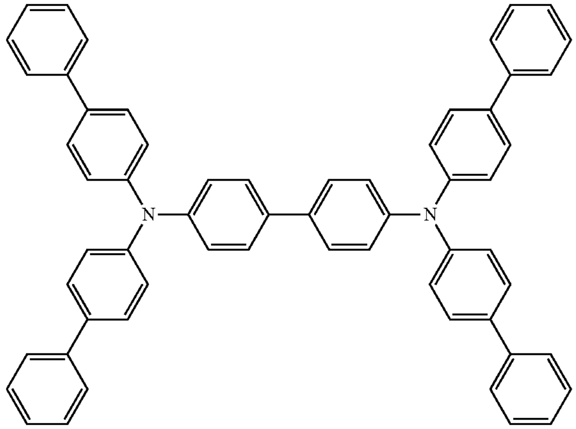

HT-2

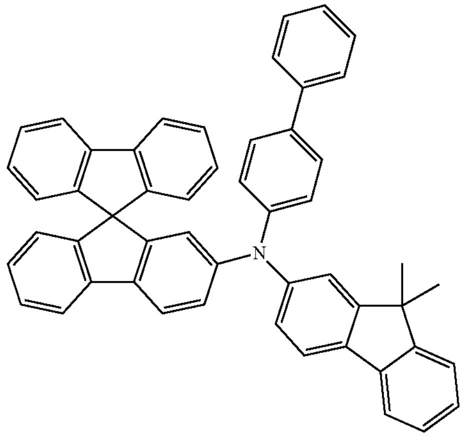

HT-3

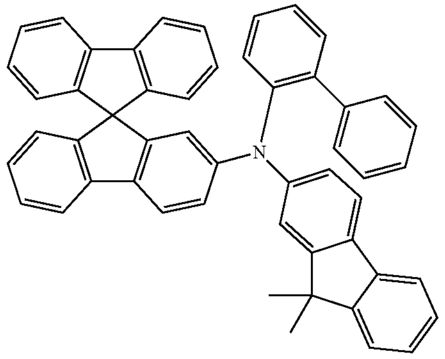

-continued
HT-4
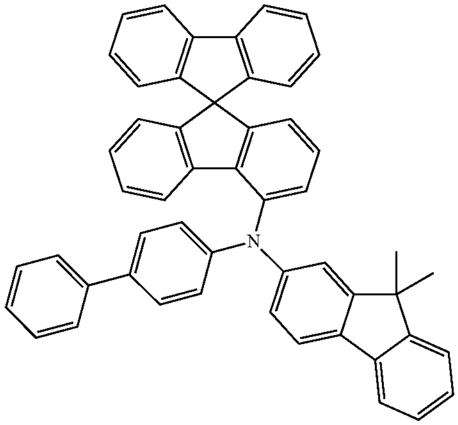
HT-5
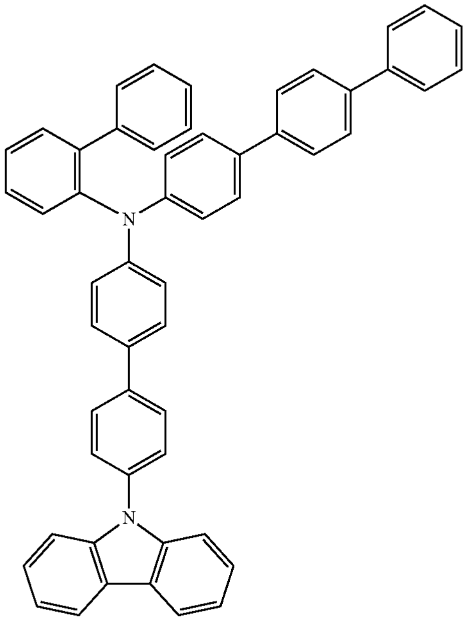
RH-1
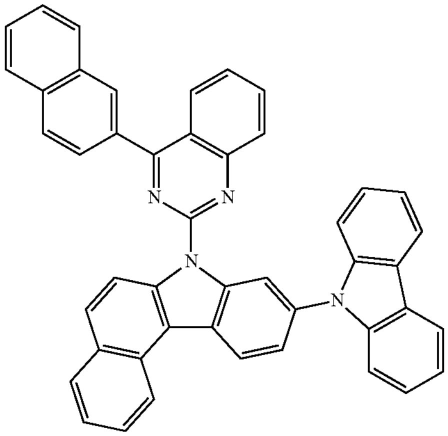
-continued
RH-2
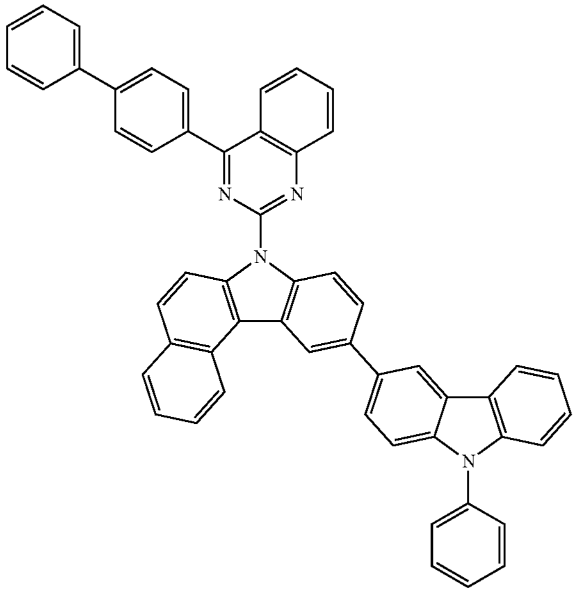
RD-1
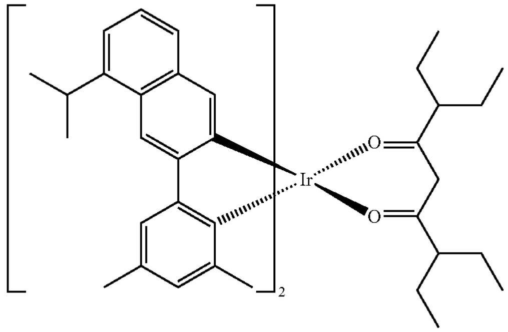
ET-1
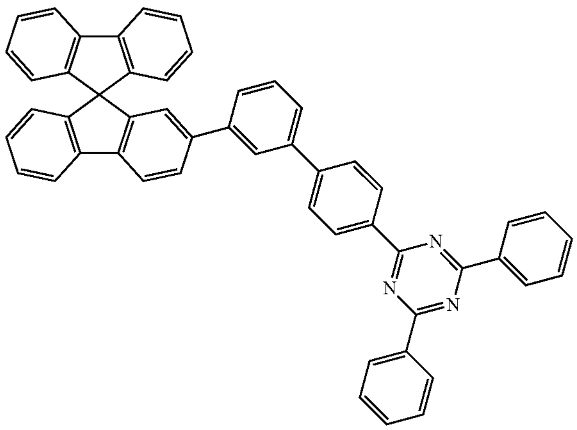

-continued

ET-2

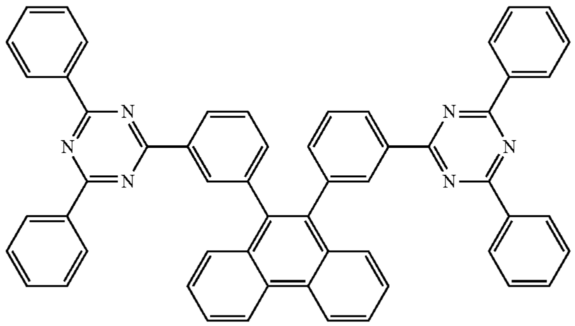

Examples 72 to 140 and Comparative Examples 14 to 26

Manufacture of Organic Light Emitting Diode

Organic light emitting diodes were manufactured in the same manner as in Example 71, except that the compounds shown in the following Table 2 were used.

Device Evaluation

The driving voltage, efficiency, service life, and light emitting color were measured by applying electric current to the organic light emitting diodes manufactured in Examples 71 to 140 and Comparative Examples 14 to 26, and the results are shown in the following Table 2. The service life in the following Table 2 indicates time taken until the initial light current value becomes 95%.

TABLE 2

| No | First hole adjusting layer | Second hole adjusting layer | Host:Dopant (thickness, Å)Dopant Content | Voltage (V) (@20mA/ $cm^2$) | Cd/A (%) (@20mA/ $cm^2$) | Color Coordinance (x, y) | Service life (T95, h) (@20mA/$cm^2$) |
|---|---|---|---|---|---|---|---|
| Example 71 | Compound 1-1 | HT-4 | Compound3-1:RD-1 (350:2%) | 4.57 | 45.8 | (0.689, 0.313) | 800 |
| Example 72 | Compound 1-1 | HT-4 | Compound3-2:RD-1 (350:2%) | 4.64 | 43.8 | (0.688, 0.312) | 850 |
| Example 73 | Compound 1-1 | HT-4 | Compound3-4:RD-1 (350:2%) | 4.67 | 43.5 | (0.689, 0.312) | 912 |
| Example 74 | Compound 1-1 | HT-4 | Compound3-5:RD-1 (350:2%) | 4.65 | 45.8 | (0.687, 0.312) | 870 |
| Example 75 | Compound 1-1 | HT-4 | Compound3-6:RD-1 (350:2%) | 4.51 | 46.3 | (0.687, 0.312) | 888 |
| Example 76 | Compound 1-2 | HT-4 | Compound2-3:RD-1 (350:2%) | 4.54 | 44.8 | (0.689, 0.313) | 867 |
| Example 77 | Compound 1-2 | HT-4 | Compound3-4:RD-1 (350:2%) | 4.27 | 45.8 | (0.687, 0.311) | 867 |
| Example 78 | Compound 1-2 | HT-4 | Compound3-5:RD-1 (350:2%) | 4.48 | 44.9 | (0.689, 0.313) | 883 |
| Example 79 | Compound 1-2 | HT-4 | Compound3-6:RD-1 (350:2%) | 4.40 | 47.5 | (0.688, 0.312) | 873 |
| Example 80 | Compound 1-2 | HT-4 | Compound3-1:RD-1 (350:2%) | 4.47 | 48.5 | (0.687, 0.311) | 864 |
| Example 81 | Compound 1-3 | HT-4 | Compound3-1:RD-1 (350:2%) | 4.67 | 47.2 | (0.687, 0.312) | 822 |
| Example 82 | Compound 1-3 | HT-4 | Compound3-3:RD-1 (350:2%) | 4.51 | 46.9 | (0.687, 0.312) | 900 |
| Example 83 | Compound 1-3 | HT-4 | Compound3-4:RD-1 (350:2%) | 4.42 | 48.5 | (0.689, 0.313) | 912 |
| Example 84 | Compound 1-3 | HT-4 | Compound3-6:RD-1 (350:2%) | 4.25 | 47.7 | (0.687, 0.312) | 878 |
| Example 85 | Compound 1-3 | HT-4 | Compound3-1:RD-1 (350:2%) | 4.25 | 48.2 | (0.689, 0.313) | 856 |
| Example 86 | Compound 1-4 | HT-4 | Compound3-2:RD-1 (350:2%) | 4.42 | 48.3 | (0.688, 0.212) | 896 |
| Example 87 | Compound 1-4 | HT-4 | Compound3-3:RD-1 (350:2%) | 4.46 | 49.2 | (0.687, 0.311) | 864 |
| Example 88 | Compound 1-4 | HT-4 | Compound3-4:RD-1 (350:2%) | 4.29 | 45.3 | (0.687, 0.312) | 874 |
| Example 89 | Compound 1-4 | HT-4 | Compound3-5:RD-1 (350:2%) | 4.69 | 44.7 | (0.689, 0.313) | 897 |
| Example 90 | Compound 1-4 | HT-4 | Compound3-6:RD-1 (350:2%) | 4.57 | 48.2 | (0.687, 0.312) | 833 |
| Example 91 | Compound 1-5 | HT-4 | Compound3-2:RD-1 (350:2%) | 4.30 | 47.3 | (0.689, 0.313) | 900 |
| Example 92 | Compound 1-5 | HT-4 | Compound3-5:RD-1 (350:2%) | 4.48 | 49.8 | (0.687, 0.311) | 812 |
| Example 93 | Compound 1-5 | HT-4 | Compound3-4:RD-1 (350:2%) | 4.52 | 49.2 | (0.687, 0.312) | 833 |
| Example 94 | Compound 1-5 | HT-4 | Compound3-3:RD-1 (350:2%) | 4.38 | 50.0 | (0.687, 0.312) | 834 |
| Example 95 | Compound 1-5 | HT-4 | Compound3-1:RD-1 (350:2%) | 4.44 | 47.5 | (0.689, 0.313) | 823 |
| Example 96 | Compound 1-6 | HT-4 | Compound3-6:RD-1 (350:2%) | 4.52 | 48.2 | (0.687, 0.312) | 813 |

TABLE 2-continued

| No | First hole adjusting layer | Second hole adjusting layer | Host:Dopant (thickness, Å)Dopant Content | Voltage (V) (@20mA/ $cm^2$) | Cd/A (%) (@20mA/ $cm^2$) | Color Coordinance (x, y) | Service life (T95, h) (@20mA/$cm^2$) |
|---|---|---|---|---|---|---|---|
| Example 97 | Compound 1-6 | HT-4 | Compound3-3:RD-1 (350:2%) | 4.22 | 47.2 | (0.689, 0.313) | 864 |
| Example 98 | Compound 1-6 | HT-4 | Compound3-4:RD-1 (350:2%) | 4.38 | 49.2 | (0.688, 0.313) | 822 |
| Example 99 | Compound 1-6 | HT-4 | Compound3-1:RD-1 (350:2%) | 4.33 | 48.3 | (0.688, 0.312) | 900 |
| Example 100 | Compound 1-6 | HT-4 | Compound3-2:RD-1 (350:2%) | 4.31 | 49.2 | (0.689, 0.213) | 912 |
| Example 101 | Compound 2-1 | HT-4 | Compound3-2:RD-1 (350:2%) | 4.23 | 45.5 | (0.687, 0.312) | 878 |
| Example 102 | Compound 2-1 | HT-4 | Compound3-1:RD-1 (350:2%) | 4.38 | 47.7 | (0.687, 0.312) | 912 |
| Example 103 | Compound 2-1 | HT-4 | Compound3-4:RD-1 (350:2%) | 4.51 | 48.2 | (0.689, 0.313) | 870 |
| Example 104 | Compound 2-1 | HT-4 | Compound3-3:RD-1 (350:2%) | 4.27 | 48.3 | (0.687, 0.311) | 888 |
| Example 105 | Compound 2-1 | HT-4 | Compound3-5:RD-1 (350:2%) | 4.32 | 49.2 | (0.689, 0.313) | 878 |
| Example 106 | Compound 2-2 | HT-4 | Compound3-6:RD-1 (350:2%) | 4.33 | 45.3 | (0.688, 0.312) | 874 |
| Example 107 | Compound 2-2 | HT-4 | Compound3-4:RD-1 (350:2%) | 4.51 | 45.8 | (0.687, 0.311) | 863 |
| Example 108 | Compound 2-2 | HT-4 | Compound3-5:RD-1 (350:2%) | 4.28 | 46.3 | (0.687, 0.312) | 846 |
| Example 109 | Compound 2-2 | HT-4 | Compound3-1:RD-1 (350:2%) | 4.57 | 44.8 | (0.687, 0.312) | 812 |
| Example 110 | Compound 2-2 | HT-4 | Compound3-2:RD-1 (350:2%) | 4.48 | 45.8 | (0.689, 0.313) | 901 |
| Example 111 | Compound 2-3 | HT-4 | Compound3-5:RD-1 (350:2%) | 4.44 | 44.9 | (0.687, 0.311) | 833 |
| Example 112 | Compound 2-3 | HT-4 | Compound3-1:RD-1 (350:2%) | 4.49 | 47.5 | (0.687, 0.312) | 877 |
| Example 113 | Compound 2-3 | HT-4 | Compound3-4:RD-1 (350:2%) | 4.67 | 48.5 | (0.687, 0.311) | 900 |
| Example 114 | Compound 2-3 | HT-4 | Compound3-3:RD-1 (350:2%) | 4.66 | 49.5 | (0.687, 0.312) | 912 |
| Example 115 | Compound 2-3 | HT-4 | Compound3-1:RD-1 (350:2%) | 4.51 | 50.2 | (0.689, 0.313) | 878 |
| Example 116 | Compound 2-4 | HT-4 | Compound3-2:RD-1 (350:2%) | 4.54 | 46.8 | (0.687, 0.312) | 856 |
| Example 117 | Compound 2-4 | HT-4 | Compound3-5:RD-1 (350:2%) | 4.27 | 49.2 | (0.689, 0.313) | 896 |
| Example 118 | Compound 2-4 | HT-4 | Compound3-1:RD-1 (350:2%) | 4.52 | 46.3 | (0.688, 0.313) | 823 |
| Example 119 | Compound 2-4 | HT-4 | Compound3-4:RD-1 (350:2%) | 4.22 | 44.8 | (0.687, 0.312) | 813 |
| Example 120 | Compound 2-4 | HT-4 | Compound3-3:RD-1 (350:2%) | 4.38 | 45.8 | (0.689, 0.313) | 864 |
| Example 121 | Compound 2-5 | HT-4 | Compound3-4:RD-1 (350:2%) | 4.33 | 44.9 | (0.687, 0.312) | 822 |
| Example 122 | Compound 2-5 | HT-4 | Compound3-1:RD-1 (350:2%) | 4.31 | 47.5 | (0.689, 0.313) | 900 |
| Example 123 | Compound 2-5 | HT-4 | Compound3-6:RD-1 (350:2%) | 4.23 | 48.5 | (0.688, 0.213) | 896 |
| Example 124 | Compound 2-5 | HT-4 | Compound3-2:RD-1 (350:2%) | 4.32 | 49.2 | (0.688, 0.312) | 864 |
| Example 125 | Compound 2-5 | HT-4 | Compound3-5:RD-1 (350:2%) | 4.33 | 45.3 | (0.689, 0.213) | 874 |
| Example 126 | Compound 2-6 | HT-4 | Compound3-3:RD-1 (350:2%) | 4.51 | 45.8 | (0.687, 0.312) | 897 |
| Example 127 | Compound 2-6 | HT-4 | Compound3-2:RD-1 (350:2%) | 4.51 | 48.2 | (0.687, 0.312) | 833 |
| Example 128 | Compound 2-6 | HT-4 | Compound3-1:RD-1 (350:2%) | 4.54 | 47.3 | (0.689, 0.313) | 912 |
| Example 129 | Compound 2-6 | HT-4 | Compound3-5:RD-1 (350:2%) | 4.27 | 49.2 | (0.687, 0.311) | 870 |
| Example 130 | Compound 2-6 | HT-4 | Compound3-6:RD-1 (350:2%) | 4.48 | 48.2 | (0.689, 0.313) | 888 |
| Example 131 | Compound 2-7 | HT-4 | Compound3-4:RD-1 (350:2%) | 4.52 | 49.3 | (0.688, 0.312) | 878 |
| Example 132 | Compound 2-7 | HT-4 | Compound3-6:RD-1 (350:2%) | 4.38 | 50.5 | (0.687, 0.311) | 874 |

TABLE 2-continued

| No | First hole adjusting layer | Second hole adjusting layer | Host:Dopant (thickness, Å)Dopant Content | Voltage (V) (@20mA/ $cm^2$) | Cd/A (%) (@20mA/ $cm^2$) | Color Coordinance (x, y) | Service life (T95, h) (@20mA/$cm^2$) |
|---|---|---|---|---|---|---|---|
| Example 133 | Compound 2-7 | HT-4 | Compound3-1:RD-1 (350:2%) | 4.44 | 49.2 | (0.687, 0.312) | 863 |
| Example 134 | Compound 2-7 | HT-4 | Compound3-2:RD-1 (350:2%) | 4.67 | 46.8 | (0.689, 0.313) | 878 |
| Example 135 | Compound 2-7 | HT-4 | Compound3-3:RD-1 (350:2%) | 4.51 | 49.5 | (0.687, 0.312) | 912 |
| Example 136 | Compound 2-8 | HT-4 | Compound3-1:RD-1 (350:2%) | 4.42 | 48.8 | (0.687, 0.312) | 870 |
| Example 137 | Compound 2-8 | HT-4 | Compound3-2:RD-1 (350:2%) | 4.25 | 47.7 | (0.689, 0.313) | 888 |
| Example 138 | Compound 2-8 | HT-4 | Compound3-4:RD-1 (350:2%) | 4.25 | 46.8 | (0.687, 0.311) | 864 |
| Example 139 | Compound 2-8 | HT-4 | Compound3-5:RD-1 (350:2%) | 4.42 | 47.8 | (0.687, 0.312) | 822 |
| Example 140 | Compound 2-8 | HT-4 | Compound3-6:RD-1 (350:2%) | 4.57 | 48.2 | (0.689, 0.313) | 900 |
| Comparative Example 14 | HT-2 | HT-4 | RH-1:RD-1 (350:2%) | 5.01 | 38.8 | (0.687, 0.312) | 680 |
| Comparative Example 15 | HT-2 | HT-4 | RH-2:RD-1 (350:2%) | 4.98 | 40.0 | (0.689, 0.313) | 666 |
| Comparative Example 16 | HT-3 | HT-4 | RH-1:RD-1 (350:2%) | 4.78 | 39.5 | (0.688, 0.313) | 648 |
| Comparative Example 17 | HT-3 | HT-4 | RH-2:RD-1 (350:2%) | 4.87 | 34.8 | (0.688, 0.312) | 712 |
| Comparative Example 18 | HT-4 | HT-5 | RH-1:RD-1 (350:2%) | 4.81 | 35.5 | (0.689, 0.312) | 650 |
| Comparative Example 19 | HT-4 | HT-5 | RH-2:RD-1 (350:2%) | 4.72 | 34.4 | (0.688, 0.312) | 651 |
| Comparative Example 20 | HT-2 | HT-4 | RH-2:RD-1 (350:2%) | 4.83 | 37.5 | (0.687, 0.311) | 645 |
| Comparative Example 21 | HT-3 | HT-4 | RH-1:RD-1 (350:2%) | 4.87 | 40.1 | (0.687, 0.312) | 689 |
| Comparative Example 22 | HT-4 | HT-4 | RH-2:RD-1 (350:2%) | 4.77 | 38.2 | (0.688, 0.313) | 700 |
| Comparative Example 23 | HT-3 | HT-4 | Compound 3-5:RD-1 (350:2%) | 4.78 | 34.7 | (0.689, 0.312) | 530 |
| Comparative Example 24 | HT-2 | HT-4 | Compound 3-1:RD-1 (350:2%) | 4.98 | 35.4 | (0.687, 0.311) | 608 |
| Comparative Example 25 | Compound 1-1 | HT-4 | RH-1:RD-1 (350:2%) | 4.88 | 31.5 | (0.687, 0.312) | 688 |
| Comparative Example 26 | Compound 2-8 | HT-4 | RH-2:RD-1 (350:2%) | 4.77 | 39.2 | (0.689, 0.312) | 649 |

In Table 2, the organic light emitting diodes in Examples 71 to 140 and Comparative Examples 14 to 26 are organic light emitting diodes including a hole adjusting layer having two layers (double layer), and the organic light emitting diodes in Examples 71 to 140 are organic light emitting diodes in which a compound of Formula 1 or 2 of the present invention is used as a material for a first hole adjusting layer in first and second hole adjusting layers and a compound of Formula 3 of the present invention is used as a host material of the light emitting layer.

Further, Comparative Examples 14 to 22 are organic light emitting diodes in which the hole adjusting material in the related art and the host material of the light emitting layer in the related art are used in the first and second hole adjusting layers, Comparative Examples 23 and 24 are organic light emitting diodes in which the hole adjusting material in the related art is used and a compound of Formula 3 of the present invention is used as the host material of the light emitting layer in the first and second hole adjusting layers, and Comparative Examples 25 and 26 are organic light emitting diodes in which a compound of Formula 1 or 2 of the present invention is used as the material for the first hole adjusting layer in the first and second hole adjusting layers, and the host material of the light emitting layer in the related art is used.

Since the organic light emitting diodes in Examples 71 to 140 include at least one of the compounds of Formulae 1 and/or 2 of the present invention, which are excellent in ability to adjust holes in a layer of a double-layered hole adjusting layer and include, as a host of a light emitting layer, a compound of Formula 3 of the present invention in which the conjugation of N unshared electron pairs with indolocarbazole and a monocyclic hetero ring is appropriately maintained, the organic light emitting diodes in Examples 71 to 140 have low driving voltage, excellent efficiency, long service life, and stability of the device as compared to the organic light emitting diodes in Comparative Examples 14 to 26.

The invention claimed is:

1. An organic light emitting diode comprising:

a positive electrode;

a negative electrode disposed to face the positive electrode;

a light emitting layer provided between the positive electrode and the negative electrode;

a hole adjusting layer having one or more layers provided between the positive electrode and the light emitting layer; and a hole transport layer, wherein the organic light emitting diode comprises on the negative electrode a capping layer comprising the following compound:

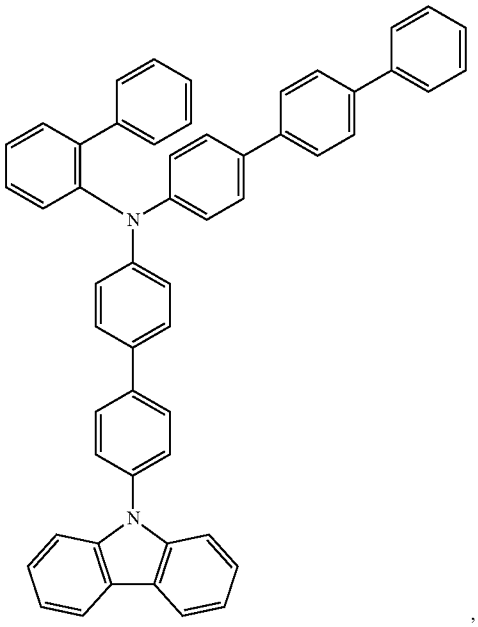

, and wherein the hole adjusting layer is positioned between the light emitting layer and the hole transport layer, and wherein one or more layers in the hole adjusting layer comprise at least one compound of Formula 1-1 to 1-3:

[Formula 1-1]

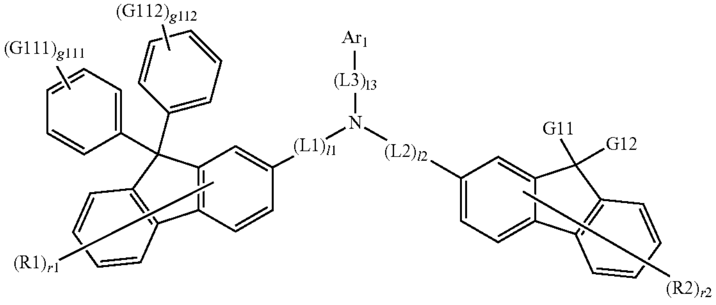

[Formula 1-2]

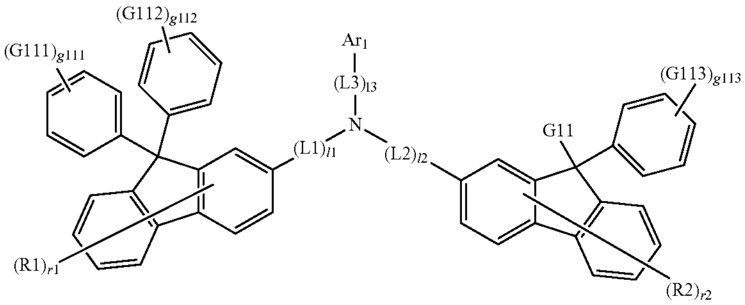

-continued

[Formula 1-3]

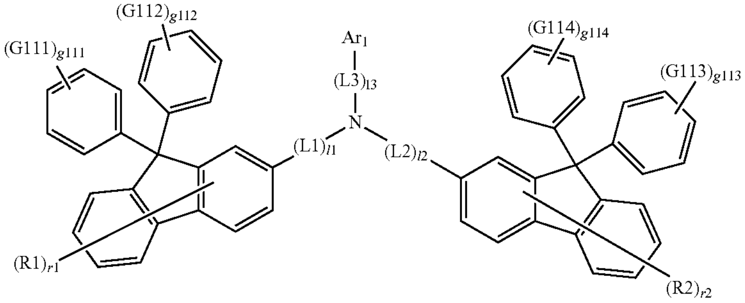

wherein in Formula 1-1 to 1-3:

L1 is a direct bond or a phenylene, and 11 is 1;

L2 is a direct bond, a phenylene, or biphenylene, and 12 is 1;

L3 is a direct bond or a phenylene, and 13 is 1;

Ar1 is a phenyl group that is unsubstituted or substituted with a phenyl group, a biphenyl group, or a terphenyl group; a biphenyl group that is unsubstituted or substituted with a phenyl group or a biphenyl group; a terphenyl group that is unsubstituted or substituted with a phenyl group; a quaterphenyl group; a naphthyl group; a fluorenyl group that is unsubstituted or substituted with one or more selected from the group consisting of a methyl group, a phenyl group, and a naphthyl group; a carbazolyl group; a dibenzofuran group; and a dibenzothiophene group;

R1 is hydrogen, deuterium, a methyl group, a t-butyl group, or a phenyl group, and r1 is 1;

R2 is hydrogen, deuterium, phenyl, biphenyl, or naphthyl, and r2 is 1;

G11 and G12 are the same as or different from each other, and are each independently an unsubstituted alkyl group;

G111 and G112 are the same as or different from each other, and are each independently hydrogen, a methyl group, or a t-butyl group;

G113 and G114 are hydrogen, and g113 and g114 are each 5;

g111 and g112 are each an integer from 1 to 5; and when g111 and g112 are each 2 or more, two or more structures in the parentheses are the same as or different from each other; and the light emitting layer comprises a host selected from among the following compounds:

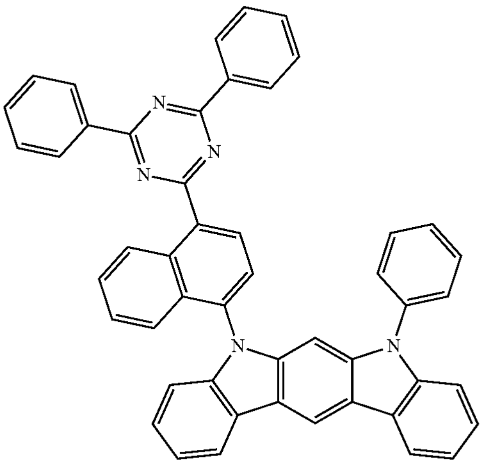

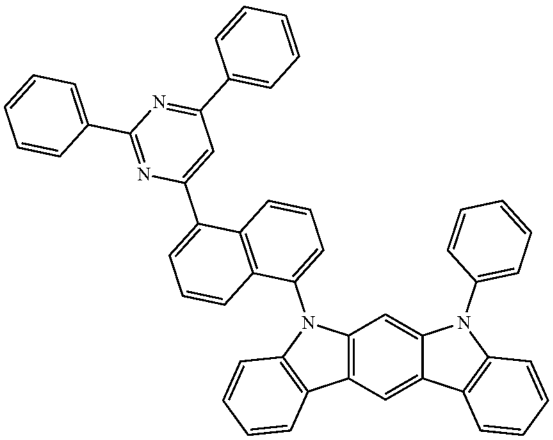

-continued
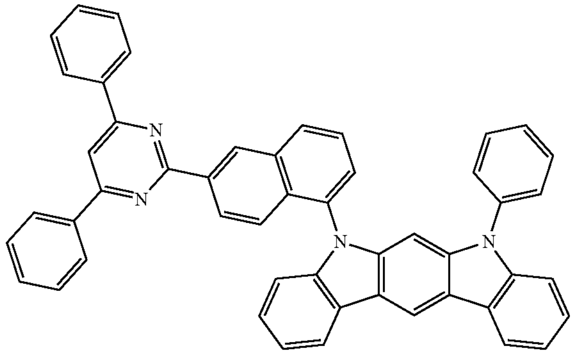
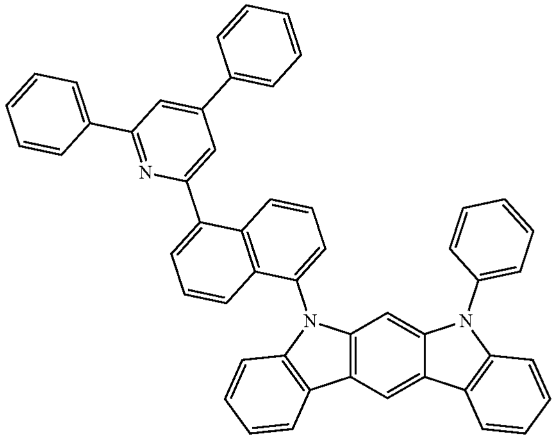
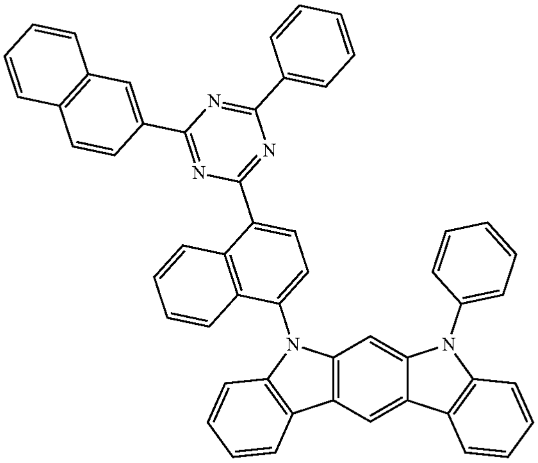
-continued
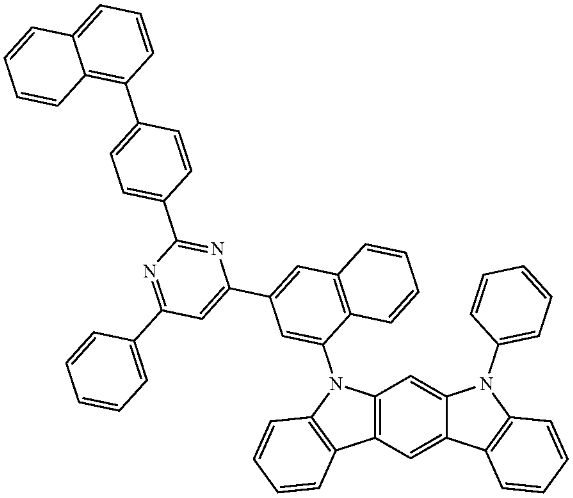
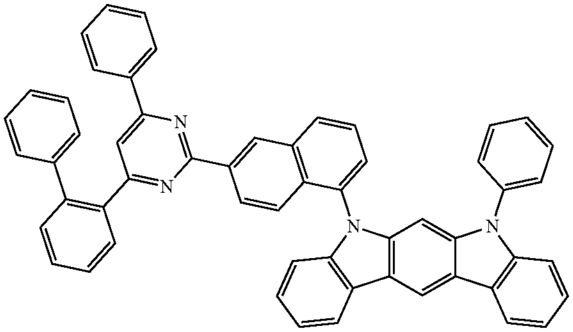
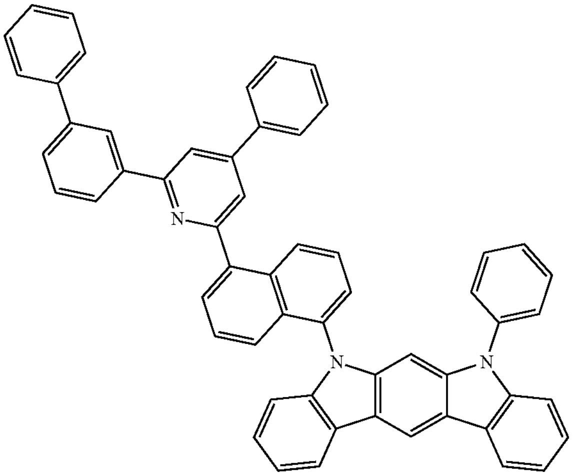

-continued
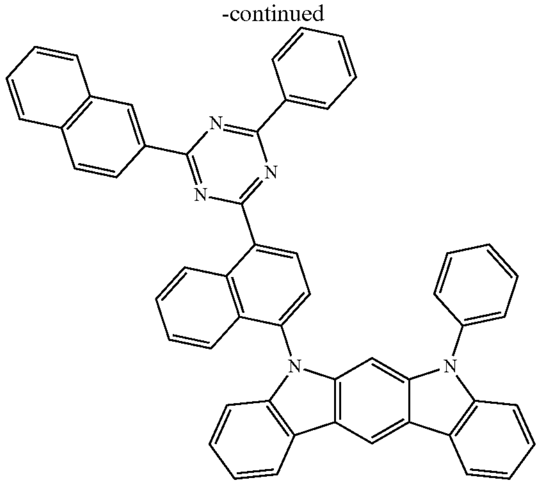
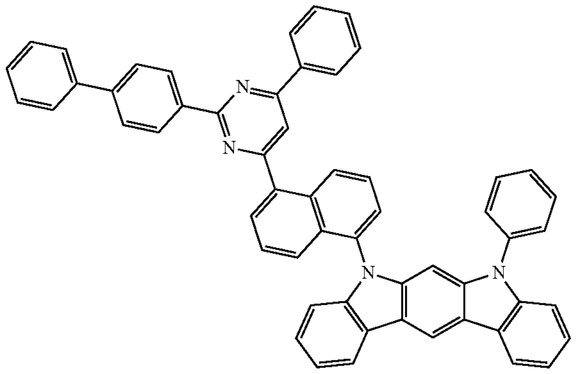
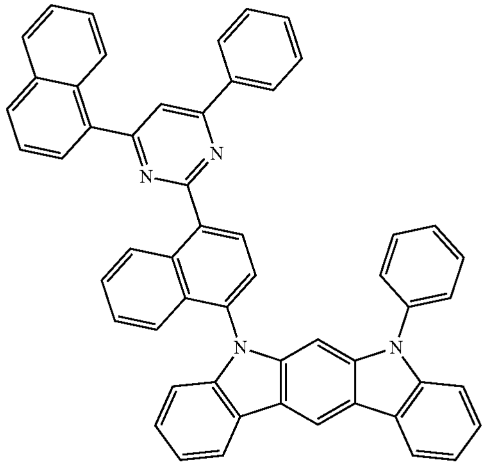
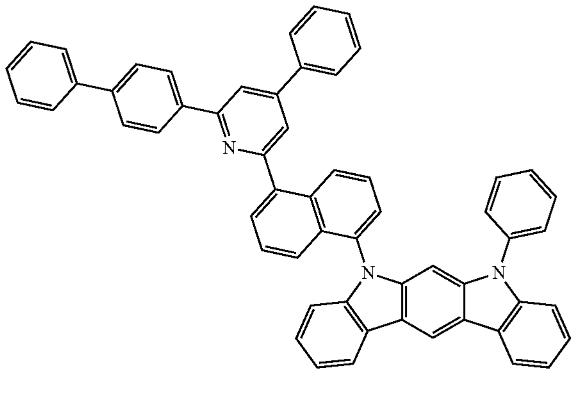
-continued
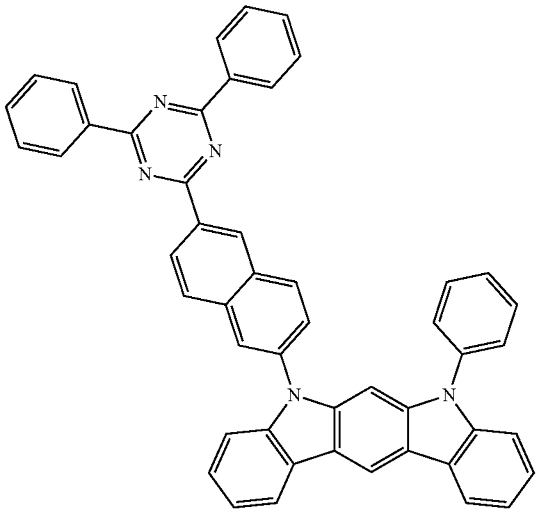
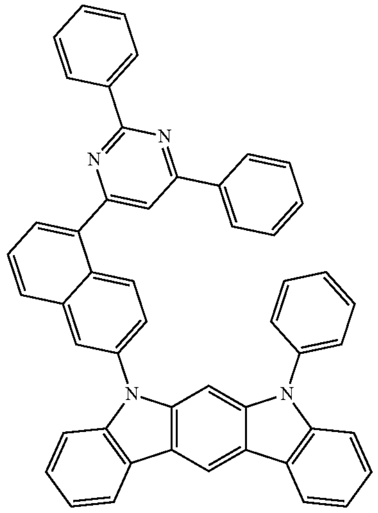
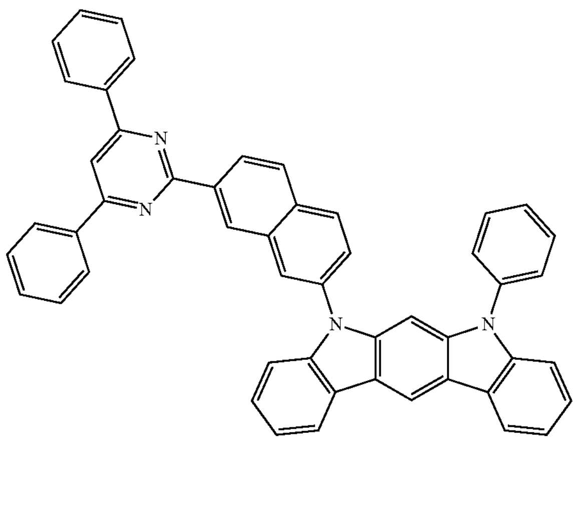

-continued
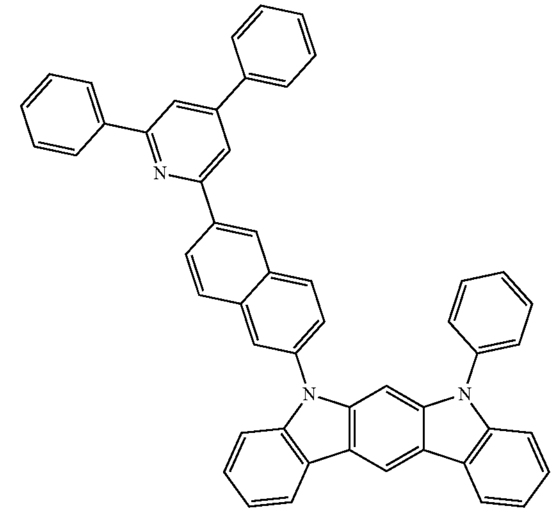
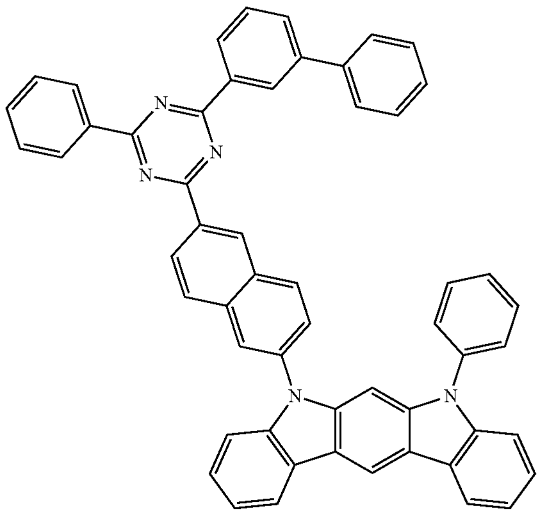
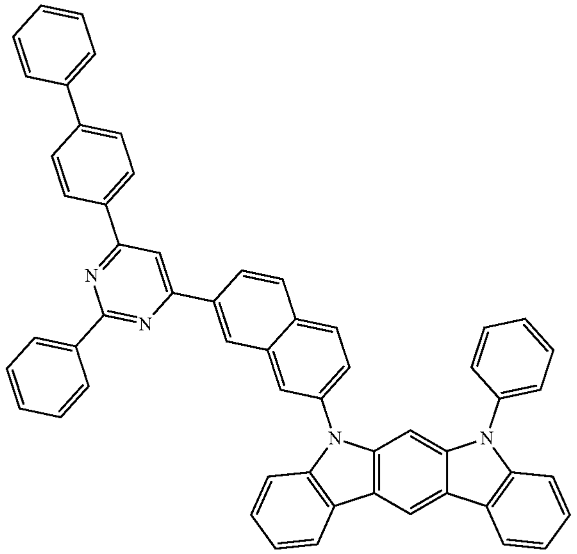
-continued
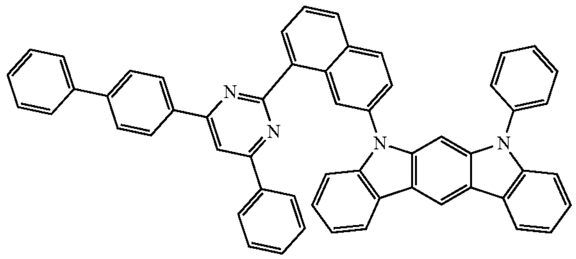
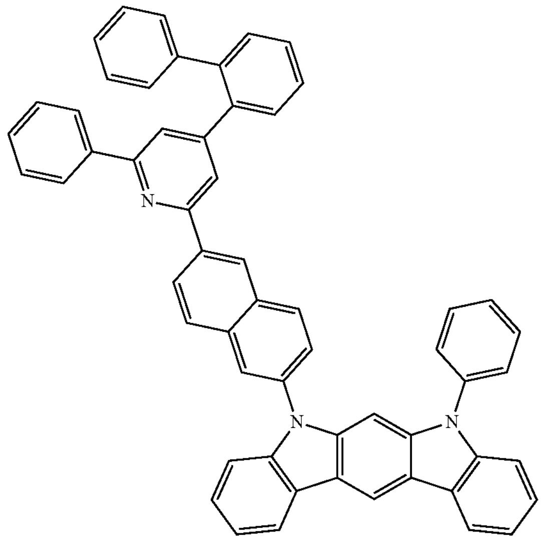
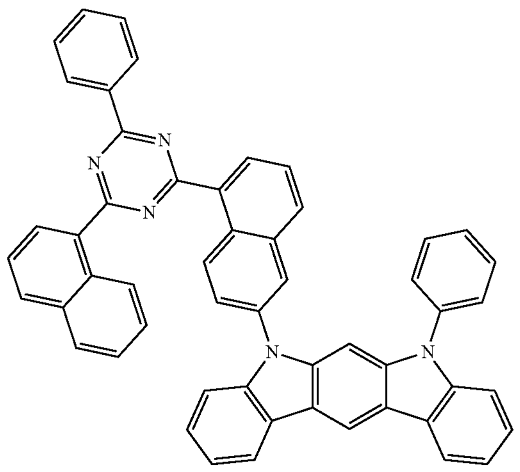

-continued
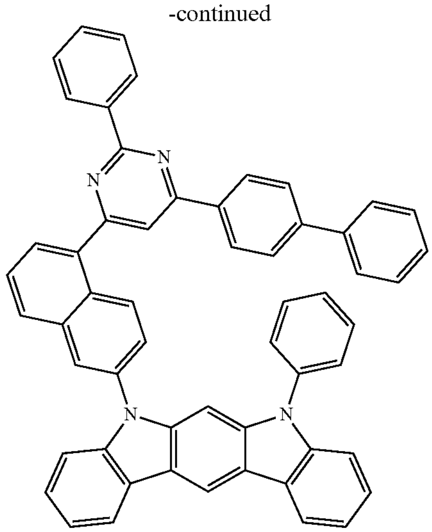
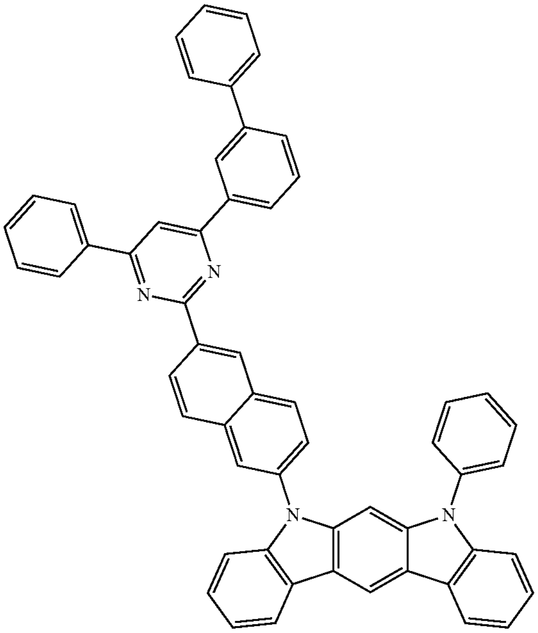
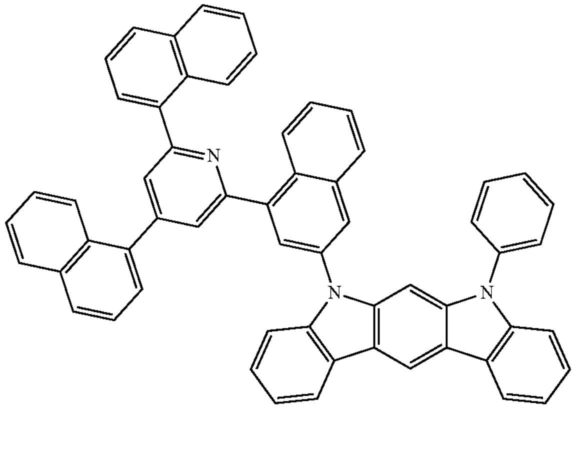
-continued
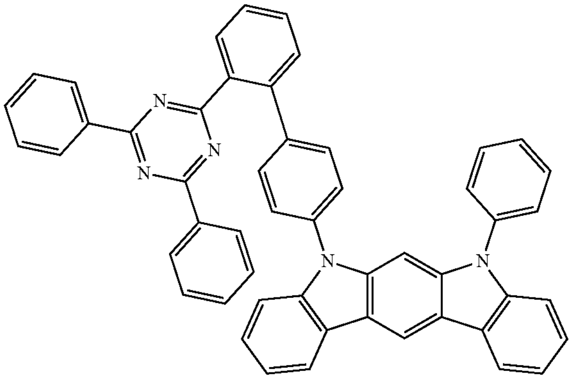
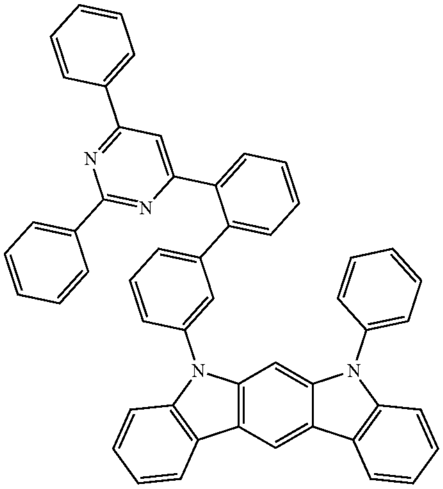
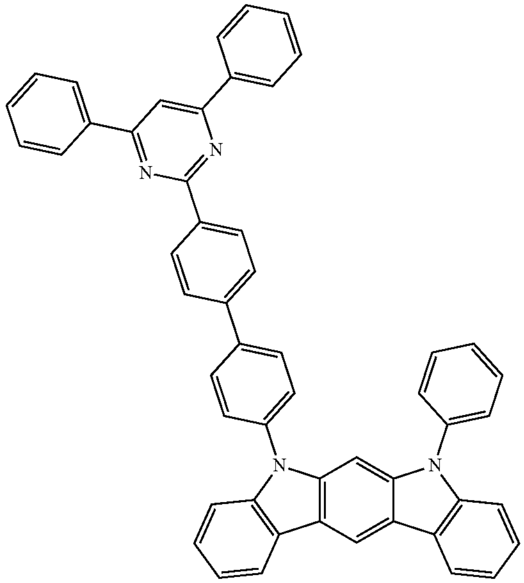

-continued
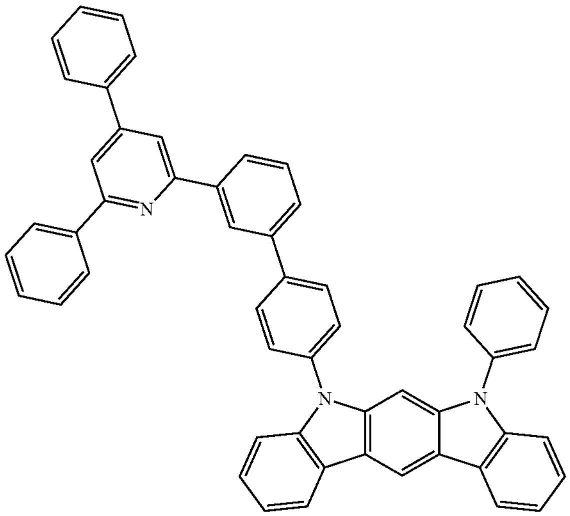
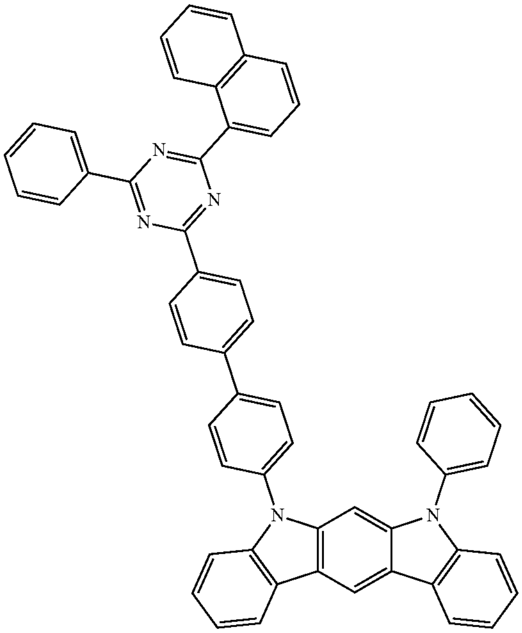
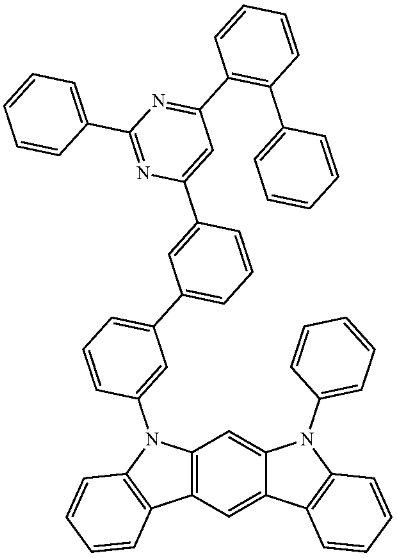
-continued
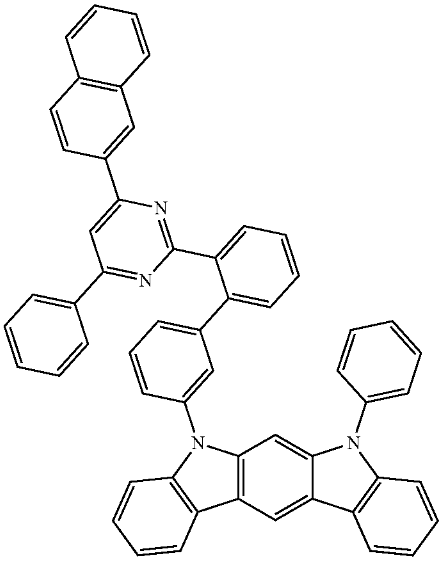
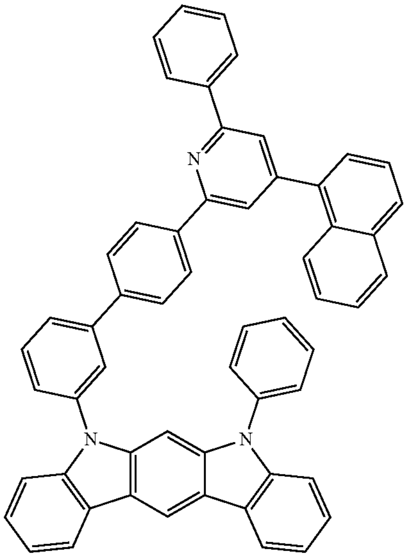

-continued

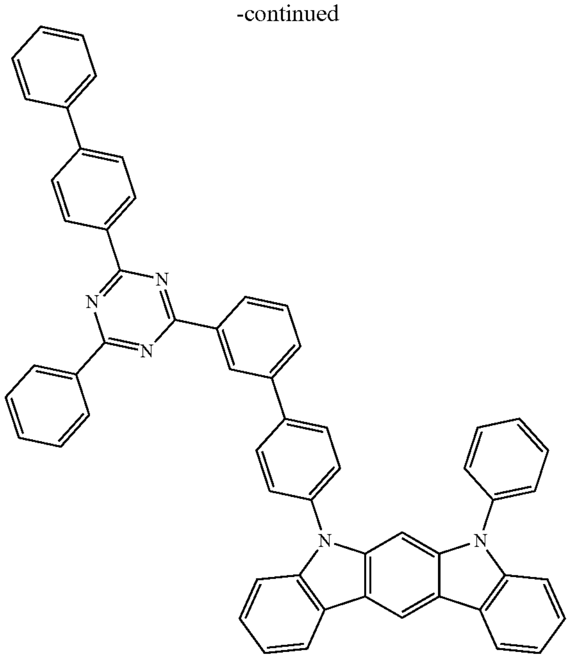

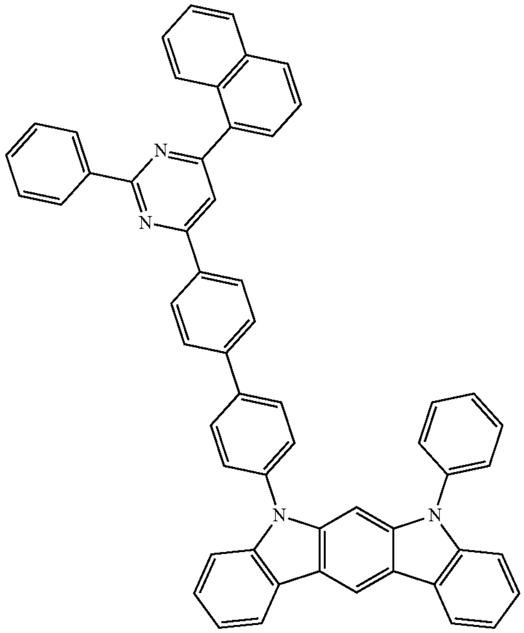

-continued

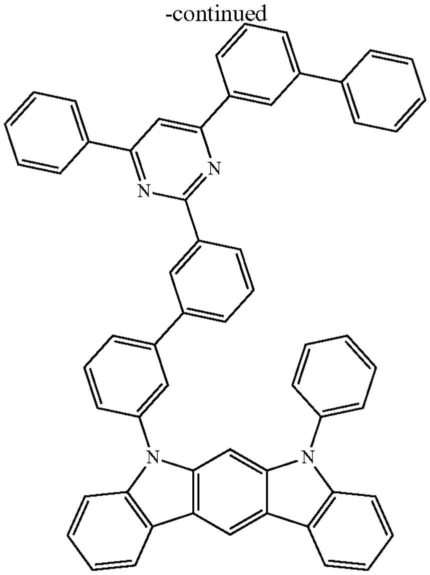

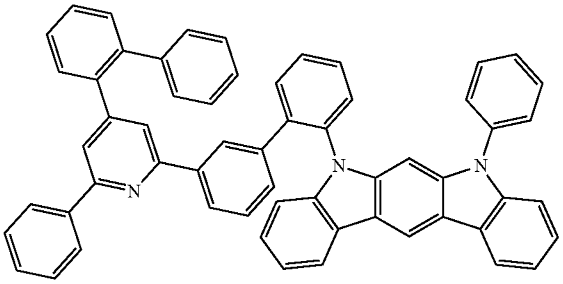

.

2. The organic light emitting diode of claim 1, wherein the hole transport layer and the hole adjusting layer are provided to be brought into contact with each other.

3. The organic light emitting diode of claim 1, wherein the hole adjusting layer and the light emitting layer are in contact with each other.

4. The organic light emitting diode of claim 1, wherein the compound of Formula 1 is selected from among the following compounds:

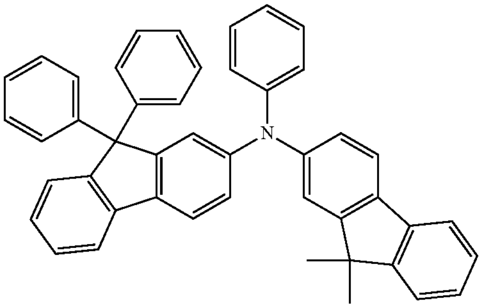

-continued
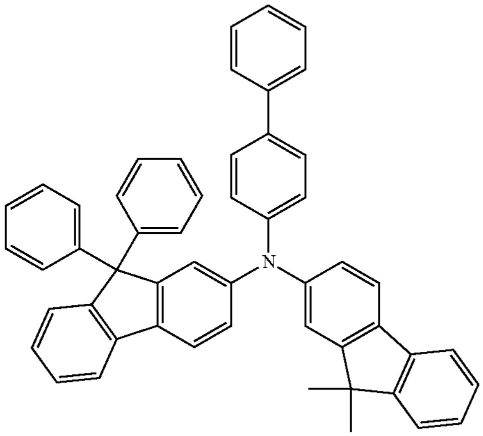
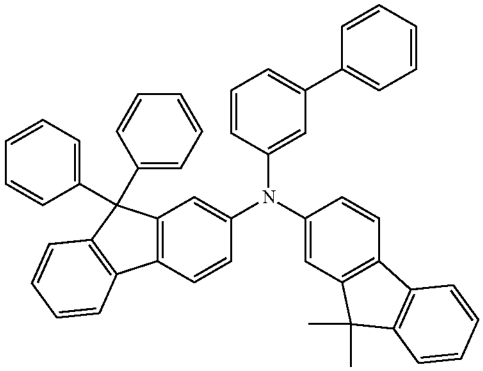
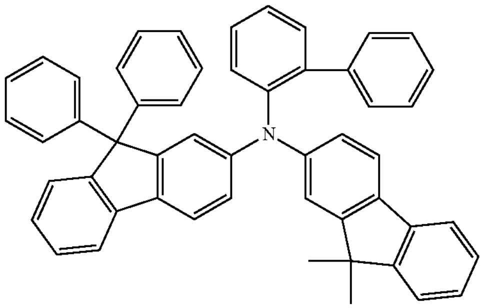
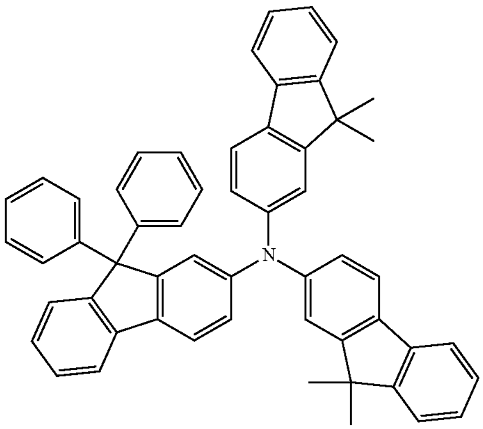
-continued
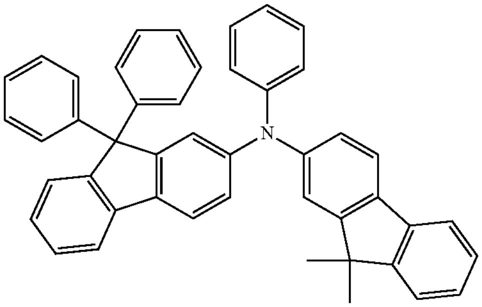
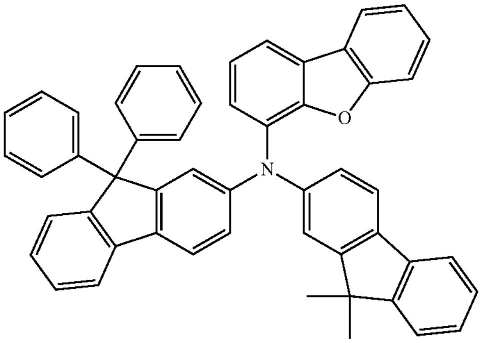
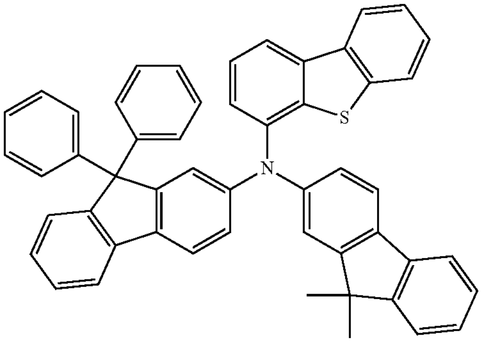
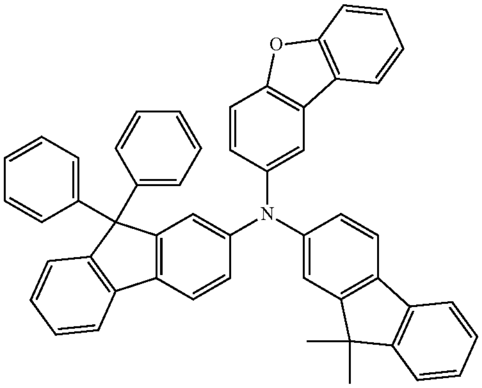

-continued
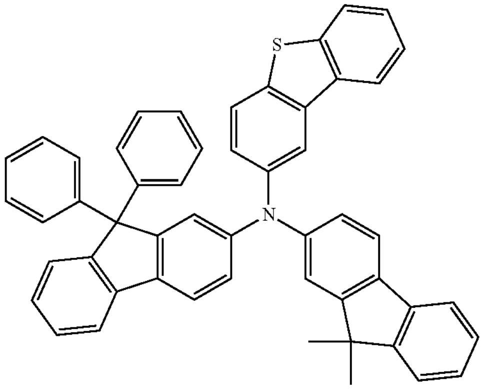
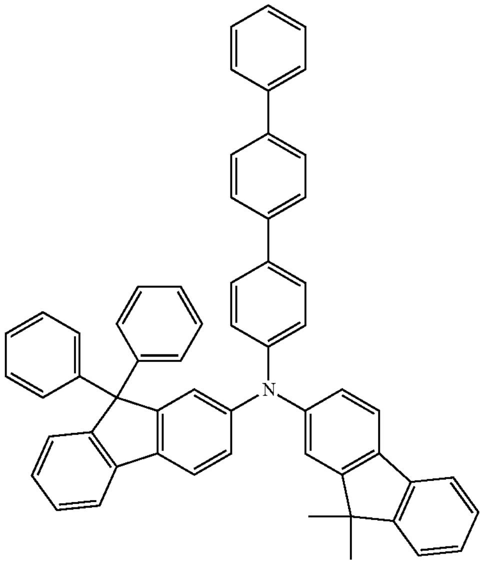
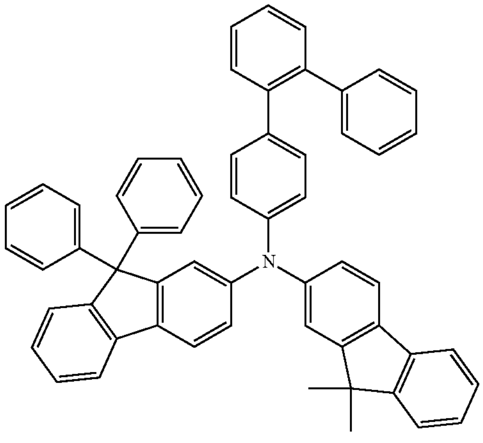
-continued
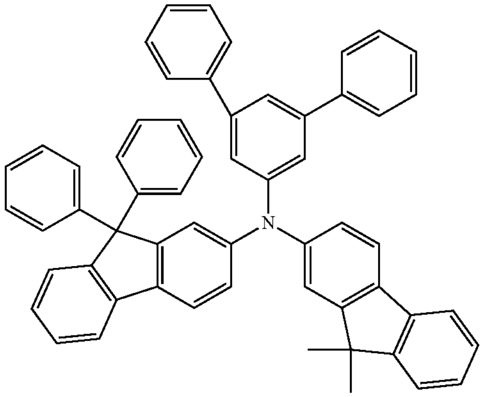
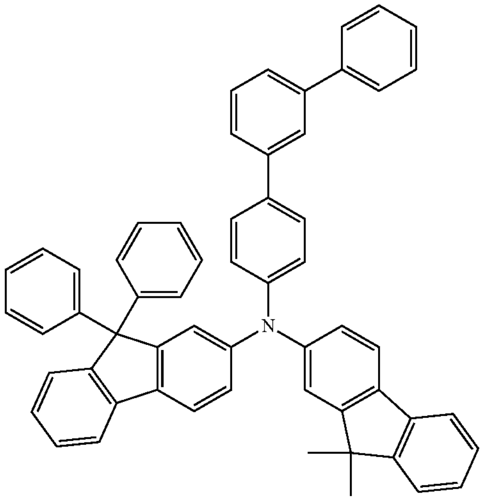
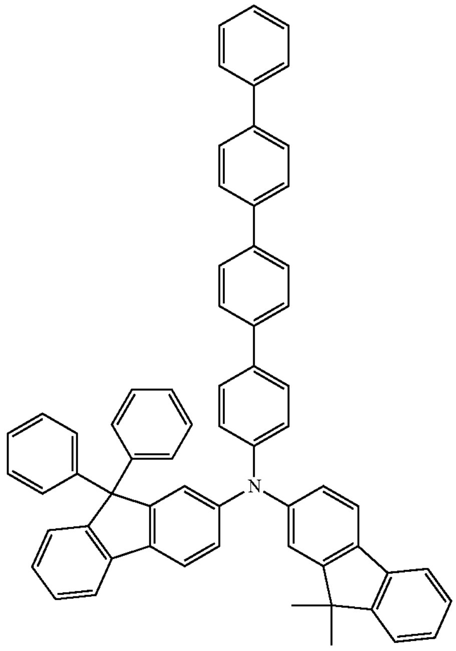

-continued
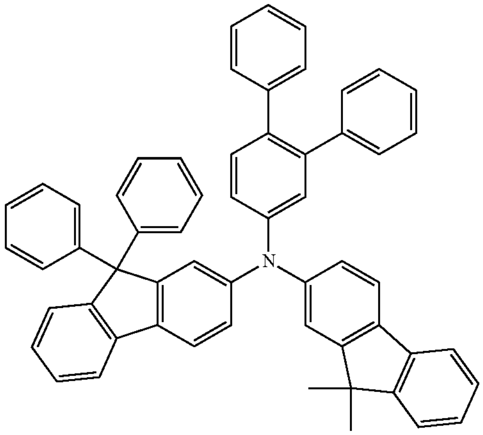
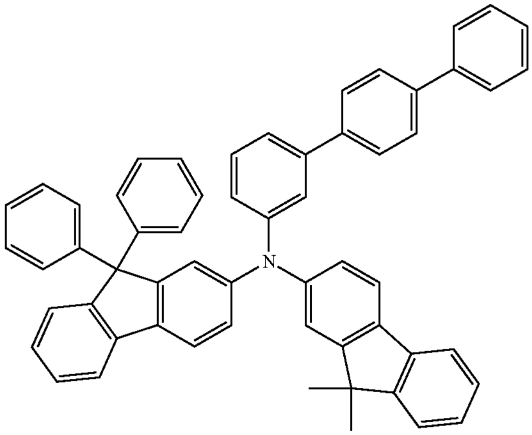
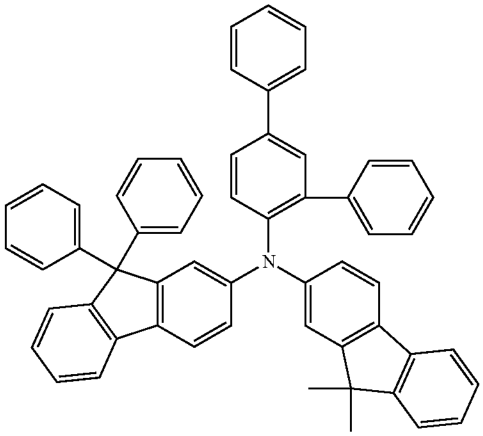
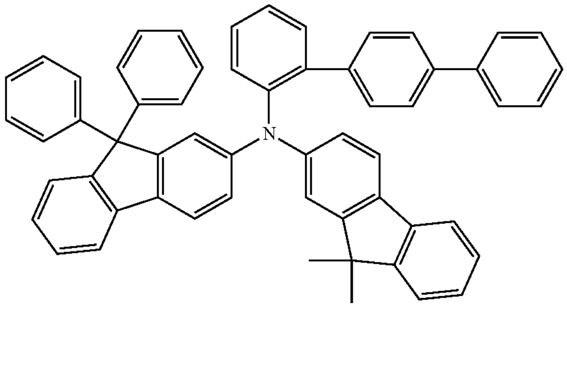
-continued
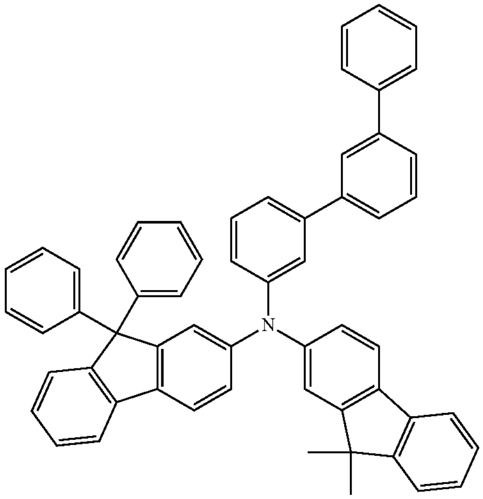
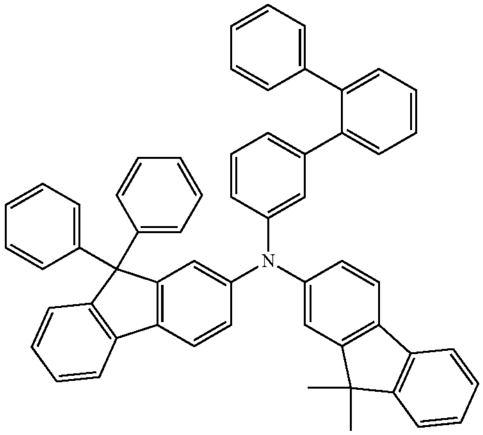
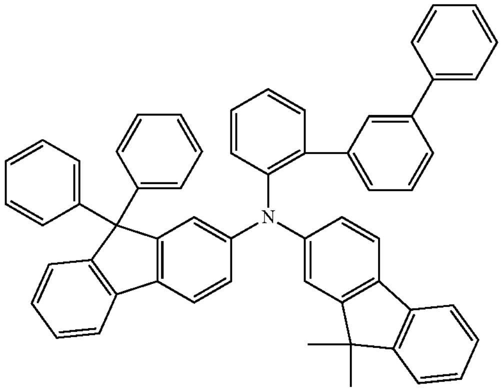
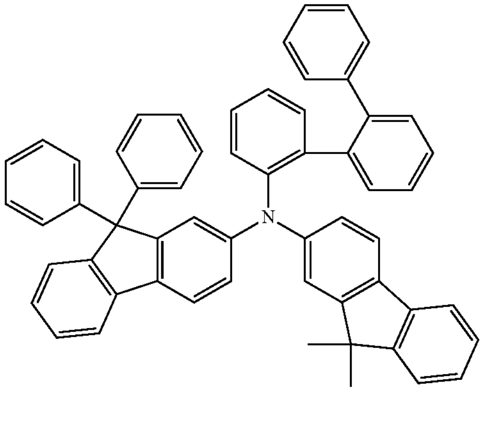

-continued
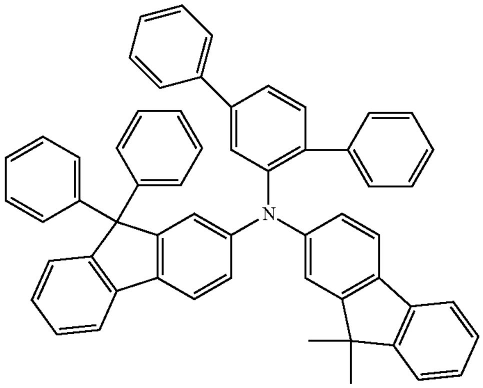
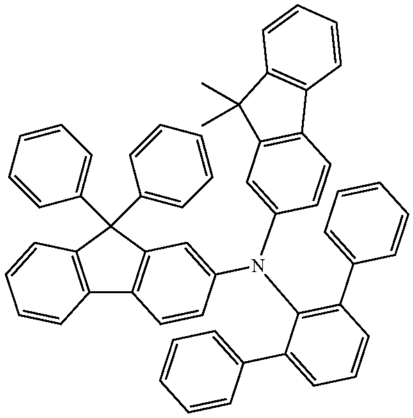
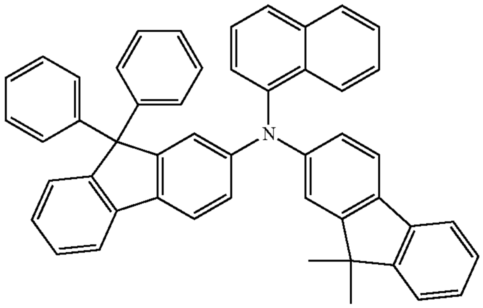
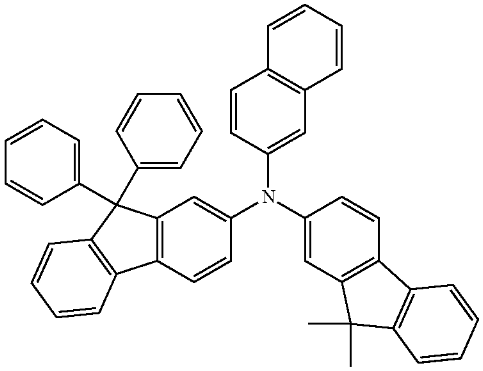
-continued
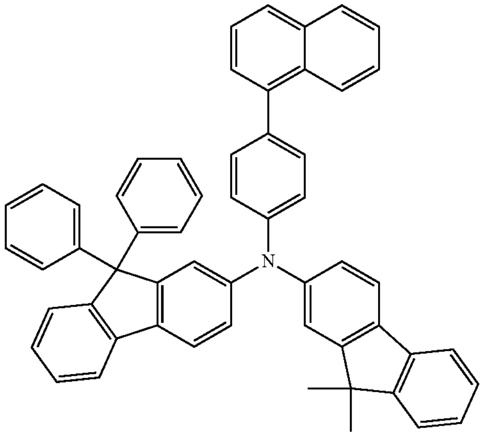
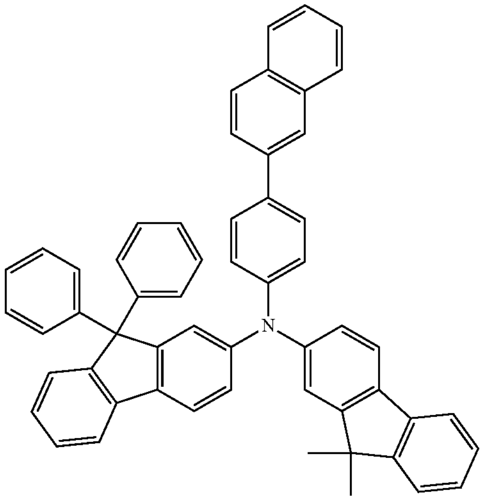
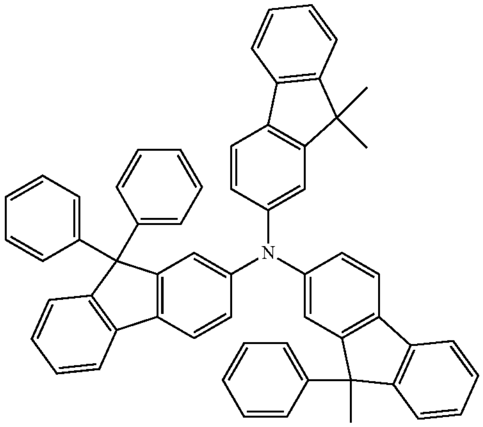

-continued
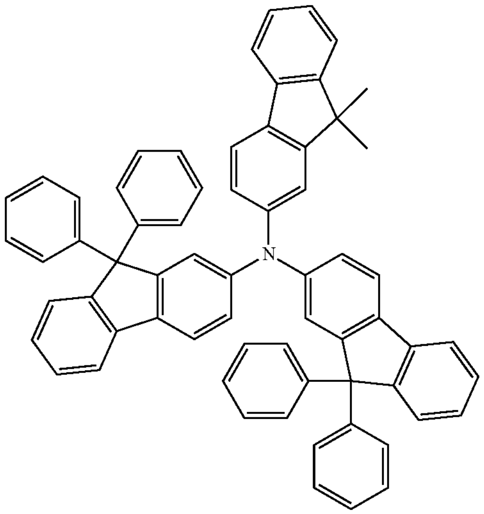 [SMILES: CC1(C)c2ccccc2-c2ccc(N(c3ccc4c(c3)C(c3ccccc3)(c3ccccc3)c3ccccc3-4)c3ccc4c(c3)C(c3ccccc3)(c3ccccc3)c3ccccc3-4)cc21]
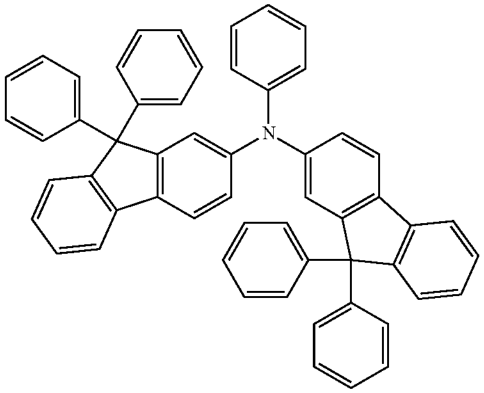
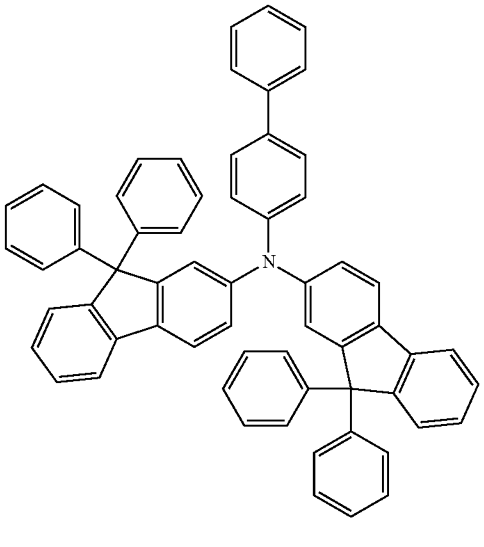
-continued
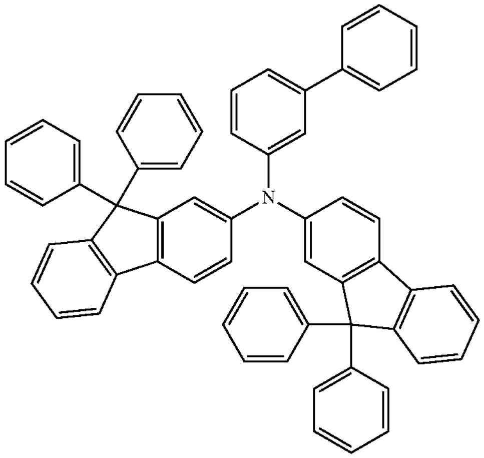
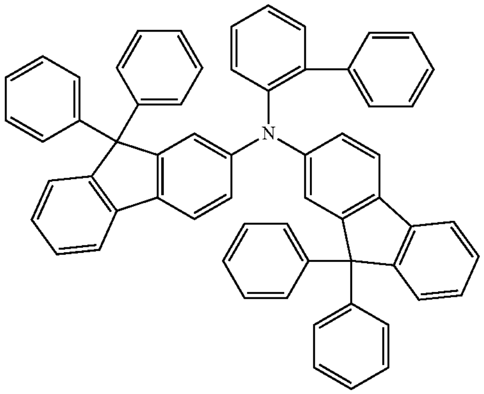
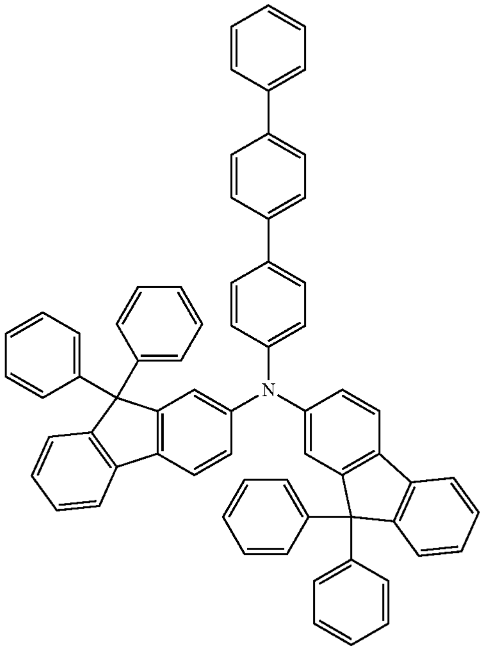

-continued
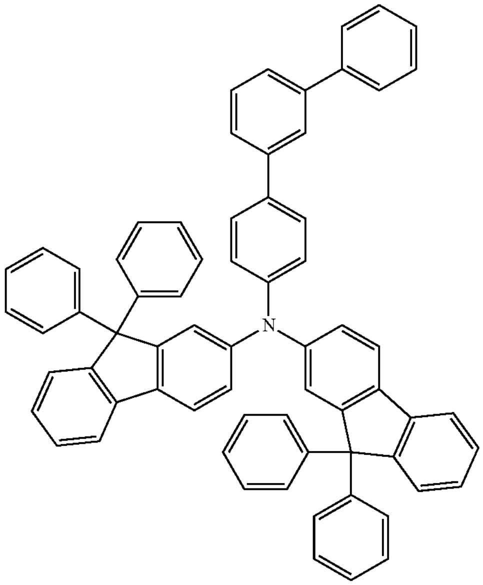
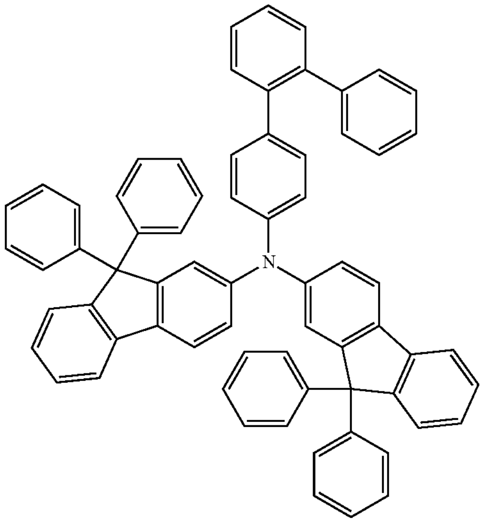
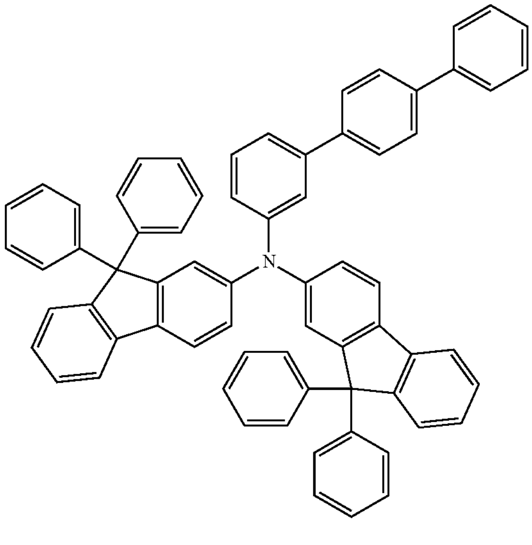
-continued
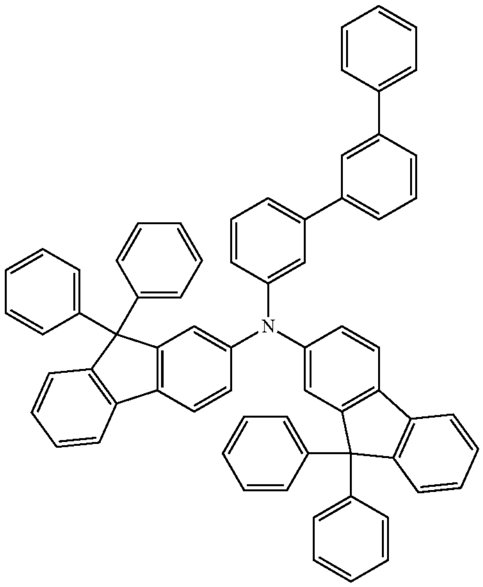
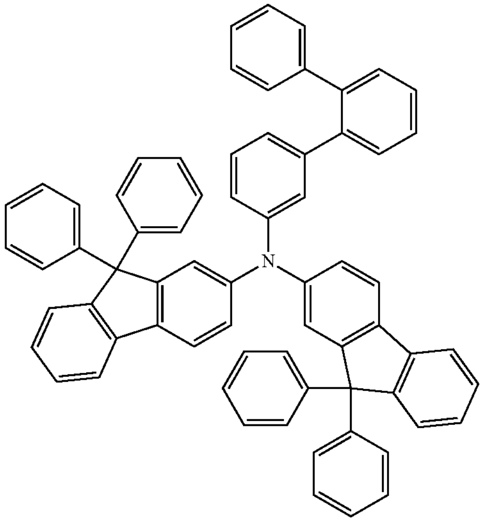
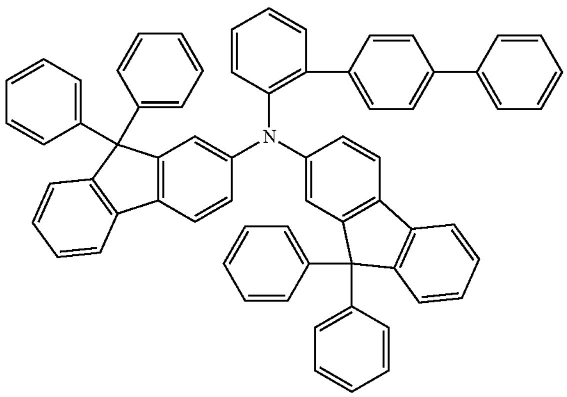

-continued
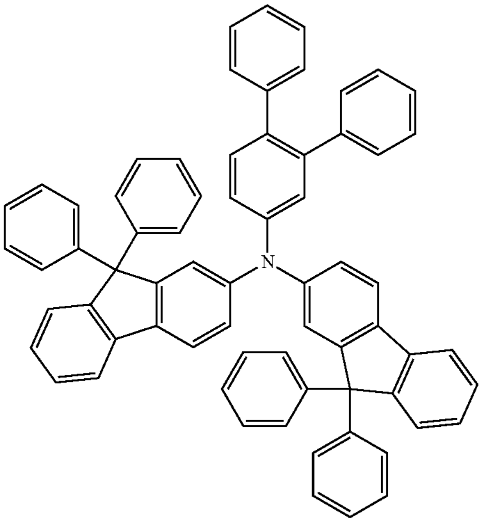
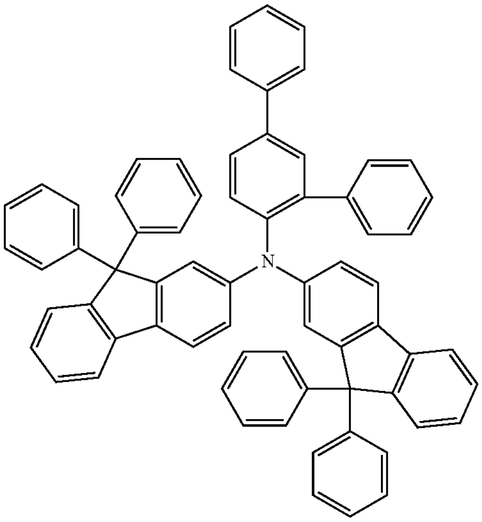
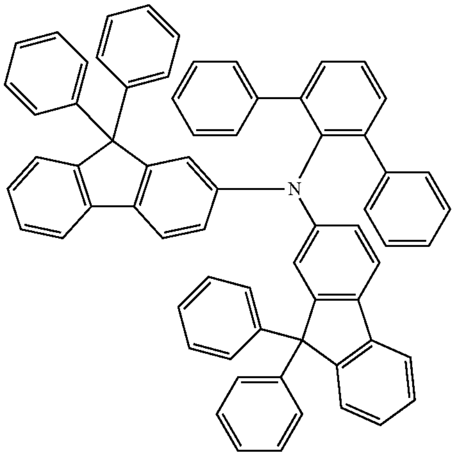
-continued
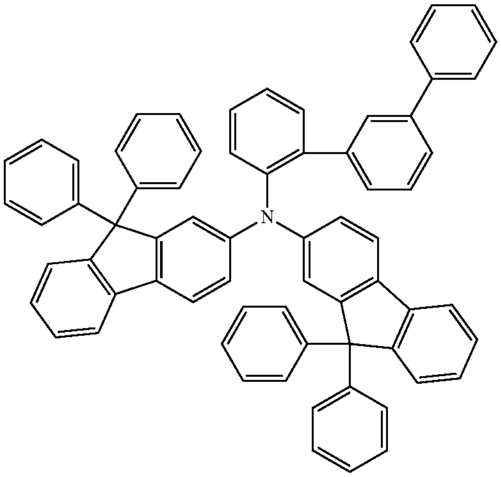
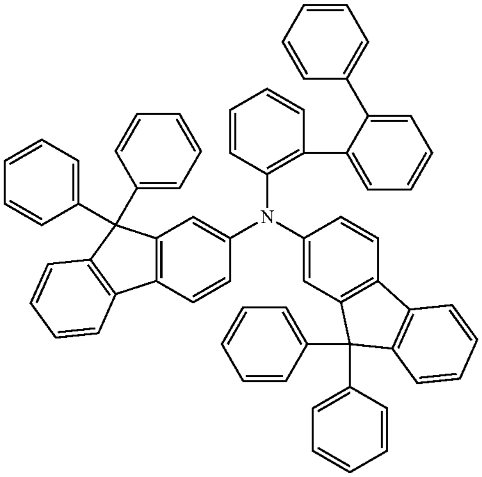
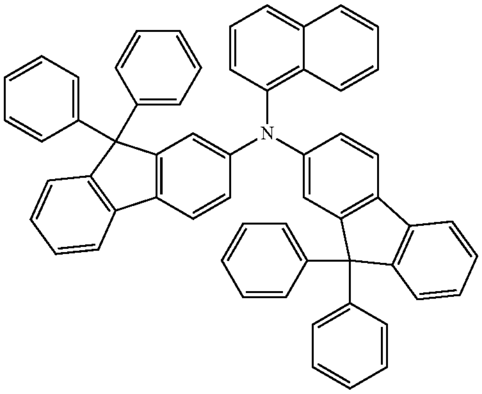

-continued
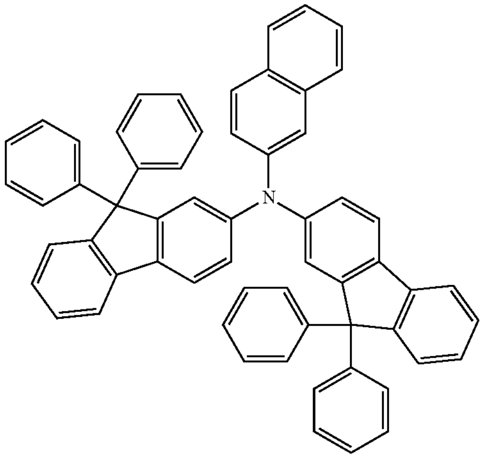
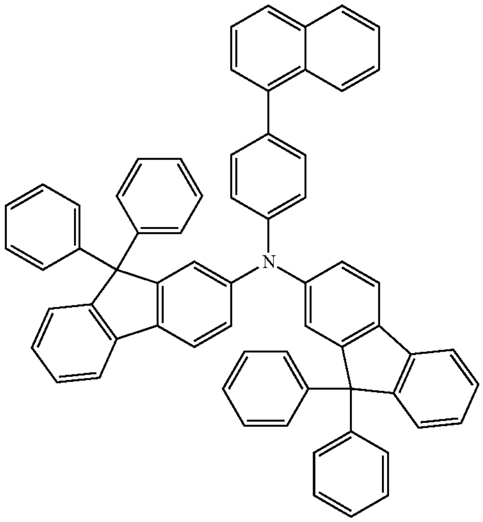
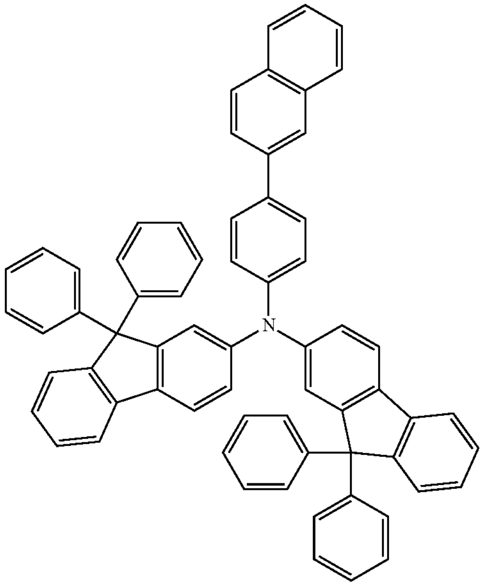
-continued
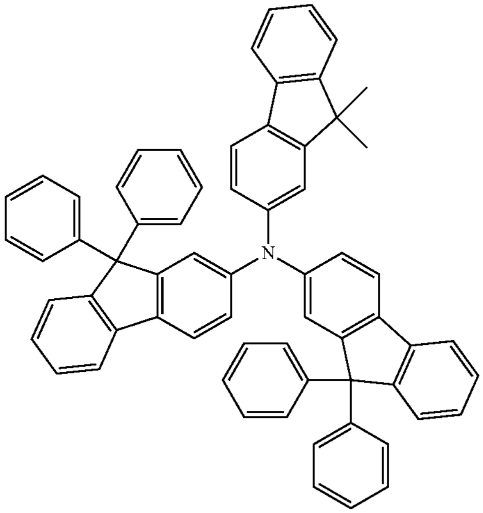
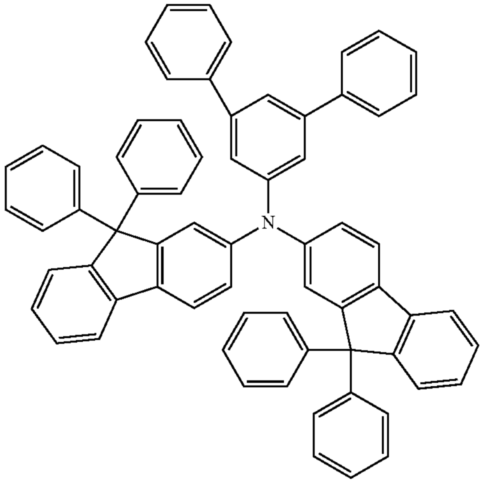
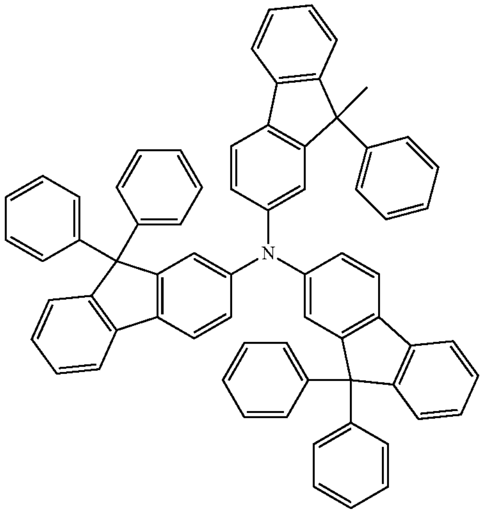

-continued
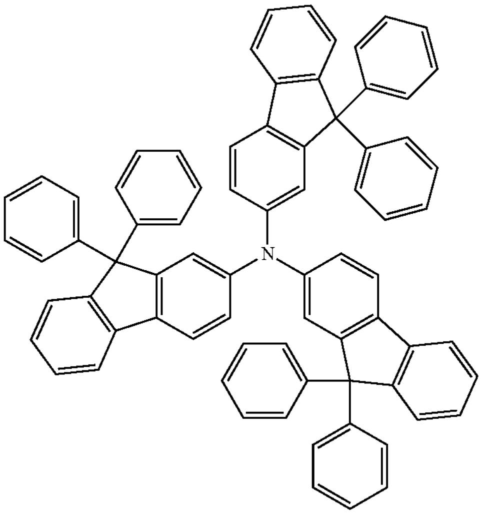
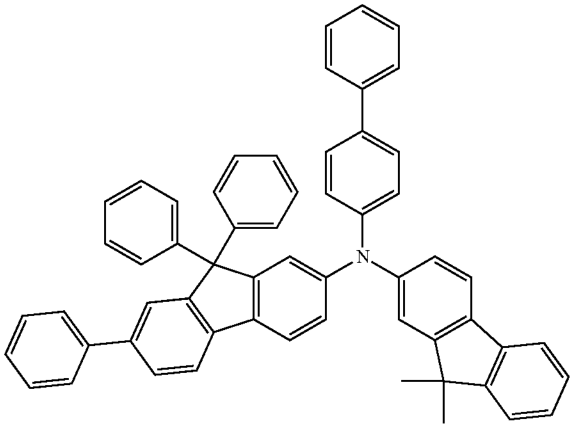
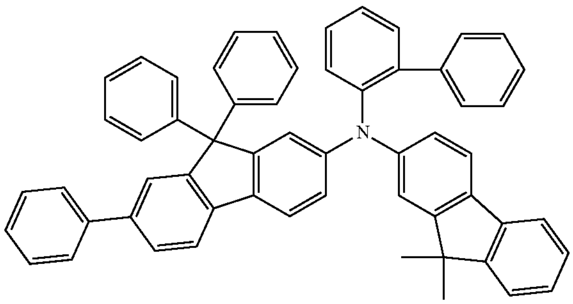
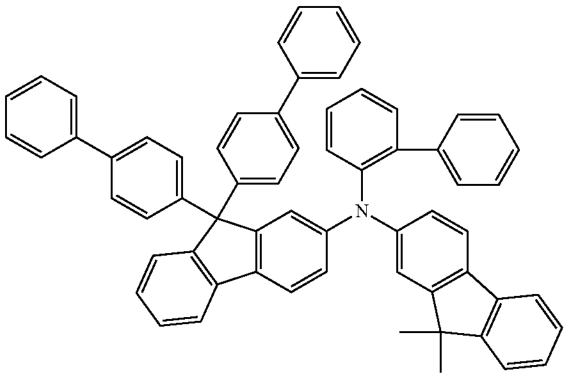
-continued
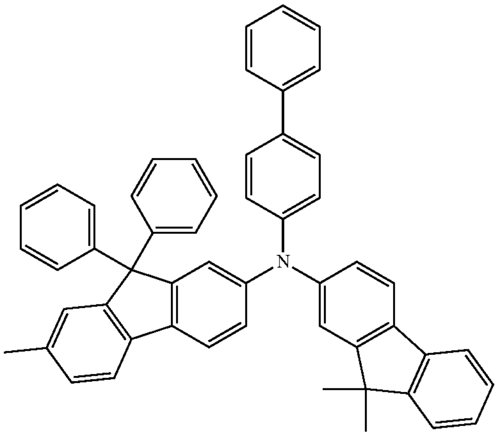
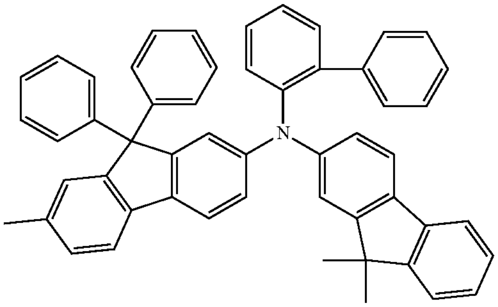
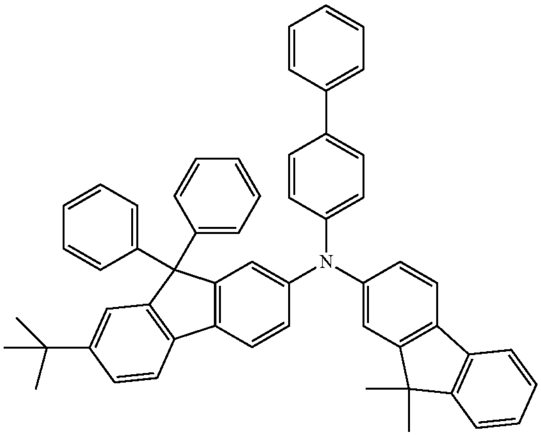
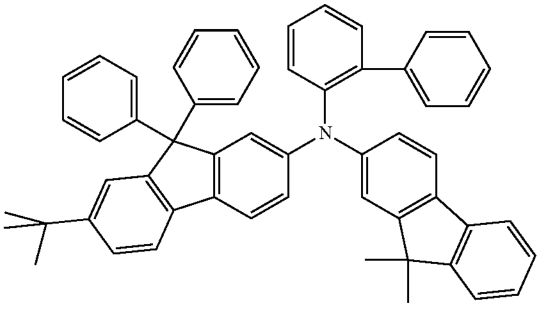

-continued
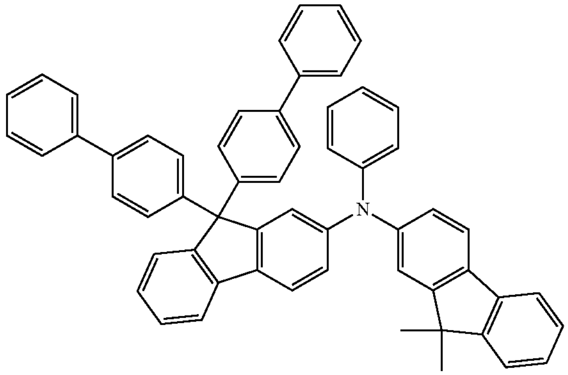
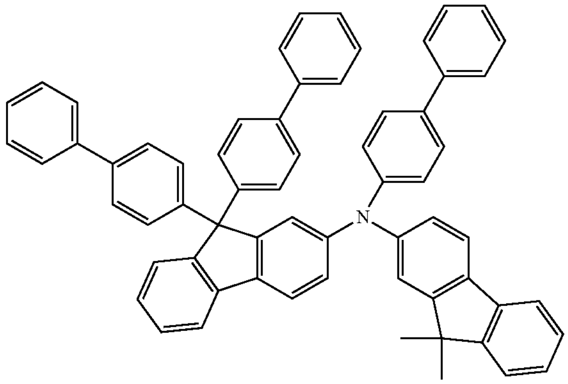
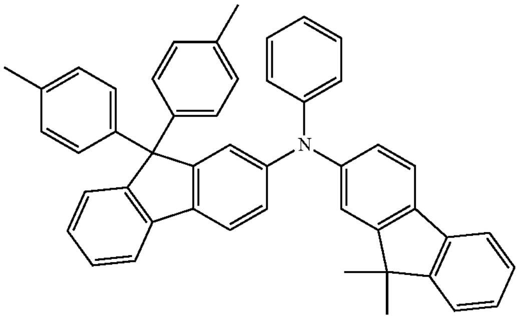
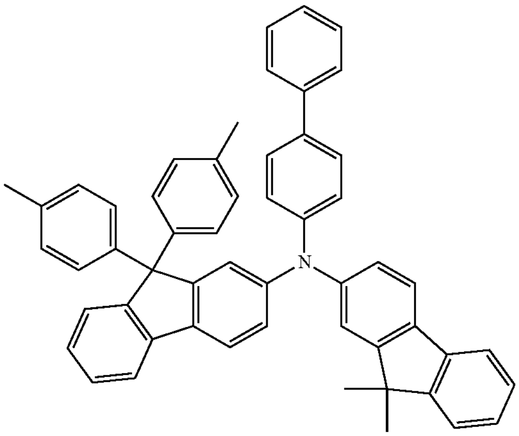
-continued
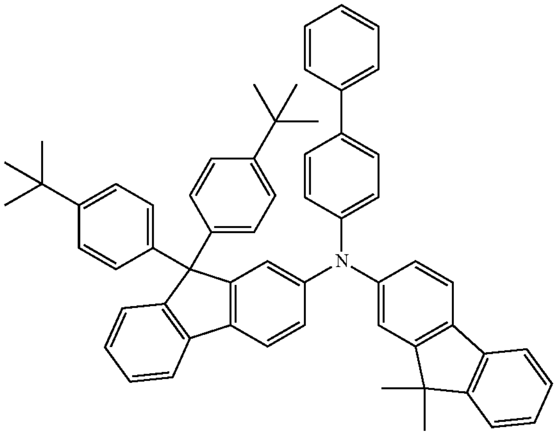
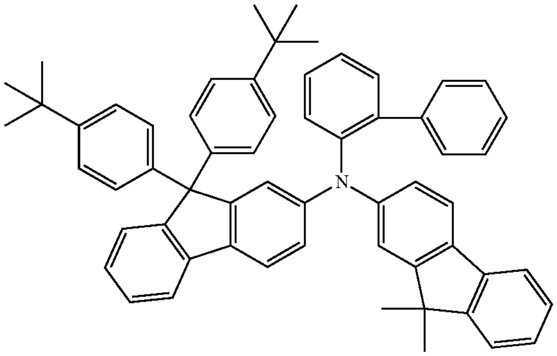
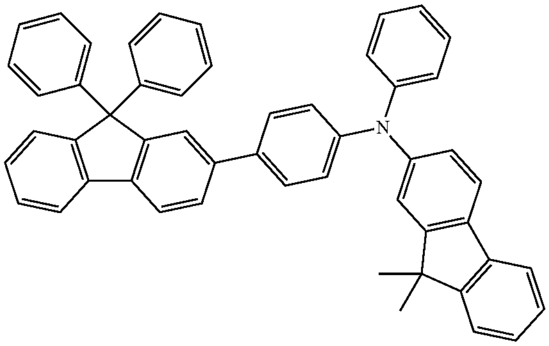
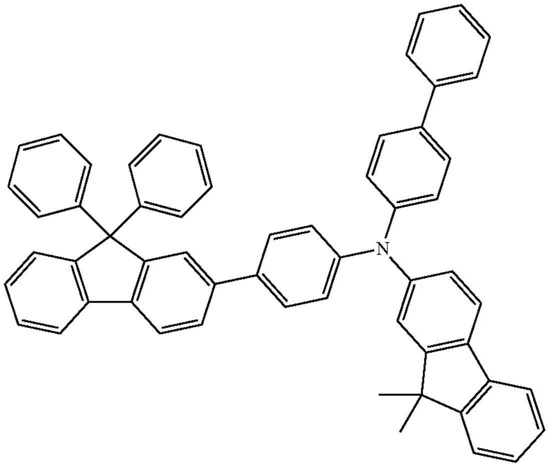

-continued
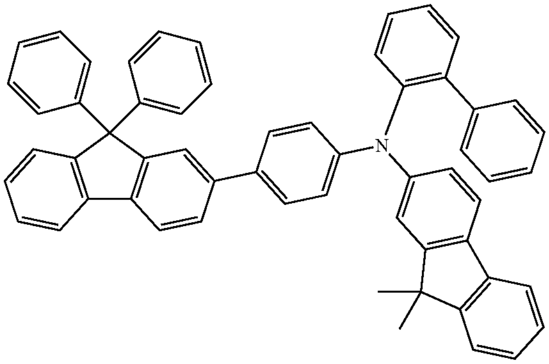
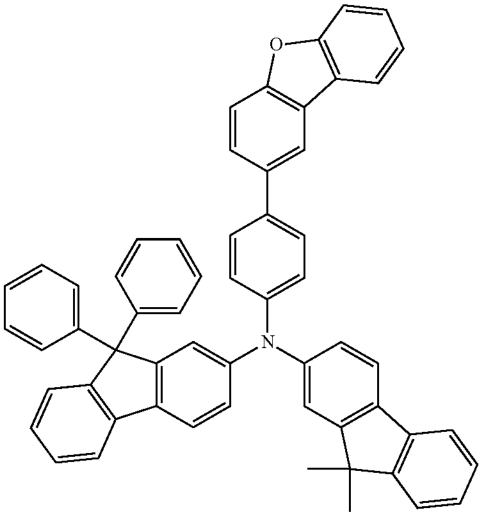
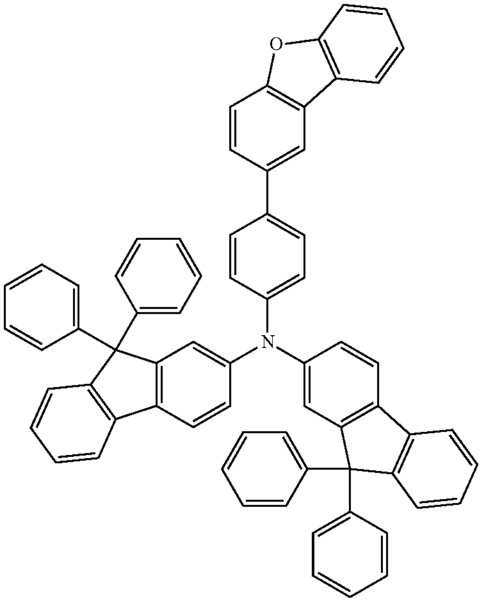
-continued
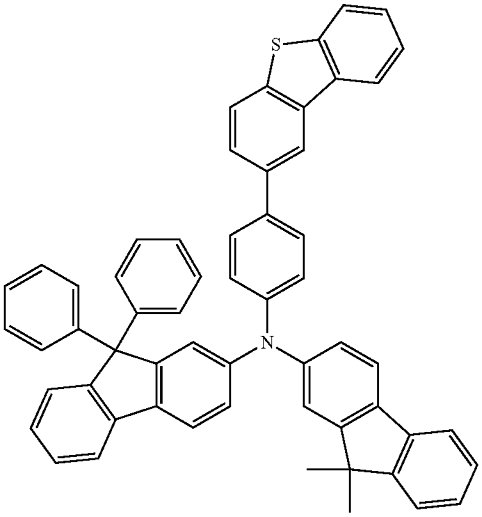
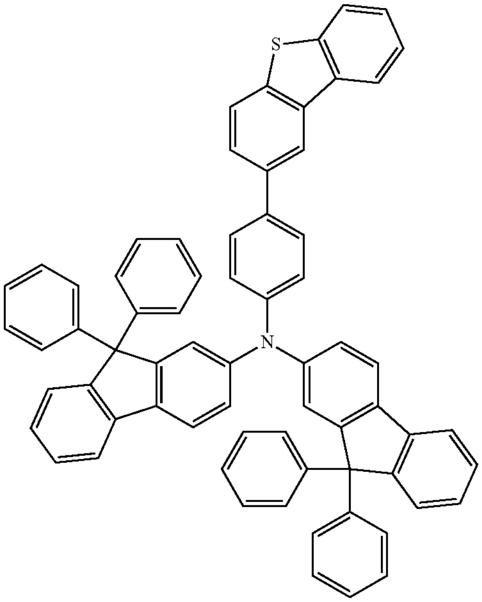
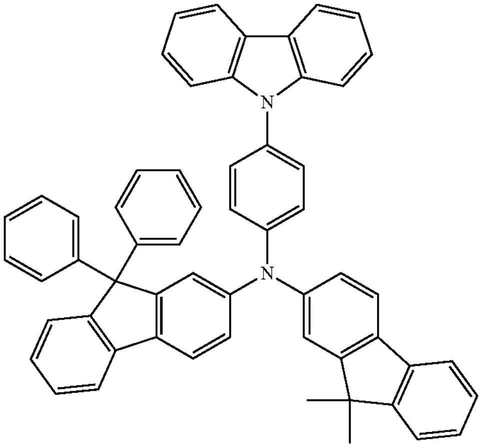

-continued
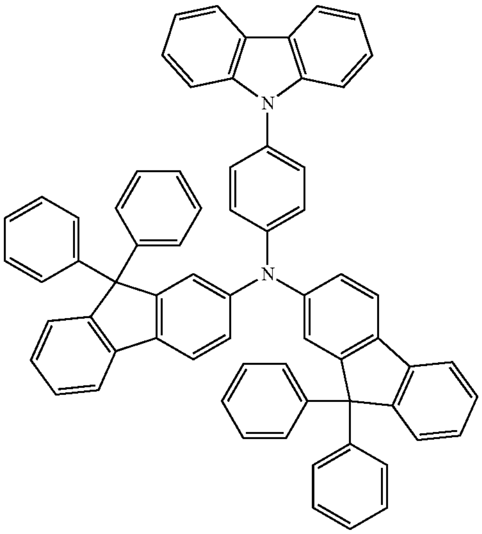
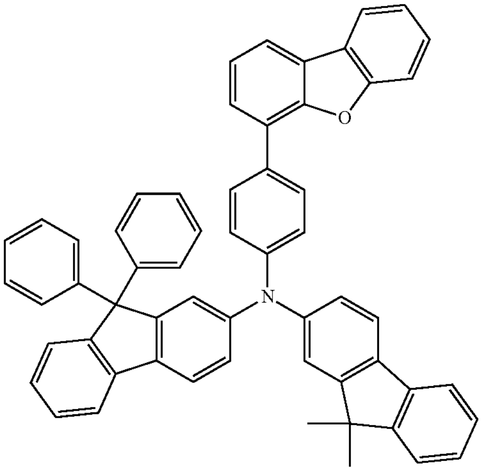
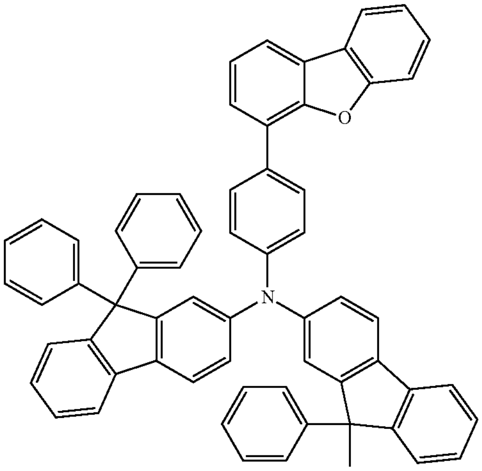
-continued
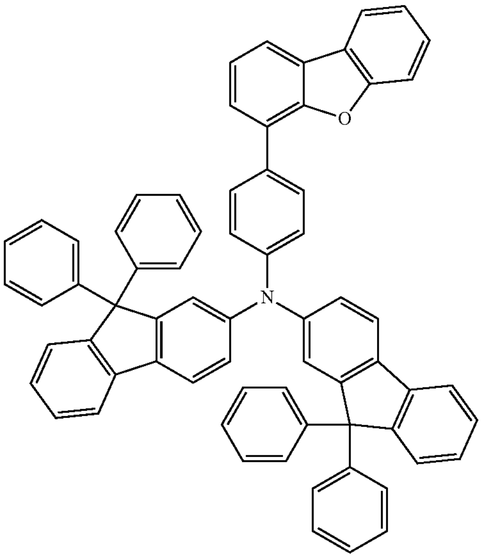
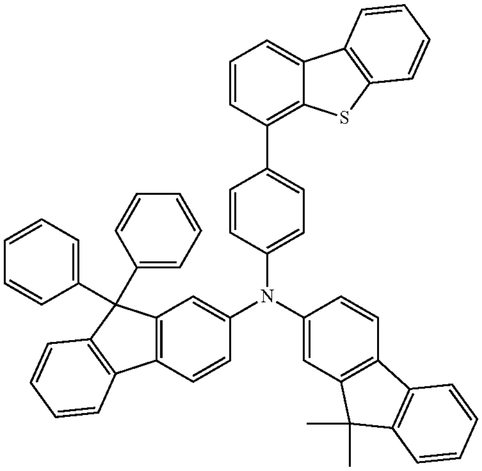
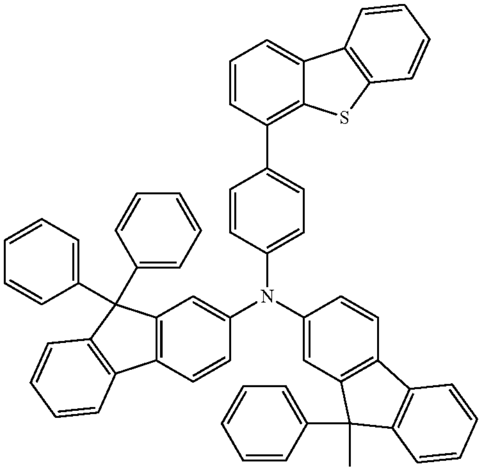

-continued
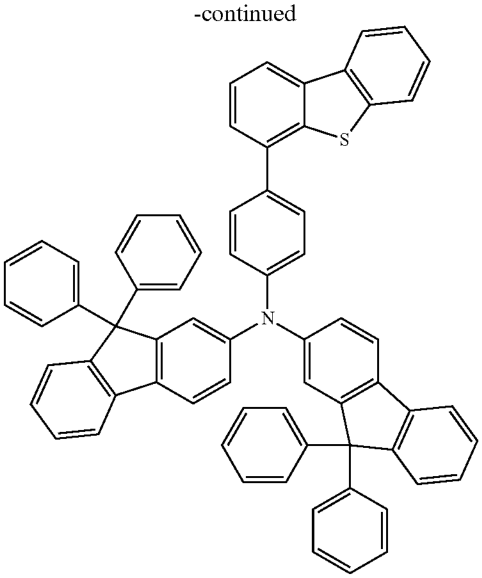
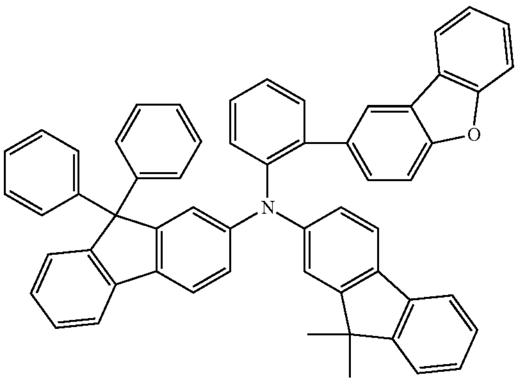
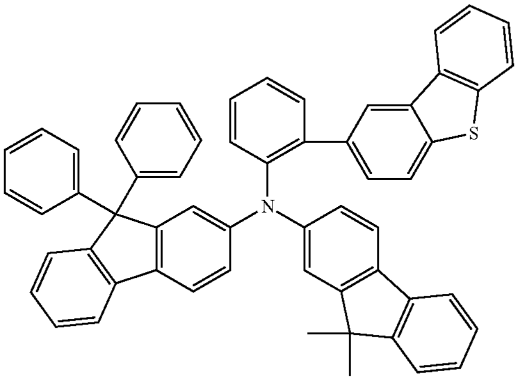
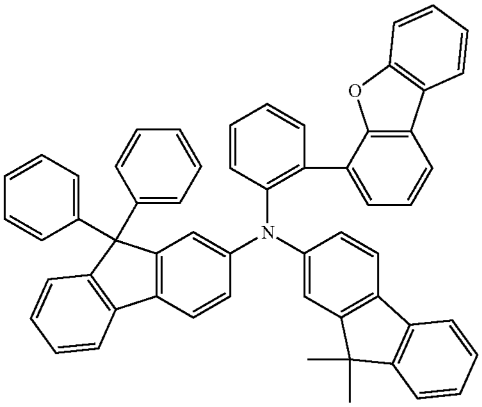
-continued
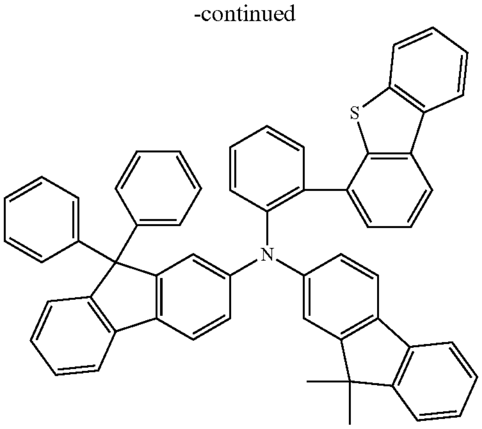
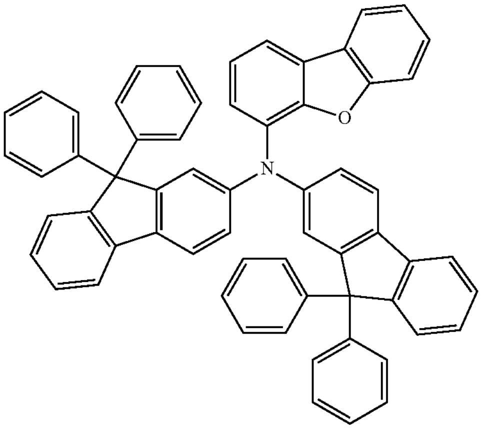
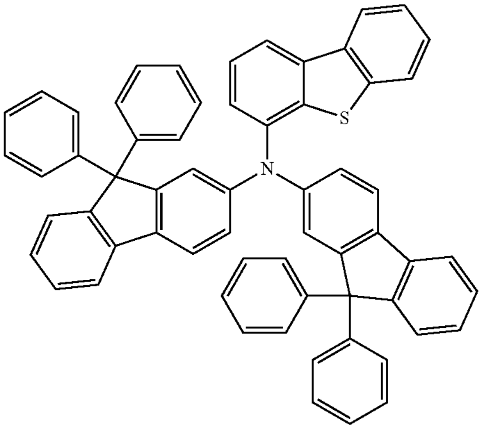
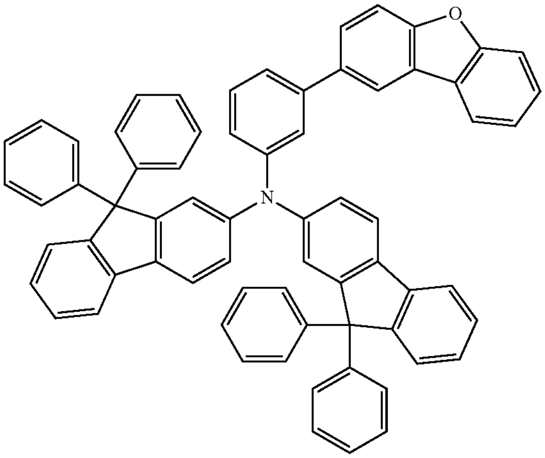

-continued
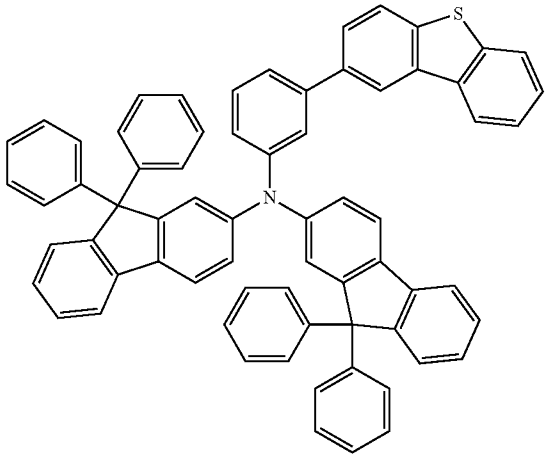
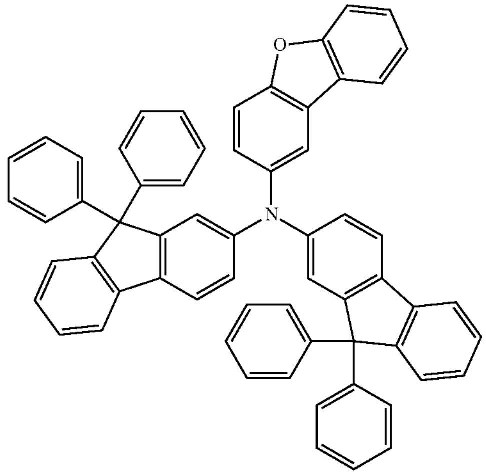
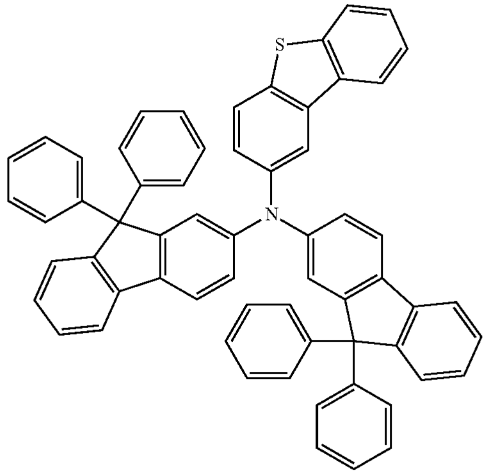
-continued
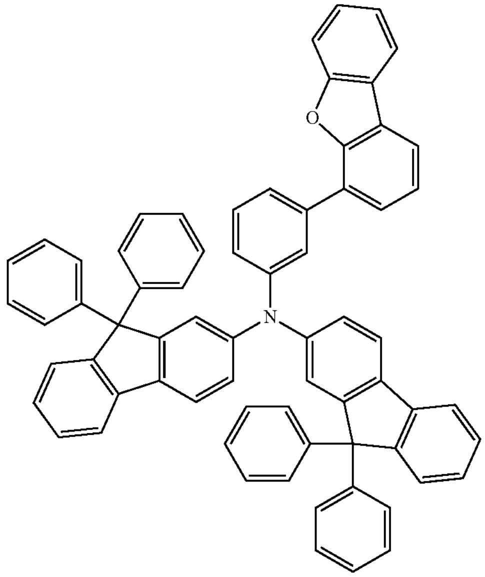
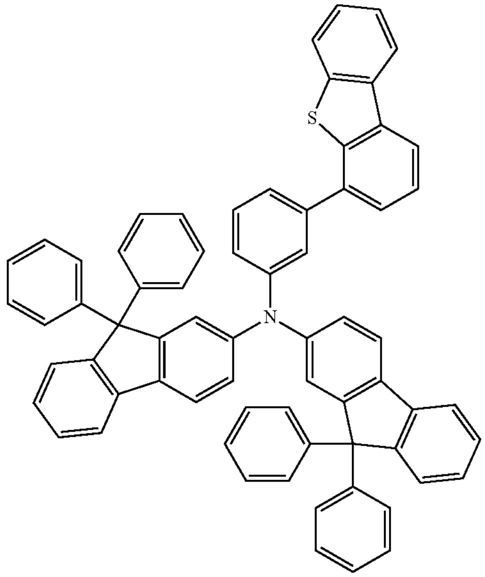
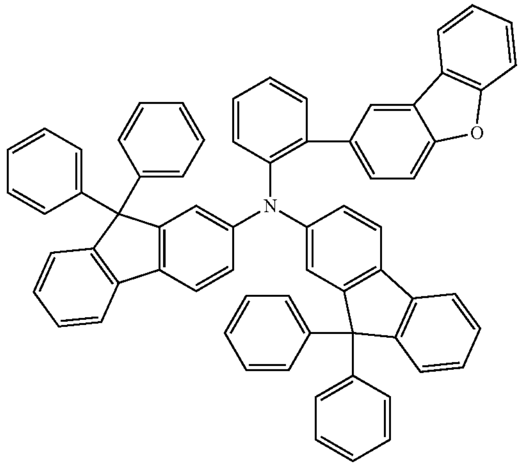

-continued
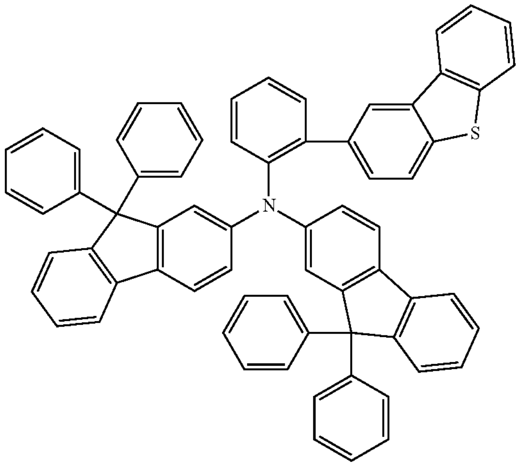
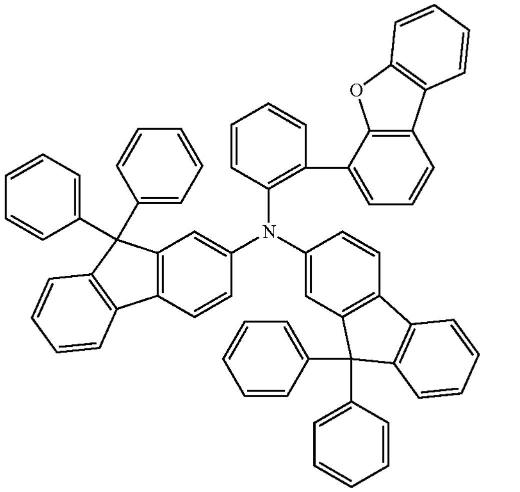
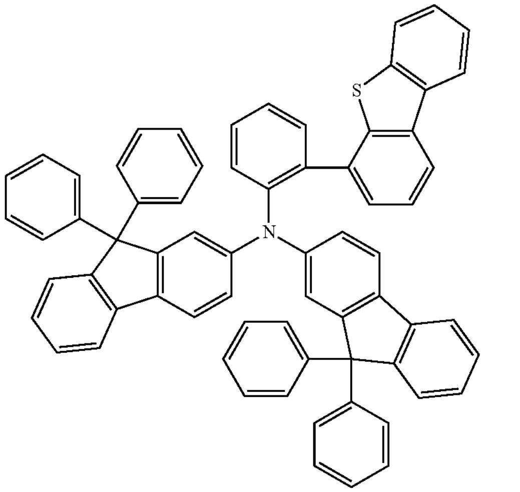
-continued
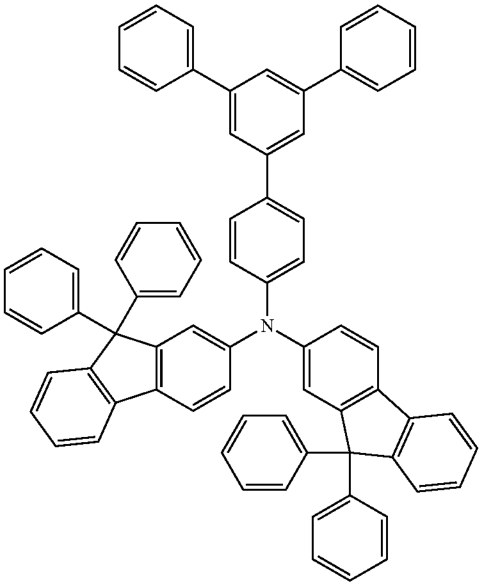
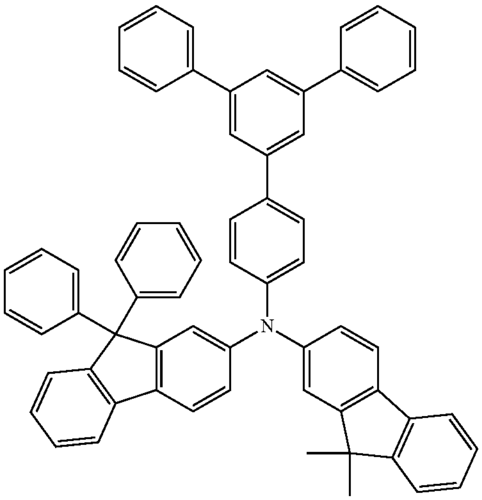
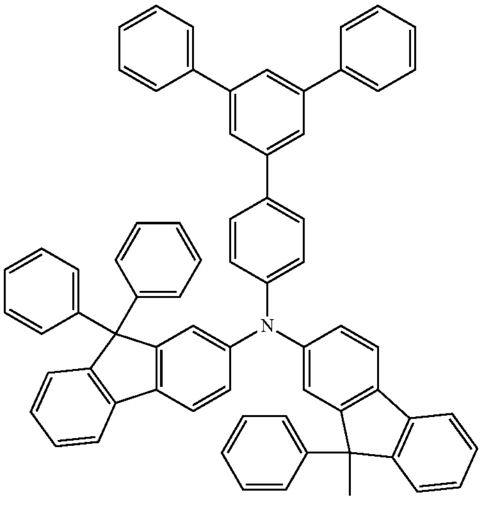

-continued
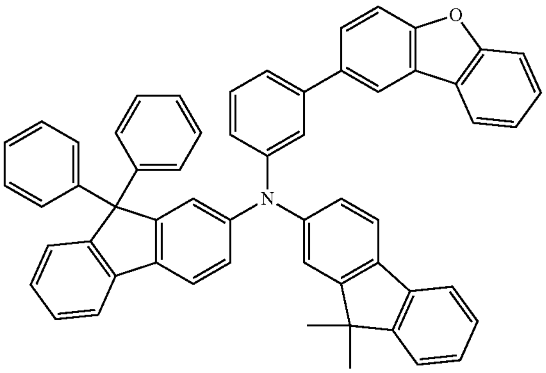
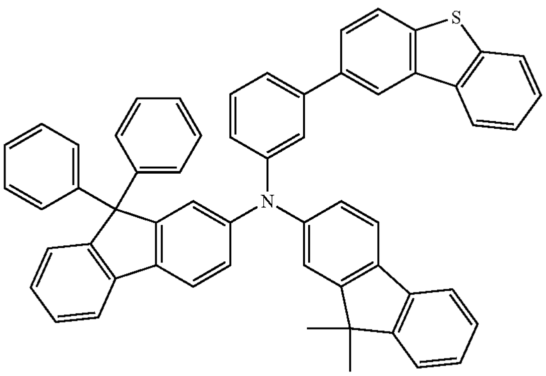
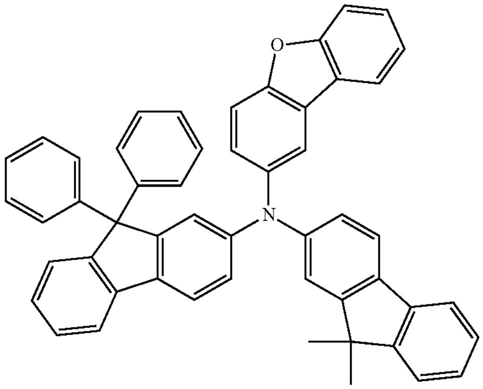
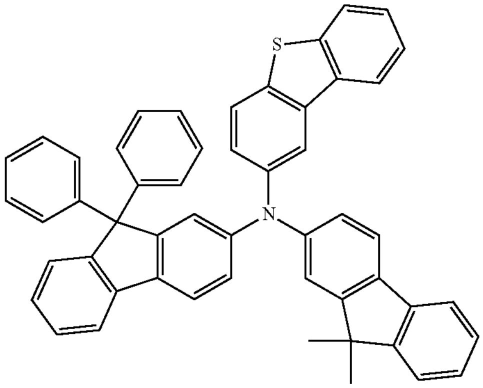
-continued
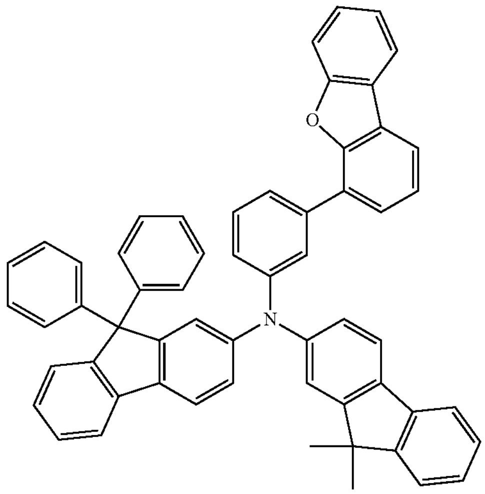
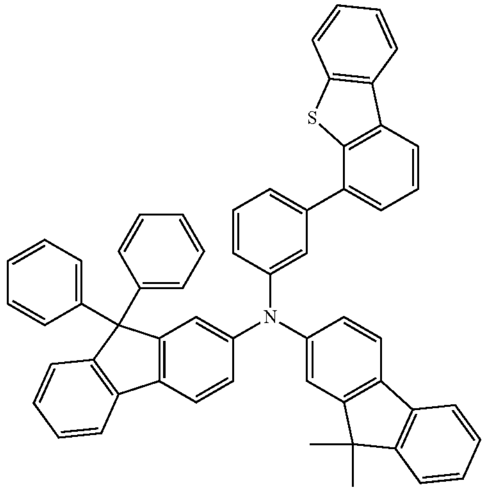
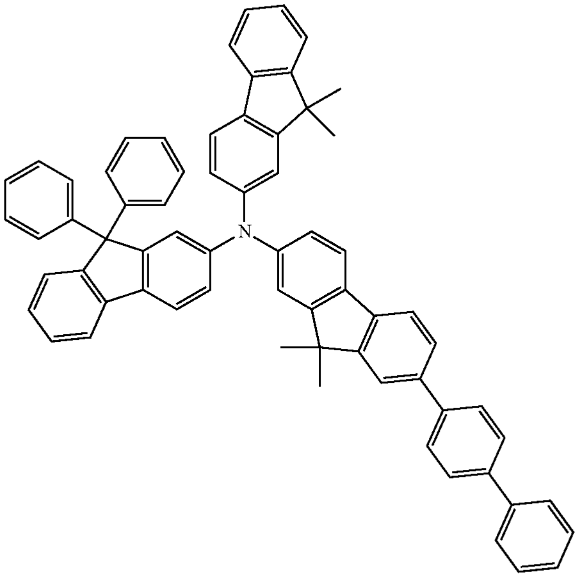

-continued
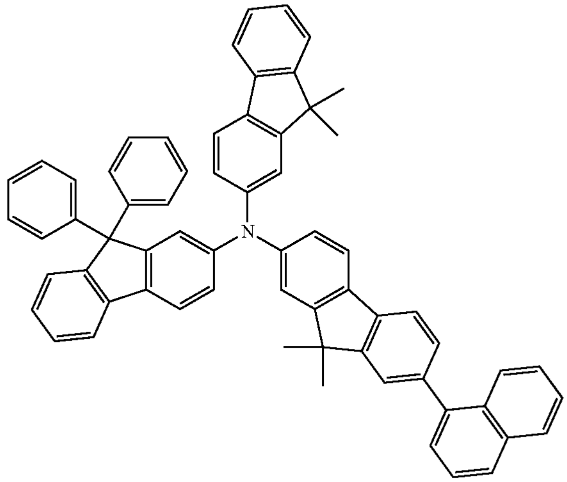
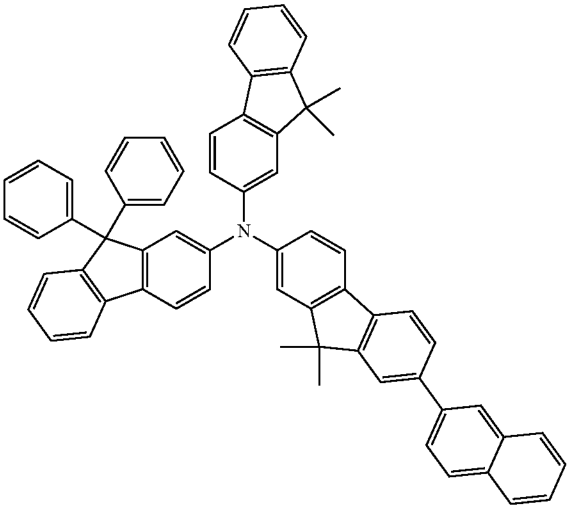
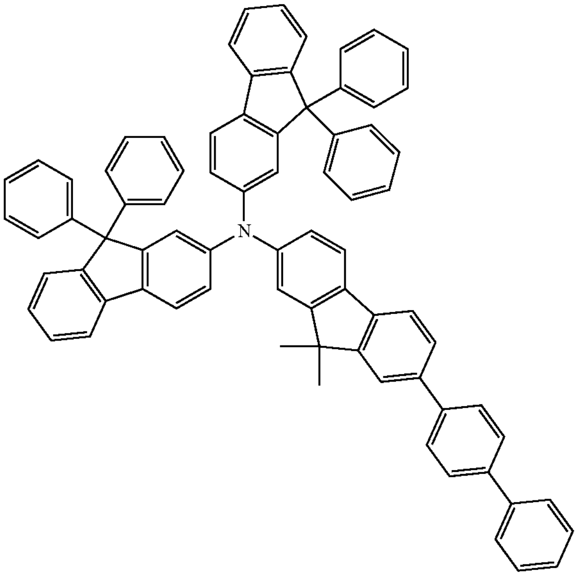
-continued
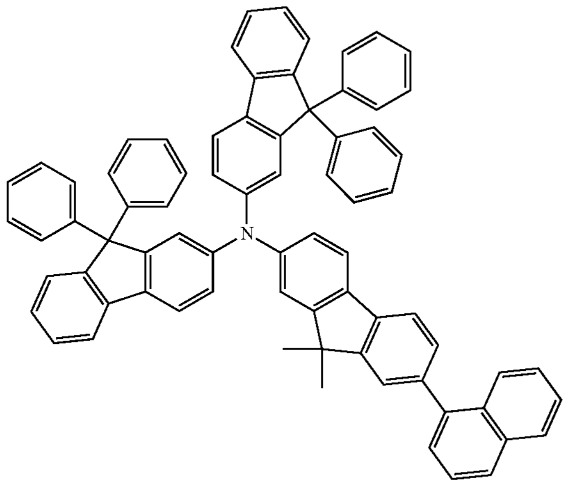
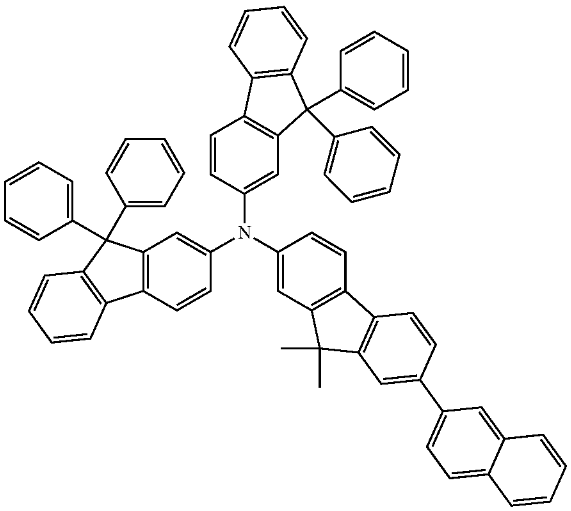
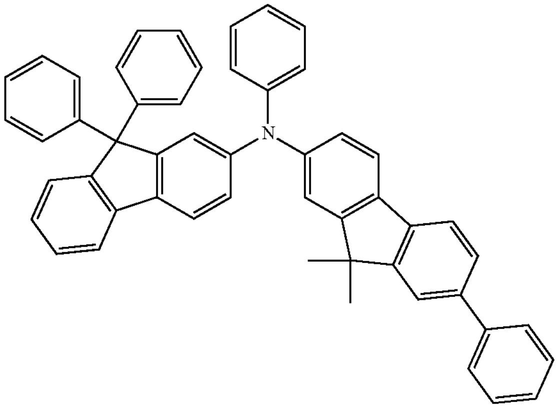

-continued
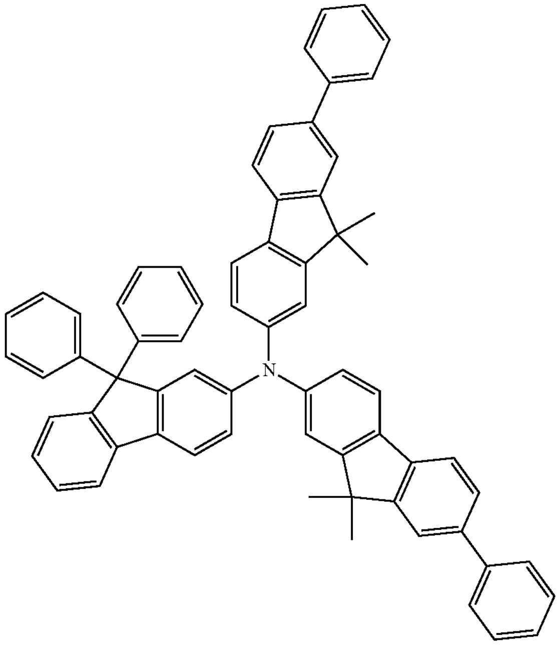
-continued
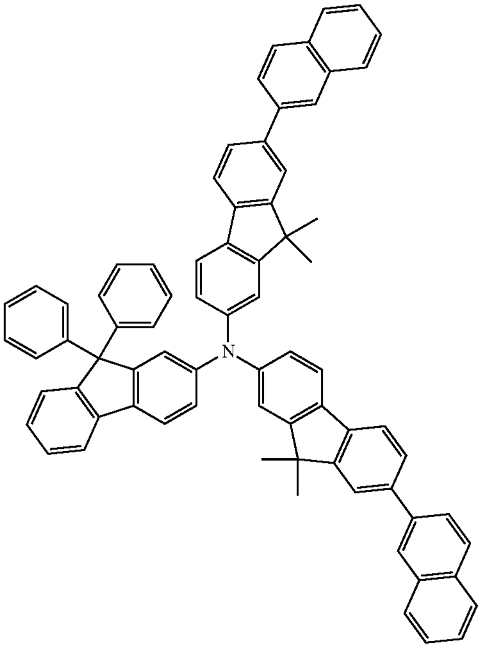
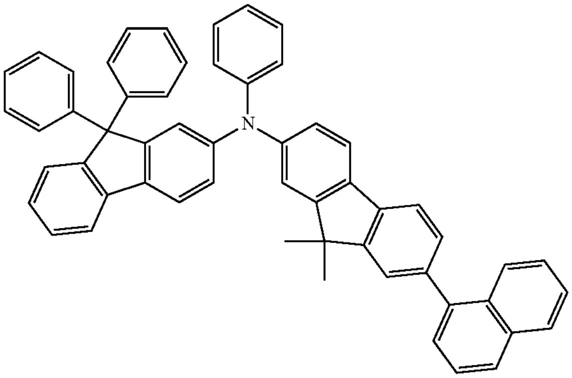
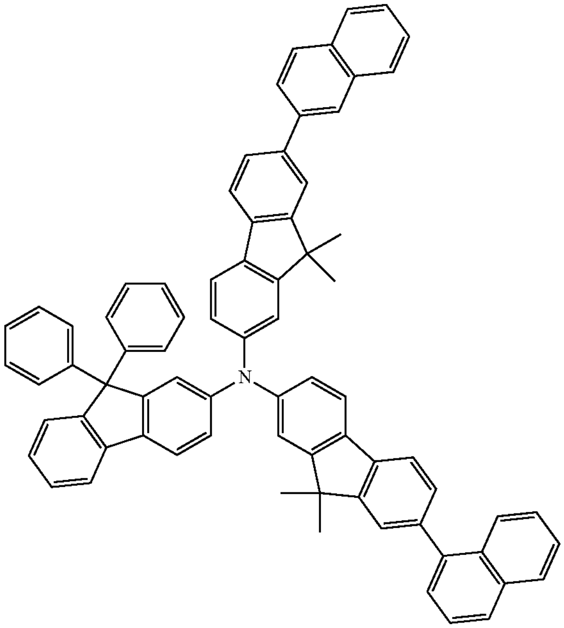
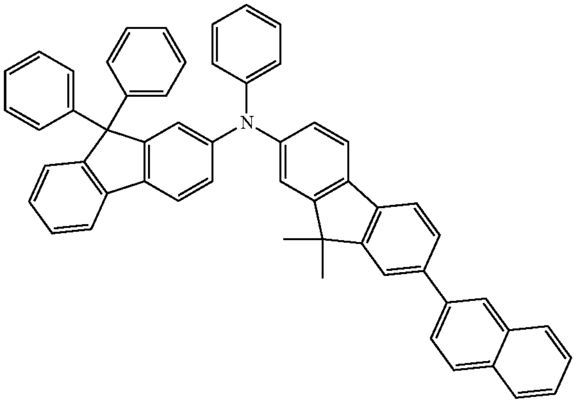

-continued
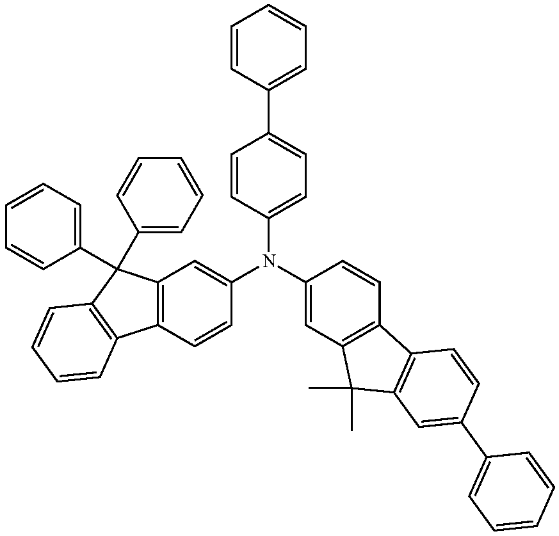
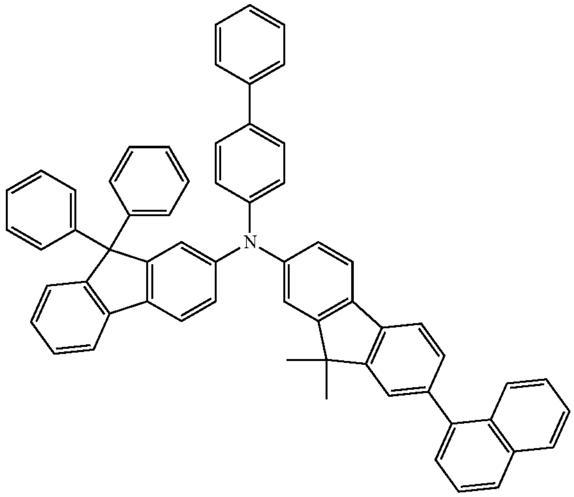
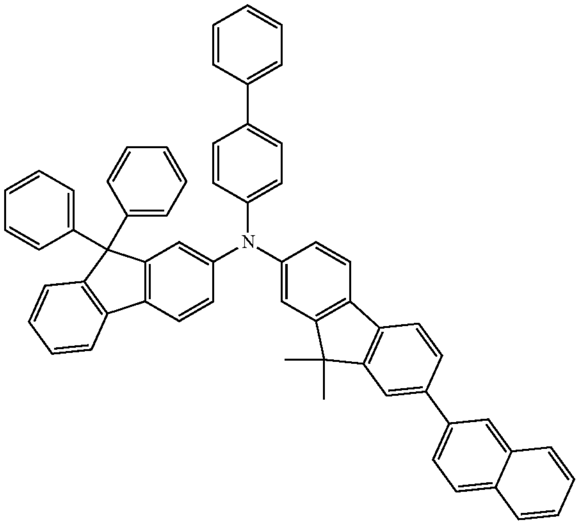
-continued
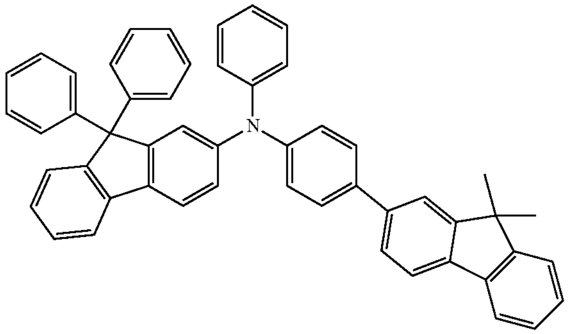
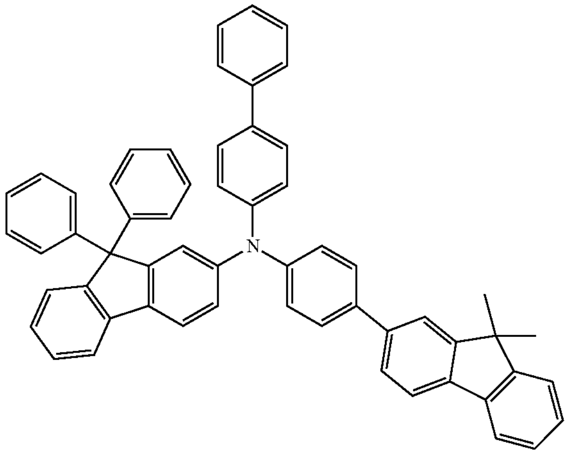
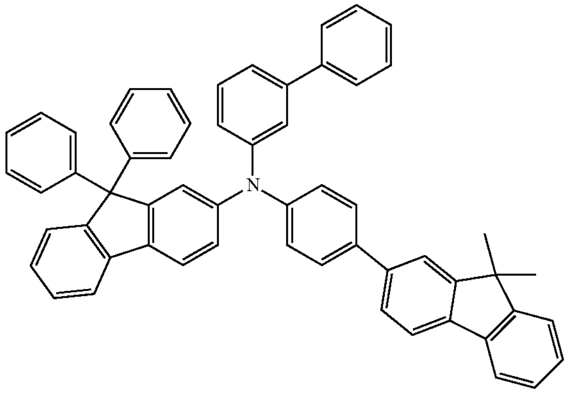
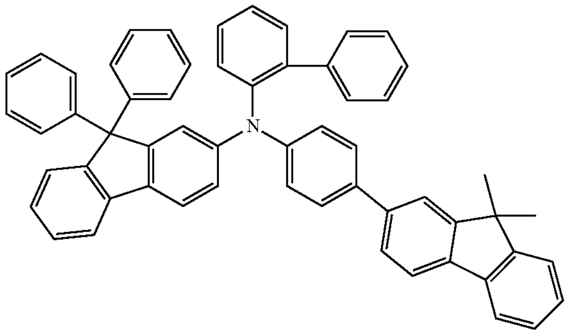

-continued
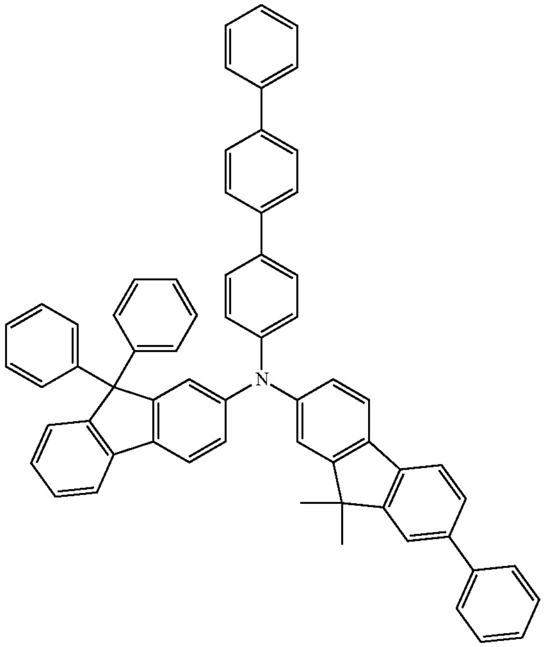
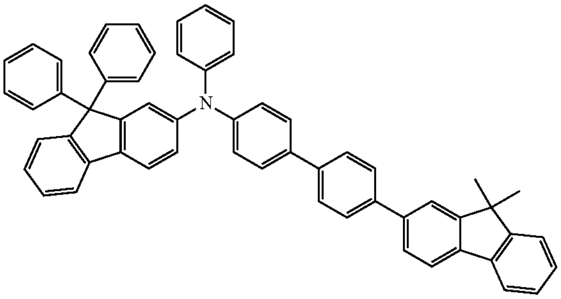
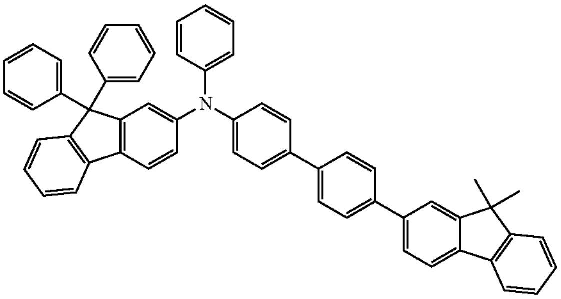
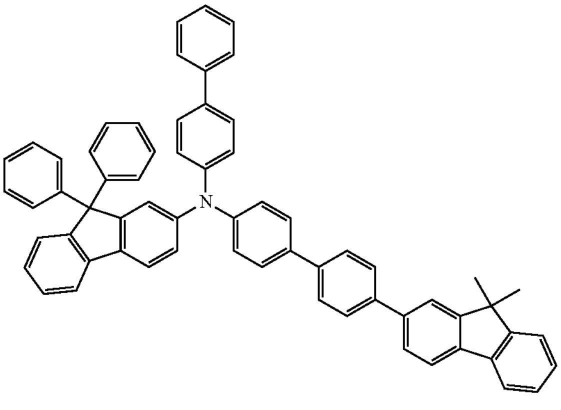
-continued
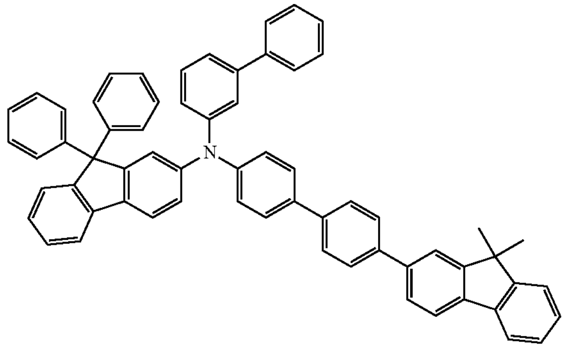
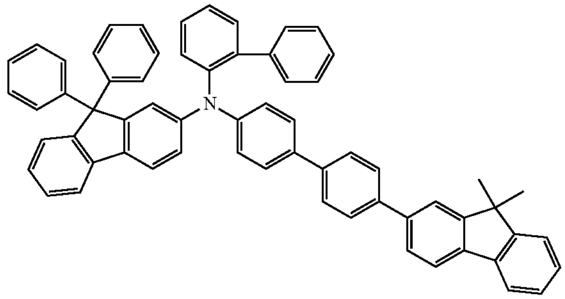
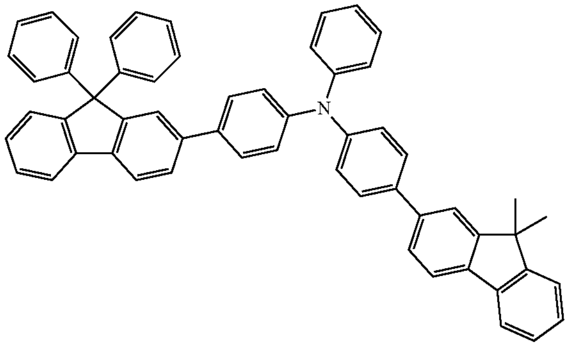
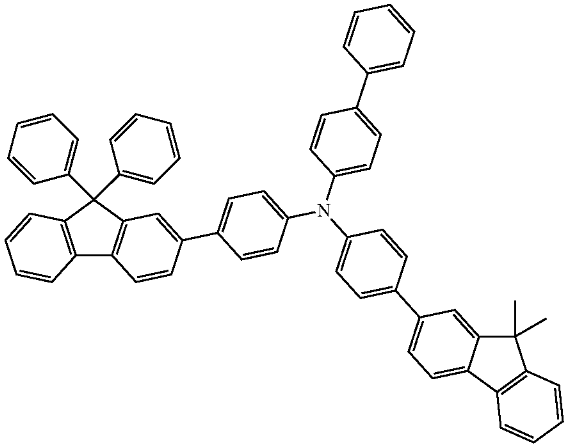

-continued
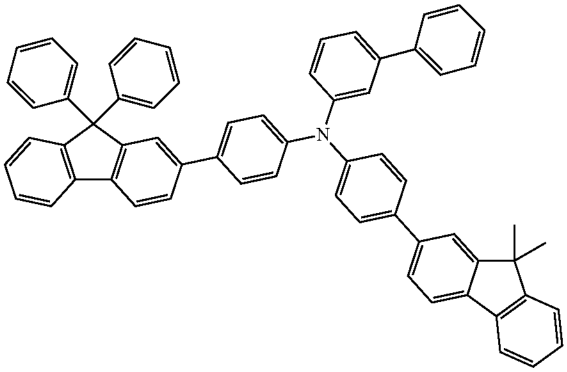
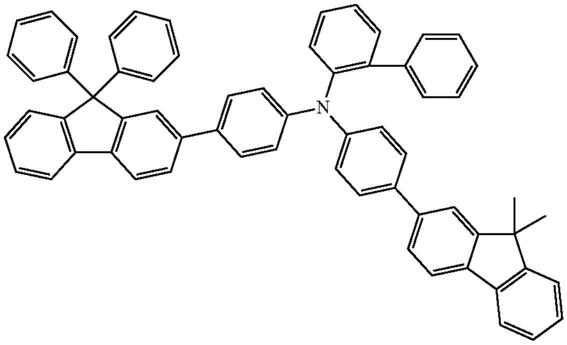
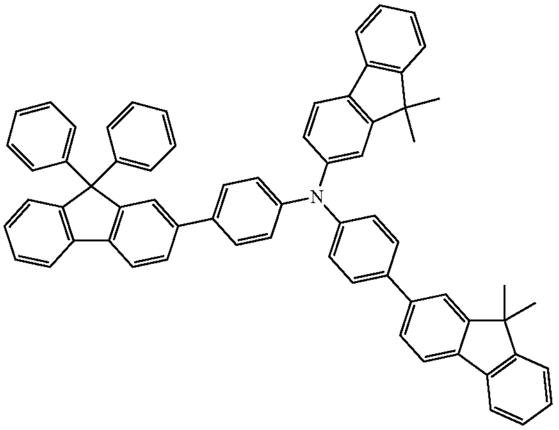
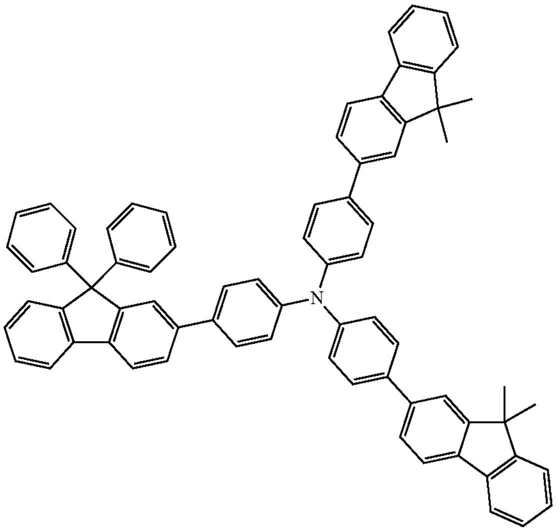
-continued
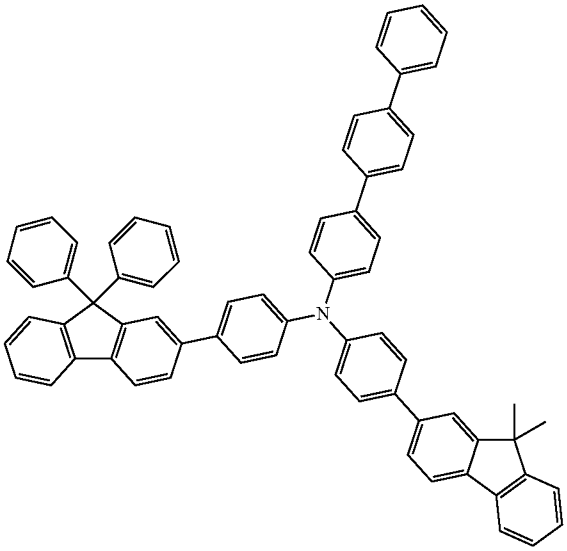
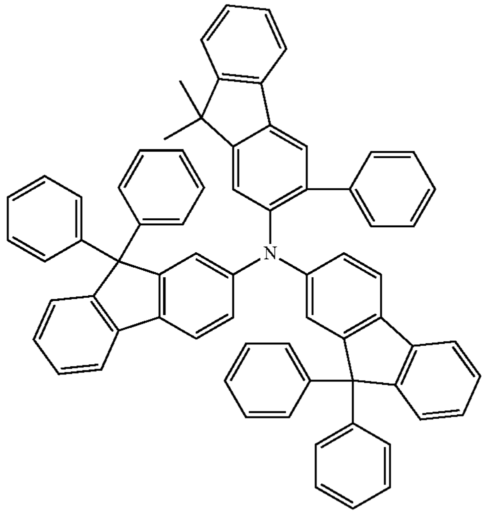
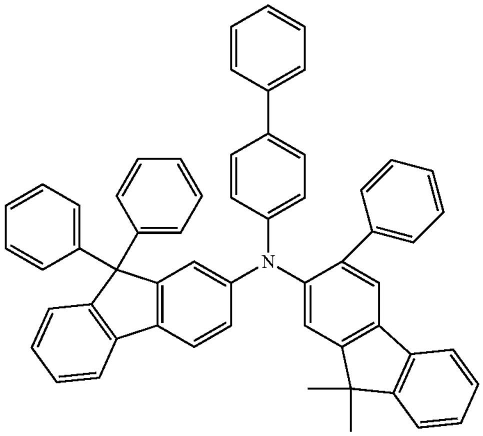

-continued
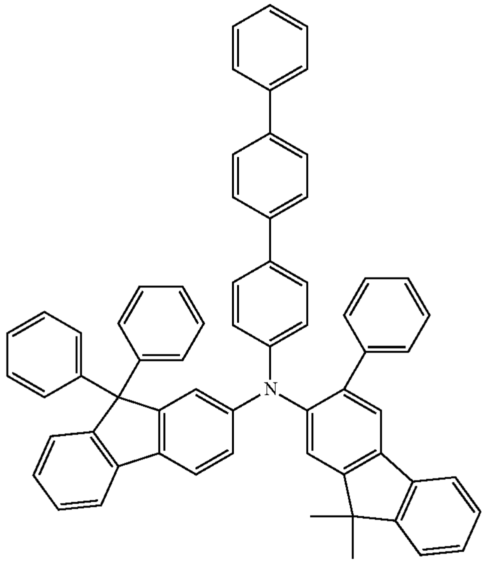
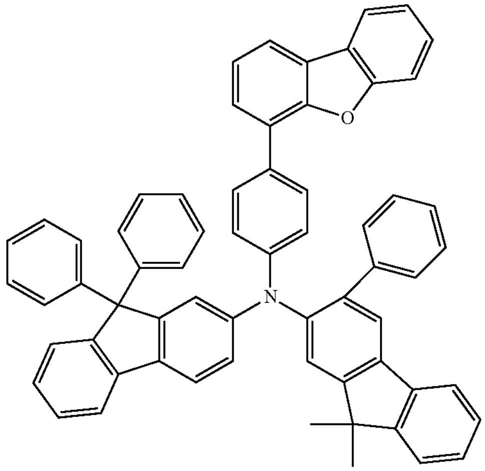
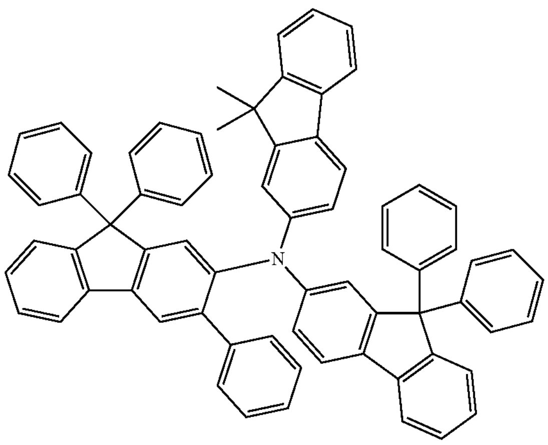
-continued
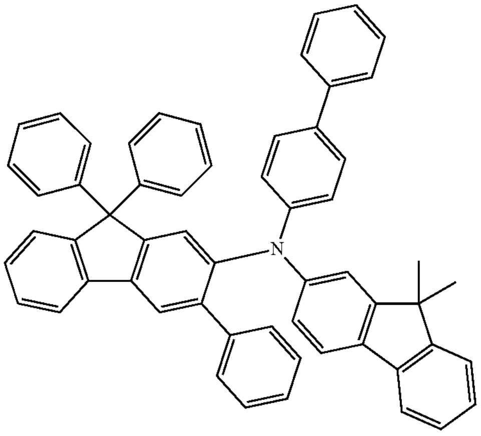
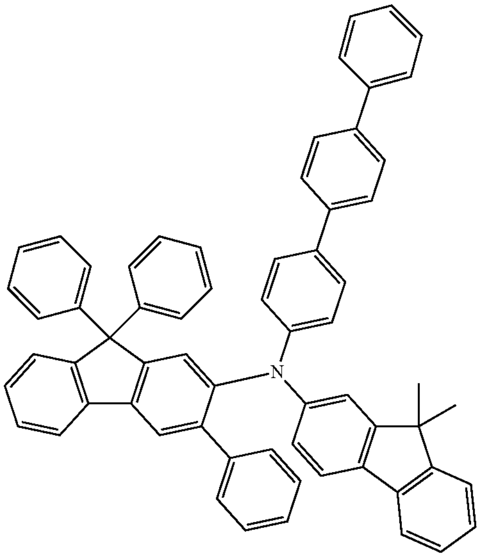
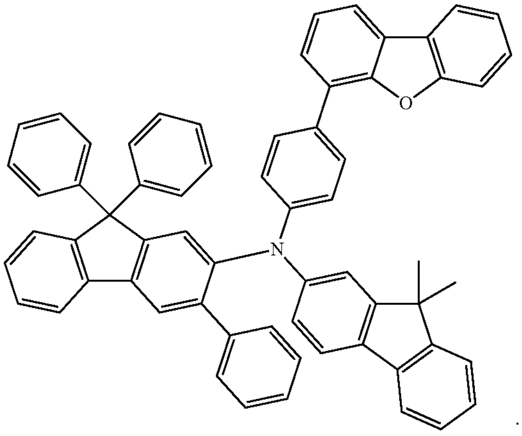
.
5. The organic light emitting diode of claim 1, wherein the dopant is one or more selected from among the following compounds:

-continued
Dp-1
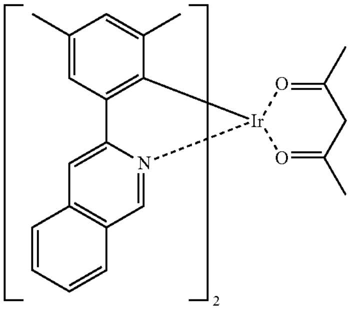
Dp-2
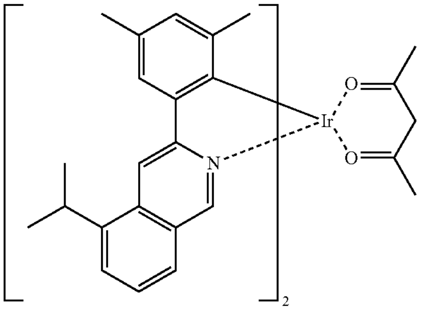
Dp-3
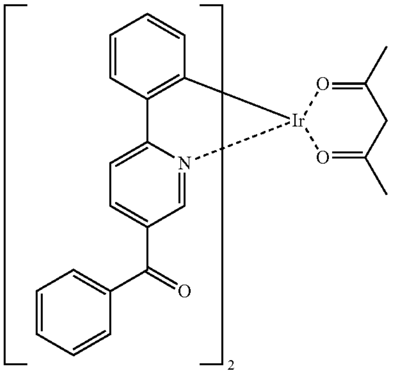
Dp-4
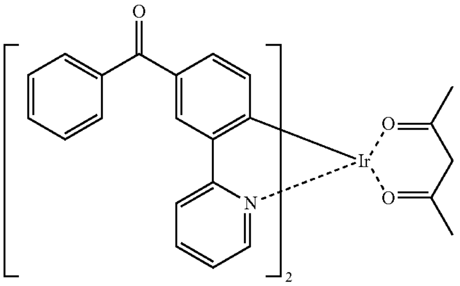
Dp-5
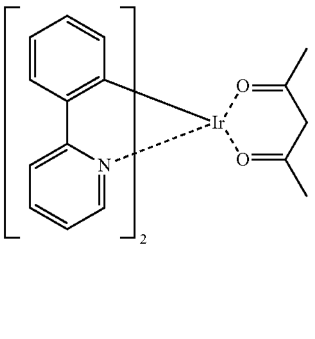
Dp-6
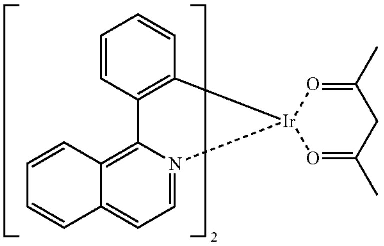
Dp-7
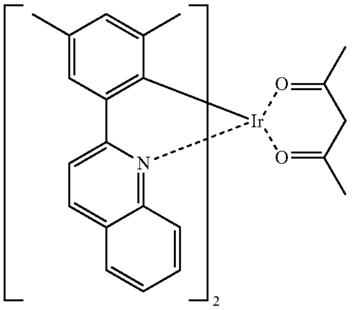
Dp-8
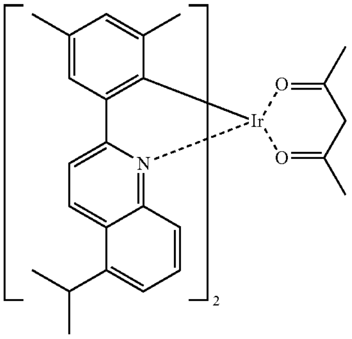
Dp-9
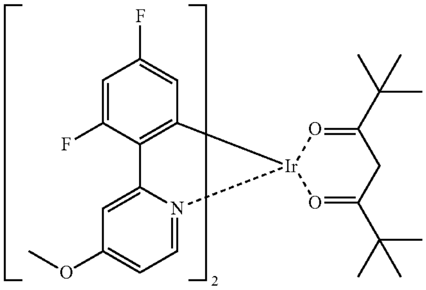
Dp-10
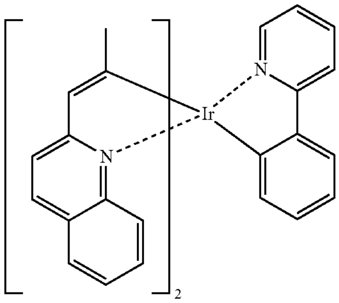

-continued
Dp-11
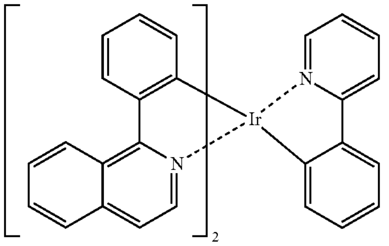
Dp-12
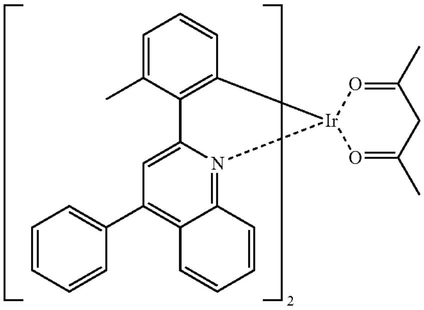
DP-13
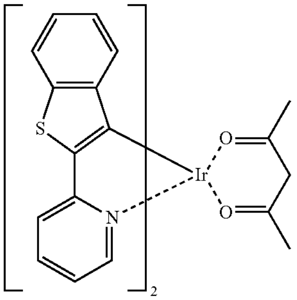
Dp-14
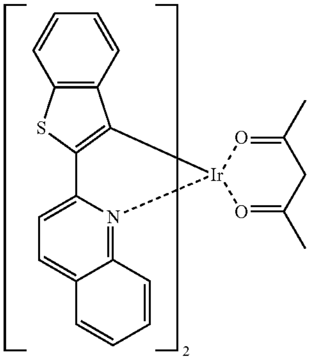
Dp-15
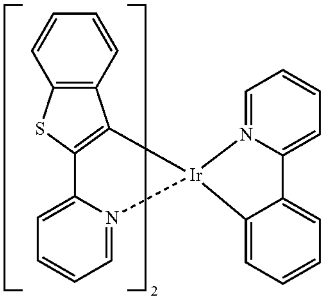
-continued
DP-16
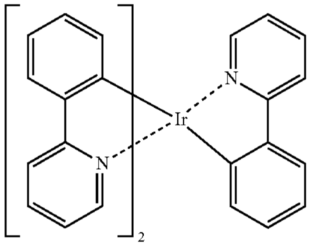
Dp-17
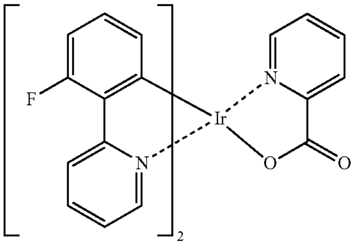
Dp-18
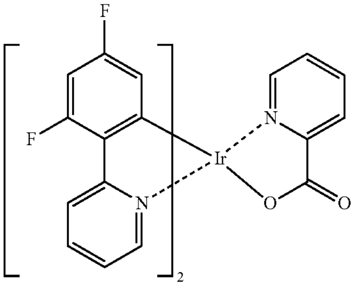
Dp-19
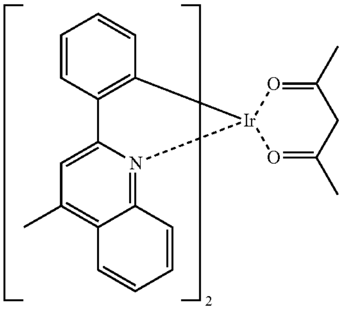
Dp-20
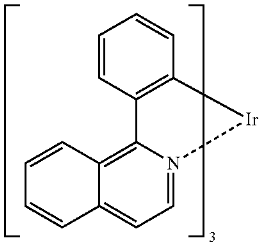
Dp-21
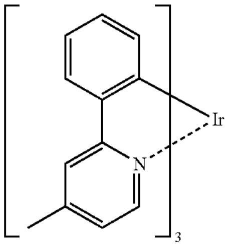

-continued
Dp-22
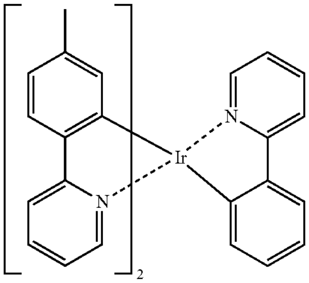
Dp-23
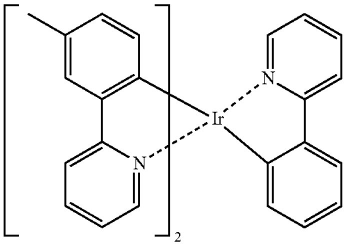
Dp-24
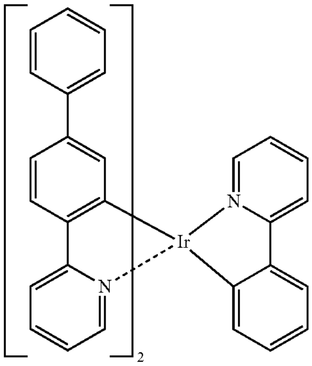
Dp-25
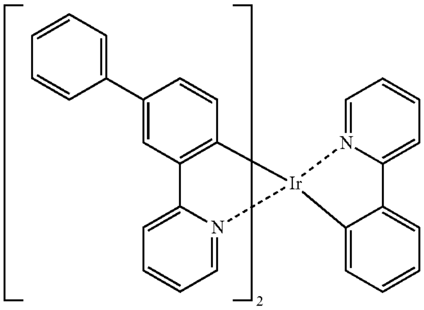
Dp-26
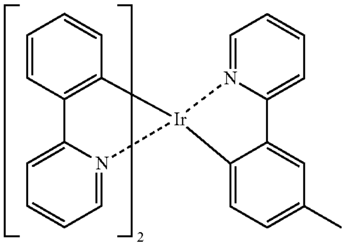
-continued
Dp-27
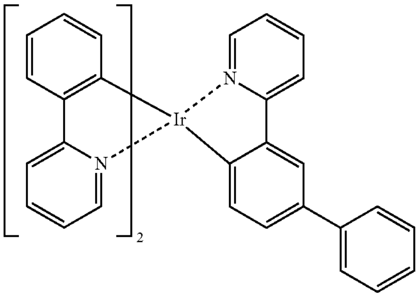
Dp-28
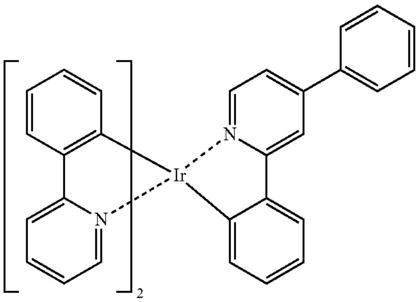
Dp-29
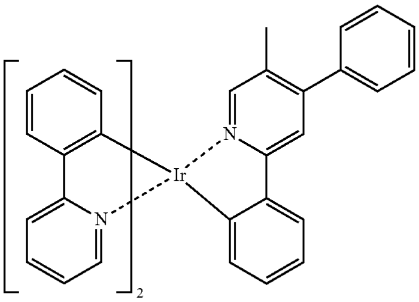
Dp-30
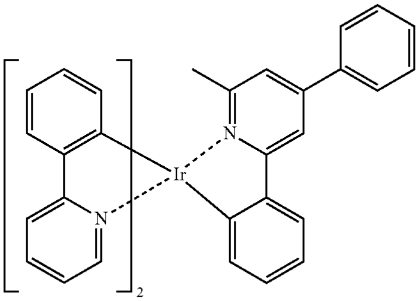
Dp-31
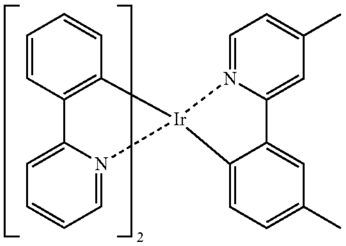

-continued
Dp-32
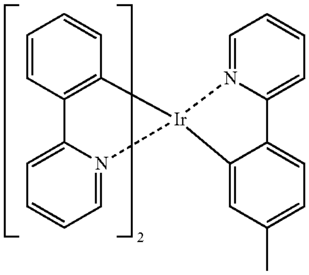
Dp-33
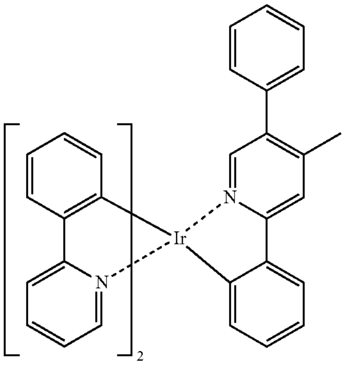
Dp-34
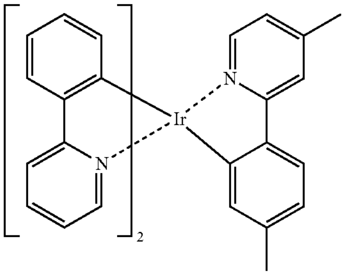
Dp-35
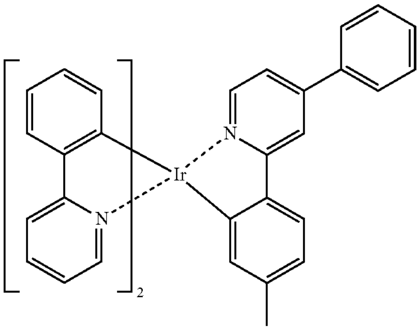
-continued
Dp-36
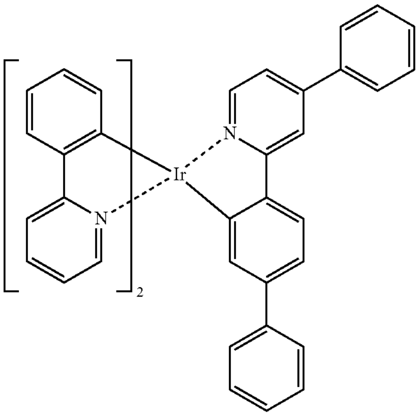
Dp-37
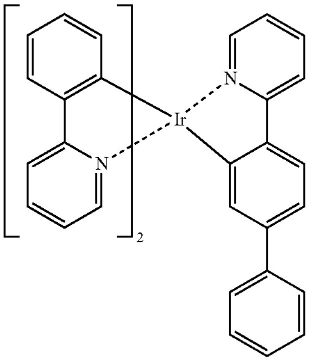
Dp-38
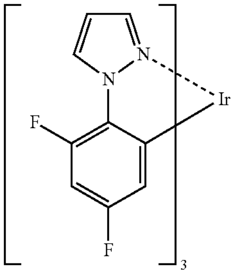
Dp-39
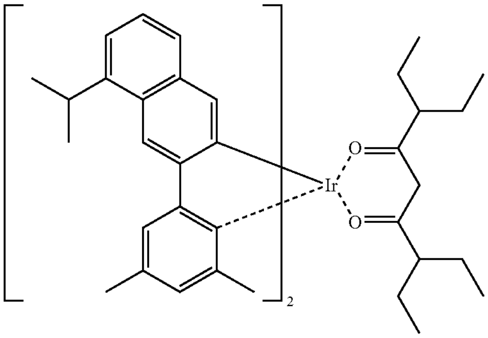
.
* * * * *